(12) United States Patent
Hadari et al.

(10) Patent No.: US 10,781,267 B2
(45) Date of Patent: *Sep. 22, 2020

(54) METHODS OF TREATING BY ADMINISTERING ANTI-KIT ANTIBODIES

(71) Applicant: Celldex Therapeutics, Inc., Hampton, NJ (US)

(72) Inventors: Yaron Hadari, Harrison, NY (US); Elizabeth M Mandel-Bausch, Pleasant Prairie, WI (US); Francis Joseph Carr, Balmedie (GB); Timothy David Jones, Babraham (GB); Laura Clare Alexandra Perry, Lidgate (GB)

(73) Assignee: Celldex Therapeutics, Inc., Hampton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/221,002

(22) Filed: Dec. 14, 2018

(65) Prior Publication Data

US 2019/0106510 A1  Apr. 11, 2019

Related U.S. Application Data

(62) Division of application No. 15/433,482, filed on Feb. 15, 2017, now Pat. No. 10,184,007, which is a division of application No. 15/084,715, filed on Mar. 30, 2016, now Pat. No. 9,605,081, which is a division of application No. 13/949,931, filed on Jul. 24, 2013, now Pat. No. 9,334,332.

(60) Provisional application No. 61/675,762, filed on Jul. 25, 2012, provisional application No. 61/675,751, filed on Jul. 25, 2012.

(51) Int. Cl.
| | | |
|---|---|---|
| *A61K 39/395* | (2006.01) | |
| *C07K 16/28* | (2006.01) | |
| *C07K 16/40* | (2006.01) | |
| *A61K 47/68* | (2017.01) | |
| *A61K 31/4045* | (2006.01) | |
| *A61K 31/506* | (2006.01) | |
| *A61K 38/19* | (2006.01) | |
| *A61K 45/06* | (2006.01) | |
| *G01N 33/566* | (2006.01) | |
| *C07K 16/32* | (2006.01) | |
| *G01N 33/574* | (2006.01) | |
| *A61K 39/00* | (2006.01) | |

(52) U.S. Cl.
CPC .......... *C07K 16/40* (2013.01); *A61K 31/4045* (2013.01); *A61K 31/506* (2013.01); *A61K 38/19* (2013.01); *A61K 39/3955* (2013.01); *A61K 39/39533* (2013.01); *A61K 39/39558* (2013.01); *A61K 45/06* (2013.01); *A61K 47/6851* (2017.08); *C07K 16/2803* (2013.01); *C07K 16/32* (2013.01); *C12Y 207/10001* (2013.01); *G01N 33/566* (2013.01); *G01N 33/5748* (2013.01); *A61K 2039/505* (2013.01); *C07K 2317/14* (2013.01); *C07K 2317/21* (2013.01); *C07K 2317/24* (2013.01); *C07K 2317/31* (2013.01); *C07K 2317/55* (2013.01); *C07K 2317/56* (2013.01); *C07K 2317/565* (2013.01); *C07K 2317/567* (2013.01); *C07K 2317/76* (2013.01); *C07K 2317/77* (2013.01); *C07K 2317/92* (2013.01); *G01N 2333/70596* (2013.01); *G01N 2333/91205* (2013.01)

(58) Field of Classification Search
None
See application file for complete search history.

(56) References Cited

U.S. PATENT DOCUMENTS

| | | |
|---|---|---|
| 5,268,358 A | 12/1993 | Fretto |
| 5,489,516 A | 2/1996 | Broudy et al. |
| 5,545,533 A | 8/1996 | Bartke et al. |
| 5,686,572 A | 11/1997 | Wolf et al. |
| 5,808,002 A | 9/1998 | Biihring |
| 5,817,310 A | 10/1998 | Ramakrishnan et al. |
| 5,882,644 A | 3/1999 | Chang et al. |
| 5,891,652 A | 4/1999 | Wolf et al. |
| 5,906,938 A | 5/1999 | Broudy et al. |
| 5,911,988 A | 6/1999 | Brownell et al. |
| 5,919,911 A | 7/1999 | Broudy et al. |

(Continued)

FOREIGN PATENT DOCUMENTS

| | | |
|---|---|---|
| EP | 0548867 A2 | 6/1993 |
| EP | 0787743 A2 | 8/1997 |

(Continued)

OTHER PUBLICATIONS

Staser et al., Jul. 2010, "Mast cells and the neurofibroma microenvironment," Blood 116(2):157-164.

(Continued)

*Primary Examiner* — Phillip Gambel
(74) *Attorney, Agent, or Firm* — Jones Day

(57) ABSTRACT

Provided herein, in one aspect, are antibodies that immunospecifically bind to a human KIT antigen comprising the fourth and/or fifth extracellular Ig-like domains (that is, D4 and/or D5 domains), polynucleotides comprising nucleotide sequences encoding such antibodies, and expression vectors and host cells for producing such antibodies. The antibodies can inhibit KIT activity, such as ligand-induced receptor phosphorylation. Also provided herein are kits and pharmaceutical compositions comprising antibodies that specifically bind to a KIT antigen, as well as methods of treating or managing a KIT-associated disorder or disease and methods of diagnosing a KIT-associated disorder or disease using the antibodies described herein.

22 Claims, 15 Drawing Sheets

Specification includes a Sequence Listing.

(56) References Cited

U.S. PATENT DOCUMENTS

| | | |
|---|---|---|
| 5,922,847 A | 7/1999 | Broudy et al. |
| 6,001,803 A | 12/1999 | Besmer et al. |
| 6,403,559 B1 | 6/2002 | Besmer et al. |
| 6,495,331 B1 | 12/2002 | Gelfand et al. |
| 6,555,367 B1 | 4/2003 | Spence et al. |
| 6,576,812 B1 | 6/2003 | Longley et al. |
| 6,977,159 B1 | 12/2005 | Longley et al. |
| 6,989,248 B2 | 1/2006 | Longley |
| 6,998,391 B2 | 2/2006 | Lyons et al. |
| 7,303,893 B1 | 12/2007 | Chien et al. |
| 7,419,777 B2 | 9/2008 | Bacus |
| 7,449,309 B2 | 11/2008 | Longley |
| 7,906,302 B2 | 3/2011 | Longley |
| 7,915,391 B2 | 3/2011 | Ng et al. |
| 7,959,942 B2 | 6/2011 | Cottone |
| 8,088,060 B2 | 1/2012 | Cottone et al. |
| 8,133,485 B2 | 3/2012 | Levi-Schaffer et al. |
| 8,133,733 B2 | 3/2012 | Khan |
| 8,278,067 B2 | 10/2012 | Longley et al. |
| 8,436,150 B2 | 5/2013 | Ng et al. |
| 8,552,157 B2 | 10/2013 | Amatulli et al. |
| 8,791,249 B2 | 7/2014 | Ng et al. |
| 9,067,986 B2 | 6/2015 | Gurney et al. |
| 9,334,332 B2 | 5/2016 | Hadari et al. |
| 9,540,443 B2 | 1/2017 | Hadari et al. |
| 9,605,081 B2 | 3/2017 | Hadari et al. |
| 10,184,007 B2 | 1/2019 | Hadari et al. |
| 10,189,907 B2 | 1/2019 | Hadari et al. |
| 10,239,943 B2 | 3/2019 | Lavallee et al. |
| 2002/0118775 A1 | 8/2002 | Persson et al. |
| 2004/0018593 A1 | 1/2004 | Jill et al. |
| 2004/0110226 A1 | 6/2004 | Lazar et al. |
| 2004/0248215 A1 | 12/2004 | Keler et al. |
| 2005/0004066 A1 | 1/2005 | Rockwell |
| 2005/0232917 A1 | 10/2005 | Pullen et al. |
| 2005/0244409 A1 | 11/2005 | Erickson-Miller et al. |
| 2005/0261175 A1 | 11/2005 | Zsebo et al. |
| 2005/0276784 A1 | 12/2005 | Besmer et al. |
| 2005/0281828 A1 | 12/2005 | Bowdish et al. |
| 2006/0019280 A1 | 1/2006 | Chen et al. |
| 2007/0004910 A1 | 1/2007 | Sexton et al. |
| 2007/0225202 A1 | 9/2007 | Andreev et al. |
| 2007/0253951 A1 | 11/2007 | Ng et al. |
| 2008/0032989 A1 | 2/2008 | Robinson et al. |
| 2008/0095775 A1 | 4/2008 | Lewis et al. |
| 2008/0213774 A1 | 9/2008 | Chen et al. |
| 2008/0260729 A1 | 10/2008 | Nash et al. |
| 2008/0274469 A1 | 11/2008 | Bastian et al. |
| 2008/0287309 A1 | 11/2008 | Bowdish et al. |
| 2009/0022740 A1 | 1/2009 | Bergstein |
| 2009/0022741 A1 | 1/2009 | Bergstein |
| 2009/0028879 A1 | 1/2009 | Bergstein |
| 2009/0075381 A1 | 3/2009 | Clarke et al. |
| 2009/0136450 A1 | 5/2009 | Chumakov et al. |
| 2009/0136497 A1 | 5/2009 | Longley et al. |
| 2009/0136517 A1 | 5/2009 | Garton et al. |
| 2009/0149389 A1 | 6/2009 | Panitch et al. |
| 2009/0169547 A1 | 7/2009 | Sahin et al. |
| 2009/0181017 A1 | 7/2009 | Hass et al. |
| 2009/0181022 A1 | 7/2009 | Nielson et al. |
| 2009/0186031 A1 | 7/2009 | Wood et al. |
| 2009/0191201 A1 | 7/2009 | Heiss et al. |
| 2009/0192133 A1 | 7/2009 | Horton |
| 2009/0233905 A1 | 9/2009 | Burke et al. |
| 2009/0246206 A1 | 10/2009 | Nielson et al. |
| 2009/0304625 A1 | 12/2009 | Husain et al. |
| 2010/0029674 A1 | 2/2010 | Tiollier et al. |
| 2010/0124569 A1 | 5/2010 | Abbot et al. |
| 2010/0129440 A1 | 5/2010 | Zhao et al. |
| 2010/0143935 A1 | 6/2010 | Davis |
| 2010/0173324 A1 | 7/2010 | Mori et al. |
| 2010/0196923 A1 | 8/2010 | Atala |
| 2010/0204058 A1 | 8/2010 | Chang et al. |
| 2010/0226927 A1 | 9/2010 | Weissman et al. |
| 2010/0298331 A1 | 11/2010 | Lee et al. |
| 2010/0316640 A1 | 12/2010 | Sundaram et al. |
| 2011/0059091 A1 | 3/2011 | Chang et al. |
| 2011/0091428 A1 | 4/2011 | Anversa |
| 2011/0123532 A1 | 5/2011 | Gurney et al. |
| 2011/0182866 A1 | 7/2011 | McNiece et al. |
| 2011/0195975 A1 | 8/2011 | Clapp et al. |
| 2011/0223165 A1 | 9/2011 | Ng et al. |
| 2011/0262465 A1 | 10/2011 | Gao et al. |
| 2011/0268776 A1 | 11/2011 | Schapira et al. |
| 2011/0281813 A1 | 11/2011 | Advani et al. |
| 2011/0293574 A1 | 12/2011 | Chute et al. |
| 2011/0311538 A1 | 12/2011 | Schlessinger et al. |
| 2011/0318351 A1 | 12/2011 | Bergstein |
| 2012/0065380 A1 | 3/2012 | Yoo et al. |
| 2012/0189633 A1 | 7/2012 | Hadari et al. |
| 2012/0328599 A1 | 12/2012 | Bae et al. |
| 2013/0011406 A1 | 1/2013 | Hadari et al. |
| 2013/0071397 A1 | 3/2013 | Schlessinger et al. |
| 2013/0184221 A9 | 7/2013 | Panitch et al. |
| 2013/0266595 A1 | 10/2013 | Flygare et al. |
| 2014/0056905 A1 | 2/2014 | Hadari et al. |
| 2014/0065168 A1 | 3/2014 | Hadari et al. |
| 2017/0073422 A1 | 3/2017 | Hadari et al. |
| 2017/0121408 A1 | 5/2017 | LaVallee et al. |
| 2019/0100598 A1 | 4/2019 | Hadari et al. |
| 2019/0153094 A1 | 5/2019 | LaVallee et al. |

FOREIGN PATENT DOCUMENTS

| | | |
|---|---|---|
| EP | 1378752 A1 | 1/2004 |
| EP | 0586445 B1 | 9/2004 |
| EP | 0889125 B1 | 8/2008 |
| JP | 2009534052 A | 9/2009 |
| JP | 2013510166 A | 3/2013 |
| WO | WO 1992/17505 A1 | 10/1992 |
| WO | WO 1992/021766 A1 | 12/1992 |
| WO | WO 1993/010805 A1 | 6/1993 |
| WO | WO 1998/41090 A1 | 9/1998 |
| WO | WO 2000/067794 A1 | 11/2000 |
| WO | WO 2001/034201 A2 | 5/2001 |
| WO | WO 2003/065995 A2 | 8/2003 |
| WO | WO 2003/091437 A1 | 11/2003 |
| WO | WO 2004/002425 A2 | 1/2004 |
| WO | WO 2005/095640 A1 | 10/2005 |
| WO | WO 2006/017173 A1 | 2/2006 |
| WO | WO 2007/004060 A2 | 1/2007 |
| WO | WO 2007/127317 A2 | 11/2007 |
| WO | WO 2008/112290 A2 | 9/2008 |
| WO | WO 2008/153926 A2 | 12/2008 |
| WO | WO 2009/082624 A2 | 7/2009 |
| WO | WO 2009/135001 A2 | 11/2009 |
| WO | WO 2009/152288 A1 | 12/2009 |
| WO | WO 2010/136508 A2 | 12/2010 |
| WO | WO 2011/057022 A1 | 5/2011 |
| WO | WO 2011/119948 A1 | 9/2011 |
| WO | WO 2012/093172 A1 | 7/2012 |
| WO | WO 2012/103165 A2 | 8/2012 |
| WO | WO 2012/154480 A1 | 11/2012 |
| WO | WO 2013/177481 A1 | 11/2013 |
| WO | WO 2014/018625 A1 | 1/2014 |
| WO | WO 2015/050959 A1 | 4/2015 |
| WO | WO 2015/112822 A1 | 7/2015 |

OTHER PUBLICATIONS

Pummi et al., Jan. 2006, "Tight junction proteins and perineurial cells in neurofibromas, " J Histochem Cytochem 54(1):53-61.

Imai and Takaoka, 2006, "Comparing antibody and small-molecule therapies for cancer", Nature Reviews Cancer 6(9): 714-727.

Adams et al., 2006, "Humanization of a recombinant monoclonal antibody to produce a therapeutic HER dimerization inhibitor, Pertuzumab", Cander Immunol Immunother, 55:717-727 (published online Sep. 3, 2005).

Amir-Zaltsman et al., 2000, "Inhibitors of protein tyrosine phosphorylation: preliminary assessment of activity by time-resolved fluorescence", Luminescence, 15:377-380.

(56) References Cited

OTHER PUBLICATIONS

Ashman et al., 1994, "Epitope mapping and functional studies with three monoclonal antibodies to the C-kit receptor tyrosine kinase", J Cell Physiol, 158(3):545-554.

Atienza et al., 2006, "Label-free and real-time cell-based kinase assay for screening selective and potent receptor tyrosine kinase inhibitors using microelectronic sensor array", J Biomolec Screening, 11(6):634-643.

Bae et al., 2000, "Arginine-rich anti-vascular endothelial growth factor peptides inhibit tumor growth and metastasis by blocking angiogenesis", J Biol Chem, 275(18):13588-13596.

Bae et al., 2010, "Asymmetric recepor contact is required for tyrosine autophosphorylation of fibroblast growth factor receptor in living cells", Proc Natl Acad Sci USA, 107(7):2866-2867.

Baselga et al., 2005, "Critical update and emerging trends in epidermal growth factor receptor targeting in cancer", J Clin Oncol, 23(11):2445-2459.

Berezov et al., 2002, "Disabling receptor ensembles with rationally designed interface peptidomimetics", J Biol Chem, 277(31):28330-28339.

Besmer et al., 1986, "A new acute transforming feline retrovirus and relationship of its oncogene v-kit with the protein kinase gene family", Nature, 320:415-421.

Binetruy-Tournaire et al., 2000, "Identification of a peptide blocking vascular endothelial growth factor (VEGF)-mediated angiogenesis", EMBO J, 19(7):1525-1533.

Blechman et al., 1993a, "Soluble c-kit proteins and antireceptor monoclonal antibodies confine the binding site of stem cell factor", J Biol Chem, 268(6):4399-4406.

Blechman et al., 1993b, "Structure-function analyses of the kit receptor for the steel factor", Stem Cells, 11:12-21.

Blechman et al., 1995a, "The fourth immunolglobulin domain of the stem cell factor receptor couples ligand binding to signal transduction", Cell, 80:103-113.

Blechman and Yarden, 1995b, "Structural aspects of receptor dimerization. C-KIT as an example", Ann N Y Acad Sci 766:344-362.

Briddell et al., 1992, "Further phenotypic characterization and isolation of human hematopoietic progenitor cells using a monoclonal antibody to the c-kit receptor", Blood 79(12):3159-3167.

Broudy et al., Jan. 1992, "Isolation and characterization of a monoclonal antibody that recognizes the human c-kit receptor", Blood 79(2):338-346.

Broudy et al., 2001, "The fifth immunoglobulin-like domain of the Kit receptor is required for proteolytic cleavage from the cell surface", Cytokine 15(4):188-195.

Carlberg and Rohrschneider, 1994, "The effect of activating mutations on dimerization, tyrosine phosphorylation and internalization of the macrophage colony stimulating factor receptor", Molec Biol Cell, 5(1):81-95.

Chen et al., 1995 Jun., "Enhancement and destruction of antibody function by somatic mutation: unequal occurrence is controlled by V gene combinatorial associations," EMBO J, 14(12):2784-2794.

Chen et al., 2008, "A crystallographic snapshot of tyrosine transphosphorylation in action", Proc Natl Acad Sci USA, 105(50):19660-19665.

Colman et al., Jan. 1994, "Effects of amino acid sequence changes on antibody-antigen interactions," Res Immunol, 145(1):33-36.

Edris et al., 2013, "Anti-KIT Monoclonal Antibody Inhibits Imatinib-resistant Gastrointestinal Stromal Tumor Growth", Proc. Natl. Acad. Sci. U S A., 110(9):3501-3506, (Epub Feb. 4, 2013).

Gedrich et al., "Regulation of Mast Cell Activity by KTN0158, a Humanized anti-KIT Monoclonal Antibody", Children's Tumor Foundation 2014 NF Conference, Jun. 7-10, 2014, Washington, D.C., Meeting Abstract.

Gedrich et al., "Regulation of Mast Cell Activity by KTN0158, a Humanized anti-KIT Monoclonal Antibody", Children's Tumor Foundation 2014 NF Conference, Jun. 7-10, 2014, Washington, D.C., Meeting Poster.

Gedrich et al., "Targeting KIT on innate immune cells enhances the antitumor activity of checkpoint inhibitors in vivo," Society for Immunotherapy of Cancer (SITC) 30th Annual Meeting, Nov. 6-8, 2015, National Harbor, MD, slide presentation on Nov. 7, 2015.

Gedrich et al., Nov. 4, 2015, "Targeting KIT on innate immune cells enhances the antitumor activity of checkpoint inhibitors in vivo," J Immunother Cancer 3(Suppl 2): O12, Meeting Abstract for Society for Immunotherapy of Cancer (SITC) 30th Annual Meeting, Nov. 6-8, 2015, National Harbor, MD.

GenBan Accession No. AAC50968.1 (KIT_Mouse), dated Feb. 6, 1997. Retrieved from the Internet: URL<http://www.ncbi.nlm.nih.gov/entrez/viewer.fcgi?db=protein&id=1817733>.

GenBan Accession No. P05532, dated May 1, 2007. Retrieved from the Internet: URL<http://www.ncbi.nlm.nih.gov/entrez/viewer.fcgi?1254373:PROT:4572902>.

Granier et al., 2007, "Structure and conformational changes in the c-terminal domain of the beta2-adrenoceptor", J Biol Chem, 282(18):13895-13905.

Harding et al., May-Jun. 2010, "The immunogenicity of humanized and fully human antibodies: residual immunogenicity resides in the CDR regions," Mabs, 2(3):256-265.

Hubbard et al., 2005, "EGF receptor inhibition: attacks on multiple fronts", Cancer Cell, 7(4):287-288.

Japanese Society for Bioinfonnatics (ed.), Encyclopedia of Bioinfomatics, Jul. 1, 2006, pp. 462-463. (English abstract).

Jeffrey et al., Jul. 2013, A potent anti-CD70 antibody-drug conjugate combining a dimeric pyrrolobenzodiazepine drug with site-specific conjugation technology:, Bioconjugate Chem 24:1256-1263.

Jiang et al., 2000, "Structure of the active core of human stem cell factor and analysis of binding to its receptor kit", EMBO J, 19(13):3192-3203.

Kussie et al., Jan. 1994, "A single engineered amino acid substitution changes antibody fine specificity," J Immunol, 152(1):146-152.

Lebron et al., 2014, "A human monoclonal antibody targeting the stem cell factor receptor (c-Kit) blocks tumor cell signaling and inhibits tumor growth", Cancer Biol Ther 15(9):1208-1218.

Lemmon et al., 1997, "Kit receptor dimerization is driven by bivalent binding of stem cell factor", J Biol Chem, 272(10):6311-6317.

Lemmon et al., 2007, "A new twist in the transmembrane signaling tool-kit", Cell, 130(2):213-215.

Lennartsson et al., 2004, "Synergistic growth of stem cell factor and granulocyte macrophage colony-stimulating factor involves kinase-dependent and -independent contributions from c-kit", J Biol Chem, 279(43):44544-44553.

Lerner et al., May 1991, "Monoclonal Antibody YB5.B8 Identifies the Human c-kit Protein Product", 77:1876-1883.

Lev et al., 1992, "A recombinant ectodomain of the receptor for the stem cell factor (SCF) retains ligand-induced receptor dimerization and antagonizes SCF-stimulated cellular responses", J Biol Chem, 267(15):10866-10873.

Lev et al., 1993, "Interspecies molecular chimeras of Kit help define the binding site of the stem cell factor", Mol Cell Biol., 13(4):2224-2234.

Liang et al., 2013, "The c-kit receptor-mediated signal transduction and tumor-related diseases", Int. J. Biol. Sci., 9(5):435-443.

Liu et al., 2007, "Structural basis for stem cell factor: KIT signaling and activation of class III receptor tyrosine kinases", The EMBO Journal, 26(3):891-901.

Lokker et al., 1997, "Functional importance of platelet-derived growth factor (PDGF) receptor extracellular immunoglobulin-like domains", J Biol Chem, 272(52):33037-33044.

London et al., "KTN0158, a humanized anti-KIT monoclonal antibody, demonstrates antitumor activity in dogs with mast cell tumors," AACR-NCI-EORTC International Conference on Molecular Targets and Cancer Therapeutics, Nov. 5-9, 2015, Boston, MA, Meeting Abstract published online Oct. 26, 2015.

London et al., "KTN0158, a humanized anti-KIT monoclonal antibody, demonstrates antitumor activity in dogs with mast cell tumors," AACR-NCI-EORTC International Conference on Molecular Targets and Cancer Therapeutics, Nov. 5-9, 2015, Boston, MA, poster presented Nov. 8, 2015.

London et al., "KTN0158, a humanized anti-KIT monoclonal antibody, demonstrates antitumor activity in dogs with mast cell

(56) References Cited

OTHER PUBLICATIONS tumors," The European Cancer Congress (ECC 2015), Sep. 25-29, 2015, Vienna, Austria, Meeting Abstract published online Sep. 11, 2015.
London et al., "KTN0158, a humanized anti-KIT monoclonal antibody, demonstrates antitumor activity in dogs with mast cell tumors," The European Cancer Congress (ECC 2015), Sep. 25-29, 2015, Vienna, Austria, poster presented Sep. 28, 2015.
Lubeski et al., "KTN0182A, an anti-KIT, pyrrolobenzodiazepine (PBD)-containing antibody-drug conjugate (ADC) demonstrates potent antitumor activity in vitro and in vivo against a broad range of tumor types", 11th Annual PEGS, May 4-8, 2015, Boston, MA, Meeting Poster.
Lubeski et al., "KTN0182A, an anti-KIT, pyrrolobenzodiazepine (PBD)-containing antibody-drug conjugate (ADC) demonstrates potent antitumor activity in vitro and in vivo against a broad range of tumor types", 11th Annual PEGS, May 4-8, 2015, Boston, MA, Meeting Abstract.
Mandel et al., "KTN0158, a Humanized Anti-KIT Monoclonal Antibody, Reduces Airway Eosinophilia in a Feline Model of Allergic Asthma", American College of Allergy, Asthma & Immunology (ACAAI) 2014 Annual Scientific Meeting, Nov. 6-10, 2014, Atlanta, GA, Meeting Poster.
Mandel et al., "Regulation of Airway Eosinophilia in a Model of Feline Allergic Asthma by KTN0158, a Humanized anti-KIT Monoclonal Antibody", American College of Allergy, Asthma & Immunology (ACAAI) 2014 Annual Scientific Meeting, Nov. 6-10, 2014, Atlanta, GA, Meeting Abstract.
Matthews et al., 1991, "A receptor tyrosine kinase cDNA isolated from a population of enriched primitive hematopoietic cells and exhibiting close genetic linkage to c-kit", Proc Natl Acad Sci USA, 88:9026-9030.
Micke et al., 2003, "Characterization of c-kit expression in small cell lung cancer: prognostic therapeutic implications", Clin Cancer Res, 9:188-194.
Nakayama and Parandoosh, 1999, "An immunoassay for assessment of receptor tyrosine kinase autophosphorylation", J Immunol Methods, 225:67-74.
Omura et al., 1997, "Immunoglobulin-like domain 4-mediated receptor-receptor interactions contribute to platelet-derived growth factor-induced receptor dimerization.", J Biol Chem, 272(19):12676-12682.
Philo et al., 1996, "Human stem cell factor dimer forms a complex with two molecules of the extracellular domain of its receptor, kit", J Biol Chem, 271(12):6895-6902.
Protein Knowledgebase (UniProtKB), P10721 (KIT_Human) [online] [retrieved on May 19, 2014]. Retrieved from the Internet http://www.uniport.org/uniprot/P10721#ref1, pp. 1-25.
Reshetnyak et al., 2013, "Structural basis for KIT receptor tyrosine kinase inhibition by antibodies targeting the D4 membrane-proximal region", Proc Natl Acad Sci USA, 110(44):17832-17837.
Roskoski et al., 2004, "The ErbB/HER receptor protein-tyrosine kinases and cancer", Biochem Biophys Res Com, 319(1):1-11.
Ruch et al., 2007, "Structure of a VEGF-VEGF receptor complex determined by electron microscopy", Nat Struct Mol Biol, 14(3):249-250.
Rudikoff et al., Mar. 1982, "Single amino acid substitution altering antigen-binding specificity," Proc Natl Acad Sci U S A, 79(6):1979-1983.
Ryan et al., 1994, "Role for the stem cell factor/KIT complex in Schwann cell neoplasia and mast cell proliferation associated with neurofibromatosis", J Neurosci Res 37(3):415-432.
Sakai et al., 2007, "Pertuzumab, a novel HER dimerization inhibitor, inhibits the growth of human lung cancer cells mediated by the HER3 signaling pathway", Cancer Sci, 98(9):1498-1503.
Schittek et al., 1992, "Natural occurrence and origin of somatically mutated memory B cells in mice", J Exp Med, 176:427-428.
Sequence Alignment, GenBan Accession No. AAC50968.1 (KIT_Mouse), dated May 1, 2007. [Retrieved from the Internet: URL<http://blast.ncbi.nlm.nih.gov/Blast.cgi>.

Shen et al., 2005, "Protein kinase inhibitors for treatment of cancer", Trends in Biopharmaceutical Industry, 1(3):15-19.
Shulman et al., 1997, "An antibody reactive with domain 4 of the platelet-derived growth beta receptor allows BB binding while inhibiting proliferation by impairing receptor dimerization", J Biol Chem, 272(28):17400-17404.
Sugimura et al., 2002, "Human-Antibody Engineering (Review)", Bioventure, 2(4): 30-33. (English abstract).
Tabone-Eglinger et al., 2008, "KIT mutations induce intracellular retention and activation of an immature form of the KIT protein in gastrointestinal stromal tumors", Clin Cancer Res 14(8):2285-2294.
Tamura et al., 2007, "Tyrosine kinases as targets for anti-inflammatory therapy", Anti-Inflammatory & Anti-Allergy Agents in Medicinal Chemistry, 6(1):47-60.
Tan et al., 2007, "Monitering interactions between receptor tyrosine kinases and their downstream effector proteins in living cells using bioluminescence resonance energy transfer", Molec Pharmacol, 72:1440-1446.
Tao et al., 2001, "Kinase insert domain receptor (KDR) extracellular immunoglobulin-like domains 4—contain structural features that block receptor dimerization and vascular endothelial g(rowth factor-induced signaling", J Biol Chem,): 276(24):21916-21923.
Uniprot Submission D2VI02_NAEGR, dated Mar. 2, 2010. Retrieved from the internet: <URL: http://www.uniprot.org/uniprot?D2VI02.txt?version=1>]; aa 155-161.
Uniprot Submission QOUL05_PHANO, dated Mar. 2, 2010. Retrieved from the Internet: <URL: http://www.uniprot.org/uniprot?QOUL05.txt?version=1>]; aa 598-608.
Wiesmann et al., 2000, "Ligand-binding sites in 1g-like domains of receptor tyrosine kinases", J Molec Med, 78(5):247-260.
Wikipedia, The Free Encyclopedia, "Humanized_antibody," [online], Retrieved from the Internet: < URL: http://en.wikipedia.org/wiki/Humanized_antibody>.
Yang et al., Oct. 2008, "Nf1-dependent tumors require a microenvironment containing Nf1+/-- and c-kit-dependent bone marrow", Cell 135(3):437-448.
Yang et al., 2010, "Direct contacts between extracellular membrane-proximal domains are required for VEGF receptor activation and cell signaling", Proc Natl Acad Sci USA, 107(5):1906-1911.
Yarden et al., 1987, "Human proto-oncogene c-kit: a new cell surface receptor tyrosine kinase for an unidentified ligand", EMBO J, 6(11):3341-3351.
Yoo et al., 2005, "Arginine-rich anti-vascular endothelial growth factor (anti_VEGF) hexapeptide inhibits collagen-induced arthritis and VEGF-stimulated productions of TNF-alpha and IL-6 by human monocytes", J Immunol, 174(9):5846-5855.
Yuzawa et al., 2007, "Structural basis for activation of the receptor tyrosine KIT by stem cell factor", Cell, 13(2):323-334.
Zhang et al., 2000, "Crystal structure of human stem cell factot: implication for stem cell factor receptor dimerization and activation", Proc Natl Acad Sci USA, 97(14):7732-7737.
Zhang et al., 2006, "An allosteric mechanism for activation of kinase domain of epidermal growth factor receptor", Cell, 125:1137-1149.
Zhang et al., 2009, "Targeting cancer with small molecule kinase inhibitors", Nature Reviews Cancer, 9:28-39.
Ashman and Griffith, Jan. 2013, "Therapeutic targeting of c-KIT in cancer," Expert Opin Investig Drugs, 22(1):103-115.
Ashman, Oct. 1999, "The biology of stem cell factor and its receptor C-kit," Int J Biochem Cell Biol, 31(10):1037-1051.
Balachandran et al., Mar. 2012, "Imatinib potentiates anti-tumor T cell responses in gastrointestinal stromal tumor through the inhibition of Ido," Nat Med, 17(9):1094-1100.
Bradding, Jun. 2008, "Asthma eosinophil disease, mast cell disease, or both?" Allergy Asthma Clin Immunol, 4(2):84-90.
Cheon et al., Mar. 2011, "Mast cell 5-lipoxygenase activity promotes intestinal polyposis in APCDelta468 mice," Cancer Res, 71(5):1627-1636.
Christiansson et al., May 2015, "The tyrosine kinase inhibitors imatinib and dasatinib reduce myeloid suppressor cells and release effector lymphocyte responses," Mol Cancer Ther, 14(5):1181-1191.

(56) References Cited

OTHER PUBLICATIONS

Coussens et al., Jun. 1999, "Inflammatory mast cells up-regulate angiogenesis during squamous epithelial carcinogenesis," Genes Dev, 13(11):1382-1397.
Finke et al., Jul. 2011, "MDSC as a mechanism of tumor escape from sunitinib mediated anti-angiogenic therapy," Int Immunopharmacol, 11(7):856-861.
Galli et al., 1999, "The regulation of mast cell and basophil development by the Kit ligand, SCF, and IL-3," in: Razin E, Rivera J ed. Signal Transduction in Mast Cells and Basophils, pp. 11-30.
Garton et al., "Inhibition of KIT in vivo modifies immune cell populations to improve the efficacy of checkpoint inhibitors in syngeneic mouse tumor models," American Association for Cancer Research (AACR) Annual Meeting, Apr. 16-20, 2016, New Orleans, LA, Meeting Abstract published online Mar. 16, 2016.
Garton et al., "Inhibition of KIT in vivo modifies immune cell populations to improve the efficacy of checkpoint inhibitors in syngeneic mouse tumor models," American Association for Cancer Research (AACR) Annual Meeting, Apr. 16-20, 2016, New Orleans, LA, poster presented on Apr. 19, 2016.
Grimbaldeston et al., Sep. 2005, "Mast cell-deficient W-sash c-kit mutant Kit W-sh/W-sh mice as a model for investigating mast cell biology in vivo," Am J Pathol, 167(3):835-848.
Jacoby, et al., Dec. 1997, "Molecular analysis of the NF2 tumor-suppressor gene in schwannomatosis," Am J Hum Genet, 61(6):1293-1302.
Joensuu, 2006, "Gastrointestinal stromal tumor (GIST)," Ann Oncol, 17 Suppl 10:x280-6.
Kao et al., Jan. 2011, "Targeting immune suppressing myeloid-derived suppressor cells in oncology," Crit Rev Oncol Hematol, 77(1):12-19.
Lammie et al., Nov. 1994, "Expression of c-kit and kit ligand proteins in normal human tissues," J Histochem Cytochem, 42(11):1417-1425.
Larmonier et al., Nov. 2008, "Imatinib mesylate inhibits CD4+ CD25+ regulatory T cell activity and enhances active immunotherapy against BCR-ABL-tumors," J Immunol, 181(10):6955-6963.
Metcalfe et al., 1997, "Mast cells," Physiol Rev, 77:1033-1079.
Miettinen and Lasota, Sep. 2005, "KIT (CD117): a review on expression in normal and neoplastic tissues, and mutations and their clinicopathologic correlation," Appl Immunohistochem Mol Morphol, 13(3):205-220.
Mukherjee et al., Jun. 2009, "Human schwannomas express activated platelet-derived growth factor receptors and c-kit and are growth inhibited by Gleevec (Imatinib Mesylate)," Cancer Res, 69(12):5099-5107.
Ozao-Choy et al., Mar. 2009, "The novel role of tyrosine kinase inhibitor in the reversal of immune suppression and modulation of tumor microenvironment for immune-based cancer therapies," Cancer Res, 69(6):2514-2522.
Pan et al., Jan. 2008, "Reversion of immune tolerance in advanced malignancy: modulation of myeloid-derived suppressor cell development by blockade of stem-cell factor function," Blood, 111(1):219-228.
Plotkin, et al., Apr. 2012, "Quantitative assessment of whole-body tumor burden in adult patients with 13/1, 13/2 neurofibromatosis," PLoS One, 7(4):e35711.
Rädinger et al., Aug. 2010, "Generation, isolation, and maintenance of human mast cells and mast cell lines," Curr Protoc Immunol, Chapter 7:Unit 7.37.
Reith et al., Mar. 1990, "W mutant mice with mild or severe developmental defects contain distinct point mutations in the kinase domain of the c-kit receptor," Genes Dev, 4(3):390-400.
Saleem et al., Jul. 15, 2012, "Cutting edge: mast cells critically augment myeloid-derived suppressor cell activity," J Immunol, 189(2):511-515.
Schlessinger, Oct. 2000, "Cell signaling by receptor tyrosine kinases," Cell, 103(2):211-225.
Soucek et al., Oct. 2007, "Mast cells are required for angiogenesis and macroscopic expansion of Myc-induced pancreatic islet tumors," Nat Med, 13(10):1211-1208.
Stahl et al., Jun. 2016, "Targeting KIT on innate immune cells to enhance the antitumor activity of checkpoint inhibitors," Immunotherapy, 8(7):767-774.
Starkey et al., Jul. 1988, "Mast-cell-deficient W/Wv mice exhibit A decreased rate of tumor angiogenesis," Int J Cancer, 42(1):48-52.
Staser et al., Nov. 2012, "Pathogenesis of plexiform neurofibroma: tumor-stromal/hematopoietic interactions in tumor progression," Annu Rev Pathol, 7:469-495.
Theoharides and Conti, May 2004, "Mast cells: the Jekyll and Hyde of tumor growth," Trends Immunol, 25(5):235-241.
Ullrich and Schlessinger, Apr. 1990, "Signal transduction by receptors with tyrosine kinase activity," Cell, 61(2):203-212.
Yang et al., Jan. 2010, "Mast cells mobilize myeloid-derived suppressor cells and Treg cells in tumor microenvironment via IL-17 pathway in murine hepatocarcinoma model," PLoS One, 5(1):e8922.
Zoog et al., Mar. 2009, "Antagonists of CD117 (cKit) signaling inhibit mast cell accumulation in healing skin wounds," Cytometry A, 75(3):189-198.
Vajdos et al., Jul. 2002, "Comprehensive functional maps of the antigen-binding site of an anti-ErbB2 antibody obtained with shotgun scanning mutagenesis," J Mol Biol 320(2):415-428.
Kodukula et al., Mar. 1991, "Biosynthesis of phosphatidylinositol glycan-anchored membrane proteins. Design of a simple protein substrate to characterize the enzyme that cleaves the cooh-terminal signal peptide" J Biol Chem 266(7): 4464-4470.
Secor et al., Mar. 2000, "Mast cells are essential for early onset and severe disease in a murine model of multiple sclerosis," J Exp Med 191(5):813-822.
Garton et al., Apr. 2017, "Anti-KIT monoclonal antibody treatment enhances the antitumor activity of immune checkpoint inhibitors by reversing tumor-induced immunosuppression," Mol Cancer Ther 16(4):671-680.
Vermersch et al., Jun. 2012, "Masitinib treatment in patients with progressive multiple sclerosis: a randomized pilot study," BMC Neurol 12:36.
Shah et al., Sep. 2015, "c-Kit as a novel potential therapeutic target in colorectal cancer," Gastroenterology 149(3): 534-537 (published online in Jul. 2015).
Lebron et al., Sep. 2014, "A human monoclonal antibody targeting the stem cell factor receptor (c-Kit) blocks tumor cell signaling and inhibits tumor growth," Cancer Biology & Therapy 15(9): 1208-1218 (published online in Jun. 2014).
Dodd et al., Sep.-Oct. 2010, "Animal models of soft-tissue sarcoma," Disease Models & Mechanisms 3(9-10): 557-566 (published online in Aug. 2010).
Brown et al., 2001, "Mechanisms underlying mast cell influence on EAE disease course," Molecular Immunology 38 (16-18): 1373-1378.
Notice of Allowance and Fee(s) Due dated May 20, 2020 in U.S. Appl. No. 16/270,116 (7 pages).

Fig. 1

```
  1  MRGARGAWDF LCVLLLLLRV QTGSSQPSVS PGEPSPPSIH PGKSDLIVRV GDEIRLLCTD PGFVKWTFEI LDETNENKQN
                                                {D1
                                                  }{D2
 81  EWITEKAEAT NTGKYTCTNK HGLSNSIYVF VRDPAKLFLV DRSLYGKEDN DTLVRCPLTD PEVTNYSLKG CQGKPLPKDL
161  RFIPDPKAGI MIKSVKRAYH RLCLHCSVDQ EGKSVLSEKF ILKVRPAFKA VPVVSVSKAS YLLREGEEFT VTCTIKDVSS
                                                            }{D3
241  SVYSTWKREN SQTKLQEKYN SWHHGDFNYE RQATLTISSA RVNDSGVFMC YANNTFGSAN VTTTLEVVDK GFINIFPMIN
                                                                                }{D4
321  TTVFVNDGEN VDLIVEYEAF PKPEHQQWIY MNRTFTDKWE DYPKSENESN IRYVSELHLT RLKGTEGGTY TFLVSNSDVN
              }{D5
401  AAIAFNVYVN TKPEILTYDR LVNGMLQCVA AGFPEPTIDW YFCPGTEQRC SASVLPVDVQ TLNSSGPPFG KLVVQSSIDS
                          }
481  SAFKHNGTVE CKAYNDVGKT SAYFNFAFKE QIHPHTLFTP LLIGFVIVAG MMCIIVMLT  YKYLQKPMYE VQWKVVEEIN
561  GNNYVYIDPT QLPYDHKWEF PRNRLSFGKT LGAGAFGKVV EATAYGLIKS DAAMTVAVKM LKPSAHLTER EALMSELKVL
641  SYLGNHMNIV NLLGACTIGG PTLVITEYCC YGDLLNFLRR KRDSFICSKQ EDHAEAALYK NLLHSKESSC SDSTNEYMDM
721  KPGVSYVVPT KADKRRSVRI GSYIERDVTP AIMEDDELAL DLEDLLSFSY QVAKGMAFLA SKNCIHRDLA ARNILLTHGR
801  ITKICDFGLA RDIKNDSNYV VKGNARLPVK WMAPESIFNC VYTFESDVWS YGIFLWELFS LGSSPYPGMP VDSKFYKMIK
881  EGFRMLSPEH APAEMYDIMK TCWDADPLKR PTFKQIVQLI EKQISESTNH IYSNLANCSP NRQKPVVDHS VRINSVGSTA
961  SSSQPLLVHD DV    (SEQ ID NO: 1)
```

KIT D4/D5 Antigen (SEQ ID NO: 14): M1-E33 + V308-H515 (SEQ ID NO: 73) + 5 x His

1 MRGARGAWDF LCVLLLLLRV QTGSSQPSVS PGEVDKGFIN IFPMINTTVF VNDGENVDLI

61 VEYEAFPKPE HQQWIYMNRT FTDKWEDYPK SENESNIRYV SELHLTRLKG TEGGTYTFLV

121 SNSDVNAAIA FNVYVNTKPE ILTYDRLVNG MLQCVAAGFP EPTIDWYFCP GTEQRCSASV

181 LPVDVQTLNS SGPPFGKLVV QSSIDSSAFK HNGTVECKAY NDVGKTSAYF NFAFKEQIHP

241 H*HHHHH*

Fig. 2

H1 VH domain

FR1
```
         10        20        30        40        50        60        70        80        90       100
CAGGTCCAGCTGGTGCAGTCTGGGGCTGAACTGAAGAAGCCTGGGGCCTCAGTGAAGCTGTCCTGCAAGGCTTCTGGCTACACTTTCACTGACTACTATA
 Q  V  Q  L  V  Q  S  G  A  E  L  K  K  P  G  A  S  V  K  L  S  C  K  A  S  G  Y  T  F  T  D  Y  Y
 1                 10                 20                 30
                                                                                        CDR1
```

FR2
```
        110       120       130       140       150       160       170       180       190       200
TAAACTGGGTGAAGCAGGCGCCCCTGGAAAGGGACTTGAGTGGATTGCAAGGATTTACCCTGGAAGTGGTAATACTTACTACAATGAGAAGTTCAAGGCAG
 I  N  W  V  K  Q  A  P  G  K  G  L  E  W  I  A  R  I  Y  P  G  S  G  N  T  Y  Y  N  E  K  F  K  G
                 40                          50 52A                         60
                 40                          50                             60
                                             CDR2                                              FR3
```

```
        210       220       230       240       250       260       270       280       290       300
GGCCACACTGACTGCAGAAAAATCCACTGCTACTATGCAGCTCAGCAGCCTACAATGCAGCTCTGCAGAGATCTGAGGACTCTGCTGTCTATTTCTGTGCAAGGGGGGTG
 A  T  L  T  A  E  K  S  T  S  T  A  Y  M  Q  L  S  S  L  R  S  E  D  S  A  V  Y  F  C  A  R  G  V
                 70                          80 82ABC                       90
                                                                            90
                                                                                      CDR3
```

FR4
```
        310       320       330       340
TACTACTTTGACTACTGGGGCCAAGGCACCACTGTCACAGTCTCCTCA
 Y  Y  F  D  Y  W  G  Q  G  T  T  V  T  V  S  S
                 100                 110
99/101                                110
```

(Kabat Numbering)
(Numerical Numbering)

Fig. 3A

H2 VH domain

FR1
```
         10        20        30        40        50        60        70        80        90       100
CAGGTCCAGCTGGTGCAGTCTGGAGCTGAGGTGAAGAAGCCTGGGGCCTCAGTGAAGCTGTCCTGCAAGGCTTCTGGCTACACTTTCACTGACTACTATA
 Q  V  Q  L  V  Q  S  G  A  E  V  K  K  P  G  A  S  V  K  L  S  C  K  A  S  G  Y  T  F  T  D  Y  Y
                  10                         20                         30
                  10                         20                         30
```
FR2                                                                                                CDR1
```
         110       120       130       140       150       160       170       180       190       200
TAAACTGGGTGAAGCAGGCCCCTGGAAAAGGGACTTGAGTGGATTGGAATTAGATATTCCTGGAAGTGGTAATACTTACTACAATGAGAAGTTCAAGGGCAG
 I  N  W  V  K  Q  A  P  G  E  G  L  E  W  I  A  R  I  Y  P  G  S  G  N  T  Y  Y  N  E  K  F  K  G  R
                  40                         50 A                         60
                  40                         50                           60
```
                                              CDR2                                                FR3
```
         210       220       230       240       250       260       270       280       290       300
GGCCACACTGACTGCAGAAAAATCCAGCACTGCCTACATGCAGCTCAGCAGCCTGAGATCTGAGGACACTGCGGTCTATTTCTGTGCAAGGGGGGTG
 A  T  L  T  A  E  K  S  S  T  A  Y  M  Q  L  S  S  L  R  S  E  D  T  A  V  Y  F  C  A  R  G  V
                  70                         80 82 A B C                         90
                                              80                                 90
```
                                                                                         CDR3
```
         310       320       330       340
TACTACTTTGACTACTGGGGCCAAGGCACCACTGTCACAGTCTCCTCA
 Y  Y  F  D  Y  W  G  Q  G  T  T  V  T  V  S  S
                  110
                  110                         99/101
```
FR4

(Kabat Numbering)
(Numerical Numbering)

Fig. 3B

H4 VH domain

FR1

```
          10         20         30         40         50         60         70         80         90        100
CAGGTCCAGCTGgtgcAGTCtGGGGCTGAGGTGAAGAAGCCTGGGGCCTCAGTGAAGGTGTCCTGCAAGGCTTCTGGCTACACTTTCACTGACTACTATA
 Q  V  Q  L  V  Q  S  G  A  E  V  K  K  P  G  A  S  V  K  V  S  C  K  A  S  G  Y  T  F  T  D  Y  Y
                    10                   20                   30
                    10                   20                   30
```

CDR1

FR2

```
         110        120        130        140        150        160        170        180        190        200
TAAACTGGGTGAGGCAGGCCAAGGCCCTGGAATGGATTGCAAGGATTTACCCTGGAAGTGGTAATACTTACTACAATGAGAAGTTCAAGGGCAG
 I  N  W  V  R  Q  A  P  G  Q  G  L  E  W  I  A  R  I  Y  P  G  S  G  N  T  Y  Y  N  E  K  F  K  G  R
                    40                             50 52 A                              60
                    40                             50                                   60
```

CDR2                                                    FR3

```
         210        220        230        240        250        260        270        280        290        300
GGCCACAATCAATGCAGACAAATCCAGCAGCACAGCCTACATGGAGCTGAGCAGCCTGAGATCTGAGGACACTGCTGTCTATTTCTGTGCAAGGGGGGTG
 A  T  I  T  A  D  K  S  S  S  T  A  Y  M  E  L  S  S  L  R  S  E  D  T  A  V  Y  F  C  A  R  G  V
                    70                   80 82 A B C                      90
                    70                             80                                   90
```

CDR3

FR4

```
         310        320        330        340
TACTACTTTGACTACTGGGGCCAAGGCACCACTGTCACAGTCTCCTCA
 Y  Y  F  D  Y  W  G  Q  G  T  T  V  T  V  S  S
                   110
                   110
 99/101
```

(Kabat Numbering)
(Numerical Numbering)

Fig. 3D

L2 VL domain

FR1

```
         10         20         30         40         50         60                    CDR1
GACATTGTGATGACCCAGTCTCCATCCTCCCTGTCCGCATCAGTAGGAGACAGGGTCACCATCACTTGCAAGGCCAGTCAGAATGTTCGTACTAATGTAG
 D  I  V  M  T  Q  S  P  S  S  L  S  A  S  V  G  D  R  V  T  I  T  C  K  A  S  Q  N  V  R  T  N  V
                      10                    20                          30
                      10                    20                          30
```

FR2

```
         110        120        130        140             CDR2    150        160              FR3    170        180        190        200
CCTGGTATCAACAGAAACCAGGGAAAGCTCCTAAGCTCCTGATTTACTCGGCATCCTACCGGTACAGTGGAGTCCCATATGCTTCACAGGCAGTGGATC
 A  W  Y  Q  Q  K  P  G  K  A  P  K  L  L  I  Y  S  A  S  Y  R  Y  S  G  V  P  D  R  F  T  G  S  G  S
                   40                    50                          60
                   40                    50                          60
```

```
         210        220        230        240        250         CDR3  260        270        280              FR4   290        300
TGGGACAGATTTCACTCTCACCATCAGTCAGCtctGCAGCCTGAAGACTTTGCAGACTATTTCTGTCAGCAATATAACAGCTATCCTCGGACGTTCGGTGGA
 G  T  D  F  T  L  T  I  S  S  L  Q  P  E  D  F  A  D  Y  F  C  Q  Q  Y  N  S  Y  P  R  T  F  G  G
                70                    80                          90
                70                    80                          90
```

```
         310        320
GGCACCAAGGTGGAAATCAAA
 G  T  K  V  E  I  K
            106 A
            107
```

(Kabat Numbering)
(Numerical Numbering)

Fig. 3G

L3 VL domain

FR1

```
         10         20         30         40         50         60         70         80         90        100
GACATTGTGATGACCCAGTCTCCATCCTCCCTGTCTGCATCAGTAGGAGACAGGGTCACCATCACTTGCAAGGCCAGTCAGAATGTGCGTACTAATGTAG
 D  I  V  M  T  Q  S  P  S  S  L  S  A  S  V  G  D  R  V  T  I  T  C  K  A  S  Q  N  V  R  T  N  V
            10                   20                    30
            10                   20                    30
```
<u>_____CDR1_____</u>

FR2 _____

```
        110        120        130        140        150        160        170        180        190        200
CCTGGTATCAACAGAAACCAGGGAAAGCTCCTAAAGCACTGATTTACTCGGCATCCTACCGGTACAGTGGAGTCCCTGATCGCTTCAGCGGCAGTGGATC
 A  W  Y  Q  Q  K  P  G  K  A  P  K  A  L  I  Y  S  A  S  Y  R  Y  S  G  V  P  D  R  F  S  G  S
                    40                   50                   60
                    40                   50                   60
```
<u>_____CDR2_____</u>        <u>_____FR3_____</u>

CDR3
```
        210        220        230        240        250        260        270        280        290        300
TGGGACAGATTTCACTCTCACCATCAGCTCTCTGCAGCCTGAAGATTTCGCAGACTATTTCTGTCAGCAATATAACAGCTATCCTCGGACGTTCGGTGGA
 G  T  D  F  T  L  T  I  S  S  L  Q  P  E  D  F  A  D  Y  F  C  Q  Q  Y  N  S  Y  P  R  T  F  G  G
                    70                   80                   90
                    70                   80                   90
```
<u>_____CDR3_____</u>   <u>__FR4__</u>

```
        310        320
GGCACCAAGGTTGGAAATCAAA
 G  T  K  V  E  I  K
       106 A
       107
```

(Kabat Numbering)
(Numerical Numbering)

Fig. 3H

QVQLVQSGAEX$_{H1}$KKPGASVKX$_{H2}$SCKASGYTFTDYYINWVX$_{H3}$QAPGKGLEWIARIYPGSGNTYYNEKFKGRX$_{H4}$TX$_{H5}$TAX$_{H6}$KSTSTAYMX$_{H7}$LSSLRSEDX$_{H8}$AVYFCARGVYFDYWGQGTTVTVSS

Fig. 4A

DIVMTQSPSX$_{K1}$LSASVGDRVTITCKASQNVRTNVAWYQQKPGKAPKX$_{K2}$LIYSASYRYSGVPDRFX$_{K3}$GSGSGTDFT
LTISSLQX$_{K4}$EDFAX$_{K5}$YX$_{K6}$CQQYNSYPRTFGGGTKVEIK

SEQUENCE LISTING

```
<160> NUMBER OF SEQ ID NOS: 333

<210> SEQ ID NO 1
<211> LENGTH: 972
<212> TYPE: PRT
<213> ORGANISM: Homo sapiens
<220> FEATURE:
<223> OTHER INFORMATION: full length human KIT

<400> SEQUENCE: 1

Met Arg Gly Ala Arg Gly Ala Trp Asp Phe Leu Cys Val Leu Leu Leu
1               5                   10                  15

Leu Leu Arg Val Gln Thr Gly Ser Ser Gln Pro Ser Val Ser Pro Gly
            20                  25                  30

Glu Pro Ser Pro Pro Ser Ile His Pro Gly Lys Ser Asp Leu Ile Val
        35                  40                  45

Arg Val Gly Asp Glu Ile Arg Leu Leu Cys Thr Asp Pro Gly Phe Val
    50                  55                  60

Lys Trp Thr Phe Glu Ile Leu Asp Glu Thr Asn Glu Asn Lys Gln Asn
65                  70                  75                  80

Glu Trp Ile Thr Glu Lys Ala Glu Ala Thr Asn Thr Gly Lys Tyr Thr
                85                  90                  95

Cys Thr Asn Lys His Gly Leu Ser Asn Ser Ile Tyr Val Phe Val Arg
            100                 105                 110

Asp Pro Ala Lys Leu Phe Leu Val Asp Arg Ser Leu Tyr Gly Lys Glu
        115                 120                 125

Asp Asn Asp Thr Leu Val Arg Cys Pro Leu Thr Asp Pro Glu Val Thr
    130                 135                 140

Asn Tyr Ser Leu Lys Gly Cys Gln Gly Lys Pro Leu Pro Lys Asp Leu
145                 150                 155                 160

Arg Phe Ile Pro Asp Pro Lys Ala Gly Ile Met Ile Lys Ser Val Lys
                165                 170                 175

Arg Ala Tyr His Arg Leu Cys Leu His Cys Ser Val Asp Gln Glu Gly
            180                 185                 190

Lys Ser Val Leu Ser Glu Lys Phe Ile Leu Lys Val Arg Pro Ala Phe
        195                 200                 205

Lys Ala Val Pro Val Val Ser Val Ser Lys Ala Ser Tyr Leu Leu Arg
```

```
            210                 215                 220
Glu Gly Glu Glu Phe Thr Val Thr Cys Thr Ile Lys Asp Val Ser Ser
225                 230                 235                 240

Ser Val Tyr Ser Thr Trp Lys Arg Glu Asn Ser Gln Thr Lys Leu Gln
                245                 250                 255

Glu Lys Tyr Asn Ser Trp His His Gly Asp Phe Asn Tyr Glu Arg Gln
                260                 265                 270

Ala Thr Leu Thr Ile Ser Ser Ala Arg Val Asn Asp Ser Gly Val Phe
            275                 280                 285

Met Cys Tyr Ala Asn Asn Thr Phe Gly Ser Ala Asn Val Thr Thr Thr
        290                 295                 300

Leu Glu Val Val Asp Lys Gly Phe Ile Asn Ile Phe Pro Met Ile Asn
305                 310                 315                 320

Thr Thr Val Phe Val Asn Asp Gly Glu Asn Val Asp Leu Ile Val Glu
                325                 330                 335

Tyr Glu Ala Phe Pro Lys Pro Glu His Gln Gln Trp Ile Tyr Met Asn
                340                 345                 350

Arg Thr Phe Thr Asp Lys Trp Glu Asp Tyr Pro Lys Ser Glu Asn Glu
            355                 360                 365

Ser Asn Ile Arg Tyr Val Ser Glu Leu His Leu Thr Arg Leu Lys Gly
        370                 375                 380

Thr Glu Gly Gly Thr Tyr Thr Phe Leu Val Ser Asn Ser Asp Val Asn
385                 390                 395                 400

Ala Ala Ile Ala Phe Asn Val Tyr Val Asn Thr Lys Pro Glu Ile Leu
                405                 410                 415

Thr Tyr Asp Arg Leu Val Asn Gly Met Leu Gln Cys Val Ala Ala Gly
            420                 425                 430

Phe Pro Glu Pro Thr Ile Asp Trp Tyr Phe Cys Pro Gly Thr Glu Gln
        435                 440                 445

Arg Cys Ser Ala Ser Val Leu Pro Val Asp Val Gln Thr Leu Asn Ser
    450                 455                 460

Ser Gly Pro Pro Phe Gly Lys Leu Val Val Gln Ser Ser Ile Asp Ser
465                 470                 475                 480

Ser Ala Phe Lys His Asn Gly Thr Val Glu Cys Lys Ala Tyr Asn Asp
                485                 490                 495

Val Gly Lys Thr Ser Ala Tyr Phe Asn Phe Ala Phe Lys Glu Gln Ile
            500                 505                 510

His Pro His Thr Leu Phe Thr Pro Leu Leu Ile Gly Phe Val Ile Val
        515                 520                 525

Ala Gly Met Met Cys Ile Ile Val Met Ile Leu Thr Tyr Lys Tyr Leu
    530                 535                 540

Gln Lys Pro Met Tyr Glu Val Gln Trp Lys Val Val Glu Glu Ile Asn
545                 550                 555                 560

Gly Asn Asn Tyr Val Tyr Ile Asp Pro Thr Gln Leu Pro Tyr Asp His
                565                 570                 575

Lys Trp Glu Phe Pro Arg Asn Arg Leu Ser Phe Gly Lys Thr Leu Gly
            580                 585                 590

Ala Gly Ala Phe Gly Lys Val Val Glu Ala Thr Ala Tyr Gly Leu Ile
        595                 600                 605

Lys Ser Asp Ala Ala Met Thr Val Ala Val Lys Met Leu Lys Pro Ser
    610                 615                 620

Ala His Leu Thr Glu Arg Glu Ala Leu Met Ser Glu Leu Lys Val Leu
625                 630                 635                 640
```

Ser Tyr Leu Gly Asn His Met Asn Ile Val Asn Leu Leu Gly Ala Cys
        645                 650                 655

Thr Ile Gly Gly Pro Thr Leu Val Ile Thr Glu Tyr Cys Cys Tyr Gly
        660                 665                 670

Asp Leu Leu Asn Phe Leu Arg Arg Lys Arg Asp Ser Phe Ile Cys Ser
        675                 680                 685

Lys Gln Glu Asp His Ala Glu Ala Leu Tyr Lys Asn Leu Leu His
    690                 695                 700

Ser Lys Glu Ser Ser Cys Ser Asp Ser Thr Asn Glu Tyr Met Asp Met
705                 710                 715                 720

Lys Pro Gly Val Ser Tyr Val Val Pro Thr Lys Ala Asp Lys Arg Arg
                725                 730                 735

Ser Val Arg Ile Gly Ser Tyr Ile Glu Arg Asp Val Thr Pro Ala Ile
                740                 745                 750

Met Glu Asp Asp Glu Leu Ala Leu Asp Leu Glu Asp Leu Leu Ser Phe
            755                 760                 765

Ser Tyr Gln Val Ala Lys Gly Met Ala Phe Leu Ala Ser Lys Asn Cys
    770                 775                 780

Ile His Arg Asp Leu Ala Ala Arg Asn Ile Leu Leu Thr His Gly Arg
785                 790                 795                 800

Ile Thr Lys Ile Cys Asp Phe Gly Leu Ala Arg Asp Ile Lys Asn Asp
                805                 810                 815

Ser Asn Tyr Val Val Lys Gly Asn Ala Arg Leu Pro Val Lys Trp Met
                820                 825                 830

Ala Pro Glu Ser Ile Phe Asn Cys Val Tyr Thr Phe Glu Ser Asp Val
            835                 840                 845

Trp Ser Tyr Gly Ile Phe Leu Trp Glu Leu Phe Ser Leu Gly Ser Ser
    850                 855                 860

Pro Tyr Pro Gly Met Pro Val Asp Ser Lys Phe Tyr Lys Met Ile Lys
865                 870                 875                 880

Glu Gly Phe Arg Met Leu Ser Pro Glu His Ala Pro Ala Glu Met Tyr
                885                 890                 895

Asp Ile Met Lys Thr Cys Trp Asp Ala Asp Pro Leu Lys Arg Pro Thr
            900                 905                 910

Phe Lys Gln Ile Val Gln Leu Ile Glu Lys Gln Ile Ser Glu Ser Thr
    915                 920                 925

Asn His Ile Tyr Ser Asn Leu Ala Asn Cys Ser Pro Asn Arg Gln Lys
930                 935                 940

Pro Val Val Asp His Ser Val Arg Ile Asn Ser Val Gly Ser Thr Ala
945                 950                 955                 960

Ser Ser Ser Gln Pro Leu Leu Val His Asp Val
                965                 970

<210> SEQ ID NO 2
<211> LENGTH: 116
<212> TYPE: PRT
<213> ORGANISM: Artificial Sequence
<220> FEATURE:
<223> OTHER INFORMATION: H1 VH domain

<400> SEQUENCE: 2

Gln Val Gln Leu Val Gln Ser Gly Ala Glu Leu Lys Lys Pro Gly Ala
1               5                   10                  15

Ser Val Lys Leu Ser Cys Lys Ala Ser Gly Tyr Thr Phe Thr Asp Tyr
            20                  25                  30

-continued

Tyr Ile Asn Trp Val Lys Gln Ala Pro Gly Lys Gly Leu Glu Trp Ile
            35                  40                  45

Ala Arg Ile Tyr Pro Gly Ser Gly Asn Thr Tyr Tyr Asn Glu Lys Phe
        50                  55                  60

Lys Gly Arg Ala Thr Leu Thr Ala Glu Lys Ser Thr Ser Thr Ala Tyr
65                  70                  75                  80

Met Gln Leu Ser Ser Leu Arg Ser Glu Asp Ser Ala Val Tyr Phe Cys
                85                  90                  95

Ala Arg Gly Val Tyr Tyr Phe Asp Tyr Trp Gly Gln Gly Thr Thr Val
            100                 105                 110

Thr Val Ser Ser
            115

<210> SEQ ID NO 3
<211> LENGTH: 116
<212> TYPE: PRT
<213> ORGANISM: Artificial Sequence
<220> FEATURE:
<223> OTHER INFORMATION: H2 VH domain

<400> SEQUENCE: 3

Gln Val Gln Leu Val Gln Ser Gly Ala Glu Val Lys Lys Pro Gly Ala
1               5                   10                  15

Ser Val Lys Leu Ser Cys Lys Ala Ser Gly Tyr Thr Phe Thr Asp Tyr
            20                  25                  30

Tyr Ile Asn Trp Val Lys Gln Ala Pro Gly Lys Gly Leu Glu Trp Ile
            35                  40                  45

Ala Arg Ile Tyr Pro Gly Ser Gly Asn Thr Tyr Tyr Asn Glu Lys Phe
        50                  55                  60

Lys Gly Arg Ala Thr Leu Thr Ala Glu Lys Ser Thr Ser Thr Ala Tyr
65                  70                  75                  80

Met Gln Leu Ser Ser Leu Arg Ser Glu Asp Thr Ala Val Tyr Phe Cys
                85                  90                  95

Ala Arg Gly Val Tyr Tyr Phe Asp Tyr Trp Gly Gln Gly Thr Thr Val
            100                 105                 110

Thr Val Ser Ser
            115

<210> SEQ ID NO 4
<211> LENGTH: 116
<212> TYPE: PRT
<213> ORGANISM: Artificial Sequence
<220> FEATURE:
<223> OTHER INFORMATION: H3 VH domain

<400> SEQUENCE: 4

Gln Val Gln Leu Val Gln Ser Gly Ala Glu Val Lys Lys Pro Gly Ala
1               5                   10                  15

Ser Val Lys Leu Ser Cys Lys Ala Ser Gly Tyr Thr Phe Thr Asp Tyr
            20                  25                  30

Tyr Ile Asn Trp Val Arg Gln Ala Pro Gly Lys Gly Leu Glu Trp Ile
            35                  40                  45

Ala Arg Ile Tyr Pro Gly Ser Gly Asn Thr Tyr Tyr Asn Glu Lys Phe
        50                  55                  60

Lys Gly Arg Ala Thr Leu Thr Ala Asp Lys Ser Thr Ser Thr Ala Tyr
65                  70                  75                  80

Met Gln Leu Ser Ser Leu Arg Ser Glu Asp Thr Ala Val Tyr Phe Cys 85                  90                  95
Ala Arg Gly Val Tyr Tyr Phe Asp Tyr Trp Gly Gln Gly Thr Thr Val
            100                 105                 110

Thr Val Ser Ser
        115

<210> SEQ ID NO 5
<211> LENGTH: 116
<212> TYPE: PRT
<213> ORGANISM: Artificial Sequence
<220> FEATURE:
<223> OTHER INFORMATION: H4 VH domain

<400> SEQUENCE: 5

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile Asn Trp Val Arg Gln Ala Pro Gly Lys Gly Leu Glu Trp Ile
        35                  40                  45

Ala Arg Ile Tyr Pro Gly Ser Gly Asn Thr Tyr Tyr Asn Glu Lys Phe
50                  55                  60

Lys Gly Arg Ala Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Gly Val Tyr Tyr Phe Asp Tyr Trp Gly Gln Gly Thr Thr Val
            100                 105                 110

Thr Val Ser Ser
        115

<210> SEQ ID NO 6
<211> LENGTH: 116
<212> TYPE: PRT
<213> ORGANISM: Artificial Sequence
<220> FEATURE:
<223> OTHER INFORMATION: H5 VH domain

<400> SEQUENCE: 6

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile Asn Trp Val Arg Gln Ala Pro Gly Lys Gly Leu Glu Trp Ile
        35                  40                  45

Ala Arg Ile Tyr Pro Gly Ser Gly Asn Thr Tyr Tyr Asn Glu Lys Phe
50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Gly Val Tyr Tyr Phe Asp Tyr Trp Gly Gln Gly Thr Thr Val
            100                 105                 110

Thr Val Ser Ser
        115

<210> SEQ ID NO 7
<211> LENGTH: 107

```
<212> TYPE: PRT
<213> ORGANISM: Artificial Sequence
<220> FEATURE:
<223> OTHER INFORMATION: L1 VL domain

<400> SEQUENCE: 7

Asp Ile Val Met Thr Gln Ser Pro Ser Phe Leu Ser Ala Ser Val Gly
1               5                   10                  15

Asp Arg Val Thr Ile Thr Cys Lys Ala Ser Gln Asn Val Arg Thr Asn
            20                  25                  30

Val Ala Trp Tyr Gln Gln Lys Pro Gly Lys Ala Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Ser Leu Gln Ser
65                  70                  75                  80

Glu Asp Phe Ala Asp Tyr Phe Cys Gln Gln Tyr Asn Ser Tyr Pro Arg
                85                  90                  95

Thr Phe Gly Gly Gly Thr Lys Val Glu Ile Lys
            100                 105

<210> SEQ ID NO 8
<211> LENGTH: 107
<212> TYPE: PRT
<213> ORGANISM: Artificial Sequence
<220> FEATURE:
<223> OTHER INFORMATION: L2 VL domain

<400> SEQUENCE: 8

Asp Ile Val Met Thr Gln Ser Pro Ser Ser Leu Ser Ala Ser Val Gly
1               5                   10                  15

Asp Arg Val Thr Ile Thr Cys Lys Ala Ser Gln Asn Val Arg Thr Asn
            20                  25                  30

Val Ala Trp Tyr Gln Gln Lys Pro Gly Lys Ala Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Ser Leu Gln Pro
65                  70                  75                  80

Glu Asp Phe Ala Asp Tyr Phe Cys Gln Gln Tyr Asn Ser Tyr Pro Arg
                85                  90                  95

Thr Phe Gly Gly Gly Thr Lys Val Glu Ile Lys
            100                 105

<210> SEQ ID NO 9
<211> LENGTH: 107
<212> TYPE: PRT
<213> ORGANISM: Artificial Sequence
<220> FEATURE:
<223> OTHER INFORMATION: L3 VL domain

<400> SEQUENCE: 9

Asp Ile Val Met Thr Gln Ser Pro Ser Ser Leu Ser Ala Ser Val Gly
1               5                   10                  15

Asp Arg Val Thr Ile Thr Cys Lys Ala Ser Gln Asn Val Arg Thr Asn
            20                  25                  30

Val Ala Trp Tyr Gln Gln Lys Pro Gly Lys Ala Pro Lys Ala Leu Ile
        35                  40                  45

Tyr Ser Ala Ser Tyr Arg Tyr Ser Gly Val Pro Asp Arg Phe Ser Gly
```

```
                        50                  55                  60

Ser Gly Ser Gly Thr Asp Phe Thr Leu Thr Ile Ser Ser Leu Gln Pro
 65                  70                  75                  80

Glu Asp Phe Ala Asp Tyr Phe Cys Gln Gln Tyr Asn Ser Tyr Pro Arg
                 85                  90                  95

Thr Phe Gly Gly Gly Thr Lys Val Glu Ile Lys
                100                 105

<210> SEQ ID NO 10
<211> LENGTH: 107
<212> TYPE: PRT
<213> ORGANISM: Artificial Sequence
<220> FEATURE:
<223> OTHER INFORMATION: L4 VL domain

<400> SEQUENCE: 10

Asp Ile Val Met Thr Gln Ser Pro Ser Ser Leu Ser Ala Ser Val Gly
  1               5                  10                  15

Asp Arg Val Thr Ile Thr Cys Lys Ala Ser Gln Asn Val Arg Thr Asn
                 20                  25                  30

Val Ala Trp Tyr Gln Gln Lys Pro Gly Lys Ala Pro Lys Ser Leu Ile
             35                  40                  45

Tyr Ser Ala Ser Tyr Arg Tyr Ser Gly Val Pro Asp Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro Arg
                 85                  90                  95

Thr Phe Gly Gly Gly Thr Lys Val Glu Ile Lys
                100                 105

<210> SEQ ID NO 11
<211> LENGTH: 116
<212> TYPE: PRT
<213> ORGANISM: Artificial Sequence
<220> FEATURE:
<223> OTHER INFORMATION: consensus sequence of a VH domain
<220> FEATURE:
<221> NAME/KEY: VARIANT
<222> LOCATION: 11, 20, 38, 68, 70, 73, 82, 91
<223> OTHER INFORMATION: Xaa = Any Amino Acid

<400> SEQUENCE: 11

Gln Val Gln Leu Val Gln Ser Gly Ala Glu Xaa Lys Lys Pro Gly Ala
  1               5                  10                  15

Ser Val Lys Xaa Ser Cys Lys Ala Ser Gly Tyr Thr Phe Thr Asp Tyr
                 20                  25                  30

Tyr Ile Asn Trp Val Xaa Gln Ala Pro Gly Lys Gly Leu Glu Trp Ile
             35                  40                  45

Ala Arg Ile Tyr Pro Gly Ser Gly Asn Thr Tyr Tyr Asn Glu Lys Phe
         50                  55                  60

Lys Gly Arg Xaa Thr Xaa Thr Ala Xaa Lys Ser Thr Ser Thr Ala Tyr
 65                  70                  75                  80

Met Xaa Leu Ser Ser Leu Arg Ser Glu Asp Xaa Ala Val Tyr Phe Cys
                 85                  90                  95

Ala Arg Gly Val Tyr Tyr Phe Asp Tyr Trp Gly Gln Gly Thr Thr Val
                100                 105                 110

Thr Val Ser Ser
            115
```

<210> SEQ ID NO 12
<211> LENGTH: 107
<212> TYPE: PRT
<213> ORGANISM: Artificial Sequence
<220> FEATURE:
<223> OTHER INFORMATION: consensus sequence of a VL domain
<220> FEATURE:
<221> NAME/KEY: VARIANT
<222> LOCATION: 10, 46, 63, 80, 85, 87
<223> OTHER INFORMATION: Xaa = Any Amino Acid

<400> SEQUENCE: 12

Asp Ile Val Met Thr Gln Ser Pro Ser Xaa Leu Ser Ala Ser Val Gly
1               5                   10                  15

Asp Arg Val Thr Ile Thr Cys Lys Ala Ser Gln Asn Val Arg Thr Asn
            20                  25                  30

Val Ala Trp Tyr Gln Gln Lys Pro Gly Lys Ala Pro Lys Xaa Leu Ile
        35                  40                  45

Tyr Ser Ala Ser Tyr Arg Tyr Ser Gly Val Pro Asp Arg Phe Xaa Gly
    50                  55                  60

Ser Gly Ser Gly Thr Asp Phe Thr Leu Thr Ile Ser Ser Leu Gln Xaa
65                  70                  75                  80

Glu Asp Phe Ala Xaa Tyr Xaa Cys Gln Gln Tyr Asn Ser Tyr Pro Arg
                85                  90                  95

Thr Phe Gly Gly Gly Thr Lys Val Glu Ile Lys
            100                 105

<210> SEQ ID NO 13

<400> SEQUENCE: 13

000

<210> SEQ ID NO 14
<211> LENGTH: 246
<212> TYPE: PRT
<213> ORGANISM: Artificial Sequence
<220> FEATURE:
<223> OTHER INFORMATION: recombinant KIT D4/D5 polypeptide

<400> SEQUENCE: 14

Met Arg Gly Ala Arg Gly Ala Trp Asp Phe Leu Cys Val Leu Leu Leu
1               5                   10                  15

Leu Leu Arg Val Gln Thr Gly Ser Ser Gln Pro Ser Val Ser Pro Gly
            20                  25                  30

Glu Val Asp Lys Gly Phe Ile Asn Ile Phe Pro Met Ile Asn Thr Thr
        35                  40                  45

Val Phe Val Asn Asp Gly Glu Asn Val Asp Leu Ile Val Glu Tyr Glu
    50                  55                  60

Ala Phe Pro Lys Pro Glu His Gln Gln Trp Ile Tyr Met Asn Arg Thr
65                  70                  75                  80

Phe Thr Asp Lys Trp Glu Asp Tyr Pro Lys Ser Glu Asn Glu Ser Asn
                85                  90                  95

Ile Arg Tyr Val Ser Glu Leu His Leu Thr Arg Leu Lys Gly Thr Glu
            100                 105                 110

Gly Gly Thr Tyr Thr Phe Leu Val Ser Asn Ser Asp Val Asn Ala Ala
        115                 120                 125

Ile Ala Phe Asn Val Tyr Val Asn Thr Lys Pro Glu Ile Leu Thr Tyr
    130                 135                 140

Asp Arg Leu Val Asn Gly Met Leu Gln Cys Val Ala Gly Phe Pro
145                 150                 155                 160

Glu Pro Thr Ile Asp Trp Tyr Phe Cys Pro Gly Thr Glu Gln Arg Cys
                165                 170                 175

Ser Ala Ser Val Leu Pro Val Asp Val Gln Thr Leu Asn Ser Ser Gly
            180                 185                 190

Pro Pro Phe Gly Lys Leu Val Val Gln Ser Ser Ile Asp Ser Ser Ala
        195                 200                 205

Phe Lys His Asn Gly Thr Val Glu Cys Lys Ala Tyr Asn Asp Val Gly
210                 215                 220

Lys Thr Ser Ala Tyr Phe Asn Phe Ala Phe Lys Glu Gln Ile His Pro
225                 230                 235                 240

His His His His His His
            245

<210> SEQ ID NO 15
<211> LENGTH: 101
<212> TYPE: PRT
<213> ORGANISM: Homo sapiens
<220> FEATURE:
<223> OTHER INFORMATION: K310 to N410 (D4 domain) of human KIT

<400> SEQUENCE: 15

Lys Gly Phe Ile Asn Ile Phe Pro Met Ile Asn Thr Thr Val Phe Val
1               5                   10                  15

Asn Asp Gly Glu Asn Val Asp Leu Ile Val Glu Tyr Glu Ala Phe Pro
            20                  25                  30

Lys Pro Glu His Gln Gln Trp Ile Tyr Met Asn Arg Thr Phe Thr Asp
        35                  40                  45

Lys Trp Glu Asp Tyr Pro Lys Ser Glu Asn Glu Ser Asn Ile Arg Tyr
    50                  55                  60

Val Ser Glu Leu His Leu Thr Arg Leu Lys Gly Thr Glu Gly Gly Thr
65                  70                  75                  80

Tyr Thr Phe Leu Val Ser Asn Ser Asp Val Asn Ala Ala Ile Ala Phe
                85                  90                  95

Asn Val Tyr Val Asn
            100

<210> SEQ ID NO 16
<211> LENGTH: 5
<212> TYPE: PRT
<213> ORGANISM: Artificial Sequence
<220> FEATURE:
<223> OTHER INFORMATION: VH CDR1

<400> SEQUENCE: 16

Asp Tyr Tyr Ile Asn
1               5

<210> SEQ ID NO 17
<211> LENGTH: 17
<212> TYPE: PRT
<213> ORGANISM: Artificial Sequence
<220> FEATURE:
<223> OTHER INFORMATION: VH CDR2

<400> SEQUENCE: 17

Arg Ile Tyr Pro Gly Ser Gly Asn Thr Tyr Tyr Asn Glu Lys Phe Lys
1               5                   10                  15

<210> SEQ ID NO 18
<211> LENGTH: 7
<212> TYPE: PRT
<213> ORGANISM: Artificial Sequence
<220> FEATURE:
<223> OTHER INFORMATION: VH CDR3

<400> SEQUENCE: 18

Gly Val Tyr Tyr Phe Asp Tyr
1               5

<210> SEQ ID NO 19
<211> LENGTH: 11
<212> TYPE: PRT
<213> ORGANISM: Artificial Sequence
<220> FEATURE:
<223> OTHER INFORMATION: VL CDR1

<400> SEQUENCE: 19

Lys Ala Ser Gln Asn Val Arg Thr Asn Val Ala
1               5                   10

<210> SEQ ID NO 20
<211> LENGTH: 7
<212> TYPE: PRT
<213> ORGANISM: Artificial Sequence
<220> FEATURE:
<223> OTHER INFORMATION: VL CDR2

<400> SEQUENCE: 20

Ser Ala Ser Tyr Arg Tyr Ser
1               5

<210> SEQ ID NO 21
<211> LENGTH: 9
<212> TYPE: PRT
<213> ORGANISM: Artificial Sequence
<220> FEATURE:
<223> OTHER INFORMATION: VL CDR3

<400> SEQUENCE: 21

Gln Gln Tyr Asn Ser Tyr Pro Arg Thr
1               5

<210> SEQ ID NO 22
<211> LENGTH: 348
<212> TYPE: DNA
<213> ORGANISM: Artificial Sequence
<220> FEATURE:
<223> OTHER INFORMATION: H1 VH domain

<400> SEQUENCE: 22
caggtccagc tggtgcagtc tggggctgag ctgaagaagc ctggggcctc agtgaagctg      60
tcctgcaagg cttctggcta cactttcact gactactata taaactgggt gaagcaggcc     120
cctggaaagg gacttgagtg gattgcaagg atttaccctg aagtggtaa tacttactac      180 aatgagaagt tcaagggcag ggccacactg actgcagaaa aatccaccag cactgcctac     240
atgcagctca gcagcctgag atctgaggac tctgctgtct atttctgtgc aaggggggtg     300
tactactttg actactgggg ccaaggcacc actgtcacag tctcctca                  348

<210> SEQ ID NO 23
<211> LENGTH: 348

<212> TYPE: DNA
<213> ORGANISM: Artificial Sequence
<220> FEATURE:
<223> OTHER INFORMATION: H2 VH domain

<400> SEQUENCE: 23

```
caggtccagc tggtgcagtc tggggctgag gtgaagaagc ctggggcctc agtgaagctg    60
tcctgcaagg cttctggcta cactttcact gactactata aaactgggt gaagcaggcc    120
cctggaaagg gacttgagtg gattgcaagg atttaccctg gaagtggtaa tacttactac    180
aatgagaagt tcaagggcag ggccacactg actgcagaaa aatccaccag cactgcctac    240
atgcagctca gcagcctgag atctgaggac actgctgtct atttctgtgc aaggggggtg    300
tactactttg actactgggg ccaaggcacc actgtcacag tctcctca               348
```

<210> SEQ ID NO 24
<211> LENGTH: 348
<212> TYPE: DNA
<213> ORGANISM: Artificial Sequence
<220> FEATURE:
<223> OTHER INFORMATION: H3 VH domain

<400> SEQUENCE: 24

```
caggtccagc tggtgcagtc tggggctgag gtgaagaagc ctggggcctc agtgaagctg    60
tcctgcaagg cttctggcta cactttcact gactactata aaactgggt gaggcaggcc    120
cctggaaagg gacttgagtg gattgcaagg atttaccctg gaagtggtaa tacttactac    180
aatgagaagt tcaagggcag ggccacactg actgcagaca aatccaccag cactgcctac    240
atgcagctca gcagcctgag atctgaggac actgctgtct atttctgtgc aaggggggtg    300
tactactttg actactgggg ccaaggcacc actgtcacag tctcctca               348
```

<210> SEQ ID NO 25
<211> LENGTH: 348
<212> TYPE: DNA
<213> ORGANISM: Artificial Sequence
<220> FEATURE:
<223> OTHER INFORMATION: H4 VH domain

<400> SEQUENCE: 25

```
caggtccagc tggtgcagtc tggggctgag gtgaagaagc ctggggcctc agtgaaggtg    60
tcctgcaagg cttctggcta cactttcact gactactata aaactgggt gaggcaggcc    120
cctggaaagg gacttgagtg gattgcaagg atttaccctg gaagtggtaa tacttactac    180
aatgagaagt tcaagggcag ggccacaatc actgcagaca aatccaccag cactgcctac    240
atggagctca gcagcctgag atctgaggac actgctgtct atttctgtgc aaggggggtg    300
tactactttg actactgggg ccaaggcacc actgtcacag tctcctca               348
```

<210> SEQ ID NO 26
<211> LENGTH: 348
<212> TYPE: DNA
<213> ORGANISM: Artificial Sequence
<220> FEATURE:
<223> OTHER INFORMATION: H5 VH domain

<400> SEQUENCE: 26

```
caggtccagc tggtgcagtc tggggctgag gtgaagaagc ctggggcctc agtgaaggtg    60
tcctgcaagg cttctggcta cactttcact gactactata aaactgggt gaggcaggcc    120
cctggaaagg gacttgagtg gattgcaagg atttaccctg gaagtggtaa tacttactac    180
```

```
aatgagaagt tcaagggcag ggtcacaatc actgcagaca atccaccag cactgcctac      240 atggagctca gcagcctgag atctgaggac actgctgtct atttctgtgc aaggggggtg     300
tactactttg actactgggg ccaaggcacc actgtcacag tctcctca                  348
```

```
<210> SEQ ID NO 27
<211> LENGTH: 321
<212> TYPE: DNA
<213> ORGANISM: Artificial Sequence
<220> FEATURE:
<223> OTHER INFORMATION: L1 VL domain

<400> SEQUENCE: 27
gacattgtga tgacccagtc tccatccttc ctgtccgcat cagtaggaga cagggtcacc      60
atcacctgca aggccagtca gaatgtgcgt actaatgtag cctggtatca acagaaacca    120
gggaaagctc ctaaagcact gatttactcg gcatcctacc ggtacagtgg agtccctgat    180
cgcttcacag gcagtggatc tgggacagat ttcactctca ccatcagctc tctgcagtct    240
gaagacttcg cagactattt ctgtcagcaa tataacagct atcctcggac gttcggtgga    300
ggcaccaagg tggaaatcaa a                                               321
```

```
<210> SEQ ID NO 28
<211> LENGTH: 321
<212> TYPE: DNA
<213> ORGANISM: Artificial Sequence
<220> FEATURE:
<223> OTHER INFORMATION: L2 VL domain

<400> SEQUENCE: 28
gacattgtga tgacccagtc tccatcctcc ctgtccgcat cagtaggaga cagggtcacc      60
atcacctgca aggccagtca gaatgtgcgt actaatgtag cctggtatca acagaaacca    120
gggaaagctc ctaaagcact gatttactcg gcatcctacc ggtacagtgg agtccctgat    180
cgcttcacag gcagtggatc tgggacagat ttcactctca ccatcagctc tctgcagcct    240
gaagacttcg cagactattt ctgtcagcaa tataacagct atcctcggac gttcggtgga    300
ggcaccaagg tggaaatcaa a                                               321
```

```
<210> SEQ ID NO 29
<211> LENGTH: 321
<212> TYPE: DNA
<213> ORGANISM: Artificial Sequence
<220> FEATURE:
<223> OTHER INFORMATION: L3 VL domain

<400> SEQUENCE: 29
gacattgtga tgacccagtc tccatcctcc ctgtccgcat cagtaggaga cagggtcacc      60
atcacctgca aggccagtca gaatgtgcgt actaatgtag cctggtatca acagaaacca    120
gggaaagctc ctaaagcact gatttactcg gcatcctacc ggtacagtgg agtccctgat    180
cgcttcagcg gcagtggatc tgggacagat ttcactctca ccatcagctc tctgcagcct    240
gaagacttcg cagactattt ctgtcagcaa tataacagct atcctcggac gttcggtgga    300
ggcaccaagg tggaaatcaa a                                               321
```

```
<210> SEQ ID NO 30
<211> LENGTH: 321
<212> TYPE: DNA
<213> ORGANISM: Artificial Sequence
<220> FEATURE:
<223> OTHER INFORMATION: L4 VL domain
```

<400> SEQUENCE: 30

```
gacattgtga tgacccagtc tccatcctcc ctgtccgcat cagtaggaga cagggtcacc      60
atcacctgca aggccagtca gaatgtgcgt actaatgtag cctggtatca acagaaacca     120
gggaaagctc ctaaatccct gatttactcg gcatcctacc ggtacagtgg agtccctgat     180
cgcttcagcg gcagtggatc tgggacagat ttcactctca ccatcagctc tctgcagcct     240
gaagacttcg caacctatta ctgtcagcaa tataacagct atcctcggac gttcggtgga     300
ggcaccaagg tggaaatcaa a                                               321
```

<210> SEQ ID NO 31
<211> LENGTH: 116
<212> TYPE: PRT
<213> ORGANISM: mouse
<220> FEATURE:
<223> OTHER INFORMATION: variable heavy chain region of anti-KIT antibody 37M

<400> SEQUENCE: 31

```
Gln Val Gln Leu Lys Gln Ser Gly Ala Glu Leu Val Arg Pro Gly Ala
1               5                   10                  15

Ser Val Lys Leu Ser Cys Lys Ala Ser Gly Tyr Thr Phe Thr Asp Tyr
            20                  25                  30

Tyr Ile Asn Trp Val Lys Gln Arg Pro Gly Gln Gly Leu Glu Trp Ile
        35                  40                  45

Ala Arg Ile Tyr Pro Gly Ser Gly Asn Thr Tyr Tyr Asn Glu Lys Phe
    50                  55                  60

Lys Gly Lys Ala Thr Leu Thr Ala Glu Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Gly Val Tyr Tyr Phe Asp Tyr Trp Gly Gln Gly Thr Thr Leu
            100                 105                 110

Thr Val Ser Ser
        115
```

<210> SEQ ID NO 32
<211> LENGTH: 108
<212> TYPE: PRT
<213> ORGANISM: mouse
<220> FEATURE:
<223> OTHER INFORMATION: VL chain region of anti-KIT antibodies 37M and 37C

<400> SEQUENCE: 32

```
Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Arg Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Asn Ser Tyr Pro Arg
                85                  90                  95
```

```
Thr Phe Gly Gly Gly Thr Lys Leu Glu Ile Lys Arg
            100                 105

<210> SEQ ID NO 33
<211> LENGTH: 30
<212> TYPE: PRT
<213> ORGANISM: Artificial Sequence
<220> FEATURE:
<223> OTHER INFORMATION: FR1 of VH domain

<400> SEQUENCE: 33

Gln Val Gln Leu Val Gln Ser Gly Ala Glu Leu Lys Lys Pro Gly Ala
1               5                   10                  15

Ser Val Lys Leu Ser Cys Lys Ala Ser Gly Tyr Thr Phe Thr
            20                  25                  30

<210> SEQ ID NO 34
<211> LENGTH: 14
<212> TYPE: PRT
<213> ORGANISM: Artificial Sequence
<220> FEATURE:
<223> OTHER INFORMATION: FR2 of VH domain

<400> SEQUENCE: 34

Trp Val Lys Gln Ala Pro Gly Lys Gly Leu Glu Trp Ile Ala
1               5                   10

<210> SEQ ID NO 35
<211> LENGTH: 32
<212> TYPE: PRT
<213> ORGANISM: Artificial Sequence
<220> FEATURE:
<223> OTHER INFORMATION: FR3 of VH domain

<400> SEQUENCE: 35

Arg Ala Thr Leu Thr Ala Glu Lys Ser Thr Ser Thr Ala Tyr Met Gln
1               5                   10                  15

Leu Ser Ser Leu Arg Ser Glu Asp Ser Ala Val Tyr Phe Cys Ala Arg
            20                  25                  30

<210> SEQ ID NO 36
<211> LENGTH: 11
<212> TYPE: PRT
<213> ORGANISM: Artificial Sequence
<220> FEATURE:
<223> OTHER INFORMATION: FR4 of VH domain

<400> SEQUENCE: 36

Trp Gly Gln Gly Thr Thr Val Thr Val Ser Ser
1               5                   10

<210> SEQ ID NO 37
<211> LENGTH: 30
<212> TYPE: PRT
<213> ORGANISM: Artificial Sequence
<220> FEATURE:
<223> OTHER INFORMATION: FR1 of VH domain

<400> SEQUENCE: 37

Gln Val Gln Leu Val Gln Ser Gly Ala Glu Val Lys Lys Pro Gly Ala
1               5                   10                  15

Ser Val Lys Leu Ser Cys Lys Ala Ser Gly Tyr Thr Phe Thr
            20                  25                  30

<210> SEQ ID NO 38
```

-continued

```
<211> LENGTH: 32
<212> TYPE: PRT
<213> ORGANISM: Artificial Sequence
<220> FEATURE:
<223> OTHER INFORMATION: FR3 of VH domain

<400> SEQUENCE: 38

Arg Ala Thr Leu Thr Ala Glu Lys Ser Thr Ser Thr Ala Tyr Met Gln
1               5                   10                  15

Leu Ser Ser Leu Arg Ser Glu Asp Thr Ala Val Tyr Phe Cys Ala Arg
            20                  25                  30

<210> SEQ ID NO 39
<211> LENGTH: 14
<212> TYPE: PRT
<213> ORGANISM: Artificial Sequence
<220> FEATURE:
<223> OTHER INFORMATION: FR2 of VH domain

<400> SEQUENCE: 39

Trp Val Arg Gln Ala Pro Gly Lys Gly Leu Glu Trp Ile Ala
1               5                   10

<210> SEQ ID NO 40
<211> LENGTH: 32
<212> TYPE: PRT
<213> ORGANISM: Artificial Sequence
<220> FEATURE:
<223> OTHER INFORMATION: FR3 of VH domain

<400> SEQUENCE: 40

Arg Ala Thr Leu Thr Ala Asp Lys Ser Thr Ser Thr Ala Tyr Met Gln
1               5                   10                  15

Leu Ser Ser Leu Arg Ser Glu Asp Thr Ala Val Tyr Phe Cys Ala Arg
            20                  25                  30

<210> SEQ ID NO 41
<211> LENGTH: 30
<212> TYPE: PRT
<213> ORGANISM: Artificial Sequence
<220> FEATURE:
<223> OTHER INFORMATION: FR1 of VH domain

<400> SEQUENCE: 41

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30

<210> SEQ ID NO 42
<211> LENGTH: 32
<212> TYPE: PRT
<213> ORGANISM: Artificial Sequence
<220> FEATURE:
<223> OTHER INFORMATION: FR3 of VH domain

<400> SEQUENCE: 42

Arg Ala Thr Ile Thr Ala Asp Lys Ser Thr Ser Thr Ala Tyr Met Glu
1               5                   10                  15

Leu Ser Ser Leu Arg Ser Glu Asp Thr Ala Val Tyr Phe Cys Ala Arg
            20                  25                  30

<210> SEQ ID NO 43
<211> LENGTH: 32
<212> TYPE: PRT
```

```
<213> ORGANISM: Artificial Sequence
<220> FEATURE:
<223> OTHER INFORMATION: FR3 of VH domain

<400> SEQUENCE: 43

Arg Val Thr Ile Thr Ala Asp Lys Ser Thr Ser Thr Ala Tyr Met Glu
1               5                   10                  15

Leu Ser Ser Leu Arg Ser Glu Asp Thr Ala Val Tyr Phe Cys Ala Arg
                20                  25                  30

<210> SEQ ID NO 44
<211> LENGTH: 23
<212> TYPE: PRT
<213> ORGANISM: Artificial Sequence
<220> FEATURE:
<223> OTHER INFORMATION: FR1 of VL domain

<400> SEQUENCE: 44

Asp Ile Val Met Thr Gln Ser Pro Ser Phe Leu Ser Ala Ser Val Gly
1               5                   10                  15

Asp Arg Val Thr Ile Thr Cys
                20

<210> SEQ ID NO 45
<211> LENGTH: 15
<212> TYPE: PRT
<213> ORGANISM: Artificial Sequence
<220> FEATURE:
<223> OTHER INFORMATION: FR2 of VL domain

<400> SEQUENCE: 45

Trp Tyr Gln Gln Lys Pro Gly Lys Ala Pro Lys Ala Leu Ile Tyr
1               5                   10                  15

<210> SEQ ID NO 46
<211> LENGTH: 32
<212> TYPE: PRT
<213> ORGANISM: Artificial Sequence
<220> FEATURE:
<223> OTHER INFORMATION: FR3 of VL domain

<400> SEQUENCE: 46

Gly Val Pro Asp Arg Phe Thr Gly Ser Gly Ser Gly Thr Asp Phe Thr
1               5                   10                  15

Leu Thr Ile Ser Ser Leu Gln Ser Glu Asp Phe Ala Asp Tyr Phe Cys
                20                  25                  30

<210> SEQ ID NO 47
<211> LENGTH: 10
<212> TYPE: PRT
<213> ORGANISM: Artificial Sequence
<220> FEATURE:
<223> OTHER INFORMATION: FR4 of VL domain

<400> SEQUENCE: 47

Phe Gly Gly Gly Thr Lys Val Glu Ile Lys
1               5                   10

<210> SEQ ID NO 48
<211> LENGTH: 23
<212> TYPE: PRT
<213> ORGANISM: Artificial Sequence
<220> FEATURE:
<223> OTHER INFORMATION: FR1 of VL domain

<400> SEQUENCE: 48
```

-continued

Asp Ile Val Met Thr Gln Ser Pro Ser Ser Leu Ser Ala Ser Val Gly
1               5                   10                  15

Asp Arg Val Thr Ile Thr Cys
            20

<210> SEQ ID NO 49
<211> LENGTH: 32
<212> TYPE: PRT
<213> ORGANISM: Artificial Sequence
<220> FEATURE:
<223> OTHER INFORMATION: FR3 of VL domain

<400> SEQUENCE: 49

Gly Val Pro Asp Arg Phe Thr Gly Ser Gly Ser Gly Thr Asp Phe Thr
1               5                   10                  15

Leu Thr Ile Ser Ser Leu Gln Pro Glu Asp Phe Ala Asp Tyr Phe Cys
            20                  25                  30

<210> SEQ ID NO 50
<211> LENGTH: 32
<212> TYPE: PRT
<213> ORGANISM: Artificial Sequence
<220> FEATURE:
<223> OTHER INFORMATION: FR3 of VL domain

<400> SEQUENCE: 50

Gly Val Pro Asp Arg Phe Ser Gly Ser Gly Ser Gly Thr Asp Phe Thr
1               5                   10                  15

Leu Thr Ile Ser Ser Leu Gln Pro Glu Asp Phe Ala Asp Tyr Phe Cys
            20                  25                  30

<210> SEQ ID NO 51
<211> LENGTH: 15
<212> TYPE: PRT
<213> ORGANISM: Artificial Sequence
<220> FEATURE:
<223> OTHER INFORMATION: FR2 of VL domain

<400> SEQUENCE: 51

Trp Tyr Gln Gln Lys Pro Gly Lys Ala Pro Lys Ser Leu Ile Tyr
1               5                   10                  15

<210> SEQ ID NO 52
<211> LENGTH: 32
<212> TYPE: PRT
<213> ORGANISM: Artificial Sequence
<220> FEATURE:
<223> OTHER INFORMATION: FR3 of VL domain

<400> SEQUENCE: 52

Gly Val Pro Asp Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 53
<211> LENGTH: 107
<212> TYPE: PRT
<213> ORGANISM: Artificial Sequence
<220> FEATURE:
<223> OTHER INFORMATION: VL chain region of Ab1

<400> SEQUENCE: 53

Asp Ile Gln Met Thr Gln Ser Pro Thr Ser Leu Ser Ala Phe Val Gly

```
                1               5                    10                   15
        Asp Arg Val Thr Ile Thr Cys Gln Ala Ser Gln Asp Ile Gly Asn Tyr
                        20                  25                  30

Leu Asn Trp Tyr Gln Gln Lys Ser Gly Glu Pro Pro Lys Leu Leu Val
                    35                  40                  45

Tyr Asp Ala Ser Phe Leu Lys Lys Gly Val Pro Ser Arg Phe Ser Gly
                50                  55                  60

Ser Gly Ser Gly Thr Gln Tyr Phe Leu Thr Ile Tyr Ser Leu Gln Pro
        65                  70                  75                  80

Glu Asp Phe Ala Thr Tyr Phe Cys Gln His Ser Asp Asn Leu Ser Val
                        85                  90                  95

Thr Phe Gly Gly Gly Thr Lys Val Glu Val Lys
                    100                 105

<210> SEQ ID NO 54
<211> LENGTH: 107
<212> TYPE: PRT
<213> ORGANISM: Artificial Sequence
<220> FEATURE:
<223> OTHER INFORMATION: VL chain region of Ab21

<400> SEQUENCE: 54

Asp Ile Gln Met Thr Gln Ser Pro Thr Ser Leu Ser Ala Phe Val Gly
        1               5                   10                  15

Asp Arg Val Thr Ile Thr Cys Gln Ala Ser Gln Asp Ile Gly Asn Tyr
                        20                  25                  30

Leu Asn Trp Tyr Gln Gln Lys Ser Gly Glu Pro Pro Lys Leu Leu Val
                    35                  40                  45

Tyr Asp Ala Ser Phe Leu Lys Lys Gly Val Pro Ser Arg Phe Ser Gly
                50                  55                  60

Ser Gly Ser Gly Thr Gln Tyr Phe Leu Thr Ile Tyr Ser Leu Gln Pro
        65                  70                  75                  80

Glu Asp Phe Ala Thr Tyr Phe Cys Gln His Ser Asp Ser Leu Ser Val
                        85                  90                  95

Thr Phe Gly Gly Gly Thr Lys Val Glu Val Lys
                    100                 105

<210> SEQ ID NO 55
<211> LENGTH: 122
<212> TYPE: PRT
<213> ORGANISM: Artificial Sequence
<220> FEATURE:
<223> OTHER INFORMATION: VH chain region of Ab1 or Ab21

<400> SEQUENCE: 55

Glu Val Gln Leu Leu Glu Ser Gly Gly Gly Leu Val Gln Pro Gly Gly
        1               5                   10                  15

Ser Leu Arg Leu Ser Cys Ala Ala Ser Gly Phe Thr Phe Ser Asn Tyr
                        20                  25                  30

Leu Met Ser Trp Val Arg Gln Ala Pro Gly Lys Gly Leu Glu Trp Val
                    35                  40                  45

Ser Ser Ile Val Pro Ser Gly Gly Phe Thr His Tyr Ala Asp Ser Val
                50                  55                  60

Lys Gly Arg Phe Thr Ile Ser Arg Asp Asn Ser Lys Asn Thr Leu Tyr
        65                  70                  75                  80

Leu Gln Met Asn Ser Leu Arg Ala Glu Asp Thr Ala Val Tyr Tyr Cys
                        85                  90                  95
```

```
Ala Arg Leu Gln Thr Gly Ser Trp Arg Val His Ala Phe Asp Ile Trp
            100                 105                 110
Gly Gln Gly Thr Met Val Thr Val Ser Ser
        115                 120

<210> SEQ ID NO 56
<211> LENGTH: 7
<212> TYPE: PRT
<213> ORGANISM: Artificial Sequence
<220> FEATURE:
<223> OTHER INFORMATION: VH CDR1 (Table 2)

<400> SEQUENCE: 56

Gly Tyr Thr Phe Thr Asp Tyr
1               5

<210> SEQ ID NO 57
<211> LENGTH: 6
<212> TYPE: PRT
<213> ORGANISM: Artificial Sequence
<220> FEATURE:
<223> OTHER INFORMATION: VH CDR2 (Table 2)

<400> SEQUENCE: 57

Tyr Pro Gly Ser Gly Asn
1               5

<210> SEQ ID NO 58
<211> LENGTH: 8
<212> TYPE: PRT
<213> ORGANISM: Artificial Sequence
<220> FEATURE:
<223> OTHER INFORMATION: VH CDR3 (Table 2)

<400> SEQUENCE: 58

Gly Val Tyr Tyr Phe Asp Tyr Trp
1               5

<210> SEQ ID NO 59
<211> LENGTH: 7
<212> TYPE: PRT
<213> ORGANISM: Artificial Sequence
<220> FEATURE:
<223> OTHER INFORMATION: VL CDR1 (Table 2)

<400> SEQUENCE: 59

Ser Gln Asn Val Arg Thr Asn
1               5

<210> SEQ ID NO 60
<211> LENGTH: 3
<212> TYPE: PRT
<213> ORGANISM: Artificial Sequence
<220> FEATURE:
<223> OTHER INFORMATION: VL CDR2 (Table 2)

<400> SEQUENCE: 60

Ser Ala Ser
1

<210> SEQ ID NO 61
<211> LENGTH: 6
<212> TYPE: PRT
<213> ORGANISM: Artificial Sequence
<220> FEATURE:
<223> OTHER INFORMATION: VL CDR3 (Table 2)
```

```
<400> SEQUENCE: 61

Tyr Asn Ser Tyr Pro Arg
1               5

<210> SEQ ID NO 62
<211> LENGTH: 4
<212> TYPE: PRT
<213> ORGANISM: Artificial Sequence
<220> FEATURE:
<223> OTHER INFORMATION: VH CDR2 (Table 2)

<400> SEQUENCE: 62

Pro Gly Ser Gly
1

<210> SEQ ID NO 63
<211> LENGTH: 6
<212> TYPE: PRT
<213> ORGANISM: Artificial Sequence
<220> FEATURE:
<223> OTHER INFORMATION: VH CDR3 (Table 2)

<400> SEQUENCE: 63

Val Tyr Tyr Phe Asp Tyr
1               5

<210> SEQ ID NO 64
<211> LENGTH: 10
<212> TYPE: PRT
<213> ORGANISM: Artificial Sequence
<220> FEATURE:
<223> OTHER INFORMATION: VH CDR1 (Table 3)

<400> SEQUENCE: 64

Gly Tyr Thr Phe Thr Asp Tyr Tyr Ile Asn
1               5                   10

<210> SEQ ID NO 65
<211> LENGTH: 10
<212> TYPE: PRT
<213> ORGANISM: Artificial Sequence
<220> FEATURE:
<223> OTHER INFORMATION: VH CDR2 (Table 3)

<400> SEQUENCE: 65

Arg Ile Tyr Pro Gly Ser Gly Asn Thr Tyr
1               5                   10

<210> SEQ ID NO 66
<211> LENGTH: 7
<212> TYPE: PRT
<213> ORGANISM: Artificial Sequence
<220> FEATURE:
<223> OTHER INFORMATION: VL CDR1 (Table 3)

<400> SEQUENCE: 66

Arg Thr Asn Val Ala Trp Tyr
1               5

<210> SEQ ID NO 67
<211> LENGTH: 10
<212> TYPE: PRT
<213> ORGANISM: Artificial Sequence
<220> FEATURE:
<223> OTHER INFORMATION: VL CDR2 (Table 3)

<400> SEQUENCE: 67
```

Ala Leu Ile Tyr Ser Ala Ser Tyr Arg Tyr
1               5                   10

<210> SEQ ID NO 68
<211> LENGTH: 8
<212> TYPE: PRT
<213> ORGANISM: Artificial Sequence
<220> FEATURE:
<223> OTHER INFORMATION: VL CDR3 (Table 3)

<400> SEQUENCE: 68

Gln Gln Tyr Asn Ser Tyr Pro Arg
1               5

<210> SEQ ID NO 69
<211> LENGTH: 116
<212> TYPE: PRT
<213> ORGANISM: Artificial Sequence
<220> FEATURE:
<223> OTHER INFORMATION: variable heavy chain region of anti-KIT
      antibody 37C

<400> SEQUENCE: 69

Gln Val Gln Leu Lys Gln Ser Gly Ala Glu Leu Val Arg Pro Gly Ala
1               5                   10                  15

Ser Val Lys Leu Ser Cys Lys Ala Ser Gly Tyr Thr Phe Thr Asp Tyr
            20                  25                  30

Tyr Ile Asn Trp Val Lys Gln Arg Pro Gly Gln Gly Leu Glu Trp Ile
        35                  40                  45

Ala Arg Ile Tyr Pro Gly Ser Gly Asn Thr Tyr Tyr Asn Glu Lys Phe
    50                  55                  60

Lys Gly Lys Ala Thr Leu Thr Ala Glu Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Gly Val Tyr Tyr Phe Asp Tyr Trp Gly Gln Gly Thr Thr Leu
            100                 105                 110

Thr Val Ser Ala
        115

<210> SEQ ID NO 70
<211> LENGTH: 6
<212> TYPE: PRT
<213> ORGANISM: Artificial Sequence
<220> FEATURE:
<223> OTHER INFORMATION: VH CDR1 (Table 3)

<400> SEQUENCE: 70

Thr Asp Tyr Tyr Ile Asn
1               5

<210> SEQ ID NO 71
<211> LENGTH: 13
<212> TYPE: PRT
<213> ORGANISM: Artificial Sequence
<220> FEATURE:
<223> OTHER INFORMATION: VH CDR2 (Table 3)

<400> SEQUENCE: 71

Trp Ile Ala Arg Ile Tyr Pro Gly Ser Gly Asn Thr Tyr
1               5                   10

```
<210> SEQ ID NO 72
<211> LENGTH: 9
<212> TYPE: PRT
<213> ORGANISM: Artificial Sequence
<220> FEATURE:
<223> OTHER INFORMATION: VH CDR3 (Table 3)

<400> SEQUENCE: 72

Ala Arg Gly Val Tyr Tyr Phe Asp Tyr
1               5

<210> SEQ ID NO 73
<211> LENGTH: 208
<212> TYPE: PRT
<213> ORGANISM: Homo sapiens
<220> FEATURE:
<223> OTHER INFORMATION: Human KIT amino acids V308 to H515

<400> SEQUENCE: 73

Val Asp Lys Gly Phe Ile Asn Ile Phe Pro Met Ile Asn Thr Thr Val
1               5                   10                  15

Phe Val Asn Asp Gly Glu Asn Val Asp Leu Ile Val Glu Tyr Glu Ala
            20                  25                  30

Phe Pro Lys Pro Glu His Gln Gln Trp Ile Tyr Met Asn Arg Thr Phe
        35                  40                  45

Thr Asp Lys Trp Glu Asp Tyr Pro Lys Ser Glu Asn Glu Ser Asn Ile
    50                  55                  60

Arg Tyr Val Ser Glu Leu His Leu Thr Arg Leu Lys Gly Thr Glu Gly
65                  70                  75                  80

Gly Thr Tyr Thr Phe Leu Val Ser Asn Ser Asp Val Asn Ala Ala Ile
                85                  90                  95

Ala Phe Asn Val Tyr Val Asn Thr Lys Pro Glu Ile Leu Thr Tyr Asp
            100                 105                 110

Arg Leu Val Asn Gly Met Leu Gln Cys Val Ala Ala Gly Phe Pro Glu
        115                 120                 125

Pro Thr Ile Asp Trp Tyr Phe Cys Pro Gly Thr Glu Gln Arg Cys Ser
    130                 135                 140

Ala Ser Val Leu Pro Val Asp Val Gln Thr Leu Asn Ser Ser Gly Pro
145                 150                 155                 160

Pro Phe Gly Lys Leu Val Val Gln Ser Ser Ile Asp Ser Ser Ala Phe
                165                 170                 175

Lys His Asn Gly Thr Val Glu Cys Lys Ala Tyr Asn Asp Val Gly Lys
            180                 185                 190

Thr Ser Ala Tyr Phe Asn Phe Ala Phe Lys Glu Gln Ile His Pro His
        195                 200                 205

<210> SEQ ID NO 74
<211> LENGTH: 11
<212> TYPE: PRT
<213> ORGANISM: Artificial Sequence
<220> FEATURE:
<223> OTHER INFORMATION: VL CDR1
<220> FEATURE:
<221> NAME/KEY: VARIANT
<222> LOCATION: 1
<223> OTHER INFORMATION: Xaa = Any Amino Acid

<400> SEQUENCE: 74

Xaa Ala Ser Gln Asn Val Arg Thr Asn Val Ala
1               5                   10
```

```
<210> SEQ ID NO 75
<211> LENGTH: 11
<212> TYPE: PRT
<213> ORGANISM: Artificial Sequence
<220> FEATURE:
<223> OTHER INFORMATION: VL CDR1
<220> FEATURE:
<221> NAME/KEY: VARIANT
<222> LOCATION: 2
<223> OTHER INFORMATION: Xaa = Any Amino Acid

<400> SEQUENCE: 75

Lys Xaa Ser Gln Asn Val Arg Thr Asn Val Ala
1               5                   10

<210> SEQ ID NO 76
<211> LENGTH: 11
<212> TYPE: PRT
<213> ORGANISM: Artificial Sequence
<220> FEATURE:
<223> OTHER INFORMATION: VL CDR1
<220> FEATURE:
<221> NAME/KEY: VARIANT
<222> LOCATION: 3
<223> OTHER INFORMATION: Xaa = Any Amino Acid

<400> SEQUENCE: 76

Lys Ala Xaa Gln Asn Val Arg Thr Asn Val Ala
1               5                   10

<210> SEQ ID NO 77
<211> LENGTH: 11
<212> TYPE: PRT
<213> ORGANISM: Artificial Sequence
<220> FEATURE:
<223> OTHER INFORMATION: VL CDR1
<220> FEATURE:
<221> NAME/KEY: VARIANT
<222> LOCATION: 4
<223> OTHER INFORMATION: Xaa = Any Amino Acid

<400> SEQUENCE: 77

Lys Ala Ser Xaa Asn Val Arg Thr Asn Val Ala
1               5                   10

<210> SEQ ID NO 78
<211> LENGTH: 11
<212> TYPE: PRT
<213> ORGANISM: Artificial Sequence
<220> FEATURE:
<223> OTHER INFORMATION: VL CDR1
<220> FEATURE:
<221> NAME/KEY: VARIANT
<222> LOCATION: 5
<223> OTHER INFORMATION: Xaa = Any Amino Acid

<400> SEQUENCE: 78

Lys Ala Ser Gln Xaa Val Arg Thr Asn Val Ala
1               5                   10

<210> SEQ ID NO 79
<211> LENGTH: 11
<212> TYPE: PRT
<213> ORGANISM: Artificial Sequence
<220> FEATURE:
<223> OTHER INFORMATION: VL CDR1
<220> FEATURE:
<221> NAME/KEY: VARIANT
<222> LOCATION: 5
<223> OTHER INFORMATION: Xaa = Ala or Gly or Thr or Tyr or Cys or Ser
```

<400> SEQUENCE: 79

Lys Ala Ser Gln Xaa Val Arg Thr Asn Val Ala
1               5                   10

<210> SEQ ID NO 80
<211> LENGTH: 11
<212> TYPE: PRT
<213> ORGANISM: Artificial Sequence
<220> FEATURE:
<223> OTHER INFORMATION: VL CDR1
<220> FEATURE:
<221> NAME/KEY: VARIANT
<222> LOCATION: 6
<223> OTHER INFORMATION: Xaa = Any Amino Acid

<400> SEQUENCE: 80

Lys Ala Ser Gln Asn Xaa Arg Thr Asn Val Ala
1               5                   10

<210> SEQ ID NO 81
<211> LENGTH: 11
<212> TYPE: PRT
<213> ORGANISM: Artificial Sequence
<220> FEATURE:
<223> OTHER INFORMATION: VL CDR1
<220> FEATURE:
<221> NAME/KEY: VARIANT
<222> LOCATION: 7
<223> OTHER INFORMATION: Xaa = Any Amino Acid

<400> SEQUENCE: 81

Lys Ala Ser Gln Asn Val Xaa Thr Asn Val Ala
1               5                   10

<210> SEQ ID NO 82
<211> LENGTH: 11
<212> TYPE: PRT
<213> ORGANISM: Artificial Sequence
<220> FEATURE:
<223> OTHER INFORMATION: VL CDR1
<220> FEATURE:
<221> NAME/KEY: VARIANT
<222> LOCATION: 8
<223> OTHER INFORMATION: Xaa = Any Amino Acid

<400> SEQUENCE: 82

Lys Ala Ser Gln Asn Val Arg Xaa Asn Val Ala
1               5                   10

<210> SEQ ID NO 83
<211> LENGTH: 11
<212> TYPE: PRT
<213> ORGANISM: Artificial Sequence
<220> FEATURE:
<223> OTHER INFORMATION: VL CDR1
<220> FEATURE:
<221> NAME/KEY: VARIANT
<222> LOCATION: 9
<223> OTHER INFORMATION: Xaa = Any Amino Acid

<400> SEQUENCE: 83

Lys Ala Ser Gln Asn Val Arg Thr Xaa Val Ala
1               5                   10

<210> SEQ ID NO 84
<211> LENGTH: 11
<212> TYPE: PRT
<213> ORGANISM: Artificial Sequence
<220> FEATURE:

```
<223> OTHER INFORMATION: VL CDR1
<220> FEATURE:
<221> NAME/KEY: VARIANT
<222> LOCATION: 9
<223> OTHER INFORMATION: Xaa = Ala or Gly or Thr or Tyr or Cys or Ser

<400> SEQUENCE: 84

Lys Ala Ser Gln Asn Val Arg Thr Xaa Val Ala
1               5                   10

<210> SEQ ID NO 85
<211> LENGTH: 11
<212> TYPE: PRT
<213> ORGANISM: Artificial Sequence
<220> FEATURE:
<223> OTHER INFORMATION: VL CDR1
<220> FEATURE:
<221> NAME/KEY: VARIANT
<222> LOCATION: 10
<223> OTHER INFORMATION: Xaa = Any Amino Acid

<400> SEQUENCE: 85

Lys Ala Ser Gln Asn Val Arg Thr Asn Xaa Ala
1               5                   10

<210> SEQ ID NO 86
<211> LENGTH: 11
<212> TYPE: PRT
<213> ORGANISM: Artificial Sequence
<220> FEATURE:
<223> OTHER INFORMATION: VL CDR1
<220> FEATURE:
<221> NAME/KEY: VARIANT
<222> LOCATION: 11
<223> OTHER INFORMATION: Xaa = Any Amino Acid

<400> SEQUENCE: 86

Lys Ala Ser Gln Asn Val Arg Thr Asn Val Xaa
1               5                   10

<210> SEQ ID NO 87
<211> LENGTH: 11
<212> TYPE: PRT
<213> ORGANISM: Artificial Sequence
<220> FEATURE:
<223> OTHER INFORMATION: VL CDR1

<400> SEQUENCE: 87

Cys Lys Ala Ser Gln Asn Val Arg Thr Asn Val
1               5                   10

<210> SEQ ID NO 88
<211> LENGTH: 11
<212> TYPE: PRT
<213> ORGANISM: Artificial Sequence
<220> FEATURE:
<223> OTHER INFORMATION: VL CDR1

<400> SEQUENCE: 88

Ile Cys Lys Ala Ser Gln Asn Val Arg Thr Asn
1               5                   10

<210> SEQ ID NO 89
<211> LENGTH: 11
<212> TYPE: PRT
<213> ORGANISM: Artificial Sequence
<220> FEATURE:
<223> OTHER INFORMATION: VL CDR1
```

```
<400> SEQUENCE: 89

Ala Ser Gln Asn Val Arg Thr Asn Val Ala Trp
1               5                   10

<210> SEQ ID NO 90
<211> LENGTH: 11
<212> TYPE: PRT
<213> ORGANISM: Artificial Sequence
<220> FEATURE:
<223> OTHER INFORMATION: VL CDR1

<400> SEQUENCE: 90

Ser Gln Asn Val Arg Thr Asn Val Ala Trp Tyr
1               5                   10

<210> SEQ ID NO 91
<211> LENGTH: 11
<212> TYPE: PRT
<213> ORGANISM: Artificial Sequence
<220> FEATURE:
<223> OTHER INFORMATION: VL CDR1

<400> SEQUENCE: 91

Gln Asn Val Arg Thr Asn Val Ala Trp Tyr Gln
1               5                   10

<210> SEQ ID NO 92
<211> LENGTH: 7
<212> TYPE: PRT
<213> ORGANISM: Artificial Sequence
<220> FEATURE:
<223> OTHER INFORMATION: VL CDR2
<220> FEATURE:
<221> NAME/KEY: VARIANT
<222> LOCATION: 1
<223> OTHER INFORMATION: Xaa = Any Amino Acid

<400> SEQUENCE: 92

Xaa Ala Ser Tyr Arg Tyr Ser
1               5

<210> SEQ ID NO 93
<211> LENGTH: 7
<212> TYPE: PRT
<213> ORGANISM: Artificial Sequence
<220> FEATURE:
<223> OTHER INFORMATION: VL CDR2
<220> FEATURE:
<221> NAME/KEY: VARIANT
<222> LOCATION: 2
<223> OTHER INFORMATION: Xaa = Any Amino Acid

<400> SEQUENCE: 93

Ser Xaa Ser Tyr Arg Tyr Ser
1               5

<210> SEQ ID NO 94
<211> LENGTH: 7
<212> TYPE: PRT
<213> ORGANISM: Artificial Sequence
<220> FEATURE:
<223> OTHER INFORMATION: VL CDR2
<220> FEATURE:
<221> NAME/KEY: VARIANT
<222> LOCATION: 3
<223> OTHER INFORMATION: Xaa = Any Amino Acid

<400> SEQUENCE: 94
```

Ser Ala Xaa Tyr Arg Tyr Ser
1               5

<210> SEQ ID NO 95
<211> LENGTH: 7
<212> TYPE: PRT
<213> ORGANISM: Artificial Sequence
<220> FEATURE:
<223> OTHER INFORMATION: VL CDR2
<220> FEATURE:
<221> NAME/KEY: VARIANT
<222> LOCATION: 4
<223> OTHER INFORMATION: Xaa = Any Amino Acid

<400> SEQUENCE: 95

Ser Ala Ser Xaa Arg Tyr Ser
1               5

<210> SEQ ID NO 96
<211> LENGTH: 7
<212> TYPE: PRT
<213> ORGANISM: Artificial Sequence
<220> FEATURE:
<223> OTHER INFORMATION: VL CDR2
<220> FEATURE:
<221> NAME/KEY: VARIANT
<222> LOCATION: 5
<223> OTHER INFORMATION: Xaa = Any Amino Acid

<400> SEQUENCE: 96

Ser Ala Ser Tyr Xaa Tyr Ser
1               5

<210> SEQ ID NO 97
<211> LENGTH: 7
<212> TYPE: PRT
<213> ORGANISM: Artificial Sequence
<220> FEATURE:
<223> OTHER INFORMATION: VL CDR2
<220> FEATURE:
<221> NAME/KEY: VARIANT
<222> LOCATION: 6
<223> OTHER INFORMATION: Xaa = Any Amino Acid

<400> SEQUENCE: 97

Ser Ala Ser Tyr Arg Xaa Ser
1               5

<210> SEQ ID NO 98
<211> LENGTH: 7
<212> TYPE: PRT
<213> ORGANISM: Artificial Sequence
<220> FEATURE:
<223> OTHER INFORMATION: VL CDR2
<220> FEATURE:
<221> NAME/KEY: VARIANT
<222> LOCATION: 7
<223> OTHER INFORMATION: Xaa = Any Amino Acid

<400> SEQUENCE: 98

Ser Ala Ser Tyr Arg Tyr Xaa
1               5

<210> SEQ ID NO 99
<211> LENGTH: 7
<212> TYPE: PRT
<213> ORGANISM: Artificial Sequence
<220> FEATURE:
<223> OTHER INFORMATION: VL CDR2

```
<400> SEQUENCE: 99

Tyr Ser Ala Ser Tyr Arg Tyr
1               5

<210> SEQ ID NO 100
<211> LENGTH: 7
<212> TYPE: PRT
<213> ORGANISM: Artificial Sequence
<220> FEATURE:
<223> OTHER INFORMATION: VL CDR2

<400> SEQUENCE: 100

Ile Tyr Ser Ala Ser Tyr Arg
1               5

<210> SEQ ID NO 101
<211> LENGTH: 7
<212> TYPE: PRT
<213> ORGANISM: Artificial Sequence
<220> FEATURE:
<223> OTHER INFORMATION: VL CDR2

<400> SEQUENCE: 101

Leu Ile Tyr Ser Ala Ser Tyr
1               5

<210> SEQ ID NO 102
<211> LENGTH: 7
<212> TYPE: PRT
<213> ORGANISM: Artificial Sequence
<220> FEATURE:
<223> OTHER INFORMATION: VL CDR2

<400> SEQUENCE: 102

Ala Ser Tyr Arg Tyr Ser Gly
1               5

<210> SEQ ID NO 103
<211> LENGTH: 7
<212> TYPE: PRT
<213> ORGANISM: Artificial Sequence
<220> FEATURE:
<223> OTHER INFORMATION: VL CDR2

<400> SEQUENCE: 103

Ser Tyr Arg Tyr Ser Gly Val
1               5

<210> SEQ ID NO 104
<211> LENGTH: 7
<212> TYPE: PRT
<213> ORGANISM: Artificial Sequence
<220> FEATURE:
<223> OTHER INFORMATION: VL CDR2

<400> SEQUENCE: 104

Tyr Arg Tyr Ser Gly Val Pro
1               5

<210> SEQ ID NO 105
<211> LENGTH: 9
<212> TYPE: PRT
<213> ORGANISM: Artificial Sequence
<220> FEATURE:
<223> OTHER INFORMATION: VL CDR3
<220> FEATURE:
<221> NAME/KEY: VARIANT
```

```
<222> LOCATION: 2
<223> OTHER INFORMATION: Xaa = Any Amino Acid

<400> SEQUENCE: 105

Gln Xaa Tyr Asn Ser Tyr Pro Arg Thr
1               5

<210> SEQ ID NO 106
<211> LENGTH: 9
<212> TYPE: PRT
<213> ORGANISM: Artificial Sequence
<220> FEATURE:
<223> OTHER INFORMATION: VL CDR3
<220> FEATURE:
<221> NAME/KEY: VARIANT
<222> LOCATION: 3
<223> OTHER INFORMATION: Xaa = Any Amino Acid

<400> SEQUENCE: 106

Gln Gln Xaa Asn Ser Tyr Pro Arg Thr
1               5

<210> SEQ ID NO 107
<211> LENGTH: 9
<212> TYPE: PRT
<213> ORGANISM: Artificial Sequence
<220> FEATURE:
<223> OTHER INFORMATION: VL CDR3
<220> FEATURE:
<221> NAME/KEY: VARIANT
<222> LOCATION: 4
<223> OTHER INFORMATION: Xaa = Any Amino Acid

<400> SEQUENCE: 107

Gln Gln Tyr Xaa Ser Tyr Pro Arg Thr
1               5

<210> SEQ ID NO 108
<211> LENGTH: 9
<212> TYPE: PRT
<213> ORGANISM: Artificial Sequence
<220> FEATURE:
<223> OTHER INFORMATION: VL CDR3
<220> FEATURE:
<221> NAME/KEY: VARIANT
<222> LOCATION: 5
<223> OTHER INFORMATION: Xaa = Any Amino Acid

<400> SEQUENCE: 108

Gln Gln Tyr Asn Xaa Tyr Pro Arg Thr
1               5

<210> SEQ ID NO 109
<211> LENGTH: 9
<212> TYPE: PRT
<213> ORGANISM: Artificial Sequence
<220> FEATURE:
<223> OTHER INFORMATION: VL CDR3
<220> FEATURE:
<221> NAME/KEY: VARIANT
<222> LOCATION: 6
<223> OTHER INFORMATION: Xaa = Any Amino Acid

<400> SEQUENCE: 109

Gln Gln Tyr Asn Ser Xaa Pro Arg Thr
1               5

<210> SEQ ID NO 110
<211> LENGTH: 9
```

<212> TYPE: PRT
<213> ORGANISM: Artificial Sequence
<220> FEATURE:
<223> OTHER INFORMATION: VL CDR3
<220> FEATURE:
<221> NAME/KEY: VARIANT
<222> LOCATION: 7
<223> OTHER INFORMATION: Xaa = Any Amino Acid

<400> SEQUENCE: 110

Gln Gln Tyr Asn Ser Tyr Xaa Arg Thr
1               5

<210> SEQ ID NO 111
<211> LENGTH: 9
<212> TYPE: PRT
<213> ORGANISM: Artificial Sequence
<220> FEATURE:
<223> OTHER INFORMATION: VL CDR3
<220> FEATURE:
<221> NAME/KEY: VARIANT
<222> LOCATION: 8
<223> OTHER INFORMATION: Xaa = Any Amino Acid

<400> SEQUENCE: 111

Gln Gln Tyr Asn Ser Tyr Pro Xaa Thr
1               5

<210> SEQ ID NO 112
<211> LENGTH: 9
<212> TYPE: PRT
<213> ORGANISM: Artificial Sequence
<220> FEATURE:
<223> OTHER INFORMATION: VL CDR3
<220> FEATURE:
<221> NAME/KEY: VARIANT
<222> LOCATION: 9
<223> OTHER INFORMATION: Xaa = Any Amino Acid

<400> SEQUENCE: 112

Gln Gln Tyr Asn Ser Tyr Pro Arg Xaa
1               5

<210> SEQ ID NO 113
<211> LENGTH: 8
<212> TYPE: PRT
<213> ORGANISM: Artificial Sequence
<220> FEATURE:
<223> OTHER INFORMATION: VL CDR3

<400> SEQUENCE: 113

Gln Gln Tyr Asn Ser Tyr Pro Arg
1               5

<210> SEQ ID NO 114
<211> LENGTH: 8
<212> TYPE: PRT
<213> ORGANISM: Artificial Sequence
<220> FEATURE:
<223> OTHER INFORMATION: VL CDR3

<400> SEQUENCE: 114

Cys Gln Gln Tyr Asn Ser Tyr Pro
1               5

<210> SEQ ID NO 115
<211> LENGTH: 8
<212> TYPE: PRT
<213> ORGANISM: Artificial Sequence

```
<220> FEATURE:
<223> OTHER INFORMATION: VL CDR3

<400> SEQUENCE: 115

Phe Cys Gln Gln Tyr Asn Ser Tyr
1               5

<210> SEQ ID NO 116
<211> LENGTH: 8
<212> TYPE: PRT
<213> ORGANISM: Artificial Sequence
<220> FEATURE:
<223> OTHER INFORMATION: VL CDR3

<400> SEQUENCE: 116

Tyr Phe Cys Gln Gln Tyr Asn Ser
1               5

<210> SEQ ID NO 117
<211> LENGTH: 8
<212> TYPE: PRT
<213> ORGANISM: Artificial Sequence
<220> FEATURE:
<223> OTHER INFORMATION: VL CDR3

<400> SEQUENCE: 117

Gln Tyr Asn Ser Tyr Pro Arg Phe
1               5

<210> SEQ ID NO 118
<211> LENGTH: 8
<212> TYPE: PRT
<213> ORGANISM: Artificial Sequence
<220> FEATURE:
<223> OTHER INFORMATION: VL CDR3

<400> SEQUENCE: 118

Tyr Asn Ser Tyr Pro Arg Phe Gly
1               5

<210> SEQ ID NO 119
<211> LENGTH: 7
<212> TYPE: PRT
<213> ORGANISM: Artificial Sequence
<220> FEATURE:
<223> OTHER INFORMATION: VL CDR3

<400> SEQUENCE: 119

Ser Tyr Pro Arg Phe Gly Gly
1               5

<210> SEQ ID NO 120
<211> LENGTH: 5
<212> TYPE: PRT
<213> ORGANISM: Artificial Sequence
<220> FEATURE:
<223> OTHER INFORMATION: VH CDR1
<220> FEATURE:
<221> NAME/KEY: VARIANT
<222> LOCATION: 1
<223> OTHER INFORMATION: Xaa = Any Amino Acid

<400> SEQUENCE: 120

Xaa Tyr Tyr Ile Asn
1               5

<210> SEQ ID NO 121
```

```
<211> LENGTH: 5
<212> TYPE: PRT
<213> ORGANISM: Artificial Sequence
<220> FEATURE:
<223> OTHER INFORMATION: VH CDR1
<220> FEATURE:
<221> NAME/KEY: VARIANT
<222> LOCATION: 2
<223> OTHER INFORMATION: Xaa = Any Amino Acid

<400> SEQUENCE: 121

Asp Xaa Tyr Ile Asn
1               5

<210> SEQ ID NO 122
<211> LENGTH: 5
<212> TYPE: PRT
<213> ORGANISM: Artificial Sequence
<220> FEATURE:
<223> OTHER INFORMATION: VH CDR1
<220> FEATURE:
<221> NAME/KEY: VARIANT
<222> LOCATION: 3
<223> OTHER INFORMATION: Xaa = Any Amino Acid

<400> SEQUENCE: 122

Asp Tyr Xaa Ile Asn
1               5

<210> SEQ ID NO 123
<211> LENGTH: 5
<212> TYPE: PRT
<213> ORGANISM: Artificial Sequence
<220> FEATURE:
<223> OTHER INFORMATION: VH CDR1
<220> FEATURE:
<221> NAME/KEY: VARIANT
<222> LOCATION: 4
<223> OTHER INFORMATION: Xaa = Any Amino Acid

<400> SEQUENCE: 123

Asp Tyr Tyr Xaa Asn
1               5

<210> SEQ ID NO 124
<211> LENGTH: 5
<212> TYPE: PRT
<213> ORGANISM: Artificial Sequence
<220> FEATURE:
<223> OTHER INFORMATION: VH CDR1
<220> FEATURE:
<221> NAME/KEY: VARIANT
<222> LOCATION: 5
<223> OTHER INFORMATION: Xaa = Any Amino Acid

<400> SEQUENCE: 124

Asp Tyr Tyr Ile Xaa
1               5

<210> SEQ ID NO 125
<211> LENGTH: 5
<212> TYPE: PRT
<213> ORGANISM: Artificial Sequence
<220> FEATURE:
<223> OTHER INFORMATION: VH CDR1

<400> SEQUENCE: 125

Thr Asp Tyr Tyr Ile
1               5
```

```
<210> SEQ ID NO 126
<211> LENGTH: 5
<212> TYPE: PRT
<213> ORGANISM: Artificial Sequence
<220> FEATURE:
<223> OTHER INFORMATION: VH CDR1

<400> SEQUENCE: 126

Phe Thr Asp Tyr Tyr
1               5

<210> SEQ ID NO 127
<211> LENGTH: 5
<212> TYPE: PRT
<213> ORGANISM: Artificial Sequence
<220> FEATURE:
<223> OTHER INFORMATION: VH CDR1

<400> SEQUENCE: 127

Thr Phe Thr Asp Tyr
1               5

<210> SEQ ID NO 128
<211> LENGTH: 5
<212> TYPE: PRT
<213> ORGANISM: Artificial Sequence
<220> FEATURE:
<223> OTHER INFORMATION: VH CDR1

<400> SEQUENCE: 128

Tyr Tyr Ile Asn Trp
1               5

<210> SEQ ID NO 129
<211> LENGTH: 6
<212> TYPE: PRT
<213> ORGANISM: Artificial Sequence
<220> FEATURE:
<223> OTHER INFORMATION: VH CDR1

<400> SEQUENCE: 129

Tyr Tyr Ile Asn Trp Val
1               5

<210> SEQ ID NO 130
<211> LENGTH: 5
<212> TYPE: PRT
<213> ORGANISM: Artificial Sequence
<220> FEATURE:
<223> OTHER INFORMATION: VH CDR1

<400> SEQUENCE: 130

Ile Asn Trp Val Arg
1               5

<210> SEQ ID NO 131
<211> LENGTH: 17
<212> TYPE: PRT
<213> ORGANISM: Artificial Sequence
<220> FEATURE:
<223> OTHER INFORMATION: VH CDR2
<220> FEATURE:
<221> NAME/KEY: VARIANT
<222> LOCATION: 1
<223> OTHER INFORMATION: Xaa = Any Amino Acid

<400> SEQUENCE: 131
```

```
Xaa Ile Tyr Pro Gly Ser Gly Asn Thr Tyr Tyr Asn Glu Lys Phe Lys
1               5                   10                  15

Gly

<210> SEQ ID NO 132
<211> LENGTH: 17
<212> TYPE: PRT
<213> ORGANISM: Artificial Sequence
<220> FEATURE:
<223> OTHER INFORMATION: VH CDR2
<220> FEATURE:
<221> NAME/KEY: VARIANT
<222> LOCATION: 2
<223> OTHER INFORMATION: Xaa = Any Amino Acid

<400> SEQUENCE: 132

Arg Xaa Tyr Pro Gly Ser Gly Asn Thr Tyr Tyr Asn Glu Lys Phe Lys
1               5                   10                  15

Gly

<210> SEQ ID NO 133
<211> LENGTH: 17
<212> TYPE: PRT
<213> ORGANISM: Artificial Sequence
<220> FEATURE:
<223> OTHER INFORMATION: VH CDR2
<220> FEATURE:
<221> NAME/KEY: VARIANT
<222> LOCATION: 3
<223> OTHER INFORMATION: Xaa = Any Amino Acid

<400> SEQUENCE: 133

Arg Ile Xaa Pro Gly Ser Gly Asn Thr Tyr Tyr Asn Glu Lys Phe Lys
1               5                   10                  15

Gly

<210> SEQ ID NO 134
<211> LENGTH: 17
<212> TYPE: PRT
<213> ORGANISM: Artificial Sequence
<220> FEATURE:
<223> OTHER INFORMATION: VH CDR2
<220> FEATURE:
<221> NAME/KEY: VARIANT
<222> LOCATION: 4
<223> OTHER INFORMATION: Xaa = Any Amino Acid

<400> SEQUENCE: 134

Arg Ile Tyr Xaa Gly Ser Gly Asn Thr Tyr Tyr Asn Glu Lys Phe Lys
1               5                   10                  15

Gly

<210> SEQ ID NO 135
<211> LENGTH: 17
<212> TYPE: PRT
<213> ORGANISM: Artificial Sequence
<220> FEATURE:
<223> OTHER INFORMATION: VH CDR2
<220> FEATURE:
<221> NAME/KEY: VARIANT
<222> LOCATION: 5
<223> OTHER INFORMATION: Xaa = Any Amino Acid

<400> SEQUENCE: 135

Arg Ile Tyr Pro Xaa Ser Gly Asn Thr Tyr Tyr Asn Glu Lys Phe Lys
1               5                   10                  15
```

Gly

```
<210> SEQ ID NO 136
<211> LENGTH: 17
<212> TYPE: PRT
<213> ORGANISM: Artificial Sequence
<220> FEATURE:
<223> OTHER INFORMATION: VH CDR2
<220> FEATURE:
<221> NAME/KEY: VARIANT
<222> LOCATION: 6
<223> OTHER INFORMATION: Xaa = Any Amino Acid

<400> SEQUENCE: 136
```

Arg Ile Tyr Pro Gly Xaa Gly Asn Thr Tyr Tyr Asn Glu Lys Phe Lys
1               5                   10                  15

Gly

```
<210> SEQ ID NO 137
<211> LENGTH: 17
<212> TYPE: PRT
<213> ORGANISM: Artificial Sequence
<220> FEATURE:
<223> OTHER INFORMATION: VH CDR2
<220> FEATURE:
<221> NAME/KEY: VARIANT
<222> LOCATION: 7
<223> OTHER INFORMATION: Xaa = Any Amino Acid

<400> SEQUENCE: 137
```

Arg Ile Tyr Pro Gly Ser Xaa Asn Thr Tyr Tyr Asn Glu Lys Phe Lys
1               5                   10                  15

Gly

```
<210> SEQ ID NO 138
<211> LENGTH: 17
<212> TYPE: PRT
<213> ORGANISM: Artificial Sequence
<220> FEATURE:
<223> OTHER INFORMATION: VH CDR2
<220> FEATURE:
<221> NAME/KEY: VARIANT
<222> LOCATION: 8
<223> OTHER INFORMATION: Xaa = Any Amino Acid

<400> SEQUENCE: 138
```

Arg Ile Tyr Pro Gly Ser Gly Xaa Thr Tyr Tyr Asn Glu Lys Phe Lys
1               5                   10                  15

Gly

```
<210> SEQ ID NO 139
<211> LENGTH: 17
<212> TYPE: PRT
<213> ORGANISM: Artificial Sequence
<220> FEATURE:
<223> OTHER INFORMATION: VH CDR2
<220> FEATURE:
<221> NAME/KEY: VARIANT
<222> LOCATION: 9
<223> OTHER INFORMATION: Xaa = Any Amino Acid

<400> SEQUENCE: 139
```

Arg Ile Tyr Pro Gly Ser Gly Asn Xaa Tyr Tyr Asn Glu Lys Phe Lys
1               5                   10                  15

Gly

```
<210> SEQ ID NO 140
<211> LENGTH: 17
<212> TYPE: PRT
<213> ORGANISM: Artificial Sequence
<220> FEATURE:
<223> OTHER INFORMATION: VH CDR2
<220> FEATURE:
<221> NAME/KEY: VARIANT
<222> LOCATION: 10
<223> OTHER INFORMATION: Xaa = Any Amino Acid

<400> SEQUENCE: 140

Arg Ile Tyr Pro Gly Ser Gly Asn Thr Xaa Tyr Asn Glu Lys Phe Lys
1               5                   10                  15

Gly

<210> SEQ ID NO 141
<211> LENGTH: 17
<212> TYPE: PRT
<213> ORGANISM: Artificial Sequence
<220> FEATURE:
<223> OTHER INFORMATION: VH CDR2
<220> FEATURE:
<221> NAME/KEY: VARIANT
<222> LOCATION: 11
<223> OTHER INFORMATION: Xaa = Any Amino Acid

<400> SEQUENCE: 141

Arg Ile Tyr Pro Gly Ser Gly Asn Thr Tyr Xaa Asn Glu Lys Phe Lys
1               5                   10                  15

Gly

<210> SEQ ID NO 142
<211> LENGTH: 17
<212> TYPE: PRT
<213> ORGANISM: Artificial Sequence
<220> FEATURE:
<223> OTHER INFORMATION: VH CDR2
<220> FEATURE:
<221> NAME/KEY: VARIANT
<222> LOCATION: 12
<223> OTHER INFORMATION: Xaa = Any Amino Acid

<400> SEQUENCE: 142

Arg Ile Tyr Pro Gly Ser Gly Asn Thr Tyr Tyr Xaa Glu Lys Phe Lys
1               5                   10                  15

Gly

<210> SEQ ID NO 143
<211> LENGTH: 17
<212> TYPE: PRT
<213> ORGANISM: Artificial Sequence
<220> FEATURE:
<223> OTHER INFORMATION: VH CDR2
<220> FEATURE:
<221> NAME/KEY: VARIANT
<222> LOCATION: 13
<223> OTHER INFORMATION: Xaa = Any Amino Acid

<400> SEQUENCE: 143

Arg Ile Tyr Pro Gly Ser Gly Asn Thr Tyr Tyr Asn Xaa Lys Phe Lys
1               5                   10                  15

Gly

<210> SEQ ID NO 144
<211> LENGTH: 17
<212> TYPE: PRT
```

```
<213> ORGANISM: Artificial Sequence
<220> FEATURE:
<223> OTHER INFORMATION: VH CDR2
<220> FEATURE:
<221> NAME/KEY: VARIANT
<222> LOCATION: 14
<223> OTHER INFORMATION: Xaa = Any Amino Acid

<400> SEQUENCE: 144

Arg Ile Tyr Pro Gly Ser Gly Asn Thr Tyr Tyr Asn Glu Xaa Phe Lys
1               5                   10                  15
Gly

<210> SEQ ID NO 145
<211> LENGTH: 17
<212> TYPE: PRT
<213> ORGANISM: Artificial Sequence
<220> FEATURE:
<223> OTHER INFORMATION: VH CDR2
<220> FEATURE:
<221> NAME/KEY: VARIANT
<222> LOCATION: 15
<223> OTHER INFORMATION: Xaa = Any Amino Acid

<400> SEQUENCE: 145

Arg Ile Tyr Pro Gly Ser Gly Asn Thr Tyr Tyr Asn Glu Lys Xaa Lys
1               5                   10                  15
Gly

<210> SEQ ID NO 146
<211> LENGTH: 17
<212> TYPE: PRT
<213> ORGANISM: Artificial Sequence
<220> FEATURE:
<223> OTHER INFORMATION: VH CDR2
<220> FEATURE:
<221> NAME/KEY: VARIANT
<222> LOCATION: 16
<223> OTHER INFORMATION: Xaa = Any Amino Acid

<400> SEQUENCE: 146

Arg Ile Tyr Pro Gly Ser Gly Asn Thr Tyr Tyr Asn Glu Lys Phe Xaa
1               5                   10                  15
Gly

<210> SEQ ID NO 147
<211> LENGTH: 17
<212> TYPE: PRT
<213> ORGANISM: Artificial Sequence
<220> FEATURE:
<223> OTHER INFORMATION: VH CDR2
<220> FEATURE:
<221> NAME/KEY: VARIANT
<222> LOCATION: 17
<223> OTHER INFORMATION: Xaa = Any Amino Acid

<400> SEQUENCE: 147

Arg Ile Tyr Pro Gly Ser Gly Asn Thr Tyr Tyr Asn Glu Lys Phe Lys
1               5                   10                  15
Xaa

<210> SEQ ID NO 148
<211> LENGTH: 16
<212> TYPE: PRT
<213> ORGANISM: Artificial Sequence
<220> FEATURE:
<223> OTHER INFORMATION: VH CDR2
```

<400> SEQUENCE: 148

Ala Arg Ile Tyr Pro Gly Ser Gly Asn Thr Tyr Tyr Asn Glu Lys Phe
1               5                   10                  15

<210> SEQ ID NO 149
<211> LENGTH: 16
<212> TYPE: PRT
<213> ORGANISM: Artificial Sequence
<220> FEATURE:
<223> OTHER INFORMATION: VH CDR2

<400> SEQUENCE: 149

Ile Ala Arg Ile Tyr Pro Gly Ser Gly Asn Thr Tyr Tyr Asn Glu Lys
1               5                   10                  15

<210> SEQ ID NO 150
<211> LENGTH: 16
<212> TYPE: PRT
<213> ORGANISM: Artificial Sequence
<220> FEATURE:
<223> OTHER INFORMATION: VH CDR2

<400> SEQUENCE: 150

Trp Ile Ala Arg Ile Tyr Pro Gly Ser Gly Asn Thr Tyr Tyr Asn Glu
1               5                   10                  15

<210> SEQ ID NO 151
<211> LENGTH: 17
<212> TYPE: PRT
<213> ORGANISM: Artificial Sequence
<220> FEATURE:
<223> OTHER INFORMATION: VH CDR2

<400> SEQUENCE: 151

Ile Tyr Pro Gly Ser Gly Asn Thr Tyr Tyr Asn Glu Lys Phe Lys Gly
1               5                   10                  15

Arg

<210> SEQ ID NO 152
<211> LENGTH: 17
<212> TYPE: PRT
<213> ORGANISM: Artificial Sequence
<220> FEATURE:
<223> OTHER INFORMATION: VH CDR2

<400> SEQUENCE: 152

Tyr Pro Gly Ser Gly Asn Thr Tyr Tyr Asn Glu Lys Phe Lys Gly Arg
1               5                   10                  15

Ala

<210> SEQ ID NO 153
<211> LENGTH: 17
<212> TYPE: PRT
<213> ORGANISM: Artificial Sequence
<220> FEATURE:
<223> OTHER INFORMATION: VH CDR2

<400> SEQUENCE: 153

Pro Gly Ser Gly Asn Thr Tyr Tyr Asn Glu Lys Phe Lys Gly Arg Ala
1               5                   10                  15

Thr

<210> SEQ ID NO 154

```
<211> LENGTH: 7
<212> TYPE: PRT
<213> ORGANISM: Artificial Sequence
<220> FEATURE:
<223> OTHER INFORMATION: VH CDR3
<220> FEATURE:
<221> NAME/KEY: VARIANT
<222> LOCATION: 1
<223> OTHER INFORMATION: Xaa = Any Amino Acid

<400> SEQUENCE: 154

Xaa Val Tyr Tyr Phe Asp Tyr
1               5

<210> SEQ ID NO 155
<211> LENGTH: 7
<212> TYPE: PRT
<213> ORGANISM: Artificial Sequence
<220> FEATURE:
<223> OTHER INFORMATION: VH CDR3
<220> FEATURE:
<221> NAME/KEY: VARIANT
<222> LOCATION: 2
<223> OTHER INFORMATION: Xaa = Any Amino Acid

<400> SEQUENCE: 155

Gly Xaa Tyr Tyr Phe Asp Tyr
1               5

<210> SEQ ID NO 156
<211> LENGTH: 7
<212> TYPE: PRT
<213> ORGANISM: Artificial Sequence
<220> FEATURE:
<223> OTHER INFORMATION: VH CDR3
<220> FEATURE:
<221> NAME/KEY: VARIANT
<222> LOCATION: 3
<223> OTHER INFORMATION: Xaa = Any Amino Acid

<400> SEQUENCE: 156

Gly Val Xaa Tyr Phe Asp Tyr
1               5

<210> SEQ ID NO 157
<211> LENGTH: 7
<212> TYPE: PRT
<213> ORGANISM: Artificial Sequence
<220> FEATURE:
<223> OTHER INFORMATION: VH CDR3
<220> FEATURE:
<221> NAME/KEY: VARIANT
<222> LOCATION: 4
<223> OTHER INFORMATION: Xaa = Any Amino Acid

<400> SEQUENCE: 157

Gly Val Tyr Xaa Phe Asp Tyr
1               5

<210> SEQ ID NO 158
<211> LENGTH: 7
<212> TYPE: PRT
<213> ORGANISM: Artificial Sequence
<220> FEATURE:
<223> OTHER INFORMATION: VH CDR3
<220> FEATURE:
<221> NAME/KEY: VARIANT
<222> LOCATION: 5
<223> OTHER INFORMATION: Xaa = Any Amino Acid

<400> SEQUENCE: 158
```

```
Gly Val Tyr Tyr Xaa Asp Tyr
1               5
```

<210> SEQ ID NO 159
<211> LENGTH: 7
<212> TYPE: PRT
<213> ORGANISM: Artificial Sequence
<220> FEATURE:
<223> OTHER INFORMATION: VH CDR3
<220> FEATURE:
<221> NAME/KEY: VARIANT
<222> LOCATION: 6
<223> OTHER INFORMATION: Xaa = Any Amino Acid

<400> SEQUENCE: 159

```
Gly Val Tyr Tyr Phe Xaa Tyr
1               5
```

<210> SEQ ID NO 160
<211> LENGTH: 7
<212> TYPE: PRT
<213> ORGANISM: Artificial Sequence
<220> FEATURE:
<223> OTHER INFORMATION: VH CDR3
<220> FEATURE:
<221> NAME/KEY: VARIANT
<222> LOCATION: 7
<223> OTHER INFORMATION: Xaa = Any Amino Acid

<400> SEQUENCE: 160

```
Gly Val Tyr Tyr Phe Asp Xaa
1               5
```

<210> SEQ ID NO 161
<211> LENGTH: 7
<212> TYPE: PRT
<213> ORGANISM: Artificial Sequence
<220> FEATURE:
<223> OTHER INFORMATION: VH CDR3

<400> SEQUENCE: 161

```
Arg Gly Val Tyr Tyr Phe Asp
1               5
```

<210> SEQ ID NO 162
<211> LENGTH: 7
<212> TYPE: PRT
<213> ORGANISM: Artificial Sequence
<220> FEATURE:
<223> OTHER INFORMATION: VH CDR3

<400> SEQUENCE: 162

```
Ala Arg Gly Val Tyr Tyr Phe
1               5
```

<210> SEQ ID NO 163
<211> LENGTH: 7
<212> TYPE: PRT
<213> ORGANISM: Artificial Sequence
<220> FEATURE:
<223> OTHER INFORMATION: VH CDR3

<400> SEQUENCE: 163

```
Cys Ala Arg Gly Val Tyr Tyr
1               5
```

<210> SEQ ID NO 164

```
<211> LENGTH: 8
<212> TYPE: PRT
<213> ORGANISM: Artificial Sequence
<220> FEATURE:
<223> OTHER INFORMATION: VH CDR3

<400> SEQUENCE: 164

Gly Val Tyr Tyr Phe Asp Tyr Trp
1               5

<210> SEQ ID NO 165
<211> LENGTH: 8
<212> TYPE: PRT
<213> ORGANISM: Artificial Sequence
<220> FEATURE:
<223> OTHER INFORMATION: VH CDR3

<400> SEQUENCE: 165

Val Tyr Tyr Phe Asp Tyr Trp Gly
1               5

<210> SEQ ID NO 166
<211> LENGTH: 8
<212> TYPE: PRT
<213> ORGANISM: Artificial Sequence
<220> FEATURE:
<223> OTHER INFORMATION: VH CDR3

<400> SEQUENCE: 166

Tyr Tyr Phe Asp Tyr Trp Gly Gln
1               5

<210> SEQ ID NO 167
<211> LENGTH: 30
<212> TYPE: PRT
<213> ORGANISM: Artificial Sequence
<220> FEATURE:
<223> OTHER INFORMATION: VH FR1
<220> FEATURE:
<221> NAME/KEY: VARIANT
<222> LOCATION: 1
<223> OTHER INFORMATION: Xaa = Any Amino Acid
<220> FEATURE:
<221> NAME/KEY: VARIANT
<222> LOCATION: 11, 20
<223> OTHER INFORMATION: Xaa = Leu or Val

<400> SEQUENCE: 167

Xaa Val Gln Leu Val Gln Ser Gly Ala Glu Xaa Lys Lys Pro Gly Ala
1               5                   10                  15

Ser Val Lys Xaa Ser Cys Lys Ala Ser Gly Tyr Thr Phe Thr
            20                  25                  30

<210> SEQ ID NO 168
<211> LENGTH: 30
<212> TYPE: PRT
<213> ORGANISM: Artificial Sequence
<220> FEATURE:
<223> OTHER INFORMATION: VH FR1
<220> FEATURE:
<221> NAME/KEY: VARIANT
<222> LOCATION: 2
<223> OTHER INFORMATION: Xaa = Any Amino Acid
<220> FEATURE:
<221> NAME/KEY: VARIANT
<222> LOCATION: 11, 20
<223> OTHER INFORMATION: Xaa = Leu or Val

<400> SEQUENCE: 168
```

```
Gln Xaa Gln Leu Val Gln Ser Gly Ala Glu Xaa Lys Lys Pro Gly Ala
1               5                   10                  15

Ser Val Lys Xaa Ser Cys Lys Ala Ser Gly Tyr Thr Phe Thr
            20                  25                  30

<210> SEQ ID NO 169
<211> LENGTH: 30
<212> TYPE: PRT
<213> ORGANISM: Artificial Sequence
<220> FEATURE:
<223> OTHER INFORMATION: VH FR1
<220> FEATURE:
<221> NAME/KEY: VARIANT
<222> LOCATION: 3
<223> OTHER INFORMATION: Xaa = Any Amino Acid
<220> FEATURE:
<221> NAME/KEY: VARIANT
<222> LOCATION: 11, 20
<223> OTHER INFORMATION: Xaa = Leu or Val

<400> SEQUENCE: 169

Gln Val Xaa Leu Val Gln Ser Gly Ala Glu Xaa Lys Lys Pro Gly Ala
1               5                   10                  15

Ser Val Lys Xaa Ser Cys Lys Ala Ser Gly Tyr Thr Phe Thr
            20                  25                  30

<210> SEQ ID NO 170
<211> LENGTH: 30
<212> TYPE: PRT
<213> ORGANISM: Artificial Sequence
<220> FEATURE:
<223> OTHER INFORMATION: VH FR1
<220> FEATURE:
<221> NAME/KEY: VARIANT
<222> LOCATION: 4
<223> OTHER INFORMATION: Xaa = Any Amino Acid
<220> FEATURE:
<221> NAME/KEY: VARIANT
<222> LOCATION: 11, 20
<223> OTHER INFORMATION: Xaa = Leu or Val

<400> SEQUENCE: 170

Gln Val Gln Xaa Val Gln Ser Gly Ala Glu Xaa Lys Lys Pro Gly Ala
1               5                   10                  15

Ser Val Lys Xaa Ser Cys Lys Ala Ser Gly Tyr Thr Phe Thr
            20                  25                  30

<210> SEQ ID NO 171
<211> LENGTH: 30
<212> TYPE: PRT
<213> ORGANISM: Artificial Sequence
<220> FEATURE:
<223> OTHER INFORMATION: VH FR1
<220> FEATURE:
<221> NAME/KEY: VARIANT
<222> LOCATION: 5
<223> OTHER INFORMATION: Xaa = Any Amino Acid
<220> FEATURE:
<221> NAME/KEY: VARIANT
<222> LOCATION: 11, 20
<223> OTHER INFORMATION: Xaa = Leu or Val

<400> SEQUENCE: 171

Gln Val Gln Leu Xaa Gln Ser Gly Ala Glu Xaa Lys Lys Pro Gly Ala
1               5                   10                  15

Ser Val Lys Xaa Ser Cys Lys Ala Ser Gly Tyr Thr Phe Thr
            20                  25                  30
```

```
<210> SEQ ID NO 172
<211> LENGTH: 30
<212> TYPE: PRT
<213> ORGANISM: Artificial Sequence
<220> FEATURE:
<223> OTHER INFORMATION: VH FR1
<220> FEATURE:
<221> NAME/KEY: VARIANT
<222> LOCATION: 6
<223> OTHER INFORMATION: Xaa = Any Amino Acid
<220> FEATURE:
<221> NAME/KEY: VARIANT
<222> LOCATION: 11, 20
<223> OTHER INFORMATION: Xaa = Leu or Val

<400> SEQUENCE: 172

Gln Val Gln Leu Val Xaa Ser Gly Ala Glu Xaa Lys Lys Pro Gly Ala
1               5                   10                  15

Ser Val Lys Xaa Ser Cys Lys Ala Ser Gly Tyr Thr Phe Thr
            20                  25                  30

<210> SEQ ID NO 173
<211> LENGTH: 30
<212> TYPE: PRT
<213> ORGANISM: Artificial Sequence
<220> FEATURE:
<223> OTHER INFORMATION: VH FR1
<220> FEATURE:
<221> NAME/KEY: VARIANT
<222> LOCATION: 7
<223> OTHER INFORMATION: Xaa = Any Amino Acid
<220> FEATURE:
<221> NAME/KEY: VARIANT
<222> LOCATION: 11, 20
<223> OTHER INFORMATION: Xaa = Leu or Val

<400> SEQUENCE: 173

Gln Val Gln Leu Val Gln Xaa Gly Ala Glu Xaa Lys Lys Pro Gly Ala
1               5                   10                  15

Ser Val Lys Xaa Ser Cys Lys Ala Ser Gly Tyr Thr Phe Thr
            20                  25                  30

<210> SEQ ID NO 174
<211> LENGTH: 30
<212> TYPE: PRT
<213> ORGANISM: Artificial Sequence
<220> FEATURE:
<223> OTHER INFORMATION: VH FR1
<220> FEATURE:
<221> NAME/KEY: VARIANT
<222> LOCATION: 8
<223> OTHER INFORMATION: Xaa = Any Amino Acid
<220> FEATURE:
<221> NAME/KEY: VARIANT
<222> LOCATION: 11, 20
<223> OTHER INFORMATION: Xaa = Leu or Val

<400> SEQUENCE: 174

Gln Val Gln Leu Val Gln Ser Xaa Ala Glu Xaa Lys Lys Pro Gly Ala
1               5                   10                  15

Ser Val Lys Xaa Ser Cys Lys Ala Ser Gly Tyr Thr Phe Thr
            20                  25                  30

<210> SEQ ID NO 175
<211> LENGTH: 30
<212> TYPE: PRT
<213> ORGANISM: Artificial Sequence
<220> FEATURE:
<223> OTHER INFORMATION: VH FR1
<220> FEATURE:
```

```
<221> NAME/KEY: VARIANT
<222> LOCATION: 9
<223> OTHER INFORMATION: Xaa = Any Amino Acid
<220> FEATURE:
<221> NAME/KEY: VARIANT
<222> LOCATION: 11, 20
<223> OTHER INFORMATION: Xaa = Leu or Val

<400> SEQUENCE: 175

Gln Val Gln Leu Val Gln Ser Gly Xaa Glu Xaa Lys Lys Pro Gly Ala
1               5                   10                  15

Ser Val Lys Xaa Ser Cys Lys Ala Ser Gly Tyr Thr Phe Thr
            20                  25                  30

<210> SEQ ID NO 176
<211> LENGTH: 30
<212> TYPE: PRT
<213> ORGANISM: Artificial Sequence
<220> FEATURE:
<223> OTHER INFORMATION: VH FR1
<220> FEATURE:
<221> NAME/KEY: VARIANT
<222> LOCATION: 10
<223> OTHER INFORMATION: Xaa = Any Amino Acid
<220> FEATURE:
<221> NAME/KEY: VARIANT
<222> LOCATION: 11, 20
<223> OTHER INFORMATION: Xaa = Leu or Val

<400> SEQUENCE: 176

Gln Val Gln Leu Val Gln Ser Gly Ala Xaa Xaa Lys Lys Pro Gly Ala
1               5                   10                  15

Ser Val Lys Xaa Ser Cys Lys Ala Ser Gly Tyr Thr Phe Thr
            20                  25                  30

<210> SEQ ID NO 177
<211> LENGTH: 30
<212> TYPE: PRT
<213> ORGANISM: Artificial Sequence
<220> FEATURE:
<223> OTHER INFORMATION: VH FR1
<220> FEATURE:
<221> NAME/KEY: VARIANT
<222> LOCATION: 11
<223> OTHER INFORMATION: Xaa = Any Amino Acid
<220> FEATURE:
<221> NAME/KEY: VARIANT
<222> LOCATION: 20
<223> OTHER INFORMATION: Xaa = Leu or Val

<400> SEQUENCE: 177

Gln Val Gln Leu Val Gln Ser Gly Ala Glu Xaa Lys Lys Pro Gly Ala
1               5                   10                  15

Ser Val Lys Xaa Ser Cys Lys Ala Ser Gly Tyr Thr Phe Thr
            20                  25                  30

<210> SEQ ID NO 178
<211> LENGTH: 30
<212> TYPE: PRT
<213> ORGANISM: Artificial Sequence
<220> FEATURE:
<223> OTHER INFORMATION: VH FR1
<220> FEATURE:
<221> NAME/KEY: VARIANT
<222> LOCATION: 12
<223> OTHER INFORMATION: Xaa = Any Amino Acid
<220> FEATURE:
<221> NAME/KEY: VARIANT
<222> LOCATION: 11, 20
<223> OTHER INFORMATION: Xaa = Leu or Val
```

```
<400> SEQUENCE: 178

Gln Val Gln Leu Val Gln Ser Gly Ala Glu Xaa Xaa Lys Pro Gly Ala
1               5                   10                  15

Ser Val Lys Xaa Ser Cys Lys Ala Ser Gly Tyr Thr Phe Thr
            20                  25                  30

<210> SEQ ID NO 179
<211> LENGTH: 30
<212> TYPE: PRT
<213> ORGANISM: Artificial Sequence
<220> FEATURE:
<223> OTHER INFORMATION: VH FR1
<220> FEATURE:
<221> NAME/KEY: VARIANT
<222> LOCATION: 13
<223> OTHER INFORMATION: Xaa = Any Amino Acid
<220> FEATURE:
<221> NAME/KEY: VARIANT
<222> LOCATION: 11, 20
<223> OTHER INFORMATION: Xaa = Leu or Val

<400> SEQUENCE: 179

Gln Val Gln Leu Val Gln Ser Gly Ala Glu Xaa Lys Xaa Pro Gly Ala
1               5                   10                  15

Ser Val Lys Xaa Ser Cys Lys Ala Ser Gly Tyr Thr Phe Thr
            20                  25                  30

<210> SEQ ID NO 180
<211> LENGTH: 30
<212> TYPE: PRT
<213> ORGANISM: Artificial Sequence
<220> FEATURE:
<223> OTHER INFORMATION: VH FR1
<220> FEATURE:
<221> NAME/KEY: VARIANT
<222> LOCATION: 14
<223> OTHER INFORMATION: Xaa = Any Amino Acid
<220> FEATURE:
<221> NAME/KEY: VARIANT
<222> LOCATION: 11, 20
<223> OTHER INFORMATION: Xaa = Leu or Val

<400> SEQUENCE: 180

Gln Val Gln Leu Val Gln Ser Gly Ala Glu Xaa Lys Lys Xaa Gly Ala
1               5                   10                  15

Ser Val Lys Xaa Ser Cys Lys Ala Ser Gly Tyr Thr Phe Thr
            20                  25                  30

<210> SEQ ID NO 181
<211> LENGTH: 30
<212> TYPE: PRT
<213> ORGANISM: Artificial Sequence
<220> FEATURE:
<223> OTHER INFORMATION: VH FR1
<220> FEATURE:
<221> NAME/KEY: VARIANT
<222> LOCATION: 15
<223> OTHER INFORMATION: Xaa = Any Amino Acid
<220> FEATURE:
<221> NAME/KEY: VARIANT
<222> LOCATION: 11, 20
<223> OTHER INFORMATION: Xaa = Leu or Val

<400> SEQUENCE: 181

Gln Val Gln Leu Val Gln Ser Gly Ala Glu Xaa Lys Lys Pro Xaa Ala
1               5                   10                  15

Ser Val Lys Xaa Ser Cys Lys Ala Ser Gly Tyr Thr Phe Thr
```

20                  25                  30

<210> SEQ ID NO 182
<211> LENGTH: 30
<212> TYPE: PRT
<213> ORGANISM: Artificial Sequence
<220> FEATURE:
<223> OTHER INFORMATION: VH FR1
<220> FEATURE:
<221> NAME/KEY: VARIANT
<222> LOCATION: 16
<223> OTHER INFORMATION: Xaa = Any Amino Acid
<220> FEATURE:
<221> NAME/KEY: VARIANT
<222> LOCATION: 11, 20
<223> OTHER INFORMATION: Xaa = Leu or Val

<400> SEQUENCE: 182

Gln Val Gln Leu Val Gln Ser Gly Ala Glu Xaa Lys Lys Pro Gly Xaa
1               5                   10                  15

Ser Val Lys Xaa Ser Cys Lys Ala Ser Gly Tyr Thr Phe Thr
            20                  25                  30

<210> SEQ ID NO 183
<211> LENGTH: 30
<212> TYPE: PRT
<213> ORGANISM: Artificial Sequence
<220> FEATURE:
<223> OTHER INFORMATION: VH FR1
<220> FEATURE:
<221> NAME/KEY: VARIANT
<222> LOCATION: 17
<223> OTHER INFORMATION: Xaa = Any Amino Acid
<220> FEATURE:
<221> NAME/KEY: VARIANT
<222> LOCATION: 11, 20
<223> OTHER INFORMATION: Xaa = Leu or Val

<400> SEQUENCE: 183

Gln Val Gln Leu Val Gln Ser Gly Ala Glu Xaa Lys Lys Pro Gly Ala
1               5                   10                  15

Xaa Val Lys Xaa Ser Cys Lys Ala Ser Gly Tyr Thr Phe Thr
            20                  25                  30

<210> SEQ ID NO 184
<211> LENGTH: 30
<212> TYPE: PRT
<213> ORGANISM: Artificial Sequence
<220> FEATURE:
<223> OTHER INFORMATION: VH FR1
<220> FEATURE:
<221> NAME/KEY: VARIANT
<222> LOCATION: 18
<223> OTHER INFORMATION: Xaa = Any Amino Acid
<220> FEATURE:
<221> NAME/KEY: VARIANT
<222> LOCATION: 11, 20
<223> OTHER INFORMATION: Xaa = Leu or Val

<400> SEQUENCE: 184

Gln Val Gln Leu Val Gln Ser Gly Ala Glu Xaa Lys Lys Pro Gly Ala
1               5                   10                  15

Ser Xaa Lys Xaa Ser Cys Lys Ala Ser Gly Tyr Thr Phe Thr
            20                  25                  30

<210> SEQ ID NO 185
<211> LENGTH: 30
<212> TYPE: PRT
<213> ORGANISM: Artificial Sequence

```
<220> FEATURE:
<223> OTHER INFORMATION: VH FR1
<220> FEATURE:
<221> NAME/KEY: VARIANT
<222> LOCATION: 19
<223> OTHER INFORMATION: Xaa = Any Amino Acid
<220> FEATURE:
<221> NAME/KEY: VARIANT
<222> LOCATION: 11, 20
<223> OTHER INFORMATION: Xaa = Leu or Val

<400> SEQUENCE: 185

Gln Val Gln Leu Val Gln Ser Gly Ala Glu Xaa Lys Lys Pro Gly Ala
1               5                   10                  15

Ser Val Xaa Xaa Ser Cys Lys Ala Ser Gly Tyr Thr Phe Thr
            20                  25                  30

<210> SEQ ID NO 186
<211> LENGTH: 30
<212> TYPE: PRT
<213> ORGANISM: Artificial Sequence
<220> FEATURE:
<223> OTHER INFORMATION: VH FR1
<220> FEATURE:
<221> NAME/KEY: VARIANT
<222> LOCATION: 11
<223> OTHER INFORMATION: Xaa = Leu or Val
<220> FEATURE:
<221> NAME/KEY: VARIANT
<222> LOCATION: 20
<223> OTHER INFORMATION: Xaa = Any Amino Acid

<400> SEQUENCE: 186

Gln Val Gln Leu Val Gln Ser Gly Ala Glu Xaa Lys Lys Pro Gly Ala
1               5                   10                  15

Ser Val Lys Xaa Ser Cys Lys Ala Ser Gly Tyr Thr Phe Thr
            20                  25                  30

<210> SEQ ID NO 187
<211> LENGTH: 30
<212> TYPE: PRT
<213> ORGANISM: Artificial Sequence
<220> FEATURE:
<223> OTHER INFORMATION: VH FR1
<220> FEATURE:
<221> NAME/KEY: VARIANT
<222> LOCATION: 11, 20
<223> OTHER INFORMATION: Xaa = Leu or Val
<220> FEATURE:
<221> NAME/KEY: VARIANT
<222> LOCATION: 21
<223> OTHER INFORMATION: Xaa = Any Amino Acid

<400> SEQUENCE: 187

Gln Val Gln Leu Val Gln Ser Gly Ala Glu Xaa Lys Lys Pro Gly Ala
1               5                   10                  15

Ser Val Lys Xaa Xaa Cys Lys Ala Ser Gly Tyr Thr Phe Thr
            20                  25                  30

<210> SEQ ID NO 188
<211> LENGTH: 30
<212> TYPE: PRT
<213> ORGANISM: Artificial Sequence
<220> FEATURE:
<223> OTHER INFORMATION: VH FR1
<220> FEATURE:
<221> NAME/KEY: VARIANT
<222> LOCATION: 11, 20
<223> OTHER INFORMATION: Xaa = Leu or Val
<220> FEATURE:
```

-continued

```
<221> NAME/KEY: VARIANT
<222> LOCATION: 22
<223> OTHER INFORMATION: Xaa = Any Amino Acid

<400> SEQUENCE: 188

Gln Val Gln Leu Val Gln Ser Gly Ala Glu Xaa Lys Lys Pro Gly Ala
1               5                   10                  15

Ser Val Lys Xaa Ser Xaa Lys Ala Ser Gly Tyr Thr Phe Thr
            20                  25                  30

<210> SEQ ID NO 189
<211> LENGTH: 30
<212> TYPE: PRT
<213> ORGANISM: Artificial Sequence
<220> FEATURE:
<223> OTHER INFORMATION: VH FR1
<220> FEATURE:
<221> NAME/KEY: VARIANT
<222> LOCATION: 11, 20
<223> OTHER INFORMATION: Xaa = Any Amino Acid
<220> FEATURE:
<221> NAME/KEY: VARIANT
<222> LOCATION: 23
<223> OTHER INFORMATION: Xaa = Any Amino Acid

<400> SEQUENCE: 189

Gln Val Gln Leu Val Gln Ser Gly Ala Glu Xaa Lys Lys Pro Gly Ala
1               5                   10                  15

Ser Val Lys Xaa Ser Cys Xaa Ala Ser Gly Tyr Thr Phe Thr
            20                  25                  30

<210> SEQ ID NO 190
<211> LENGTH: 30
<212> TYPE: PRT
<213> ORGANISM: Artificial Sequence
<220> FEATURE:
<223> OTHER INFORMATION: VH FR1
<220> FEATURE:
<221> NAME/KEY: VARIANT
<222> LOCATION: 11, 20
<223> OTHER INFORMATION: Xaa = Leu or Val
<220> FEATURE:
<221> NAME/KEY: VARIANT
<222> LOCATION: 24
<223> OTHER INFORMATION: Xaa = Any Amino Acid

<400> SEQUENCE: 190

Gln Val Gln Leu Val Gln Ser Gly Ala Glu Xaa Lys Lys Pro Gly Ala
1               5                   10                  15

Ser Val Lys Xaa Ser Cys Lys Xaa Ser Gly Tyr Thr Phe Thr
            20                  25                  30

<210> SEQ ID NO 191
<211> LENGTH: 30
<212> TYPE: PRT
<213> ORGANISM: Artificial Sequence
<220> FEATURE:
<223> OTHER INFORMATION: VH FR1
<220> FEATURE:
<221> NAME/KEY: VARIANT
<222> LOCATION: 11, 20
<223> OTHER INFORMATION: Xaa = Leu or Val
<220> FEATURE:
<221> NAME/KEY: VARIANT
<222> LOCATION: 25
<223> OTHER INFORMATION: Xaa = Any Amino Acid

<400> SEQUENCE: 191

Gln Val Gln Leu Val Gln Ser Gly Ala Glu Xaa Lys Lys Pro Gly Ala
```

```
                        1               5                   10                  15
Ser Val Lys Xaa Ser Cys Lys Ala Xaa Gly Tyr Thr Phe Thr
                        20                  25                  30

<210> SEQ ID NO 192
<211> LENGTH: 30
<212> TYPE: PRT
<213> ORGANISM: Artificial Sequence
<220> FEATURE:
<223> OTHER INFORMATION: VH FR1
<220> FEATURE:
<221> NAME/KEY: VARIANT
<222> LOCATION: 11, 20
<223> OTHER INFORMATION: Xaa = Leu or Val
<220> FEATURE:
<221> NAME/KEY: VARIANT
<222> LOCATION: 26
<223> OTHER INFORMATION: Xaa = Any Amino Acid

<400> SEQUENCE: 192

Gln Val Gln Leu Val Gln Ser Gly Ala Glu Xaa Lys Lys Pro Gly Ala
1               5                   10                  15
Ser Val Lys Xaa Ser Cys Lys Ala Ser Xaa Tyr Thr Phe Thr
                        20                  25                  30

<210> SEQ ID NO 193
<211> LENGTH: 30
<212> TYPE: PRT
<213> ORGANISM: Artificial Sequence
<220> FEATURE:
<223> OTHER INFORMATION: VH FR1
<220> FEATURE:
<221> NAME/KEY: VARIANT
<222> LOCATION: 11, 20
<223> OTHER INFORMATION: Xaa = Leu or Val
<220> FEATURE:
<221> NAME/KEY: VARIANT
<222> LOCATION: 27
<223> OTHER INFORMATION: Xaa = Any Amino Acid

<400> SEQUENCE: 193

Gln Val Gln Leu Val Gln Ser Gly Ala Glu Xaa Lys Lys Pro Gly Ala
1               5                   10                  15
Ser Val Lys Xaa Ser Cys Lys Ala Ser Gly Xaa Thr Phe Thr
                        20                  25                  30

<210> SEQ ID NO 194
<211> LENGTH: 30
<212> TYPE: PRT
<213> ORGANISM: Artificial Sequence
<220> FEATURE:
<223> OTHER INFORMATION: VH FR1
<220> FEATURE:
<221> NAME/KEY: VARIANT
<222> LOCATION: 11, 20
<223> OTHER INFORMATION: Xaa = Leu or Val
<220> FEATURE:
<221> NAME/KEY: VARIANT
<222> LOCATION: 28
<223> OTHER INFORMATION: Xaa = Any Amino Acid

<400> SEQUENCE: 194

Gln Val Gln Leu Val Gln Ser Gly Ala Glu Xaa Lys Lys Pro Gly Ala
1               5                   10                  15
Ser Val Lys Xaa Ser Cys Lys Ala Ser Gly Tyr Xaa Phe Thr
                        20                  25                  30

<210> SEQ ID NO 195
```

```
<211> LENGTH: 30
<212> TYPE: PRT
<213> ORGANISM: Artificial Sequence
<220> FEATURE:
<223> OTHER INFORMATION: VH FR1
<220> FEATURE:
<221> NAME/KEY: VARIANT
<222> LOCATION: 11, 20
<223> OTHER INFORMATION: Xaa = Leu or Val
<220> FEATURE:
<221> NAME/KEY: VARIANT
<222> LOCATION: 29
<223> OTHER INFORMATION: Xaa = Any Amino Acid

<400> SEQUENCE: 195

Gln Val Gln Leu Val Gln Ser Gly Ala Glu Xaa Lys Lys Pro Gly Ala
1               5                   10                  15

Ser Val Lys Xaa Ser Cys Lys Ala Ser Gly Tyr Thr Xaa Thr
            20                  25                  30

<210> SEQ ID NO 196
<211> LENGTH: 30
<212> TYPE: PRT
<213> ORGANISM: Artificial Sequence
<220> FEATURE:
<223> OTHER INFORMATION: VH FR1
<220> FEATURE:
<221> NAME/KEY: VARIANT
<222> LOCATION: 11, 20
<223> OTHER INFORMATION: Xaa = Leu or Val
<220> FEATURE:
<221> NAME/KEY: VARIANT
<222> LOCATION: 30
<223> OTHER INFORMATION: Xaa = Any Amino Acid

<400> SEQUENCE: 196

Gln Val Gln Leu Val Gln Ser Gly Ala Glu Xaa Lys Lys Pro Gly Ala
1               5                   10                  15

Ser Val Lys Xaa Ser Cys Lys Ala Ser Gly Tyr Thr Phe Xaa
            20                  25                  30

<210> SEQ ID NO 197
<211> LENGTH: 14
<212> TYPE: PRT
<213> ORGANISM: Artificial Sequence
<220> FEATURE:
<223> OTHER INFORMATION: VH FR2
<220> FEATURE:
<221> NAME/KEY: VARIANT
<222> LOCATION: 1
<223> OTHER INFORMATION: Xaa = Any Amino Acid
<220> FEATURE:
<221> NAME/KEY: VARIANT
<222> LOCATION: 3
<223> OTHER INFORMATION: Xaa = Arg or Lys

<400> SEQUENCE: 197

Xaa Val Xaa Gln Ala Pro Gly Lys Gly Leu Glu Trp Ile Ala
1               5                   10

<210> SEQ ID NO 198
<211> LENGTH: 14
<212> TYPE: PRT
<213> ORGANISM: Artificial Sequence
<220> FEATURE:
<223> OTHER INFORMATION: VH FR2
<220> FEATURE:
<221> NAME/KEY: VARIANT
<222> LOCATION: 2
<223> OTHER INFORMATION: Xaa = Any Amino Acid
<220> FEATURE:
```

```
<221> NAME/KEY: VARIANT
<222> LOCATION: 3
<223> OTHER INFORMATION: Xaa = Arg or Lys

<400> SEQUENCE: 198

Trp Xaa Xaa Gln Ala Pro Gly Lys Gly Leu Glu Trp Ile Ala
1               5                   10

<210> SEQ ID NO 199
<211> LENGTH: 14
<212> TYPE: PRT
<213> ORGANISM: Artificial Sequence
<220> FEATURE:
<223> OTHER INFORMATION: VH FR2
<220> FEATURE:
<221> NAME/KEY: VARIANT
<222> LOCATION: 3
<223> OTHER INFORMATION: Xaa = Any Amino Acid

<400> SEQUENCE: 199

Trp Val Xaa Gln Ala Pro Gly Lys Gly Leu Glu Trp Ile Ala
1               5                   10

<210> SEQ ID NO 200
<211> LENGTH: 14
<212> TYPE: PRT
<213> ORGANISM: Artificial Sequence
<220> FEATURE:
<223> OTHER INFORMATION: VH FR2
<220> FEATURE:
<221> NAME/KEY: VARIANT
<222> LOCATION: 3
<223> OTHER INFORMATION: Xaa = Arg or Lys
<220> FEATURE:
<221> NAME/KEY: VARIANT
<222> LOCATION: 4
<223> OTHER INFORMATION: Xaa = Any Amino Acid

<400> SEQUENCE: 200

Trp Val Xaa Xaa Ala Pro Gly Lys Gly Leu Glu Trp Ile Ala
1               5                   10

<210> SEQ ID NO 201
<211> LENGTH: 14
<212> TYPE: PRT
<213> ORGANISM: Artificial Sequence
<220> FEATURE:
<223> OTHER INFORMATION: VH FR2
<220> FEATURE:
<221> NAME/KEY: VARIANT
<222> LOCATION: 3
<223> OTHER INFORMATION: Xaa = Arg or Lys
<220> FEATURE:
<221> NAME/KEY: VARIANT
<222> LOCATION: 5
<223> OTHER INFORMATION: Xaa = Any Amino Acid

<400> SEQUENCE: 201

Trp Val Xaa Gln Xaa Pro Gly Lys Gly Leu Glu Trp Ile Ala
1               5                   10

<210> SEQ ID NO 202
<211> LENGTH: 14
<212> TYPE: PRT
<213> ORGANISM: Artificial Sequence
<220> FEATURE:
<223> OTHER INFORMATION: VH FR2
<220> FEATURE:
<220> FEATURE:
<221> NAME/KEY: VARIANT
<222> LOCATION: 3
```

```
<223> OTHER INFORMATION: Xaa = Arg or Lys
<220> FEATURE:
<220> FEATURE:
<221> NAME/KEY: VARIANT
<222> LOCATION: 6
<223> OTHER INFORMATION: Xaa = Any Amino Acid

<400> SEQUENCE: 202

Trp Val Xaa Gln Ala Xaa Gly Lys Gly Leu Glu Trp Ile Ala
1               5                   10

<210> SEQ ID NO 203
<211> LENGTH: 14
<212> TYPE: PRT
<213> ORGANISM: Artificial Sequence
<220> FEATURE:
<223> OTHER INFORMATION: VH FR2
<220> FEATURE:
<221> NAME/KEY: VARIANT
<222> LOCATION: 3
<223> OTHER INFORMATION: Xaa = Arg or Lys
<220> FEATURE:
<221> NAME/KEY: VARIANT
<222> LOCATION: 7
<223> OTHER INFORMATION: Xaa = Any Amino Acid

<400> SEQUENCE: 203

Trp Val Xaa Gln Ala Pro Xaa Lys Gly Leu Glu Trp Ile Ala
1               5                   10

<210> SEQ ID NO 204
<211> LENGTH: 14
<212> TYPE: PRT
<213> ORGANISM: Artificial Sequence
<220> FEATURE:
<223> OTHER INFORMATION: VH FR2
<220> FEATURE:
<221> NAME/KEY: VARIANT
<222> LOCATION: 3
<223> OTHER INFORMATION: Xaa = Arg or Lys
<220> FEATURE:
<221> NAME/KEY: VARIANT
<222> LOCATION: 8
<223> OTHER INFORMATION: Xaa = Any Amino Acid

<400> SEQUENCE: 204

Trp Val Xaa Gln Ala Pro Gly Xaa Gly Leu Glu Trp Ile Ala
1               5                   10

<210> SEQ ID NO 205
<211> LENGTH: 14
<212> TYPE: PRT
<213> ORGANISM: Artificial Sequence
<220> FEATURE:
<223> OTHER INFORMATION: VH FR2
<220> FEATURE:
<221> NAME/KEY: VARIANT
<222> LOCATION: 3
<223> OTHER INFORMATION: Xaa = Arg or Lys
<220> FEATURE:
<221> NAME/KEY: VARIANT
<222> LOCATION: 9
<223> OTHER INFORMATION: Xaa = Any Amino Acid

<400> SEQUENCE: 205

Trp Val Xaa Gln Ala Pro Gly Lys Xaa Leu Glu Trp Ile Ala
1               5                   10

<210> SEQ ID NO 206
<211> LENGTH: 14
<212> TYPE: PRT
```

```
<213> ORGANISM: Artificial Sequence
<220> FEATURE:
<223> OTHER INFORMATION: VH FR2
<220> FEATURE:
<221> NAME/KEY: VARIANT
<222> LOCATION: 3
<223> OTHER INFORMATION: Xaa = Arg or Lys
<220> FEATURE:
<221> NAME/KEY: VARIANT
<222> LOCATION: 10
<223> OTHER INFORMATION: Xaa = Any Amino Acid

<400> SEQUENCE: 206

Trp Val Xaa Gln Ala Pro Gly Lys Gly Xaa Glu Trp Ile Ala
1               5                   10

<210> SEQ ID NO 207
<211> LENGTH: 14
<212> TYPE: PRT
<213> ORGANISM: Artificial Sequence
<220> FEATURE:
<223> OTHER INFORMATION: VH FR2
<220> FEATURE:
<221> NAME/KEY: VARIANT
<222> LOCATION: 3
<223> OTHER INFORMATION: Xaa = Arg or Lys
<220> FEATURE:
<221> NAME/KEY: VARIANT
<222> LOCATION: 11
<223> OTHER INFORMATION: Xaa = Any Amino Acid

<400> SEQUENCE: 207

Trp Val Xaa Gln Ala Pro Gly Lys Gly Leu Xaa Trp Ile Ala
1               5                   10

<210> SEQ ID NO 208
<211> LENGTH: 14
<212> TYPE: PRT
<213> ORGANISM: Artificial Sequence
<220> FEATURE:
<223> OTHER INFORMATION: VH FR2
<220> FEATURE:
<221> NAME/KEY: VARIANT
<222> LOCATION: 3
<223> OTHER INFORMATION: Xaa = Arg or Lys
<220> FEATURE:
<221> NAME/KEY: VARIANT
<222> LOCATION: 12
<223> OTHER INFORMATION: Xaa = Any Amino Acid

<400> SEQUENCE: 208

Trp Val Xaa Gln Ala Pro Gly Lys Gly Leu Glu Xaa Ile Ala
1               5                   10

<210> SEQ ID NO 209
<211> LENGTH: 14
<212> TYPE: PRT
<213> ORGANISM: Artificial Sequence
<220> FEATURE:
<223> OTHER INFORMATION: VH FR2
<220> FEATURE:
<221> NAME/KEY: VARIANT
<222> LOCATION: 3
<223> OTHER INFORMATION: Xaa = Arg or Lys
<220> FEATURE:
<221> NAME/KEY: VARIANT
<222> LOCATION: 13
<223> OTHER INFORMATION: Xaa = Any Amino Acid

<400> SEQUENCE: 209

Trp Val Xaa Gln Ala Pro Gly Lys Gly Leu Glu Trp Xaa Ala
1               5                   10
```

<210> SEQ ID NO 210
<211> LENGTH: 14
<212> TYPE: PRT
<213> ORGANISM: Artificial Sequence
<220> FEATURE:
<223> OTHER INFORMATION: VH FR2
<220> FEATURE:
<221> NAME/KEY: VARIANT
<222> LOCATION: 3
<223> OTHER INFORMATION: Xaa = Arg or Lys
<220> FEATURE:
<221> NAME/KEY: VARIANT
<222> LOCATION: 14
<223> OTHER INFORMATION: Xaa = Any Amino Acid

<400> SEQUENCE: 210

Trp Val Xaa Gln Ala Pro Gly Lys Gly Leu Glu Trp Ile Xaa
1               5                   10

<210> SEQ ID NO 211
<211> LENGTH: 32
<212> TYPE: PRT
<213> ORGANISM: Artificial Sequence
<220> FEATURE:
<223> OTHER INFORMATION: VH FR3
<220> FEATURE:
<221> NAME/KEY: VARIANT
<222> LOCATION: 1
<223> OTHER INFORMATION: Xaa = Any Amino Acid
<220> FEATURE:
<221> NAME/KEY: VARIANT
<222> LOCATION: 2
<223> OTHER INFORMATION: Xaa = Ala or Val
<220> FEATURE:
<221> NAME/KEY: VARIANT
<222> LOCATION: 4
<223> OTHER INFORMATION: Xaa = Ile or Leu
<220> FEATURE:
<221> NAME/KEY: VARIANT
<222> LOCATION: 16
<223> OTHER INFORMATION: Xaa = Glu or Gln
<220> FEATURE:
<221> NAME/KEY: VARIANT
<222> LOCATION: 25
<223> OTHER INFORMATION: Xaa = Ser or Thr

<400> SEQUENCE: 211

Xaa Xaa Thr Xaa Thr Ala Asp Lys Ser Thr Ser Thr Ala Tyr Met Xaa
1               5                   10                  15

Leu Ser Ser Leu Arg Ser Glu Asp Xaa Ala Val Tyr Phe Cys Ala Arg
            20                  25                  30

<210> SEQ ID NO 212
<211> LENGTH: 32
<212> TYPE: PRT
<213> ORGANISM: Artificial Sequence
<220> FEATURE:
<223> OTHER INFORMATION: VH FR3
<220> FEATURE:
<221> NAME/KEY: VARIANT
<222> LOCATION: 2
<223> OTHER INFORMATION: Xaa = Any Amino Acid
<220> FEATURE:
<221> NAME/KEY: VARIANT
<222> LOCATION: 4
<223> OTHER INFORMATION: Xaa = Ile or Leu
<220> FEATURE:
<221> NAME/KEY: VARIANT
<222> LOCATION: 16
<223> OTHER INFORMATION: Xaa = Glu or Gln
<220> FEATURE:
<221> NAME/KEY: VARIANT

```
<222> LOCATION: 25
<223> OTHER INFORMATION: Xaa = Ser or Thr

<400> SEQUENCE: 212

Arg Xaa Thr Xaa Thr Ala Asp Lys Ser Thr Ser Thr Ala Tyr Met Xaa
1               5                   10                  15

Leu Ser Ser Leu Arg Ser Glu Asp Xaa Ala Val Tyr Phe Cys Ala Arg
            20                  25                  30

<210> SEQ ID NO 213
<211> LENGTH: 32
<212> TYPE: PRT
<213> ORGANISM: Artificial Sequence
<220> FEATURE:
<223> OTHER INFORMATION: VH FR3
<220> FEATURE:
<221> NAME/KEY: VARIANT
<222> LOCATION: 2
<223> OTHER INFORMATION: Xaa = Ala or Val
<220> FEATURE:
<221> NAME/KEY: VARIANT
<222> LOCATION: 3
<223> OTHER INFORMATION: Xaa = Any Amino Acid
<220> FEATURE:
<221> NAME/KEY: VARIANT
<222> LOCATION: 4
<223> OTHER INFORMATION: Xaa = Ile or Leu
<220> FEATURE:
<221> NAME/KEY: VARIANT
<222> LOCATION: 16
<223> OTHER INFORMATION: Xaa = Glu or Gln
<220> FEATURE:
<221> NAME/KEY: VARIANT
<222> LOCATION: 25
<223> OTHER INFORMATION: Xaa = Ser or Thr

<400> SEQUENCE: 213

Arg Xaa Xaa Xaa Thr Ala Asp Lys Ser Thr Ser Thr Ala Tyr Met Xaa
1               5                   10                  15

Leu Ser Ser Leu Arg Ser Glu Asp Xaa Ala Val Tyr Phe Cys Ala Arg
            20                  25                  30

<210> SEQ ID NO 214
<211> LENGTH: 32
<212> TYPE: PRT
<213> ORGANISM: Artificial Sequence
<220> FEATURE:
<223> OTHER INFORMATION: VH FR3
<220> FEATURE:
<221> NAME/KEY: VARIANT
<222> LOCATION: 2
<223> OTHER INFORMATION: Xaa = Ala or Val
<220> FEATURE:
<221> NAME/KEY: VARIANT
<222> LOCATION: 4
<223> OTHER INFORMATION: Xaa = Any Amino Acid
<220> FEATURE:
<221> NAME/KEY: VARIANT
<222> LOCATION: 16
<223> OTHER INFORMATION: Xaa = Glu or Gln
<220> FEATURE:
<221> NAME/KEY: VARIANT
<222> LOCATION: 25
<223> OTHER INFORMATION: Xaa = Ser or Thr

<400> SEQUENCE: 214

Arg Xaa Thr Xaa Thr Ala Asp Lys Ser Thr Ser Thr Ala Tyr Met Xaa
1               5                   10                  15

Leu Ser Ser Leu Arg Ser Glu Asp Xaa Ala Val Tyr Phe Cys Ala Arg
            20                  25                  30
```

```
<210> SEQ ID NO 215
<211> LENGTH: 32
<212> TYPE: PRT
<213> ORGANISM: Artificial Sequence
<220> FEATURE:
<223> OTHER INFORMATION: VH FR3
<220> FEATURE:
<221> NAME/KEY: VARIANT
<222> LOCATION: 2
<223> OTHER INFORMATION: Xaa = Any Amino Acid
<220> FEATURE:
<221> NAME/KEY: VARIANT
<222> LOCATION: 4
<223> OTHER INFORMATION: Xaa = Ile or Leu
<220> FEATURE:
<221> NAME/KEY: VARIANT
<222> LOCATION: 5
<223> OTHER INFORMATION: Xaa = Any Amino Acid
<220> FEATURE:
<221> NAME/KEY: VARIANT
<222> LOCATION: 16
<223> OTHER INFORMATION: Xaa = Glu or Gln
<220> FEATURE:
<221> NAME/KEY: VARIANT
<222> LOCATION: 25
<223> OTHER INFORMATION: Xaa = Ser or Thr

<400> SEQUENCE: 215

Arg Xaa Thr Xaa Xaa Ala Asp Lys Ser Thr Ser Thr Ala Tyr Met Xaa
 1               5                  10                  15

Leu Ser Ser Leu Arg Ser Glu Asp Xaa Ala Val Tyr Phe Cys Ala Arg
             20                  25                  30

<210> SEQ ID NO 216
<211> LENGTH: 32
<212> TYPE: PRT
<213> ORGANISM: Artificial Sequence
<220> FEATURE:
<223> OTHER INFORMATION: VH FR3
<220> FEATURE:
<221> NAME/KEY: VARIANT
<222> LOCATION: 2
<223> OTHER INFORMATION: Xaa = Any Amino Acid
<220> FEATURE:
<221> NAME/KEY: VARIANT
<222> LOCATION: 4
<223> OTHER INFORMATION: Xaa = Ile or Leu
<220> FEATURE:
<221> NAME/KEY: VARIANT
<222> LOCATION: 6
<223> OTHER INFORMATION: Xaa = Any Amino Acid
<220> FEATURE:
<221> NAME/KEY: VARIANT
<222> LOCATION: 16
<223> OTHER INFORMATION: Xaa = Glu or Gln
<220> FEATURE:
<221> NAME/KEY: VARIANT
<222> LOCATION: 25
<223> OTHER INFORMATION: Xaa = Ser or Thr

<400> SEQUENCE: 216

Arg Xaa Thr Xaa Thr Xaa Asp Lys Ser Thr Ser Thr Ala Tyr Met Xaa
 1               5                  10                  15

Leu Ser Ser Leu Arg Ser Glu Asp Xaa Ala Val Tyr Phe Cys Ala Arg
             20                  25                  30

<210> SEQ ID NO 217
<211> LENGTH: 32
<212> TYPE: PRT
<213> ORGANISM: Artificial Sequence
<220> FEATURE:
<223> OTHER INFORMATION: VH FR3
```

```
<220> FEATURE:
<221> NAME/KEY: VARIANT
<222> LOCATION: 2
<223> OTHER INFORMATION: Xaa = Any Amino Acid
<220> FEATURE:
<221> NAME/KEY: VARIANT
<222> LOCATION: 4
<223> OTHER INFORMATION: Xaa = Ile or Leu
<220> FEATURE:
<221> NAME/KEY: VARIANT
<222> LOCATION: 7
<223> OTHER INFORMATION: Xaa = Any Amino Acid
<220> FEATURE:
<221> NAME/KEY: VARIANT
<222> LOCATION: 16
<223> OTHER INFORMATION: Xaa = Glu or Gln
<220> FEATURE:
<221> NAME/KEY: VARIANT
<222> LOCATION: 25
<223> OTHER INFORMATION: Xaa = Ser or Thr

<400> SEQUENCE: 217

Arg Xaa Thr Xaa Thr Ala Xaa Lys Ser Thr Ser Thr Ala Tyr Met Xaa
 1               5                  10                  15

Leu Ser Ser Leu Arg Ser Glu Asp Xaa Ala Val Tyr Phe Cys Ala Arg
             20                  25                  30

<210> SEQ ID NO 218
<211> LENGTH: 32
<212> TYPE: PRT
<213> ORGANISM: Artificial Sequence
<220> FEATURE:
<223> OTHER INFORMATION: VH FR3
<220> FEATURE:
<221> NAME/KEY: VARIANT
<222> LOCATION: 2
<223> OTHER INFORMATION: Xaa = Any Amino Acid
<220> FEATURE:
<221> NAME/KEY: VARIANT
<222> LOCATION: 4
<223> OTHER INFORMATION: Xaa = Ile or Leu
<220> FEATURE:
<221> NAME/KEY: VARIANT
<222> LOCATION: 8
<223> OTHER INFORMATION: Xaa = Any Amino Acid
<220> FEATURE:
<221> NAME/KEY: VARIANT
<222> LOCATION: 16
<223> OTHER INFORMATION: Xaa = Glu or Gln
<220> FEATURE:
<221> NAME/KEY: VARIANT
<222> LOCATION: 25
<223> OTHER INFORMATION: Xaa = Ser or Thr

<400> SEQUENCE: 218

Arg Xaa Thr Xaa Thr Ala Asp Xaa Ser Thr Ser Thr Ala Tyr Met Xaa
 1               5                  10                  15

Leu Ser Ser Leu Arg Ser Glu Asp Xaa Ala Val Tyr Phe Cys Ala Arg
             20                  25                  30

<210> SEQ ID NO 219
<211> LENGTH: 32
<212> TYPE: PRT
<213> ORGANISM: Artificial Sequence
<220> FEATURE:
<223> OTHER INFORMATION: VH FR3
<220> FEATURE:
<221> NAME/KEY: VARIANT
<222> LOCATION: 2
<223> OTHER INFORMATION: Xaa = Any Amino Acid
<220> FEATURE:
<221> NAME/KEY: VARIANT
<222> LOCATION: 4
```

```
<223> OTHER INFORMATION: Xaa = Ile or Leu
<220> FEATURE:
<221> NAME/KEY: VARIANT
<222> LOCATION: 9
<223> OTHER INFORMATION: Xaa = Any Amino Acid
<220> FEATURE:
<221> NAME/KEY: VARIANT
<222> LOCATION: 16
<223> OTHER INFORMATION: Xaa = Glu or Gln
<220> FEATURE:
<221> NAME/KEY: VARIANT
<222> LOCATION: 25
<223> OTHER INFORMATION: Xaa = Ser or Thr

<400> SEQUENCE: 219

Arg Xaa Thr Xaa Thr Ala Asp Lys Xaa Thr Ser Thr Ala Tyr Met Xaa
 1               5                  10                  15

Leu Ser Ser Leu Arg Ser Glu Asp Xaa Ala Val Tyr Phe Cys Ala Arg
             20                  25                  30

<210> SEQ ID NO 220
<211> LENGTH: 32
<212> TYPE: PRT
<213> ORGANISM: Artificial Sequence
<220> FEATURE:
<223> OTHER INFORMATION: VH FR3
<220> FEATURE:
<221> NAME/KEY: VARIANT
<222> LOCATION: 2
<223> OTHER INFORMATION: Xaa = Any Amino Acid
<220> FEATURE:
<221> NAME/KEY: VARIANT
<222> LOCATION: 4
<223> OTHER INFORMATION: Xaa = Ile or Leu
<220> FEATURE:
<221> NAME/KEY: VARIANT
<222> LOCATION: 10
<223> OTHER INFORMATION: Xaa = Any Amino Acid
<220> FEATURE:
<221> NAME/KEY: VARIANT
<222> LOCATION: 16
<223> OTHER INFORMATION: Xaa = Glu or Gln
<220> FEATURE:
<221> NAME/KEY: VARIANT
<222> LOCATION: 25
<223> OTHER INFORMATION: Xaa = Ser or Thr

<400> SEQUENCE: 220

Arg Xaa Thr Xaa Thr Ala Asp Lys Ser Xaa Ser Thr Ala Tyr Met Xaa
 1               5                  10                  15

Leu Ser Ser Leu Arg Ser Glu Asp Xaa Ala Val Tyr Phe Cys Ala Arg
             20                  25                  30

<210> SEQ ID NO 221
<211> LENGTH: 32
<212> TYPE: PRT
<213> ORGANISM: Artificial Sequence
<220> FEATURE:
<223> OTHER INFORMATION: VH FR3
<220> FEATURE:
<221> NAME/KEY: VARIANT
<222> LOCATION: 2
<223> OTHER INFORMATION: Xaa = Any Amino Acid
<220> FEATURE:
<221> NAME/KEY: VARIANT
<222> LOCATION: 4
<223> OTHER INFORMATION: Xaa = Ile or Leu
<220> FEATURE:
<221> NAME/KEY: VARIANT
<222> LOCATION: 11
<223> OTHER INFORMATION: Xaa = Any Amino Acid
<220> FEATURE:
<221> NAME/KEY: VARIANT
```

```
<222> LOCATION: 16
<223> OTHER INFORMATION: Xaa = Glu or Gln
<220> FEATURE:
<221> NAME/KEY: VARIANT
<222> LOCATION: 25
<223> OTHER INFORMATION: Xaa = Ser or Thr

<400> SEQUENCE: 221

Arg Xaa Thr Xaa Thr Ala Asp Lys Ser Thr Xaa Thr Ala Tyr Met Xaa
1               5                   10                  15

Leu Ser Ser Leu Arg Ser Glu Asp Xaa Ala Val Tyr Phe Cys Ala Arg
            20                  25                  30

<210> SEQ ID NO 222
<211> LENGTH: 32
<212> TYPE: PRT
<213> ORGANISM: Artificial Sequence
<220> FEATURE:
<223> OTHER INFORMATION: VH FR3
<220> FEATURE:
<221> NAME/KEY: VARIANT
<222> LOCATION: 2
<223> OTHER INFORMATION: Xaa = Any Amino Acid
<220> FEATURE:
<221> NAME/KEY: VARIANT
<222> LOCATION: 4
<223> OTHER INFORMATION: Xaa = Ile or Leu
<220> FEATURE:
<221> NAME/KEY: VARIANT
<222> LOCATION: 12
<223> OTHER INFORMATION: Xaa = Any Amino Acid
<220> FEATURE:
<221> NAME/KEY: VARIANT
<222> LOCATION: 16
<223> OTHER INFORMATION: Xaa = Glu or Gln
<220> FEATURE:
<221> NAME/KEY: VARIANT
<222> LOCATION: 25
<223> OTHER INFORMATION: Xaa = Ser or Thr

<400> SEQUENCE: 222

Arg Xaa Thr Xaa Thr Ala Asp Lys Ser Thr Ser Xaa Ala Tyr Met Xaa
1               5                   10                  15

Leu Ser Ser Leu Arg Ser Glu Asp Xaa Ala Val Tyr Phe Cys Ala Arg
            20                  25                  30

<210> SEQ ID NO 223
<211> LENGTH: 32
<212> TYPE: PRT
<213> ORGANISM: Artificial Sequence
<220> FEATURE:
<223> OTHER INFORMATION: VH FR3
<220> FEATURE:
<221> NAME/KEY: VARIANT
<222> LOCATION: 2
<223> OTHER INFORMATION: Xaa = Any Amino Acid
<220> FEATURE:
<221> NAME/KEY: VARIANT
<222> LOCATION: 4
<223> OTHER INFORMATION: Xaa = Ile or Leu
<220> FEATURE:
<221> NAME/KEY: VARIANT
<222> LOCATION: 13
<223> OTHER INFORMATION: Xaa = Any Amino Acid
<220> FEATURE:
<221> NAME/KEY: VARIANT
<222> LOCATION: 16
<223> OTHER INFORMATION: Xaa = Glu or Gln
<220> FEATURE:
<221> NAME/KEY: VARIANT
<222> LOCATION: 25
<223> OTHER INFORMATION: Xaa = Ser or Thr
```

<400> SEQUENCE: 223

Arg Xaa Thr Xaa Thr Ala Asp Lys Ser Thr Ser Thr Xaa Tyr Met Xaa
1               5                   10                  15

Leu Ser Ser Leu Arg Ser Glu Asp Xaa Ala Val Tyr Phe Cys Ala Arg
            20                  25                  30

<210> SEQ ID NO 224
<211> LENGTH: 32
<212> TYPE: PRT
<213> ORGANISM: Artificial Sequence
<220> FEATURE:
<223> OTHER INFORMATION: VH FR3
<220> FEATURE:
<221> NAME/KEY: VARIANT
<222> LOCATION: 2
<223> OTHER INFORMATION: Xaa = Any Amino Acid
<220> FEATURE:
<221> NAME/KEY: VARIANT
<222> LOCATION: 4
<223> OTHER INFORMATION: Xaa = Ile or Leu
<220> FEATURE:
<221> NAME/KEY: VARIANT
<222> LOCATION: 14
<223> OTHER INFORMATION: Xaa = Any Amino Acid
<220> FEATURE:
<221> NAME/KEY: VARIANT
<222> LOCATION: 16
<223> OTHER INFORMATION: Xaa = Glu or Gln
<220> FEATURE:
<221> NAME/KEY: VARIANT
<222> LOCATION: 25
<223> OTHER INFORMATION: Xaa = Ser or Thr

<400> SEQUENCE: 224

Arg Xaa Thr Xaa Thr Ala Asp Lys Ser Thr Ser Thr Ala Xaa Met Xaa
1               5                   10                  15

Leu Ser Ser Leu Arg Ser Glu Asp Xaa Ala Val Tyr Phe Cys Ala Arg
            20                  25                  30

<210> SEQ ID NO 225
<211> LENGTH: 32
<212> TYPE: PRT
<213> ORGANISM: Artificial Sequence
<220> FEATURE:
<223> OTHER INFORMATION: VH FR3
<220> FEATURE:
<221> NAME/KEY: VARIANT
<222> LOCATION: 2
<223> OTHER INFORMATION: Xaa = Any Amino Acid
<220> FEATURE:
<221> NAME/KEY: VARIANT
<222> LOCATION: 4
<223> OTHER INFORMATION: Xaa = Ile or Leu
<220> FEATURE:
<221> NAME/KEY: VARIANT
<222> LOCATION: 15
<223> OTHER INFORMATION: Xaa = Any Amino Acid
<220> FEATURE:
<221> NAME/KEY: VARIANT
<222> LOCATION: 16
<223> OTHER INFORMATION: Xaa = Glu or Gln
<220> FEATURE:
<221> NAME/KEY: VARIANT
<222> LOCATION: 25
<223> OTHER INFORMATION: Xaa = Ser or Thr

<400> SEQUENCE: 225

Arg Xaa Thr Xaa Thr Ala Asp Lys Ser Thr Ser Thr Ala Tyr Xaa Xaa
1               5                   10                  15

Leu Ser Ser Leu Arg Ser Glu Asp Xaa Ala Val Tyr Phe Cys Ala Arg
            20                  25                  30

```
<210> SEQ ID NO 226
<211> LENGTH: 32
<212> TYPE: PRT
<213> ORGANISM: Artificial Sequence
<220> FEATURE:
<223> OTHER INFORMATION: VH FR3
<220> FEATURE:
<221> NAME/KEY: VARIANT
<222> LOCATION: 2
<223> OTHER INFORMATION: Xaa = Any Amino Acid
<220> FEATURE:
<221> NAME/KEY: VARIANT
<222> LOCATION: 4
<223> OTHER INFORMATION: Xaa = Ile or Leu
<220> FEATURE:
<221> NAME/KEY: VARIANT
<222> LOCATION: 16
<223> OTHER INFORMATION: Xaa = Any Amino Acid
<220> FEATURE:
<221> NAME/KEY: VARIANT
<222> LOCATION: 25
<223> OTHER INFORMATION: Xaa = Ser or Thr

<400> SEQUENCE: 226

Arg Xaa Thr Xaa Thr Ala Asp Lys Ser Thr Ser Thr Ala Tyr Met Xaa
1               5                   10                  15

Leu Ser Ser Leu Arg Ser Glu Asp Xaa Ala Val Tyr Phe Cys Ala Arg
            20                  25                  30

<210> SEQ ID NO 227
<211> LENGTH: 32
<212> TYPE: PRT
<213> ORGANISM: Artificial Sequence
<220> FEATURE:
<223> OTHER INFORMATION: VH FR3
<220> FEATURE:
<221> NAME/KEY: VARIANT
<222> LOCATION: 2
<223> OTHER INFORMATION: Xaa = Any Amino Acid
<220> FEATURE:
<221> NAME/KEY: VARIANT
<222> LOCATION: 4
<223> OTHER INFORMATION: Xaa = Ile or Leu
<220> FEATURE:
<221> NAME/KEY: VARIANT
<222> LOCATION: 16
<223> OTHER INFORMATION: Xaa = Glu or Gln
<220> FEATURE:
<221> NAME/KEY: VARIANT
<222> LOCATION: 17
<223> OTHER INFORMATION: Xaa = Any Amino Acid
<220> FEATURE:
<221> NAME/KEY: VARIANT
<222> LOCATION: 25
<223> OTHER INFORMATION: Xaa = Ser or Thr

<400> SEQUENCE: 227

Arg Xaa Thr Xaa Thr Ala Asp Lys Ser Thr Ser Thr Ala Tyr Met Xaa
1               5                   10                  15

Xaa Ser Ser Leu Arg Ser Glu Asp Xaa Ala Val Tyr Phe Cys Ala Arg
            20                  25                  30

<210> SEQ ID NO 228
<211> LENGTH: 32
<212> TYPE: PRT
<213> ORGANISM: Artificial Sequence
<220> FEATURE:
<223> OTHER INFORMATION: VH FR3
<220> FEATURE:
<221> NAME/KEY: VARIANT
<222> LOCATION: 2
```

```
<223> OTHER INFORMATION: Xaa = Any Amino Acid
<220> FEATURE:
<221> NAME/KEY: VARIANT
<222> LOCATION: 4
<223> OTHER INFORMATION: Xaa = Ile or Leu
<220> FEATURE:
<221> NAME/KEY: VARIANT
<222> LOCATION: 16
<223> OTHER INFORMATION: Xaa = Glu or Gln
<220> FEATURE:
<221> NAME/KEY: VARIANT
<222> LOCATION: 18
<223> OTHER INFORMATION: Xaa = Any Amino Acid
<220> FEATURE:
<221> NAME/KEY: VARIANT
<222> LOCATION: 25
<223> OTHER INFORMATION: Xaa = Ser or Thr

<400> SEQUENCE: 228

Arg Xaa Thr Xaa Thr Ala Asp Lys Ser Thr Ser Thr Ala Tyr Met Xaa
 1               5                  10                  15

Leu Xaa Ser Leu Arg Ser Glu Asp Xaa Ala Val Tyr Phe Cys Ala Arg
            20                  25                  30

<210> SEQ ID NO 229
<211> LENGTH: 32
<212> TYPE: PRT
<213> ORGANISM: Artificial Sequence
<220> FEATURE:
<223> OTHER INFORMATION: VH FR3
<220> FEATURE:
<221> NAME/KEY: VARIANT
<222> LOCATION: 2
<223> OTHER INFORMATION: Xaa = Any Amino Acid
<220> FEATURE:
<221> NAME/KEY: VARIANT
<222> LOCATION: 4
<223> OTHER INFORMATION: Xaa = Ile or Leu
<220> FEATURE:
<221> NAME/KEY: VARIANT
<222> LOCATION: 16
<223> OTHER INFORMATION: Xaa = Glu or Gln
<220> FEATURE:
<221> NAME/KEY: VARIANT
<222> LOCATION: 19
<223> OTHER INFORMATION: Xaa = Any Amino Acid
<220> FEATURE:
<221> NAME/KEY: VARIANT
<222> LOCATION: 25
<223> OTHER INFORMATION: Xaa = Ser or Thr

<400> SEQUENCE: 229

Arg Xaa Thr Xaa Thr Ala Asp Lys Ser Thr Ser Thr Ala Tyr Met Xaa
 1               5                  10                  15

Leu Ser Xaa Leu Arg Ser Glu Asp Xaa Ala Val Tyr Phe Cys Ala Arg
            20                  25                  30

<210> SEQ ID NO 230
<211> LENGTH: 32
<212> TYPE: PRT
<213> ORGANISM: Artificial Sequence
<220> FEATURE:
<223> OTHER INFORMATION: VH FR3
<220> FEATURE:
<221> NAME/KEY: VARIANT
<222> LOCATION: 2
<223> OTHER INFORMATION: Xaa = Any Amino Acid
<220> FEATURE:
<221> NAME/KEY: VARIANT
<222> LOCATION: 4
<223> OTHER INFORMATION: Xaa = Ile or Leu
<220> FEATURE:
<221> NAME/KEY: VARIANT
```

```
<222> LOCATION: 16
<223> OTHER INFORMATION: Xaa = Glu or Gln
<220> FEATURE:
<221> NAME/KEY: VARIANT
<222> LOCATION: 20
<223> OTHER INFORMATION: Xaa = Any Amino Acid
<220> FEATURE:
<221> NAME/KEY: VARIANT
<222> LOCATION: 25
<223> OTHER INFORMATION: Xaa = Ser or Thr

<400> SEQUENCE: 230

Arg Xaa Thr Xaa Thr Ala Asp Lys Ser Thr Ser Thr Ala Tyr Met Xaa
1               5                   10                  15

Leu Ser Ser Xaa Arg Ser Glu Asp Xaa Ala Val Tyr Phe Cys Ala Arg
            20                  25                  30

<210> SEQ ID NO 231
<211> LENGTH: 32
<212> TYPE: PRT
<213> ORGANISM: Artificial Sequence
<220> FEATURE:
<223> OTHER INFORMATION: VH FR3
<220> FEATURE:
<221> NAME/KEY: VARIANT
<222> LOCATION: 2
<223> OTHER INFORMATION: Xaa = Any Amino Acid
<220> FEATURE:
<221> NAME/KEY: VARIANT
<222> LOCATION: 4
<223> OTHER INFORMATION: Xaa = Ile or Leu
<220> FEATURE:
<221> NAME/KEY: VARIANT
<222> LOCATION: 16
<223> OTHER INFORMATION: Xaa = Glu or Gln
<220> FEATURE:
<221> NAME/KEY: VARIANT
<222> LOCATION: 21
<223> OTHER INFORMATION: Xaa = Any Amino Acid
<220> FEATURE:
<221> NAME/KEY: VARIANT
<222> LOCATION: 25
<223> OTHER INFORMATION: Xaa = Ser or Thr

<400> SEQUENCE: 231

Arg Xaa Thr Xaa Thr Ala Asp Lys Ser Thr Ser Thr Ala Tyr Met Xaa
1               5                   10                  15

Leu Ser Ser Leu Xaa Ser Glu Asp Xaa Ala Val Tyr Phe Cys Ala Arg
            20                  25                  30

<210> SEQ ID NO 232
<211> LENGTH: 32
<212> TYPE: PRT
<213> ORGANISM: Artificial Sequence
<220> FEATURE:
<223> OTHER INFORMATION: VH FR3
<220> FEATURE:
<221> NAME/KEY: VARIANT
<222> LOCATION: 2
<223> OTHER INFORMATION: Xaa = Any Amino Acid
<220> FEATURE:
<221> NAME/KEY: VARIANT
<222> LOCATION: 4
<223> OTHER INFORMATION: Xaa = Ile or Leu
<220> FEATURE:
<221> NAME/KEY: VARIANT
<222> LOCATION: 16
<223> OTHER INFORMATION: Xaa = Glu or Gln
<220> FEATURE:
<221> NAME/KEY: VARIANT
<222> LOCATION: 22
<223> OTHER INFORMATION: Xaa = Any Amino Acid
<220> FEATURE:
```

<221> NAME/KEY: VARIANT
<222> LOCATION: 25
<223> OTHER INFORMATION: Xaa = Ser or Thr

<400> SEQUENCE: 232

Arg Xaa Thr Xaa Thr Ala Asp Lys Ser Thr Ser Thr Ala Tyr Met Xaa
1               5                   10                  15

Leu Ser Ser Leu Arg Xaa Glu Asp Xaa Ala Val Tyr Phe Cys Ala Arg
            20                  25                  30

<210> SEQ ID NO 233
<211> LENGTH: 32
<212> TYPE: PRT
<213> ORGANISM: Artificial Sequence
<220> FEATURE:
<223> OTHER INFORMATION: VH FR3
<220> FEATURE:
<221> NAME/KEY: VARIANT
<222> LOCATION: 2
<223> OTHER INFORMATION: Xaa = Any Amino Acid
<220> FEATURE:
<221> NAME/KEY: VARIANT
<222> LOCATION: 4
<223> OTHER INFORMATION: Xaa = Ile or Leu
<220> FEATURE:
<221> NAME/KEY: VARIANT
<222> LOCATION: 16
<223> OTHER INFORMATION: Xaa = Glu or Gln
<220> FEATURE:
<221> NAME/KEY: VARIANT
<222> LOCATION: 23
<223> OTHER INFORMATION: Xaa = Any Amino Acid
<220> FEATURE:
<221> NAME/KEY: VARIANT
<222> LOCATION: 25
<223> OTHER INFORMATION: Xaa = Ser or Thr

<400> SEQUENCE: 233

Arg Xaa Thr Xaa Thr Ala Asp Lys Ser Thr Ser Thr Ala Tyr Met Xaa
1               5                   10                  15

Leu Ser Ser Leu Arg Ser Xaa Asp Xaa Ala Val Tyr Phe Cys Ala Arg
            20                  25                  30

<210> SEQ ID NO 234
<211> LENGTH: 32
<212> TYPE: PRT
<213> ORGANISM: Artificial Sequence
<220> FEATURE:
<223> OTHER INFORMATION: VH FR3
<220> FEATURE:
<221> NAME/KEY: VARIANT
<222> LOCATION: 2
<223> OTHER INFORMATION: Xaa = Any Amino Acid
<220> FEATURE:
<221> NAME/KEY: VARIANT
<222> LOCATION: 4
<223> OTHER INFORMATION: Xaa = Ile or Leu
<220> FEATURE:
<221> NAME/KEY: VARIANT
<222> LOCATION: 16
<223> OTHER INFORMATION: Xaa = Glu or Gln
<220> FEATURE:
<221> NAME/KEY: VARIANT
<222> LOCATION: 24
<223> OTHER INFORMATION: Xaa = Any Amino Acid
<220> FEATURE:
<221> NAME/KEY: VARIANT
<222> LOCATION: 25
<223> OTHER INFORMATION: Xaa = Ser or Thr

<400> SEQUENCE: 234

Arg Xaa Thr Xaa Thr Ala Asp Lys Ser Thr Ser Thr Ala Tyr Met Xaa

```
                1               5                   10                  15
Leu Ser Ser Leu Arg Ser Glu Xaa Xaa Ala Val Tyr Phe Cys Ala Arg
            20                  25                  30

<210> SEQ ID NO 235
<211> LENGTH: 32
<212> TYPE: PRT
<213> ORGANISM: Artificial Sequence
<220> FEATURE:
<223> OTHER INFORMATION: VH FR3
<220> FEATURE:
<221> NAME/KEY: VARIANT
<222> LOCATION: 2
<223> OTHER INFORMATION: Xaa = Any Amino Acid
<220> FEATURE:
<221> NAME/KEY: VARIANT
<222> LOCATION: 4
<223> OTHER INFORMATION: Xaa = Ile or Leu
<220> FEATURE:
<221> NAME/KEY: VARIANT
<222> LOCATION: 16
<223> OTHER INFORMATION: Xaa = Glu or Gln
<220> FEATURE:
<221> NAME/KEY: VARIANT
<222> LOCATION: 25
<223> OTHER INFORMATION: Xaa = Any Amino Acid

<400> SEQUENCE: 235

Arg Xaa Thr Xaa Thr Ala Asp Lys Ser Thr Ser Thr Ala Tyr Met Xaa
1               5                   10                  15

Leu Ser Ser Leu Arg Ser Glu Asp Xaa Ala Val Tyr Phe Cys Ala Arg
            20                  25                  30

<210> SEQ ID NO 236
<211> LENGTH: 32
<212> TYPE: PRT
<213> ORGANISM: Artificial Sequence
<220> FEATURE:
<223> OTHER INFORMATION: VH FR3
<220> FEATURE:
<221> NAME/KEY: VARIANT
<222> LOCATION: 2
<223> OTHER INFORMATION: Xaa = Any Amino Acid
<220> FEATURE:
<221> NAME/KEY: VARIANT
<222> LOCATION: 4
<223> OTHER INFORMATION: Xaa = Ile or Leu
<220> FEATURE:
<221> NAME/KEY: VARIANT
<222> LOCATION: 16
<223> OTHER INFORMATION: Xaa = Glu or Gln
<220> FEATURE:
<221> NAME/KEY: VARIANT
<222> LOCATION: 25
<223> OTHER INFORMATION: Xaa = Ser or Thr
<220> FEATURE:
<221> NAME/KEY: VARIANT
<222> LOCATION: 26
<223> OTHER INFORMATION: Xaa = Any Amino Acid

<400> SEQUENCE: 236

Arg Xaa Thr Xaa Thr Ala Asp Lys Ser Thr Ser Thr Ala Tyr Met Xaa
1               5                   10                  15

Leu Ser Ser Leu Arg Ser Glu Asp Xaa Xaa Val Tyr Phe Cys Ala Arg
            20                  25                  30

<210> SEQ ID NO 237
<211> LENGTH: 32
<212> TYPE: PRT
<213> ORGANISM: Artificial Sequence
<220> FEATURE:
```

```
<223> OTHER INFORMATION: VH FR3
<220> FEATURE:
<221> NAME/KEY: VARIANT
<222> LOCATION: 2
<223> OTHER INFORMATION: Xaa = Any Amino Acid
<220> FEATURE:
<221> NAME/KEY: VARIANT
<222> LOCATION: 4
<223> OTHER INFORMATION: Xaa = Ile or Leu
<220> FEATURE:
<221> NAME/KEY: VARIANT
<222> LOCATION: 16
<223> OTHER INFORMATION: Xaa = Glu or Gln
<220> FEATURE:
<221> NAME/KEY: VARIANT
<222> LOCATION: 25
<223> OTHER INFORMATION: Xaa = Ser or Thr
<220> FEATURE:
<221> NAME/KEY: VARIANT
<222> LOCATION: 27
<223> OTHER INFORMATION: Xaa = Any Amino Acid

<400> SEQUENCE: 237

Arg Xaa Thr Xaa Thr Ala Asp Lys Ser Thr Ser Thr Ala Tyr Met Xaa
 1               5                  10                  15

Leu Ser Ser Leu Arg Ser Glu Asp Xaa Ala Xaa Tyr Phe Cys Ala Arg
             20                  25                  30

<210> SEQ ID NO 238
<211> LENGTH: 32
<212> TYPE: PRT
<213> ORGANISM: Artificial Sequence
<220> FEATURE:
<223> OTHER INFORMATION: VH FR3
<220> FEATURE:
<221> NAME/KEY: VARIANT
<222> LOCATION: 2
<223> OTHER INFORMATION: Xaa = Any Amino Acid
<220> FEATURE:
<221> NAME/KEY: VARIANT
<222> LOCATION: 4
<223> OTHER INFORMATION: Xaa = Ile or Leu
<220> FEATURE:
<221> NAME/KEY: VARIANT
<222> LOCATION: 16
<223> OTHER INFORMATION: Xaa = Glu or Gln
<220> FEATURE:
<221> NAME/KEY: VARIANT
<222> LOCATION: 25
<223> OTHER INFORMATION: Xaa = Ser or Thr
<220> FEATURE:
<221> NAME/KEY: VARIANT
<222> LOCATION: 28
<223> OTHER INFORMATION: Xaa = Any Amino Acid

<400> SEQUENCE: 238

Arg Xaa Thr Xaa Thr Ala Asp Lys Ser Thr Ser Thr Ala Tyr Met Xaa
 1               5                  10                  15

Leu Ser Ser Leu Arg Ser Glu Asp Xaa Ala Val Xaa Phe Cys Ala Arg
             20                  25                  30

<210> SEQ ID NO 239
<211> LENGTH: 32
<212> TYPE: PRT
<213> ORGANISM: Artificial Sequence
<220> FEATURE:
<223> OTHER INFORMATION: VH FR3
<220> FEATURE:
<221> NAME/KEY: VARIANT
<222> LOCATION: 2
<223> OTHER INFORMATION: Xaa = Any Amino Acid
<220> FEATURE:
<221> NAME/KEY: VARIANT
```

```
<222> LOCATION: 4
<223> OTHER INFORMATION: Xaa = Ile or Leu
<220> FEATURE:
<221> NAME/KEY: VARIANT
<222> LOCATION: 16
<223> OTHER INFORMATION: Xaa = Glu or Gln
<220> FEATURE:
<221> NAME/KEY: VARIANT
<222> LOCATION: 25
<223> OTHER INFORMATION: Xaa = Ser or Thr
<220> FEATURE:
<221> NAME/KEY: VARIANT
<222> LOCATION: 29
<223> OTHER INFORMATION: Xaa = Any Amino Acid

<400> SEQUENCE: 239

Arg Xaa Thr Xaa Thr Ala Asp Lys Ser Thr Ser Thr Ala Tyr Met Xaa
 1               5                  10                  15

Leu Ser Ser Leu Arg Ser Glu Asp Xaa Ala Val Tyr Xaa Cys Ala Arg
            20                  25                  30

<210> SEQ ID NO 240
<211> LENGTH: 32
<212> TYPE: PRT
<213> ORGANISM: Artificial Sequence
<220> FEATURE:
<223> OTHER INFORMATION: VH FR3
<220> FEATURE:
<221> NAME/KEY: VARIANT
<222> LOCATION: 2
<223> OTHER INFORMATION: Xaa = Any Amino Acid
<220> FEATURE:
<221> NAME/KEY: VARIANT
<222> LOCATION: 4
<223> OTHER INFORMATION: Xaa = Ile or Leu
<220> FEATURE:
<221> NAME/KEY: VARIANT
<222> LOCATION: 16
<223> OTHER INFORMATION: Xaa = Glu or Gln
<220> FEATURE:
<221> NAME/KEY: VARIANT
<222> LOCATION: 25
<223> OTHER INFORMATION: Xaa = Ser or Thr
<220> FEATURE:
<221> NAME/KEY: VARIANT
<222> LOCATION: 30
<223> OTHER INFORMATION: Xaa = Any Amino Acid

<400> SEQUENCE: 240

Arg Xaa Thr Xaa Thr Ala Asp Lys Ser Thr Ser Thr Ala Tyr Met Xaa
 1               5                  10                  15

Leu Ser Ser Leu Arg Ser Glu Asp Xaa Ala Val Tyr Phe Xaa Ala Arg
            20                  25                  30

<210> SEQ ID NO 241
<211> LENGTH: 32
<212> TYPE: PRT
<213> ORGANISM: Artificial Sequence
<220> FEATURE:
<223> OTHER INFORMATION: VH FR3
<220> FEATURE:
<221> NAME/KEY: VARIANT
<222> LOCATION: 2
<223> OTHER INFORMATION: Xaa = Any Amino Acid
<220> FEATURE:
<221> NAME/KEY: VARIANT
<222> LOCATION: 4
<223> OTHER INFORMATION: Xaa = Ile or Leu
<220> FEATURE:
<221> NAME/KEY: VARIANT
<222> LOCATION: 16
<223> OTHER INFORMATION: Xaa = Glu or Gln
<220> FEATURE:
```

```
<221> NAME/KEY: VARIANT
<222> LOCATION: 25
<223> OTHER INFORMATION: Xaa = Ser or Thr
<220> FEATURE:
<221> NAME/KEY: VARIANT
<222> LOCATION: 31
<223> OTHER INFORMATION: Xaa = Any Amino Acid

<400> SEQUENCE: 241

Arg Xaa Thr Xaa Thr Ala Asp Lys Ser Thr Ser Thr Ala Tyr Met Xaa
1               5                   10                  15

Leu Ser Ser Leu Arg Ser Glu Asp Xaa Ala Val Tyr Phe Cys Xaa Arg
            20                  25                  30

<210> SEQ ID NO 242
<211> LENGTH: 32
<212> TYPE: PRT
<213> ORGANISM: Artificial Sequence
<220> FEATURE:
<223> OTHER INFORMATION: VH FR3
<220> FEATURE:
<221> NAME/KEY: VARIANT
<222> LOCATION: 2
<223> OTHER INFORMATION: Xaa = Any Amino Acid
<220> FEATURE:
<221> NAME/KEY: VARIANT
<222> LOCATION: 4
<223> OTHER INFORMATION: Xaa = Ile or Leu
<220> FEATURE:
<221> NAME/KEY: VARIANT
<222> LOCATION: 16
<223> OTHER INFORMATION: Xaa = Glu or Gln
<220> FEATURE:
<221> NAME/KEY: VARIANT
<222> LOCATION: 25
<223> OTHER INFORMATION: Xaa = Ser or Thr
<220> FEATURE:
<221> NAME/KEY: VARIANT
<222> LOCATION: 32
<223> OTHER INFORMATION: Xaa = Any Amino Acid

<400> SEQUENCE: 242

Arg Xaa Thr Xaa Thr Ala Asp Lys Ser Thr Ser Thr Ala Tyr Met Xaa
1               5                   10                  15

Leu Ser Ser Leu Arg Ser Glu Asp Xaa Ala Val Tyr Phe Cys Ala Xaa
            20                  25                  30

<210> SEQ ID NO 243
<211> LENGTH: 11
<212> TYPE: PRT
<213> ORGANISM: Artificial Sequence
<220> FEATURE:
<223> OTHER INFORMATION: VH FR4
<220> FEATURE:
<221> NAME/KEY: VARIANT
<222> LOCATION: 1
<223> OTHER INFORMATION: Xaa = Any Amino Acid

<400> SEQUENCE: 243

Xaa Gly Gln Gly Thr Thr Val Thr Val Ser Ser
1               5                   10

<210> SEQ ID NO 244
<211> LENGTH: 11
<212> TYPE: PRT
<213> ORGANISM: Artificial Sequence
<220> FEATURE:
<223> OTHER INFORMATION: VH FR4
<220> FEATURE:
<221> NAME/KEY: VARIANT
<222> LOCATION: 2
```

<223> OTHER INFORMATION: Xaa = Any Amino Acid

<400> SEQUENCE: 244

Trp Xaa Gln Gly Thr Thr Val Thr Val Ser Ser
1               5                   10

<210> SEQ ID NO 245
<211> LENGTH: 11
<212> TYPE: PRT
<213> ORGANISM: Artificial Sequence
<220> FEATURE:
<223> OTHER INFORMATION: VH FR4
<220> FEATURE:
<221> NAME/KEY: VARIANT
<222> LOCATION: 3
<223> OTHER INFORMATION: Xaa = Any Amino Acid

<400> SEQUENCE: 245

Trp Gly Xaa Gly Thr Thr Val Thr Val Ser Ser
1               5                   10

<210> SEQ ID NO 246
<211> LENGTH: 11
<212> TYPE: PRT
<213> ORGANISM: Artificial Sequence
<220> FEATURE:
<223> OTHER INFORMATION: VH FR4
<220> FEATURE:
<221> NAME/KEY: VARIANT
<222> LOCATION: 4
<223> OTHER INFORMATION: Xaa = Any Amino Acid

<400> SEQUENCE: 246

Trp Gly Gln Xaa Thr Thr Val Thr Val Ser Ser
1               5                   10

<210> SEQ ID NO 247
<211> LENGTH: 11
<212> TYPE: PRT
<213> ORGANISM: Artificial Sequence
<220> FEATURE:
<223> OTHER INFORMATION: VH FR4
<220> FEATURE:
<221> NAME/KEY: VARIANT
<222> LOCATION: 5
<223> OTHER INFORMATION: Xaa = Any Amino Acid

<400> SEQUENCE: 247

Trp Gly Gln Gly Xaa Thr Val Thr Val Ser Ser
1               5                   10

<210> SEQ ID NO 248
<211> LENGTH: 11
<212> TYPE: PRT
<213> ORGANISM: Artificial Sequence
<220> FEATURE:
<223> OTHER INFORMATION: VH FR4
<220> FEATURE:
<221> NAME/KEY: VARIANT
<222> LOCATION: 6
<223> OTHER INFORMATION: Xaa = Any Amino Acid

<400> SEQUENCE: 248

Trp Gly Gln Gly Thr Xaa Val Thr Val Ser Ser
1               5                   10

<210> SEQ ID NO 249
<211> LENGTH: 11
<212> TYPE: PRT

```
<213> ORGANISM: Artificial Sequence
<220> FEATURE:
<223> OTHER INFORMATION: VH FR4
<220> FEATURE:
<221> NAME/KEY: VARIANT
<222> LOCATION: 7
<223> OTHER INFORMATION: Xaa = Any Amino Acid

<400> SEQUENCE: 249

Trp Gly Gln Gly Thr Thr Xaa Thr Val Ser Ser
1               5                   10

<210> SEQ ID NO 250
<211> LENGTH: 11
<212> TYPE: PRT
<213> ORGANISM: Artificial Sequence
<220> FEATURE:
<223> OTHER INFORMATION: VH FR4
<220> FEATURE:
<221> NAME/KEY: VARIANT
<222> LOCATION: 8
<223> OTHER INFORMATION: Xaa = Any Amino Acid

<400> SEQUENCE: 250

Trp Gly Gln Gly Thr Thr Val Xaa Val Ser Ser
1               5                   10

<210> SEQ ID NO 251
<211> LENGTH: 11
<212> TYPE: PRT
<213> ORGANISM: Artificial Sequence
<220> FEATURE:
<223> OTHER INFORMATION: VH FR4
<220> FEATURE:
<221> NAME/KEY: VARIANT
<222> LOCATION: 9
<223> OTHER INFORMATION: Xaa = Any Amino Acid

<400> SEQUENCE: 251

Trp Gly Gln Gly Thr Thr Val Thr Xaa Ser Ser
1               5                   10

<210> SEQ ID NO 252
<211> LENGTH: 11
<212> TYPE: PRT
<213> ORGANISM: Artificial Sequence
<220> FEATURE:
<223> OTHER INFORMATION: VH FR4
<220> FEATURE:
<221> NAME/KEY: VARIANT
<222> LOCATION: 10
<223> OTHER INFORMATION: Xaa = Any Amino Acid

<400> SEQUENCE: 252

Trp Gly Gln Gly Thr Thr Val Thr Val Xaa Ser
1               5                   10

<210> SEQ ID NO 253
<211> LENGTH: 11
<212> TYPE: PRT
<213> ORGANISM: Artificial Sequence
<220> FEATURE:
<223> OTHER INFORMATION: VH FR4
<220> FEATURE:
<221> NAME/KEY: VARIANT
<222> LOCATION: 11
<223> OTHER INFORMATION: Xaa = Any Amino Acid

<400> SEQUENCE: 253

Trp Gly Gln Gly Thr Thr Val Thr Val Ser Xaa
```

<210> SEQ ID NO 254
<211> LENGTH: 23
<212> TYPE: PRT
<213> ORGANISM: Artificial Sequence
<220> FEATURE:
<223> OTHER INFORMATION: VL FR1
<220> FEATURE:
<221> NAME/KEY: VARIANT
<222> LOCATION: 1
<223> OTHER INFORMATION: Xaa = Any Amino Acid
<220> FEATURE:
<221> NAME/KEY: VARIANT
<222> LOCATION: 10
<223> OTHER INFORMATION: Xaa = Phe or Ser

<400> SEQUENCE: 254

Xaa Ile Val Met Thr Gln Ser Pro Ser Xaa Leu Ser Ala Ser Val Gly
1               5                   10                  15

Asp Arg Val Thr Ile Thr Cys
            20

<210> SEQ ID NO 255
<211> LENGTH: 23
<212> TYPE: PRT
<213> ORGANISM: Artificial Sequence
<220> FEATURE:
<223> OTHER INFORMATION: VL FR1
<220> FEATURE:
<221> NAME/KEY: VARIANT
<222> LOCATION: 2
<223> OTHER INFORMATION: Xaa = Any Amino Acid
<220> FEATURE:
<221> NAME/KEY: VARIANT
<222> LOCATION: 10
<223> OTHER INFORMATION: Xaa = Phe or Ser

<400> SEQUENCE: 255

Asp Xaa Val Met Thr Gln Ser Pro Ser Xaa Leu Ser Ala Ser Val Gly
1               5                   10                  15

Asp Arg Val Thr Ile Thr Cys
            20

<210> SEQ ID NO 256
<211> LENGTH: 23
<212> TYPE: PRT
<213> ORGANISM: Artificial Sequence
<220> FEATURE:
<223> OTHER INFORMATION: VL FR1
<220> FEATURE:
<221> NAME/KEY: VARIANT
<222> LOCATION: 3
<223> OTHER INFORMATION: Xaa = Any Amino Acid
<220> FEATURE:
<221> NAME/KEY: VARIANT
<222> LOCATION: 10
<223> OTHER INFORMATION: Xaa = Phe or Ser

<400> SEQUENCE: 256

Asp Ile Xaa Met Thr Gln Ser Pro Ser Xaa Leu Ser Ala Ser Val Gly
1               5                   10                  15

Asp Arg Val Thr Ile Thr Cys
            20

<210> SEQ ID NO 257
<211> LENGTH: 23
<212> TYPE: PRT
<213> ORGANISM: Artificial Sequence

```
<220> FEATURE:
<223> OTHER INFORMATION: VL FR1
<220> FEATURE:
<221> NAME/KEY: VARIANT
<222> LOCATION: 4
<223> OTHER INFORMATION: Xaa = Any Amino Acid
<220> FEATURE:
<221> NAME/KEY: VARIANT
<222> LOCATION: 10
<223> OTHER INFORMATION: Xaa = Phe or Ser

<400> SEQUENCE: 257

Asp Ile Val Xaa Thr Gln Ser Pro Ser Xaa Leu Ser Ala Ser Val Gly
1               5                   10                  15

Asp Arg Val Thr Ile Thr Cys
            20

<210> SEQ ID NO 258
<211> LENGTH: 23
<212> TYPE: PRT
<213> ORGANISM: Artificial Sequence
<220> FEATURE:
<223> OTHER INFORMATION: VL FR1
<220> FEATURE:
<221> NAME/KEY: VARIANT
<222> LOCATION: 5
<223> OTHER INFORMATION: Xaa = Any Amino Acid
<220> FEATURE:
<221> NAME/KEY: VARIANT
<222> LOCATION: 10
<223> OTHER INFORMATION: Xaa = Phe or Ser

<400> SEQUENCE: 258

Asp Ile Val Met Xaa Gln Ser Pro Ser Xaa Leu Ser Ala Ser Val Gly
1               5                   10                  15

Asp Arg Val Thr Ile Thr Cys
            20

<210> SEQ ID NO 259
<211> LENGTH: 23
<212> TYPE: PRT
<213> ORGANISM: Artificial Sequence
<220> FEATURE:
<223> OTHER INFORMATION: VL FR1
<220> FEATURE:
<221> NAME/KEY: VARIANT
<222> LOCATION: 6
<223> OTHER INFORMATION: Xaa = Any Amino Acid
<220> FEATURE:
<221> NAME/KEY: VARIANT
<222> LOCATION: 10
<223> OTHER INFORMATION: Xaa = Phe or Ser

<400> SEQUENCE: 259

Asp Ile Val Met Thr Xaa Ser Pro Ser Xaa Leu Ser Ala Ser Val Gly
1               5                   10                  15

Asp Arg Val Thr Ile Thr Cys
            20

<210> SEQ ID NO 260
<211> LENGTH: 23
<212> TYPE: PRT
<213> ORGANISM: Artificial Sequence
<220> FEATURE:
<223> OTHER INFORMATION: VL FR1
<220> FEATURE:
<221> NAME/KEY: VARIANT
<222> LOCATION: 7
<223> OTHER INFORMATION: Xaa = Any Amino Acid
<220> FEATURE:
```

```
<221> NAME/KEY: VARIANT
<222> LOCATION: 10
<223> OTHER INFORMATION: Xaa = Phe or Ser

<400> SEQUENCE: 260

Asp Ile Val Met Thr Gln Xaa Pro Ser Xaa Leu Ser Ala Ser Val Gly
1               5                   10                  15

Asp Arg Val Thr Ile Thr Cys
            20

<210> SEQ ID NO 261
<211> LENGTH: 23
<212> TYPE: PRT
<213> ORGANISM: Artificial Sequence
<220> FEATURE:
<223> OTHER INFORMATION: VL FR1
<220> FEATURE:
<221> NAME/KEY: VARIANT
<222> LOCATION: 8
<223> OTHER INFORMATION: Xaa = Any Amino Acid
<220> FEATURE:
<221> NAME/KEY: VARIANT
<222> LOCATION: 10
<223> OTHER INFORMATION: Xaa = Phe or Ser

<400> SEQUENCE: 261

Asp Ile Val Met Thr Gln Ser Xaa Ser Xaa Leu Ser Ala Ser Val Gly
1               5                   10                  15

Asp Arg Val Thr Ile Thr Cys
            20

<210> SEQ ID NO 262
<211> LENGTH: 23
<212> TYPE: PRT
<213> ORGANISM: Artificial Sequence
<220> FEATURE:
<223> OTHER INFORMATION: VL FR1
<220> FEATURE:
<221> NAME/KEY: VARIANT
<222> LOCATION: 9
<223> OTHER INFORMATION: Xaa = Any Amino Acid
<220> FEATURE:
<221> NAME/KEY: VARIANT
<222> LOCATION: 10
<223> OTHER INFORMATION: Xaa = Phe or Ser

<400> SEQUENCE: 262

Asp Ile Val Met Thr Gln Ser Pro Xaa Xaa Leu Ser Ala Ser Val Gly
1               5                   10                  15

Asp Arg Val Thr Ile Thr Cys
            20

<210> SEQ ID NO 263
<211> LENGTH: 23
<212> TYPE: PRT
<213> ORGANISM: Artificial Sequence
<220> FEATURE:
<223> OTHER INFORMATION: VL FR1
<220> FEATURE:
<221> NAME/KEY: VARIANT
<222> LOCATION: 10
<223> OTHER INFORMATION: Xaa = Any Amino Acid

<400> SEQUENCE: 263

Asp Ile Val Met Thr Gln Ser Pro Ser Xaa Leu Ser Ala Ser Val Gly
1               5                   10                  15

Asp Arg Val Thr Ile Thr Cys
            20
```

<210> SEQ ID NO 264
<211> LENGTH: 23
<212> TYPE: PRT
<213> ORGANISM: Artificial Sequence
<220> FEATURE:
<223> OTHER INFORMATION: VL FR1
<220> FEATURE:
<221> NAME/KEY: VARIANT
<222> LOCATION: 10
<223> OTHER INFORMATION: Xaa = Phe or Ser
<220> FEATURE:
<221> NAME/KEY: VARIANT
<222> LOCATION: 11
<223> OTHER INFORMATION: Xaa = Any Amino Acid

<400> SEQUENCE: 264

Asp Ile Val Met Thr Gln Ser Pro Ser Xaa Xaa Ser Ala Ser Val Gly
1               5                   10                  15

Asp Arg Val Thr Ile Thr Cys
            20

<210> SEQ ID NO 265
<211> LENGTH: 23
<212> TYPE: PRT
<213> ORGANISM: Artificial Sequence
<220> FEATURE:
<223> OTHER INFORMATION: VL FR1
<220> FEATURE:
<221> NAME/KEY: VARIANT
<222> LOCATION: 10
<223> OTHER INFORMATION: Xaa = Phe or Ser
<220> FEATURE:
<221> NAME/KEY: VARIANT
<222> LOCATION: 12
<223> OTHER INFORMATION: Xaa = Any Amino Acid

<400> SEQUENCE: 265

Asp Ile Val Met Thr Gln Ser Pro Ser Xaa Leu Xaa Ala Ser Val Gly
1               5                   10                  15

Asp Arg Val Thr Ile Thr Cys
            20

<210> SEQ ID NO 266
<211> LENGTH: 23
<212> TYPE: PRT
<213> ORGANISM: Artificial Sequence
<220> FEATURE:
<223> OTHER INFORMATION: VL FR1
<220> FEATURE:
<221> NAME/KEY: VARIANT
<222> LOCATION: 10
<223> OTHER INFORMATION: Xaa = Phe or Ser
<220> FEATURE:
<221> NAME/KEY: VARIANT
<222> LOCATION: 13
<223> OTHER INFORMATION: Xaa = Any Amino Acid

<400> SEQUENCE: 266

Asp Ile Val Met Thr Gln Ser Pro Ser Xaa Leu Ser Xaa Ser Val Gly
1               5                   10                  15

Asp Arg Val Thr Ile Thr Cys
            20

<210> SEQ ID NO 267
<211> LENGTH: 23
<212> TYPE: PRT
<213> ORGANISM: Artificial Sequence
<220> FEATURE:

```
<223> OTHER INFORMATION: VL FR1
<220> FEATURE:
<221> NAME/KEY: VARIANT
<222> LOCATION: 10
<223> OTHER INFORMATION: Xaa = Phe or Ser
<220> FEATURE:
<221> NAME/KEY: VARIANT
<222> LOCATION: 14
<223> OTHER INFORMATION: Xaa = Any Amino Acid

<400> SEQUENCE: 267

Asp Ile Val Met Thr Gln Ser Pro Ser Xaa Leu Ser Ala Xaa Val Gly
1               5                   10                  15

Asp Arg Val Thr Ile Thr Cys
            20

<210> SEQ ID NO 268
<211> LENGTH: 23
<212> TYPE: PRT
<213> ORGANISM: Artificial Sequence
<220> FEATURE:
<223> OTHER INFORMATION: VL FR1
<220> FEATURE:
<221> NAME/KEY: VARIANT
<222> LOCATION: 10
<223> OTHER INFORMATION: Xaa = Phe or Ser
<220> FEATURE:
<221> NAME/KEY: VARIANT
<222> LOCATION: 15
<223> OTHER INFORMATION: Xaa = Any Amino Acid

<400> SEQUENCE: 268

Asp Ile Val Met Thr Gln Ser Pro Ser Xaa Leu Ser Ala Ser Xaa Gly
1               5                   10                  15

Asp Arg Val Thr Ile Thr Cys
            20

<210> SEQ ID NO 269
<211> LENGTH: 23
<212> TYPE: PRT
<213> ORGANISM: Artificial Sequence
<220> FEATURE:
<223> OTHER INFORMATION: VL FR1
<220> FEATURE:
<221> NAME/KEY: VARIANT
<222> LOCATION: 10
<223> OTHER INFORMATION: Xaa = Phe or Ser
<220> FEATURE:
<221> NAME/KEY: VARIANT
<222> LOCATION: 16
<223> OTHER INFORMATION: Xaa = Any Amino Acid

<400> SEQUENCE: 269

Asp Ile Val Met Thr Gln Ser Pro Ser Xaa Leu Ser Ala Ser Val Xaa
1               5                   10                  15

Asp Arg Val Thr Ile Thr Cys
            20

<210> SEQ ID NO 270
<211> LENGTH: 23
<212> TYPE: PRT
<213> ORGANISM: Artificial Sequence
<220> FEATURE:
<223> OTHER INFORMATION: VL FR1
<220> FEATURE:
<221> NAME/KEY: VARIANT
<222> LOCATION: 10
<223> OTHER INFORMATION: Xaa = Phe or Ser
<220> FEATURE:
<221> NAME/KEY: VARIANT
```

<222> LOCATION: 17
<223> OTHER INFORMATION: Xaa = Any Amino Acid

<400> SEQUENCE: 270

Asp Ile Val Met Thr Gln Ser Pro Ser Xaa Leu Ser Ala Ser Val Gly
1               5                   10                  15

Xaa Arg Val Thr Ile Thr Cys
            20

<210> SEQ ID NO 271
<211> LENGTH: 23
<212> TYPE: PRT
<213> ORGANISM: Artificial Sequence
<220> FEATURE:
<223> OTHER INFORMATION: VL FR1
<220> FEATURE:
<221> NAME/KEY: VARIANT
<222> LOCATION: 10
<223> OTHER INFORMATION: Xaa = Phe or Ser
<220> FEATURE:
<221> NAME/KEY: VARIANT
<222> LOCATION: 18
<223> OTHER INFORMATION: Xaa = Any Amino Acid

<400> SEQUENCE: 271

Asp Ile Val Met Thr Gln Ser Pro Ser Xaa Leu Ser Ala Ser Val Gly
1               5                   10                  15

Asp Xaa Val Thr Ile Thr Cys
            20

<210> SEQ ID NO 272
<211> LENGTH: 23
<212> TYPE: PRT
<213> ORGANISM: Artificial Sequence
<220> FEATURE:
<223> OTHER INFORMATION: VL FR1
<220> FEATURE:
<221> NAME/KEY: VARIANT
<222> LOCATION: 10
<223> OTHER INFORMATION: Xaa = Phe or Ser
<220> FEATURE:
<221> NAME/KEY: VARIANT
<222> LOCATION: 19
<223> OTHER INFORMATION: Xaa = Any Amino Acid

<400> SEQUENCE: 272

Asp Ile Val Met Thr Gln Ser Pro Ser Xaa Leu Ser Ala Ser Val Gly
1               5                   10                  15

Asp Arg Xaa Thr Ile Thr Cys
            20

<210> SEQ ID NO 273
<211> LENGTH: 23
<212> TYPE: PRT
<213> ORGANISM: Artificial Sequence
<220> FEATURE:
<223> OTHER INFORMATION: VL FR1
<220> FEATURE:
<221> NAME/KEY: VARIANT
<222> LOCATION: 10
<223> OTHER INFORMATION: Xaa = Phe or Ser
<220> FEATURE:
<221> NAME/KEY: VARIANT
<222> LOCATION: 20
<223> OTHER INFORMATION: Xaa = Any Amino Acid

<400> SEQUENCE: 273

Asp Ile Val Met Thr Gln Ser Pro Ser Xaa Leu Ser Ala Ser Val Gly
1               5                   10                  15

Asp Arg Val Xaa Ile Thr Cys
            20

<210> SEQ ID NO 274
<211> LENGTH: 23
<212> TYPE: PRT
<213> ORGANISM: Artificial Sequence
<220> FEATURE:
<223> OTHER INFORMATION: VL FR1
<220> FEATURE:
<221> NAME/KEY: VARIANT
<222> LOCATION: 10
<223> OTHER INFORMATION: Xaa = Phe or Ser
<220> FEATURE:
<221> NAME/KEY: VARIANT
<222> LOCATION: 21
<223> OTHER INFORMATION: Xaa = Any Amino Acid

<400> SEQUENCE: 274

Asp Ile Val Met Thr Gln Ser Pro Ser Xaa Leu Ser Ala Ser Val Gly
1               5                   10                  15

Asp Arg Val Thr Xaa Thr Cys
            20

<210> SEQ ID NO 275
<211> LENGTH: 23
<212> TYPE: PRT
<213> ORGANISM: Artificial Sequence
<220> FEATURE:
<223> OTHER INFORMATION: VL FR1
<220> FEATURE:
<221> NAME/KEY: VARIANT
<222> LOCATION: 10
<223> OTHER INFORMATION: Xaa = Phe or Ser
<220> FEATURE:
<221> NAME/KEY: VARIANT
<222> LOCATION: 22
<223> OTHER INFORMATION: Xaa = Any Amino Acid

<400> SEQUENCE: 275

Asp Ile Val Met Thr Gln Ser Pro Ser Xaa Leu Ser Ala Ser Val Gly
1               5                   10                  15

Asp Arg Val Thr Ile Xaa Cys
            20

<210> SEQ ID NO 276
<211> LENGTH: 23
<212> TYPE: PRT
<213> ORGANISM: Artificial Sequence
<220> FEATURE:
<223> OTHER INFORMATION: VL FR1
<220> FEATURE:
<221> NAME/KEY: VARIANT
<222> LOCATION: 10
<223> OTHER INFORMATION: Xaa = Phe or Ser
<220> FEATURE:
<221> NAME/KEY: VARIANT
<222> LOCATION: 23
<223> OTHER INFORMATION: Xaa = Any Amino Acid

<400> SEQUENCE: 276

Asp Ile Val Met Thr Gln Ser Pro Ser Xaa Leu Ser Ala Ser Val Gly
1               5                   10                  15

Asp Arg Val Thr Ile Thr Xaa
            20

<210> SEQ ID NO 277
<211> LENGTH: 15

```
<212> TYPE: PRT
<213> ORGANISM: Artificial Sequence
<220> FEATURE:
<223> OTHER INFORMATION: VL FR2
<220> FEATURE:
<221> NAME/KEY: VARIANT
<222> LOCATION: 1
<223> OTHER INFORMATION: Xaa = Any Amino Acid
<220> FEATURE:
<221> NAME/KEY: VARIANT
<222> LOCATION: 12
<223> OTHER INFORMATION: Xaa = Ser or Ala

<400> SEQUENCE: 277

Xaa Tyr Gln Gln Lys Pro Gly Lys Ala Pro Lys Xaa Leu Ile Tyr
1               5                   10                  15

<210> SEQ ID NO 278
<211> LENGTH: 15
<212> TYPE: PRT
<213> ORGANISM: Artificial Sequence
<220> FEATURE:
<223> OTHER INFORMATION: VL FR2
<220> FEATURE:
<221> NAME/KEY: VARIANT
<222> LOCATION: 2
<223> OTHER INFORMATION: Xaa = Any Amino Acid
<220> FEATURE:
<221> NAME/KEY: VARIANT
<222> LOCATION: 12
<223> OTHER INFORMATION: Xaa = Ser or Ala

<400> SEQUENCE: 278

Trp Xaa Gln Gln Lys Pro Gly Lys Ala Pro Lys Xaa Leu Ile Tyr
1               5                   10                  15

<210> SEQ ID NO 279
<211> LENGTH: 15
<212> TYPE: PRT
<213> ORGANISM: Artificial Sequence
<220> FEATURE:
<223> OTHER INFORMATION: VL FR2
<220> FEATURE:
<221> NAME/KEY: VARIANT
<222> LOCATION: 3
<223> OTHER INFORMATION: Xaa = Any Amino Acid
<220> FEATURE:
<221> NAME/KEY: VARIANT
<222> LOCATION: 12
<223> OTHER INFORMATION: Xaa = Ser or Ala

<400> SEQUENCE: 279

Trp Tyr Xaa Gln Lys Pro Gly Lys Ala Pro Lys Xaa Leu Ile Tyr
1               5                   10                  15

<210> SEQ ID NO 280
<211> LENGTH: 15
<212> TYPE: PRT
<213> ORGANISM: Artificial Sequence
<220> FEATURE:
<223> OTHER INFORMATION: VL FR2
<220> FEATURE:
<221> NAME/KEY: VARIANT
<222> LOCATION: 4
<223> OTHER INFORMATION: Xaa = Any Amino Acid
<220> FEATURE:
<221> NAME/KEY: VARIANT
<222> LOCATION: 12
<223> OTHER INFORMATION: Xaa = Ser or Ala

<400> SEQUENCE: 280

Trp Tyr Gln Xaa Lys Pro Gly Lys Ala Pro Lys Xaa Leu Ile Tyr
```

<210> SEQ ID NO 281
<211> LENGTH: 15
<212> TYPE: PRT
<213> ORGANISM: Artificial Sequence
<220> FEATURE:
<223> OTHER INFORMATION: VL FR2
<220> FEATURE:
<221> NAME/KEY: VARIANT
<222> LOCATION: 5
<223> OTHER INFORMATION: Xaa = Any Amino Acid
<220> FEATURE:
<221> NAME/KEY: VARIANT
<222> LOCATION: 12
<223> OTHER INFORMATION: Xaa = Ser or Ala

<400> SEQUENCE: 281

Trp Tyr Gln Gln Xaa Pro Gly Lys Ala Pro Lys Xaa Leu Ile Tyr
1               5                   10                  15

<210> SEQ ID NO 282
<211> LENGTH: 15
<212> TYPE: PRT
<213> ORGANISM: Artificial Sequence
<220> FEATURE:
<223> OTHER INFORMATION: VL FR2
<220> FEATURE:
<221> NAME/KEY: VARIANT
<222> LOCATION: 6
<223> OTHER INFORMATION: Xaa = Any Amino Acid
<220> FEATURE:
<221> NAME/KEY: VARIANT
<222> LOCATION: 12
<223> OTHER INFORMATION: Xaa = Ser or Ala

<400> SEQUENCE: 282

Trp Tyr Gln Gln Lys Xaa Gly Lys Ala Pro Lys Xaa Leu Ile Tyr
1               5                   10                  15

<210> SEQ ID NO 283
<211> LENGTH: 15
<212> TYPE: PRT
<213> ORGANISM: Artificial Sequence
<220> FEATURE:
<223> OTHER INFORMATION: VL FR2
<220> FEATURE:
<221> NAME/KEY: VARIANT
<222> LOCATION: 7
<223> OTHER INFORMATION: Xaa = Any Amino Acid
<220> FEATURE:
<221> NAME/KEY: VARIANT
<222> LOCATION: 12
<223> OTHER INFORMATION: Xaa = Ser or Ala

<400> SEQUENCE: 283

Trp Tyr Gln Gln Lys Pro Xaa Lys Ala Pro Lys Xaa Leu Ile Tyr
1               5                   10                  15

<210> SEQ ID NO 284
<211> LENGTH: 15
<212> TYPE: PRT
<213> ORGANISM: Artificial Sequence
<220> FEATURE:
<223> OTHER INFORMATION: VL FR2
<220> FEATURE:
<221> NAME/KEY: VARIANT
<222> LOCATION: 8
<223> OTHER INFORMATION: Xaa = Any Amino Acid
<220> FEATURE:
<221> NAME/KEY: VARIANT
<222> LOCATION: 12

<223> OTHER INFORMATION: Xaa = Ser or Ala

<400> SEQUENCE: 284

Trp Tyr Gln Gln Lys Pro Gly Xaa Ala Pro Lys Xaa Leu Ile Tyr
1               5                   10                  15

<210> SEQ ID NO 285
<211> LENGTH: 15
<212> TYPE: PRT
<213> ORGANISM: Artificial Sequence
<220> FEATURE:
<223> OTHER INFORMATION: VL FR2
<220> FEATURE:
<221> NAME/KEY: VARIANT
<222> LOCATION: 9
<223> OTHER INFORMATION: Xaa = Any Amino Acid
<220> FEATURE:
<221> NAME/KEY: VARIANT
<222> LOCATION: 12
<223> OTHER INFORMATION: Xaa = Ser or Ala

<400> SEQUENCE: 285

Trp Tyr Gln Gln Lys Pro Gly Lys Xaa Pro Lys Xaa Leu Ile Tyr
1               5                   10                  15

<210> SEQ ID NO 286
<211> LENGTH: 15
<212> TYPE: PRT
<213> ORGANISM: Artificial Sequence
<220> FEATURE:
<223> OTHER INFORMATION: VL FR2
<220> FEATURE:
<221> NAME/KEY: VARIANT
<222> LOCATION: 10
<223> OTHER INFORMATION: Xaa = Any Amino Acid
<220> FEATURE:
<221> NAME/KEY: VARIANT
<222> LOCATION: 12
<223> OTHER INFORMATION: Xaa = Ser or Ala

<400> SEQUENCE: 286

Trp Tyr Gln Gln Lys Pro Gly Lys Ala Xaa Lys Xaa Leu Ile Tyr
1               5                   10                  15

<210> SEQ ID NO 287
<211> LENGTH: 15
<212> TYPE: PRT
<213> ORGANISM: Artificial Sequence
<220> FEATURE:
<223> OTHER INFORMATION: VL FR2
<220> FEATURE:
<221> NAME/KEY: VARIANT
<222> LOCATION: 11
<223> OTHER INFORMATION: Xaa = Any Amino Acid
<220> FEATURE:
<221> NAME/KEY: VARIANT
<222> LOCATION: 12
<223> OTHER INFORMATION: Xaa = Ser or Ala

<400> SEQUENCE: 287

Trp Tyr Gln Gln Lys Pro Gly Lys Ala Pro Xaa Xaa Leu Ile Tyr
1               5                   10                  15

<210> SEQ ID NO 288
<211> LENGTH: 15
<212> TYPE: PRT
<213> ORGANISM: Artificial Sequence
<220> FEATURE:
<223> OTHER INFORMATION: VL FR2
<220> FEATURE:
<221> NAME/KEY: VARIANT

```
<222> LOCATION: 12
<223> OTHER INFORMATION: Xaa = Any Amino Acid

<400> SEQUENCE: 288

Trp Tyr Gln Gln Lys Pro Gly Lys Ala Pro Lys Xaa Leu Ile Tyr
1               5                   10                  15

<210> SEQ ID NO 289
<211> LENGTH: 15
<212> TYPE: PRT
<213> ORGANISM: Artificial Sequence
<220> FEATURE:
<223> OTHER INFORMATION: VL FR2
<220> FEATURE:
<221> NAME/KEY: VARIANT
<222> LOCATION: 12
<223> OTHER INFORMATION: Xaa = Ser or Ala
<220> FEATURE:
<221> NAME/KEY: VARIANT
<222> LOCATION: 13
<223> OTHER INFORMATION: Xaa = Any Amino Acid

<400> SEQUENCE: 289

Trp Tyr Gln Gln Lys Pro Gly Lys Ala Pro Lys Xaa Xaa Ile Tyr
1               5                   10                  15

<210> SEQ ID NO 290
<211> LENGTH: 15
<212> TYPE: PRT
<213> ORGANISM: Artificial Sequence
<220> FEATURE:
<223> OTHER INFORMATION: VL FR2
<220> FEATURE:
<221> NAME/KEY: VARIANT
<222> LOCATION: 12
<223> OTHER INFORMATION: Xaa = Ser or Ala
<220> FEATURE:
<221> NAME/KEY: VARIANT
<222> LOCATION: 14
<223> OTHER INFORMATION: Xaa = Any Amino Acid

<400> SEQUENCE: 290

Trp Tyr Gln Gln Lys Pro Gly Lys Ala Pro Lys Xaa Leu Xaa Tyr
1               5                   10                  15

<210> SEQ ID NO 291
<211> LENGTH: 15
<212> TYPE: PRT
<213> ORGANISM: Artificial Sequence
<220> FEATURE:
<223> OTHER INFORMATION: VL FR2
<220> FEATURE:
<221> NAME/KEY: VARIANT
<222> LOCATION: 12
<223> OTHER INFORMATION: Xaa = Ser or Ala
<220> FEATURE:
<221> NAME/KEY: VARIANT
<222> LOCATION: 15
<223> OTHER INFORMATION: Xaa = Any Amino Acid

<400> SEQUENCE: 291

Trp Tyr Gln Gln Lys Pro Gly Lys Ala Pro Lys Xaa Leu Ile Xaa
1               5                   10                  15

<210> SEQ ID NO 292
<211> LENGTH: 32
<212> TYPE: PRT
<213> ORGANISM: Artificial Sequence
<220> FEATURE:
<223> OTHER INFORMATION: VL FR3
<220> FEATURE:
```

<221> NAME/KEY: VARIANT
<222> LOCATION: 1
<223> OTHER INFORMATION: Xaa = Any Amino Acid
<220> FEATURE:
<221> NAME/KEY: VARIANT
<222> LOCATION: 7
<223> OTHER INFORMATION: Xaa = Ser or Thr
<220> FEATURE:
<221> NAME/KEY: VARIANT
<222> LOCATION: 24
<223> OTHER INFORMATION: Xaa = Pro or Ser
<220> FEATURE:
<221> NAME/KEY: VARIANT
<222> LOCATION: 29
<223> OTHER INFORMATION: Xaa = Asp or Thr
<220> FEATURE:
<221> NAME/KEY: VARIANT
<222> LOCATION: 31
<223> OTHER INFORMATION: Xaa = Phe or Tyr

<400> SEQUENCE: 292

Xaa Val Pro Asp Arg Phe Xaa Gly Ser Gly Ser Gly Thr Asp Phe Thr
1               5                   10                  15

Leu Thr Ile Ser Ser Leu Gln Xaa Glu Asp Phe Ala Xaa Tyr Xaa Cys
            20                  25                  30

<210> SEQ ID NO 293
<211> LENGTH: 32
<212> TYPE: PRT
<213> ORGANISM: Artificial Sequence
<220> FEATURE:
<223> OTHER INFORMATION: VL FR3
<220> FEATURE:
<221> NAME/KEY: VARIANT
<222> LOCATION: 2
<223> OTHER INFORMATION: Xaa = Any Amino Acid
<220> FEATURE:
<221> NAME/KEY: VARIANT
<222> LOCATION: 7
<223> OTHER INFORMATION: Xaa = Ser or Thr
<220> FEATURE:
<221> NAME/KEY: VARIANT
<222> LOCATION: 24
<223> OTHER INFORMATION: Xaa = Pro or Ser
<220> FEATURE:
<221> NAME/KEY: VARIANT
<222> LOCATION: 29
<223> OTHER INFORMATION: Xaa = Asp or Thr
<220> FEATURE:
<221> NAME/KEY: VARIANT
<222> LOCATION: 31
<223> OTHER INFORMATION: Xaa = Phe or Tyr

<400> SEQUENCE: 293

Gly Xaa Pro Asp Arg Phe Xaa Gly Ser Gly Ser Gly Thr Asp Phe Thr
1               5                   10                  15

Leu Thr Ile Ser Ser Leu Gln Xaa Glu Asp Phe Ala Xaa Tyr Xaa Cys
            20                  25                  30

<210> SEQ ID NO 294
<211> LENGTH: 32
<212> TYPE: PRT
<213> ORGANISM: Artificial Sequence
<220> FEATURE:
<223> OTHER INFORMATION: VL FR3
<220> FEATURE:
<221> NAME/KEY: VARIANT
<222> LOCATION: 3
<223> OTHER INFORMATION: Xaa = Any Amino Acid
<220> FEATURE:
<221> NAME/KEY: VARIANT
<222> LOCATION: 7
<223> OTHER INFORMATION: Xaa = Ser or Thr

```
<220> FEATURE:
<221> NAME/KEY: VARIANT
<222> LOCATION: 24
<223> OTHER INFORMATION: Xaa = Pro or Ser
<220> FEATURE:
<221> NAME/KEY: VARIANT
<222> LOCATION: 29
<223> OTHER INFORMATION: Xaa = Asp or Thr
<220> FEATURE:
<221> NAME/KEY: VARIANT
<222> LOCATION: 31
<223> OTHER INFORMATION: Xaa = Phe  or Tyr

<400> SEQUENCE: 294

Gly Val Xaa Asp Arg Phe Xaa Gly Ser Gly Ser Gly Thr Asp Phe Thr
1               5                   10                  15

Leu Thr Ile Ser Ser Leu Gln Xaa Glu Asp Phe Ala Xaa Tyr Xaa Cys
            20                  25                  30

<210> SEQ ID NO 295
<211> LENGTH: 32
<212> TYPE: PRT
<213> ORGANISM: Artificial Sequence
<220> FEATURE:
<223> OTHER INFORMATION: VL FR3
<220> FEATURE:
<221> NAME/KEY: VARIANT
<222> LOCATION: 4
<223> OTHER INFORMATION: Xaa = Any Amino Acid
<220> FEATURE:
<221> NAME/KEY: VARIANT
<222> LOCATION: 7
<223> OTHER INFORMATION: Xaa = Ser or Thr
<220> FEATURE:
<221> NAME/KEY: VARIANT
<222> LOCATION: 24
<223> OTHER INFORMATION: Xaa = Pro or Ser
<220> FEATURE:
<221> NAME/KEY: VARIANT
<222> LOCATION: 29
<223> OTHER INFORMATION: Xaa = Asp or Thr
<220> FEATURE:
<221> NAME/KEY: VARIANT
<222> LOCATION: 31
<223> OTHER INFORMATION: Xaa = Phe  or Tyr

<400> SEQUENCE: 295

Gly Val Pro Xaa Arg Phe Xaa Gly Ser Gly Ser Gly Thr Asp Phe Thr
1               5                   10                  15

Leu Thr Ile Ser Ser Leu Gln Xaa Glu Asp Phe Ala Xaa Tyr Xaa Cys
            20                  25                  30

<210> SEQ ID NO 296
<211> LENGTH: 32
<212> TYPE: PRT
<213> ORGANISM: Artificial Sequence
<220> FEATURE:
<223> OTHER INFORMATION: VL FR3
<220> FEATURE:
<221> NAME/KEY: VARIANT
<222> LOCATION: 5
<223> OTHER INFORMATION: Xaa = Any Amino Acid
<220> FEATURE:
<221> NAME/KEY: VARIANT
<222> LOCATION: 7
<223> OTHER INFORMATION: Xaa = Ser or Thr
<220> FEATURE:
<221> NAME/KEY: VARIANT
<222> LOCATION: 24
<223> OTHER INFORMATION: Xaa = Pro or Ser
<220> FEATURE:
<221> NAME/KEY: VARIANT
<222> LOCATION: 29
```

```
<223> OTHER INFORMATION: Xaa = Asp or Thr
<220> FEATURE:
<221> NAME/KEY: VARIANT
<222> LOCATION: 31
<223> OTHER INFORMATION: Xaa = Phe or Tyr

<400> SEQUENCE: 296

Gly Val Pro Asp Xaa Phe Xaa Gly Ser Gly Ser Gly Thr Asp Phe Thr
1               5                   10                  15

Leu Thr Ile Ser Ser Leu Gln Xaa Glu Asp Phe Ala Xaa Tyr Xaa Cys
            20                  25                  30

<210> SEQ ID NO 297
<211> LENGTH: 32
<212> TYPE: PRT
<213> ORGANISM: Artificial Sequence
<220> FEATURE:
<223> OTHER INFORMATION: VL FR3
<220> FEATURE:
<221> NAME/KEY: VARIANT
<222> LOCATION: 6
<223> OTHER INFORMATION: Xaa = Any Amino Acid
<220> FEATURE:
<221> NAME/KEY: VARIANT
<222> LOCATION: 7
<223> OTHER INFORMATION: Xaa = Ser or Thr
<220> FEATURE:
<221> NAME/KEY: VARIANT
<222> LOCATION: 24
<223> OTHER INFORMATION: Xaa = Pro or Ser
<220> FEATURE:
<221> NAME/KEY: VARIANT
<222> LOCATION: 29
<223> OTHER INFORMATION: Xaa = Asp or Thr
<220> FEATURE:
<221> NAME/KEY: VARIANT
<222> LOCATION: 31
<223> OTHER INFORMATION: Xaa = Phe or Tyr

<400> SEQUENCE: 297

Gly Val Pro Asp Arg Xaa Xaa Gly Ser Gly Ser Gly Thr Asp Phe Thr
1               5                   10                  15

Leu Thr Ile Ser Ser Leu Gln Xaa Glu Asp Phe Ala Xaa Tyr Xaa Cys
            20                  25                  30

<210> SEQ ID NO 298
<211> LENGTH: 32
<212> TYPE: PRT
<213> ORGANISM: Artificial Sequence
<220> FEATURE:
<223> OTHER INFORMATION: VL FR3
<220> FEATURE:
<221> NAME/KEY: VARIANT
<222> LOCATION: 7
<223> OTHER INFORMATION: Xaa = Any Amino Acid
<220> FEATURE:
<221> NAME/KEY: VARIANT
<222> LOCATION: 24
<223> OTHER INFORMATION: Xaa = Pro or Ser
<220> FEATURE:
<221> NAME/KEY: VARIANT
<222> LOCATION: 29
<223> OTHER INFORMATION: Xaa = Asp or Thr
<220> FEATURE:
<221> NAME/KEY: VARIANT
<222> LOCATION: 31
<223> OTHER INFORMATION: Xaa = Phe or Tyr

<400> SEQUENCE: 298

Gly Val Pro Asp Arg Phe Xaa Gly Ser Gly Ser Gly Thr Asp Phe Thr
1               5                   10                  15
```

Leu Thr Ile Ser Ser Leu Gln Xaa Glu Asp Phe Ala Xaa Tyr Xaa Cys
            20                  25                  30

<210> SEQ ID NO 299
<211> LENGTH: 32
<212> TYPE: PRT
<213> ORGANISM: Artificial Sequence
<220> FEATURE:
<223> OTHER INFORMATION: VL FR3
<220> FEATURE:
<221> NAME/KEY: VARIANT
<222> LOCATION: 7
<223> OTHER INFORMATION: Xaa = Ser or Thr
<220> FEATURE:
<221> NAME/KEY: VARIANT
<222> LOCATION: 8
<223> OTHER INFORMATION: Xaa = Any Amino Acid
<220> FEATURE:
<221> NAME/KEY: VARIANT
<222> LOCATION: 24
<223> OTHER INFORMATION: Xaa = Pro or Ser
<220> FEATURE:
<221> NAME/KEY: VARIANT
<222> LOCATION: 29
<223> OTHER INFORMATION: Xaa = Asp or Thr
<220> FEATURE:
<221> NAME/KEY: VARIANT
<222> LOCATION: 31
<223> OTHER INFORMATION: Xaa = Phe or Tyr

<400> SEQUENCE: 299

Gly Val Pro Asp Arg Phe Xaa Xaa Ser Gly Ser Gly Thr Asp Phe Thr
1               5                   10                  15

Leu Thr Ile Ser Ser Leu Gln Xaa Glu Asp Phe Ala Xaa Tyr Xaa Cys
            20                  25                  30

<210> SEQ ID NO 300
<211> LENGTH: 32
<212> TYPE: PRT
<213> ORGANISM: Artificial Sequence
<220> FEATURE:
<223> OTHER INFORMATION: VL FR3
<220> FEATURE:
<221> NAME/KEY: VARIANT
<222> LOCATION: 7
<223> OTHER INFORMATION: Xaa = Ser or Thr
<220> FEATURE:
<221> NAME/KEY: VARIANT
<222> LOCATION: 9
<223> OTHER INFORMATION: Xaa = Any Amino Acid
<220> FEATURE:
<221> NAME/KEY: VARIANT
<222> LOCATION: 24
<223> OTHER INFORMATION: Xaa = Pro or Ser
<220> FEATURE:
<221> NAME/KEY: VARIANT
<222> LOCATION: 29
<223> OTHER INFORMATION: Xaa = Asp or Thr
<220> FEATURE:
<221> NAME/KEY: VARIANT
<222> LOCATION: 31
<223> OTHER INFORMATION: Xaa = Phe or Tyr

<400> SEQUENCE: 300

Gly Val Pro Asp Arg Phe Xaa Gly Xaa Gly Ser Gly Thr Asp Phe Thr
1               5                   10                  15

Leu Thr Ile Ser Ser Leu Gln Xaa Glu Asp Phe Ala Xaa Tyr Xaa Cys
            20                  25                  30

<210> SEQ ID NO 301
<211> LENGTH: 32
<212> TYPE: PRT

```
<213> ORGANISM: Artificial Sequence
<220> FEATURE:
<223> OTHER INFORMATION: VL FR3
<220> FEATURE:
<221> NAME/KEY: VARIANT
<222> LOCATION: 7
<223> OTHER INFORMATION: Xaa = Ser or Thr
<220> FEATURE:
<221> NAME/KEY: VARIANT
<222> LOCATION: 10
<223> OTHER INFORMATION: Xaa = Any Amino Acid
<220> FEATURE:
<221> NAME/KEY: VARIANT
<222> LOCATION: 24
<223> OTHER INFORMATION: Xaa = Pro or Ser
<220> FEATURE:
<221> NAME/KEY: VARIANT
<222> LOCATION: 29
<223> OTHER INFORMATION: Xaa = Asp or Thr
<220> FEATURE:
<221> NAME/KEY: VARIANT
<222> LOCATION: 31
<223> OTHER INFORMATION: Xaa = Phe or Tyr

<400> SEQUENCE: 301

Gly Val Pro Asp Arg Phe Xaa Gly Ser Xaa Ser Gly Thr Asp Phe Thr
1               5                   10                  15

Leu Thr Ile Ser Ser Leu Gln Xaa Glu Asp Phe Ala Xaa Tyr Xaa Cys
            20                  25                  30

<210> SEQ ID NO 302
<211> LENGTH: 32
<212> TYPE: PRT
<213> ORGANISM: Artificial Sequence
<220> FEATURE:
<223> OTHER INFORMATION: VL FR3
<220> FEATURE:
<221> NAME/KEY: VARIANT
<222> LOCATION: 7
<223> OTHER INFORMATION: Xaa = Ser or Thr
<220> FEATURE:
<221> NAME/KEY: VARIANT
<222> LOCATION: 11
<223> OTHER INFORMATION: Xaa = Any Amino Acid
<220> FEATURE:
<221> NAME/KEY: VARIANT
<222> LOCATION: 24
<223> OTHER INFORMATION: Xaa = Pro or Ser
<220> FEATURE:
<221> NAME/KEY: VARIANT
<222> LOCATION: 29
<223> OTHER INFORMATION: Xaa = Asp or Thr
<220> FEATURE:
<221> NAME/KEY: VARIANT
<222> LOCATION: 31
<223> OTHER INFORMATION: Xaa = Phe or Tyr

<400> SEQUENCE: 302

Gly Val Pro Asp Arg Phe Xaa Gly Ser Gly Xaa Gly Thr Asp Phe Thr
1               5                   10                  15

Leu Thr Ile Ser Ser Leu Gln Xaa Glu Asp Phe Ala Xaa Tyr Xaa Cys
            20                  25                  30

<210> SEQ ID NO 303
<211> LENGTH: 32
<212> TYPE: PRT
<213> ORGANISM: Artificial Sequence
<220> FEATURE:
<223> OTHER INFORMATION: VL FR3
<220> FEATURE:
<221> NAME/KEY: VARIANT
<222> LOCATION: 7
<223> OTHER INFORMATION: Xaa = Ser or Thr
```

```
<220> FEATURE:
<221> NAME/KEY: VARIANT
<222> LOCATION: 12
<223> OTHER INFORMATION: Xaa = Any Amino Acid
<220> FEATURE:
<221> NAME/KEY: VARIANT
<222> LOCATION: 24
<223> OTHER INFORMATION: Xaa = Pro or Ser
<220> FEATURE:
<221> NAME/KEY: VARIANT
<222> LOCATION: 29
<223> OTHER INFORMATION: Xaa = Asp or Thr
<220> FEATURE:
<221> NAME/KEY: VARIANT
<222> LOCATION: 31
<223> OTHER INFORMATION: Xaa = Phe  or Tyr

<400> SEQUENCE: 303

Gly Val Pro Asp Arg Phe Xaa Gly Ser Gly Ser Xaa Thr Asp Phe Thr
 1               5                  10                  15

Leu Thr Ile Ser Ser Leu Gln Xaa Glu Asp Phe Ala Xaa Tyr Xaa Cys
            20                  25                  30

<210> SEQ ID NO 304
<211> LENGTH: 32
<212> TYPE: PRT
<213> ORGANISM: Artificial Sequence
<220> FEATURE:
<223> OTHER INFORMATION: VL FR3
<220> FEATURE:
<221> NAME/KEY: VARIANT
<222> LOCATION: 7
<223> OTHER INFORMATION: Xaa = Ser or Thr
<220> FEATURE:
<221> NAME/KEY: VARIANT
<222> LOCATION: 13
<223> OTHER INFORMATION: Xaa = Any Amino Acid
<220> FEATURE:
<221> NAME/KEY: VARIANT
<222> LOCATION: 24
<223> OTHER INFORMATION: Xaa = Pro or Ser
<220> FEATURE:
<221> NAME/KEY: VARIANT
<222> LOCATION: 29
<223> OTHER INFORMATION: Xaa = Asp or Thr
<220> FEATURE:
<221> NAME/KEY: VARIANT
<222> LOCATION: 31
<223> OTHER INFORMATION: Xaa = Phe  or Tyr

<400> SEQUENCE: 304

Gly Val Pro Asp Arg Phe Xaa Gly Ser Gly Ser Gly Xaa Asp Phe Thr
 1               5                  10                  15

Leu Thr Ile Ser Ser Leu Gln Xaa Glu Asp Phe Ala Xaa Tyr Xaa Cys
            20                  25                  30

<210> SEQ ID NO 305
<211> LENGTH: 32
<212> TYPE: PRT
<213> ORGANISM: Artificial Sequence
<220> FEATURE:
<223> OTHER INFORMATION: VL FR3
<220> FEATURE:
<221> NAME/KEY: VARIANT
<222> LOCATION: 7
<223> OTHER INFORMATION: Xaa = Ser or Thr
<220> FEATURE:
<221> NAME/KEY: VARIANT
<222> LOCATION: 14
<223> OTHER INFORMATION: Xaa = Any Amino Acid
<220> FEATURE:
<221> NAME/KEY: VARIANT
<222> LOCATION: 24
```

```
<223> OTHER INFORMATION: Xaa = Pro or Ser
<220> FEATURE:
<221> NAME/KEY: VARIANT
<222> LOCATION: 29
<223> OTHER INFORMATION: Xaa = Asp or Thr
<220> FEATURE:
<221> NAME/KEY: VARIANT
<222> LOCATION: 31
<223> OTHER INFORMATION: Xaa = Phe  or Tyr

<400> SEQUENCE: 305

Gly Val Pro Asp Arg Phe Xaa Gly Ser Gly Ser Gly Thr Xaa Phe Thr
1               5                   10                  15

Leu Thr Ile Ser Ser Leu Gln Xaa Glu Asp Phe Ala Xaa Tyr Xaa Cys
            20                  25                  30

<210> SEQ ID NO 306
<211> LENGTH: 32
<212> TYPE: PRT
<213> ORGANISM: Artificial Sequence
<220> FEATURE:
<223> OTHER INFORMATION: VL FR3
<220> FEATURE:
<221> NAME/KEY: VARIANT
<222> LOCATION: 7
<223> OTHER INFORMATION: Xaa = Ser or Thr
<220> FEATURE:
<221> NAME/KEY: VARIANT
<222> LOCATION: 15
<223> OTHER INFORMATION: Xaa = Any Amino Acid
<220> FEATURE:
<221> NAME/KEY: VARIANT
<222> LOCATION: 24
<223> OTHER INFORMATION: Xaa = Pro or Ser
<220> FEATURE:
<221> NAME/KEY: VARIANT
<222> LOCATION: 29
<223> OTHER INFORMATION: Xaa = Asp or Thr
<220> FEATURE:
<221> NAME/KEY: VARIANT
<222> LOCATION: 31
<223> OTHER INFORMATION: Xaa = Phe  or Tyr

<400> SEQUENCE: 306

Gly Val Pro Asp Arg Phe Xaa Gly Ser Gly Ser Gly Thr Asp Xaa Thr
1               5                   10                  15

Leu Thr Ile Ser Ser Leu Gln Xaa Glu Asp Phe Ala Xaa Tyr Xaa Cys
            20                  25                  30

<210> SEQ ID NO 307
<211> LENGTH: 32
<212> TYPE: PRT
<213> ORGANISM: Artificial Sequence
<220> FEATURE:
<223> OTHER INFORMATION: VL FR3
<220> FEATURE:
<221> NAME/KEY: VARIANT
<222> LOCATION: 7
<223> OTHER INFORMATION: Xaa = Ser or Thr
<220> FEATURE:
<221> NAME/KEY: VARIANT
<222> LOCATION: 16
<223> OTHER INFORMATION: Xaa = Any Amino Acid
<220> FEATURE:
<221> NAME/KEY: VARIANT
<222> LOCATION: 24
<223> OTHER INFORMATION: Xaa = Pro or Ser
<220> FEATURE:
<221> NAME/KEY: VARIANT
<222> LOCATION: 29
<223> OTHER INFORMATION: Xaa = Asp or Thr
<220> FEATURE:
<221> NAME/KEY: VARIANT
```

```
<222> LOCATION: 31
<223> OTHER INFORMATION: Xaa = Phe or Tyr

<400> SEQUENCE: 307

Gly Val Pro Asp Arg Phe Xaa Gly Ser Gly Ser Gly Thr Asp Phe Xaa
1               5                   10                  15

Leu Thr Ile Ser Ser Leu Gln Xaa Glu Asp Phe Ala Xaa Tyr Xaa Cys
            20                  25                  30

<210> SEQ ID NO 308
<211> LENGTH: 32
<212> TYPE: PRT
<213> ORGANISM: Artificial Sequence
<220> FEATURE:
<223> OTHER INFORMATION: VL FR3
<220> FEATURE:
<221> NAME/KEY: VARIANT
<222> LOCATION: 7
<223> OTHER INFORMATION: Xaa = Ser or Thr
<220> FEATURE:
<221> NAME/KEY: VARIANT
<222> LOCATION: 17
<223> OTHER INFORMATION: Xaa = Any Amino Acid
<220> FEATURE:
<221> NAME/KEY: VARIANT
<222> LOCATION: 24
<223> OTHER INFORMATION: Xaa = Pro or Ser
<220> FEATURE:
<221> NAME/KEY: VARIANT
<222> LOCATION: 29
<223> OTHER INFORMATION: Xaa = Asp or Thr
<220> FEATURE:
<221> NAME/KEY: VARIANT
<222> LOCATION: 31
<223> OTHER INFORMATION: Xaa = Phe or Tyr

<400> SEQUENCE: 308

Gly Val Pro Asp Arg Phe Xaa Gly Ser Gly Ser Gly Thr Asp Phe Thr
1               5                   10                  15

Xaa Thr Ile Ser Ser Leu Gln Xaa Glu Asp Phe Ala Xaa Tyr Xaa Cys
            20                  25                  30

<210> SEQ ID NO 309
<211> LENGTH: 32
<212> TYPE: PRT
<213> ORGANISM: Artificial Sequence
<220> FEATURE:
<223> OTHER INFORMATION: VL FR3
<220> FEATURE:
<221> NAME/KEY: VARIANT
<222> LOCATION: 7
<223> OTHER INFORMATION: Xaa = Ser or Thr
<220> FEATURE:
<221> NAME/KEY: VARIANT
<222> LOCATION: 18
<223> OTHER INFORMATION: Xaa = Any Amino Acid
<220> FEATURE:
<221> NAME/KEY: VARIANT
<222> LOCATION: 24
<223> OTHER INFORMATION: Xaa = Pro or Ser
<220> FEATURE:
<221> NAME/KEY: VARIANT
<222> LOCATION: 29
<223> OTHER INFORMATION: Xaa = Asp or Thr
<220> FEATURE:
<221> NAME/KEY: VARIANT
<222> LOCATION: 31
<223> OTHER INFORMATION: Xaa = Phe or Tyr

<400> SEQUENCE: 309

Gly Val Pro Asp Arg Phe Xaa Gly Ser Gly Ser Gly Thr Asp Phe Thr
1               5                   10                  15
```

```
Leu Xaa Ile Ser Ser Leu Gln Xaa Glu Asp Phe Ala Xaa Tyr Xaa Cys
        20                  25                  30

<210> SEQ ID NO 310
<211> LENGTH: 32
<212> TYPE: PRT
<213> ORGANISM: Artificial Sequence
<220> FEATURE:
<223> OTHER INFORMATION: VL FR3
<220> FEATURE:
<221> NAME/KEY: VARIANT
<222> LOCATION: 7
<223> OTHER INFORMATION: Xaa = Ser or Thr
<220> FEATURE:
<221> NAME/KEY: VARIANT
<222> LOCATION: 19
<223> OTHER INFORMATION: Xaa = Any Amino Acid
<220> FEATURE:
<221> NAME/KEY: VARIANT
<222> LOCATION: 24
<223> OTHER INFORMATION: Xaa = Pro or Ser
<220> FEATURE:
<221> NAME/KEY: VARIANT
<222> LOCATION: 29
<223> OTHER INFORMATION: Xaa = Asp or Thr
<220> FEATURE:
<221> NAME/KEY: VARIANT
<222> LOCATION: 31
<223> OTHER INFORMATION: Xaa = Phe  or Tyr

<400> SEQUENCE: 310

Gly Val Pro Asp Arg Phe Xaa Gly Ser Gly Ser Gly Thr Asp Phe Thr
1               5                   10                  15

Leu Thr Xaa Ser Ser Leu Gln Xaa Glu Asp Phe Ala Xaa Tyr Xaa Cys
        20                  25                  30

<210> SEQ ID NO 311
<211> LENGTH: 32
<212> TYPE: PRT
<213> ORGANISM: Artificial Sequence
<220> FEATURE:
<223> OTHER INFORMATION: VL FR3
<220> FEATURE:
<221> NAME/KEY: VARIANT
<222> LOCATION: 7
<223> OTHER INFORMATION: Xaa = Ser or Thr
<220> FEATURE:
<221> NAME/KEY: VARIANT
<222> LOCATION: 20
<223> OTHER INFORMATION: Xaa = Any Amino Acid
<220> FEATURE:
<221> NAME/KEY: VARIANT
<222> LOCATION: 24
<223> OTHER INFORMATION: Xaa = Pro or Ser
<220> FEATURE:
<221> NAME/KEY: VARIANT
<222> LOCATION: 29
<223> OTHER INFORMATION: Xaa = Asp or Thr
<220> FEATURE:
<221> NAME/KEY: VARIANT
<222> LOCATION: 31
<223> OTHER INFORMATION: Xaa = Phe  or Tyr

<400> SEQUENCE: 311

Gly Val Pro Asp Arg Phe Xaa Gly Ser Gly Ser Gly Thr Asp Phe Thr
1               5                   10                  15

Leu Thr Ile Xaa Ser Leu Gln Xaa Glu Asp Phe Ala Xaa Tyr Xaa Cys
        20                  25                  30

<210> SEQ ID NO 312
<211> LENGTH: 32
```

```
<212> TYPE: PRT
<213> ORGANISM: Artificial Sequence
<220> FEATURE:
<223> OTHER INFORMATION: VL FR3
<220> FEATURE:
<221> NAME/KEY: VARIANT
<222> LOCATION: 7
<223> OTHER INFORMATION: Xaa = Ser or Thr
<220> FEATURE:
<221> NAME/KEY: VARIANT
<222> LOCATION: 21
<223> OTHER INFORMATION: Xaa = Any Amino Acid
<220> FEATURE:
<221> NAME/KEY: VARIANT
<222> LOCATION: 24
<223> OTHER INFORMATION: Xaa = Pro or Ser
<220> FEATURE:
<221> NAME/KEY: VARIANT
<222> LOCATION: 29
<223> OTHER INFORMATION: Xaa = Asp or Thr
<220> FEATURE:
<221> NAME/KEY: VARIANT
<222> LOCATION: 31
<223> OTHER INFORMATION: Xaa = Phe  or Tyr

<400> SEQUENCE: 312

Gly Val Pro Asp Arg Phe Xaa Gly Ser Gly Ser Gly Thr Asp Phe Thr
1               5                   10                  15

Leu Thr Ile Ser Xaa Leu Gln Xaa Glu Asp Phe Ala Xaa Tyr Xaa Cys
                20                  25                  30

<210> SEQ ID NO 313
<211> LENGTH: 32
<212> TYPE: PRT
<213> ORGANISM: Artificial Sequence
<220> FEATURE:
<223> OTHER INFORMATION: VL FR3
<220> FEATURE:
<221> NAME/KEY: VARIANT
<222> LOCATION: 7
<223> OTHER INFORMATION: Xaa = Ser or Thr
<220> FEATURE:
<221> NAME/KEY: VARIANT
<222> LOCATION: 22
<223> OTHER INFORMATION: Xaa = Any Amino Acid
<220> FEATURE:
<221> NAME/KEY: VARIANT
<222> LOCATION: 24
<223> OTHER INFORMATION: Xaa = Pro or Ser
<220> FEATURE:
<221> NAME/KEY: VARIANT
<222> LOCATION: 29
<223> OTHER INFORMATION: Xaa = Asp or Thr
<220> FEATURE:
<221> NAME/KEY: VARIANT
<222> LOCATION: 31
<223> OTHER INFORMATION: Xaa = Phe  or Tyr

<400> SEQUENCE: 313

Gly Val Pro Asp Arg Phe Xaa Gly Ser Gly Ser Gly Thr Asp Phe Thr
1               5                   10                  15

Leu Thr Ile Ser Ser Xaa Gln Xaa Glu Asp Phe Ala Xaa Tyr Xaa Cys
                20                  25                  30

<210> SEQ ID NO 314
<211> LENGTH: 32
<212> TYPE: PRT
<213> ORGANISM: Artificial Sequence
<220> FEATURE:
<223> OTHER INFORMATION: VL FR3
<220> FEATURE:
<221> NAME/KEY: VARIANT
<222> LOCATION: 7
```

```
<223> OTHER INFORMATION: Xaa = Ser or Thr
<220> FEATURE:
<221> NAME/KEY: VARIANT
<222> LOCATION: 23
<223> OTHER INFORMATION: Xaa = Any Amino Acid
<220> FEATURE:
<221> NAME/KEY: VARIANT
<222> LOCATION: 24
<223> OTHER INFORMATION: Xaa = Pro or Ser
<220> FEATURE:
<221> NAME/KEY: VARIANT
<222> LOCATION: 29
<223> OTHER INFORMATION: Xaa = Asp or Thr
<220> FEATURE:
<221> NAME/KEY: VARIANT
<222> LOCATION: 31
<223> OTHER INFORMATION: Xaa = Phe or Tyr

<400> SEQUENCE: 314

Gly Val Pro Asp Arg Phe Xaa Gly Ser Gly Ser Gly Thr Asp Phe Thr
1               5                   10                  15

Leu Thr Ile Ser Ser Leu Xaa Xaa Glu Asp Phe Ala Xaa Tyr Xaa Cys
            20                  25                  30

<210> SEQ ID NO 315
<211> LENGTH: 32
<212> TYPE: PRT
<213> ORGANISM: Artificial Sequence
<220> FEATURE:
<223> OTHER INFORMATION: VL FR3
<220> FEATURE:
<221> NAME/KEY: VARIANT
<222> LOCATION: 7
<223> OTHER INFORMATION: Xaa = Ser or Thr
<220> FEATURE:
<221> NAME/KEY: VARIANT
<222> LOCATION: 24
<223> OTHER INFORMATION: Xaa = Any Amino Acid
<220> FEATURE:
<221> NAME/KEY: VARIANT
<222> LOCATION: 29
<223> OTHER INFORMATION: Xaa = Asp or Thr
<220> FEATURE:
<221> NAME/KEY: VARIANT
<222> LOCATION: 31
<223> OTHER INFORMATION: Xaa = Phe or Tyr

<400> SEQUENCE: 315

Gly Val Pro Asp Arg Phe Xaa Gly Ser Gly Ser Gly Thr Asp Phe Thr
1               5                   10                  15

Leu Thr Ile Ser Ser Leu Gln Xaa Glu Asp Phe Ala Xaa Tyr Xaa Cys
            20                  25                  30

<210> SEQ ID NO 316
<211> LENGTH: 32
<212> TYPE: PRT
<213> ORGANISM: Artificial Sequence
<220> FEATURE:
<223> OTHER INFORMATION: VL FR3
<220> FEATURE:
<221> NAME/KEY: VARIANT
<222> LOCATION: 7
<223> OTHER INFORMATION: Xaa = Ser or Thr
<220> FEATURE:
<221> NAME/KEY: VARIANT
<222> LOCATION: 24
<223> OTHER INFORMATION: Xaa = Pro or Ser
<220> FEATURE:
<221> NAME/KEY: VARIANT
<222> LOCATION: 25
<223> OTHER INFORMATION: Xaa = Any Amino Acid
<220> FEATURE:
<221> NAME/KEY: VARIANT
```

<222> LOCATION: 29
<223> OTHER INFORMATION: Xaa = Asp or Thr
<220> FEATURE:
<221> NAME/KEY: VARIANT
<222> LOCATION: 31
<223> OTHER INFORMATION: Xaa = Phe or Tyr

<400> SEQUENCE: 316

Gly Val Pro Asp Arg Phe Xaa Gly Ser Gly Ser Gly Thr Asp Phe Thr
1               5                   10                  15

Leu Thr Ile Ser Ser Leu Gln Xaa Xaa Asp Phe Ala Xaa Tyr Xaa Cys
            20                  25                  30

<210> SEQ ID NO 317
<211> LENGTH: 32
<212> TYPE: PRT
<213> ORGANISM: Artificial Sequence
<220> FEATURE:
<223> OTHER INFORMATION: VL FR3
<220> FEATURE:
<221> NAME/KEY: VARIANT
<222> LOCATION: 7
<223> OTHER INFORMATION: Xaa = Ser or Thr
<220> FEATURE:
<221> NAME/KEY: VARIANT
<222> LOCATION: 24
<223> OTHER INFORMATION: Xaa = Pro or Ser
<220> FEATURE:
<221> NAME/KEY: VARIANT
<222> LOCATION: 26
<223> OTHER INFORMATION: Xaa = Any Amino Acid
<220> FEATURE:
<221> NAME/KEY: VARIANT
<222> LOCATION: 29
<223> OTHER INFORMATION: Xaa = Asp or Thr
<220> FEATURE:
<221> NAME/KEY: VARIANT
<222> LOCATION: 31
<223> OTHER INFORMATION: Xaa = Phe or Tyr

<400> SEQUENCE: 317

Gly Val Pro Asp Arg Phe Xaa Gly Ser Gly Ser Gly Thr Asp Phe Thr
1               5                   10                  15

Leu Thr Ile Ser Ser Leu Gln Xaa Glu Xaa Phe Ala Xaa Tyr Xaa Cys
            20                  25                  30

<210> SEQ ID NO 318
<211> LENGTH: 32
<212> TYPE: PRT
<213> ORGANISM: Artificial Sequence
<220> FEATURE:
<223> OTHER INFORMATION: VL FR3
<220> FEATURE:
<221> NAME/KEY: VARIANT
<222> LOCATION: 7
<223> OTHER INFORMATION: Xaa = Ser or Thr
<220> FEATURE:
<221> NAME/KEY: VARIANT
<222> LOCATION: 24
<223> OTHER INFORMATION: Xaa = Pro or Ser
<220> FEATURE:
<221> NAME/KEY: VARIANT
<222> LOCATION: 27
<223> OTHER INFORMATION: Xaa = Any Amino Acid
<220> FEATURE:
<221> NAME/KEY: VARIANT
<222> LOCATION: 29
<223> OTHER INFORMATION: Xaa = Asp or Thr
<220> FEATURE:
<221> NAME/KEY: VARIANT
<222> LOCATION: 31
<223> OTHER INFORMATION: Xaa = Phe or Tyr

<400> SEQUENCE: 318

Gly Val Pro Asp Arg Phe Xaa Gly Ser Gly Ser Gly Thr Asp Phe Thr
1               5                   10                  15

Leu Thr Ile Ser Ser Leu Gln Xaa Glu Asp Xaa Ala Xaa Tyr Xaa Cys
            20                  25                  30

<210> SEQ ID NO 319
<211> LENGTH: 32
<212> TYPE: PRT
<213> ORGANISM: Artificial Sequence
<220> FEATURE:
<223> OTHER INFORMATION: VL FR3
<220> FEATURE:
<221> NAME/KEY: VARIANT
<222> LOCATION: 7
<223> OTHER INFORMATION: Xaa = Ser or Thr
<220> FEATURE:
<221> NAME/KEY: VARIANT
<222> LOCATION: 24
<223> OTHER INFORMATION: Xaa = Pro or Ser
<220> FEATURE:
<221> NAME/KEY: VARIANT
<222> LOCATION: 28
<223> OTHER INFORMATION: Xaa = Any Amino Acid
<220> FEATURE:
<221> NAME/KEY: VARIANT
<222> LOCATION: 29
<223> OTHER INFORMATION: Xaa = Asp or Thr
<220> FEATURE:
<221> NAME/KEY: VARIANT
<222> LOCATION: 31
<223> OTHER INFORMATION: Xaa = Phe or Tyr

<400> SEQUENCE: 319

Gly Val Pro Asp Arg Phe Xaa Gly Ser Gly Ser Gly Thr Asp Phe Thr
1               5                   10                  15

Leu Thr Ile Ser Ser Leu Gln Xaa Glu Asp Phe Xaa Xaa Tyr Xaa Cys
            20                  25                  30

<210> SEQ ID NO 320
<211> LENGTH: 32
<212> TYPE: PRT
<213> ORGANISM: Artificial Sequence
<220> FEATURE:
<223> OTHER INFORMATION: VL FR3
<220> FEATURE:
<221> NAME/KEY: VARIANT
<222> LOCATION: 7
<223> OTHER INFORMATION: Xaa = Ser or Thr
<220> FEATURE:
<221> NAME/KEY: VARIANT
<222> LOCATION: 24
<223> OTHER INFORMATION: Xaa = Pro or Ser
<220> FEATURE:
<221> NAME/KEY: VARIANT
<222> LOCATION: 29
<223> OTHER INFORMATION: Xaa = Any Amino Acid
<220> FEATURE:
<221> NAME/KEY: VARIANT
<222> LOCATION: 31
<223> OTHER INFORMATION: Xaa = Phe or Tyr

<400> SEQUENCE: 320

Gly Val Pro Asp Arg Phe Xaa Gly Ser Gly Ser Gly Thr Asp Phe Thr
1               5                   10                  15

Leu Thr Ile Ser Ser Leu Gln Xaa Glu Asp Phe Ala Xaa Tyr Xaa Cys
            20                  25                  30

<210> SEQ ID NO 321
<211> LENGTH: 32

```
<212> TYPE: PRT
<213> ORGANISM: Artificial Sequence
<220> FEATURE:
<223> OTHER INFORMATION: VL FR3
<220> FEATURE:
<221> NAME/KEY: VARIANT
<222> LOCATION: 7
<223> OTHER INFORMATION: Xaa = Ser or Thr
<220> FEATURE:
<221> NAME/KEY: VARIANT
<222> LOCATION: 24
<223> OTHER INFORMATION: Xaa = Pro or Ser
<220> FEATURE:
<221> NAME/KEY: VARIANT
<222> LOCATION: 29
<223> OTHER INFORMATION: Xaa = Asp or Thr
<220> FEATURE:
<221> NAME/KEY: VARIANT
<222> LOCATION: 30
<223> OTHER INFORMATION: Xaa = Any Amino Acid
<220> FEATURE:
<221> NAME/KEY: VARIANT
<222> LOCATION: 31
<223> OTHER INFORMATION: Xaa = Phe  or Tyr

<400> SEQUENCE: 321

Gly Val Pro Asp Arg Phe Xaa Gly Ser Gly Ser Gly Thr Asp Phe Thr
1               5                   10                  15

Leu Thr Ile Ser Ser Leu Gln Xaa Glu Asp Phe Ala Xaa Xaa Xaa Cys
            20                  25                  30

<210> SEQ ID NO 322
<211> LENGTH: 32
<212> TYPE: PRT
<213> ORGANISM: Artificial Sequence
<220> FEATURE:
<223> OTHER INFORMATION: VL FR3
<220> FEATURE:
<221> NAME/KEY: VARIANT
<222> LOCATION: 7
<223> OTHER INFORMATION: Xaa = Ser or Thr
<220> FEATURE:
<221> NAME/KEY: VARIANT
<222> LOCATION: 24
<223> OTHER INFORMATION: Xaa = Pro or Ser
<220> FEATURE:
<221> NAME/KEY: VARIANT
<222> LOCATION: 29
<223> OTHER INFORMATION: Xaa = Asp or Thr
<220> FEATURE:
<221> NAME/KEY: VARIANT
<222> LOCATION: 31
<223> OTHER INFORMATION: Xaa = Any Amino Acid

<400> SEQUENCE: 322

Gly Val Pro Asp Arg Phe Xaa Gly Ser Gly Ser Gly Thr Asp Phe Thr
1               5                   10                  15

Leu Thr Ile Ser Ser Leu Gln Xaa Glu Asp Phe Ala Xaa Tyr Xaa Cys
            20                  25                  30

<210> SEQ ID NO 323
<211> LENGTH: 32
<212> TYPE: PRT
<213> ORGANISM: Artificial Sequence
<220> FEATURE:
<223> OTHER INFORMATION: VL FR3
<220> FEATURE:
<221> NAME/KEY: VARIANT
<222> LOCATION: 7
<223> OTHER INFORMATION: Xaa = Ser or Thr
<220> FEATURE:
<221> NAME/KEY: VARIANT
<222> LOCATION: 24
```

```
<223> OTHER INFORMATION: Xaa = Pro or Ser
<220> FEATURE:
<221> NAME/KEY: VARIANT
<222> LOCATION: 29
<223> OTHER INFORMATION: Xaa = Asp or Thr
<220> FEATURE:
<221> NAME/KEY: VARIANT
<222> LOCATION: 31
<223> OTHER INFORMATION: Xaa = Phe or Tyr
<220> FEATURE:
<221> NAME/KEY: VARIANT
<222> LOCATION: 32
<223> OTHER INFORMATION: Xaa = Any Amino Acid

<400> SEQUENCE: 323

Gly Val Pro Asp Arg Phe Xaa Gly Ser Gly Ser Gly Thr Asp Phe Thr
1               5                   10                  15

Leu Thr Ile Ser Ser Leu Gln Xaa Glu Asp Phe Ala Xaa Tyr Xaa Xaa
            20                  25                  30

<210> SEQ ID NO 324
<211> LENGTH: 10
<212> TYPE: PRT
<213> ORGANISM: Artificial Sequence
<220> FEATURE:
<223> OTHER INFORMATION: VL FR4
<220> FEATURE:
<221> NAME/KEY: VARIANT
<222> LOCATION: 1
<223> OTHER INFORMATION: Xaa = Any Amino Acid

<400> SEQUENCE: 324

Xaa Gly Gly Gly Thr Lys Val Glu Ile Lys
1               5                   10

<210> SEQ ID NO 325
<211> LENGTH: 10
<212> TYPE: PRT
<213> ORGANISM: Artificial Sequence
<220> FEATURE:
<223> OTHER INFORMATION: VL FR4
<220> FEATURE:
<221> NAME/KEY: VARIANT
<222> LOCATION: 2
<223> OTHER INFORMATION: Xaa = Any Amino Acid

<400> SEQUENCE: 325

Phe Xaa Gly Gly Thr Lys Val Glu Ile Lys
1               5                   10

<210> SEQ ID NO 326
<211> LENGTH: 10
<212> TYPE: PRT
<213> ORGANISM: Artificial Sequence
<220> FEATURE:
<223> OTHER INFORMATION: VL FR4
<220> FEATURE:
<221> NAME/KEY: VARIANT
<222> LOCATION: 3
<223> OTHER INFORMATION: Xaa = Any Amino Acid

<400> SEQUENCE: 326

Phe Gly Xaa Gly Thr Lys Val Glu Ile Lys
1               5                   10

<210> SEQ ID NO 327
<211> LENGTH: 10
<212> TYPE: PRT
<213> ORGANISM: Artificial Sequence
<220> FEATURE:
```

```
<223> OTHER INFORMATION: VL FR4
<220> FEATURE:
<221> NAME/KEY: VARIANT
<222> LOCATION: 4
<223> OTHER INFORMATION: Xaa = Any Amino Acid

<400> SEQUENCE: 327

Phe Gly Gly Xaa Thr Lys Val Glu Ile Lys
1               5                   10

<210> SEQ ID NO 328
<211> LENGTH: 10
<212> TYPE: PRT
<213> ORGANISM: Artificial Sequence
<220> FEATURE:
<223> OTHER INFORMATION: VL FR4
<220> FEATURE:
<221> NAME/KEY: VARIANT
<222> LOCATION: 5
<223> OTHER INFORMATION: Xaa = Any Amino Acid

<400> SEQUENCE: 328

Phe Gly Gly Gly Xaa Lys Val Glu Ile Lys
1               5                   10

<210> SEQ ID NO 329
<211> LENGTH: 10
<212> TYPE: PRT
<213> ORGANISM: Artificial Sequence
<220> FEATURE:
<223> OTHER INFORMATION: VL FR4
<220> FEATURE:
<221> NAME/KEY: VARIANT
<222> LOCATION: 6
<223> OTHER INFORMATION: Xaa = Any Amino Acid

<400> SEQUENCE: 329

Phe Gly Gly Gly Thr Xaa Val Glu Ile Lys
1               5                   10

<210> SEQ ID NO 330
<211> LENGTH: 10
<212> TYPE: PRT
<213> ORGANISM: Artificial Sequence
<220> FEATURE:
<223> OTHER INFORMATION: VL FR4
<220> FEATURE:
<221> NAME/KEY: VARIANT
<222> LOCATION: 7
<223> OTHER INFORMATION: Xaa = Any Amino Acid

<400> SEQUENCE: 330

Phe Gly Gly Gly Thr Lys Xaa Glu Ile Lys
1               5                   10

<210> SEQ ID NO 331
<211> LENGTH: 10
<212> TYPE: PRT
<213> ORGANISM: Artificial Sequence
<220> FEATURE:
<223> OTHER INFORMATION: VL FR4
<220> FEATURE:
<221> NAME/KEY: VARIANT
<222> LOCATION: 8
<223> OTHER INFORMATION: Xaa = Any Amino Acid

<400> SEQUENCE: 331

Phe Gly Gly Gly Thr Lys Val Xaa Ile Lys
1               5                   10
```

```
<210> SEQ ID NO 332
<211> LENGTH: 10
<212> TYPE: PRT
<213> ORGANISM: Artificial Sequence
<220> FEATURE:
<223> OTHER INFORMATION: VL FR4
<220> FEATURE:
<221> NAME/KEY: VARIANT
<222> LOCATION: 9
<223> OTHER INFORMATION: Xaa = Any Amino Acid

<400> SEQUENCE: 332

Phe Gly Gly Gly Thr Lys Val Glu Xaa Lys
1               5                   10

<210> SEQ ID NO 333
<211> LENGTH: 10
<212> TYPE: PRT
<213> ORGANISM: Artificial Sequence
<220> FEATURE:
<223> OTHER INFORMATION: VL FR4
<220> FEATURE:
<221> NAME/KEY: VARIANT
<222> LOCATION: 10
<223> OTHER INFORMATION: Xaa = Any Amino Acid

<400> SEQUENCE: 333

Phe Gly Gly Gly Thr Lys Val Glu Ile Xaa
1               5                   10
```

METHODS OF TREATING BY ADMINISTERING ANTI-KIT ANTIBODIES

This application is a divisional application of U.S. patent application Ser. No. 15/433,482, filed Feb. 15, 2017, which is a divisional application of U.S. patent application Ser. No. 15/084,715, filed Mar. 30, 2016, which is a divisional application of U.S. patent application Ser. No. 13/949,931, filed Jul. 24, 2013, which claims the benefit, under 35 U.S.C. § 119(e), of U.S. Provisional Application No. 61/675,751 filed on Jul. 25, 2012 and U.S. Provisional Application No. 61/675,762 filed on Jul. 25, 2012; the foregoing applications are hereby incorporated by reference in their entireties.

The instant application contains a Sequence Listing, which is being concurrently submitted as an ASCII text file named "Sequence_Listing_12638-059-999.TXT", created Jul. 24, 2013, and being 151,683 bytes in size. The Sequence Listing is hereby incorporated by reference in its entirety.

1. FIELD

Provided herein are antibodies that specifically bind to a KIT polypeptide, antigen-binding fragments thereof, conjugates of such antibodies, polynucleotides encoding such antibodies, vectors and host cells for producing such antibodies, kits and pharmaceutical compositions comprising antibodies that immunospecifically bind to a KIT antigen, uses and methods for treating or managing a KIT-associated disorder, and diagnostic methods.

2. BACKGROUND

KIT (or c-Kit) is a type III receptor tyrosine kinase encoded by the c-kit gene. KIT comprises five extracellular immunoglobulin (Ig)-like domains, a single transmembrane region, an inhibitory cytoplasmic juxtamembrane domain, and a split cytoplasmic kinase domain separated by a kinase insert segment (see, e.g., Yarden et al., Nature, 1986, 323: 226-232; Ullrich and Schlessinger, Cell, 1990, 61:203-212; Clifford et al., J. Biol. Chem., 2003, 278:31461-31464). The human c-kit gene encoding the KIT receptor has been cloned as described by Yarden et al., EMBO J., 1987, 6:3341-3351. KIT is also known as CD117 or stem cell factor receptor ("SCFR"), because it is the receptor for the stem cell factor ("SCF") ligand (also known as Steel Factor or Kit Ligand). SCF ligand binding to the first three extracellular Ig-like domains of KIT induces receptor dimerization, and thereby activates intrinsic tyrosine kinase activity through the phosphorylation of specific tyrosine residues in the juxtamembrane and kinase domains (see, e.g., Weiss and Schlessinger, Cell, 1998, 94:277-280; Clifford et al., J. Biol. Chem., 2003, 278:31461-31464). Members of the Stat, Src, ERK, and AKT signaling pathways have been shown to be downstream signal transducers of KIT signaling.

The fourth (D4) and fifth (D5) extracellular Ig-like domains of KIT are believed to mediate receptor dimerization (see, e.g., International Patent Application Publication No. WO 2008/153926; Yuzawa et al., Cell, 2007, 130:323-334).

Expression of KIT has been detected in various cell types, such as mast cells, stem cells, brain cells, melanoblasts, ovary cells, and cancer cells (e.g., leukemia cells). Studies of loss-of-function KIT mutations indicate that KIT is important for the normal growth of hematopoietic progenitor cells, mast cells, melanocytes, primordial germ cells, and the interstitial cells of Cajal (see, e.g., Besmer, P., Curr. Opin. Cell Biol., 1991, 3:939-946; Lyman et al., Blood, 1998, 91:1101-1134; Ashman, L. K., Int. J. Biochem. Cell Biol., 1999, 31:1037-1051; Kitamura et al., Mutat. Res., 2001, 477:165-171; Mol et al., J. Biol. Chem., 2003, 278:31461-31464). Moreover, KIT plays an important role in hematopoiesis, melanogenesis, and gametogenesis (see Ueda et al., Blood, 2002, 99:3342-3349).

Abnormal KIT activity has been implicated in connection with a number of cancers. For example, gain-of-function KIT mutations resulting in SCF-independent, constitutive activation of KIT are found in certain cancer cells and are associated with certain cancers such as leukemia (e.g., chronic myelogenous leukemia) and gastrointestinal stromal tumors (see, e.g., Mol et al., J. Biol. Chem., 2003, 278: 31461-31464).

3. SUMMARY

Provided herein, in one aspect, are antibodies, antigen-binding fragments thereof, and conjugates thereof, that immunospecifically bind to a domain 4 (D4) (or D4 region) of the extracellular domain of KIT (e.g., human KIT) and inhibit a KIT activity, as well as related compositions, reagents and methods.

In one aspect, provided herein is an antibody, or an antigen binding fragment thereof, which immunospecifically binds to a D4 of human KIT, comprising:
(i) a light chain variable region ("VL") comprising a VL CDR1, VL CDR2, and VL CDR3 having the amino acid sequences of SEQ ID NO: 19, SEQ ID NO: 20, and SEQ ID NO: 21, respectively; and
(ii) a heavy chain variable region ("VH") comprising VH CDR1, VH CDR2, and VH CDR3 having the amino acid sequences of SEQ ID NO: 16, SEQ ID NO: 17, and SEQ ID NO: 18, respectively.

In one embodiment, the VL and VH of an antibody provided herein or an antigen-binding fragment thereof are non-immunogenic in a human. In a particular embodiment, the antibody can be expressed in Chinese hamster ovary (CHO) cells at a titer of at least 0.45 µg/mL. In a particular embodiment, the antibody can be expressed in Chinese hamster ovary (CHO) cells at a titer of at least 0.3 µg/mL, at least 0.6 µg/mL, at least 0.75 µg/mL, or at least 1 µg/mL.

In a certain aspect, provided herein is antibody, or an antigen-binding fragment thereof, or a conjugate thereof, which immunospecifically binds to a D4 of human KIT, comprising:
a light chain variable region ("VL") comprising the amino acid sequence: DIVMTQSPSX$_{K1}$LSASVGDRVTITCKASQN VRTNVAWYQQKPGKAPKX$_{K2}$LIYSAS YRYSGVPDRFX$_{K3}$GSGSGTDFTLTIS SLQX$_{K4}$EDFAX$_{K5}$YX$_{K6}$CQQYNSYPRTFGGGT KVEIK (SEQ ID NO: 12), wherein X$_{K1}$ is an amino acid with an aromatic or aliphatic hydroxyl side chain, X$_{K2}$ is an amino acid with an aliphatic or aliphatic hydroxyl side chain, X$_{K3}$ is an amino acid with an aliphatic hydroxyl side chain, X$_{K4}$ is an amino acid with an aliphatic hydroxyl side chain or is P, X$_{K5}$ is an amino acid with a charged or acidic side chain, and X$_{K6}$ is an amino acid with an aromatic side chain; and
a heavy chain variable region ("VH") comprising a VH CDR1, VH CDR2, and VH CDR3 comprising the amino acid sequences of SEQ ID NO: 16, SEQ ID NO: 17, and SEQ ID NO: 18, respectively.

In a particular aspect, provided herein is antibody (or a fragment thereof or a conjugate thereof), which immunospecifically binds to a D4 of human KIT, comprising:

(i) a VL comprising a VL CDR1, VL CDR2, and VL CDR3 having the amino acid sequences of SEQ ID NO: 19, SEQ ID NO: 20, and SEQ ID NO: 21, respectively; and (ii) a VH comprising the amino acid sequence: QVQLVQSGAEX$_{H1}$KKPGASVKX$_{H2}$SCKASGY TFTDYYINWVX$_{H3}$QAPGKGLEWIA RIYPGSGNTYYNEKFKGRX$_{H4}$TX$_{H5}$TAX$_{H6}$KST STAYMX$_{H7}$LSSLRSEDX$_{H8}$AVYFCA RGVYYFDY-WGQGTTVTVSS (SEQ ID NO: 11), wherein X$_{H1}$ is an amino acid with an aliphatic side chain, X$_{H2}$ is an amino acid with an aliphatic side chain, X$_{H3}$ is an amino acid with a polar or basic side chain, X$_{H4}$ is an amino acid with an aliphatic side chain, X$_{H5}$ is an amino acid with an aliphatic side chain, X$_{H6}$ is an amino acid with an acidic side chain, X$_{H7}$ is an amino acid with an acidic or amide derivative side chain, and X$_{H8}$ is an amino acid with an aliphatic hydroxyl side chain.

In a particular embodiment, X$_{K1}$ is the amino acid F or S, X$_{K2}$ is the amino acid A or S, X$_{K3}$ is the amino acid T or S, X$_{K4}$ is the amino acid S or P, X$_{K5}$ is the amino acid D or T, and X$_{K6}$ is the amino acid F or Y.

In a certain embodiment, X$_{K1}$ is the amino acid S, X$_{K2}$ is the amino acid A, X$_{K3}$ is the amino acid T, X$_{K4}$ is the amino acid P, X$_{K5}$ is the amino acid D, and X$_{K6}$ is the amino acid F.

In a particular embodiment, X$_{K1}$ is the amino acid F, X$_{K2}$ is the amino acid A, X$_{K3}$ is the amino acid T, X$_{K4}$ is the amino acid S, X$_{K5}$ is the amino acid D, and X$_{K6}$ is the amino acid F.

In a particular embodiment, X$_{K1}$ is the amino acid F or S, X$_{K2}$ is the amino acid A, X$_{K3}$ is the amino acid T, X$_{K4}$ is the amino acid S or P, X$_{K5}$ is the amino acid D, and X$_{K6}$ is the amino acid F.

In a particular embodiment, X$_{K1}$ is the amino acid S, X$_{K2}$ is the amino acid A, X$_{K3}$ is the amino acid T, X$_{K4}$ is the amino acid P, X$_{K5}$ is the amino acid D, and X$_{K6}$ is the amino acid F.

In a particular embodiment, X$_{K1}$ is the amino acid S, X$_{K2}$ is the amino acid S, X$_{K3}$ is the amino acid S, X$_{K4}$ is the amino acid P, X$_{K5}$ is the amino acid T, and X$_{K6}$ is the amino acid Y.

In one embodiment, X$_{H1}$ is the amino acid L or V, X$_{H2}$ is the amino acid L or V, X$_{H3}$ is the amino acid K or R, X$_{H4}$ is the amino acid V or A, X$_{H5}$ is the amino acid L or I, X$_{H6}$ is the amino acid E or D, X$_{H7}$ is the amino acid Q or E, and X$_{H8}$ is the amino acid S or T.

In a specific embodiment, X$_{H1}$ is the amino acid V, X$_{H2}$ is the amino acid L or V, X$_{H3}$ is the amino acid R or Q, X$_{H4}$ is the amino acid A, X$_{H5}$ is the amino acid L or I, X$_{H6}$ is the amino acid D, X$_{H7}$ is the amino acid Q or E, and X$_{H8}$ is the amino acid T.

In a specific embodiment, X$_{H1}$ is the amino acid V, X$_{H2}$ is the amino acid L, X$_{H3}$ is the amino acid R, X$_{H4}$ is the amino acid A, X$_{H5}$ is the amino acid L, X$_{H6}$ is the amino acid D, X$_{H7}$ is the amino acid Q, and X$_{H8}$ is the amino acid T.

In a certain embodiment, X$_{H1}$ is the amino acid V, X$_{H2}$ is the amino acid V, X$_{H3}$ is the amino acid R, X$_{H4}$ is the amino acid A, X$_{H5}$ is the amino acid I, X$_{H6}$ is the amino acid D, X$_{H7}$ is the amino acid E, and X$_{H8}$ is the amino acid T.

In a certain embodiment, X$_{H1}$ is the amino acid L, X$_{H2}$ is the amino acid L, X$_{H3}$ is the amino acid K, X$_{H4}$ is the amino acid A, X$_{H5}$ is the amino acid L, X$_{H6}$ is the amino acid E, X$_{H7}$ is the amino acid Q, and X$_{H8}$ is the amino acid S.

In a certain embodiment, X$_{H1}$ is the amino acid V, X$_{H2}$ is the amino acid L, X$_{H3}$ is the amino acid K, X$_{H4}$ is the amino acid A, X$_{H5}$ is the amino acid L, X$_{H6}$ is the amino acid E, X$_{H7}$ is the amino acid Q, and X$_{H8}$ is the amino acid T.

In a certain embodiment, X$_{H1}$ is the amino acid V, X$_{H2}$ is the amino acid V, X$_{H3}$ is the amino acid R, X$_{H4}$ is the amino acid V, X$_{H5}$ is the amino acid I, X$_{H6}$ is the amino acid D, X$_{H7}$ is the amino acid E, and X$_{H8}$ is the amino acid T.

In a particular embodiment, X$_{K1}$ to X$_{K6}$ is an amino acid set forth in Table 6A, and/or X$_{H1}$ to X$_{H8}$ is an amino acid set forth in Table 6B.

In a particular aspect, provided herein is antibody, or an antigen-binding fragment thereof, or a conjugate thereof, which immunospecifically binds to a D4 of human KIT, comprising:

i) a VL comprising an amino acid sequence that is: at least 90% identical to SEQ ID NO: 7, at least 88% identical to SEQ ID NO: 8, at least 87% identical to SEQ ID NO: 9, or at least 84% identical to SEQ ID NO: 10; and ii) a VH comprising an amino acid sequence that is: at least 93% identical to SEQ ID NO: 2, at least 92% identical to SEQ ID NO: 3, at least 90% identical to SEQ ID NO: 4, at least 87% identical to SEQ ID NO: 5, or at least 86% identical to SEQ ID NO: 6.

In a certain aspect, provided herein is antibody, or an antigen-binding fragment thereof, or a conjugate thereof, which immunospecifically binds to a D4 region of human KIT, comprising:

i) a light chain variable region ("VL") comprising the amino acid sequence: DIVMTQSPSX$_{K1}$LSASVGDRVTITCKASQN VRTNVAWYQQKPGKAPKX$_{K2}$LIYSAS YRYSGVPDRFX$_{K3}$GSGSGTDFTLTISSLQX$_{K4}$EDF AX$_{K5}$YX$_{K6}$CQQYNSYPRTFGGG TKVEIK (SEQ ID NO: 12), wherein X$_{K1}$ is an amino acid with an aromatic or aliphatic hydroxyl side chain, X$_{K2}$ is an amino acid with an aliphatic or aliphatic hydroxyl side chain, X$_{K3}$ is an amino acid with an aliphatic hydroxyl side chain, X$_{K4}$ is an amino acid with an aliphatic hydroxyl side chain or is P, X$_{K5}$ is an amino acid with a charged or acidic side chain, and X$_{K6}$ is an amino acid with an aromatic side chain; and (ii) a VH comprising the amino acid sequence: QVQLVQSGAEX$_{H1}$KKPGASVKX$_{H2}$SCKASGYT FTDYYINWVX$_{H3}$QAPGKGLEWIA RIYPGSGNTYYNEKFKGRX$_{H4}$TX$_{H5}$TAX$_{H6}$KSTS TAYMX$_{H7}$LSSLRSEDX$_{H8}$AVYFCA RGVYYFDY-WGQGTTVTVSS (SEQ ID NO: 11), wherein X$_{H1}$ is an amino acid with an aliphatic side chain, X$_{H2}$ is an amino acid with an aliphatic side chain, X$_{H3}$ is an amino acid with a polar or basic side chain, X$_{H4}$ is an amino acid with an aliphatic side chain, X$_{H5}$ is an amino acid with an aliphatic side chain, X$_{H6}$ is an amino acid with an acidic side chain, X$_{H7}$ an amino acid with an acidic or amide derivative side chain, and X$_{H8}$ is an amino acid with an aliphatic hydroxyl side chain.

In a particular embodiment, X$_{K1}$ to X$_{K6}$ is an amino acid set forth in Table 6A, and/or X$_{H1}$ to X$_{H8}$ is an amino acid set forth in Table 6B.

In a particular embodiment, an antibody described herein specifically binds to CHO cells recombinantly expressing wild-type KIT with an EC$_{50}$ of about 150 pM or less as determined by flow cytometry. In a particular embodiment, an antibody described herein specifically binds to a recombinant D4/D5 region of human KIT with an EC$_{50}$ of about 600 pM or less, or about 250 pM to about 600 pM, as determined by flow cytometry. In a certain embodiment, an antibody described herein inhibits tyrosine phosphorylation of KIT with an $IC_{50}$ of about 600 pM or less as determined by ELISA.

In a specific embodiment, an antibody described herein can be expressed in CHO cells with a titer of at least 1.0 μg/mL, or at least 1.1 μg/mL, or at least 1.2 μg/mL.

In a particular embodiment, an antibody described herein further comprises a human light chain constant region and a human heavy chain constant region. In one embodiment, the human light chain constant region of an antibody described herein is a human kappa light chain constant region. In a particular embodiment, the human heavy chain constant region of an antibody described herein is a human gamma heavy chain constant region.

In a certain embodiment, an antibody described herein is a human IgG1 or IgG4 antibody. In a certain embodiment, an antibody described herein is an antigen-binding fragment or a Fab fragment. In a specific embodiment, an antibody described herein is an antigen-binding fragment or a Fab fragment. In a particular embodiment, an antibody described herein is a bispecific antibody. In a certain embodiment, an antibody described herein is internalized by a cell.

In a particular aspect, provided herein is a conjugate comprising an antibody described herein, or a KIT-binding fragment thereof, linked to an agent. In a specific embodiment, the agent is a toxin. In a certain embodiment, the toxin is abrin, ricin A, pseudomonas exotoxin, cholera toxin, or diphtheria toxin. In one embodiment, the conjugate is internalized by a cell.

In a certain aspect, provided herein is a pharmaceutical composition comprising a conjugate described herein and a pharmaceutically acceptable carrier.

In another aspect, provided herein is a pharmaceutical composition comprising an antibody described herein and a pharmaceutically acceptable carrier.

In a particular aspect, provided herein is a polynucleotide comprising nucleotide sequences encoding a VH chain region, a VL chain region, or both a VL chain region and a VH chain region, of an antibody described herein.

In a specific embodiment, a polynucleotide (e.g., isolated polynucleotide) provided herein comprises SEQ ID NO: 22, 23, 24, 25, or 26 encoding a VH. In a certain embodiment, a polynucleotide (e.g., isolated polynucleotide) provided herein comprises SEQ ID NO: 27, 28, 29, or 30 encoding a VL. In a particular embodiment, a polynucleotide (e.g., isolated polynucleotide) or a population of polynucleotides (e.g., population of isolated polynucleotides) provided herein comprises SEQ ID NO: 22, 23, 24, 25, or 26 encoding a VH, and SEQ ID NO: 27, 28, 29, or 30 encoding a VL.

In a particular embodiment, a polynucleotide (e.g., isolated polynucleotide) or a population of polynucleotides (e.g., population of isolated polynucleotides) provided herein comprises SEQ ID NO: 22 encoding a VH, and SEQ ID NO: 27 encoding a VL.

In a particular embodiment, a polynucleotide (e.g., isolated polynucleotide) or a population of polynucleotides (e.g., population of isolated polynucleotides) provided herein comprises SEQ ID NO: 22 encoding a VH, and SEQ ID NO: 28 encoding a VL.

In a particular embodiment, a polynucleotide (e.g., isolated polynucleotide) or a population of polynucleotides (e.g., population of isolated polynucleotides) provided herein comprises SEQ ID NO: 22 encoding a VH, and SEQ ID NO: 29 encoding a VL.

In a particular embodiment, a polynucleotide (e.g., isolated polynucleotide) or a population of polynucleotides (e.g., population of isolated polynucleotides) provided herein comprises SEQ ID NO: 22 encoding a VH, and SEQ ID NO: 30 encoding a VL.

In a particular embodiment, a polynucleotide (e.g., isolated polynucleotide) or a population of polynucleotides (e.g., population of isolated polynucleotides) provided herein comprises SEQ ID NO: 23 encoding a VH, and SEQ ID NO: 27 encoding a VL.

In a particular embodiment, a polynucleotide (e.g., isolated polynucleotide) or a population of polynucleotides (e.g., population of isolated polynucleotides) provided herein comprises SEQ ID NO: 23 encoding a VH, and SEQ ID NO: 28 encoding a VL.

In a particular embodiment, a polynucleotide (e.g., isolated polynucleotide) or a population of polynucleotides (e.g., population of isolated polynucleotides) provided herein comprises SEQ ID NO: 23 encoding a VH, and SEQ ID NO: 29 encoding a VL.

In a particular embodiment, a polynucleotide (e.g., isolated polynucleotide) or a population of polynucleotides (e.g., population of isolated polynucleotides) provided herein comprises SEQ ID NO: 23 encoding a VH, and SEQ ID NO: 30 encoding a VL.

In a particular embodiment, a polynucleotide (e.g., isolated polynucleotide) or a population of polynucleotides (e.g., population of isolated polynucleotides) provided herein comprises SEQ ID NO: 24 encoding a VH, and SEQ ID NO: 27 encoding a VL.

In a particular embodiment, a polynucleotide (e.g., isolated polynucleotide) or a population of polynucleotides (e.g., population of isolated polynucleotides) provided herein comprises SEQ ID NO: 24 encoding a VH, and SEQ ID NO: 28 encoding a VL.

In a particular embodiment, a polynucleotide (e.g., isolated polynucleotide) or a population of polynucleotides (e.g., population of isolated polynucleotides) provided herein comprises SEQ ID NO: 24 encoding a VH, and SEQ ID NO: 29 encoding a VL.

In a particular embodiment, a polynucleotide (e.g., isolated polynucleotide) or a population of polynucleotides (e.g., population of isolated polynucleotides) provided herein comprises SEQ ID NO: 24 encoding a VH, and SEQ ID NO: 30 encoding a VL.

In a particular embodiment, a polynucleotide (e.g., isolated polynucleotide) or a population of polynucleotides (e.g., population of isolated polynucleotides) provided herein comprises SEQ ID NO: 25 encoding a VH, and SEQ ID NO: 27 encoding a VL.

In a particular embodiment, a polynucleotide (e.g., isolated polynucleotide) or a population of polynucleotides (e.g., population of isolated polynucleotides) provided herein comprises SEQ ID NO: 25 encoding a VH, and SEQ ID NO: 28 encoding a VL.

In a particular embodiment, a polynucleotide (e.g., isolated polynucleotide) or a population of polynucleotides (e.g., population of isolated polynucleotides) provided herein comprises SEQ ID NO: 25 encoding a VH, and SEQ ID NO: 29 encoding a VL.

In a particular embodiment, a polynucleotide (e.g., isolated polynucleotide) or a population of polynucleotides (e.g., population of isolated polynucleotides) provided herein comprises SEQ ID NO: 25 encoding a VH, and SEQ ID NO: 30 encoding a VL.

In a particular embodiment, a polynucleotide (e.g., isolated polynucleotide) or a population of polynucleotides (e.g., population of isolated polynucleotides) provided herein comprises SEQ ID NO: 26 encoding a VH, and SEQ ID NO: 27 encoding a VL.

In a particular embodiment, a polynucleotide (e.g., isolated polynucleotide) or a population of polynucleotides (e.g., population of isolated polynucleotides) provided herein comprises SEQ ID NO: 26 encoding a VH, and SEQ ID NO: 28 encoding a VL.

In a particular embodiment, a polynucleotide (e.g., isolated polynucleotide) or a population of polynucleotides (e.g., population of isolated polynucleotides) provided herein comprises SEQ ID NO: 26 encoding a VH, and SEQ ID NO: 29 encoding a VL.

In a particular embodiment, a polynucleotide (e.g., isolated polynucleotide) or a population of polynucleotides (e.g., population of isolated polynucleotides) provided herein comprises SEQ ID NO: 26 encoding a VH, and SEQ ID NO: 30 encoding a VL.

In one aspect, provided herein is a vector comprising a polynucleotide described herein for expressing an anti-KIT antibody or a fragment thereof. In a certain embodiment, a vector provided herein is a mammalian expression vector.

In a certain aspect, provided herein is a host cell comprising a vector provided herein or one or more polynucleotides provided herein for expressing an anti-KIT antibody or a fragment thereof.

In a particular aspect, provided herein is a cell producing an antibody described herein. In one embodiment, a cell provided herein comprises one or more polynucleotides described herein, wherein the cell can express an antibody which specifically binds to a D4 of human KIT. In a certain embodiment, the cell comprises a vector described herein.

In a specific aspect, provided herein is a kit comprising an antibody (or antigen-binding fragment thereof or conjugate thereof) described herein. In a particular embodiment, a kit comprises a conjugate described herein.

In a certain aspect, provided herein is a method for treating or managing a KIT-associated disorder (e.g., cancer), comprising administering to a subject in need thereof a therapeutically effective amount of an antibody described herein or an antigen-binding fragment thereof or a conjugate thereof.

In one aspect, provided herein is a method for treating or managing a KIT-associated disorder, comprising administering to a subject in need thereof a therapeutically effective amount of a conjugate described herein.

In a particular embodiment, the KIT-associated disorder is cancer, an inflammatory condition, or fibrosis. In a specific embodiment, the cancer is leukemia, chronic myelogenous leukemia, lung cancer, small cell lung cancer, or gastrointestinal stromal tumors. In one embodiment, the cancer is refractory to treatment by a tyrosine kinase inhibitor. In a further embodiment embodiment, the tyrosine kinase inhibitor is imatinib mesylate or SU11248.

In a certain embodiment, a method provided herein further comprises administering a second agent. In a specific embodiment, the second agent is a chemotherapeutic agent, tyrosine kinase inhibitor, a histone deacetylase inhibitor, an antibody, or a cytokine. In a particular embodiment, the tyrosine kinase inhibitor is imatinib mesylate or SU11248.

In a specific aspect, provided herein is a method for diagnosing a subject with a KIT-associated disorder comprising contacting cells or a sample obtained from the subject with an antibody described herein (or an antigen-binding fragment thereof or a conjugate thereof) and detecting the expression level of KIT in the cells or the sample. For example, detection of the binding of an antibody described herein to a KIT antigen present in the cell or sample can be correlated to the expression level of KIT in the cell or sample. In a particular embodiment, the antibody is conjugated to a detectable molecule. In a certain embodiment, the detectable molecule is an enzyme, a fluorescent molecule, a luminescent molecule, or a radioactive molecule.

In a particular aspect, provided herein is a method for inhibiting KIT activity in a cell expressing KIT comprising contacting the cell with an effective amount of an antibody described herein (or an antigen-binding fragment thereof or a conjugate thereof).

In a particular aspect, provided herein is a method for inducing or enhancing apoptosis in a cell expressing KIT comprising contacting the cell with an effective amount an antibody described herein (or an antigen-binding fragment thereof or a conjugate thereof).

In a particular aspect, provided herein is a method for inducing cell differentiation comprising contacting a cell expressing KIT with an effective amount of an antibody described herein (or an antigen-binding fragment thereof or a conjugate thereof). In a particular embodiment, the cell is a stem cell.

In a certain aspect, provided herein is a method of making an antibody which immunospecifically binds to a D4 region of human KIT comprising culturing a cell or host cell described herein. In a certain aspect, provided herein is a method of making an antibody which immunospecifically binds to a D4 region of human KIT comprising expressing the antibody using a cell or host cell described herein. In a particular embodiment, the cell is an isolated cell. In a particular embodiment, the method further comprises the step of purifying the antibody obtained from the cell or host cell.

In one aspect, provided herein is an antibody or antigen-binding fragment thereof, which immunospecifically binds to a D4 region of human KIT, wherein said antibody or antigen-binding fragment thereof comprises:
(i) a light chain variable region ("VL") comprising a VL CDR1, VL CDR2, and VL CDR3 selected from the group set forth in Tables 10-12; and
(ii) a heavy chain variable region ("VH") comprising VH CDR1, VH CDR2, and VH CDR3 selected from the group set forth in Tables 13-15.

In a certain aspect, described herein is an antibody or antigen-binding fragment thereof, wherein said antibody or antigen-binding fragment thereof comprises:
(i) VL comprising a VL FR1, VL FR2, VL FR3, AND VL FR4 selected from the group set forth in Tables 20-23; and
(ii) a VH comprising Vh FR1, VH FR2, VH FR3, and VH FR4 selected from the group set forth in Tables 16-19.

In a particular aspect, the antibody or antigen-binding fragment described herein comprises an Fc region with an amino acid modification. In a certain aspect, the antibody or antigen-binding fragment described herein comprises an Fc region which is an IgG1 isotype or an IgG4 isotype. In one aspect, the antibody or antigen-binding fragment described herein is a humanized antibody. In a particular aspect, the antibody or antigen-binding fragment thereof described herein is a bispecific antibody.

In a certain aspect, described herein is an antibody or antigen-binding fragment thereof which is conjugated to another agent.

In one aspect, provided herein is a composition comprising an antibody or antigen-binding fragment thereof described herein.

In a particular aspect, provided herein is a polynucleotide comprising nucleotide sequences encoding a VH chain region, a VL chain region, or both a VL chain region and a VH chain region, of an antibody or antigen-binding fragment thereof described herein (e.g., antibody or antigen binding fragment thereof comprising sequences set forth in Tables 10-15). Also provided is a vector comprising the polynucleotide described herein. In one aspect, the vector is a mammalian expression vector.

In a certain aspect, provided herein is a host cell comprising a vector of or one or more polynucleotides described herein. In one aspect, provided herein is a cell producing an antibody or antigen-binding fragment thereof described herein (e.g., antibody or antigen binding fragment thereof comprising sequences set forth in Tables 10-15).

In a particular aspect, provided herein is a kit comprising an antibody or antigen-binding fragment thereof described herein (e.g., antibody or antigen binding fragment thereof comprising sequences set forth in Tables 10-15).

In a certain aspect, provided herein is a method for treating or managing a KIT-associated disorder, comprising administering to a subject in need thereof a therapeutically effective amount of an antibody or antigen-binding fragment thereof described herein (e.g., antibody or antigen binding fragment thereof comprising sequences set forth in Tables 10-15). In one embodiment, the KIT-associated disorder is cancer, an inflammatory condition, or fibrosis. In a particular embodiment, the cancer is leukemia, chronic myelogenous leukemia, lung cancer, small cell lung cancer, or gastrointestinal stromal tumors.

In a particular aspect, the method for treating or managing a KIT-associated disorder described herein further comprises administering a second agent. In a particular embodiment, the second agent is a chemotherapeutic agent, tyrosine kinase inhibitor, a histone deacetylase inhibitor, an antibody, a cytokine, an HSP90 inhibitor, a PGP inhibitor, or a proteosome inhibitor.

In one aspect, provided herein is a method for diagnosing a subject with a KIT-associated disorder comprising contacting cells or a sample obtained from the subject with an antibody or antigen-binding fragment thereof described herein (e.g., antibody or antigen binding fragment thereof comprising sequences set forth in Tables 10-15) and detecting the expression level of KIT in the cells or the sample. In a certain embodiment, the antibody is conjugated to a detectable molecule.

In a certain aspect, provided herein is a method for inhibiting KIT activity in a cell expressing KIT comprising contacting the cell with an effective amount of an antibody or antigen-binding fragment thereof described herein (e.g., antibody or antigen binding fragment thereof comprising sequences set forth in Tables 10-15).

A method for inducing or enhancing apoptosis in a cell expressing KIT comprising contacting the cell with an effective amount of an antibody or antigen-binding fragment thereof described herein (e.g., antibody or antigen binding fragment thereof comprising sequences set forth in Tables 10-15).

A method of making an antibody which immunospecifically binds to a D4 region of human KIT comprising culturing, and/or expressing the antibody using, a cell described herein.

4. BRIEF DESCRIPTION OF THE FIGURES

FIG. 1 depicts the amino acid sequence of full length human KIT (SEQ ID NO: 1), GenBank™ accession number AAC50969. The first through fifth extracellular Ig-like domains (i.e., D1, D2, D3, D4, and D5) are indicated; " " depicts the amino-terminal residue of each domain and "1" depicts the carboxyl-terminal residue of each domain. The D1 domain is depicted at P34 to R112, the D2 domain is depicted at D113 to P206, the D3 domain is depicted at A207 to D309, the D4 domain is depicted at K310 to N410 (SEQ ID NO: 15), the hinge region between D4 and D5 is located at V409 to N410, and the D5 domain is depicted at T411 to K509. Also, the D1/D2 hinge region is located at D113 to L117; the D2/D3 hinge region is located at P206 to A210; and the D3/D4 hinge region is located at D309 to G311. The D4/D5 region comprises K310 to K509. The transmembrane domain comprises residues F525 to Q545, and the kinase domain comprises residues K589 to 5933.

FIG. 2 depicts the amino acid sequence of a recombinant KIT D4/D5. Human KIT amino acids V308 to H515 (SEQ ID NO: 73) are depicted in bold. The polypeptide depicted (SEQ ID NO: 14) contains (i) the first 33 amino acids (i.e., M1 to E33) of the amino terminus of human KIT (including the signal peptide, underlined, not bold), (ii) the D4/D5 region of human KIT (bold), and (iii) a 5×His tag (italics) at the carboxyl terminus.

FIG. 3A depicts the amino acid sequence (SEQ ID NO: 2) of the H1 VH domain, and a DNA (SEQ ID NO:22) encoding the amino acid sequence. The framework regions (FR1, FR2, FR3, and FR4), and CDRs (CDR1, CDR2, and CDR3) are indicated. Both Kabat numbering and numerical numbering of the amino acid residues are indicated.

FIG. 3B depicts the amino acid sequence (SEQ ID NO: 3) of the H2 VH domain and a DNA (SEQ ID NO:23) encoding the amino acid sequence. The framework regions (FR1, FR2, FR3, and FR4), and CDRs (CDR1, CDR2, and CDR3) are indicated. Both Kabat numbering and numerical numbering of the amino acid residues are indicated.

FIG. 3C depicts the amino acid sequence (SEQ ID NO: 4) of the H3 VH domain and a DNA (SEQ ID NO:24) encoding the amino acid sequence. The framework regions (FR1, FR2, FR3, and FR4), and CDRs (CDR1, CDR2, and CDR3) are indicated. Both Kabat numbering and numerical numbering of the amino acid residues are indicated.

FIG. 3D depicts the amino acid sequence (SEQ ID NO: 5) of the H4 VH domain and a DNA (SEQ ID NO:25) encoding the amino acid sequence. The framework regions (FR1, FR2, FR3, and FR4), and CDRs (CDR1, CDR2, and CDR3) are indicated. Both Kabat numbering and numerical numbering of the amino acid residues are indicated.

FIG. 3E depicts the amino acid sequence (SEQ ID NO: 6) of the H5 VH domain and a DNA (SEQ ID NO:26) encoding the amino acid sequence. The framework regions (FR1, FR2, FR3, and FR4), and CDRs (CDR1, CDR2, and CDR3) are indicated. Both Kabat numbering and numerical numbering of the amino acid residues are indicated.

FIG. 3F depicts the amino acid sequence (SEQ ID NO: 7) of the L1 VL domain and a DNA (SEQ ID NO:27) encoding the amino acid sequence. The framework regions (FR1, FR2, FR3, and FR4), and CDRs (CDR1, CDR2, and CDR3) are indicated. Both Kabat numbering and numerical numbering of the amino acid residues are indicated.

FIG. 3G depicts the amino acid sequence (SEQ ID NO: 8) of the L2 VL domain and a DNA (SEQ ID NO:28) encoding the amino acid sequence. The framework regions (FR1, FR2, FR3, and FR4), and CDRs (CDR1, CDR2, and CDR3) are indicated. Both Kabat numbering and numerical numbering of the amino acid residues are indicated.

FIG. 3H depicts the amino acid sequence (SEQ ID NO: 9) of the L3 VL domain and a DNA (SEQ ID NO:29) encoding the amino acid sequence. The framework regions (FR1, FR2, FR3, and FR4), and CDRs (CDR1, CDR2, and CDR3)

are indicated. Both Kabat numbering and numerical numbering of the amino acid residues are indicated.

FIG. 3I depicts the amino acid sequence (SEQ ID NO: 10) of the L4 VL domain and a DNA (SEQ ID NO:30) encoding the amino acid sequence. The framework regions (FR1, FR2, FR3, and FR4), and CDRs (CDR1, CDR2, and CDR3) are indicated. Both Kabat numbering and numerical numbering of the amino acid residues are indicated.

FIG. 4A depicts the consensus sequence (SEQ ID NO: 11) of a VH domain. $X_{H1-H8}$ indicate amino acids which can be any amino acid.

FIG. 4B depicts the consensus sequence (SEQ ID NO: 12) of a VL domain. $X_{K1-K6}$ indicate amino acids which can be any amino acid.

5. DETAILED DESCRIPTION

Figure 3C:
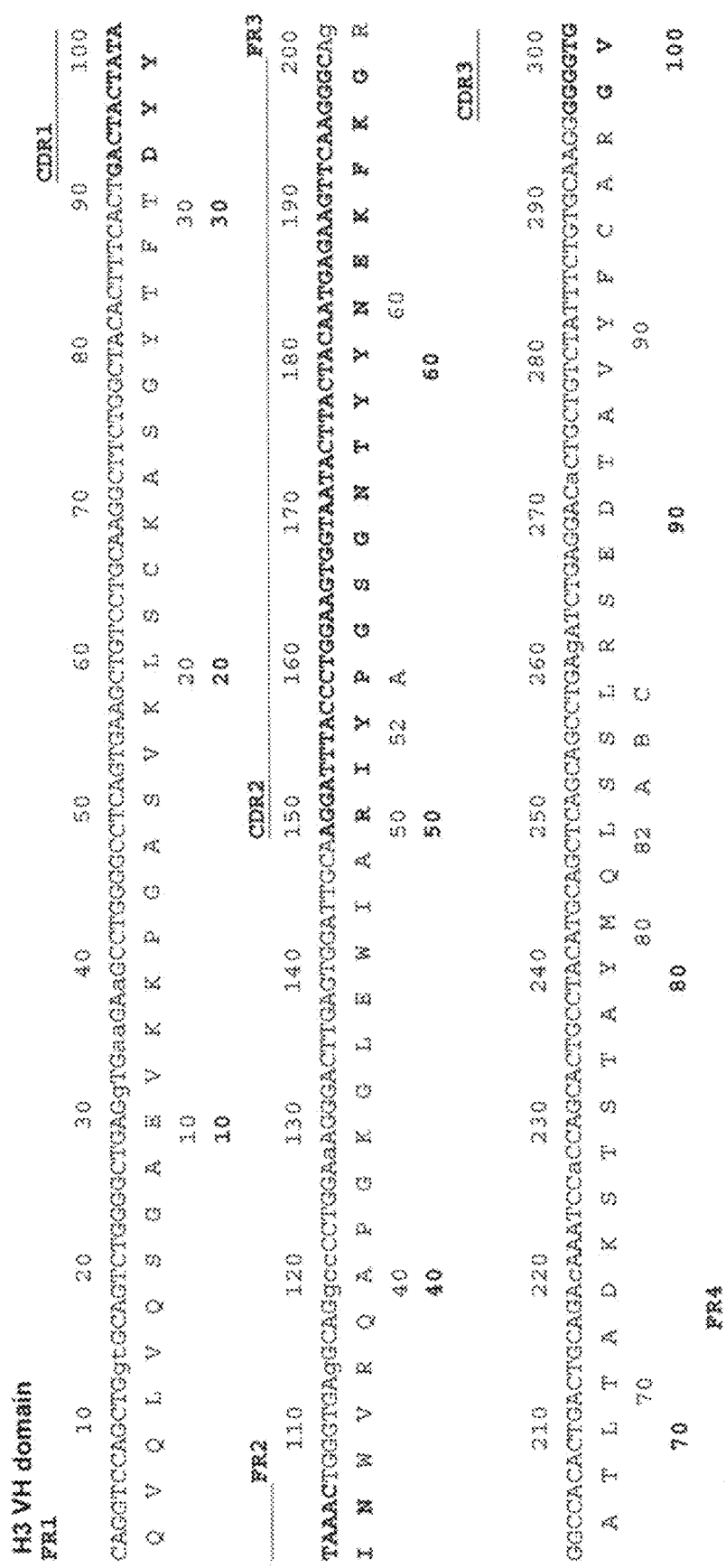
Figure 3E:
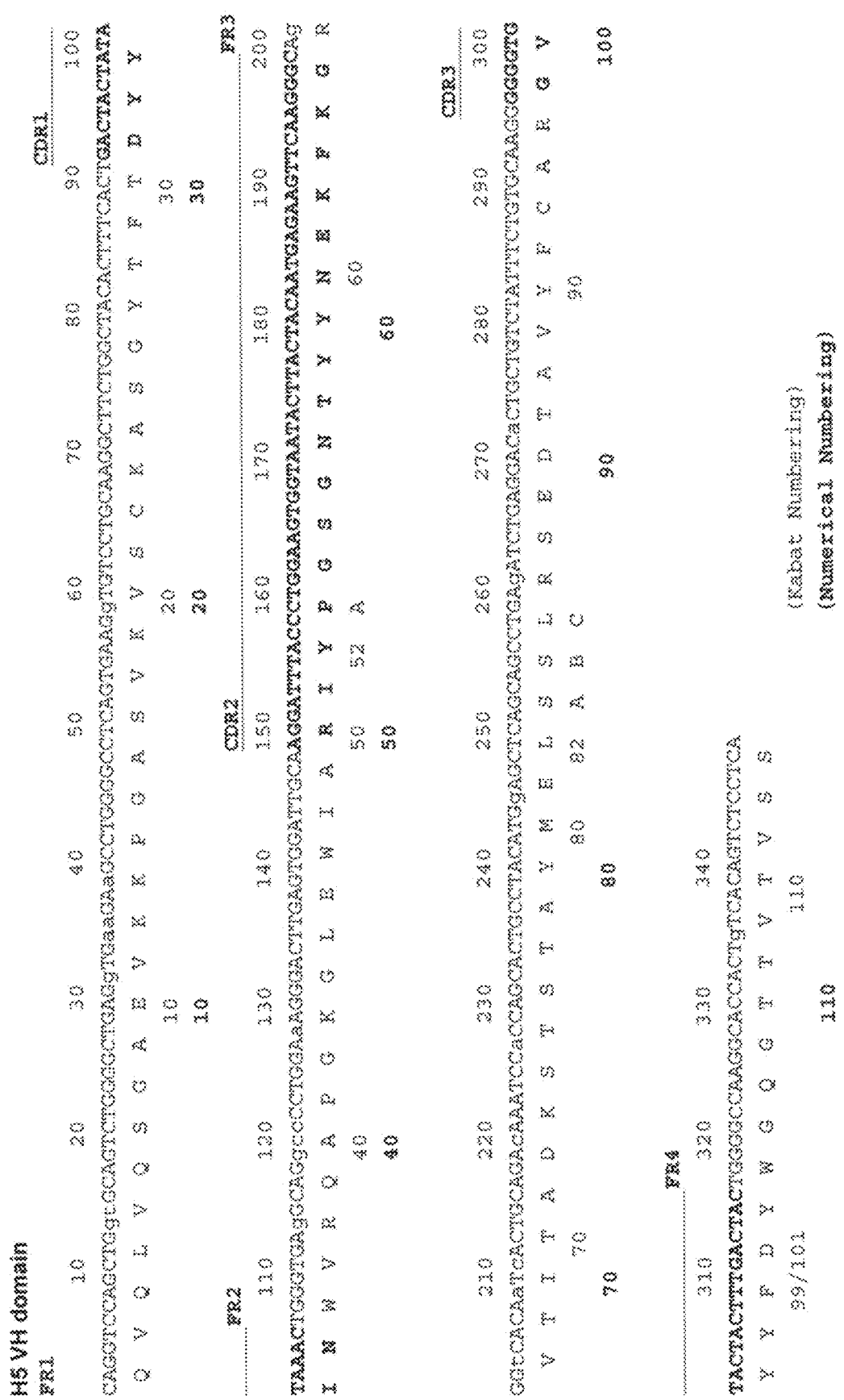
Figure 3F:
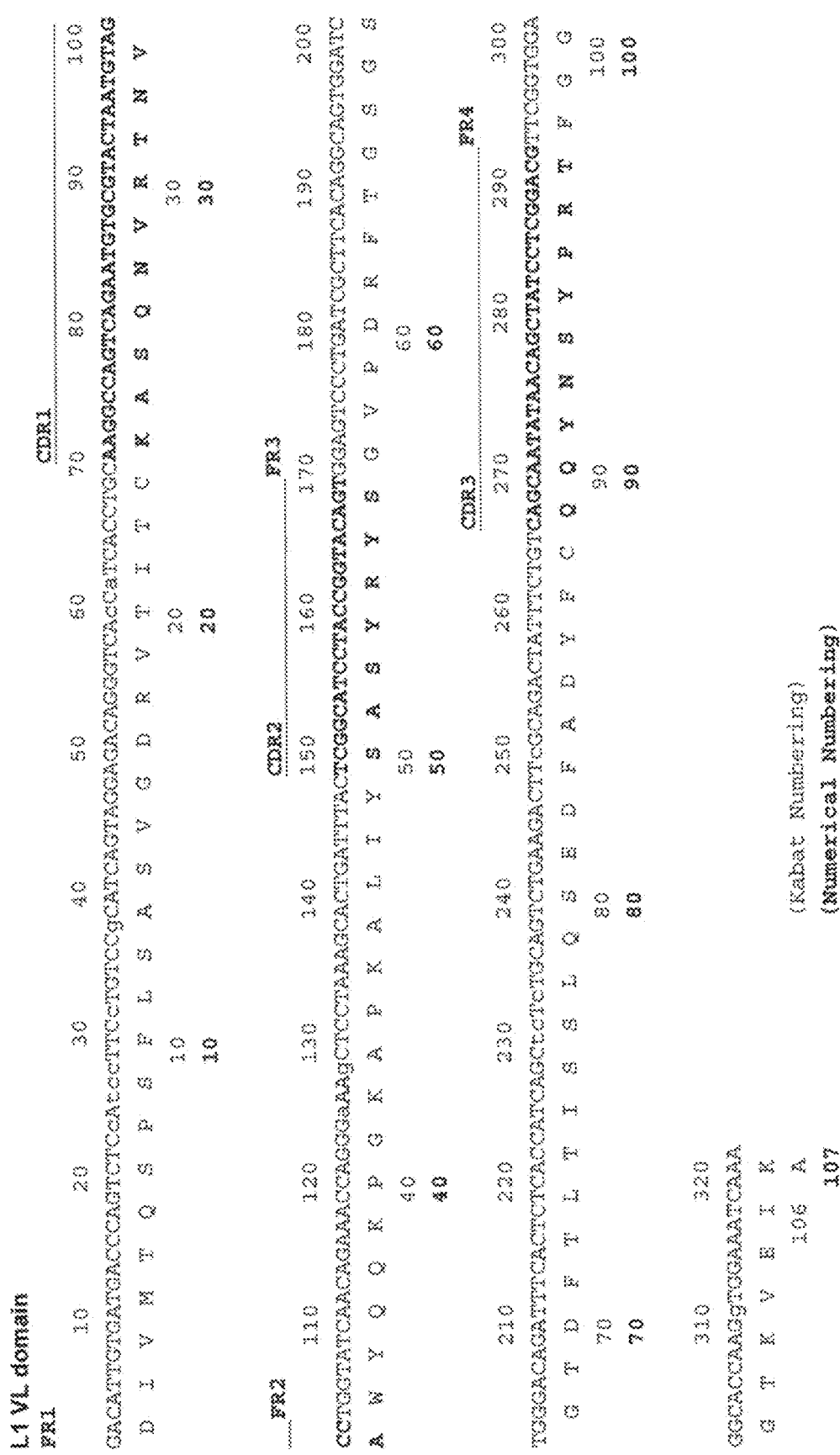
Figure 31:
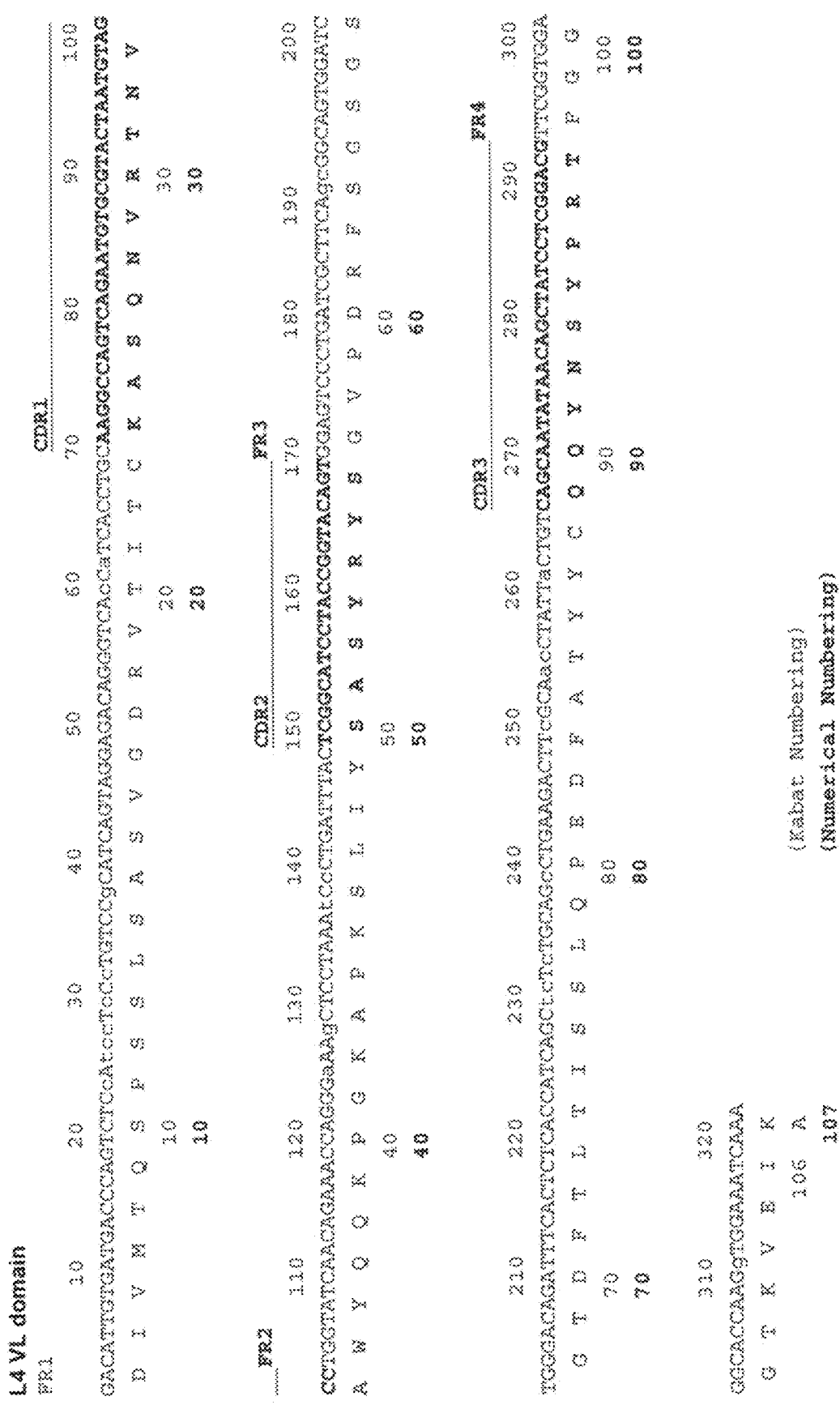

Unless defined otherwise, all technical and scientific terms used herein have the same meaning as is commonly understood by one of ordinary skill in the art.

As used herein, the terms "about" or "approximately" mean within plus or minus 10% of a given value or range.

Provided herein are antibodies, and antigen-binding fragments thereof, that immunospecifically bind to a KIT polypeptide (e.g., a KIT polypeptide containing a human KIT D4 domain), and conjugates thereof. Also provided are isolated nucleic acids (polynucleotides) encoding such antibodies, and antigen-binding fragments thereof. Further provided are vectors (e.g., expression vectors) and cells (e.g., host cells) comprising nucleic acids encoding such antibodies or antigen-binding fragments thereof. Also provided are methods of making such antibodies, cells, e.g., host cells. Also provided herein are methods and uses for treating or managing a KIT-associated disorder or disease (e.g., cancer, inflammatory condition, or fibrosis) or one or more effects of such KIT-associated disorder or disease comprising administering one or more antibodies described herein, or an antigen-binding fragment thereof or a conjugate thereof. Also provided herein is are methods for diagnosing a KIT-associated disorder or disease (e.g., cancer, inflammatory condition, or fibrosis) comprising contacting a sample with one or more antibodies (or antigen-binding fragment thereof) described herein and determining the expression level of KIT in the sample relative to a reference sample (e.g., a control sample). Further provided herein are methods and uses for inhibiting KIT activity in a cell expressing KIT comprising contacting the cell with an effective amount of an antibody or an antigen-binding fragment thereof. Also further provided herein are methods for inducing or enhancing cell differentiation or apoptosis in a cell expressing KIT comprising contacting the cell with an effective amount of an antibody or antibodies described herein.

As used herein, the terms "D4/D5 region" or "D4/D5 domain" refer to a region within a KIT polypeptide spanning the fourth Ig-like extracellular ("D4") domain, the fifth Ig-like extracellular ("D5") domain, and the hinge region in between the D4 and D5 domains ("D4-D5 hinge region"), of KIT, in the following order from the amino terminus to the carboxyl terminus: D4, D4-D5 hinge region, and D5. As used herein, amino acids V308 to H515 of FIG. 1 and the polypeptide depicted at FIG. 2 herein are considered examples of a D4/D5 region or domain.

As used herein, the terms "KIT" or "KIT receptor" or "KIT polypeptide" refer to any form of full-length KIT including, but not limited to, native KIT, an isoform of KIT, an interspecies KIT homolog, or a KIT variant, e.g., naturally occurring (for example, allelic or splice variant, or mutant, e.g., somatic mutant) or artificially constructed variant (for example, a recombinant or chemically modified variant). KIT is a type III receptor tyrosine kinase encoded by the c-kit gene (see, e.g., Yarden et al., Nature, 1986, 323:226-232; Ullrich and Schlessinger, Cell, 1990, 61:203-212; Clifford et al., J. Biol. Chem., 2003, 278:31461-31464; Yarden et al., EMBO J., 1987, 6:3341-3351; Mol et al., J. Biol. Chem., 2003, 278:31461-31464). GenBank™ accession number NM_000222 provides an exemplary human KIT nucleic acid sequence. GenBank™ accession numbers NP_001087241, P10721, and AAC50969 provide exemplary human KIT amino acid sequences. GenBank™ accession number AAH75716 provides an exemplary murine KIT amino acid sequence. Native KIT comprises five extracellular immunoglobulin (Ig)-like domains (D1, D2, D3, D4, D5), a single transmembrane region, an inhibitory cytoplasmic juxtamembrane domain, and a split cytoplasmic kinase domain separated by a kinase insert segment (see, e.g., Yarden et al., Nature, 1986, 323:226-232; Ullrich and Schlessinger, Cell, 1990, 61:203-212; Clifford et al., J. Biol. Chem., 2003, 278:31461-31464). An exemplary amino acid sequence of the D4/D5 region of human KIT is provided in FIG. 1, at amino acid residues V308 to H515. In a specific embodiment, KIT is human KIT. In a particular embodiment, KIT can exist as a monomer, dimer, multimer, native form, or denatured form.

In the context of a peptide or a polypeptide, the term "fragment" as used herein refers to a peptide or polypeptide that comprises a less than full length amino acid sequence. Such a fragment can arise, for example, from a truncation at the amino terminus, a truncation at the carboxy terminus, and/or an internal deletion of a residue(s) from the amino acid sequence. Fragments can, for example, result from alternative RNA splicing or from in vivo protease activity. In certain embodiments, KIT fragments or antibody fragments (e.g., antibody fragments that immunospecifically bind to a KIT polypeptide) include polypeptides comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least contiguous 100 amino acid residues, at least 125 contiguous amino acid residues, at least 150 contiguous amino acid residues, at least 175 contiguous amino acid residues, at least 200 contiguous amino acid residues, or at least 250 contiguous amino acid residues of the amino acid sequence of a KIT polypeptide or an antibody (e.g., an antibody that immunospecifically binds to a KIT polypeptide), respectively. In a specific embodiment, a fragment of a KIT polypeptide or an antibody (e.g., an antibody that immunospecifically binds to a KIT polypeptide) retains at least 1, at least 2, or at least 3 functions of the polypeptide or antibody.

As used herein, the term "host cell" refers to a particular cell that comprises an exogenous nucleic acid molecule, e.g., a cell that has been transfected or transformed with a nucleic acid molecule, and the progeny or potential progeny of such a parent cell. Progeny of such a cell may not be identical to the parent cell due to mutations or environmental influences that can occur in succeeding generations or integration of the nucleic acid molecule into the host cell genome.

5.1 Antibodies

As used herein, the terms "antibody" and "immunoglobulin" and "Ig" are terms of art and can be used interchangeably herein and refer to a molecule with an antigen binding site that immunospecifically binds an antigen.

As used herein, an "antigen" is a moiety or molecule that contains an epitope, and, as such, also is specifically bound by antibody. In a specific embodiment, the antigen, to which an antibody described herein binds, is KIT (e.g., human KIT), or a fragment thereof, for example, an extracellular domain of KIT (e.g., human KIT) or a D4 region of KIT (e.g., human KIT).

As used herein, an "epitope" is a term in the art and refers to a localized region of an antigen to which an antibody can specifically bind. A region or a polypeptide contributing to an epitope can be contiguous amino acids of the polypeptide or an epitope can come together from two or more non-contiguous regions of the polypeptide.

As used herein, the terms "antigen binding domain," "antigen binding region," "antigen binding fragment," and similar terms refer to a portion of an antibody molecule which comprises the amino acid residues that interact with an antigen and confer on the antibody molecule its specificity for the antigen (e.g., the complementarity determining regions (CDR)). The antigen binding region can be derived from any animal species, such as rodents (e.g., mouse, rat or hamster) and humans. The CDRs of an antibody molecule can be determined by any method well known to one of skill in the art. In particular, the CDRs can be determined according to the Kabat numbering system (see Kabat et al. (1991) *Sequences of Proteins of Immunological Interest.* (U.S. Department of Health and Human Services, Washington, D.C.) 5$^{th}$ ed.). In certain aspects, the CDRs of an antibody can be determined according to (i) the Chothia numbering scheme, which will be referred to herein as the "Chothia CDRs" (see, e.g., Chothia and Lesk, 1987, J. Mol. Biol., 196:901-917; Al-Lazikani et al., 1997, J. Mol. Biol., 273:927-948; and U.S. Pat. No. 7,709,226); or (ii) the IMGT numbering system, for example, as described in Lefranc, M.-P., 1999, The Immunologist, 7:132-136 and Lefranc, M.-P. et al., 1999, Nucleic Acids Res., 27:209-212.

As used herein, a "conformational epitope" or "non-linear epitope" or "discontinuous epitope" refers to one comprised of at least two amino acids which are not consecutive amino acids in a single protein chain. For example, a conformational epitope can be comprised of two or more amino acids which are separated by a stretch of intervening amino acids but which are close enough to be recognized by an antibody (e.g., an anti-KIT antibody) described herein as a single epitope. As a further example, amino acids which are separated by intervening amino acids on a single protein chain, or amino acids which exist on separate protein chains, can be brought into proximity due to the conformational shape of a protein structure or complex to become a conformational epitope which can be bound by an anti-KIT antibody described herein. It will be appreciated by one of skill in the art that, in general, a linear epitope bound by an anti-KIT antibody described herein may or may not be dependent on the secondary, tertiary, or quaternary structure of the KIT receptor. For example, in some embodiments, an anti-KIT antibody described herein binds to a group of amino acids regardless of whether they are folded in a natural three dimensional protein structure. In other embodiments, an anti-KIT antibody described herein does not recognize the individual amino acid residues making up the epitope, and require a particular conformation (bend, twist, turn or fold) in order to recognize and bind the epitope.

As used herein, the term "constant region" or "constant domain" refers to an antibody portion, e.g., a carboxyl terminal portion of a light and/or heavy chain which is not directly involved in binding of an antibody to antigen but which exhibits various effector functions, such as interaction with the Fc receptor. The terms refer to a portion of an immunoglobulin molecule having a generally more conserved amino acid sequence relative to an immunoglobulin variable domain.

As used herein, the term "heavy chain" when used in reference to an antibody refers to any distinct types, e.g., alpha ($\alpha$), delta ($\delta$), epsilon ($\epsilon$), gamma ($\gamma$) and mu ($\mu$), based on the amino acid sequence of the constant domain, which give rise to IgA, IgD, IgE, IgG and IgM classes of antibodies, respectively, including subclasses of IgG, e.g., IgG$_1$, IgG$_2$, IgG$_3$ and IgG$_4$. In a specific embodiment, the heavy chain is a human heavy chain.

As used herein, the terms "immunospecifically binds," "immunospecifically recognizes," "specifically binds," and "specifically recognizes" are analogous terms in the context of antibodies and refer to molecules that bind to an antigen (e.g., epitope or immune complex) as such binding is understood by one skilled in the art. For example, a molecule that specifically binds to an antigen may bind to other peptides or polypeptides, generally with lower affinity as determined by, e.g., immunoassays, Biacore™, KinExA 3000 instrument (Sapidyne Instruments, Boise, Id.), or other assays known in the art. In a specific embodiment, molecules that immunospecifically bind to an antigen bind to the antigen with a $K_a$ that is at least 2 logs, 2.5 logs, 3 logs, 4 logs or greater than the $K_a$ when the molecules bind to another antigen. In another specific embodiment, molecules that immunospecifically bind to an antigen do not cross react with other proteins. In another specific embodiment, molecules that immunospecifically bind to an antigen do not cross react with other non-KIT proteins.

As used herein, an "isolated" or "purified" antibody is substantially free of cellular material or other contaminating proteins from the cell or tissue source from which the antibody is derived, or substantially free of chemical precursors or other chemicals when chemically synthesized.

The terms "Kabat numbering," and like terms are recognized in the art and refer to a system of numbering amino acid residues in the heavy and light chain variable regions of an antibody, or an antigen binding portion thereof (Kabat et al. (1971) *Ann. NY Acad. Sci.* 190:382-391 and, Kabat et al. (1991) *Sequences of Proteins of Immunological Interest*, Fifth Edition, U.S. Department of Health and Human Services, NIH Publication No. 91-3242). Using the Kabat numbering system, CDRs within an antibody heavy chain molecule are typically present at amino acid positions 31 to 35 ("CDR1"), amino acid positions 50 to 65 ("CDR2"), and amino acid positions 95 to 102 ("CDR3"). Using the Kabat numbering system, CDRs within an antibody light chain molecule are typically present at amino acid positions 24 to 34 (CDR1), amino acid positions 50 to 56 (CDR2), and amino acid positions 89 to 97 (CDR3).

As used herein, the term "light chain" when used in reference to an antibody refers to any distinct types, e.g., kappa (κ) of lambda (λ) based on the amino acid sequence of the constant domains. Light chain amino acid sequences are well known in the art. In specific embodiments, the light chain is a human light chain.

As used herein, the term "monoclonal antibody" refers to an antibody obtained from a population of homogenous or substantially homogeneous antibodies, and each monoclonal antibody will typically recognize a single epitope on the antigen. The term "monoclonal" is not limited to any particular method for making the antibody. Generally, a population of monoclonal antibodies can be generated by cells, a population of cells, or a cell line. In specific embodiments, a "monoclonal antibody," as used herein, is an antibody produced by a single hybridoma or other cell (e.g., host cell producing a recombinant antibody), wherein the antibody immunospecifically binds to a KIT epitope (e.g., an epitope of a D4 of human KIT) as determined, e.g., by ELISA or other antigen-binding or competitive binding assay known in the art or in the Examples provided herein. Monoclonal antibodies described herein can, for example, be made by the hybridoma method as described in Kohler et al.; Nature, 256:495 (1975) or can be isolated from phage libraries using the techniques as described herein, for example. Other methods for the preparation of clonal cell lines and of monoclonal antibodies expressed thereby are well known in the art (see, for example, Chapter 11 in: *Short Protocols in Molecular Biology*, (2002) 5th Ed., Ausubel et al., eds., John Wiley and Sons, New York).

As used herein, the term "polyclonal antibodies" refers to an antibody population that includes a variety of different antibodies directed to the same and to different epitopes within an antigen or antigens. Methods for producing polyclonal antibodies are known in the art (See, e.g., see, for example, Chapter 11 in: *Short Protocols in Molecular Biology*, (2002) 5th Ed., Ausubel et al., eds., John Wiley and Sons, New York).

As used herein, the term "recombinant human antibody" includes human antibodies that are isolated, prepared, expressed, or created by recombinant means, such as antibodies expressed using a recombinant expression vector transfected into a host cell, antibodies isolated from a recombinant, combinatorial human antibody library, antibodies isolated from an animal (e.g., a mouse, rabbit, goat, or cow) that is transgenic and/or transchromosomal for human immunoglobulin genes (see e.g., Taylor, L. D. et al. (1992) *Nucl. Acids Res.* 20:6287-6295) or antibodies prepared, expressed, created or isolated by any other means that involves creation, e.g., via synthesis, genetic engineering of DNA sequences that encode human immunoglobulin sequences, or splicing of sequences that encode human immunoglobulins, e.g., human immunoglobulin gene sequences, to other such sequences. Such recombinant human antibodies can have variable and constant regions derived from human germline immunoglobulin sequences. In certain embodiments, the amino acid sequences of such recombinant human antibodies have been modified such thus the amino acid sequences of the VH and/or VL regions of the recombinant antibodies are sequences that, while derived from and related to human germline VH and VL sequences, do not naturally exist within the human antibody germline repertoire in vivo. As a non-limiting example, a recombinant human antibody can be obtained by assembling several human sequence fragments into a composite human sequence of a recombinant human antibody.

As used herein, the terms "variable region" or "variable domain" refer to a portion of an antibody, generally, a portion of a light or heavy chain, typically about the amino-terminal 110 to 120 amino acids in the mature heavy chain and about 90 to 100 amino acids in the mature light chain, which differ extensively in sequence among antibodies and are used in the binding and specificity of a particular antibody for its particular antigen. The variability in sequence is concentrated in those regions called complementarity determining regions (CDRs) while the more highly conserved regions in the variable domain are called framework regions (FR). Without wishing to be bound by any particular mechanism or theory, it is believed that the CDRs of the light and heavy chains are primarily responsible for the interaction of the antibody with antigen. In a specific embodiment, numbering of amino acid positions of antibodies described herein is according to the EU Index, as in Kabat et al. (1991) *Sequences of Proteins of Immunological Interest*, Fifth Edition, U.S. Department of Health and Human Services, NIH Publication No. 91-3242 ("Kabat et al."). In certain aspects, the CDRs of an antibody can be determined according to (i) the Chothia numbering scheme, which will be referred to herein as the "Chothia CDRs" (see, e.g., Chothia and Lesk, 1987, J. Mol. Biol., 196:901-917; Al-Lazikani et al., 1997, J. Mol. Biol., 273:927-948; and U.S. Pat. No. 7,709,226); or (ii) the IMGT numbering system, for example, as described in Lefranc, M.-P., 1999, The Immunologist, 7:132-136 and Lefranc, M.-P. et al., 1999, Nucleic Acids Res., 27:209-212. In certain embodiments, the variable region is a human variable region. In certain embodiments, the variable region comprises rodent or murine CDRs and human framework regions (FRs). In particular embodiments, the variable region is a primate (e.g., non-human primate) variable region. In certain embodiments, the variable region comprises rodent or murine CDRs and primate (e.g., non-human primate) framework regions (FRs). As a non-limiting example, a variable region described herein is obtained from assembling two or more fragments of human sequences into a composite human sequence.

In specific aspects, provided herein are antibodies (including antigen-binding fragments thereof), such as humanized antibodies, that immunospecifically bind to a D4 of human KIT and a D4/D5 region of KIT, e.g., human KIT. Amino acid residues V308 to H515 (SEQ ID NO: 73) of FIGS. 1 and 2 represent an exemplary D4/D5 region of human KIT, and amino acids K310 to N410 (SEQ ID NO: 15), as depicted in FIGS. 1 and 2, represent an exemplary D4 of human KIT. In another specific embodiment, an antibody described herein (or an antigen-binding fragment thereof) immunospecifically binds to a D5 domain of KIT, e.g., human KIT, with lower affinity than to a D4 domain of KIT, e.g., human KIT. In a particular embodiment, an antibody described herein (or an antigen-binding fragment thereof) immunospecifically binds to a D4 domain of KIT, e.g., human KIT, with higher affinity than to a D5 domain of KIT, e.g., human KIT; for example, the higher affinity is at least 10 fold, 20 fold, 50 fold, 100 fold, 500 fold, or 1000 fold as determined by methods known in the art, e.g., ELISA or Biacore assays.

In a specific embodiment, an antibody described herein (or an antigen-binding fragment thereof) immunospecifically binds to a D4 or D4/D5 region of KIT, e.g., human KIT, and has higher affinity for a KIT antigen consisting essentially of a D4 domain only than a KIT antigen consisting essentially of a D5 domain only. In a particular embodiment, an antibody described herein (or an antigen-binding fragment thereof) immunospecifically binds to a D4 or D4/D5 region of KIT, e.g., human KIT, and has at least 1 fold, 2 fold, 3 fold, 4 fold, 5 fold, or 10 fold higher affinity for a KIT antigen consisting essentially of a D4 domain only than a KIT antigen consisting essentially of a D5 domain only. In a particular embodiment, an antibody described herein (or an antigen-binding fragment thereof) immunospecifically binds to a D4 or D4/D5 region of KIT, e.g., human KIT, and has higher binding affinity (e.g., approximately a 2 fold to 3 fold higher affinity) for a KIT antigen consisting essentially of a D4 domain only or a D4/D5 region only, than a KIT antigen consisting essentially of a D5 domain only.

In a particular embodiment, an antibody described herein (or an antigen-binding fragment thereof) immunospecifically binds to a KIT antigen comprising or consisting essentially of the amino acid sequence of SEQ ID NO: 15. In a specific embodiment, an antibody described herein (or an antigen-binding fragment thereof) immunospecifically binds to a D4 domain of KIT, e.g., human KIT. In a particular embodiment, an antibody described herein immunospecifically binds to a KIT antigen comprising or consisting essentially of a D4 of human KIT. In a particular embodiment, an antibody described herein (or an antigen-binding fragment thereof) immunospecifically binds to a KIT antigen comprising or consisting essentially of the amino acid sequence of SEQ ID NO: 14 or 73.

In particular aspects, provided herein are antibodies or antigen-binding fragments thereof, which immunospecifically bind to a KIT polypeptide (e.g., a D4 region of KIT, for example, human KIT, e.g., SEQ ID NO: 15 [a human D4 sequence]) and comprise an amino acid sequence as described herein.

In specific aspects, described herein are antibodies (e.g., human or humanized antibodies), including antigen-binding fragments thereof, comprising:
(i) VH CDRs of a VH domain comprising the amino acid sequence of SEQ ID NO: 31 (QVQLKQSGAELVRP-GASVKLSCKASGYTFTDYYINWVKQRPGQ-GLEWIARIYPG SGNTYYNEKFKGKATL-TAEKSSSTAYMQLSSLTSEDSAVYFCARGV YYFDYWGQ GTTLTVSS) or SEQ ID NO: 69 (QVQLKQSGAELVRPGASVKLSCKASGYTFT-DYYINWVKQRPGQGLEWIARIYPG SGN-TYYNEKFKGKATLTAEKSSSTAYMQLSSLTSED-SAVYFCARGVYYFDYWGQ GTTLTVSA), and
(ii) VL CDRs of a VL domain comprising the amino acid sequence of SEQ ID NO: 32 (DIVMTQSQKFMSTS-VGDRVS VTCKASQNVRTNVAWYQQKPGQSP-KALIYSASYRYSGVPDRFTGSGSGTDFTLTI SNVQSEDLADYFCQQYNSYPRTFGGGT-KLEIKR).

In a specific embodiment, an antibody (e.g., a human or humanized antibody) described herein, which immunospecifically binds to a KIT polypeptide (e.g., the D4 region of human KIT), comprises the VH CDRs (SEQ ID NOs: 16-18) and VL CDRs (SEQ ID NOs: 19-21) described in Table 1. In a specific embodiment, an antibody (e.g., a human or humanized antibody) described herein, which immunospecifically binds to a KIT polypeptide (e.g., the D4 region of human KIT), comprises the VH CDRs and VL CDRs described in Table 2 (e.g., set 1 or set 2). In a certain embodiment, an antibody (e.g., a human or humanized antibody) described herein, which immunospecifically binds to a KIT polypeptide (e.g., the D4 region of human KIT), comprises the VH CDRs and VL CDRs described in Table 3 (AbM CDRs or Contact CDRs).

TABLE 1

CDR Amino Acid Sequences

| | amino acid sequence | SEQ ID NO: |
|---|---|---|
| VL CDR1 | KASQNVRTNVA | 19 |
| VL CDR2 | SASYRYS | 20 |
| VL CDR3 | QQYNSYPRT | 21 |
| VH CDR1 | DYYIN | 16 |
| VH CDR2 | RIYPGSGNTYYNEKFKG | 17 |
| VH CDR3 | GVYYFDY | 18 |

TABLE 2

CDR Amino Acid Sequences

| | Set 1 | | Set 2 | |
|---|---|---|---|---|
| | amino acid sequence | SEQ ID NO: | amino acid sequence | SEQ ID NO: |
| VL CDR1 | KASQNVRTNVA | 19 | SQNVRTN | 59 |
| VL CDR2 | SASYRYS | 20 | SAS | 60 |
| VL CDR3 | QQYNSYPRT | 21 | YNSYPR | 61 |
| VH CDR1 | GYTFTDY | 56 | GYTFTDY | 56 |
| VH CDR2 | YPGSGN | 57 | PGSG | 62 |
| VH CDR3 | GVYYFDYW | 58 | VYYFDY | 63 |

TABLE 3

CDR Amino Acid Sequences

| | AbM | | Contact | |
|---|---|---|---|---|
| | amino acid sequence | SEQ ID NO: | amino acid sequence | SEQ ID NO: |
| VL CDR1 | KASQNVRTNVA | 19 | RTNVAWY | 66 |
| VL CDR2 | SASYRYS | 20 | ALIYSASYRY | 67 |
| VL CDR3 | QQYNSYPRT | 21 | QQYNSYPR | 68 |
| VH CDR1 | GYTFTDYYIN | 64 | TDYYIN | 70 |
| VH CDR2 | RIYPGSGNTY | 65 | WIARIYPGSGNTY | 71 |
| VH CDR3 | GVYYFDYW | 58 | ARGVYYFDY | 72 |

TABLE 4

VL and VH domains of Antibodies Hum1-20

| VL domain | VH domain | | | | |
|---|---|---|---|---|---|
| | H1 (SEQ ID NO: 2) | H2 (SEQ ID NO: 3) | H3 (SEQ ID NO: 4) | H4 (SEQ ID NO: 5) | H5 (SEQ ID NO: 6) |
| L1 (SEQ ID NO: 7) | Hum1 | Hum2 | Hum3 | Hum4 | Hum5 |
| L2 (SEQ ID NO: 8) | Hum6 | Hum7 | Hum8 | Hum9 | Hum10 |
| L3 (SEQ ID NO: 9) | Hum11 | Hum12 | Hum13 | Hum14 | Hum15 |
| L4 (SEQ ID NO: 10) | Hum16 | Hum17 | Hum18 | Hum19 | Hum20 |

In certain aspects, provided herein are VH domains (e.g., H1, H2, H3, H4 and H5 comprising SEQ ID NOs: 2-6, respectively) and VL domains (e.g., L1, L2, L3, and L4 comprising SEQ ID NOs: 7-10, respectively). In certain embodiments, provided herein are antibodies comprising such VH and VL domains, as set forth, for example, in Table 4 (i.e., antibodies Hum1-Hum20). In particular embodiments, these antibodies comprise VH CDRs1-3 and VL CDRs 1-3 comprising SEQ ID NOs: 16-18 and 19-21, respectively.

In certain embodiments, an antibody described herein, or an antigen-binding fragment thereof, comprises a variable light (VL) chain region comprising an amino acid sequence described herein, for example, any one of SEQ ID NOs: 7-10 (e.g., see FIGS. 3F-3I) or SEQ ID NO: 12.

In certain embodiments, an antibody described herein, or an antigen-binding fragment thereof, comprises a variable heavy (VH) chain region comprising an amino acid sequence described herein, for example any one of SEQ ID NOs: 2-6 (e.g., see FIGS. 3A-3E) or SEQ ID NO: 11.

For example, described herein is an antibody that immunospecifically binds to a KIT polypeptide (e.g., the D4 region of human KIT) and comprises (i) the VH domain H1 (SEQ ID NO: 2), H2 (SEQ ID NO: 3), H3 (SEQ ID NO: 4), H4 (SEQ ID NO: 5), or H5 (SEQ ID NO: 6) and/or (ii) the VL domain L1 (SEQ ID NO: 7), L2 (SEQ ID NO: 8), L3 (SEQ ID NO: 9), or L4 (SEQ ID NO: 10). In a particular example, an antibody described herein, or an antigen-binding fragment thereof, can immunospecifically bind to a KIT polypeptide (e.g., the D4 region of human KIT) and comprise a VH domain and/or a VL domain of any one of antibodies Hum1-Hum20 (see Table 4). In a particular example, an antibody described herein, or an antigen-binding fragment thereof, comprises a VH domain and/or a VL domain of any one of antibodies Hum4, Hum8, Hum10, or Hum17.

In a particular embodiment, an antibody, which immunospecifically binds to a KIT polypeptide (e.g., the D4 region of human KIT), comprises H1 (SEQ ID NO: 2) and L1 (SEQ ID NO: 7). In a particular embodiment, an antibody, which immunospecifically binds to a KIT polypeptide (e.g., the D4 region of human KIT), comprises H1 (SEQ ID NO: 2) and L2 (SEQ ID NO: 8). In a specific embodiment, an antibody, which immunospecifically binds to a KIT polypeptide (e.g., the D4 region of human KIT), comprises H1 (SEQ ID NO: 2) and L3 (SEQ ID NO: 9). In a specific embodiment, an antibody, which immunospecifically binds to a KIT polypeptide (e.g., the D4 region of human KIT), comprises H1 (SEQ ID NO: 2) and L4 (SEQ ID NO: 10). In a specific embodiment, an antibody, which immunospecifically binds to a KIT polypeptide (e.g., the D4 region of human KIT), comprises H2 (SEQ ID NO: 3) and L1 (SEQ ID NO: 7). In a specific embodiment, an antibody, which immunospecifically binds to a KIT polypeptide (e.g., the D4 region of human KIT), comprises H2 (SEQ ID NO: 3) and L2 (SEQ ID NO: 8). In a specific embodiment, an antibody, which immunospecifically binds to a KIT polypeptide (e.g., the D4 region of human KIT), comprises H2 (SEQ ID NO: 3) and L3 (SEQ ID NO: 9). In a specific embodiment, an antibody, which immunospecifically binds to a KIT polypeptide (e.g., the D4 region of human KIT), comprises H2 (SEQ ID NO: 3) and L4 (SEQ ID NO: 10). In a specific embodiment, an antibody, which immunospecifically binds to a KIT polypeptide (e.g., the D4 region of human KIT), comprises H3 (SEQ ID NO: 4) and L1 (SEQ ID NO: 7). In a specific embodiment, an antibody, which immunospecifically binds to a KIT polypeptide (e.g., the D4 region of human KIT), comprises H3 (SEQ ID NO: 4) and L2 (SEQ ID NO: 8). In a specific embodiment, an antibody, which immunospecifically binds to a KIT polypeptide (e.g., the D4 region of human KIT), comprises H3 (SEQ ID NO: 4) and L3 (SEQ ID NO: 9). In a specific embodiment, an antibody, which immunospecifically binds to a KIT polypeptide (e.g., the D4 region of human KIT), comprises H3 (SEQ ID NO: 4) and L4 (SEQ ID NO: 10). In a specific embodiment, an antibody, which immunospecifically binds to a KIT polypeptide (e.g., the D4 region of human KIT), comprises H4 (SEQ ID NO: 5) and L1 (SEQ ID NO: 7). In a specific embodiment, an antibody, which immunospecifically binds to a KIT polypeptide (e.g., the D4 region of human KIT), comprises H4 (SEQ ID NO: 5) and L2 (SEQ ID NO: 8). In a specific embodiment, an antibody, which immunospecifically binds to a KIT polypeptide (e.g., the D4 region of human KIT), comprises H4 (SEQ ID NO: 5) and L3 (SEQ ID NO: 9). In a specific embodiment, an antibody, which immunospecifically binds to a KIT polypeptide (e.g., the D4 region of human KIT), comprises H4 (SEQ ID NO: 5) and L4 (SEQ ID NO: 10). In a specific embodiment, an antibody, which immunospecifically binds to a KIT polypeptide (e.g., the D4 region of human KIT), comprises H5 (SEQ ID NO: 6) and L1 (SEQ ID NO: 7). In a specific embodiment, an antibody, which immunospecifically binds to a KIT polypeptide (e.g., the D4 region of human KIT), comprises H5 (SEQ ID NO: 6) and L2 (SEQ ID NO: 8). In a specific embodiment, an antibody, which immunospecifically binds to a KIT polypeptide (e.g., the D4 region of human KIT), comprises H5 (SEQ ID NO: 6) and L3 (SEQ ID NO: 9). In a specific embodiment, an antibody, which immunospecifically binds to a KIT polypeptide (e.g., the D4 region of human KIT), comprises H5 (SEQ ID NO: 6) and L4 (SEQ ID NO: 10).

In certain aspects, an antibody, or an antigen-binding fragment thereof, is non-immunogenic in a human. In a particular embodiment, a non-immunogenic amino acid sequence is devoid of epitopes identified to be binders to human MEW class II, e.g., epitopes that are non-human germline binders to human MHC class II. In a particular embodiment, amino acid sequences substantially devoid of epitopes identified to be binders to human MHC class II, e.g., epitopes that are non-human germline binders to human MHC class II. For example, in silico tools to identify the location of both B- and T-cell epitopes and to assess the potential for immunogenicity have been developed, and such tools provide an alternative to in vitro or in vivo immunogenicity assays. For example, computational epitope prediction methods and manually curated databases containing experimentally derived epitope data have been developed (See Bryson et al., Biodrugs, 2010, 24(1): 1-8).

Non-limiting examples of epitope databases include the Immune Epitope Database (IEDB) and the proprietary T Cell Epitope Database™ (TCED™). Such epitope databases can be used alone or in combination with in vitro assays described in the art, e.g., MHC class II binding assays and T cell activation or proliferation assays. Alternatively, such in vitro assays can be used independently of such epitope databases. Methods for determining immunogenicity of an agent, such as an antibody, or for removing or reducing immunogenicity of an agent, such as an antibody, have been described in the art, see, e.g., Altschul et al., Nucleic Acids Res., 1997, 25:3389-3402; Baker et al., Curr. Opin. Drug Discov. Devel., 2007, 10:219; Hill et al., Arthritis Res. Ther., 2003, 1:R40-R48; Jones et al., J. Thromb. Haemost., 2005, 3:991-1000; Holgate et al., IDrugs, 2009, 12:233-237; Jones et al., Methods Mol. Biol., 2009, 525:405-423; and Baker et al., Curr. Drug Saf., 2010, 5:308-313. In a particular embodiment, an antibody described herein which immunospecifically binds to a D4 region of human KIT comprises a VH domain and a VL domain that are not immunogenic, as determined by the T Cell Epitope Database™ (TCED™). In a certain embodiment, an antibody described herein immunospecifically binds to a D4 region of human KIT, and comprises a VH domain and a VL domain that are not immunogenic, as determined by an in vitro assay described in the art, see, e.g., Wang et al., 2008, PLoS Coomputational Biology, 2008, 4(4):e1000048; and Arnold et al., 2002, J. Immunol., 169:739-749.

In certain aspects, provided herein is an antibody (e.g., human or humanized antibody) or an antigen-binding fragment thereof, which immunospecifically binds to a KIT polypeptide (e.g., the D4 region of human KIT), comprising a VH domain that has at least 93% sequence identity to H1 (SEQ ID NO: 2). In a particular embodiment, an antibody, which immunospecifically binds to a KIT polypeptide (e.g., the D4 region of human KIT), comprises a VH domain that has at least 94%, or at least 95%, or at least 96%, or at least 97%, or at least 98%, or at least 99% sequence identity to H1 (SEQ ID NO: 2). In a particular embodiment, the VH domain is non-immunogenic, for example as determined by the absence of epitopes that binds to MEW class II, e.g., non-human germline binders to MEW class II. In a certain embodiment, such antibody or antigen-binding fragment thereof comprises a VH domain comprising VH CDR1, VH CDR2, and VH CDR3 comprising the amino acid sequences of SEQ ID NOs: 16-18, respectively.

In certain aspects, provided herein is an antibody or an antigen-binding fragment thereof, which immunospecifically binds to a KIT polypeptide (e.g., the D4 region of human KIT), comprising a VH domain that has at least 92% sequence identity to H2 (SEQ ID NO: 3). In a particular embodiment, an antibody, which immunospecifically binds to a KIT polypeptide (e.g., the D4 region of human KIT), or antigen-binding fragment thereof, comprises a VH domain that has at least 93%, at least 94%, or at least 95%, or at least 96%, or at least 97%, or at least 98%, or at least 99% sequence identity to H2 (SEQ ID NO: 3). In a particular embodiment, the VH domain is non-immunogenic, for example as determined by the absence of epitopes that bind to MEW class II, e.g., non-human germline binders to MEW class II. In a certain embodiment, such antibody, or antigen-binding fragment thereof, comprises a VH domain comprising VH CDR1, VH CDR2, and VH CDR3 comprising the amino acid sequences of SEQ ID NOs: 16-18, respectively.

In certain aspects, provided herein is an antibody or an antigen-binding fragment thereof, which immunospecifically binds to a KIT polypeptide (e.g., the D4 region of human KIT), comprising a VH domain that has at least 90% sequence identity to H3 (SEQ ID NO: 4). In a particular embodiment, an antibody or an antigen-binding fragment thereof, which immunospecifically binds to a KIT polypeptide (e.g., the D4 region of human KIT), comprises a VH domain that has at least 92%, at least 93%, at least 94%, or at least 95%, or at least 96%, or at least 97%, or at least 98%, or at least 99% sequence identity to H3 (SEQ ID NO: 4). In a particular embodiment, the VH domain is non-immunogenic, for example as determined by the absence of epitopes that binds to MHC class II, e.g., non-human germline binders to MEW class II. In a certain embodiment, such antibody or antigen-binding fragment thereof comprises a VH domain comprising VH CDR1, VH CDR2, and VH CDR3 comprising the amino acid sequences of SEQ ID NOs: 16-18, respectively.

In certain aspects, provided herein is an antibody or an antigen-binding fragment thereof, which immunospecifically binds to a KIT polypeptide (e.g., the D4 region of human KIT), comprising a VH domain that has at least 87% sequence identity to H4 (SEQ ID NO: 5). In a particular embodiment, an antibody or an antigen-binding fragment thereof, which immunospecifically binds to a KIT polypeptide (e.g., the D4 region of human KIT), comprises a VH domain that has at least 92%, at least 93%, at least 94%, or at least 95%, or at least 96%, or at least 97%, or at least 98%, or at least 99% sequence identity to H4 (SEQ ID NO: 5). In a particular embodiment, the VH domain is non-immunogenic, for example as determined by the absence of epitopes that binds to MHC class II, e.g., non-human germline binders to MEW class II. In a certain embodiment, such antibody or antigen-binding fragment thereof comprises a VH domain comprising VH CDR1, VH CDR2, and VH CDR3 comprising the amino acid sequences of SEQ ID NOs: 16-18, respectively.

In certain aspects, provided herein is an antibody or an antigen-binding fragment thereof, which immunospecifically binds to a KIT polypeptide (e.g., the D4 region of human KIT), comprising a VH domain that has at least 86% sequence identity to H5 (SEQ ID NO: 6). In a particular embodiment, an antibody or an antigen-binding fragment thereof, which immunospecifically binds to a KIT polypeptide (e.g., the D4 region of human KIT), comprises a VH domain that has at least 92%, at least 93%, at least 94%, or at least 95%, or at least 96%, or at least 97%, or at least 98%, or at least 99% sequence identity to H5 (SEQ ID NO: 6). In a particular embodiment, the VH domain is non-immunogenic, for example as determined by the absence of epitopes that binds to MHC class II, e.g., non-human germline binders to MEW class II. In a certain embodiment, such antibody or antigen-binding fragment thereof comprises a VH domain comprising VH CDR1, VH CDR2, and VH CDR3 comprising the amino acid sequences of SEQ ID NOs: 16-18, respectively.

In certain aspects, provided herein is an antibody or an antigen-binding fragment thereof, which immunospecifically binds to a KIT polypeptide (e.g., the D4 region of human KIT), comprising a VL domain that has at least 90% sequence identity to L1 (SEQ ID NO: 7). In a particular embodiment, an antibody or an antigen-binding fragment thereof, which immunospecifically binds to a KIT polypeptide (e.g., the D4 region of human KIT), comprises a VL domain that has at least 92%, at least 93%, at least 94%, or at least 95%, or at least 96%, or at least 97%, or at least 98%, or at least 99% sequence identity to L1 (SEQ ID NO: 7). In a particular embodiment, the VL domain is non-immunogenic, for example as determined by the absence of epitopes that binds to MHC class II, e.g., non-human germline binders to MEW class II. In a certain embodiment, such antibody or antigen-binding fragment thereof comprises a VL domain comprising VL CDR1, VL CDR2, and VL CDR3 comprising the amino acid sequences of SEQ ID NO: 19-21, respectively.

In certain aspects, provided herein is an antibody or an antigen-binding fragment thereof, which immunospecifically binds to a KIT polypeptide (e.g., the D4 region of human KIT), comprising a VL domain that has at least 88% sequence identity to L2 (SEQ ID NO: 8). In a particular embodiment, an antibody, which immunospecifically binds to a KIT polypeptide (e.g., the D4 region of human KIT), comprises a VL domain that has at least 92%, at least 93%, at least 94%, or at least 95%, or at least 96%, or at least 97%, or at least 98%, or at least 99% sequence identity to L2 (SEQ ID NO: 8). In a particular embodiment, the VL domain is non-immunogenic, for example as determined by the absence of epitopes that binds to MHC class II, e.g., non-human germline binders to MHC class II. In a certain embodiment, such antibody or antigen-binding fragment thereof comprises a VL domain comprising VL CDR1, VL CDR2, and VL CDR3 comprising the amino acid sequences of SEQ ID NO: 19-21, respectively.

In certain aspects, provided herein is an antibody or an antigen-binding fragment thereof, which immunospecifically binds to a KIT polypeptide (e.g., the D4 region of human KIT), comprising a VL domain that has at least 87% sequence identity to L3 (SEQ ID NO: 9). In a particular embodiment, an antibody or an antigen-binding fragment thereof, which immunospecifically binds to a KIT polypeptide (e.g., the D4 region of human KIT), comprises a VL domain that has at least 92%, at least 93%, at least 94%, or at least 95%, or at least 96%, or at least 97%, or at least 98%, or at least 99% sequence identity to L3 (SEQ ID NO: 9). In a particular embodiment, the VL domain is non-immunogenic, for example as determined by the absence of epitopes that binds to MHC class II, e.g., non-human germline binders to MHC class II. In a certain embodiment, such antibody or antigen-binding fragment thereof comprises a VL domain comprising VL CDR1, VL CDR2, and VL CDR3 comprising the amino acid sequences of SEQ ID NO: 19-21, respectively.

In certain aspects, provided herein is an antibody or an antigen-binding fragment thereof, which immunospecifically binds to a KIT polypeptide (e.g., the D4 region of human KIT), comprising a VL domain that has at least 84% sequence identity to L4 (SEQ ID NO: 10). In a particular embodiment, an antibody or an antigen-binding fragment thereof, which immunospecifically binds to a KIT polypeptide (e.g., the D4 region of human KIT), comprises a VL domain that has at least 92%, at least 93%, at least 94%, or at least 95%, or at least 96%, or at least 97%, or at least 98%, or at least 99% sequence identity to L4 (SEQ ID NO: 10). In a particular embodiment, the VL domain is non-immunogenic, for example as determined by the absence of epitopes that binds to MHC class II, e.g., non-human germline binders to MHC class II. In a certain embodiment, such antibody or antigen-binding fragment thereof comprises a VL domain comprising VL CDR1, VL CDR2, and VL CDR3 comprising the amino acid sequences of SEQ ID NO: 19-21, respectively.

In specific embodiments, provided herein is an antibody (e.g., human or humanized antibody) or an antigen-binding fragment thereof, which immunospecifically binds to a KIT polypeptide (e.g., the D4 region of human KIT), comprising (i) a VH domain comprising an amino acid sequence that has at least 93% or at least 95% sequence identity to H1 (SEQ ID NO: 2); and (ii) a VL domain comprising an amino acid sequence that has at least 90% or at least 92% sequence identity to L1 (SEQ ID NO: 7). In a particular embodiment, the VL and VH domains are non-immunogenic, for example as determined by the absence of epitopes that binds to MHC class II, e.g., non-human germline binders to MEW class II. In a certain embodiment, such antibody or antigen-binding fragment thereof comprises VL CDRs 1-3 comprising the amino acid sequences of SEQ ID NOs: 19-21, respectively, and VH CDRs 1-3 comprising the amino acid sequences of SEQ ID NOs: 16-18, respectively.

In specific embodiments, provided herein is an antibody (e.g., human or humanized antibody) or an antigen-binding fragment thereof, which immunospecifically binds to a KIT polypeptide (e.g., the D4 region of human KIT), comprising (i) a VH domain comprising an amino acid sequence that has at least 92% or at least 94% sequence identity to H2 (SEQ ID NO: 3); and (ii) a VL domain comprising an amino acid sequence that has at least 90% or at least 92% sequence identity to L1 (SEQ ID NO: 7). In a particular embodiment, the VL and VH domains are non-immunogenic, for example as determined by the absence of epitopes that binds to MHC class II, e.g., non-human germline binders to MEW class II. In a certain embodiment, such antibody or antigen-binding fragment thereof comprises VL CDRs 1-3 comprising the amino acid sequences of SEQ ID NOs: 19-21, respectively, and VH CDRs 1-3 comprising the amino acid sequences of SEQ ID NOs: 16-18, respectively.

In specific embodiments, provided herein is an antibody (e.g., human or humanized antibody) or an antigen-binding fragment thereof, which immunospecifically binds to a KIT polypeptide (e.g., the D4 region of human KIT), comprising (i) a VH domain comprising an amino acid sequence that has at least 90% or at least 92% sequence identity to H3 (SEQ ID NO: 4); and (ii) a VL domain comprising an amino acid sequence that has at least 90% or at least 92% sequence identity to L1 (SEQ ID NO: 7). In a particular embodiment, the VL and VH domains are non-immunogenic, for example as determined by the absence of epitopes that binds to MHC class II, e.g., non-human germline binders to MEW class II. In a certain embodiment, such antibody or antigen-binding fragment thereof comprises VL CDRs 1-3 comprising the amino acid sequences of SEQ ID NOs: 19-21, respectively, and VH CDRs 1-3 comprising the amino acid sequences of SEQ ID NOs: 16-18, respectively.

In specific embodiments, provided herein is an antibody (e.g., human or humanized antibody) or an antigen-binding fragment thereof, which immunospecifically binds to a KIT polypeptide (e.g., the D4 region of human KIT), comprising (i) a VH domain comprising an amino acid sequence that has at least 87% or at least 90% sequence identity to H4 (SEQ ID NO: 5); and (ii) a VL domain comprising an amino acid sequence that has at least 90% or at least 92% sequence identity to L1 (SEQ ID NO: 7). In a particular embodiment, the VL and VH domains are non-immunogenic, for example as determined by the absence of epitopes that binds to MHC class II, e.g., non-human germline binders to MEW class II. In a certain embodiment, such antibody or antigen-binding fragment thereof comprises VL CDRs 1-3 comprising the amino acid sequences of SEQ ID NOs: 19-21, respectively, and VH CDRs 1-3 comprising the amino acid sequences of SEQ ID NOs: 16-18, respectively.

In specific embodiments, provided herein is an antibody (e.g., human or humanized antibody) or an antigen-binding fragment thereof, which immunospecifically binds to a KIT polypeptide (e.g., the D4 region of human KIT), comprising (i) a VH domain comprising an amino acid sequence that has at least 86% or at least 88% sequence identity to H5 (SEQ ID NO: 6); and (ii) a VL domain comprising an amino acid sequence that has at least 90% or at least 92% sequence identity to L1 (SEQ ID NO: 7). In a particular embodiment, the VL and VH domains are non-immunogenic, for example as determined by the absence of epitopes that binds to MHC class II, e.g., non-human germline binders to MEW class II. In a certain embodiment, such antibody or antigen-binding fragment thereof comprises VL CDRs 1-3 comprising the amino acid sequences of SEQ ID NOs: 19-21, respectively, and VH CDRs 1-3 comprising the amino acid sequences of SEQ ID NOs: 16-18, respectively.

In specific embodiments, provided herein is an antibody (e.g., human or humanized antibody) or an antigen-binding fragment thereof, which immunospecifically binds to a KIT polypeptide (e.g., the D4 region of human KIT), comprising (i) a VH domain comprising an amino acid sequence that has at least 93% or at least 95% sequence identity to H1 (SEQ ID NO: 2); and (ii) a VL domain comprising an amino acid sequence that has at least 88% or at least 90% sequence identity to L2 (SEQ ID NO: 8). In a particular embodiment, the VL and VH domains are non-immunogenic, for example as determined by the absence of epitopes that binds to MHC class II, e.g., non-human germline binders to MEW class II. In a certain embodiment, such antibody or antigen-binding fragment thereof comprises VL CDRs 1-3 comprising the amino acid sequences of SEQ ID NOs: 19-21, respectively, and VH CDRs 1-3 comprising the amino acid sequences of SEQ ID NOs: 16-18, respectively.

In specific embodiments, provided herein is an antibody (e.g., human or humanized antibody) or an antigen-binding fragment thereof, which immunospecifically binds to a KIT polypeptide (e.g., the D4 region of human KIT), comprising (i) a VH domain comprising an amino acid sequence that has at least 92% or at least 94% sequence identity to H2 (SEQ ID NO: 3); and (ii) a VL domain comprising an amino acid sequence that has at least 88% or at least 90% sequence identity to L2 (SEQ ID NO: 8). In a particular embodiment, the VL and VH domains are non-immunogenic, for example as determined by the absence of epitopes that binds to MHC class II, e.g., non-human germline binders to MEW class II. In a certain embodiment, such antibody or antigen-binding fragment thereof comprises VL CDRs 1-3 comprising the amino acid sequences of SEQ ID NOs: 19-21, respectively, and VH CDRs 1-3 comprising the amino acid sequences of SEQ ID NOs: 16-18, respectively.

In specific embodiments, provided herein is an antibody (e.g., human or humanized antibody) or an antigen-binding fragment thereof, which immunospecifically binds to a KIT polypeptide (e.g., the D4 region of human KIT), comprising (i) a VH domain comprising an amino acid sequence that has at least 90% or at least 92% sequence identity to H3 (SEQ ID NO: 4); and (ii) a VL domain comprising an amino acid sequence that has at least 88% or at least 90% sequence identity to L2 (SEQ ID NO: 8). In a particular embodiment, the VL and VH domains are non-immunogenic, for example as determined by the absence of epitopes that binds to MHC class II, e.g., non-human germline binders to MEW class II. In a certain embodiment, such antibody or antigen-binding fragment thereof comprises VL CDRs 1-3 comprising the amino acid sequences of SEQ ID NOs: 19-21, respectively, and VH CDRs 1-3 comprising the amino acid sequences of SEQ ID NOs: 16-18, respectively.

In specific embodiments, provided herein is an antibody (e.g., human or humanized antibody) or an antigen-binding fragment thereof, which immunospecifically binds to a KIT polypeptide (e.g., the D4 region of human KIT), comprising (i) a VH domain comprising an amino acid sequence that has at least 87% or at least 90% sequence identity to H4 (SEQ ID NO: 5); and (ii) a VL domain comprising an amino acid sequence that has at least 88% or at least 90% sequence identity to L2 (SEQ ID NO: 8). In a particular embodiment, the VL and VH domains are non-immunogenic, for example as determined by the absence of epitopes that binds to MHC class II, e.g., non-human germline binders to MEW class II. In a certain embodiment, such antibody or antigen-binding fragment thereof comprises VL CDRs 1-3 comprising the amino acid sequences of SEQ ID NOs: 19-21, respectively, and VH CDRs 1-3 comprising the amino acid sequences of SEQ ID NOs: 16-18, respectively.

In specific embodiments, provided herein is an antibody (e.g., human or humanized antibody) or an antigen-binding fragment thereof, which immunospecifically binds to a KIT polypeptide (e.g., the D4 region of human KIT), comprising (i) a VH domain comprising an amino acid sequence that has at least 86% or at least 88% sequence identity to H5 (SEQ ID NO: 6); and (ii) a VL domain comprising an amino acid sequence that has at least 88% or at least 90% sequence identity to L2 (SEQ ID NO: 8). In a particular embodiment, the VL and VH domains are non-immunogenic, for example as determined by the absence of epitopes that binds to MHC class II, e.g., non-human germline binders to MEW class II. In a certain embodiment, such antibody or antigen-binding fragment thereof comprises VL CDRs 1-3 comprising the amino acid sequences of SEQ ID NOs: 19-21, respectively, and VH CDRs 1-3 comprising the amino acid sequences of SEQ ID NOs: 16-18, respectively.

In specific embodiments, provided herein is an antibody (e.g., human or humanized antibody) or an antigen-binding fragment thereof, which immunospecifically binds to a KIT polypeptide (e.g., the D4 region of human KIT), comprising (i) a VH domain comprising an amino acid sequence that has at least 93% or at least 95% sequence identity to H1 (SEQ ID NO: 2); and (ii) a VL domain comprising an amino acid sequence that has at least 87% or at least 90% sequence identity to L3 (SEQ ID NO: 9). In a particular embodiment, the VL and VH domains are non-immunogenic, for example as determined by the absence of epitopes that binds to MHC class II, e.g., non-human germline binders to MEW class II. In a certain embodiment, such antibody or antigen-binding fragment thereof comprises VL CDRs 1-3 comprising the amino acid sequences of SEQ ID NOs: 19-21, respectively, and VH CDRs 1-3 comprising the amino acid sequences of SEQ ID NOs: 16-18, respectively.

In specific embodiments, provided herein is an antibody (e.g., human or humanized antibody) or an antigen-binding fragment thereof, which immunospecifically binds to a KIT polypeptide (e.g., the D4 region of human KIT), comprising (i) a VH domain comprising an amino acid sequence that has at least 92% or at least 94% sequence identity to H2 (SEQ ID NO: 3); and (ii) a VL domain comprising an amino acid sequence that has at least 87% or at least 90% sequence identity to L3 (SEQ ID NO: 9). In a particular embodiment, the VL and VH domains are non-immunogenic, for example as determined by the absence of epitopes that binds to MHC class II, e.g., non-human germline binders to MEW class II. In a certain embodiment, such antibody or antigen-binding fragment thereof comprises VL CDRs 1-3 comprising the amino acid sequences of SEQ ID NOs: 19-21, respectively, and VH CDRs 1-3 comprising the amino acid sequences of SEQ ID NOs: 16-18, respectively.

In specific embodiments, provided herein is an antibody (e.g., human or humanized antibody) or an antigen-binding fragment thereof, which immunospecifically binds to a KIT polypeptide (e.g., the D4 region of human KIT), comprising (i) a VH domain comprising an amino acid sequence that has at least 90% or at least 92% sequence identity to H3 (SEQ ID NO: 4); and (ii) a VL domain comprising an amino acid sequence that has at least 87% or at least 90% sequence identity to L3 (SEQ ID NO: 9). In a particular embodiment, the VL and VH domains are non-immunogenic, for example as determined by the absence of epitopes that binds to MHC class II, e.g., non-human germline binders to MEW class II. In a certain embodiment, such antibody or antigen-binding fragment thereof comprises VL CDRs 1-3 comprising the amino acid sequences of SEQ ID NOs: 19-21, respectively, and VH CDRs 1-3 comprising the amino acid sequences of SEQ ID NOs: 16-18, respectively.

In specific embodiments, provided herein is an antibody (e.g., human or humanized antibody) or an antigen-binding fragment thereof, which immunospecifically binds to a KIT polypeptide (e.g., the D4 region of human KIT), comprising (i) a VH domain comprising an amino acid sequence that has at least 87% or at least 90% sequence identity to H4 (SEQ ID NO: 5); and (ii) a VL domain comprising an amino acid sequence that has at least 87% or at least 90% sequence identity to L3 (SEQ ID NO: 9). In a particular embodiment, the VL and VH domains are non-immunogenic, for example as determined by the absence of epitopes that binds to MHC class II, e.g., non-human germline binders to MEW class II. In a certain embodiment, such antibody or antigen-binding fragment thereof comprises VL CDRs 1-3 comprising the amino acid sequences of SEQ ID NOs: 19-21, respectively, and VH CDRs 1-3 comprising the amino acid sequences of SEQ ID NOs: 16-18, respectively.

In specific embodiments, provided herein is an antibody (e.g., human or humanized antibody) or an antigen-binding fragment thereof, which immunospecifically binds to a KIT polypeptide (e.g., the D4 region of human KIT), comprising (i) a VH domain comprising an amino acid sequence that has at least 86% or at least 88% sequence identity to H5 (SEQ ID NO: 6); and (ii) a VL domain comprising an amino acid sequence that has at least 87% or at least 90% sequence identity to L3 (SEQ ID NO: 9). In a particular embodiment, the VL and VH domains are non-immunogenic, for example as determined by the absence of epitopes that binds to MHC class II, e.g., non-human germline binders to MEW class II. In a certain embodiment, such antibody or antigen-binding fragment thereof comprises VL CDRs 1-3 comprising the amino acid sequences of SEQ ID NOs: 19-21, respectively, and VH CDRs 1-3 comprising the amino acid sequences of SEQ ID NOs: 16-18, respectively.

In specific embodiments, provided herein is an antibody (e.g., human or humanized antibody) or an antigen-binding fragment thereof, which immunospecifically binds to a KIT polypeptide (e.g., the D4 region of human KIT), comprising (i) a VH domain comprising an amino acid sequence that has at least 93% or at least 95% sequence identity to H1 (SEQ ID NO: 2); and (ii) a VL domain comprising an amino acid sequence that has at least 84% or at least 86% sequence identity to L4 (SEQ ID NO: 10). In a particular embodiment, the VL and VH domains are non-immunogenic, for example as determined by the absence of epitopes that binds to MHC class II, e.g., non-human germline binders to MEW class II. In a certain embodiment, such antibody or antigen-binding fragment thereof comprises VL CDRs 1-3 comprising the amino acid sequences of SEQ ID NOs: 19-21, respectively, and VH CDRs 1-3 comprising the amino acid sequences of SEQ ID NOs: 16-18, respectively.

In specific embodiments, provided herein is an antibody (e.g., human or humanized antibody) or an antigen-binding fragment thereof, which immunospecifically binds to a KIT polypeptide (e.g., the D4 region of human KIT), comprising (i) a VH domain comprising an amino acid sequence that has at least 92% or at least 94% sequence identity to H2 (SEQ ID NO: 3); and (ii) a VL domain comprising an amino acid sequence that has at least 84% or at least 86% sequence identity to L4 (SEQ ID NO: 10). In a particular embodiment, the VL and VH domains are non-immunogenic, for example as determined by the absence of epitopes that binds to MHC class II, e.g., non-human germline binders to MEW class II. In a certain embodiment, such antibody or antigen-binding fragment thereof comprises VL CDRs 1-3 comprising the amino acid sequences of SEQ ID NOs: 19-21, respectively, and VH CDRs 1-3 comprising the amino acid sequences of SEQ ID NOs: 16-18, respectively.

In specific embodiments, provided herein is an antibody (e.g., human or humanized antibody) or an antigen-binding fragment thereof, which immunospecifically binds to a KIT polypeptide (e.g., the D4 region of human KIT), comprising (i) a VH domain comprising an amino acid sequence that has at least 90% or at least 92% sequence identity to H3 (SEQ ID NO: 4); and (ii) a VL domain comprising an amino acid sequence that has at least 84% or at least 86% sequence identity to L4 (SEQ ID NO: 10). In a particular embodiment, the VL and VH domains are non-immunogenic, for example as determined by the absence of epitopes that binds to MHC class II, e.g., non-human germline binders to MEW class II. In a certain embodiment, such antibody or antigen-binding fragment thereof comprises VL CDRs 1-3 comprising the amino acid sequences of SEQ ID NOs: 19-21, respectively, and VH CDRs 1-3 comprising the amino acid sequences of SEQ ID NOs: 16-18, respectively.

In specific embodiments, provided herein is an antibody (e.g., human or humanized antibody) or an antigen-binding fragment thereof, which immunospecifically binds to a KIT polypeptide (e.g., the D4 region of human KIT), comprising (i) a VH domain comprising an amino acid sequence that has at least 87% or at least 90% sequence identity to H4 (SEQ ID NO: 5); and (ii) a VL domain comprising an amino acid sequence that has at least 84% or at least 86% sequence identity to L4 (SEQ ID NO: 10). In a particular embodiment, the VL and VH domains are non-immunogenic, for example as determined by the absence of epitopes that binds to MHC class II, e.g., non-human germline binders to MEW class II. In a certain embodiment, such antibody or antigen-binding fragment thereof comprises VL CDRs 1-3 comprising the amino acid sequences of SEQ ID NOs: 19-21, respectively, and VH CDRs 1-3 comprising the amino acid sequences of SEQ ID NOs: 16-18, respectively.

In specific embodiments, provided herein is an antibody (e.g., human or humanized antibody) or an antigen-binding fragment thereof, which immunospecifically binds to a KIT polypeptide (e.g., the D4 region of human KIT), comprising (i) a VH domain comprising an amino acid sequence that has at least 86% or at least 88% sequence identity to H5 (SEQ ID NO: 6); and (ii) a VL domain comprising an amino acid sequence that has at least 84% or at least 86% sequence identity to L4 (SEQ ID NO: 10). In a particular embodiment, the VL and VH domains are non-immunogenic, for example as determined by the absence of epitopes that binds to MHC class II, e.g., non-human germline binders to MEW class II. In a certain embodiment, such antibody or antigen-binding fragment thereof comprises VL CDRs 1-3 comprising the amino acid sequences of SEQ ID NOs: 19-21, respectively, and VH CDRs 1-3 comprising the amino acid sequences of SEQ ID NOs: 16-18, respectively.

To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions×100%). In one embodiment, the two sequences are the same length. In a certain embodiment, the percent identity is determined over the entire length of an amino acid sequence or nucleotide sequence.

The determination of percent identity between two sequences (e.g., amino acid sequences or nucleic acid sequences) can also be accomplished using a mathematical algorithm. A preferred, non-limiting example of a mathematical algorithm utilized for the comparison of two sequences is the algorithm of Karlin and Altschul, 1990, Proc. Natl. Acad. Sci. U.S.A. 87:2264 2268, modified as in Karlin and Altschul, 1993, Proc. Natl. Acad. Sci. U.S.A. 90:5873 5877. Such an algorithm is incorporated into the NBLAST and XBLAST programs of Altschul et al., 1990, J. Mol. Biol. 215:403. BLAST nucleotide searches can be performed with the NBLAST nucleotide program parameters set, e.g., for score=100, wordlength=12 to obtain nucleotide sequences homologous to a nucleic acid molecules described herein. BLAST protein searches can be performed with the XBLAST program parameters set, e.g., to score 50, wordlength=3 to obtain amino acid sequences homologous to a protein molecule described herein. To obtain gapped alignments for comparison purposes, Gapped BLAST can be utilized as described in Altschul et al., 1997, Nucleic Acids Res. 25:3389 3402. Alternatively, PSI BLAST can be used to perform an iterated search which detects distant relationships between molecules (Id.). When utilizing BLAST, Gapped BLAST, and PSI Blast programs, the default parameters of the respective programs (e.g., of XBLAST and NBLAST) can be used (see, e.g., National Center for Biotechnology Information (NCBI) on the worldwide web, ncbi.nlm.nih.gov). Another preferred, non limiting example of a mathematical algorithm utilized for the comparison of sequences is the algorithm of Myers and Miller, 1988, CABIOS 4:11 17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, typically only exact matches are counted.

In a particular aspect, provided herein is an antibody or an antigen-binding fragment thereof, which immunospecifically binds to a KIT polypeptide (e.g., the D4 region of human KIT), comprises: (i) a VH domain comprising VH CDR1, VH CDR2, and VH CDR3 comprising the amino acid sequences of SEQ ID NOs: 16-18, respectively, and one, two, three or four framework regions of H1, H2, H3, H4 or H5 (see Table 5A); and/or (ii) a VL domain comprising VL CDR1, VL CDR2, and VL CDR3 comprising the amino acid sequences of SEQ ID NO: 19-21, respectively, and one, two, three or four framework regions of L1, L2, L3, or L4 (see Table 5B).

In one embodiment, an antibody described herein, which immunospecifically binds to a KIT polypeptide (e.g., the D4 region of human KIT), comprises a VH domain comprising VH CDR1, VH CDR2, and VH CDR3 comprising the amino acid sequences of SEQ ID NOs: 16-18, respectively, and framework region FR1 of H1, H2, H3, H4 or H5. In one embodiment, an antibody described herein, which immunospecifically binds to a KIT polypeptide (e.g., the D4 region of human KIT), comprises a VH domain comprising VH CDR1, VH CDR2, and VH CDR3 comprising the amino acid sequences of SEQ ID NOs: 16-18, respectively, and framework region FR2 of H1, H2, H3, H4 or H5. In one embodiment, an antibody described herein, which immunospecifically binds to a KIT polypeptide (e.g., the D4 region of human KIT), comprises a VH domain comprising VH CDR1, VH CDR2, and VH CDR3 comprising the amino acid sequences of SEQ ID NOs: 16-18, respectively, and framework region FR3 of H1, H2, H3, H4 or H5. In one embodiment, an antibody described herein, which immunospecifically binds to a KIT polypeptide (e.g., the D4 region of human KIT), comprises a VH domain comprising VH CDR1, VH CDR2, and VH CDR3 comprising the amino acid sequences of SEQ ID NOs: 16-18, respectively, and framework region FR4 of H1, H2, H3, H4 or H5.

In one embodiment, an antibody described herein, which immunospecifically binds to a KIT polypeptide (e.g., the D4 region of human KIT), comprises a VH domain comprising VH CDR1, VH CDR2, and VH CDR3 comprising the amino acid sequences of SEQ ID NOs: 16-18, respectively, and framework regions FR1 and FR2 of H1, H2, H3, H4 or H5. In one embodiment, an antibody described herein, which immunospecifically binds to a KIT polypeptide (e.g., the D4 region of human KIT), comprises a VH domain comprising VH CDR1, VH CDR2, and VH CDR3 comprising the amino acid sequences of SEQ ID NOs: 16-18, respectively, and framework regions FR1, FR2, and FR3 of H1, H2, H3, H4 or H5. In one embodiment, an antibody described herein, which immunospecifically binds to a KIT polypeptide (e.g., the D4 region of human KIT), comprises a VH domain comprising VH CDR1, VH CDR2, and VH CDR3 comprising the amino acid sequences of SEQ ID NOs: 16-18, respectively, and framework regions FR1, FR2, FR3, and FR4 of H1, H2, H3, H4 or H5.

In one embodiment, an antibody described herein, which immunospecifically binds to a KIT polypeptide (e.g., the D4 region of human KIT), comprises a VH domain comprising VH CDR1, VH CDR2, and VH CDR3 comprising the amino acid sequences of SEQ ID NOs: 16-18, respectively, and framework regions FR1 and FR3 of H1, H2, H3, H4 or H5. In one embodiment, an antibody described herein, which immunospecifically binds to a KIT polypeptide (e.g., the D4 region of human KIT), comprises a VH domain comprising VH CDR1, VH CDR2, and VH CDR3 comprising the amino acid sequences of SEQ ID NOs: 16-18, respectively, and framework regions FR1, FR3, and FR4 of H1, H2, H3, H4 or H5.

In one embodiment, an antibody described herein, which immunospecifically binds to a KIT polypeptide (e.g., the D4 region of human KIT), comprises a VH domain comprising VH CDR1, VH CDR2, and VH CDR3 comprising the amino acid sequences of SEQ ID NOs: 16-18, respectively, and framework regions FR1 and FR4 of H1, H2, H3, H4 or H5.

In one embodiment, an antibody described herein, which immunospecifically binds to a KIT polypeptide (e.g., the D4 region of human KIT), comprises a VH domain comprising VH CDR1, VH CDR2, and VH CDR3 comprising the amino acid sequences of SEQ ID NOs: 16-18, respectively, and framework regions FR1, FR2, and FR4 of H1, H2, H3, H4 or H5.

In one embodiment, a human or humanized antibody described herein, which immunospecifically binds to a KIT polypeptide (e.g., the D4 region of human KIT), comprises a VH domain comprising VH CDR1, VH CDR2, and VH CDR3 comprising the amino acid sequences of SEQ ID NOs: 16-18, respectively, and framework regions FR2 and FR3 of H1, H2, H3, H4 or H5. In one embodiment, an antibody described herein, which immunospecifically binds to a KIT polypeptide (e.g., the D4 region of human KIT), comprises a VH domain comprising VH CDR1, VH CDR2, and VH CDR3 comprising the amino acid sequences of SEQ ID NOs: 16-18, respectively, and framework regions FR2, FR3, and FR4 of H1, H2, H3, H4 or H5.

In one embodiment, an antibody described herein, which immunospecifically binds to a KIT polypeptide (e.g., the D4 region of human KIT), comprises a VH domain comprising VH CDR1, VH CDR2, and VH CDR3 comprising the amino acid sequences of SEQ ID NOs: 16-18, respectively, and framework regions FR3 and FR4 of H1, H2, H3, H4 or H5.

In one embodiment, an antibody described herein, which immunospecifically binds to a KIT polypeptide (e.g., the D4 region of human KIT), comprises a VL domain comprising VL CDR1, VL CDR2, and VL CDR3 comprising the amino acid sequences of SEQ ID NOs: 19-21, respectively, and framework region FR1 of L1, L2, L3, or L4. In one embodiment, an antibody described herein, which immunospecifically binds to a KIT polypeptide (e.g., the D4 region of human KIT), comprises a VL domain comprising VL CDR1, VL CDR2, and VL CDR3 comprising the amino acid sequences of SEQ ID NOs: 19-21, respectively, and framework region FR2 of L1, L2, L3, or L4. In one embodiment, an antibody described herein, which immunospecifically binds to a KIT polypeptide (e.g., the D4 region of human KIT), comprises a VL domain comprising VL CDR1, VL CDR2, and VL CDR3 comprising the amino acid sequences of SEQ ID NOs: 19-21, respectively, and framework region FR3 of L1, L2, L3, or L4. In one embodiment, an antibody described herein, which immunospecifically binds to a KIT polypeptide (e.g., the D4 region of human KIT), comprises a VL domain comprising VL CDR1, VL CDR2, and VL CDR3 comprising the amino acid sequences of SEQ ID NOs: 19-21, respectively, and framework region FR4 of L1, L2, L3, or L4.

In one embodiment, an antibody described herein, which immunospecifically binds to a KIT polypeptide (e.g., the D4 region of human KIT), comprises a VL domain comprising VL CDR1, VL CDR2, and VL CDR3 comprising the amino acid sequences of SEQ ID NOs: 19-21, respectively, and framework regions FR1 and FR2 of L1, L2, L3, or L4. In one embodiment, an antibody described herein, which immunospecifically binds to a KIT polypeptide (e.g., the D4 region of human KIT), comprises a VL domain comprising VL CDR1, VL CDR2, and VL CDR3 comprising the amino acid sequences of SEQ ID NOs: 19-21, respectively, and framework regions FR1, FR2, FR3, and FR4 of L1, L2, L3, or L4.

In one embodiment, an antibody described herein, which immunospecifically binds to a KIT polypeptide (e.g., the D4 region of human KIT), comprises a VL domain comprising VL CDR1, VL CDR2, and VL CDR3 comprising the amino acid sequences of SEQ ID NOs: 19-21, respectively, and framework regions FR1 and FR3 of L1, L2, L3, or L4. In one embodiment, an antibody described herein, which immunospecifically binds to a KIT polypeptide (e.g., the D4 region of human KIT), comprises a VL domain comprising VL CDR1, VL CDR2, and VL CDR3 comprising the amino acid sequences of SEQ ID NOs: 19-21, respectively, and framework regions FR1, FR3, and FR4 of L1, L2, L3, or L4.

In one embodiment, an antibody described herein, which immunospecifically binds to a KIT polypeptide (e.g., the D4 region of human KIT), comprises a VL domain comprising VL CDR1, VL CDR2, and VL CDR3 comprising the amino acid sequences of SEQ ID NOs: 19-21, respectively, and framework regions FR1 and FR4 of L1, L2, L3, or L4.

In one embodiment, an antibody described herein, which immunospecifically binds to a KIT polypeptide (e.g., the D4 region of human KIT), comprises a VL domain comprising VL CDR1, VL CDR2, and VL CDR3 comprising the amino acid sequences of SEQ ID NOs: 19-21, respectively, and framework regions FR1, FR2, and FR4 of L1, L2, L3, or L4.

In one embodiment, an antibody described herein, which immunospecifically binds to a KIT polypeptide (e.g., the D4 region of human KIT), comprises a VL domain comprising VL CDR1, VL CDR2, and VL CDR3 comprising the amino acid sequences of SEQ ID NOs: 19-21, respectively, and framework regions FR2 and FR3 of L1, L2, L3, or L4. In one embodiment, an antibody described herein, which immunospecifically binds to a KIT polypeptide (e.g., the D4 region of human KIT), comprises a VL domain comprising VL CDR1, VL CDR2, and VL CDR3 comprising the amino acid sequences of SEQ ID NOs: 19-21, respectively, and framework regions FR2, FR3, and FR4 of L1, L2, L3, or L4.

In one embodiment, an antibody described herein, which immunospecifically binds to a KIT polypeptide (e.g., the D4 region of human KIT), comprises a VL domain comprising VL CDR1, VL CDR2, and VL CDR3 comprising the amino acid sequences of SEQ ID NOs: 19-21, respectively, and framework regions FR3 and FR4 of L1, L2, L3, or L4.

In a particular aspect, provided herein is an antibody or an antigen-binding fragment thereof, which immunospecifically binds to a KIT polypeptide (e.g., the D4 region of human KIT), comprising: (i) a VH domain comprising VH CDR1, VH CDR2, and VH CDR3 comprising the amino acid sequences of SEQ ID NOs: 16-18, respectively, and framework regions FR1-FR4 of any one of VH domains HH257-HH281 (see Table 5C); and (ii) a VL domain comprising VL CDR1, VL CDR2, and VL CDR3 comprising the amino acid sequences of SEQ ID NO: 19-21, respectively, and FR1-FR4 of any one of VL domains LL65-LL76 (see Table 5D).

In a particular aspect, provided herein is an antibody or an antigen-binding fragment thereof, which immunospecifically binds to a KIT polypeptide (e.g., the D4 region of human KIT), comprising: (i) a VH domain comprising VH CDR1, VH CDR2, and VH CDR3 comprising a combination of amino acid sequences set forth in Table 2 or 3, and framework regions FR1-FR4 of any one of VH domains H1-H5 (Table 5A) and HH257-HH281 (see Table 5C); and (ii) a VL domain comprising VL CDR1, VL CDR2, and VL CDR3 comprising a combination of amino acid sequences set forth in either Table 2 (set 1 or set 2) or 3 (AbM or Contact CDRs), respectively, and FR1-FR4 of any one of VL domains L1-L4 (Table 5B) and LL65-LL76 (see Table 5D).

In a particular aspect, provided herein is an antibody or an antigen-binding fragment thereof, which immunospecifically binds to a KIT polypeptide (e.g., the D4 region of human KIT), comprising: (i) a VH domain comprising VH CDR1, VH CDR2, and VH CDR3 comprising a combination of amino acid sequences set forth in Table 2 or 3, and corresponding framework regions FR1-FR4 comprising sequences flanking the VH CDRs for example, as depicted in any one of FIGS. 3A-3I; and (ii) a VL domain comprising VL CDR1, VL CDR2, and VL CDR3 comprising a combination of amino acid sequences set forth in in either Table 2 (set 1 or set 2) or 3 (AbM or Contact CDRs), respectively, and corresponding framework regions FR1-FR4 comprising sequences flanking the VL CDRs, for example as depicted in any one of FIGS. 3A-3I.

TABLE 5A

VH domain Framework Regions (FRs)

| | VH FR1 | VH FR2 | VH FR3 | VH FR4 |
|---|---|---|---|---|
| H1 | QVQLVQSGAELKKPGAS VKLSCKASGYTFT (SEQ ID NO: 33) | WVKQAPGKGLEWIA (SEQ ID NO: 34) | RATLTAEKSTSTAYMQLSS LRSEDSAVYFCAR (SEQ ID NO: 35) | WGQGTTVTVSS (SEQ ID NO: 36) |
| H2 | QVQLVQSGAEVKKPGAS VKLSCKASGYTFT (SEQ ID NO: 37) | WVKQAPGKGLEWIA (SEQ ID NO: 34) | RATLTAEKSTSTAYMQLSS LRSEDTAVYFCAR (SEQ ID NO: 38) | WGQGTTVTVSS (SEQ ID NO: 36) |
| H3 | QVQLVQSGAEVKKPGAS VKVLSCKASGYTFT (SEQ ID NO: 37) | WVRQAPGKGLEWIA (SEQ ID NO: 39) | RATLTADKSTSTAYMQLSS LRSEDTAVYFCAR (SEQ ID NO: 40) | WGQGTTVTVSS (SEQ ID NO: 36) |
| H4 | QVQLVQSGAEVKKPGAS VKVSCKASGYTFT (SEQ ID NO: 41) | WVRQAPGKGLEWIA (SEQ ID NO: 39) | RATITADKSTSTAYMELSS LRSEDTAVYFCAR (SEQ ID NO: 42) | WGQGTTVTVSS (SEQ ID NO: 36) |
| H5 | QVQLVQSGAEVKKPGAS VKVSCKASGYTFT (SEQ ID NO: 41) | WVRQAPGKGLEWIA (SEQ ID NO: 39) | RVTITADKSTSTAYMELSS LRSEDTAVYFCAR (SEQ ID NO: 43) | WGQGTTVTVSS (SEQ ID NO: 36) |

TABLE 5B

VL domain Framework Regions (FRs)

| | VL FR1 | VL FR2 | VL FR3 | VL FR4 |
|---|---|---|---|---|
| L1 | DIVMTQSPSFLSASV GDRVTITC (SEQ ID NO: 44) | WYQQKPGKAPKALIY (SEQ ID NO: 45) | GVPDRFTGSGSGTDFTLT ISSLQSEDFADYFC (SEQ ID NO: 46) | FGGGTKVEIK (SEQ ID NO: 47) |
| L2 | DIVMTQSPSSLSASV GDRVTITC (SEQ ID NO: 48) | WYQQKPGKAPKALIY (SEQ ID NO: 45) | GVPDRFTGSGSGTDFTLT ISSLQPEDFADYFC (SEQ ID NO: 49) | FGGGTKVEIK (SEQ ID NO: 47) |
| L3 | DIVMTQSPSSLSASV GDRVTITC (SEQ ID NO: 48) | WYQQKPGKAPKALIY (SEQ ID NO: 45) | GVPDRFSGSGSGTDFTLT ISSLQPEDFADYFC (SEQ ID NO: 50) | FGGGTKVEIK (SEQ ID NO: 47) |
| L4 | DIVMTQSPSSLSASV GDRVTITC (SEQ ID NO: 48) | WYQQKPGKAPKSLIY (SEQ ID NO: 51) | GVPDRFSGSGSGTDFTLT ISSLQPDEFATYYC (SEQ ID NO: 52) | FGGGTKVEIK (SEQ ID NO: 47) |

TABLE 5C

Framework region sequences of VH domains HH257 to HH281

| VH domain | VH FR1 | VH FR2 | VH FR3 | VH FR4 |
|---|---|---|---|---|
| HH257 | SEQ ID NO: 33 | SEQ ID NO: 39 | SEQ ID NO: 35 | SEQ ID NO: 36 |
| HH258 | SEQ ID NO: 33 | SEQ ID NO: 34 | SEQ ID NO: 38 | SEQ ID NO: 36 |
| HH259 | SEQ ID NO: 33 | SEQ ID NO: 39 | SEQ ID NO: 38 | SEQ ID NO: 36 |
| HH260 | SEQ ID NO: 33 | SEQ ID NO: 34 | SEQ ID NO: 40 | SEQ ID NO: 36 |
| HH261 | SEQ ID NO: 33 | SEQ ID NO: 39 | SEQ ID NO: 40 | SEQ ID NO: 36 |
| HH262 | SEQ ID NO: 33 | SEQ ID NO: 34 | SEQ ID NO: 42 | SEQ ID NO: 36 |
| HH263 | SEQ ID NO: 33 | SEQ ID NO: 39 | SEQ ID NO: 42 | SEQ ID NO: 36 |
| HH264 | SEQ ID NO: 33 | SEQ ID NO: 34 | SEQ ID NO: 43 | SEQ ID NO: 36 |

TABLE 5C-continued

Framework region sequences of VH domains HH257 to HH281

| VH domain | VH FR1 | VH FR2 | VH FR3 | VH FR4 |
|---|---|---|---|---|
| HH265 | SEQ ID NO: 33 | SEQ ID NO: 39 | SEQ ID NO: 43 | SEQ ID NO: 36 |
| HH266 | SEQ ID NO: 37 | SEQ ID NO: 34 | SEQ ID NO: 35 | SEQ ID NO: 36 |
| HH267 | SEQ ID NO: 37 | SEQ ID NO: 39 | SEQ ID NO: 35 | SEQ ID NO: 36 |
| HH268 | SEQ ID NO: 37 | SEQ ID NO: 39 | SEQ ID NO: 38 | SEQ ID NO: 36 |
| HH269 | SEQ ID NO: 37 | SEQ ID NO: 34 | SEQ ID NO: 40 | SEQ ID NO: 36 |
| HH270 | SEQ ID NO: 37 | SEQ ID NO: 34 | SEQ ID NO: 42 | SEQ ID NO: 36 |
| HH271 | SEQ ID NO: 37 | SEQ ID NO: 39 | SEQ ID NO: 42 | SEQ ID NO: 36 |
| HH272 | SEQ ID NO: 37 | SEQ ID NO: 34 | SEQ ID NO: 43 | SEQ ID NO: 36 |
| HH273 | SEQ ID NO: 37 | SEQ ID NO: 39 | SEQ ID NO: 43 | SEQ ID NO: 36 |
| HH274 | SEQ ID NO: 41 | SEQ ID NO: 34 | SEQ ID NO: 35 | SEQ ID NO: 36 |
| HH275 | SEQ ID NO: 41 | SEQ ID NO: 39 | SEQ ID NO: 35 | SEQ ID NO: 36 |
| HH276 | SEQ ID NO: 41 | SEQ ID NO: 34 | SEQ ID NO: 38 | SEQ ID NO: 36 |
| HH277 | SEQ ID NO: 41 | SEQ ID NO: 39 | SEQ ID NO: 38 | SEQ ID NO: 36 |
| HH278 | SEQ ID NO: 41 | SEQ ID NO: 34 | SEQ ID NO: 40 | SEQ ID NO: 36 |
| HH279 | SEQ ID NO: 41 | SEQ ID NO: 39 | SEQ ID NO: 40 | SEQ ID NO: 36 |
| HH280 | SEQ ID NO: 41 | SEQ ID NO: 34 | SEQ ID NO: 42 | SEQ ID NO: 36 |
| HH281 | SEQ ID NO: 41 | SEQ ID NO: 34 | SEQ ID NO: 43 | SEQ ID NO: 36 |

TABLE 5D

Framework region sequences of VL domains LL65 to LL76

| VL domain | VL FR1 | VL FR2 | VL FR3 | VL FR4 |
|---|---|---|---|---|
| LL65 | SEQ ID NO: 44 | SEQ ID NO: 51 | SEQ ID NO: 46 | SEQ ID NO: 47 |
| LL66 | SEQ ID NO: 44 | SEQ ID NO: 45 | SEQ ID NO: 49 | SEQ ID NO: 47 |
| LL67 | SEQ ID NO: 44 | SEQ ID NO: 51 | SEQ ID NO: 49 | SEQ ID NO: 47 |
| LL68 | SEQ ID NO: 44 | SEQ ID NO: 45 | SEQ ID NO: 50 | SEQ ID NO: 47 |
| LL69 | SEQ ID NO: 44 | SEQ ID NO: 51 | SEQ ID NO: 50 | SEQ ID NO: 47 |
| LL70 | SEQ ID NO: 44 | SEQ ID NO: 45 | SEQ ID NO: 52 | SEQ ID NO: 47 |
| LL71 | SEQ ID NO: 44 | SEQ ID NO: 51 | SEQ ID NO: 52 | SEQ ID NO: 47 |
| LL72 | SEQ ID NO: 48 | SEQ ID NO: 45 | SEQ ID NO: 46 | SEQ ID NO: 47 |
| LL73 | SEQ ID NO: 48 | SEQ ID NO: 51 | SEQ ID NO: 46 | SEQ ID NO: 47 |
| LL74 | SEQ ID NO: 48 | SEQ ID NO: 51 | SEQ ID NO: 49 | SEQ ID NO: 47 |
| LL75 | SEQ ID NO: 48 | SEQ ID NO: 51 | SEQ ID NO: 50 | SEQ ID NO: 47 |
| LL76 | SEQ ID NO: 48 | SEQ ID NO: 45 | SEQ ID NO: 52 | SEQ ID NO: 47 |

In a particular aspect, provided herein is an antibody (e.g., human or humanized antibody) or an antigen-binding fragment thereof, which immunospecifically binds to a KIT polypeptide (e.g., the D4 region of human KIT), comprising: (i) a VH domain comprising the amino acid sequence: QVQLVQSGAEX$_{H1}$KKPGASVKX$_{H2}$SCKASGYTFT DYYINWVX$_{H3}$QAPGKGLEWIARIYPGS GNTYYNEKFKGRX$_{H4}$TX$_{H5}$TAX$_{H6}$KSTSTAYMX$_{H7}$ LSSLRSEDX$_{H8}$AVYFCARGVYYFDYW GQGTTVTVSS (SEQ ID NO: 11), wherein X$_{H1}$ at Kabat position 11, X$_{H2}$ at Kabat position 20, X$_{H3}$ at Kabat position 38, X$_{H4}$ at Kabat position 67, X$_{H5}$ at Kabat position 69, X$_{H6}$ at Kabat position 72, X$_{H7}$ at Kabat position 81, and X$_{H8}$ at Kabat position 87 are independently selected from any amino acid; and/or (ii) a VL domain comprising the amino acid sequence DIVMTQSPSX$_{K1}$LSASVGDRVTITCKASQNVRT NVAWYQQKPGKAPKX$_{K2}$LIYSASYRYSG VPDRFX$_{K3}$GSGSGTDFTLTISSLQX$_{K4}$EDFAX$_{K5}$YX$_{K6}$ CQQYNSYPRTFGGGTKVEIK (SEQ ID NO: 12), wherein X$_{K1}$ at Kabat position 10, X$_{K2}$ at Kabat position 46, X$_{K3}$ at Kabat position 63, X$_{K4}$ at Kabat position 80, X$_{K5}$ at Kabat position 85, and X$_{K6}$ at Kabat position 87 are independently selected from any amino acid. In a particular embodiment, the VH and/or VL domain is non-immunogenic, for example as determined by the absence of epitopes that binds to MHC class II, e.g., non-human germline binders to MHC class II.

In a particular aspect, provided herein is an antibody, which immunospecifically binds to a KIT polypeptide (e.g., the D4 region of human KIT), comprising: (i) a VH domain comprising the amino acid sequence: QVQLVQSGAEX$_{H1}$KKPGASVKX$_{H2}$SCKASGYTF TDYYINWVX$_{H3}$QAPGKGLEWIARIYPGS GNTYYNEKFKGRX$_{H4}$TX$_{H5}$TAX$_{H6}$KSTSTAYMX$_{H7}$ LSSLRSEDX$_{H8}$AVYFCARGVYYFDYW GQGTTVTVSS (SEQ ID NO: 11), wherein X$_{H1}$ at Kabat position 11, X$_{H2}$ at Kabat position 20, X$_{H3}$ at Kabat position 38, X$_{H4}$ at Kabat position 67, X$_{H5}$ at Kabat position 69, X$_{H6}$ at Kabat position 72, X$_{H7}$ at Kabat position 81, and X$_{H8}$ at Kabat position 87 are selected from the combination of amino acids set forth in Table 6B; and/or (ii) a VL domain comprising the amino acid sequence: DIVMTQSPSX$_{K1}$LSASVGDRVTITCKASQNVRTNV WYQQKPGKAPKX$_{K2}$LIYSASYRYSG VPDRFX$_{K3}$GSGSGTDFTLTISSLQX$_{K4}$EDFAX$_{K5}$YX$_{K6}$ CQQYNSYPRTFGGGTKVEIK (SEQ ID NO: 12), wherein X$_{K1}$ at Kabat position 10, X$_{K2}$ at Kabat position 46, X$_{K3}$ at Kabat position 63, X$_{K4}$ at Kabat position 80, X$_{K5}$ at Kabat position 85, and X$_{K6}$ at Kabat position 87 are selected from the combination of amino acids set forth in Table 6A. In a particular embodiment, the VH and/or VL domain is non-immunogenic, for example as determined by the absence of epitopes that binds to MHC class II, e.g., non-human germline binders to MHC class II.

In one embodiment, X$_{H1}$ at Kabat position 11 is an amino acid with an aliphatic side chain (e.g., hydrophobic side chain, or nonpolar side chain branched-chain amino acid (BCAA)), such as L or V. In one embodiment, $X_{H2}$ at Kabat position 20 is an amino acid with an aliphatic side chain (e.g., hydrophobic side chain, or nonpolar side chain branched-chain amino acid (BCAA)), such as L or V. In one embodiment, $X_{H3}$ at Kabat position 38 is an amino acid with a polar side chain (e.g., hydrophilic side chain, basic side chain, or charged side chain, e.g., positively charged side chain or negatively charged side chain), such as K or R. In one embodiment, $X_{H4}$ at Kabat position 67 is an amino acid with an aliphatic side chain (e.g., hydrophobic side chain, or nonpolar side chain branched-chain amino acid (BCAA)), such as V or A. In one embodiment, $X_{H5}$ at Kabat position 69 is an amino acid with an aliphatic side chain (e.g., hydrophobic side chain, or nonpolar side chain branched-chain amino acid (BCAA)), such as L or I. In one embodiment, $X_{H6}$ at Kabat position 72 is an amino acid with an acidic side chain, such as E or D. In one embodiment, $X_{H7}$ at Kabat position 81 is an amino acid with an acidic side chain or its amide derivative, such as Q (uncharged/amide derivative of E) or E. In one embodiment, $X_{H8}$ at Kabat position 87 is an amino acid with an aliphatic hydroxyl group or a hydrophilic side chain, such as S or T.

In one embodiment, $X_{H1}$ at Kabat position 11 is an aliphatic amino acid, such as a branched-chain amino acid (BCAA), for example V; $X_{H2}$ at Kabat position 20 is an aliphatic amino acid, such as a branched-chain amino acid (BCAA), for example L; $X_{H3}$ at Kabat position 38 is an amino acid with a polar side chain, such as R; $X_{H4}$ at Kabat position 67 is an amino acid with an aliphatic side chain, such as A; $X_{H5}$ at Kabat position 69 is an amino acid with an aliphatic side chain, such as L; $X_{H6}$ at Kabat position 72 is an amino acid with a polar side chain, such as D; $X_{H7}$ at Kabat position 81 is an amino acid with an an amide derivative of an acidic amino acid, such as Q; and $X_{H8}$ at Kabat position 87 is an amino acid with an aliphatic hydroxyl side chain, such as T.

In one embodiment, $X_{H1}$ at Kabat position 11 is an aliphatic amino acid, such as a branched-chain amino acid (BCAA), for example V; $X_{H2}$ at Kabat position 20 is an aliphatic amino acid, such as a branched-chain amino acid (BCAA), for example V; $X_{H3}$ at Kabat position 38 is an amino acid with a polar side chain, such as R; $X_{H4}$ at Kabat position 67 is an amino acid with an aliphatic side chain, such as A; $X_{H5}$ at Kabat position 69 is an amino acid with an aliphatic side chain, such as I; $X_{H6}$ at Kabat position 72 is an amino acid with a polar side chain, such as D; $X_{H7}$ at Kabat position 81 is an acidic amino acid, such as E; and $X_{H8}$ at Kabat position 87 is an amino acid with an aliphatic hydroxyl side chain, such as T.

In a specific embodiment, $X_{K1}$ at Kabat position 10 is an aromatic amino acid such as F or an amino acid with an aliphatic hydroxyl side chain such as S. In a certain embodiment, $X_{K2}$ at Kabat position 46 is an amino acid with an aliphatic side chain (e.g., hydrophobic amino acid) such as A or an amino acid with an aliphatic hydroxyl side chain such as S. In one embodiment, $X_{K3}$ at Kabat position 63 is an amino acid with an aliphatic hydroxyl side chain such as T or S. In a specific embodiment, $X_{K4}$ at Kabat position 80 is an amino acid with an aliphatic hydroxyl side chain such as S or an aromatic amino acid such as P. In a certain embodiment, $X_{K5}$ at Kabat position 85 is an acidic amino acid such as D or an amino acid with an aliphatic hydroxyl side chain such as T. In one embodiment, $X_{K6}$ at Kabat position 87 is an aromatic amino acid such as F or Y.

In a specific embodiment, $X_{K1}$ at Kabat position 10 is an amino acid with an aliphatic hydroxyl side chain such as S; $X_{K2}$ at Kabat position 46 is an amino acid with an aliphatic side chain (e.g., hydrophobic amino acid) such as A; $X_{K3}$ at Kabat position 63 is an amino acid with an aliphatic hydroxyl side chain such as T; $X_{K4}$ at Kabat position 80 is an aromatic amino acid such as P; $X_{K5}$ at Kabat position 85 is an acidic amino acid such as D; and $X_{K6}$ at Kabat position 87 is an aromatic amino acid such as F.

In a specific embodiment, $X_{K1}$ at Kabat position 10 is an aromatic amino acid such as F; $X_{K2}$ at Kabat position 46 is an amino acid with an aliphatic side chain (e.g., hydrophobic amino acid) such as A; $X_{K3}$ at Kabat position 63 is an amino acid with an aliphatic hydroxyl side chain such as T; $X_{K4}$ at Kabat position 80 is an aliphatic hydroxyl side chain such as S; $X_{K5}$ at Kabat position 85 is an acidic amino acid such as D; and $X_{K6}$ at Kabat position 87 is an aromatic amino acid such as F.

In a particular particular embodiment, an antibody described herein or a antigen-binding fragment thereof, which immunospecifically binds to a KIT polypeptide (e.g., the D4 region of human KIT), comprises: (i) a VH domain comprising the amino acid sequence: QVQLVQSGAEX$_{H1}$KKPGASVKX$_{H2}$SCKASGYTFTD YYINWVX$_{H3}$QAPGKGLEWIARIYPGS GNTYYNEKFKGRX$_{H4}$TX$_{H5}$TAX$_{H6}$KSTSTAYMX$_{H7}$LS SLRSEDX$_{H8}$AVYFCARGVYYFDYW GQGTTVTVSS (SEQ ID NO: 11), wherein $X_{H1}$ at Kabat position 11 is an amino acid with an aliphatic side chain such as V, $X_{H2}$ at Kabat position 20 is an amino acid with an aliphatic side chain such as L, $X_{H3}$ at Kabat position 38 is an amino acid with a polar side chain such as K, $X_{H4}$ at Kabat position 67 is an amino acid with an aliphatic side chain such as A, $X_{H5}$ at Kabat position 69 is an amino acid with an aliphatic side chain such as L, $X_{H6}$ at Kabat position 72 is an acidic amino acid such as D, $X_{H7}$ at Kabat position 81 is an acidic amino acid or an amide derivative thereof such as Q, and $X_{H8}$ at Kabat position 87 is an amino acid with an aliphatic hydroxyl side chain such as T; and (ii) a VL domain comprising the amino acid sequence DIVMTQSPSX$_{K1}$LSASVGDRVTITCKASQNVRTNVA WYQQKPGKAPKX$_{K2}$LIYSASYRYSG VPDRFX$_{K3}$GSGSGTDFTLTISSLQX$_{K4}$EDFAX$_{K5}$YX$_{K6}$ CQQYNSYPRTFGGGTKVEIK (SEQ ID NO: 12), wherein $X_{K1}$ at Kabat position 10 is an amino acid with an aliphatic hydroxyl side chain such as S, $X_{K2}$ at Kabat position 46 is an amino acid with an aliphatic side chain such as A, $X_{K3}$ at Kabat position 63 is an amino acid with an aliphatic hydroxyl side chain such as T, $X_{K4}$ at Kabat position 80 is an aromatic amino acid such as P, $X_{K5}$ at Kabat position 85 is an acidic amino acid such as D, and $X_{K6}$ at Kabat position 87 is an aromatic amino acid such as F.

In a particular particular embodiment, an antibody described herein or a antigen-binding fragment thereof, which immunospecifically binds to a KIT polypeptide (e.g., the D4 region of human KIT), comprises: (i) a VH domain comprising the amino acid sequence: QVQLVQSGAEX$_{H1}$KKPGASVKX$_{H2}$SCKASGYTFTD YYINWVX$_{H3}$QAPGKGLEWIARIYPGS GNTYYNEKFKGRX$_{H4}$TX$_{H5}$TAX$_{H6}$KSTSTAYMX$_{H7}$ LSSLRSEDX$_{H8}$AVYFCARGVYYFDYW GQGTTVTVSS (SEQ ID NO: 11), wherein $X_{H1}$ at Kabat position 11 is an amino acid with an aliphatic side chain such as V, $X_{H2}$ at Kabat position 20 is an amino acid with an aliphatic side chain such as V, $X_{H3}$ at Kabat position 38 is an amino acid with a polar side chain such as R, $X_{H4}$ at Kabat position 67 is an amino acid with an aliphatic side chain such as A, $X_{H5}$ at Kabat position 69 is an amino acid with an aliphatic side chain such as I, $X_{H6}$ at Kabat position 72 is an acidic amino acid such as D, $X_{H7}$ at Kabat position 81 is an acidic amino acid such as E, and $X_{H8}$ at Kabat position 87 is an amino acid with an aliphatic hydroxyl side chain such as T; and (ii) a VL domain comprising the amino acid sequence DIVMTQSPSX$_{K1}$LSASVGDRVTITCKASQNVRTNV AWYQQKPGKAPKX$_{K2}$LIYSASYRYSG VPDRFX$_{K3}$GSGSGTDFTLTISSLQX$_{K4}$EDFAX$_{K5}$YX$_{K6}$ CQQYNSYPRTFGGGTKVEIK (SEQ ID NO: 12), wherein $X_{K1}$ at Kabat position 10 is an aromatic amino acid such as F, $X_{K2}$ at Kabat position 46 is an amino acid with an aliphatic side chain such as A, $X_{K3}$ at Kabat position 63 is an amino acid with an aliphatic hydroxyl side chain such as T, $X_{K4}$ at Kabat position 80 is an amino acid with an aliphatic hydroxyl side chain such as S, $X_{K5}$ at Kabat position 85 is an acidic amino acid such as D, and $X_{K6}$ at Kabat position 87 is an aromatic amino acid such as F.

In a particular embodiment, an antibody described herein or an antigen-binding fragment thereof, which immunospecifically binds to a KIT polypeptide (e.g., the D4 region of human KIT), comprises (i) a VH domain comprising VH CDR1, VH CDR2, and VH CDR3 comprising the amino acid sequences of SEQ ID NOs: 16-18, respectively; and (ii) a VL domain comprising SEQ ID NO: 7, 8, 9, or 10.

In a particular embodiment, an antibody described herein or an antigen-binding fragment thereof, which immunospecifically binds to a KIT polypeptide (e.g., the D4 region of human KIT), comprises (i) a VH domain comprising VH CDR1, VH CDR2, and VH CDR3 comprising the amino acid sequences of SEQ ID NOs: 16-18, respectively; and (ii) a VL domain comprising the amino acid sequence DIVMTQSPSX$_{K1}$LSASVGDRVTITCKASQNVRTNV AWYQQKPGKAPKX$_{K2}$LIYSASYRYSG VPDRFX$_{K3}$GSGSGTDFTLTISSLQX$_{K4}$EDFAX$_{K5}$YX$_{K6}$ CQQYNSYPRTFGGGTKVEIK (SEQ ID NO: 12), wherein $X_{K1}$ at Kabat position 10, $X_{K2}$ at Kabat position 46, $X_{K3}$ at Kabat position 63, $X_{K4}$ at Kabat position 80, $X_{K5}$ at Kabat position 85, and $X_{K6}$ at Kabat position 87 are selected from the combination of amino acids set forth in Table 6A.

In a particular embodiment, an antibody described herein or an antigen-binding fragment thereof, which immunospecifically binds to a KIT polypeptide (e.g., the D4 region of human KIT), comprises (i) a VH domain comprising the amino acid sequence of SEQ ID NO: 2, 3, 4, or 5; and (ii) a VL domain comprising VL CDR1, VL CDR2, and VL CDR3 comprising the amino acid sequences of SEQ ID NOs: 19-21, respectively.

In a particular embodiment, an antibody described herein or an antigen-binding fragment thereof, which immunospecifically binds to a KIT polypeptide (e.g., the D4 region of human KIT), comprises (i) a VH domain comprising the amino acid sequence: QVQLVQSGAEX$_{H1}$KKPGASVKX$_{H2}$SCKASGYTFT DYYINWVX$_{H3}$QAPGKGLEWIARIYPGS GNTYYNEKFKGRX$_{H4}$TX$_{H5}$TAX$_{H6}$KSTSTAYMX$_{H7}$ LSSLRSEDX$_{H8}$AVYFCARGVYYFDYW GQGTTVTVSS (SEQ ID NO: 11), wherein $X_{H1}$ at Kabat position 11, $X_{H2}$ at Kabat position 20, $X_{H3}$ at Kabat position 38, $X_{H4}$ at Kabat position 67, $X_{H5}$ at Kabat position 69, $X_{H6}$ at Kabat position 72, $X_{H7}$ at Kabat position 81, and $X_{H8}$ at Kabat position 87 are selected from the combination of amino acids set forth in Table 6B; and (ii) a VL domain comprising VL CDR1, VL CDR2, and VL CDR3 comprising the amino acid sequences of SEQ ID NOs: 19-21, respectively.

TABLE 6A

VK domain Amino Acid Substitutions

| | $X_{K1}$ | $X_{K2}$ | $X_{K3}$ | $X_{K4}$ | $X_{K5}$ | $X_{K6}$ |
|---|---|---|---|---|---|---|
| Kabat position | 10 | 46 | 63 | 80 | 85 | 87 |
| Numerical position of SEQ ID NO: 12 | 10 | 46 | 63 | 80 | 85 | 87 |
| Amino acid side chain | Aromatic or aliphatic hydroxyl | Aliphatic or aliphatic hydroxyl | aliphatic hydroxyl | Proline or aliphatic hydroxyl | Charged or acidic | aromatic |
| L1 | F | A | T | S | D | F |
| L2 | S | A | T | P | D | F |
| L3 | S | A | T | P | D | F |
| L4 | S | S | S | P | T | Y |
| LL1 | S | A | T | S | D | F |
| LL2 | F | S | T | S | D | F |
| LL3 | S | S | T | S | D | F |
| LL4 | F | A | S | S | D | F |
| LL5 | S | A | S | S | D | F |
| LL6 | F | S | S | S | D | F |
| LL7 | S | S | S | S | D | F |
| LL8 | F | A | T | P | D | F |
| LL9 | S | A | T | P | D | F |
| LL10 | F | S | T | P | D | F |
| LL11 | S | S | T | P | D | F |
| LL12 | F | A | S | P | D | F |
| LL13 | S | A | S | P | D | F |
| LL14 | F | S | S | P | D | F |
| LL15 | S | S | S | P | D | F |
| LL16 | F | A | T | S | T | F |
| LL17 | S | A | T | S | T | F |
| LL18 | F | S | T | S | T | F |
| LL19 | S | S | T | S | T | F |
| LL20 | F | A | S | S | T | F |
| LL21 | S | A | S | S | T | F |
| LL22 | F | S | S | S | T | F |
| LL23 | S | S | S | S | T | F |
| LL24 | F | A | T | P | T | F |
| LL25 | S | A | T | P | T | F |

TABLE 6A-continued

VK domain Amino Acid Substitutions

| | $X_{K1}$ | $X_{K2}$ | $X_{K3}$ | $X_{K4}$ | $X_{K5}$ | $X_{K6}$ |
|---|---|---|---|---|---|---|
| LL26 | F | S | T | P | T | F |
| LL27 | S | S | T | P | T | F |
| LL28 | F | A | S | P | T | F |
| LL29 | S | A | S | P | T | F |
| LL30 | F | S | S | P | T | F |
| LL31 | S | S | S | P | T | F |
| LL32 | S | A | T | S | D | Y |
| LL33 | F | S | T | S | D | Y |
| LL34 | S | S | T | S | D | Y |
| LL35 | F | A | S | S | D | Y |
| LL36 | S | A | S | S | D | Y |
| LL37 | F | S | S | S | D | Y |
| LL38 | S | S | S | S | D | Y |
| LL39 | F | A | T | P | D | Y |
| LL40 | S | A | T | P | D | Y |
| LL41 | F | S | T | P | D | Y |
| LL42 | S | S | T | P | D | Y |
| LL43 | F | A | S | P | D | Y |
| LL44 | S | A | S | P | D | Y |
| LL45 | F | S | S | P | D | Y |
| LL46 | S | S | S | P | D | Y |
| LL47 | F | A | T | S | T | Y |
| LL48 | S | A | T | S | T | Y |
| LL49 | F | S | T | S | T | Y |
| LL50 | S | S | T | S | T | Y |
| LL51 | F | A | S | S | T | Y |
| LL52 | S | A | S | S | T | Y |
| LL53 | F | S | S | S | T | Y |
| LL54 | S | S | S | S | T | Y |
| LL55 | F | A | T | P | T | Y |
| LL56 | S | A | T | P | T | Y |
| LL57 | F | S | T | P | T | Y |
| LL58 | S | S | T | P | T | Y |
| LL59 | F | A | S | P | T | Y |
| LL60 | S | A | S | P | T | Y |
| LL61 | F | S | S | P | T | Y |
| LL62 | S | S | S | P | T | Y |

TABLE 6B

VH domain Amino Acid Substitutions

| | $X_{H1}$ | $X_{H2}$ | $X_{H3}$ | $X_{H4}$ | $X_{H5}$ | $X_{H6}$ | $X_{H7}$ | $X_{H8}$ |
|---|---|---|---|---|---|---|---|---|
| Kabat position | 11 | 20 | 38 | 67 | 69 | 72 | 81 | 87 |
| Numerical position of SEQ ID NO: 11 | 11 | 20 | 38 | 68 | 70 | 73 | 82 | 91 |
| Amino acid side chain | Aliphatic | Aliphatic | Polar or basic | Aliphatic | Aliphatic | Acidic | Acidic or amide derivative | aliphatic hydroxyl |
| H1 | L | L | K | A | L | E | Q | S |
| H2 | V | L | K | A | L | E | Q | T |
| H3 | V | L | R | A | L | D | Q | T |
| H4 | V | V | R | A | I | D | E | T |
| H5 | V | V | R | V | I | D | E | T |
| HH1 | L | L | K | A | L | E | Q | S |
| HH2 | V | L | K | A | L | E | Q | S |
| HH3 | L | V | K | A | L | E | Q | S |
| HH4 | V | V | K | A | L | E | Q | S |
| HH5 | L | L | R | A | L | E | Q | S |
| HH6 | V | L | R | A | L | E | Q | S |
| HH7 | L | V | R | A | L | E | Q | S |
| HH8 | V | V | R | A | L | E | Q | S |
| HH9 | L | L | K | V | L | E | Q | S |
| HH10 | V | L | K | V | L | E | Q | S |
| HH11 | L | V | K | V | L | E | Q | S |
| HH12 | V | V | K | V | L | E | Q | S |
| HH13 | L | L | R | V | L | E | Q | S |
| HH14 | V | L | R | V | L | E | Q | S |
| HH15 | L | V | R | V | L | E | Q | S |
| HH16 | V | V | R | V | L | E | Q | S |
| HH17 | L | L | K | A | I | E | Q | S |
| HH18 | V | L | K | A | I | E | Q | S |

TABLE 6B-continued

VH domain Amino Acid Substitutions

| | $X_{H1}$ | $X_{H2}$ | $X_{H3}$ | $X_{H4}$ | $X_{H5}$ | $X_{H6}$ | $X_{H7}$ | $X_{H8}$ |
|---|---|---|---|---|---|---|---|---|
| HH19 | L | V | K | A | I | E | Q | S |
| HH20 | V | V | K | A | I | E | Q | S |
| HH21 | L | L | R | A | I | E | Q | S |
| HH22 | V | L | R | A | I | E | Q | S |
| HH23 | L | V | R | A | I | E | Q | S |
| HH24 | V | V | R | A | I | E | Q | S |
| HH25 | L | L | K | V | I | E | Q | S |
| HH26 | V | L | K | V | I | E | Q | S |
| HH27 | L | V | K | V | I | E | Q | S |
| HH28 | V | V | K | V | I | E | Q | S |
| HH29 | L | L | R | V | I | E | Q | S |
| HH30 | V | L | R | V | I | E | Q | S |
| HH31 | L | V | R | V | I | E | Q | S |
| HH32 | V | V | R | V | I | E | Q | S |
| HH33 | L | L | K | A | L | D | Q | S |
| HH34 | V | L | K | A | L | D | Q | S |
| HH35 | L | V | K | A | L | D | Q | S |
| HH36 | V | V | K | A | L | D | Q | S |
| HH37 | L | L | R | A | L | D | Q | S |
| HH38 | V | L | R | A | L | D | Q | S |
| HH39 | L | V | R | A | L | D | Q | S |
| HH40 | V | V | R | A | L | D | Q | S |
| HH41 | L | L | K | V | L | D | Q | S |
| HH42 | V | L | K | V | L | D | Q | S |
| HH43 | L | V | K | V | L | D | Q | S |
| HH44 | V | V | K | V | L | D | Q | S |
| HH45 | L | L | R | V | L | D | Q | S |
| HH46 | V | L | R | V | L | D | Q | S |
| HH47 | L | V | R | V | L | D | Q | S |
| HH48 | V | V | R | V | L | D | Q | S |
| HH49 | L | L | K | A | I | D | Q | S |
| HH50 | V | L | K | A | I | D | Q | S |
| HH51 | L | V | K | A | I | D | Q | S |
| HH52 | V | V | K | A | I | D | Q | S |
| HH53 | L | L | R | A | I | D | Q | S |
| HH54 | V | L | R | A | I | D | Q | S |
| HH55 | L | V | R | A | I | D | Q | S |
| HH56 | V | V | R | A | I | D | Q | S |
| HH57 | L | L | K | V | I | D | Q | S |
| HH58 | V | L | K | V | I | D | Q | S |
| HH59 | L | V | K | V | I | D | Q | S |
| HH60 | V | V | K | V | I | D | Q | S |
| HH61 | L | L | R | V | I | D | Q | S |
| HH62 | V | L | R | V | I | D | Q | S |
| HH63 | L | V | R | V | I | D | Q | S |
| HH64 | V | V | R | V | I | D | Q | S |
| HH65 | L | L | K | A | L | E | E | S |
| HH66 | V | L | K | A | L | E | E | S |
| HH67 | L | V | K | A | L | E | E | S |
| HH68 | V | V | K | A | L | E | E | S |
| HH69 | L | L | R | A | L | E | E | S |
| HH70 | V | L | R | A | L | E | E | S |
| HH71 | L | V | R | A | L | E | E | S |
| HH72 | V | V | R | A | L | E | E | S |
| HH73 | L | L | K | V | L | E | E | S |
| HH74 | V | L | K | V | L | E | E | S |
| HH75 | L | V | K | V | L | E | E | S |
| HH76 | V | V | K | V | L | E | E | S |
| HH77 | L | L | R | V | L | E | E | S |
| HH78 | V | L | R | V | L | E | E | S |
| HH79 | L | V | R | V | L | E | E | S |
| HH80 | V | V | R | V | L | E | E | S |
| HH81 | L | L | K | A | I | E | E | S |
| HH82 | V | L | K | A | I | E | E | S |
| HH83 | L | V | K | A | I | E | E | S |
| HH84 | V | V | K | A | I | E | E | S |
| HH85 | L | L | R | A | I | E | E | S |
| HH86 | V | L | R | A | I | E | E | S |
| HH87 | L | V | R | A | I | E | E | S |
| HH88 | V | V | R | A | I | E | E | S |
| HH89 | L | L | K | V | I | E | E | S |
| HH90 | V | L | K | V | I | E | E | S |
| HH91 | L | V | K | V | I | E | E | S |
| HH92 | V | V | K | V | I | E | E | S |
| HH93 | L | L | R | V | I | E | E | S |
| HH94 | V | L | R | V | I | E | E | S |
| HH95 | L | V | R | V | I | E | E | S |

TABLE 6B-continued

VH domain Amino Acid Substitutions

| | $X_{H1}$ | $X_{H2}$ | $X_{H3}$ | $X_{H4}$ | $X_{H5}$ | $X_{H6}$ | $X_{H7}$ | $X_{H8}$ |
|---|---|---|---|---|---|---|---|---|
| HH96 | V | V | R | V | I | E | E | S |
| HH97 | L | L | K | A | L | D | E | S |
| HH98 | V | L | K | A | L | D | E | S |
| HH99 | L | V | K | A | L | D | E | S |
| HH100 | V | V | K | A | L | D | E | S |
| HH101 | L | L | R | A | L | D | E | S |
| HH102 | V | L | R | A | L | D | E | S |
| HH103 | L | V | R | A | L | D | E | S |
| HH104 | V | V | R | A | L | D | E | S |
| HH105 | L | L | K | V | L | D | E | S |
| HH106 | V | L | K | V | L | D | E | S |
| HH107 | L | V | K | V | L | D | E | S |
| HH108 | V | V | K | V | L | D | E | S |
| HH109 | L | L | R | V | L | D | E | S |
| HH110 | V | L | R | V | L | D | E | S |
| HH111 | L | V | R | V | L | D | E | S |
| HH112 | V | V | R | V | L | D | E | S |
| HH113 | L | L | K | A | I | D | E | S |
| HH114 | V | L | K | A | I | D | E | S |
| HH115 | L | V | K | A | I | D | E | S |
| HH116 | V | V | K | A | I | D | E | S |
| HH117 | L | L | R | A | I | D | E | S |
| HH118 | V | L | R | A | I | D | E | S |
| HH119 | L | V | R | A | I | D | E | S |
| HH120 | V | V | R | A | I | D | E | S |
| HH121 | L | L | K | V | I | D | E | S |
| HH122 | V | L | K | V | I | D | E | S |
| HH123 | L | V | K | V | I | D | E | S |
| HH124 | V | V | K | V | I | D | E | S |
| HH125 | L | L | R | V | I | D | E | S |
| HH126 | V | L | R | V | I | D | E | S |
| HH127 | L | V | R | V | I | D | E | S |
| HH128 | V | V | R | V | I | D | E | S |
| HH129 | L | L | K | A | L | E | Q | T |
| HH130 | V | L | K | A | L | E | Q | T |
| HH131 | L | V | K | A | L | E | Q | T |
| HH132 | V | V | K | A | L | E | Q | T |
| HH133 | L | L | R | A | L | E | Q | T |
| HH134 | V | L | R | A | L | E | Q | T |
| HH135 | L | V | R | A | L | E | Q | T |
| HH136 | V | V | R | A | L | E | Q | T |
| HH137 | L | L | K | V | L | E | Q | T |
| HH138 | V | L | K | V | L | E | Q | T |
| HH139 | L | V | K | V | L | E | Q | T |
| HH140 | V | V | K | V | L | E | Q | T |
| HH141 | L | L | R | V | L | E | Q | T |
| HH142 | V | L | R | V | L | E | Q | T |
| HH143 | L | V | R | V | L | E | Q | T |
| HH144 | V | V | R | V | L | E | Q | T |
| HH145 | L | L | K | A | I | E | Q | T |
| HH146 | V | L | K | A | I | E | Q | T |
| HH147 | L | V | K | A | I | E | Q | T |
| HH148 | V | V | K | A | I | E | Q | T |
| HH149 | L | L | R | A | I | E | Q | T |
| HH150 | V | L | R | A | I | E | Q | T |
| HH151 | L | V | R | A | I | E | Q | T |
| HH152 | V | V | R | A | I | E | Q | T |
| HH153 | L | L | K | V | I | E | Q | T |
| HH154 | V | L | K | V | I | E | Q | T |
| HH155 | L | V | K | V | I | E | Q | T |
| HH156 | V | V | K | V | I | E | Q | T |
| HH157 | L | L | R | V | I | E | Q | T |
| HH158 | V | L | R | V | I | E | Q | T |
| HH159 | L | V | R | V | I | E | Q | T |
| HH160 | V | V | R | V | I | E | Q | T |
| HH161 | L | L | K | A | L | D | Q | T |
| HH162 | V | L | K | A | L | D | Q | T |
| HH163 | L | V | K | A | L | D | Q | T |
| HH164 | V | V | K | A | L | D | Q | T |
| HH165 | L | L | R | A | L | D | Q | T |
| HH166 | V | L | R | A | L | D | Q | T |
| HH167 | L | V | R | A | L | D | Q | T |
| HH168 | V | V | R | A | L | D | Q | T |
| HH169 | L | L | K | V | L | D | Q | T |
| HH170 | V | L | K | V | L | D | Q | T |
| HH171 | L | V | K | V | L | D | Q | T |
| HH172 | V | V | K | V | L | D | Q | T |

TABLE 6B-continued

VH domain Amino Acid Substitutions

| | $X_{H1}$ | $X_{H2}$ | $X_{H3}$ | $X_{H4}$ | $X_{H5}$ | $X_{H6}$ | $X_{H7}$ | $X_{H8}$ |
|---|---|---|---|---|---|---|---|---|
| HH173 | L | L | R | V | L | D | Q | T |
| HH174 | V | L | R | V | L | D | Q | T |
| HH175 | L | V | R | V | L | D | Q | T |
| HH176 | V | V | R | V | L | D | Q | T |
| HH177 | L | L | K | A | I | D | Q | T |
| HH178 | V | L | K | A | I | D | Q | T |
| HH179 | L | V | K | A | I | D | Q | T |
| HH180 | V | V | K | A | I | D | Q | T |
| HH181 | L | L | R | A | I | D | Q | T |
| HH182 | V | L | R | A | I | D | Q | T |
| HH183 | L | V | R | A | I | D | Q | T |
| HH184 | V | V | R | A | I | D | Q | T |
| HH185 | L | L | K | V | I | D | Q | T |
| HH186 | V | L | K | V | I | D | Q | T |
| HH187 | L | V | K | V | I | D | Q | T |
| HH188 | V | V | K | V | I | D | Q | T |
| HH189 | L | L | R | V | I | D | Q | T |
| HH190 | V | L | R | V | I | D | Q | T |
| HH191 | L | V | R | V | I | D | Q | T |
| HH192 | V | V | R | V | I | D | Q | T |
| HH193 | L | L | K | A | L | E | E | T |
| HH194 | V | L | K | A | L | E | E | T |
| HH195 | L | V | K | A | L | E | E | T |
| HH196 | V | V | K | A | L | E | E | T |
| HH197 | L | L | R | A | L | E | E | T |
| HH198 | V | L | R | A | L | E | E | T |
| HH199 | L | V | R | A | L | E | E | T |
| HH200 | V | V | R | A | L | E | E | T |
| HH201 | L | L | K | V | L | E | E | T |
| HH202 | V | L | K | V | L | E | E | T |
| HH203 | L | V | K | V | L | E | E | T |
| HH204 | V | V | K | V | L | E | E | T |
| HH205 | L | L | R | V | L | E | E | T |
| HH206 | V | L | R | V | L | E | E | T |
| HH207 | L | V | R | V | L | E | E | T |
| HH208 | V | V | R | V | L | E | E | T |
| HH209 | L | L | K | A | I | E | E | T |
| HH210 | V | L | K | A | I | E | E | T |
| HH211 | L | V | K | A | I | E | E | T |
| HH212 | V | V | K | A | I | E | E | T |
| HH213 | L | L | R | A | I | E | E | T |
| HH214 | V | L | R | A | I | E | E | T |
| HH215 | L | V | R | A | I | E | E | T |
| HH216 | V | V | R | A | I | E | E | T |
| HH217 | L | L | K | V | I | E | E | T |
| HH218 | V | L | K | V | I | E | E | T |
| HH219 | L | V | K | V | I | E | E | T |
| HH220 | V | V | K | V | I | E | E | T |
| HH221 | L | L | R | V | I | E | E | T |
| HH222 | V | L | R | V | I | E | E | T |
| HH223 | L | V | R | V | I | E | E | T |
| HH224 | V | V | R | V | I | E | E | T |
| HH225 | L | L | K | A | L | D | E | T |
| HH226 | V | L | K | A | L | D | E | T |
| HH227 | L | V | K | A | L | D | E | T |
| HH228 | V | V | K | A | L | D | E | T |
| HH229 | L | L | R | A | L | D | E | T |
| HH230 | V | L | R | A | L | D | E | T |
| HH231 | L | V | R | A | L | D | E | T |
| HH232 | V | V | R | A | L | D | E | T |
| HH233 | L | L | K | V | L | D | E | T |
| HH234 | V | L | K | V | L | D | E | T |
| HH235 | L | V | K | V | L | D | E | T |
| HH236 | V | V | K | V | L | D | E | T |
| HH237 | L | L | R | V | L | D | E | T |
| HH238 | V | L | R | V | L | D | E | T |
| HH239 | L | V | R | V | L | D | E | T |
| HH240 | V | V | R | V | L | D | E | T |
| HH241 | L | L | K | A | I | D | E | T |
| HH242 | V | L | K | A | I | D | E | T |
| HH243 | L | V | K | A | I | D | E | T |
| HH244 | V | V | K | A | I | D | E | T |
| HH245 | L | L | R | A | I | D | E | T |
| HH246 | V | L | R | A | I | D | E | T |
| HH247 | L | V | R | A | I | D | E | T |
| HH248 | V | V | R | A | I | D | E | T |
| HH249 | L | L | K | V | I | D | E | T |

TABLE 6B-continued

| | VH domain Amino Acid Substitutions | | | | | | | |
|---|---|---|---|---|---|---|---|---|
| | $X_{H1}$ | $X_{H2}$ | $X_{H3}$ | $X_{H4}$ | $X_{H5}$ | $X_{H6}$ | $X_{H7}$ | $X_{H8}$ |
| HH250 | V | L | K | V | I | D | E | T |
| HH251 | L | V | K | V | I | D | E | T |
| HH252 | V | V | K | V | I | D | E | T |
| HH253 | L | L | R | V | I | D | E | T |
| HH254 | V | L | R | V | I | D | E | T |
| HH255 | L | V | R | V | I | D | E | T |
| HH256 | V | V | R | V | I | D | E | T |

In a specific embodiment, the position (i.e., boundary) of a VL chain region described herein relative to the constant region may change by one, two, three, or four amino acid positions so long as immunospecific binding to KIT (e.g., the D4 region of human KIT) is maintained (e.g., substantially maintained, for example, at least 50%, at least 60%, at least 70%, at least 80%, at least 90%, at least 95%). In a specific embodiment, the position (i.e., boundary) of a VH chain region described herein relative to the constant region may change by one, two, three, or four amino acid positions so long as immunospecific binding to KIT (e.g., the D4 region of human KIT) is maintained (e.g., substantially maintained, for example, at least 50%, at least 60%, at least 70%, at least 80%, at least 90%, at least 95%).

In specific aspects, provided herein is a moiety comprising VH CDRs and/or VL CDRs described herein, for example as set forth in Tables 1-3 and 10-15, wherein the VH CDRs and VL CDRs are arranged in a spatial orientation that confers specific binding to a D4 region of human KIT.

In specific aspects, provided herein is a moiety comprising VH CDRs comprising the amino acid sequences of SEQ ID NOs: 16-18 and VL CDRs comprising the amino acid sequences of SEQ ID NOs: 19-21, VH CDRs comprising the amino acid sequences of SEQ ID NOs: 56, 62 and 63 and VL CDRs comprising the amino acid sequences of SEQ ID NOs: 59-61, VH CDRs comprising the amino acid sequences of SEQ ID NOs: 70-72 and VL CDRs comprising the amino acid sequences of SEQ ID NOs: 66-68, wherein the VH CDRs and VL CDRs are arranged in a spatial orientation that confers specific binding to a D4 region of human KIT. In certain embodiments, the moiety is an antibody or an antigen-binding fragment thereof. In a particular embodiment, the moiety is a protein, such as a fusion protein comprising an Fc region.

In specific aspects, provided herein is a moiety comprising VH CDRs selected from Tables 13-15 and/or VL CDRs selected from Tables 10-12, wherein the VH CDRs and VL CDRs are arranged in a spatial orientation that confers specific binding to a D4 region of human KIT. In certain embodiments, the moiety is an antibody or an antigen-binding fragment thereof. In a particular embodiment, the moiety is a protein, such as a fusion protein comprising an Fc region.

In specific aspects, provided herein is a moiety, such as an antibody or an antigen-binding fragment thereof, comprising VH CDRs 1-3 and VL CDRs 1-3 selected from the ones presented in Tables 10-15, wherein the VH CDRs and VL CDRs are arranged in a spatial orientation that confers specific binding to a D4 region of human KIT. In particular aspects, a moiety described herein comprises linkers, such as peptide linkers, that link the VH CDRs 1-3 and/or VL CDRs 1-3 in the spatial orientation that confers specific binding to a D4 region of human KIT.

In particular aspects, a moiety described herein comprises linkers, such as peptide linkers, that links the VH CDRs and/or VL CDRs in a spatial orientation that confers specific binding to a D4 region of human KIT.

In certain aspects, provided herein is an antibody or an antigen-binding fragment thereof comprising VL CDRs 1-3 and VH CDRs 1-3 selected from the ones presented in Tables 10-15, wherein the antibody or antigen-binding fragment thereof immunospecifically binds a D4 region of KIT, such as human KIT.

In a specific embodiment, the "X" amino acid of a CDR in any one of Tables 10-15 is any naturally occurring amino acid that maintains specific binding affinity to a D4 region of human KIT. In a specific embodiment, the "X" amino acid of a CDR in any one of Tables 10-15 is a non-natural amino acid that maintains specific binding affinity to a D4 region of human KIT. In a specific embodiment, the "X" amino acid of a CDR in any one of Tables 10-15 is a conservative substitution of the corresponding amino acid of the CDRs having the amino acid sequences of SEQ ID NOs: 16-21, wherein specific binding affinity to a D4 region of human KIT is maintained.

In a specific embodiment, the "X" amino acid of a CDR in any one of Tables 10-15 is, independently, amino acid A, G, T, K, or L. In a particular embodiment, the "X" amino acid of a CDR in any one of Tables 10-15 is amino acid A, G, T, Y, C, or S. In certain aspects of these embodiments, specific binding affinity to a D4 region of human KIT is maintained.

In a certain embodiment, an antibody described herein or an antigen-binding fragment thereof comprises VH CDRs and/or VL CDRs selected from those presented in Tables 10-15.

In a particular embodiment, a CDR, such as any one of VL CDRs 1-3 and VH CDRs 1-3 depicted in Tables 10-15, comprises one or more (e.g., two, three, four, or five) "X" amino acids, wherein each "X" amino acid can be any amino acid which can maintain specific binding of the antibody or fragment thereof to a D4 region of human KIT.

TABLE 10

| VL CDR1 | |
|---|---|
| VL CDR1 | SEQ ID NO: |
| K A S Q N V R T N V A | 19 |
| X A S Q N V R T N V A | 74 |
| K X S Q N V R T N V A | 75 |
| K A X Q N V R T N V A | 76 |
| K A S X N V R T N V A | 77 |
| K A S Q X V R T N V A | 78 |

TABLE 10-continued

VL CDR1

| VL CDR1 | SEQ ID NO: |
|---|---|
| K A S Q (A/G/T/Y/C/S) V R T N V A | 79 |
| K A S Q N X R T N V A | 80 |
| K A S Q N V X T N V A | 81 |
| K A S Q N V R X N V A | 82 |
| K A S Q N V R T X V A | 83 |
| K A S Q N V R T (A/G/T/Y/C/S) V A | 84 |
| K A S Q N V R T N X A | 85 |
| K A S Q N V R T N V X | 86 |
| C K A S Q N V R T N V | 87 |
| I C K A S Q N V R T N | 88 |
| A S Q N V R T N V A W | 89 |
| S Q N V R T N V A W Y | 90 |
| Q N V R T N V A W Y Q | 91 |

TABLE 11

VL CDR2

| VL CDR2 | SEQ ID NO: |
|---|---|
| S A S Y R Y S | 20 |
| X A S Y R Y S | 92 |
| S X S Y R Y S | 93 |
| S A X Y R Y S | 94 |
| S A S X R Y S | 95 |
| S A S Y X Y S | 96 |
| S A S Y R X S | 97 |
| S A S Y R Y X | 98 |
| Y S A S Y R Y | 99 |
| I Y S A S Y R | 100 |
| L I Y S A S Y | 101 |
| A S Y R Y S G | 102 |
| S Y R Y S G V | 103 |
| Y R Y S G V P | 104 |

TABLE 12

VL CDR3

| VL CDR3 | SEQ ID NO: |
|---|---|
| Q Q Y N S Y P R T | 21 |
| Q X Y N S Y P R T | 105 |

TABLE 12-continued

VL CDR3

| VL CDR3 | SEQ ID NO: |
|---|---|
| Q Q X N S Y P R T | 106 |
| Q Q Y X S Y P R T | 107 |
| Q Q Y N X Y P R T | 108 |
| Q Q Y N S X P R T | 109 |
| Q Q Y N S Y X R T | 110 |
| Q Q Y N S Y P X T | 111 |
| Q Q Y N S Y P R X | 112 |
| Q Q Y N S Y P R | 113 |
| C Q Q Y N S Y P | 114 |
| F C Q Q Y N S Y | 115 |
| Y F C Q Q Y N S | 116 |
| Q Y N S Y P R F | 117 |
| Y N S Y P R F G | 118 |
| S Y P R F G G | 119 |

TABLE 13

VH CDR1

| VH CDR1 | SEQ ID NO: |
|---|---|
| D Y Y I N | 16 |
| X Y Y I N | 120 |
| D X Y I N | 121 |
| D Y X I N | 122 |
| D Y Y X N | 123 |
| D Y Y I X | 124 |
| T D Y Y I | 125 |
| F T D Y Y | 126 |
| T F T D Y | 127 |
| Y Y I N W | 128 |
| Y Y I N W V | 129 |
| I N W V R | 130 |

TABLE 14

VH CDR2

| VH CDR2 | SEQ ID NO: |
|---|---|
| R I Y P G S G N T Y Y N E K F K G | 17 |
| X I Y P G S G N T Y Y N E K F K G | 131 |
| R X Y P G S G N T Y Y N E K F K G | 132 |

TABLE 14-continued

VH CDR2

| VH CDR2 | SEQ ID NO: |
|---|---|
| R I X P G S G N T Y Y N E K F K G | 133 |
| R I Y X G S G N T Y Y N E K F K G | 134 |
| R I Y P X S G N T Y Y N E K F K G | 135 |
| R I Y P G X G N T Y Y N E K F K G | 136 |
| R I Y P G S X N T Y Y N E K F K G | 137 |
| R I Y P G S G X T Y Y N E K F K G | 138 |
| R I Y P G S G N X Y Y N E K F K G | 139 |
| R I Y P G S G N T X Y N E K F K G | 140 |
| R I Y P G S G N T Y X N E K F K G | 141 |
| R I Y P G S G N T Y Y X E K F K G | 142 |
| R I Y P G S G N T Y Y N X K F K G | 143 |
| R I Y P G S G N T Y Y N E X F K G | 144 |
| R I Y P G S G N T Y Y N E K X K G | 145 |
| R I Y P G S G N T Y Y N E K F X G | 146 |
| R I Y P G S G N T Y Y N E K F K X | 147 |
| A R I Y P G S G N T Y Y N E K F | 148 |
| I A R I Y P G S G N T Y Y N E K | 149 |
| W I A R I Y P G S G N T Y Y N E | 150 |
| I Y P G S G N T Y Y N E K F K G R | 151 |
| Y P G S G N T Y Y N E K F K G R A | 152 |
| P G S G N T Y Y N E K F K G R A T | 153 |

TABLE 15

VH CDR3

| VH CDR3 | SEQ ID NO: |
|---|---|
| G V Y Y F D Y | 18 |
| X V Y Y F D Y | 154 |
| G X Y Y F D Y | 155 |
| G V X Y F D Y | 156 |
| G V Y X F D Y | 157 |
| G V Y Y X D Y | 158 |
| G V Y Y F X Y | 159 |
| G V Y Y F D X | 160 |
| R G V Y Y F D | 161 |
| A R G V Y Y F | 162 |
| C A R G V Y Y | 163 |
| G V Y Y F D Y W | 164 |

TABLE 15-continued

VH CDR3

| VH CDR3 | SEQ ID NO: |
|---|---|
| V Y Y F D Y W G | 165 |
| Y Y F D Y W G Q | 166 |

In certain aspects, provided herein is an antibody or an antigen-binding fragment thereof comprising VL FRs 1-4 selected from the ones presented in Tables 20-23 and/or VH FRs 1-4 selected from the ones presented in Tables 16-19, wherein the antibody or antigen-binding fragment thereof immunospecifically binds a D4 region of KIT, such as human KIT.

In a specific embodiment, the "X" amino acid of an FR in any one of Tables 16-23 is any naturally occurring amino acid that maintains specific binding affinity to a D4 region of human KIT. In a specific embodiment, the "X" amino acid of a CDR in any one of Tables 16-23 is a non-natural amino acid that maintains specific binding affinity to a D4 region of human KIT. In a specific embodiment, the "X" amino acid of a CDR in any one of Tables 16-23 is a conservative substitution of the corresponding amino acid of the CDRs having the amino acid sequences of SEQ ID NOs: 16-21, wherein specific binding affinity to a D4 region of human KIT is maintained.

In a specific embodiment, the "X" amino acid of a CDR in any one of Tables 16-23 is amino acid A, G, T, K, or L. In a particular embodiment, the "X" amino acid of a CDR in any one of Tables 16-23 is amino acid A, G, T, Y, C, or S. In certain aspects of these embodiments, specific binding affinity to a D4 region of human KIT is maintained. In a certain embodiment, an antibody described herein or an antigen-binding fragment thereof comprises VH CDRs and/or VL CDRs selected from those presented in Tables 16-23.

In a particular embodiment, an FR, such as any one of VL FRs 1-4 and VH FRs 1-4 depicted in Tables 16-23, comprises one or more (e.g., two, three, four, or five) "X" amino acids, wherein each "X" amino acid can be any amino acid which can maintain specific binding of the antibody or fragment thereof to a D4 region of human KIT.

TABLE 16

VH FR1

| | VH FR1 | SEQ ID NO: |
|---|---|---|
| H1 | QVQLVQSGAELKKPGASVKLSCKASGYTFT | 33 |
| H2/H3 | QVQLVQSGAEVKKPGASVKLSCKASGYTFT | 37 |
| H4/H5 | QVQLVQSGAEVKKPGASVKVSCKASGYTFT | 41 |
| | XVQLVQSGAE(L/V)KKPGASVK(L/V)SCKASGYTFT | 167 |
| | QXQLVQSGAE(L/V)KKPGASVK(L/V)SCKASGYTFT | 168 |
| | QVXLVQSGAE(L/V)KKPGASVK(L/V)SCKASGYTFT | 169 |
| | QVQXVQSGAE(L/V)KKPGASVK(L/V)SCKASGYTFT | 170 |
| | QVQLXQSGAE(L/V)KKPGASVK(L/V)SCKASGYTFT | 171 |
| | QVQLVXSGAE(L/V)KKPGASVK(L/V)SCKASGYTFT | 172 |
| | QVQLVQXGAE(L/V)KKPGASVK(L/V)SCKASGYTFT | 173 |

TABLE 16-continued

| VH FR1 | SEQ ID NO: |
|---|---|
| QVQLVQSXAE(L/V)KKPGASVK(L/V)SCKASGYTFT | 174 |
| QVQLVQSGXE(L/V)KKPGASVK(L/V)SCKASGYTFT | 175 |
| QVQLVQSGAX(L/V)KKPGASVK(L/V)SCKASGYTFT | 176 |
| QVQLVQSGAEXKKPGASVK(L/V)SCKASGYTFT | 177 |
| QVQLVQSGAE(L/V)XKPGASVK(L/V)SCKASGYTFT | 178 |
| QVQLVQSGAE(L/V)KXPGASVK(L/V)SCKASGYTFT | 179 |
| QVQLVQSGAE(L/V)KKXGASVK(L/V)SCKASGYTFT | 180 |
| QVQLVQSGAE(L/V)KKPXASVK(L/V)SCKASGYTFT | 181 |
| QVQLVQSGAE(L/V)KKPGXSVK(L/V)SCKASGYTFT | 182 |
| QVQLVQSGAE(L/V)KKPGAXVK(L/V)SCKASGYTFT | 183 |
| QVQLVQSGAE(L/V)KKPGASXK(L/V)SCKASGYTFT | 184 |
| QVQLVQSGAE(L/V)KKPGASVX(L/V)SCKASGYTFT | 185 |
| QVQLVQSGAE(L/V)KKPGASVKXSCKASGYTFT | 186 |
| QVQLVQSGAE(L/V)KKPGASVK(L/V)XCKASGYTFT | 187 |
| QVQLVQSGAE(L/V)KKPGASVK(L/V)SXKASGYTFT | 188 |
| QVQLVQSGAE(L/V)KKPGASVK(L/V)SCXASGYTFT | 189 |
| QVQLVQSGAE(L/V)KKPGASVK(L/V)SCKXSGYTFT | 190 |
| QVQLVQSGAE(L/V)KKPGASVK(L/V)SCKAXGYTFT | 191 |
| QVQLVQSGAE(L/V)KKPGASVK(L/V)SCKASXYTFT | 192 |
| QVQLVQSGAE(L/V)KKPGASVK(L/V)SCKASGXTFT | 193 |
| QVQLVQSGAE(L/V)KKPGASVK(L/V)SCKASGYXFT | 194 |
| QVQLVQSGAE(L/V)KKPGASVK(L/V)SCKASGYTXT | 195 |
| QVQLVQSGAE(L/V)KKPGASVK(L/V)SCKASGYTFX | 196 |

TABLE 17

| | VH FR2 | SEQ ID NO: |
|---|---|---|
| H1/H2 | WVKQAPGKGLEWIA | 34 |
| H3/H4/H5 | WVRQAPGKGLEWIA | 39 |
| | XV(R/K)QAPGKGLEWIA | 197 |
| | WX(R/K)QAPGKGLEWIA | 198 |
| | WVXQAPGKGLEWIA | 199 |
| | WV(R/K)XAPGKGLEWIA | 200 |
| | WV(R/K)QXPGKGLEWIA | 201 |
| | WV(R/K)QAXGKGLEWIA | 202 |
| | WV(R/K)QAPXKGLEWIA | 203 |
| | WV(R/K)QAPGXGLEWIA | 204 |
| | WV(R/K)QAPGKXLEWIA | 205 |
| | WV(R/K)QAPGKGXEWIA | 206 |
| | WV(R/K)QAPGKGLXWIA | 207 |
| | WV(R/K)QAPGKGLEXIA | 208 |
| | WV(R/K)QAPGKGLEWXA | 209 |
| | WV(R/K)QAPGKGLEWIX | 210 |

TABLE 18

| | VH FR3 | SEQ ID NO: |
|---|---|---|
| H1 | RATLTAEKSTSTAYMQLSSLRSEDSAVYFCAR | 35 |
| H2 | RATLTAEKSTSTAYMQLSSLRSEDTAVYFCAR | 38 |
| H3 | RATLTADKSTSTAYMQLSSLRSEDTAVYFCAR | 40 |
| H4 | RATITADKSTSTAYMELSSLRSEDTAVYFCAR | 42 |
| H5 | RVTITADKSTSTAYMELSSLRSEDTAVYFCAR | 43 |
| | X(A/V)T(I/L)TADKSTSTAYM(E/Q)LSSLRSED(S/T)AVYFCAR | 211 |
| | RXT(I/L)TADKSTSTAYM(E/Q)LSSLRSED(S/T)AVYFCAR | 212 |
| | R(A/V)X(I/L)TADKSTSTAYM(E/Q)LSSLRSED(S/T)AVYFCAR | 213 |
| | R(A/V)TXTADKSTSTAYM(E/Q)LSSLRSED(S/T)AVYFCAR | 214 |
| | R(A/V)T(I/L)XADKSTSTAYM(E/Q)LSSLRSED(S/T)AVYFCAR | 215 |
| | R(A/V)T(I/L)TXDKSTSTAYM(E/Q)LSSLRSED(S/T)AVYFCAR | 216 |

TABLE 18-continued

VH FR3

| VH FR3 | SEQ ID NO: |
|---|---|
| R(A/V)T(I/L)TAXKSTSTAYM(E/Q)LSSLRSED(S/T)AVYFCAR | 217 |
| R(A/V)T(I/L)TADXSTSTAYM(E/Q)LSSLRSED(S/T)AVYFCAR | 218 |
| R(A/V)T(I/L)TADKXTSTAYM(E/Q)LSSLRSED(S/T)AVYFCAR | 219 |
| R(A/V)T(I/L)TADKSXSTAYM(E/Q)LSSLRSED(S/T)AVYFCAR | 220 |
| R(A/V)T(I/L)TADKSTXTAYM(E/Q)LSSLRSED(S/T)AVYFCAR | 221 |
| R(A/V)T(I/L)TADKSTSXAYM(E/Q)LSSLRSED(S/T)AVYFCAR | 222 |
| R(A/V)T(I/L)TADKSTSTXYM(E/Q)LSSLRSED(S/T)AVYFCAR | 223 |
| R(A/V)T(I/L)TADKSTSTAXM(E/Q)LSSLRSED(S/T)AVYFCAR | 224 |
| R(A/V)T(I/L)TADKSTSTAYX(E/Q)LSSLRSED(S/T)AVYFCAR | 225 |
| R(A/V)T(I/L)TADKSTSTAYMXLSSLRSED(S/T)AVYFCAR | 226 |
| R(A/V)T(I/L)TADKSTSTAYM(E/Q)XSSLRSED(S/T)AVYFCAR | 227 |
| R(A/V)T(I/L)TADKSTSTAYM(E/Q)LXSLRSED(S/T)AVYFCAR | 228 |
| R(A/V)T(I/L)TADKSTSTAYM(E/Q)LSXLRSED(S/T)AVYFCAR | 229 |
| R(A/V)T(I/L)TADKSTSTAYM(E/Q)LSSXRSED(S/T)AVYFCAR | 230 |
| R(A/V)T(I/L)TADKSTSTAYM(E/Q)LSSLXSED(S/T)AVYFCAR | 231 |
| R(A/V)T(I/L)TADKSTSTAYM(E/Q)LSSLRXED(S/T)AVYFCAR | 232 |
| R(A/V)T(I/L)TADKSTSTAYM(E/Q)LSSLRSXD(S/T)AVYFCAR | 233 |
| R(A/V)T(I/L)TADKSTSTAYM(E/Q)LSSLRSEX(S/T)AVYFCAR | 234 |
| R(A/V)T(I/L)TADKSTSTAYM(E/Q)LSSLRSEDXAVYFCAR | 235 |
| R(A/V)T(I/L)TADKSTSTAYM(E/Q)LSSLRSED(S/T)XVYFCAR | 236 |
| R(A/V)T(I/L)TADKSTSTAYM(E/Q)LSSLRSED(S/T)AXYFCAR | 237 |
| R(A/V)T(I/L)TADKSTSTAYM(E/Q)LSSLRSED(S/T)AVXFCAR | 238 |
| R(A/V)T(I/L)TADKSTSTAYM(E/Q)LSSLRSED(S/T)AVYXCAR | 239 |
| R(A/V)T(I/L)TADKSTSTAYM(E/Q)LSSLRSED(S/T)AVYFXAR | 240 |
| R(A/V)T(I/L)TADKSTSTAYM(E/Q)LSSLRSED(S/T)AVYFCXR | 241 |
| R(A/V)T(I/L)TADKSTSTAYM(E/Q)LSSLRSED(S/T)AVYFCAX | 242 |

TABLE 19

VH FR4

| | VH FR4 | SEQ ID NO: |
|---|---|---|
| H1-H5 | WGQGTTVTVSS | 36 |
| | XGQGTTVTVSS | 243 |
| | WXQGTTVTVSS | 244 |
| | WGXGTTVTVSS | 245 |
| | WGQXTTVTVSS | 246 |
| | WGQGXTVTVSS | 247 |
| | WGQGTXVTVSS | 248 |

TABLE 19-continued

VH FR4

| VH FR4 | SEQ ID NO: |
|---|---|
| WGQGTTXTVSS | 249 |
| WGQGTTVXVSS | 250 |
| WGQGTTVTXSS | 251 |
| WGQGTTVTVXS | 252 |
| WGQGTTVTVSX | 253 |

TABLE 20

VL FR1

| | VL R1 | SEQ ID NO: |
|---|---|---|
| L1 | DIVMTQSPSFLSASVGDRVTITC | 44 |
| L2/L3/L4 | DIVMTQSPSSLSASVGDRVTITC | 48 |
| | XIVMTQSPS(F/S)LSASVGDRVTITC | 254 |
| | DXVMTQSPS(F/S)LSASVGDRVTITC | 255 |
| | DIXMTQSPS(F/S)LSASVGDRVTITC | 256 |
| | DIVXTQSPS(F/S)LSASVGDRVTITC | 257 |
| | DIVMXQSPS(F/S)LSASVGDRVTITC | 258 |
| | DIVMTXSPS(F/S)LSASVGDRVTITC | 259 |
| | DIVMTQXPS(F/S)LSASVGDRVTITC | 260 |
| | DIVMTQSXS(F/S)LSASVGDRVTITC | 261 |
| | DIVMTQSPX(F/S)LSASVGDRVTITC | 262 |
| | DIVMTQSPSXLSASVGDRVTITC | 263 |
| | DIVMTQSPS(F/S)XSASVGDRVTITC | 264 |
| | DIVMTQSPS(F/S)LXASVGDRVTITC | 265 |
| | DIVMTQSPS(F/S)LSXSVGDRVTITC | 266 |
| | DIVMTQSPS(F/S)LSAXVGDRVTITC | 267 |
| | DIVMTQSPS(F/S)LSASXGDRVTITC | 268 |
| | DIVMTQSPS(F/S)LSASVXDRVTITC | 269 |
| | DIVMTQSPS(F/S)LSASVGXRVTITC | 270 |
| | DIVMTQSPS(F/S)LSASVGDXVTITC | 271 |
| | DIVMTQSPS(F/S)LSASVGDRXTITC | 272 |
| | DIVMTQSPS(F/S)LSASVGDRVXITC | 273 |
| | DIVMTQSPS(F/S)LSASVGDRVTXTC | 274 |
| | DIVMTQSPS(F/S)LSASVGDRVTIXC | 275 |
| | DIVMTQSPS(F/S)LSASVGDRVTITX | 276 |

TABLE 21

VL FR2

| | VL FR2 | SEQ ID NO: |
|---|---|---|
| L1/L2/L3 | WYQQKPGKAPKALIY | 45 |
| L4 | WYQQKPGKAPKSLIY | 51 |
| | XYQQKPGKAPK(S/A)LIY | 277 |
| | WXQQKPGKAPK(S/A)LIY | 278 |
| | WXXQKPGKAPK(S/A)LIY | 279 |
| | WYQXKPGKAPK(S/A)LIY | 280 |
| | WYQQXPGKAPK(S/A)LIY | 281 |
| | WYQQKXGKAPK(S/A)LIY | 282 |
| | WYQQKPXKAPK(S/A)LIY | 283 |
| | WYQQKPGXPK(S/A)LIY | 284 |
| | WYQQKPGKXPK(S/A)LIY | 285 |
| | WYQQKPGKAXK(S/A)LIY | 286 |
| | WYQQKPGKAPX(S/A)LIY | 287 |
| | WYQQKPGKAPKXLIY | 288 |
| | WYQQKPGKAPK(S/A)XIY | 289 |
| | WYQQKPGKAPK(S/A)LXY | 290 |
| | WYQQKPGKAPK(S/A)LIX | 291 |

TABLE 22

VL FR3

| | VL FR3 | SEQ ID NO: |
|---|---|---|
| L1 | GVPDRFTGSGSGTDFTLTISSLQSEDFADYFC | 46 |
| L2 | GVPDRFTGSGSGTDFTLTISSLQPEDFADYFC | 49 |
| L3 | GVPDRFSGSGSGTDFTLTISSLQPEDFADYFC | 50 |
| L4 | GVPDRFSGSGSGTDFTLTISSLQPEDFATYYC | 52 |
| | XVPDRF(S/T)GSGSGTDFTLTISSLQ(P/S)EDFA(D/T)Y(F/Y)C | 292 |
| | GXPDRF(S/T)GSGSGTDFTLTISSLQ(P/S)EDFA(D/T)Y(F/Y)C | 293 |
| | GVXDRF(S/T)GSGSGTDFTLTISSLQ(P/S)EDFA(D/T)Y(F/Y)C | 294 |
| | GVPXRF(S/T)GSGSGTDFTLTISSLQ(P/S)EDFA(D/T)Y(F/Y)C | 295 |
| | GVPDXF(S/T)GSGSGTDFTLTISSLQ(P/S)EDFA(D/T)Y(F/Y)C | 296 |
| | GVPDRX(S/T)GSGSGTDFTLTISSLQ(P/S)EDFA(D/T)Y(F/Y)C | 297 |

TABLE 22-continued

VL FR3

| VL FR3 | SEQ ID NO: |
|---|---|
| GVPDRFXGSGSGTDFTLTISSLQ(P/S)EDFA(D/T)Y(F/Y)C | 298 |
| GVPDRF(S/T)XSGSGTDFTLTISSLQ(P/S)EDFA(D/T)Y(F/Y)C | 299 |
| GVPDRF(S/T)GXSGTDFTLTISSLQ(P/S)EDFA(D/T)Y(F/Y)C | 300 |
| GVPDRF(S/T)GSXGTDFTLTISSLQ(P/S)EDFA(D/T)Y(F/Y)C | 301 |
| GVPDRF(S/T)GSGXTDFTLTISSLQ(P/S)EDFA(D/T)Y(F/Y)C | 302 |
| GVPDRF(S/T)GSGSXDFTLTISSLQ(P/S)EDFA(D/T)Y(F/Y)C | 303 |
| GVPDRF(S/T)GSGSGXFTLTISSLQ(P/S)EDFA(D/T)Y(F/Y)C | 304 |
| GVPDRF(S/T)GSGSGTXTLTISSLQ(P/S)EDFA(D/T)Y(F/Y)C | 305 |
| GVPDRF(S/T)GSGSGTDXLTISSLQ(P/S)EDFA(D/T)Y(F/Y)C | 306 |
| GVPDRF(S/T)GSGSGTDFXTISSLQ(P/S)EDFA(D/T)Y(F/Y)C | 307 |
| GVPDRF(S/T)GSGSGTDFTXISSLQ(P/S)EDFA(D/T)Y(F/Y)C | 308 |
| GVPDRF(S/T)GSGSGTDFTLXSSLQ(P/S)EDFA(D/T)Y(F/Y)C | 309 |
| GVPDRF(S/T)GSGSGTDFTLTXSLQ(P/S)EDFA(D/T)Y(F/Y)C | 310 |
| GVPDRF(S/T)GSGSGTDFTLTIXSLQ(P/S)EDFA(D/T)Y(F/Y)C | 311 |
| GVPDRF(S/T)GSGSGTDFTLTISXLQ(P/S)EDFA(D/T)Y(F/Y)C | 312 |
| GVPDRF(S/T)GSGSGTDFTLTISSXQ(P/S)EDFA(D/T)Y(F/Y)C | 313 |
| GVPDRF(S/T)GSGSGTDFTLTISSLX(P/S)EDFA(D/T)Y(F/Y)C | 314 |
| GVPDRF(S/T)GSGSGTDFTLTISSLQXEDFA(D/T)Y(F/Y)C | 315 |
| GVPDRF(S/T)GSGSGTDFTLTISSLQ(P/S)XDFA(D/T)Y(F/Y)C | 316 |
| GVPDRF(S/T)GSGSGTDFTLTISSLQ(P/S)EXFA(D/T)Y(F/Y)C | 317 |
| GVPDRF(S/T)GSGSGTDFTLTISSLQ(P/S)EDXA(D/T)Y(F/Y)C | 318 |
| GVPDRF(S/T)GSGSGTDFTLTISSLQ(P/S)EDFX(D/T)Y(F/Y)C | 319 |
| GVPDRF(S/T)GSGSGTDFTLTISSLQ(P/S)EDFAXY(F/Y)C | 320 |
| GVPDRF(S/T)GSGSGTDFTLTISSLQ(P/S)EDFA(D/T)X(F/Y)C | 321 |
| GVPDRF(S/T)GSGSGTDFTLTISSLQ(P/S)EDFA(D/T)YXC | 322 |
| GVPDRF(S/T)GSGSGTDFTLTISSLQ(P/S)EDFA(D/T)Y(F/Y)X | 323 |

TABLE 23

VL FR4

| | VL FR4 | SEQ ID NO: |
|---|---|---|
| L1-L4 | FGGGTKVEIK | 47 |
| | XGGGTKVEIK | 324 |
| | FXGGTKVEIK | 325 |
| | FGXGTKVEIK | 326 |
| | FGGXTKVEIK | 327 |
| | FGGGXKVEIK | 328 |
| | FGGGTXVEIK | 329 |
| | FGGGTKXEIK | 330 |
| | FGGGTKVXIK | 331 |
| | FGGGTKVEXK | 332 |
| | FGGGTKVEIX | 333 |

In one aspect, an antibody described herein comprises an Fc region that comprises one or more amino acid deletions, additions and/or modifications.

An "Fc region," as used herein, includes polypeptides comprising a constant region of an antibody excluding the first constant region immunoglobulin domain, and thus refers to the last two constant region immunoglobulin domains of IgA, IgD, and IgG, the last three constant region immunoglobulin domains of IgE and IgM, and the flexible hinge N-terminal to these domains. For IgA and IgM, an Fc region may include the J chain. For IgG, an Fc region may comprise immunoglobulin domains Cgamma2 and Cgamma3 (Cγ2 and Cγ3) and the hinge between Cgamma1 (Cγ1) and Cgamma2 (Cγ2). Although the boundaries of an Fc region may vary, the human IgG heavy chain Fc region generally comprises residues C226 or P230 to its carboxyl-terminus, wherein the numbering is according to the EU index as in Kabat et al. (1991, NIH Publication 91-3242, National Technical Information Service, Springfield, Va.). The "EU index as set forth in Kabat" refers to the residue numbering of the human IgG1 EU antibody as described in Kabat et al. supra. In a certain embodiment, an Fc region comprises a non-naturally occurring Fc region. In certain aspects, one or more polymorphisms are present one or more Fc positions, including but not limited to Kabat 270, 272, 312, 315, 356, and 358.

In one aspect, provided herein is an antibody, as described herein, which specifically binds to a D4 region of KIT, or an antigen-binding fragment thereof, comprising an Fc region which has altered binding properties for an Fc ligand (e.g., an Fc receptor, such as C1q) relative to a comparable antibody (e.g., one having the same amino acid sequence except having a wild type Fc region).

The affinities and binding properties of an Fc region for its ligand, may be determined by a variety of in vitro assay methods (biochemical or immunological based assays) known in the art for determining Fc-FcγR interactions, i.e., specific binding of an Fc region to an FcγR including but not limited to, equilibrium methods (e.g., enzyme-linked immunoabsorbent assay (ELISA), or radioimmunoassay (RIA)), or kinetics (e.g., BIACORE® analysis), and other methods such as indirect binding assays, competitive inhibition assays, fluorescence resonance energy transfer (FRET), gel electrophoresis and chromatography (e.g., gel filtration). These and other methods may utilize a label on one or more of the components being examined and/or employ a variety of detection methods including but not limited to chromogenic, fluorescent, luminescent, or isotopic labels.

In one embodiment, an Fc region of an antibody described herein has enhanced binding to one or more Fc ligand relative to a comparable molecule. In a specific embodiment, an Fc region of an antibody described herein has enhanced binding to an Fc receptor. In another specific embodiment, an Fc region of an antibody described herein has enhanced binding to the Fc receptor FcγRIIIA. In one specific embodiment, an Fc region of an antibody described herein has enhanced binding to the Fc receptor FcRn. In another specific embodiment, an Fc region of an antibody described herein has enhanced binding to C1q relative to a comparable molecule.

In a certain aspect, the serum half-life of proteins comprising Fc regions may be increased by increasing the binding affinity of the Fc region for FcRn. In one embodiment, an Fc region of an antibody described herein has enhanced serum half-life relative to comparable molecule.

"Antibody-dependent cell-mediated cytotoxicity" or "ADCC" refers to a form of cytotoxicity in which secreted Ig bound onto Fc receptors (FcRs) present on certain cytotoxic cells (e.g., Natural Killer (NK) cells, neutrophils, and macrophages) enables these cytotoxic cells to bind specifically to an antigen-bearing target cell and subsequently kill the target cell with cytotoxins. Specific high-affinity IgG antibodies directed to the surface of target cells "arm" the cytotoxic cells, for such killing. Lysis of the target cell involves direct cell-to-cell contact, and does not involve complement. It is contemplated that, in addition to antibodies, other proteins comprising Fc regions, specifically Fc fusion proteins, having the capacity to bind specifically to an antigen-bearing target cell will be able to effect cell-mediated cytotoxicity. For simplicity, the cell-mediated cytotoxicity resulting from the activity of an Fc fusion protein is also referred to herein as ADCC activity.

The ability of any particular protein, e.g., antibody, comprising an Fc region to mediate lysis of the target cell by ADCC can be assayed. To assess ADCC activity, of an Fc region, a target cell-binding antibody comprising the Fc region is added to target cells in combination with immune effector cells, which may be activated by the antigen-antibody complexes resulting in cytolysis of the target cell. Cytolysis is generally detected by the release of label (e.g. radioactive substrates, fluorescent dyes or natural intracellular proteins) from the lysed cells. Useful effector cells for such assays include peripheral blood mononuclear cells (PBMC) and Natural Killer (NK) cells. Specific examples of in vitro ADCC assays are described in Wisecarver et al., 1985 79:277-282; Bruggemann et al., 1987, J Exp. Med. 166:1351-1361; Wilkinson et al., 2001, J Immunol. Methods 258:183-191; Patel et al., 1995 J Immunol. Methods 184: 29-38. Alternatively, or additionally, ADCC activity of a protein comprising an Fc region may be assessed in vivo, e.g., in a animal model such as that disclosed in Clynes et al., 1998, Proc. Natl. Acad. Sci. USA 95:652-656.

In one embodiment, a protein, e.g., an antibody described herein, comprising an Fc region has enhanced ADCC activity relative to a comparable protein, e.g., antibody. In another specific embodiment, an antibody described herein comprising an Fc region has enhanced binding to the Fc receptor FcγRIIIA and has enhanced ADCC activity relative to a comparable antibody. In some embodiments, an antibody described herein comprising an Fc region has both enhanced ADCC activity and enhanced serum half-life relative to a comparable antibody.

"Complement dependent cytotoxicity" and "CDC" refer to the lysing of a target cell in the presence of complement. The complement activation pathway is initiated by the binding of the first component of the complement system (C1q) to a molecule, an antibody for example, complexed with a cognate antigen. To assess complement activation, a CDC assay, as described in Gazzano-Santoro et al., 1996, J. Immunol. Methods, 202:163, may be performed, for example. In one embodiment, an antibody described herein comprising an Fc region has enhanced CDC activity relative to a comparable antibody. In other embodiments, an antibody described herein comprising an Fc region has both enhanced CDC activity and enhanced serum half life relative to a comparable antibody.

In one embodiment, an antibody described herein comprises an Fc region that comprises an amino acid modification (e.g., substitution, deletion or addition, or a non-naturally occurring amino acid residue) at one or more positions (e.g., at one, two, three, or four positions) selected from the group consisting of 234, 235, 236, 239, 240, 241, 243, 244, 245, 247, 252, 254, 256, 262, 263, 264, 265, 266, 267, 269, 296, 297, 298, 299, 313, 325, 326, 327, 328, 329, 330, 332, 333, and 334 as numbered by the EU index as set forth in Kabat. Optionally, the Fc region may comprise an amino acid modification (e.g., substitution, deletion or addition) or a non-naturally occurring amino acid residue at additional and/or alternative positions known to one skilled in the art (see, e.g., U.S. Pat. Nos. 5,624,821; 6,277,375; 6,737,056; PCT Patent Publications WO 01/58957; WO 04/016750;

WO 04/029207; WO 04/035752 and WO 05/040217, each of which is incorporated herein in its entirety, but particularly for the disclosure of such modifications). In a further embodiment, one or more functions of an Fc region is maintained (e.g., substantially maintained, for example, at least 50%, at least 60%, at least 70%, at least 80%, at least 90%, at least 95%) by the Fc region comprising an amino acid modification (e.g., substitution, deletion or addition) or a non-naturally occurring amino acid residue at one or more positions. For example, such Fc functions can include effector function, such as CDC or ADCC, or binding affinity to an Fc receptor. In a certain embodiment, the Fc region, comprising an amino acid modification (e.g., substitution, deletion or addition) or a non-naturally occurring amino acid residue at one or more positions, exhibits at least one or more enhanced Fc activity, e.g., enhanced half-life, or enhanced effector function, such as ADCC or CDC. In a particular embodiment, the Fc region, comprising an amino acid modification (e.g., substitution, deletion or addition) or a non-naturally occurring amino acid residue at one or more positions, exhibits decreased Fc activity, e.g., decreased stability/half-life, or decreased effector function, such as ADCC or CDC.

In a specific embodiment, an antibody described herein comprises an Fc region, wherein the Fc region comprises at least one (e.g., one, two, three, or four) amino acid modification (e.g., substitution, deletion or addition) or at least one non-naturally occurring amino acid residue (e.g., one, two, three, or four) selected from the group consisting of 234D, 234E, 234N, 234Q, 234T, 234H, 234Y, 234I, 234V, 234F, 235A, 235D, 235R, 235W, 235P, 235S, 235N, 235Q, 235T, 235H, 235Y, 235I, 235V, 235F, 236E, 239D, 239E, 239N, 239Q, 239F, 239T, 239H, 239Y, 240I, 240A, 240T, 240M, 241W, 241L, 241Y, 241E, 241 R. 243W, 243L 243Y, 243R, 243Q, 244H, 245A, 247V, 247G, 252Y, 254T, 256E, 262I, 262A, 262T, 262E, 263I, 263A, 263T, 263M, 264L, 264I, 264W, 264T, 264R, 264F, 264M, 264Y, 264E, 265G, 265N, 265Q, 265Y, 265F, 265V, 265I, 265L, 265H, 265T, 266I, 266A, 266T, 266M, 267Q, 267L, 269H, 269Y, 269F, 269R, 296E, 296Q, 296D, 296N, 296S, 296T, 296L, 296I, 296H, 269G, 297S, 297D, 297E, 298H, 298I, 298T, 298F, 299I, 299L, 299A, 299S, 299V, 299H, 299F, 299E, 313F, 325Q, 325L, 325I, 325D, 325E, 325A, 325T, 325V, 325H, 327G, 327W, 327N, 327L, 328S, 328M, 328D, 328E, 328N, 328Q, 328F, 328I, 328V, 328T, 328H, 328A, 329F, 329H, 329Q, 330K, 330G, 330T, 330C, 330L, 330Y, 330V, 330I, 330F, 330R, 330H, 332D, 332S, 332W, 332F, 332E, 332N, 332Q, 332T, 332H, 332Y, and 332A as numbered by the EU index as set forth in Kabat. Optionally, the Fc region may comprise additional and/or alternative non-naturally occurring amino acid residues known to one skilled in the art (see, e.g., U.S. Pat. Nos. 5,624,821; 6,277,375; 6,737,056; PCT Patent Publications WO 01/58957; WO 04/016750; WO 04/029207; WO 04/035752 and WO 05/040217).

In a certain aspect, provided herein is an antibody comprising an Fc region, wherein the Fc region comprises at least a non-naturally occurring amino acid at one or more positions selected from the group consisting of 239, 330 and 332, as numbered by the EU index as set forth in Kabat. In a specific embodiment, provided herein is an antibody comprising an Fc region, wherein the Fc region comprises at least one non-naturally occurring amino acid selected from the group consisting of 239D, 330L and 332E, as numbered by the EU index as set forth in Kabat. Optionally, the Fc region may further comprise additional non-naturally occurring amino acid at one or more positions selected from the group consisting of 252, 254, and 256, as numbered by the EU index as set forth in Kabat. In a specific embodiment, provided herein is an antibody comprising an Fc region, wherein the Fc region comprises at least one non-naturally occurring amino acid selected from the group consisting of 239D, 330L and 332E, as numbered by the EU index as set forth in Kabat and at least one non-naturally occurring amino acid at one or more positions are selected from the group consisting of 252Y, 254T and 256E, as numbered by the EU index as set forth in Kabat. In one embodiment, an Fc region comprising such sequence exhibits one or more Fc activity, for example, binding affinity to an Fc receptor or effector function, such as ADCC or CDC. In a specific embodiment, an Fc region comprising such sequence exhibits reduced Fc activity, for example, reduced binding affinity to an Fc receptor or reduced effector function, such as ADCC or CDC. In a particular embodiment, an Fc region comprising such sequence exhibits enhanced Fc activity, for example, enhanced half-life, enhanced binding affinity to an Fc receptor, or enhanced effector function, such as ADCC or CDC.

Non-limiting examples of Fc region modifications are provided in Ghetie et al., 1997, Nat Biotech. 15:637-40; Duncan et al, 1988, Nature 332:563-564; Lund et al., 1991, J. Immunol 147:2657-2662; Lund et al, 1992, Mol Immunol 29:53-59; Alegre et al, 1994, Transplantation 57:1537-1543; Hutchins et al., 1995, Proc Natl. Acad Sci USA 92:11980-11984; Jefferis et al, 1995, Immunol Lett. 44:111-117; Lund et al., 1995, Faseb J 9:115-119; Jefferis et al, 1996, Immunol Lett 54:101-104; Lund et al, 1996, J Immunol 157:4963-4969; Armour et al., 1999, Eur J Immunol 29:2613-2624; Idusogie et al, 2000, J Immunol 164:4178-4184; Reddy et al, 2000, J Immunol 164:1925-1933; Xu et al., 2000, Cell Immunol 200:16-26; Idusogie et al, 2001, J Immunol 166: 2571-2575; Shields et al., 2001, J Biol Chem 276:6591-6604; Jefferis et al, 2002, Immunol Lett 82:57-65; Presta et al., 2002, Biochem Soc Trans 30:487-490); U.S. Pat. Nos. 5,624,821; 5,885,573; 5,677,425; 6,165,745; 6,277,375; 5,869,046; 6,121,022; 5,624,821; 5,648,260; 6,528,624; 6,194,551; 6,737,056; 6,821,505; 6,277,375; 8,163,882; 7,355,008; 7,960,512; 8,039,592; 8,039,359; 8,101,720; 7,214,775; 7,682,610; 7,741,442; U.S. Patent Publication Nos. 2004/0002587 and PCT Publications WO 94/29351; WO 99/58572; WO 00/42072; WO 04/029207; WO 04/099249; WO 04/063351.

In a particular embodiment, an antibody described herein comprises one or more (e.g., one, two, three, or four) modifications to an IgG1 Fc region, such as a human IgG1 Fc region. In a certain embodiment, an antibody described herein comprises one or more (e.g., one, two, three, or four) modifications to an IgG2 Fc region, such as a human IgG2 Fc region. In one embodiment, an antibody described herein comprises one or more (e.g., one, two, three, or four) modifications to an IgG4 Fc region, such as a human IgG4 Fc region.

In some aspects, an antibody described herein comprises an Fc region, wherein the Fc region comprises one or more (e.g., one, two, three, or four) glycoform modifications (e.g., removal or substitution of one or more glycoforms), such as engineered glycoforms, i.e., a carbohydrate composition that is covalently attached to a molecule comprising an Fc region. Engineered glycoforms may be useful for a variety of purposes, including but not limited to enhancing or reducing effector function. Engineered glycoforms may be generated by any method known to one skilled in the art, for example by using engineered or variant expression strains, by co-expression with one or more enzymes, for example DI N-acetylglucosaminyltransferase III (GnTI11), by expressing a molecule comprising an Fc region in various organisms or cell lines from various organisms, or by modifying carbohydrate(s) after the molecule comprising Fc region has been expressed. Methods for generating engineered glycoforms are known in the art, and include but are not limited to those described in Umana et al, 1999, Nat. Biotechnol 17:176-180; Davies et al., 20017 Biotechnol Bioeng 74:288-294; Shields et al, 2002, J Biol Chem 277:26733-26740; Shinkawa et al., 2003, J Biol Chem 278:3466-3473) U.S. Pat. No. 6,602,684; U.S. application Ser. No. 10/277,370; U.S. application Ser. No. 10/113,929; PCT WO 00/61739A1; PCT WO 01/292246A1; PCT WO 02/311140A1; PCT WO 02/30954A1; WO 00061739; US 20030115614; and Okazaki et al., 2004, JMB, 336: 1239-49. Methods for generating modified glycoforms of an antibody described herein are described in the art, and include but are not limited to those described in U.S. Pat. Nos. 7,517,670; 8,021,856; 8,080,415; 8,084,222; 7,700,321; and 8,071,336.

In a particular embodiment, glycosylation of an Fc region can be modified to increase or decrease effector function. Accordingly, in one embodiment, an Fc region of an antibody described herein comprises modified glycosylation of amino acid residues. In another embodiment, the modified glycosylation of amino acid residues results in lowered effector function, such as ADCC or CDC. In another embodiment, the modified glycosylation of the amino acid residues results in increased effector function. In some embodiments, the glycosylation patterns of the antibodies provided herein are modified to enhance ADCC and CDC effector function (see, for example, Shields et al., (2002) JBC. 277:26733; Shinkawa et al., (2003) JBC. 278:3466 and Okazaki et al., (2004) J. Mol. Biol., 336: 1239). In a specific embodiment, such modified glycosylation is different than glycosylation of an Fc region found naturally in vivo, or such modified glycosylation is a non-naturally occurring glycosylation of an Fc region. For example, modified glycosylation of an Fc region can be achieved by modifying an amino acid or by expressing the protein/antibody in a cell that has been engineered to contain a different glycosylation machinery than its parental cell that has not been modified. In this regard, such a cell can be engineered to not express a certain glycosylation enzyme or to express a certain glycosylation enzyme that is not present in the parental cell.

Methods for generating non-naturally occurring Fc regions are known in the art. For example, amino acid substitutions and/or deletions can be generated by mutagenesis methods, including, but not limited to, site-directed mutagenesis (Kunkel, Proc. Natl. Acad. Sci. USA 82:488-492 (1985)), PCR mutagenesis (Higuchi, in "PCR Protocols: A Guide to Methods and Applications", Academic Press, San Diego, pp. 177-183 (1990)), and cassette mutagenesis (Wells et al., Gene 34:315-323 (1985)). Site-directed mutagenesis can be performed by the overlap-extension PCR method (Higuchi, in "PCR Technology: Principles and Applications for DNA Amplification", Stockton Press, New York, pp. 61-70 (1989)). Alternatively, the technique of overlap-extension PCR (Higuchi, ibid.) can be used to introduce any desired mutation(s) into a target sequence (the starting DNA). Other methods useful for the generation of Fc region modifications are known in the art (see, e.g., U.S. Pat. Nos. 5,624,821; 5,885,573; 5,677,425; 6,165,745; 6,277,375; 5,869,046; 6,121,022; 5,624,821; 5,648,260; 6,528,624; 6,194,551; 6,737,056; 6,821,505; 6,277,375; U.S. Patent Publication Nos. 2004/0002587 and PCT Publications WO 94/29351; WO 99/58572; WO 00/42072; WO 02/060919; WO 04/029207; WO 04/099249; WO 04/063351).

In a specific embodiment, the Fc region has reduced fucosylation. In another embodiment, the Fc region is afucosylated (see for examples, U.S. Patent Application Publication No. 2005/0226867).

In a certain aspect, an antibody described herein is a non-fucosylated antibody, for example an Fc region of the antibody does not contain sugar chains with a fucose, e.g., a fucose bound to N-acetylglucosamines (see, e.g., U.S. Pat. Nos. 7,214,775; 7,682,610; and 7,741,442). Methods for making non-fucosylated antibodies are known in the art, see, e.g., U.S. Pat. No. 7,708,992. For example, non-fucosylated antibodies can be generated using engineered host cells, see, e.g., U.S. Pat. Nos. 6,946,292; 7,425,446; 8,067,232; 7,846,725; and 7,393,683. Knock-out animals for generating non-fucosylated antibodies also have been described, see, e.g., U.S. Pat. No. 7,737,325. In a particular embodiment, a non-fucosylated antibody described herein, which specifically binds to a D4 region of human KIT, exhibits increased ADCC.

In a particular aspect, an antibody described herein comprises a fucose content of less than 100%, for example, less than 65%, relative to the fucose content of a reference antibody (see, e.g., U.S. Pat. Nos. 7,931,895 and 7,846,434). In a certain embodiment, an antibody described herein is characterized by a fucose content wherein at least about 60% of the N-linked oligosaccharides, e.g. N-linked oligosaccharides in the CH2-derived domains, contain no fucose. In specific embodiments, the percentage of N-linked oligosaccharides, e.g. N-linked oligosaccharides in the CH2-derived domains, that contain no fucose is at least about 65%, about 70%, about 75%, about 80%, about 85%, about 90%, about 95% or more, and exhibits altered effector function, for example enhanced ADCC or reduced ADCC. In a particular embodiment, an antibody described herein, which specifically binds to a D4 region of human KIT, comprises a fucose content of less than 65% and exhibits increased ADCC.

In particular aspects, an antibody described herein comprises an Fc region with altered FcγR binding activity displaying reduced binding to an FcγR and comprises an amino acid modification at any one or more (e.g., one, two, three, or four) of amino acid positions 238, 239, 248, 249, 252, 254, 265, 268, 269, 270, 272, 278, 289, 292, 293, 294, 295, 296, 298, 301, 303, 322, 324, 327, 329, 333, 335, 338, 340, 373, 376, 382, 388, 389, 414, 416, 419, 434, 435, 437, 438 or 439 of the Fc region, wherein the numbering of the residues in the Fc region is that of the EU index as in Kabat (see, e.g., U.S. Pat. No. 7,183,387). For example, an antibody described herein comprising an Fc region displays reduced binding to an FcγRI and comprise an amino acid modification at any one or more (one, two, three, or four) of amino acid positions 238, 265, 269, 270, 327 or 329 of the Fc region, wherein the numbering of the residues in the Fc region is that of the EU index as in Kabat.

In a particular embodiment, an antibody described herein comprising an Fc region displays reduced binding to an FcγRII and comprises an amino acid modification at any one or more (e.g., one, two, three, or four) of amino acid positions 238, 265, 269, 270, 292, 294, 295, 298, 303, 324, 327, 329, 333, 335, 338, 373, 376, 414, 416, 419, 435, 438 or 439 of the Fc region, wherein the numbering of the residues in the Fc region is that of the EU index as in Kabat.

In a specific embodiment, an antibody described herein comprising an Fc region displays reduced binding to an FcγRIII and comprises an amino acid modification at one or more (e.g., one, two, three, or four) of amino acid positions 238, 239, 248, 249, 252, 254, 265, 268, 269, 270, 272, 278, 289, 293, 294, 295, 296, 301, 303, 322, 327, 329, 338, 340, 373, 376, 382, 388, 389, 416, 434, 435 or 437 of the Fc region, wherein the numbering of the residues in the Fc region is that of the EU index as in Kabat.

In certain aspects, the serum half-life of a protein, such as an antibody described herein, comprising an Fc region, is increased by increasing the binding affinity of an Fc region for FcRn.

In a particular embodiment, an antibody described herein or an antigen-binding fragment thereof specifically binds to a KIT polypeptide (e.g., the D4 region of human KIT) with an $EC_{50}$ (half maximal effective concentration) value of about 50 nM or less as determined by ELISA.

In a particular embodiment, an antibody described herein or an antigen-binding fragment thereof specifically binds to a KIT polypeptide (e.g., the D4 region of human KIT) with an $EC_{50}$ value of about 150 pM or less as determined by FACs with CHO-WT-KIT cells (CHO cells engineered to recombinantly express wild-type human KIT).

In a particular embodiment, an antibody described herein or an antigen-binding fragment thereof, which specifically binds to a KIT polypeptide (e.g., the D4 region of human KIT), is capable of blocking KIT phosphorylation with $IC_{50}$ (50% inhibition concentration) value of about 600 pM or less.

In a particular embodiment, an antibody described herein or an antigen-binding fragment thereof, which specifically binds to a KIT polypeptide (e.g., the D4 region of human KIT), be recombinantly expressed in CHO cells at an average titer of at least 0.5 µg/mL. In a particular embodiment, an antibody described herein or an antigen-binding fragment thereof, which specifically binds to a KIT polypeptide (e.g., the D4 region of human KIT), be recombinantly expressed in CHO cells at an average titer of at least 1.0 µg/mL.

In a specific embodiment, an antibody described herein or an antigen-binding fragment thereof, which specifically binds to a KIT polypeptide (e.g., the D4 region of human KIT), comprises a VH domain and a VL domain that are non-immunogenic, for example, the VH domain and VL domain do not contain T cell epitopes.

In particular embodiments, an antibody described herein (or an antigen-binding fragment thereof) does not bind the extracellular ligand binding site of KIT, e.g., the SCF binding site of KIT. In particular embodiments, an antibody described herein (or an antigen-binding fragment thereof) does not inhibit ligand binding to KIT, e.g., does not inhibit KIT ligand (e.g., SCF) binding to KIT.

In specific aspects, antibodies (e.g., human or humanized antibodies) described herein are inhibitory antibodies, that is, antibodies that inhibit (e.g., partially inhibit) KIT activity, i.e., one or more KIT activities. In a specific embodiment, partial inhibition of a KIT activity results in, for example, about 25% to about 65% or 75% inhibition. In a specific embodiment, partial inhibition of a KIT activity results in, for example, about 35% to about 85% or 95% inhibition. Non-limiting examples of KIT activities include KIT dimerization, KIT phosphorylation (e.g., tyrosine phosphorylation), signaling downstream of KIT (e.g., Stat, AKT, MAPK, or Ras signaling), induction or enhancement of gene transcription (e.g., c-Myc), induction or enhancement of cell proliferation or cell survival. In a particular embodiment, an antibody described herein inhibits KIT phosphorylation (e.g., ligand-induced phosphorylation). In a specific embodiment, an antibody described herein inhibits KIT tyrosine phosphorylation in the KIT cytoplasmic domain. In another particular embodiment, an antibody described herein inhibits cell proliferation. In yet another particular embodiment, an antibody described herein inhibits cell survival. In a specific embodiment, an antibody described herein induces apoptosis. In another specific embodiment, an antibody described herein induces cell differentiation, e.g., cell differentiation in a cell expressing KIT, e.g., human KIT. In a particular embodiment, an antibody described herein inhibits KIT activity but does not inhibit KIT dimerization. In another particular embodiment, an antibody described herein inhibits KIT activity and does not inhibit ligand binding to KIT, e.g., does not inhibit KIT ligand (e.g., SCF) binding to KIT, but does inhibit KIT dimerization.

In a particular embodiment, an antibody described herein inhibits a KIT activity, such as ligand-induced tyrosine phosphorylation of a KIT cytoplasmic domain, by about 25% to about 65% or 75%, as determined by a cell-based phosphorylation assay well known in the art, for example, the cell-based phosphorylation assay described herein. In a certain embodiment, an antibody described herein inhibits a KIT activity, such as ligand-induced tyrosine phosphorylation of a KIT cytoplasmic domain, by about 35% to about 85% or 95%, as determined by a cell-based phosphorylation assay well known in the art, for example, the cell-based phosphorylation assay described herein. In a particular embodiment, an antibody described herein, or an antigen-binding fragment thereof or a conjugate thereof, inhibits a KIT activity, such as ligand-induced tyrosine phosphorylation of a KIT cytoplasmic domain, with a 50% inhibition concentration ($IC_{50}$) of less than about 600 pM, or less than about 500 pM, or less than about 250 pM, as determined by a cell-based phosphorylation assay well known in the art, for example, the cell-based phosphorylation assay described herein. In a specific embodiment, the $IC_{50}$ is less than about 550 pM or 200 pM. In a specific embodiment, the $IC_{50}$ is in the range of about 50 pM to about 225 pM, or in the range of 100 pM to about 600 pM. In a specific embodiment, the $IC_{50}$ is in the range of about 50 pM to about 550 pM, or about 50 pM to about 600 pM, or about 150 pM to about 550 pM.

In a specific embodiment, an antibody described herein, or an antigen-binding fragment thereof or a conjugate thereof, (i) immunospecifically binds to a KIT polypeptide comprising the D4 region of human KIT, (ii) inhibits KIT phosphorylation (e.g., tyrosine phosphorylation), and (iii) does not affect KIT ligand (e.g., SCF) binding to KIT. In yet another specific embodiment, such an antibody does not inhibit KIT dimerization. In yet another specific embodiment, such an antibody can be recombinantly expressed by CHO cells at an average titer of at least 0.5 µg/mL, for example at least 1.0 µg/mL. In a further specific embodiment, such an antibody comprises a VH domain and a VL domain that are non-immunogenic, for example, the VH domain and VL domain do not contain T cell epitopes.

In other specific embodiments, an antibody described herein, or an antigen-binding fragment thereof or a conjugate thereof, immunospecifically binds to a monomeric form of KIT (e.g., human KIT). In particular embodiments, an antibody described herein does not immunospecifically bind to a monomeric form of KIT (e.g., human KIT). In specific embodiments, an antibody described herein, or an antigen-binding fragment thereof or a conjugate thereof, immunospecifically binds to a dimeric form of KIT (e.g., human KIT). In specific embodiments, an antibody described herein, or an antigen-binding fragment thereof or a conjugate thereof, does not bind to a monomeric form of KIT and specifically binds to a dimeric form of KIT or multimeric form of KIT. In certain embodiments, an antibody has higher affinity for a KIT monomer than a KIT dimer. In certain embodiments, an antibody has higher affinity for a KIT monomer than a KIT multimer.

In specific embodiments, an anti-KIT antibody described herein (or an antigen-binding fragment thereof or a conjugate thereof) specifically binds to a native isoform or native variant of KIT (that is a naturally occurring isoform or variant of KIT in an animal (e.g., monkey, mouse, goat, donkey, dog, cat, rabbit, pig, rat, human, frog, or bird) that can be isolated from an animal, preferably a human). In particular embodiments, an antibody described herein immunospecifically binds to human KIT or a fragment thereof. In specific embodiments, an anti-KIT antibody described herein (or an antigen-binding fragment thereof or a conjugate thereof) specifically binds to human KIT or a fragment thereof and does not specifically bind to a non-human KIT (e.g., monkey, mouse, goat, donkey, dog, cat, rabbit, pig, rat, or bird) or a fragment thereof. In specific embodiments, an anti-KIT antibody described herein (or an antigen-binding fragment thereof or a conjugate thereof) specifically binds to human KIT or a fragment thereof and does not specifically bind to murine KIT. In certain embodiments, an anti-KIT antibody described herein specifically binds to human KIT or a fragment thereof (e.g., a D4 region of human KIT) and to canine (dog) and non-human primate (e.g., monkey) KIT. In certain embodiments, an anti-KIT antibody described herein specifically binds to human KIT or a fragment thereof (e.g., a D4 region of human KIT) and to canine (dog) KIT. In certain embodiments, an anti-KIT antibody described herein specifically binds to human KIT or a fragment thereof (e.g., a D4 region of human KIT) and to non-human primate (e.g., monkey) KIT. In certain embodiments, an anti-KIT antibody described herein specifically binds to human KIT or a fragment thereof (e.g., a D4 region of human KIT) and to canine (dog) and non-human primate (e.g., monkey) KIT, but does not specifically bind to murine KIT or a fragment thereof (e.g., a D4 region of murine KIT).

In certain embodiments, an antibody described herein or antigen-binding fragment thereof binds to an extracellular domain of human KIT comprising a mutation, for example a somatic mutation associated with cancer (e.g., GIST), such as a mutation in exon 9 of human KIT wherein the Ala and Tyr residues at positions 502 and 503 are duplicated. In certain embodiments, an antibody described herein or antigen-binding fragment thereof binds to an extracellular domain of wild-type human KIT and an extracellular domain of human KIT comprising a mutation, for example a somatic mutation associated with cancer (e.g., GIST), such as a mutation in exon 9 of human KIT wherein the Ala and Tyr residues at positions 502 and 503 are duplicated (see, e.g., Marcia et al., (2000) Am. J. Pathol. 156(3):791-795; and Debiec-Rychter et al., (2004) European Journal of Cancer. 40:689-695, which are both incorporated herein by reference in their entireties, describing KIT mutations).

In certain embodiments, an antibody described herein or antigen-binding fragment thereof binds to an extracellular domain of human KIT which is glycosylated. In certain embodiments, an antibody described herein or antigen-binding fragment thereof binds to two different glycosylated forms of an extracellular domain of human KIT. For example, two forms of human KIT with different molecular weights, indicating different glycosylation patterns, have been observed by immunoblotting. In certain embodiments, an antibody described herein may specifically bind to both of these forms of human KIT which have different glycosylation patterns, e.g., one form is more glycosylated than the other. In certain embodiments, an antibody described herein or antigen-binding fragment thereof binds to an extracellular domain of human KIT which is not glycosylated.

In a particular embodiment, an antibody described herein does not immunospecifically bind to a KIT epitope described by International Patent Application No. WO 2008/153926, for example an epitope consisting essentially of the amino acid sequence SELHLTRLKGTEGGTYT (SEQ ID NO: 38) or LTRLKGTEGG (SEQ ID NO: 39).

In certain embodiments, an anti-KIT antibody described herein is not an antibody selected from the group consisting of: SR-1 antibody (see U.S. Patent Application Publication No. US 2007/0253951 A1; International Patent Application Publication No. WO 2007/127317); anti-KIT antibody obtained from hybridoma cell lines DSM ACC 2007, DSM ACC 2008, or DSM ACC 2009, which have been deposited at the Deutsche Sammlung von Mikroorganismen und Zellkulturen GmbH, DSM, Mascheroder Weg 1 b, D-38124 Braumschweig, Germany (see U.S. Pat. No. 5,545,533; International Patent Application Publication No. WO 92/021766); antibody produced by hybridoma cell line DSM ACC 2247 (or A3C6E2; Deposit No. DSM ACC 2247, at the Deutsche Sammlung von Mikroorganismen und Zellkulturen GmbH, DSM, Mascheroder Weg 1 b, D-38124 Braumschweig, Germany) (see U.S. Pat. No. 5,808,002); and anti-KIT antibodies designated K27, K44, K45, K49, K57, K69, and K94 (see, e.g., Blechman et al., Stem Cells, 1993, 11:12-21; Blechman et al., Cell, 1995, 80:103-113; Lev et al., Mol. Cell. Biol., 1993, 13:2224-2234; and European Patent Application Publication No. EP0548867 A2). In certain embodiments, an anti-KIT antibody described herein does not comprise a CDR of an antibody selected from such group. In particular embodiments, an anti-KIT antibody described herein does not comprise one or more (e.g., two, three, four, five, or six) CDRs (e.g., 3 VL CDRs and/or 3 VH CDRs) of an antibody selected from such group. In another embodiment, an antibody described herein is not competitively blocked (e.g., competitively blocked in a dose-dependent manner) by one of those antibodies, for example, as determined by competition binding assays (e.g., ELISAs). In certain embodiments, an anti-KIT antibody described herein is not antibody Ab1 or Ab21, which is described in U.S. Provisional Application No. 61/426,387, filed Dec. 22, 2010. In certain embodiments, an anti-KIT antibody described herein is not an antibody selected from the group consisting of: Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, and Ab21, as described in U.S. Provisional Application No. 61/426,387, filed Dec. 22, 2010 and Ab24-Ab192 as described in PCT International Patent Application No. PCT/US2011/29980 filed Mar. 25, 2011. In certain embodiments, an anti-KIT antibody described herein does not comprise a CDR, or one or more CDRs (e.g., 3 VL CDRs and/or 3VH CDRs), of an antibody selected from the group consisting of: Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab20, and Ab21, as described in U.S. Provisional Application No. 61/426,387, filed Dec. 22, 2010, and Ab24-Ab192 as described in PCT International Patent Application No. PCT/US2011/29980 filed Mar. 25, 2011. In particular embodiments, an anti-KIT antibody described herein does not comprise a CDR, or one or more CDRs (e.g., 3 VL CDRs and/or 3VH CDRs), VL chain region, or VH chain region of an antibody selected from the antibodies (e.g., antibodies Ab1-Ab21 and Ab24-Ab192) described in U.S. Provisional Application No. 61/426,387 filed Dec. 22, 2010 or PCT International Patent Application No. PCT/US2011/29980 filed Mar. 25, 2011. In certain embodiments, an anti-KIT antibody described herein is not antibody Ab1 or Ab21, or an antibody comprising CDRs (e.g., one, two, three, four, five, or six CDRs) of antibody Ab1 or Ab21, as described in U.S. Provisional Application No. 61/426,387, filed Dec. 22, 2010. In a particular embodiment, an antibody described herein is not antibody 37M or 37C as described in PCT International Patent Application No. PCT/US2012/022471 filed Jan. 25, 2012. In a certain embodiment, an antibody described herein does not comprise a VL domain comprising SEQ ID NO: 32 or a VH domain comprising SEQ ID NO: 31.

In a particular embodiment, an antibody described herein or antigen-binding fragment thereof, which immunospecifically bind to a KIT polypeptide (e.g., the D4 region of KIT, for example, human KIT), does not comprise one or more (e.g., two, three, four, five, or six) CDRs (e.g., VL CDR1, VL CDR2, VL CDR3, VH CDR1, VH CDR2, and VH CDR3) of an antibody described in US Patent Application Publication NO. US 2008/0287309, for example antibody 36C1, 84H7, 63C10, or 65A12.

In a specific embodiment, an antibody described herein is not a human or humanized version of an antibody produced by the hybridoma (BA7.3C.9) having the American Type Culture Collection (ATCC) Accession number HB10716, as described for example in U.S. Pat. No. 5,919,911 or 5,489,516. In another specific embodiment, an antibody described herein does not comprise the CDRs (e.g., VL CDR1, VL CDR2, VL CDR3, VH CDR1, VH CDR2, and/or VH CDR3) of the antibody produced by the hybridoma (BA7.3C.9) having the American Type Culture Collection (ATCC) Accession number HB10716, as described for example in U.S. Pat. No. 5,919,911 or 5,489,516. In another specific embodiment, an antibody described herein does not comprise the CDRs of the SR-1 antibody described for example in U.S. Pat. No. 5,919,911 or 5,489,516 or U.S. Patent Application Publication No. US 2007/0253951 A1 (see, e.g., ¶ [0032] or ¶ [0023]). In a further embodiment, an antibody described herein is not an antibody of the antibody produced by the hybridoma (BA7.3C.9) having the American Type Culture Collection (ATCC) Accession number HB10716, as described for example in U.S. Pat. No. 5,919, 911 or 5,489,516.

In a specific embodiment, an antibody described herein is not the humanized antibodies of the SR-1 antibody as described in U.S. Patent Application Publication No. US 2007/0253951 A1. In a specific embodiment, an antibody described herein does not comprise one or more amino acid sequences selected from the group consisting of: SEQ ID NO: 2, SEQ ID NO: 4, SEQ ID NO: 6, SEQ ID NO: 8, and SEQ ID NO: 10 referenced in U.S. Patent Application Publication No. US 2007/0253951 A1. In a particular embodiment, an antibody described herein does not comprise the amino acid sequences of SEQ ID NOs: 2 and 4 or of SEQ ID NOs: 2 and 6 referenced in U.S. Patent Application Publication No. US 2007/0253951 A1. In a specific embodiment, an antibody described herein does not comprise one or more amino acid sequence that is at least 90% identical to the amino acid sequence selected from the group consisting of: SEQ ID NO: 2, SEQ ID NO: 4, SEQ ID NO: 6, SEQ ID NO: 8, and SEQ ID NO: 10 referenced in U.S. Patent Application Publication No. US 2007/0253951 A1. In a particular embodiment, an antibody described herein does not comprise one or more CDRs described in U.S. Patent Application Publication No. US 2007/0253951 A1, for example, amino acids 44 to 58 of SEQ ID NO: 8 (VL CDR1 of antibody SR-1; RASESVDIYGNSFMH), amino acids 74 to 80 of SEQ ID NO: 8 (VL CDR2 of antibody SR-1; LASNLES), amino acids 111 to 121 of SEQ ID NO: 8 (VL CDR3 of antibody SR-1; QQNNEDPYT), amino acids 50 to 54 of SEQ ID NO: 10 (VH CDR1 of antibody SR-1; SYNMH), amino acids 69 to 85 of SEQ ID NO: 10 (VH CDR2 of antibody SR-1; VIYSGNGDTSYNQKFKG), and/or amino acids 118 to 125 of SEQ ID NO: 10 (VH CDR3 of antibody SR-1; RDTRFGN), where SEQ ID NOs: 8 and 10 are those referenced in U.S. Patent Application Publication No. US 2007/0253951 A1 (see, e.g., ¶ [0032] or ¶ [0023]). In a particular embodiment, an antibody described herein does not comprise one or more CDRs described in U.S. Patent Application Publication No. US 2007/0253951 A1, for example, amino acids 43 to 58 of SEQ ID NO: 2 (VL CDR1), amino acids 74 to 80 of SEQ ID NO: 2 (VL CDR2), amino acids 113 to 121 of SEQ ID NO: 2 (VL CDR3), amino acids 50 to 54 of SEQ ID NO: 4 (VH CDR1), amino acids 69 to 85 of SEQ ID NO: 4 (VH CDR2), and/or amino acids 118 to 125 of SEQ ID NO: 4 (VH CDR3), where SEQ ID NOs: 2 and 4 are those referenced in U.S. Patent Application Publication No. US 2007/0253951 A1. In a particular embodiment, an antibody described herein is not an antibody of antibody SR-1 as described in U.S. Patent Application Publication No. US 2007/0253951 A1.

In a specific embodiment, an antibody described herein is not an antibody selected from the group consisting of: antibody Anti-S100, ACK2, and ACK4 as described in U.S. Pat. No. 6,989,248 or 7,449,309. In a particular embodiment, an antibody described herein is not a human or humanized version of an antibody selected from such group. In a specific embodiment, an antibody described herein is not an antibody comprising one or more CDRs (e.g., 3 VL CDRs and/or 3 VH CDRs) of an antibody selected from the group consisting of: antibody Anti-S100, ACK2, and ACK4 as described in U.S. Pat. No. 6,989,248 or 7,449,309.

In certain aspects, competition binding assays can be used to assist in identifying a target epitope of an antibody or to determine whether an antibody is competitively blocked, e.g., in a dose dependent manner, by another antibody for example, an antibody that binds essentially the same epitope, or overlapping epitopes, as a reference antibody, when the two antibodies recognize identical or sterically overlapping epitopes in competition binding assays such as competition ELISA assays, which can be configured in all number of different formats, using either labeled antigen or labeled antibody. Numerous types of competitive binding assays are known, for example: solid phase direct or indirect radioimmunoassay (MA), solid phase direct or indirect enzyme immunoassay (EIA), sandwich competition assay (see Stahli et al., (1983) Methods in Enzymology 9:242); solid phase direct biotin-avidin EIA (see Kirkland et al., (1986) J. Immunol. 137:3614); solid phase direct labeled assay, solid phase direct labeled sandwich assay (see Harlow and Lane, (1988) Antibodies: A Laboratory Manual, Cold Spring Harbor Press); solid phase direct label RIA using 1-125 label (see Morel et al., (1988) Mol. Immunol. 25(1): 7); solid phase direct biotin-avidin EIA (Cheung et al., (1990) Virology 176:546); and direct labeled MA. (Moldenhauer et al., (1990) Scand J. Immunol. 32:77). Typically, such an assay involves the use of purified antigen (e.g., KIT, such as extracellular domain of KIT or a D4 region of KIT) bound to a solid surface or cells bearing either of these, an unlabeled test immunoglobulin and a labeled reference immunoglobulin. Competitive inhibition can be measured by determining the amount of label bound to the solid surface or cells in the presence of the test immunoglobulin. Usually the test immunoglobulin is present in excess. In certain aspects, when a competing antibody is present in excess, it will inhibit specific binding of a reference antibody to a common antigen by at least 50-55%, 55-60%, 60-65%, 65-70% 70-75% or more. In a common version of this assay, the antigen is immobilized on a 96-well plate. The ability of unlabeled antibodies to block the binding of labeled antibodies to the antigen is then measured using radioactive or enzyme labels. For further details see, for example, Wagener et al., J. Immunol., 1983, 130:2308-2315; Wagener et al., J. Immunol. Methods, 1984, 68:269-274; Kuroki et al., Cancer Res., 1990, 50:4872-4879; Kuroki et al., Immunol. Invest., 1992, 21:523-538; Kuroki et al., Hybridoma, 1992, 11:391-407, and Using Antibodies: A Laboratory Manual, Ed Harlow and David Lane editors (Cold Springs Harbor Laboratory Press, Cold Springs Harbor, N.Y., 1999), pp. 386-389.

In certain aspects, an antibody described herein which immunospecifically binds to a D4 region of a KIT polypeptide (e.g., human KIT polypeptide) may be described by its VL chain region (e.g., any one of SEQ ID NOs: 7-10) or VH chain region (e.g., any one of SEQ ID NOs: 2-6), or by its 3 VL CDRs or its 3 VH CDRs. See, for example, Rader et al., 1998, Proc. Natl. Acad. Sci. USA, 95: 8910-8915, which is incorporated herein by reference in its entirety, which describes the humanization of the mouse anti-$\alpha v \beta 3$ antibody by identifying a complementing light chain or heavy chain from a human light chain or heavy chain library, respectively, resulting in humanized antibody variants having affinities as high or higher than the affinity of the original antibody. See also, Clackson et al., 1991, Nature, 352:624-628, which is incorporated herein by reference in its entirety, describing methods of producing antibodies that bind a specific antigen by using a specific VL (or VH) domain and screening a library for the complimentary variable domains. The screen produced 14 new partners for a specific VH domains and 13 new partners for a specific VL domain, which were strong binders as determined by ELISA.

Thus, in certain aspects, provided herein is an antibody, which immunospecifically binds to a D4 region of a KIT polypeptide (e.g., human KIT polypeptide), comprising a VL domain comprising the amino acid sequence of SEQ ID NO: 7 or 8. In some embodiments, provided herein is an antibody, which immunospecifically binds to a D4 region of a KIT polypeptide (e.g., human KIT polypeptide), comprising a VH domain comprising the amino acid sequence of SEQ ID NO: 4 or 5.

In certain aspects, the CDRs of an antibody described herein is determined according to the method of Chothia and Lesk, 1987, J. Mol. Biol., 196:901-917, which will be referred to herein as the "Chothia CDRs" (see also, e.g., U.S. Pat. No. 7,709,226). Using the Kabat numbering system of numbering amino acid residues in the VH chain region and VL chain region, Chothia CDRs within an antibody heavy chain molecule are typically present at amino acid positions 26 to 32 ("CDR1"), amino acid positions 53 to 55 ("CDR2"), and amino acid positions 96 to 101 ("CDR3"). Using the Kabat numbering system of numbering amino acid residues in the VH chain region and VL chain region, Chothia CDRs within an antibody light chain molecule are typically present at amino acid positions 26 to 33 (CDR1), amino acid positions 50 to 52 (CDR2), and amino acid positions 91 to 96 (CDR3).

In a specific embodiment, the position of a CDR along the VH and/or VL region of an antibody described herein may vary by one, two, three or four amino acid positions so long as immunospecific binding to KIT (e.g., the D4 region of human KIT) is maintained (e.g., substantially maintained, for example, at least 50%, at least 60%, at least 70%, at least 80%, at least 90%, at least 95%). For example, in one embodiment, the position defining a CDR of an antibody described herein may vary by shifting the N-terminal and/or C-terminal boundary of the CDR by one, two, three, or four, amino acids, relative to the CDR position depicted in FIGS. 3A-3I, so long as immunospecific binding to KIT (e.g., the D4 region) is maintained (e.g., substantially maintained, for example, at least 50%, at least 60%, at least 70%, at least 80%, at least 90%, at least 95%).

In specific aspects, provided herein is an antibody comprising an antibody light chain and heavy chain, e.g., a separate light chain and heavy chain. With respect to the light chain, in a specific embodiment, the light chain of an antibody described herein is a kappa light chain. In another specific embodiment, the light chain of an antibody described herein is a lambda light chain. In yet another specific embodiment, the light chain of an antibody described herein is a human kappa light chain or a human lambda light chain. In a particular embodiment, an antibody described herein, which immunospecifically binds to a KIT polypeptide (e.g., a KIT polypeptide comprising a D4 region of KIT, for example human KIT (e.g., SEQ ID NO: 15)) comprises a light chain wherein the amino acid sequence of the VL chain region comprises any amino acid sequence described herein (e.g., SEQ ID NO: 7, 8, 9, or 10), and wherein the constant region of the light chain comprises the amino acid sequence of a human kappa light chain constant region. Non-limiting examples of human light chain constant region sequences have been described in the art, e.g., see U.S. Pat. No. 5,693,780 and Kabat et al. (1991) *Sequences of Proteins of Immunological Interest*, Fifth Edition, U.S. Department of Health and Human Services, NIH Publication No. 91-3242.

With respect to the heavy chain, in a specific embodiment, the heavy chain of an antibody described herein can be an alpha ($\alpha$), delta ($\delta$), epsilon ($\varepsilon$), gamma ($\gamma$) or mu ($\mu$) heavy chain. In another specific embodiment, the heavy chain of an antibody described can comprise a human alpha ($\alpha$), delta ($\delta$), epsilon ($\varepsilon$), gamma ($\gamma$) or mu ($\mu$) heavy chain. In a particular embodiment, an antibody described herein, which immunospecifically binds to a KIT polypeptide (e.g., a KIT polypeptide comprising a KIT polypeptide comprising a D4 region of KIT, for example human KIT (e.g., SEQ ID NO: 15)), comprises a heavy chain wherein the amino acid sequence of the VH chain region can comprise any amino acid sequence described herein (e.g., any of SEQ ID NOs: 2-6), and wherein the constant region of the heavy chain comprises the amino acid sequence of a human gamma ($\gamma$) heavy chain constant region. Non-limiting examples of human heavy chain constant region sequences have been described in the art, e.g., see U.S. Pat. No. 5,693,780 and Kabat et al. (1991) *Sequences of Proteins of Immunological Interest*, Fifth Edition, U.S. Department of Health and Human Services, NIH Publication No. 91-3242.

In a specific embodiment, an antibody described herein, which immunospecifically binds to a KIT polypeptide (e.g., a D4 region of KIT, for example human KIT) comprises a VL chain region and a VH chain region comprising any amino acid sequences described herein, and wherein the constant regions comprise the amino acid sequences of the constant regions of an IgG, IgE, IgM, IgD, IgA or IgY immunoglobulin molecule, or a human IgG, IgE, IgM, IgD, IgA or IgY immunoglobulin molecule. In another specific embodiment, an antibody described herein, which immunospecifically binds to a KIT polypeptide (e.g., a D4 region of KIT, for example human KIT) comprises a VL chain region and a VH chain region comprising any amino acid sequences described herein, and wherein the constant regions comprise the amino acid sequences of the constant regions of an IgG, IgE, IgM, IgD, IgA or IgY immunoglobulin molecule, any class (e.g., IgG1, IgG2, IgG3, IgG4, IgA1 and IgA2), or any subclass (e.g., IgG2a and IgG2b) of immunoglobulin molecule. In a particular embodiment, the constant regions comprise the amino acid sequences of the constant regions of a human IgG, IgE, IgM, IgD, IgA or IgY immunoglobulin molecule, any class (e.g., IgG1, IgG2, IgG3, IgG4, IgA1 and IgA2), or any subclass (e.g., IgG2a and IgG2b) of immunoglobulin molecule.

In yet another specific embodiment, an antibody described herein, which immunospecifically binds to a KIT polypeptide (e.g., a D4 region of KIT, for example human KIT), comprises a VL chain region and a VH chain region comprising any amino acid sequences described herein (e.g., any one of SEQ ID NOs: 2-6 and/or any one of SEQ ID NOs: 7-10), and wherein the constant regions comprise the amino acid sequences of the constant regions of a human IgG1 or human IgG4. In a particular embodiment, an antibody described herein, which immunospecifically binds to a KIT polypeptide (e.g., a D4 region of KIT, for example human KIT) comprises a VL chain region and a VH chain region comprising any amino acid sequences described herein, and wherein the constant regions comprise the amino acid sequences of the constant region of a human IgG1.

In specific embodiments, an antibody described herein, which immunospecifically bind to a KIT polypeptide, e.g., a human KIT polypeptide, for example, a D4 region of KIT (e.g., human KIT, for example SEQ ID NO: 15), comprises framework regions (e.g., framework regions of the VL domain and/or VH domain) that are human framework regions or derived from human framework regions. Non-limiting examples of human framework regions are described in the art, e.g., see Kabat et al. (1991) *Sequences of Proteins of Immunological Interest*, Fifth Edition, U.S. Department of Health and Human Services, NIH Publication No. 91-3242). In a certain embodiment, an antibody described herein comprises framework regions (e.g., framework regions of the VL domain and/or VH domain) that are primate (e.g., non-human primate) framework regions or derived from primate (e.g., non-human primate) framework regions.

In certain examples, an antibody described herein comprises framework regions (e.g., framework regions of the VL domain and/or VH domain) that are not primate (e.g., non-human primate, for example, ape such as Old World ape) framework regions or derived from primate (e.g., non-human primate) framework regions.

In certain examples, with respect to any of these antibodies described herein, the VL chain region does not comprise non-human primate (e.g., ape such as Old World ape) framework regions or is derived from non-human primate (e.g., ape such as Old World ape) framework regions. In certain other embodiments, the VH chain region does not comprise non-human primate (e.g., ape such as Old World ape) framework regions or is derived from non-human primate (e.g., ape such as Old World ape) framework regions.

Non-limiting examples of non-human primate framework regions include those from Old World apes, e.g., *Pan troglodytes, Pan paniscus* or *Gorilla gorilla*; chimpanzee *Pan troglodytes*; Old World monkey such as Old World monkey from the genus *Macaca*; and cynomolgus monkey *Macaca cynomolgus*. Non-limiting examples of non-human primate framework sequences are described in U.S. Patent Application Publication No. US 2005/0208625.

In certain aspects, also provided herein are antibodies, which immunospecifically binds to a KIT polypeptide (e.g., a D4 region of KIT, for example human KIT), comprising one or more amino acid residue substitutions, e.g., in the VL chain region or VH chain region, for example, the CDRs or FRs. In specific embodiments, none of the amino acid residue substitutions are located within the CDRs. In specific embodiments, all of the amino acid substitutions are in the FRs (see, e.g., Tables 5A-6B). In a certain embodiment, an amino acid substitution is a conservative amino acid substitution.

As used herein, a "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

In particular embodiments, the glycosylation of antibodies described herein is modified. For example, an aglycosylated antibody can be made (i.e., the antibody lacks glycosylation) or an antibody comprising a mutation or substitution at one or more glycosylation sites to eliminate glycosylation at the one or more glycosylation sites can be made. Glycosylation can be altered to, for example, increase the affinity of the antibody for a target antigen (e.g., human KIT, for example, a D4 region of human KIT). Such carbohydrate modifications can be accomplished by, for example, altering one or more sites of glycosylation within the antibody sequence. For example, one or more amino acid substitutions can be made that result in elimination of one or more variable region (e.g., VL and/or VH CDRs or VL and/or VH FRs) glycosylation sites to thereby eliminate glycosylation at that site. Such aglycosylation can increase the affinity of the antibody for antigen (e.g., human KIT, for example, a D4 region of human KIT). Such an approach is described in further detail in U.S. Pat. Nos. 5,714,350 and 6,350,861.

Glycosylation can occur via N-linked (or asparagine-linked) glycosylation or O-linked glycosylation. N-linked glycosylation involves carbohydrate modification at the side-chain $NH_2$ group of an asparagine amino acid in a polypeptide. O-linked glycosylation involves carbohydrate modification at the hydroxyl group on the side chain of a serine, threonine, or hydroxylysine amino acid.

In specific embodiments, an asparagine (N) residue within a VH (e.g., SEQ ID NO: 2, 3, 4, 5, or 6) or VL region (e.g., SEQ ID NO: 7, 8, 9, or 10) of an antibody described herein is substituted with a serine (S) or another amino acid (e.g., alanine, glycine, glutamine, threonine, tyrosine, cysteine). In other specific embodiments, an asparagine (N) residue within a VH CDR (e.g., VH CDR1, VH CDR2, and/or VH CDR3 comprising the sequences of SEQ ID NOs: 16-18, respectively) and/or a VL CDR (e.g., VL CDR1, VL CDR2, and/or VL CDR3 comprising the sequences of SEQ ID NOs: 19-21, respectively) of an antibody described herein is substituted with a serine (S) or another amino acid (e.g., alanine, glycine, glutamine, threonine, tyrosine, cysteine). In other specific embodiments, an asparagine (N) residue within a VH FR (e.g., VH FR1, VH FR2, VH FR3 and/or VH FR4 as set forth in Tables 5A, 5C, and 6B) and/or a VL FR (e.g., VL FR1, VL FR2, VL FR3, and/or VL FR4 as set forth in Table 5B, 5D, and 6A) of an antibody described herein is substituted with a serine (S) or another amino acid (e.g., alanine, glycine, glutamine, threonine, tyrosine, cysteine).

In certain embodiments, aglycosylated antibodies can be produced in bacterial cells which lack the necessary glycosylation machinery. Cells with altered glycosylation machinery have been described in the art and can be used as host cells in which to express recombinant antibodies described herein to thereby produce an antibody with altered glycosylation. See, for example, Shields, R. L. et al. (2002) J. Biol. Chem. 277:26733-26740; Umana et al. (1999) Nat. Biotech. 17:176-1, as well as, European Patent No: EP 1,176,195; PCT Publications WO 03/035835; WO 99/54342.

In certain embodiments, one or more modifications can be made to the Fc region of an antibody described here, generally, to alter one or more functional properties of the antibody, such as serum half-life, complement fixation, Fc receptor binding, and/or antibody-dependent cellular cytotoxicity. These modifications are described, for example, in International Patent Application Publication No. WO 2008/153926 A2.

In specific embodiments, an asparagine (N) residue within the constant region of a heavy chain and/or the constant region of a light region of an antibody described herein is substituted with a serine (S) or another amino acid (e.g., alanine, glycine, glutamine, threonine, tyrosine, cysteine).

In specific embodiments, an asparagine (N) residue within a heavy chain and/or a light region of an antibody described herein is substituted with a serine (S) or another amino acid (e.g., alanine, glycine, glutamine, threonine, tyrosine, cysteine).

Provided herein are antibodies that immunospecifically bind to KIT antigen and that can modulate KIT activity. In certain embodiments, an antibody provided herein immunospecifically binds to a KIT polypeptide, e.g., a human KIT polypeptide, and inhibits a KIT activity. KIT activity can relate to any activity of KIT known or described in the art, e.g., KIT receptor dimerization, KIT receptor phosphorylation (tyrosine phosphorylation), signaling downstream of the KIT receptor (e.g., AKT, MAPK/ERK, Ras, Stat1, Stat3, or Stat5 signaling), KIT ligand (e.g., SCF) induced transcriptional regulation (e.g., SCF-induced transcriptional activation of c-Myc), induction or enhancement of cell proliferation, or cell survival. KIT activity or KIT function are used interchangeably herein. In certain aspects, KIT activity is induced by KIT ligand (e.g., SCF) binding to KIT receptor. In particular aspects, KIT activity can be induced or enhanced by gain-of-function mutations which can result, for example, in dimerization and constitutively active KIT signaling (see, e.g., Mol et al., J. Biol. Chem., 2003, 278: 31461-31464; Hirota et al., J. Pathology, 2001, 193:505-510). Such gain-of-function can allow for KIT receptor dimerization and KIT signaling to occur in the absence of KIT ligand (e.g., SCF) binding to KIT receptor. In certain embodiments, an increase in KIT activity or signaling can occur, in the absence of KIT ligand (e.g., SCF) binding KIT receptor, due to high (or overexpression) expression of KIT receptors. High or overexpression of KIT in a cell refers to an expression level which is at least about 10%, 20%, 30%, 40%, 50%, 60%, 70%, 80%, 90%, or 100% more than the expression level of a reference cell known to have normal KIT expression or KIT activity or more than the average expression level of KIT in a population of cells or samples known to have normal KIT expression or KIT activity. Expression levels of KIT can be assessed by methods described herein or known to one of skill in the art (e.g., Western blotting or immunohistochemistry). In particular embodiments, KIT activity that is higher than normal KIT activity can lead to cellular transformation, neoplasia, and tumorogenesis. In particular embodiments, KIT activity that is higher than normal KIT activity can lead to other KIT-associated disorders or diseases.

In certain embodiments, an anti-KIT antibody described herein does not block or inhibit binding of KIT ligand (e.g., SCF) to KIT receptor. In certain embodiments, an anti-KIT antibody described herein only negligibly (e.g., less than about 2% or 3%) inhibits or reduces binding of KIT ligand (e.g., SCF) to KIT receptor. In certain embodiments, an anti-KIT antibody described herein does not induce or enhance dissociation of KIT ligand (e.g., SCF) from the KIT receptor. In certain embodiments, an anti-KIT antibody described herein only negligibly (e.g., less than about 2% or 3%) induces or enhances dissociation of KIT ligand (e.g., SCF) from the KIT receptor.

In certain embodiments, an anti-KIT antibody described herein does not block or inhibit KIT receptor dimerization. In certain embodiments, an anti-KIT antibody described herein only negligibly (e.g., less than about 2% or 3% or within a standard of error or deviation) inhibits or reduces KIT receptor dimerization. In certain embodiments, an anti-KIT antibody described herein does not induce or enhance KIT receptor dimer dissociation. In certain embodiments, an anti-KIT antibody described herein only negligibly (e.g., less than about 2% or 3% or within a standard of error or deviation) induces or enhances KIT receptor dimer dissociation. In a particular embodiment, an anti-KIT antibody described herein can specifically bind to a KIT receptor dimer and do not block or inhibit KIT receptor dimerization. In a particular embodiment, an anti-KIT antibody described herein can specifically bind to a KIT receptor monomer and do not block or inhibit KIT receptor dimerization.

In certain aspects, as an inhibitor of KIT activity, an antibody described herein can block or inhibit (e.g., partially inhibit) dimerization of KIT. Generally, KIT receptor dimerization is induced when KIT ligand binds to KIT. Thus, in specific embodiments, antibodies described herein specifically bind to KIT and block or inhibit (e.g., partially inhibit) dimerization of KIT receptors by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art, e.g., immunoprecipitation assay, relative to dimerization of KIT receptors in the presence of KIT ligand stimulation without any antibody or with an unrelated antibody (e.g., an antibody that does not immunospecifically bind to KIT). In a specific embodiment, antibodies described herein specifically bind to KIT and partially inhibit dimerization of KIT receptors by about 25% to 75%. Blocking or inhibition (e.g., partial inhibition) of dimerization of KIT receptors by antibodies described herein can be assessed in the presences of KIT ligand stimulation. For example, cells expressing KIT are contacted with KIT ligand in the presence or absence of anti-KIT antibodies described herein, and the level of KIT receptor dimerization is determined. In certain embodiments, KIT ligand induced KIT receptor dimerization in the absence of anti-KIT antibody is at least about 1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold higher than KIT receptor dimerization in the presence of anti-KIT antibody as assessed by methods described herein or known to one of skill in the art (e.g., immunoprecipitation assays). Tyrosine phosphorylation of one or more residues in the cytoplasmic domain of KIT can be an indicator of KIT receptor dimerization.

In certain embodiments, an antibody described herein can inhibit (e.g., partially inhibit) KIT activity by at least about 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein and/or known to one of skill in the art, relative to KIT activity in the presence of KIT ligand stimulation without any antibody or with an unrelated antibody (e.g., an antibody that does not immunospecifically bind to KIT). In certain embodiments, an antibody described herein can inhibit (e.g., partially inhibit) KIT activity by at least about 25% to about 65% as assessed by methods described herein and/or known to one of skill in the art, relative to KIT activity in the presence of KIT ligand stimulation without any antibody or with an unrelated antibody (e.g., an antibody that does not immunospecifically bind to KIT). Non-limiting examples of KIT activity can include KIT receptor phosphorylation, KIT receptor signaling, KIT ligand (e.g., SCF) mediated cell proliferation, KIT ligand (e.g., SCF) mediated cell survival, and transcriptional activation of a KIT target gene (e.g., c-Myc).

As an inhibitor of KIT activity, an antibody described herein (or an antigen-binding fragment thereof, or a conjugate thereof) can block (e.g., partially block) or inhibit (e.g., partially inhibit) phosphorylation of KIT, specifically tyrosine phosphorylation of one or more residues in the cytoplasmic domain of KIT. Generally, KIT receptor dimerization and phosphorylation is induced when KIT ligand binds to KIT. However, in certain aspects, KIT receptor dimerization and/or phosphorylation can occur independently of KIT ligand binding to KIT receptor. For example KIT receptor dimerization and/or phosphorylation can occur due to gain-of-function mutations or overexpression of KIT.

Non-limiting examples of tyrosine residues in the cytoplasmic domain of murine KIT that can be phosphorylated, e.g., upon ligand stimulation, include 544, 546, 552, 567, 569, 577, 608, 645, 671, 674, 702, 719, 728, 745, 772, 821, 844, 853, 868, 878, 898, and 934 (see Ueda et al., Blood, 2002, 99:3342-3349). The corresponding tyrosine residues in the cytoplasmic domain of human KIT can be readily determined. Non-limiting examples of tyrosine residues in the cytoplasmic domain of human KIT (e.g., GenBank Accession No. P10721) that can be phosphorylated, e.g., upon ligand stimulation, include residues 568, 570, 703, 721, 730, 747, 823, 900, and 936. In a specific embodiment, an anti-KIT antibody described herein can inhibit receptor phosphorylation at tyrosine residue 719 of murine KIT. In another specific embodiment, an anti-KIT antibody described herein can inhibit receptor phosphorylation at tyrosine residue 703 or 721 of human KIT.

Thus, in specific embodiments, antibodies described herein (or an antigen-binding fragment thereof, or a conjugate thereof) specifically bind to KIT and block or inhibit tyrosine phosphorylation in the cytoplasmic domain of KIT by at least about 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art, e.g., ELISA assay as described in section 6 or immunoblotting assay, relative to phosphorylation in the presence of KIT ligand stimulation without any antibody or with an unrelated antibody (e.g., an antibody that does not immunospecifically bind to KIT). In particular embodiments, antibodies described herein specifically bind to KIT and block or inhibit tyrosine phosphorylation in the cytoplasmic domain of KIT by at least about 25%, optionally to about 65% or 75%, as assessed by methods described herein or known to one of skill in the art, e.g., ELISA assay as described in section 6 or immunoblotting assay. In certain embodiments, antibodies described herein specifically bind to KIT and block or inhibit tyrosine phosphorylation of the cytoplasmic domain of KIT by at least about 25% to about 80% as assessed by methods described herein or known to one of skill in the art, e.g., ELISA assay as described in section 6 or immunoblotting assay. In specific embodiments, antibodies described herein specifically bind to KIT and block or inhibit tyrosine phosphorylation of the cytoplasmic domain of KIT with an $IC_{50}$ of less than about 600 pM, or less than about 550 pM, or less than about 500 pM, or less than about 400 pM or less than about 300 pM as assessed by methods described herein (e.g., phosphorylation inhibition assay with CHO cells expressing wild-type KIT as described in Section 6 below) or known to one of skill in the art. In specific embodiments, antibodies described herein specifically bind to KIT and block or inhibit tyrosine phosphorylation of the cytoplasmic domain of KIT with an $IC_{50}$ of less than about 600 pM. In specific embodiments, antibodies described herein specifically bind to KIT and block or inhibit tyrosine phosphorylation of the cytoplasmic domain of KIT with an $IC_{50}$ of less than about 550 pM. In specific embodiments, antibodies described herein specifically bind to KIT and block or inhibit tyrosine phosphorylation of the cytoplasmic domain of KIT with an $IC_{50}$ in the range of about 100 pM to about 500 pM, about 25 pM to about 550 pM, or about 40 pM to about 600 pM, or about 50 pM to about 350 pM. For example, an $IC_{50}$ for inhibition of tyrosine phosphorylation can be determined by assaying lysates from cells, e.g., CHO cells, recombinantly expressing KIT, in ELISA which detects tyrosine phosphorylation, for example, as described in Section 6 below. In certain embodiments, cells, e.g., CHO cells, recombinantly expressing KIT, are sorted, e.g., sorted to select for cells highly expressing KIT, prior to use in the phosphorylation inhibition assays. In some embodiments, the cells are not sorted prior to use in the phosphorylation inhibition assays.

In specific embodiments, antibodies described herein (or an antigen-binding fragment thereof, or a conjugate thereof) specifically bind to KIT and reduce tyrosine phosphorylation of the cytoplasmic domain of KIT by at least about 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art, e.g., ELISA assay as described in section 6 or immunoblotting assay, relative to phosphorylation in the presence of KIT ligand stimulation without any antibody or with an unrelated antibody (e.g., an antibody that does not immunospecifically bind to KIT). In specific embodiments, antibodies described herein (or an antigen-binding fragment thereof, or a conjugate thereof) specifically bind to KIT and reduce tyrosine phosphorylation of the cytoplasmic domain of KIT by at least about 25% or 35%, optionally to about 75% as assessed by methods described herein or known to one of skill in the art, e.g., ELISA assay as described in section 6 or immunoblotting assay, relative to phosphorylation in the presence of KIT ligand stimulation without any antibody or with an unrelated antibody (e.g., an antibody that does not immunospecifically bind to KIT).

In specific embodiments, antibodies described herein specifically bind to KIT and block or inhibit phosphorylation of one or more tyrosine residues in the cytoplasmic domain of KIT by at least about 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art, e.g., immunoblotting assay, relative to phosphorylation in the presence of KIT ligand stimulation without any antibody or with an unrelated antibody (e.g., an antibody that does not immunospecifically bind to KIT). In specific embodiments, blocking or inhibition (e.g., partial inhibition) of phosphorylation of one or more tyrosine residues of the cytoplasmic domain of KIT by antibodies described herein can be assessed upon KIT ligand stimulation. For example, cells expressing KIT are contacted with KIT ligand in the presence or absence of anti-KIT antibodies described herein, and the level of phosphorylation of one or more tyrosine residues in the cytoplasmic domain of KIT can be determined. In certain embodiments, KIT ligand induced phosphorylation of one or more tyrosine residues of the cytoplasmic domain of KIT the absence of anti-KIT antibody is at least about 1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold higher than KIT ligand induced phosphorylation of one or more tyrosine residues of the cytoplasmic domain of KIT in the presence of anti-KIT antibody, as assessed by methods described herein or known to one of skill in the art (e.g., immunoblotting assays), relative to phosphorylation in the presence of KIT ligand stimulation without any antibody or with an unrelated antibody (e.g., an antibody that does not immunospecifically bind to KIT).

In specific embodiments, antibodies described herein (or an antigen-binding fragment thereof, or a conjugate thereof) specifically bind to KIT and induce or enhance KIT receptor internalization by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art, relative to internalization in the presence of an unrelated antibody (e.g., an antibody that does not immunospecifically bind to KIT). In specific embodiments, antibodies described herein (or an antigen-binding fragment thereof, or a conjugate thereof) specifically bind to KIT and induce or enhance KIT receptor internalization by at least about 25% or 35%, optionally to about 75%, as assessed by methods described herein or known to one of skill in the art, relative to internalization in the presence of an unrelated antibody (e.g., an antibody that does not immunospecifically bind to KIT). In specific embodiments, antibodies described herein specifically bind to KIT and induce or enhance KIT receptor internalization by at least about 1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold as assessed by methods described herein or known to one of skill in the art, relative to internalization in the presence of an unrelated antibody (e.g., an antibody that does not immunospecifically bind to KIT). Techniques for the quantitation or visualization of cell surface receptors are well known in the art and include a variety of fluorescent and radioactive techniques. For example, one method involves incubating the cells with a radiolabeled anti-receptor antibody. Alternatively, the natural ligand of the receptor can be conjugated to a fluorescent molecule or radioactive-label and incubated with the cells. Additional receptor internalization assays are well known in the art and are described in, for example, Jimenez et al., Biochemical Pharmacology, 1999, 57:1125-1131; Bernhagen et al., Nature Medicine, 2007, 13:587-596; and Conway et al., J. Cell Physiol., 2001, 189:341-55.

In specific embodiments, antibodies described herein specifically bind to KIT and induce or enhance KIT receptor turnover by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art (e.g., pulse-chase assay), relative to turnover in the presence of an unrelated antibody (e.g., an antibody that does not immunospecifically bind to KIT). In specific embodiments, antibodies described herein (or an antigen-binding fragment thereof, or a conjugate thereof) specifically bind to KIT and induce or enhance KIT receptor turnover by at least about 25% or 35%, optionally to about 75%, as assessed by methods described herein or known to one of skill in the art (e.g., pulse-chase assay), relative to turnover in the presence of an unrelated antibody (e.g., an antibody that does not immunospecifically bind to KIT). In specific embodiments, antibodies described herein specifically bind to KIT and induce or enhance KIT receptor turnover by at least about 1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold as assessed by methods described herein or known to one of skill in the art (e.g., pulse-chase assay), relative to turnover in the presence of an unrelated antibody (e.g., an antibody that does not immunospecifically bind to KIT). Methods for the determining receptor turnover are well known in the art. For example, cells expressing KIT can be pulse-labeled using $^{35}$S-EXPRESS Protein Labeling mix (NEG772, NEN Life Science Products), washed and chased with unlabeled medium for a period of time before protein lysates from the labeled cells are immunoprecipitated using an anti-KIT antibody and resolved by SDS-PAGE and visualized (e.g., exposed to a PhosphoImager screen (Molecular Dynamics), scanned using the Typhoon8600 scanner (Amersham), and analyzed using ImageQuant software (Molecular Dynamics)) (see, e.g., Chan et al., Development, 2004, 131:5551-5560).

In specific embodiments, antibodies described herein specifically bind to KIT and induce or enhance KIT receptor degradation by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art (e.g., pulse-chase assays), relative to degradation in the presence of an unrelated antibody (e.g., an antibody that does not immunospecifically bind to KIT). In specific embodiments, antibodies described herein specifically bind to KIT and induce or enhance KIT receptor degradation by at least about 25% or 35%, optionally to about 75%, as assessed by methods described herein or known to one of skill in the art (e.g., pulse-chase assays), relative to degradation in the presence of an unrelated antibody (e.g., an antibody that does not immunospecifically bind to KIT). In specific embodiments, antibodies described herein specifically bind to KIT and induce or enhance KIT receptor degradation by at least about 1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold as assessed by methods described herein or known to one of skill in the art (e.g., pulse-chase assays), relative to degradation in the presence of an unrelated antibody (e.g., an antibody that does not immunospecifically bind to KIT).

Techniques for quantitating or monitoring ubiquitination and/or degradation (e.g., kinetics or rate of degradation) of cell surface receptors are well known in the art and involve a variety of fluorescent and radioactive techniques (see, e.g., International Patent Application Publication No. WO 2008/153926 A2). For example, pulse chase experiments or experiments using radiolabeled ligands such as $^{125}$I-SCF can be carried out to quantitatively measure degradation of KIT.

Moreover, signaling events downstream of KIT receptor phosphorylation can serve as indicators of KIT activity. For example, KIT ligand (e.g., SCF) binding to its receptor KIT stimulates several distinct signaling pathways, including for example members of Src family kinases, phosphatidylinositol (PI) 3-kinases, and Ras mitogen-activated protein kinase (MAPK) (see Munugalavadla et al., Mol. Cell. Biol., 2005, 25:6747-6759). Phosphorylated tyrosines in the cytoplasmic domain of KIT can provide for binding sites for SH2 domain-containing proteins, which include, but are not limited to, proteins of the p21Ras-mitogen activated protein kinase (MAPK) pathway, the p85 subunit of PI 3-kinase, phospholipase C-gamma$_1$, the Grb2 adaptor protein, the Src family kinases (SFKs), Cbl, CRKL, p62Dok-1, SHP1, and SHP2 (see Ueda et al., Blood, 2002, 99:3342-3349).

Thus, in certain aspects, anti-KIT antibodies described herein which act as inhibitors of KIT activity can inhibit signaling of a member of the Src family kinases, PI 3-kinases, or Ras-MAPK. In particular embodiments, anti-KIT antibodies described herein which act as inhibitors of KIT activity can inhibit binding (or inhibit interaction), to the cytoplasmic domain of KIT, of one or more SH2 domain-containing proteins, such as proteins of the p21Ras-MAPK pathway, the p85 subunit of PI 3-kinase, phospholipase C-gamma1, the Grb2 adaptor protein, a member of the SFK, Cbl, CRKL, p62Dok-1, SHP1, and SHP2. In certain embodiments, anti-KIT antibodies described herein which act as inhibitors of KIT activity can inhibit activation by KIT of one or more SH2 domain-containing proteins, such as proteins of the p21Ras-MAPK pathway, the p85 subunit of PI 3-kinase, phospholipase C-gamma1, the Grb2 adaptor protein, a member of the SFK, Cbl, CRKL, p62Dok-1, SHP1, and SHP2.

In particular embodiments, anti-KIT antibodies described herein which act as inhibitors of KIT activity can inhibit downstream signaling such as phosphorylation of MAPK, phosphorylation of AKT, or phosphorylation of Stat1, Stat3, or Stat5. Thus, in certain embodiments, an anti-KIT antibody described herein can inhibit or reduce phosphorylation of MAPK (e.g., KIT ligand (e.g., SCF) induced phosphorylation of MAPK) by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art, e.g., Western blot or ELISA assay as described in section 6 or immunoblotting assay, relative to phosphorylation in the presence of KIT ligand stimulation without any antibody or with an unrelated antibody (e.g., an antibody that does not immunospecifically bind to KIT). In certain embodiments, an anti-KIT antibody described herein can inhibit or reduce phosphorylation of AKT (e.g., KIT ligand (e.g., SCF) induced phosphorylation of AKT) by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art, e.g., Western blot or ELISA assay as described in section 6 or immunoblotting assay, relative to phosphorylation in the presence of KIT ligand stimulation without any antibody or with an unrelated antibody (e.g., an antibody that does not immunospecifically bind to KIT). In particular embodiments, an anti-KIT antibody described herein can inhibit or reduce phosphorylation of Stat3 (e.g., KIT ligand (e.g., SCF) induced phosphorylation of Stat3) by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art, e.g., Western blot or ELISA assay as described in section 6 or immunoblotting assay, relative to phosphorylation in the presence of KIT ligand stimulation without any antibody or with an unrelated antibody (e.g., an antibody that does not immunospecifically bind to KIT). In particular embodiments, an anti-KIT antibody described herein can inhibit or reduce phosphorylation of Stat1 or Stat5 (e.g., KIT ligand (e.g., SCF) induced phosphorylation) by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art, e.g., Western blot or ELISA assay as described in section 6 or immunoblotting assay, relative to phosphorylation in the presence of KIT ligand stimulation without any antibody or with an unrelated antibody (e.g., an antibody that does not immunospecifically bind to KIT).

In certain aspects, an anti-KIT antibody described herein which can act as an inhibitor of KIT activity or activity can inhibit cellular proliferation of cells (e.g., cancer cells such as TF-1 cells) that express KIT and that respond to KIT signaling (e.g., cells that proliferate in response to KIT ligand stimulation and KIT signaling). Cell proliferation assays are described in the art and can be readily carried out by one of skill in the art. For example, cell proliferation can be assayed by measuring Bromodeoxyuridine (BrdU) incorporation (see, e.g., Hoshino et al., 1986, Int. J. Cancer 38, 369; Campana et al., 1988, J. Immunol. Meth. 107:79) or (3H) thymidine incorporation (see, e.g., Blechman et al., Cell, 1995, 80:103-113; Chen, J., 1996, Oncogene 13:1395-403; Jeoung, J., 1995, J. Biol. Chem. 270:18367 73), by direct cell count at various time intervals (e.g., 12-hour or 24-hour intervals), or by detecting changes in transcription, translation or activity of known genes such as proto-oncogenes (e.g., fos, myc) or cell cycle markers (Rb, cdc2, cyclin A, D1, D2, D3, E, etc). The levels of such protein and mRNA and activity can be determined by any method well known in the art. For example, protein can be quantitated by known immunodiagnostic methods such as ELISA, Western blotting or immunoprecipitation using antibodies, including commercially available antibodies. mRNA can be quantitated using methods that are well known and routine in the art, for example, using northern analysis, RNase protection, or polymerase chain reaction in connection with reverse transcription.

In specific embodiments, antibodies described herein specifically bind to KIT and inhibit cell proliferation by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art (e.g., BrdU incorporation assay). In specific embodiments, antibodies described herein specifically bind to KIT and inhibit cell proliferation by at least about 1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold as assessed by methods described herein or known to one of skill in the art (e.g., BrdU incorporation assay).

In certain aspects, an anti-KIT antibody described herein, which can act as an inhibitor of KIT activity, can reduce or inhibit survival of cells that express KIT and that respond to KIT signaling (e.g., cells that proliferate in response to KIT ligand stimulation and KIT signaling). Cell survival assays are described in the art and can be readily carried out by one of skill in the art. For example, cell viability can be assessed by using trypan-blue staining or other cell death or viability markers known in the art. In a specific embodiment, the level of cellular ATP is measured to determined cell viability. In specific embodiments, cell viability is measured in three-day and seven-day periods using an assay standard in the art, such as the CellTiter-Glo Assay Kit (Promega) which measures levels of intracellular ATP. A reduction in cellular ATP is indicative of a cytotoxic effect. In another specific embodiment, cell viability can be measured in the neutral red uptake assay. In other embodiments, visual observation for morphological changes can include enlargement, granularity, cells with ragged edges, a filmy appearance, rounding, detachment from the surface of the well, or other changes. These changes are given a designation of T (100% toxic), PVH (partially toxic—very heavy—80%), PH (partially toxic—heavy—60%), P (partially toxic—40%), Ps (partially toxic—slight—20%), or 0 (no toxicity—0%), conforming to the degree of cytotoxicity seen. A 50% cell inhibitory (cytotoxic) concentration ($IC_{50}$) is determined by regression analysis of these data.

In specific embodiments, antibodies described herein specifically bind to KIT and inhibit (e.g, partially inhibit) cell (e.g., cancer cell) survival by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art (e.g., trypan blue exclusion assay). In specific embodiments, antibodies described herein specifically bind to KIT and inhibit cell (e.g., cancer cell) survival by at least about 1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold as assessed by methods described herein or known to one of skill in the art (e.g., trypan blue assay).

In certain aspects, an anti-KIT antibody described herein, which can act as an inhibitor of KIT activity, is capable of inducing apoptosis (i.e., programmed cell death) of cells (e.g., cancer cells, such as MOTE cells) that express KIT and that respond to KIT signaling (e.g., cells that proliferate in response to KIT ligand stimulation and KIT signaling). Apoptosis is described in the art and can be readily carried out by one of skill in the art. For example, flow cytometry can be used to detect activated caspase 3, an apoptosis-mediating enzyme, in cells undergoing apoptosis, or Western blotting can be used to detect cleavage of poly(ADP-ribose) polymerase (PARP) (see, e.g., Smolich et al., Blood, 2001, 97:1413-1421). Cleavage of PARP is an indicator of apoptosis. In specific embodiments, antibodies described herein specifically bind to KIT and induce or enhance apoptosis by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art (e.g., flow cytometry to detect activated caspase 3). In specific embodiments, antibodies described herein specifically bind to KIT and induce or enhance apoptosis by at least about 1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold as assessed by methods described herein or known to one of skill in the art (e.g., flow cytometry to detect activated caspase 3).

In certain aspects, an anti-KIT antibody described herein, which can act as an inhibitor of KIT activity, is capable of inhibiting or decreasing anchorage independent cell growth (e.g., colony formation) by cells (e.g., H526 cells or CHO cells expressing exogenous KIT) that express KIT and that respond to KIT signaling (e.g., cells that proliferate in response to KIT ligand stimulation and KIT signaling), as measured by methods commonly known in the art, e.g., soft agar assay. In specific embodiments, antibodies described herein (or an antigen-binding fragment thereof, or a conjugate thereof) specifically bind to KIT and inhibit or decrease anchorage independent cell growth by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art (e.g., soft agar assay). In specific embodiments, antibodies described herein (or an antigen-binding fragment thereof, or a conjugate thereof) specifically bind to KIT and inhibit or decrease anchorage independent cell growth by at least about 25% or 35%, optionally to about 75%, as assessed by methods described herein or known to one of skill in the art (e.g., soft agar assay). In specific embodiments, antibodies described herein specifically bind to KIT and inhibit or decrease anchorage independent cell growth by at least about 1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold as assessed by methods described herein or known to one of skill in the art (e.g., soft agar assay).

Cells and cell lines which are appropriate for use in the assays described herein relating to KIT activity are readily available (e.g., ATCC) or can be readily identified using methods known in the art. For example, cells and/or cell lines that express KIT endogenously or that possess KIT signaling or activity are known to one of skill in the art. In certain embodiments, cells or cell lines that are appropriate for use in the assays described herein can express KIT, either endogenously or recombinantly. In particular embodiments, cells or cell lines for use in cell proliferation assays can express KIT, endogenously or recombinantly, and proliferate or increase proliferation in response to KIT ligand (e.g., SCF) stimulation. Cells or cell lines for use in cell viability assays can express KIT, endogenously or recombinantly, and exert changes in cell viability in response to KIT ligand (e.g., SCF) stimulation. Cells or cell lines for use in apoptosis assays can express KIT, endogenously or recombinantly, and exert changes in apoptosis in response to KIT ligand (e.g., SCF) stimulation.

Non-limiting examples of cells that can be used in the methods and assays described herein include primary cells, cancer cells, transformed cells, stem cells, mast cells, primordial germ cells, oocytes, spermatocytes, embryonic stem cells, hematopoietic cells, erythroleukemia cells (e.g., F36P and TF-1 cell lines), human myeloid leukemia cell lines, such as MOTE cells; gastrointestinal stromal tumor cell lines such as ST-882, GIST-T1, GIST48, GIST48B, GIST430, and GIST882; neuroblastoma cell lines such as SK-N-SH, SK-SY5Y, H-EP1, SK-N-BE(2), SK-N-BE(ZkM17), SK-N-BE(2)C, LA-N-1, or LA-N-1-5s; Ewing's sarcoma cell lines such as TC71, TC32, RD-ES, 5838, A4573, EWS-925, NCI-EWS-94, and NCI-EWS-95; and small cell lung carcinoma cell lines such as H526, ECC12, TMK1, MKN7, GCIY, and HGC27.

Alternatively, cells and cell lines that express KIT, e.g., human KIT, can routinely be generated recombinantly. Non-limiting examples of cells that can be engineered to express KIT recombinantly include COS cells, HEK 293 cells, CHO cells, fibroblasts (e.g., human fibroblasts) such as NIH3T3 cells, and MEFS. In a specific embodiment, cells for use in the methods described herein are CHO cells, for example CHO cells from the CHO GS System™ (Lonza). In a particular embodiment, these engineered cells exogenously expressing full-length human KIT (e.g., SEQ ID NO: 1).

In certain aspects, an anti-KIT antibody described herein, which can act as an inhibitor of KIT activity, is capable of inhibiting tumor growth or inducing tumor regression in mouse model studies. For example, tumor cell lines can be introduced into nude mice, and the mice can be administered with anti-KIT antibodies described herein one or more times, and tumor progression of the injected tumor cells can be monitored over a period of weeks and/or months. In some cases, administration of anti-KIT antibodies to the nude mice can occur prior to introduction of the tumor cell lines. Any appropriate tumor cell line (e.g., tumor cell line expressing KIT) can be used in the mouse xenograft models described herein. Non-limiting examples of tumor cell lines for use in these xenograft mouse models include megakaryoblastic leukemia cell lines such as MO7e; gastrointestinal stromal tumor cell lines such as ST-882, GIST-T1, GIST430, GIST48, GIST48B and GIST882; human erythroleukemic cell lines such as HEL and TF-1; human promyelocytic leukemia cell line, HL60; neuroblastoma cell lines such as SK-N-SH, SK-SY5Y, H-EP1, SK-N-BE(2), SK-N-BE (ZkM17), SK-N-BE(2)C, LA-N-1, or LA-N-1-5s; Ewing's sarcoma cell lines such as TC71, TC32, RD-ES, 5838, A4573, EWS-925, NCI-EWS-94, and NCI-EWS-95; and small cell lung carcinoma cell lines such as H526, DMS153, DMS79, ECC12, TMK1, MKN7, GCIY, and HGC27. In a specific embodiments, a tumor cell line for use in a xenograft mouse model is the GIST882, GIST430, GIST48, GIST48B, HEL, HL60, H526, DMS153, or DMS79 cell line. In certain embodiments, suitable cell lines for use in xenograft tumor models can be generated by recombinantly expressing KIT in cell. In specific embodiments, antibodies described herein (or an antigen-binding fragment thereof, or a conjugate thereof) specifically bind to KIT and inhibit tumor grow or induce tumor regression in a mouse model by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art. In specific embodiments, antibodies described herein (or an antigen-binding fragment thereof, or a conjugate thereof) specifically bind to KIT and inhibit tumor grow or induce tumor regression in a mouse model by at least about 25% or 35%, optionally to about 75%, as assessed by methods described herein or known to one of skill in the art. In specific embodiments, antibodies described herein specifically bind to KIT and inhibit tumor grow or induce tumor regression in a mouse model by at least about 1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold as assessed by methods described herein or known to one of skill in the art. Determining tumor growth inhibition or tumor regression can be assessed by monitoring tumor size over a period of time, such as by physical measurement of palpable tumors, or other visual detection methods. For example, tumor cell lines can be generated to recombinantly express a visualization agent, such as green fluorescent protein (GFP) or luciferase, then in vivo visualization of GFP can be carried out by microscopy, and in vivo visualization of luciferase can be carried out by administering luciferase substrate to the xenograft mice and detecting luminescent due to the luciferase enzyme processing the luciferase substrate. The degree or level of detection of GFP or luciferase correlates to the size of the tumor in the xenograft mice.

In certain aspects, anti-KIT antibodies described herein bind specifically to KIT antigen and can increase survival of animals in tumor xenograft models. In specific embodiments, antibodies described herein (or an antigen-binding fragment thereof, or a conjugate thereof) specifically bind to KIT and increase survival of mice in tumor xenograft models by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art. In specific embodiments, antibodies described herein (or an antigen-binding fragment thereof, or a conjugate thereof) specifically bind to KIT and increase survival of mice in tumor xenograft models by at least about 25% or 35%, optionally to about 75%, as assessed by methods described herein or known to one of skill in the art. In specific embodiments, antibodies described herein specifically bind to KIT and increase survival of mice in tumor xenograft models by at least about 1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold as assessed by methods described herein or known to one of skill in the art. Survival can be determined by plotting a survival curve of number of surviving mice against time (e.g., days or weeks) after tumor cell line injection.

Provided herein are antibodies that immunospecifically bind a KIT polypeptide, e.g., a human KIT polypeptide, e.g., a D4 region of KIT, for example, human KIT, with a particular affinity.

"Affinity" of an antibody described herein for an epitope (e.g., KIT epitope) is a term well understood in the art and refers to the extent, or strength, of binding of an antibody to an epitope. Affinity can be measured and/or expressed in a number of ways known in the art, including, but not limited to, equilibrium dissociation constant ($K_D$ or $K_d$), apparent equilibrium dissociation constant ($K_D'$ or $K_d'$), and $IC_{50}$ (amount needed to effect 50% inhibition in a competition assay). It is understood that, for purposes described herein, an affinity is an average affinity for a given population of antibodies which bind to an epitope. Values of $K_D'$ described herein in terms of milligram (mg) Ig per mL or mg/mL indicate mg Ig per mL of serum, although plasma can be used. When antibody affinity is used as a basis for administration of the treatment methods described herein, or selection for the treatment methods described herein, antibody affinity can be measured before and/or during treatment, and the values obtained can be used by a clinician in assessing whether a human patient is an appropriate candidate for treatment.

In specific aspects, provided herein are antibodies (or antigen-binding fragments thereof, or conjugates thereof) that have a high binding affinity (e.g., antibodies having a $K_D$ of less than 250 nM, 100 nM, 50 nM, 10 nM, 1 nM, 500 pM, 200 pM, 100 pM, or 50 pM) for a KIT antigen, preferably a human KIT antigen, in particular the D4/D5 region of a human KIT.

In specific embodiments, an antibody described herein (or an antigen-binding fragment thereof, or a conjugate thereof) immunospecifically binds to a KIT antigen (e.g., a D4/D5 region of KIT, for example human KIT), and has a dissociation constant ($K_D$) of less than 500,000 pM (500 nM), less than 100,000 pM (100 nM), less than 50,000 pM (50 nM), less than 10,000 pM (10 nM), less than 3,000 pM (3 nM), less than 2,500 pM (2.5 nM), less than 2,000 pM, less than 1,500 pM, less than 1,000 pM, less than 750 pM, less than 500 pM, less than 250 pM, less than 200 pM, less than 150 pM, less than 100 pM, less than 75 pM as assessed using an assay described herein or known to one of skill in the art (e.g., a Biacore™ assay) (Biacore™ International AB, Uppsala, Sweden). In a specific embodiment, an antibody described herein (or an antigen-binding fragment thereof, or a conjugate thereof) immunospecifically binds to a KIT antigen (e.g., a D4/D5 region of KIT, for example human KIT), and has a $K_D$ in the range of from 25 to 100,000 pM, 25 to 75,000 pM, 25 to 50,000 pM, 25 to 40,000 pM, 25 to 30,000 pM, 25 to 20,000 pM, 25 to 10,000 pM, 25 to 1,000 pM, 25 to 500 pM, 25 to 250 pM, 25 to 100 pM, or 25 to 50 pM as assessed using methods described herein or known to one of skill in the art (e.g., a Biacore™ assay, assay using KinExA 3000 instrument). In a particular embodiment, an antibody described herein (or an antigen-binding fragment thereof, or a conjugate thereof) immunospecifically binds to a KIT antigen (e.g., a D4 region of KIT, for example human KIT), and has a $K_D$ of about 100 pM to about 250 nM, or any value in between, as assessed using methods described herein or known to one of skill in the art (e.g., a Biacore™ assay, assay using KinExA 3000 instrument).

In specific embodiments, an anti-KIT antibody (or an antigen-binding fragment thereof, or a conjugate thereof) immunospecifically binds to a KIT antigen (e.g., a D4 region of KIT, for example human KIT), and has a concentration at 50% binding to antigen of less than 3000 pM (3 nM), less than 2500 pM (2.5 nM), less than 2000 pM, less than 1500 pM, less than 1000 pM, less than 750 pM, less than 500 pM, less than 250 pM, less than 200 pM, less than 150 pM, less than 100 pM, less than 75 pM as assessed using an assay described herein or known to one of skill in the art (e.g., solid phase ELISA as described in section 6). In a specific embodiment, an antibody described herein (or an antigen-binding fragment thereof, or a conjugate thereof) immunospecifically binds to a KIT antigen (e.g., a D4 region of KIT, for example human KIT), and has a concentration at 50% binding to antigen in the range of from 25 to 500,000 pM (500 nM), 25 to 250,000 pM (250 nM), 25 to 100,000 pM (100 nM), 25 to 75,000 pM (75 nM), 25 to 50,000 pM (50 nM), 25 to 40,000 pM (40 nM), 25 to 30,000 pM (30 nM), 25 to 20,000 pM (20 nM), 25 to 10,000 pM (10 nM), 25 to 1,000 pM (1 nM), 25 to 500 pM, 25 to 250 pM, 25 to 100 pM, or 25 to 50 pM as assessed using methods described herein or known to one of skill in the art (e.g., solid phase ELISA as described in section 6). In a particular embodiment, an antibody described herein (or an antigen-binding fragment thereof, or a conjugate thereof) immunospecifically binds to a KIT antigen (e.g., a D4 region of KIT, for example human KIT), and has a concentration at 50% binding to antigen of about 1 nM to about 25 nM, or any value in between, as assessed using methods described herein or known to one of skill in the art (e.g., solid phase ELISA as described in section 6). In a particular embodiment, an antibody described herein (or an antigen-binding fragment thereof, or a conjugate thereof) immunospecifically binds to a KIT antigen (e.g., a D4 region of KIT, for example human KIT), and has a concentration at 50% binding to antigen of about 50 pM to about 500 pM, or any value in between, as assessed using methods described herein or known to one of skill in the art (e.g., solid phase ELISA as described in section 6). In a particular embodiment, an antibody described herein (or an antigen-binding fragment thereof, or a conjugate thereof) immunospecifically binds to KIT antigen (e.g., a D4 region of KIT, for example human KIT), and has a concentration at 50% binding of about 0.5 nM, 0.25 nM, 0.1 nM, 1 nM, 1.5 nM, 2 nM, 2.5 nM, 3 nM, 3.5 nM, 4 nM, 4.5 nM, 5 nM, 5.5 nM, 6 nM, 6.5 nM, 7 nM, 8 nM, 9 nM, 10 nM, 11 nM, 12 nM, 13 nM, 14 nM, 15 nM, 16 nM, 17 nM, 18 nM, 19 nM, 20 nM, 30 nM, 40 nM, 50 nM, 60 nM, 70 nM, 80 nM, 90 nM, 100 nM, 150 nM, 200 nM, 250 nM, 300 nM, 350 nM, 400 nM, or 500 nM, or less, as assessed using methods described herein or known to one of skill in the art (e.g., solid phase ELISA as described in section 6). In a particular embodiment, antibodies described herein immunospecifically bind to KIT antigen (e.g., a D4 region of KIT, for example human KIT), and have a concentration at 50% binding from about 100 pM to about 10 nM, as assessed using methods described herein or known to one of skill in the art (e.g., ELISA, assay using KinExA 3000 instrument, or Biacore™ assay).

Methods for determining affinity of an antibody to its target antigen are readily available and described in the art. For example, the affinities and binding properties of an antibody for its target antigen, can be determined by a variety of in vitro assay methods (biochemical or immunological based assays) known in the art such as equilibrium methods (e.g., enzyme-linked immunoabsorbent assay (ELISA), or radioimmunoassay (RIA)), or kinetics (e.g., Biacore™ analysis), and other methods such as indirect binding assays, competitive inhibition assays, fluorescence resonance energy transfer (FRET), immunoprecipitation, gel electrophoresis and chromatography (e.g., gel filtration). These and other methods can utilize a label on one or more of the components being examined and/or employ a variety of detection methods including but not limited to chromogenic, fluorescent, luminescent, or isotopic labels. In certain embodiments, use of labels is not necessary, e.g., Biacore™ systems utilize the natural phenomenon of surface plasmon resonance (SPR) to deliver data in real time, without the use of labels. A detailed description of binding affinities and kinetics can be found in Paul, W. E., ed., *Fundamental Immunology*, 4th Ed. (Lippincott-Raven, Philadelphia 1999), which focuses on antibody-immunogen interactions.

In certain aspects, the affinity of an antibody described herein for a KIT antigen, e.g., human KIT, for example a D4 region of KIT (e.g., human KIT), can be characterized indirectly using cell-based assays. For example, cells expressing KIT on their cell membrane surface can be contacted with anti-KIT antibodies, and cellular activities downstream of KIT can be determined using assays known in the art. For examples, phosphorylation of the cytoplasmic domain of KIT can be determined by immunoblotting (or Western blotting) following contacting the cells with an anti-KIT antibody; cellular extracts are obtained and processed for immunoblotting (e.g., subjecting the cellular extracts to sodium dodecyl sulfate polyacrylamide gel electrophoresis (SDS-PAGE) and transferring the proteins separated on the gel to a membrane (e.g., nitrocellulose or polyvinylidene fluoride (PVDF)) with an antibody that specifically binds to a phosphorylated tyrosine in the cytoplasmic domain of KIT, but does not bind an unphosphorylated tyrosine.

In certain embodiments, an anti-KIT antibody described herein specifically binds to a KIT antigen, e.g., human KIT, for example a D4 region of KIT (e.g., human KIT), and induces or enhances dimerization and phosphorylation of KIT, in the presence or absence of the KIT ligand SCF. In some embodiments, an anti-KIT antibody described herein can inhibit or decrease KIT ligand, e.g., SCF, binding to KIT (i.e., an anti-KIT antibody can compete with a KIT ligand, e.g., SCF, for binding to KIT). In such case, cells can be contacted with an anti-KIT antibody and a KIT ligand, and the degree of inhibition of KIT phosphorylation can be determined as an indication of the degree of the anti-KIT antibody competing with the KIT ligand for binding to KIT.

Antibodies include, but are not limited to, monoclonal antibodies, recombinantly produced antibodies, multispecific antibodies (including bi-specific antibodies), human antibodies, humanized antibodies, chimeric antibodies, synthetic antibodies, tetrameric antibodies comprising two heavy chain and two light chain molecule, an antibody light chain monomer, an antibody heavy chain monomer, an antibody light chain dimer, an antibody heavy chain dimer, an antibody light chain-antibody heavy chain pair, intrabodies, heteroconjugate antibodies, single domain antibodies, monovalent antibodies, single chain antibodies or single-chain Fvs (scFv) (e.g., including monospecific, bispecific, etc.), camelized antibodies, affybodies, Fab fragments, F(ab') fragments, disulfide-linked Fvs (sdFv), anti-idiotypic (anti-Id) antibodies (including, e.g., anti-anti-Id antibodies), and epitope-binding fragments of any of the above. In certain embodiments, antibodies described herein refer to polyclonal antibody populations. Antibodies can be of any type (e.g., IgG, IgE, IgM, IgD, IgA or IgY), any class, (e.g., $IgG_1$, $IgG_2$, $IgG_3$, $IgG_4$, $IgA_1$ or $IgA_2$), or any subclass (e.g., IgG2a or IgG2b) of immunoglobulin molecule. In certain embodiments, antibodies described herein are IgG antibodies, or a class (e.g., human $IgG_1$ or $IgG_4$) or subclass thereof. In specific embodiments, a monoclonal antibody is an antibody produced by a single hybridoma or other cell, wherein the antibody immunospecifically binds to a D4 region of human KIT epitope as determined, e.g., by ELISA or other antigen-binding or competitive binding assay known in the art or in the Examples provided herein. The term "monoclonal" is not limited to any particular method for making the antibody.

In a particular embodiment, an antibody provided herein is a Fab fragment that immunospecifically binds to a KIT polypeptide, such as the D4 region of KIT. In a specific embodiment, antibodies described herein are monoclonal antibodies or isolated monoclonal antibodies. In another specific embodiment, an antibody described herein is a humanized monoclonal antibody. In a particular embodiment, an antibody described herein is a recombinant antibody, for example, a recombinant human antibody, recombinant humanized antibody or a recombinant monoclonal antibody. In certain embodiments, an antibody described herein contains non-human amino acid sequences, e.g., non-human CDRs or non-human (e.g., non-human primate) framework residues.

In particular embodiments provided herein, recombinant antibodies can be isolated, prepared, expressed, or created by recombinant means, such as antibodies expressed using a recombinant expression vector transfected into a host cell, antibodies isolated from a recombinant, combinatorial antibody library, or antibodies prepared, expressed, created or isolated by any other means that involves creation, e.g., via synthesis, genetic engineering of DNA sequences that encode human immunoglobulin sequences, or splicing of sequences that encode human immunoglobulins, e.g., human immunoglobulin gene sequences, to other such sequences. In certain embodiments, the amino acid sequences of such recombinant antibodies have been modified such thus the amino acid sequences of such antibodies, e.g., VH and/or VL regions, are sequences that do not naturally exist within an organism's antibody germline repertoire in vivo, for example a murine or human germline repertoire. In a particular embodiment, a recombinant antibody can be obtained by assembling several sequence fragments that naturally exist in an organism (e.g., primate, such as human) into a composite sequence of a recombinant antibody, wherein the composite sequence does not naturally exist within an organism (e.g., primate such as human).

Antibodies provided herein include immunoglobulin molecules of any type (e.g., IgG, IgE, IgM, IgD, IgA and IgY), class (e.g., IgG1, IgG2, IgG3, IgG4, IgA1 and IgA2) or subclass of immunoglobulin molecule. In a specific embodiment, an antibody provided herein is an IgG antibody (e.g., human IgG antibody), or a class (e.g., human IgG1 or IgG4) or subclass thereof. In another specific embodiment, an antibody described herein is an IgG1 (e.g., human IgG1 (isotype a, z, or f)) or IgG4 antibody. In certain embodiments, an antibody described herein is a whole or entire antibody, e.g., a whole or entire humanized, human, or composite human antibody.

Antibodies provided herein can include antibody fragments that retain the ability to specifically bind to an antigen, e.g., KIT epitope (e.g., a KIT epitope within a KIT polypeptide containing a D4 region of human KIT). In a specific embodiment, fragments include Fab fragments (an antibody fragment that contains the antigen-binding domain and comprises a light chain and part of a heavy chain (i.e., the VH and CH1 domains of a heavy chain) bridged by a disulfide bond); Fab' (an antibody fragment containing a single antigen-binding domain comprising an Fab and an additional portion of the heavy chain through the hinge region); F(ab')₂ (two Fab' molecules joined by interchain disulfide bonds in the hinge regions of the heavy chains; the Fab' molecules can be directed toward the same or different epitopes); a bispecific Fab (a Fab molecule having two antigen binding domains, each of which can be directed to a different epitope); a single chain Fab chain comprising a variable region, also known as a sFv (the variable, antigen-binding determinative region of a single light and heavy chain of an antibody linked together by a chain of 10-25 amino acids); a disulfide-linked Fv, or dsFv (the variable, antigen-binding determinative region of a single light and heavy chain of an antibody linked together by a disulfide bond); a camelized VH (the variable, antigen-binding determinative region of a single heavy chain of an antibody in which some amino acids at the VH interface are those found in the heavy chain of naturally occurring camel antibodies); a bispecific sFv (a sFv or a dsFv molecule having two antigen-binding domains, each of which can be directed to a different epitope); a diabody (a dimerized sFv formed when the VH domain of a first sFv assembles with the VL domain of a second sFv and the VL domain of the first sFv assembles with the VH domain of the second sFv; the two antigen-binding regions of the diabody can be directed towards the same or different epitopes); and a triabody (a trimerized sFv, formed in a manner similar to a diabody, but in which three antigen-binding domains are created in a single complex; the three antigen binding domains can be directed towards the same or different epitopes). Antibodies provided herein can also include one or more CDR sequences of an antibody. The CDR sequences can be linked together on a scaffold when two or more CDR sequences are present. In certain embodiments, an antibody comprises a single-chain Fv ("scFv"). scFvs are antibody fragments comprising the VH and VL domains of an antibody, wherein these domains are present in a single polypeptide chain. Generally, the scFv polypeptide further comprises a polypeptide linker between the VH and VL domains which enables the scFv to form the desired structure for antigen binding. For a review of scFvs, see Pluckthun in *The Pharmacology of Monoclonal Antibodies*, vol. 113, Rosenburg and Moore eds. Springer-Verlag, New York, pp. 269-315 (1994). Without being bound by any particular theories, Fv molecules can be able to penetrate tissues because of their small size. A whole antibody can be enzymatically cleaved by pepsin to produce a F(ab')$_2$ fragment, or can be enzymatically cleaved by papain to produce two Fab fragments.

In certain embodiments, antibodies described herein are human, composite human, or humanized monoclonal antibodies. In a particular embodiment, an antibody described herein is an engineered antibody, for example, antibody produced by recombinant methods. In a specific embodiment, an antibody described herein is a humanized antibody comprising one or more non-human (e.g., rodent or murine) CDRs and one or more human framework regions (FR), and optionally human heavy chain constant region and/or light chain constant region. In a specific embodiment, an antibody described herein comprises one or more primate (or non-human primate) framework regions. In a specific embodiment, an antibody described herein does not comprise non-human primate framework regions.

Antibodies provided herein can include antibodies comprising chemical modifications, for example, antibodies which have been chemically modified, e.g., by covalent attachment of any type of molecule to the antibody. For example, but not by way of limitation, an anti-KIT antibody can be glycosylated, acetylated, pegylated, phosphorylated, or amidated, can be derivitized via protective/blocking groups, or can further comprise a cellular ligand and or other protein or peptide, etc. For example, an antibody provided herein can be chemically modified, e.g., by glycosylation, acetylation, pegylation, phosphorylation, amidation, derivatization by known protecting/blocking groups, proteolytic cleavage, linkage to a cellular ligand or other protein, etc. Further, an anti-KIT antibody described herein can contain one or more non-classical amino acids.

In a particular embodiment, provided herein is an anti-KIT antibody which has been modified in a manner suitable for large scale manufacturing, e.g., the manufacturing platform of Lonza (Basel, Switzerland). For example, the BI-HEX® technology platform (Boehringer Ingleheim, Germany) can be used to adapt the anti-KIT antibodies described herein for suitable large scale manufacturing in recombinant mammalian cell expression systems. Such adaptation can involve cloning polynucleotide sequences encoding the necessary domains of an anti-KIT antibody, such as one or more CDRs or FRs, into a suitable expression vector which also contains polynucleotide sequences encoding suitable constant regions, so that an entire antibody is produced. The polynucleotide sequences provided by the expression vectors are nucleotide sequences which can be optimized to maximize antibody yield and stability for cell culture manufacturing conditions and purification processes.

5.1.1. Conjugates

In some embodiments, provided herein are antibodies (e.g., human or humanized antibodies), or antigen-binding fragments thereof, conjugated or recombinantly fused to a diagnostic, detectable or therapeutic agent or any other molecule. The conjugated or recombinantly fused antibodies can be useful, e.g., for monitoring or prognosing the onset, development, progression and/or severity of a KIT-associated disorder or disease, for example, as part of a clinical testing procedure, such as determining the efficacy of a particular therapy. The conjugated or recombinantly fused antibodies can be useful, e.g., for treating or managing a KIT-associated disorder (e.g., cancer), or for treating or managing effects of a KIT-associated disorder (e.g., cancer). Antibodies described herein can also be conjugated to a molecule (e.g., polyethylene glycol) which can affect one or more biological and/or molecular properties of the antibodies, for example, stability (e.g., in serum), half-life, solubility, and antigenicity.

In a particular aspect, provided herein is a conjugate comprising an agent (e.g., therapeutic agent) linked to an antibody described herein (or an antigen-binding fragment thereof), which antibody immunospecifically binds to a D4 region of human KIT (e.g., SEQ ID NO: 15). In a specific embodiment, a conjugated antibody specifically binds a D4 region of KIT (e.g., human KIT), and comprises an antibody comprising the CDRs set forth in Table 1, or Table 2, or Table 3. In a specific embodiment, a conjugated antibody specifically binds a D4 region of KIT (e.g., human KIT) and comprises a VL chain region comprising VL CDR1, VL CDR2, and VL CDR3 having the amino acid sequence of SEQ ID NO: 19, 20, and 21, respectively, and/or a VH chain region comprising VH CDR1, VH CDR2, and VH CDR3 having the amino acid sequence of SEQ ID NO: 16, 17, and 18, respectively. In a specific embodiment, a conjugated antibody specifically binds a D4 region of KIT (e.g., human KIT), and comprises any one of antibodies Hum1-Hum20. In a specific embodiment, a conjugated antibody provided herein specifically binds a D4 region of KIT (e.g., human KIT), and comprises an antibody comprising a VL and/or VH comprising CDRs selected from Table 1, or Table 2, or Table 3, and FRs selected from Tables 5A-5D. In a specific embodiment, a conjugated antibody provided herein specifically binds a D4 region of KIT (e.g., human KIT), and comprises an antibody comprising a VL comprising SEQ ID NO: 12 and/or VH comprising SEQ ID NO: 11. In one embodiment, an antibody that is conjugated is one that binds a D4 region of human KIT with an affinity, for example, an EC50 of about 200 pM or less. In another embodiment, an antibody that is conjugated is one that inhibits a biological activity of KIT. In specific embodiments, a conjugate comprises an antibody described herein and a molecule (e.g., therapeutic or drug moiety), wherein the antibody is linked directly to the molecule, or by way of one or more linkers. In certain embodiments, an antibody is covalently conjugated to a molecule. In a particular embodiment, an antibody is noncovalently conjugated to a molecule. In specific embodiments, an antibody described herein, e.g., an antibody conjugated to an agent, binds to wild-type human KIT. In certain embodiments, an antibody described herein, e.g., antibody conjugated to an agent, binds to an extracellular domain of human KIT comprising a mutation, for example a somatic mutation associated with cancer (e.g., GIST), such as a mutation in exon 9 of human KIT wherein the Ala and Tyr residues at positions 502 and 503 are duplicated.

Such diagnosis and detection can be accomplished, for example, by coupling the antibody to detectable molecules or substances including, but not limited to, various enzymes, such as, but not limited to, horseradish peroxidase, alkaline phosphatase, beta-galactosidase, or acetylcholinesterase;

prosthetic groups, such as, but not limited to, streptavidin/biotin and avidin/biotin; fluorescent materials, such as, but not limited to, umbelliferone, fluorescein, fluorescein isothiocynate, rhodamine, dichlorotriazinylamine fluorescein, dansyl chloride or phycoerythrin; luminescent materials, such as, but not limited to, luminol; bioluminescent materials, such as but not limited to, luciferase, luciferin, and aequorin; radioactive materials, such as, but not limited to, iodine ($^{131}$I, $^{125}$I, $^{123}$I, and $^{121}$I), carbon ($^{14}$C), sulfur ($^{35}$S), tritium ($^{3}$H), indium ($^{115}$In, $^{113}$In, $^{112}$In, and $^{111}$In), technetium ($^{99}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, and $^{117}$Sn; and positron emitting metals using various positron emission tomographies, and non-radioactive paramagnetic metal ions.

Provided are antibodies described herein, or antigen-binding fragments thereof, conjugated or recombinantly fused to a therapeutic moiety (or one or more therapeutic moieties) and uses of such antibodies. The antibody can be conjugated or recombinantly fused to a therapeutic moiety, such as a cytotoxin, e.g., a cytostatic or cytocidal agent, a therapeutic agent or a radioactive metal ion, e.g., alpha-emitters. A cytotoxin or cytotoxic agent includes any agent that is detrimental to cells. Therapeutic moieties include, but are not limited to, auristatin or a derivative thereof, e.g., monomethyl auristatin E (MMAE), monomethyl auristatin F (MMAF), auristatin PYE, and auristatin E (AE) (see, e.g., U.S. Pat. No. 7,662,387 and U.S. Pat. Application Publication Nos. 2008/0300192 and 2008/0025989, each of which is incorporated herein by reference); a microtubule-disrupting agent, e.g., maytansine or a derivative thereof, e.g., maytansinoid DM1 (see, e.g., U.S. Pat. Nos. 7,851,432, 7,575,748, and 5,416,064, each of which is incorporated herein by reference); a prodrug, e.g., a prodrug of a CC-1065 (rachelmycin) analogue; antimetabolites (e.g., methotrexate, 6-mercaptopurine, 6-thioguanine, cytarabine, 5-fluorouracil decarbazine); alkylating agents (e.g., mechlorethamine, thioepa chlorambucil, melphalan, carmustine (BCNU) and lomustine (CCNU), cyclothosphamide, busulfan, dibromomannitol, streptozotocin, mitomycin C, and cisdichlorodiamine platinum (II) (DDP), and cisplatin); minor-groove-binding alkylating agent; anthracyclines (e.g., daunorubicin (formerly daunomycin) and doxorubicin); antibiotics (e.g., d actinomycin (formerly actinomycin), bleomycin, mithramycin, and anthramycin (AMC)); Auristatin molecules (e.g., auristatin PHE, bryostatin 1, and solastatin 10; see Woyke et al., Antimicrob. Agents Chemother. 46:3802-8 (2002), Woyke et al., Antimicrob. Agents Chemother. 45:3580-4 (2001), Mohammad et al., Anticancer Drugs 12:735-40 (2001), Wall et al., Biochem. Biophys. Res. Commun. 266:76-80 (1999), Mohammad et al., Int. J. Oncol. 15:367-72 (1999), all of which are incorporated herein by reference); hormones (e.g., glucocorticoids, progestins, androgens, and estrogens), DNA-repair enzyme inhibitors (e.g., etoposide or topotecan), kinase inhibitors (e.g., compound ST1571, imatinib mesylate (Kantarjian et al., Clin Cancer Res. 8(7):2167-76 (2002)); cytotoxic agents (e.g., paclitaxel, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucorticoids, procaine, tetracaine, lidocaine, propranolol, and puromycin and analogs or homologs thereof and those compounds disclosed in U.S. Pat. Nos. 6,245,759, 6,399,633, 6,383,790, 6,335,156, 6,271,242, 6,242,196, 6,218,410, 6,218,372, 6,057,300, 6,034,053, 5,985,877, 5,958,769, 5,925,376, 5,922,844, 5,911,995, 5,872,223, 5,863,904, 5,840,745, 5,728,868, 5,648,239, 5,587,459, each of which is incorporated herein by reference with respect to such compound disclosure); farnesyl transferase inhibitors (e.g., R115777, BMS-214662, and those disclosed by, for example, U.S. Pat. Nos. 6,458,935, 6,451, 812, 6,440,974, 6,436,960, 6,432,959, 6,420,387, 6,414,145, 6,410,541, 6,410,539, 6,403,581, 6,399,615, 6,387,905, 6,372,747, 6,369,034, 6,362,188, 6,342,765, 6,342,487, 6,300,501, 6,268,363, 6,265,422, 6,248,756, 6,239,140, 6,232,338, 6,228,865, 6,228,856, 6,225,322, 6,218,406, 6,211,193, 6,187,786, 6,169,096, 6,159,984, 6,143,766, 6,133,303, 6,127,366, 6,124,465, 6,124,295, 6,103,723, 6,093,737, 6,090,948, 6,080,870, 6,077,853, 6,071,935, 6,066,738, 6,063,930, 6,054,466, 6,051,582, 6,051,574, and 6,040,305, each of which is incorporated herein by reference with respect to such inhibitor disclosure); topoisomerase inhibitors (e.g., camptothecin; irinotecan; SN-38; topotecan; 9-aminocamptothecin; GG-211 (GI 147211); DX-8951f; IST-622; rubitecan; pyrazoloacridine; XR-5000; saintopin; UCE6; UCE1022; TAN-1518A; TAN 1518B; KT6006; KT6528; ED-110; NB-506; ED-110; NB-506; and rebeccamycin); bulgarein; DNA minor groove binders such as Hoescht dye 33342 and Hoechst dye 33258; nitidine; fagaronine; epiberberine; coralyne; beta-lapachone; BC-4-1; bisphosphonates (e.g., alendronate, cimadronte, clodronate, tiludronate, etidronate, ibandronate, neridronate, olpandronate, risedronate, piridronate, pamidronate, zolendronate) HMG-CoA reductase inhibitors, (e.g., lovastatin, simvastatin, atorvastatin, pravastatin, fluvastatin, statin, cerivastatin, lescol, lupitor, rosuvastatin and atorvastatin); antisense oligonucleotides (e.g., those disclosed in the U.S. Pat. Nos. 6,277,832, 5,998,596, 5,885,834, 5,734,033, and 5,618,709, each of which is incorporated herein by reference with respect to such oligonucleotides); adenosine deaminase inhibitors (e.g., Fludarabine phosphate and 2-Chlorodeoxyadenosine); ibritumomab tiuxetan (Zevalin®); tositumomab (Bexxar®)) and pharmaceutically acceptable salts, solvates, clathrates, and prodrugs thereof. In one embodiment, an antibody that is conjugated to such therapeutic/drug moiety is one that binds a D4 region of human KIT with an affinity of less than about 200 pM. In another embodiment, an antibody that is conjugated to such therapeutic/drug moiety is one that inhibits a biological activity of KIT. In a specific embodiment, an antibody that is conjugated to such therapeutic/drug moiety is one that comprises the CDRs set forth in Table 1 (e.g., VL CDR1, VL CDR2, and VL CDR3 having the amino acid sequence of SEQ ID NO: 19, 20, and 21, respectively, and/or a VH chain region comprising VH CDR1, VH CDR2, and VH CDR3 having the amino acid sequence of SEQ ID NO: 16, 17, and 18, respectively), or Table 2, or Table 3. In a specific embodiment, an antibody that is conjugated to such therapeutic/drug moiety is one that comprises a VL comprising SEQ ID NO: 7, 8, 9, 10, or 12 or a sequence set forth in Tables 5B and 5D, and/or VH comprising SEQ ID NO: 2, 3, 4, 5, 6, or 11 or a sequence set forth in Tables 5A and 5C.

In particular embodiments, a therapeutic moiety or drug moiety is an antitubulin drug, such as an auristatin or a derivative thereof. Non-limiting examples of auristatins include monomethyl auristatin E (MMAE), monomethyl auristatin F (MMAF), auristatin PYE, and auristatin E (AE) (see, e.g., U.S. Pat. No. 7,662,387 and U.S. Pat. Application Publication Nos. 2008/0300192 and 2008/0025989, each of which is incorporated herein by reference). In certain embodiments, a therapeutic moiety or drug moiety is a microtubule-disrupting agent such as maytansine or a derivative thereof, e.g., maytansinoid DM1 or DM4 (see, e.g., U.S. Pat. Nos. 7,851,432, 7,575,748, and 5,416,064, each of which is incorporated herein by reference). In certain embodiments, a therapeutic moiety or drug moiety is a prodrug, e.g., a prodrug of a CC-1065 (rachelmycin) analogue (see, e.g., U.S. Patent Application Publication No. 2008/0279868, and PCT International Patent Application Publication Nos. WO 2009/017394, WO 2010/062171, and WO 2007/089149, each of which is incorporated herein by reference). In one embodiment, an antibody that is conjugated to such therapeutic/drug moiety is one that binds a D4 region of human KIT with an affinity of less than about 200 pM. In another embodiment, an antibody that is conjugated to such therapeutic/drug moiety is one that inhibits a biological activity of KIT. In a specific embodiment, an antibody (e.g., human or humanized antibody) that is conjugated to such therapeutic/drug moiety is one that comprises the CDRs set forth in Table 1 (e.g., VL CDR1, VL CDR2, and VL CDR3 having the amino acid sequence of SEQ ID NO: 19, 20, and 21, respectively, and/or a VH chain region comprising VH CDR1, VH CDR2, and VH CDR3 having the amino acid sequence of SEQ ID NO: 16, 17, and 18, respectively), or Table 2, or Table 3. In a specific embodiment, an antibody (e.g., human or humanized antibody) that is conjugated to such therapeutic/drug moiety is one that comprises a VL comprising SEQ ID NO: 7, 8, 9, 10, or 12 or a sequence set forth in Tables 5B and 5D, and/or VH comprising SEQ ID NO: 2, 3, 4, 5, 6, or 11 or a sequence set forth in Tables 5A and 5C.

In a specific embodiment, the antibody and therapeutic/drug agent are conjugated by way of one or more linkers. In another specific embodiment, the antibody and therapeutic/drug agent are conjugated directly.

In specific embodiments, non-limiting examples of therapeutic moieties or drug moieties for conjugation to an antibody described herein include calicheamicins (e.g., LL-E33288 complex, for example, gamma-calicheamicin, see, e.g., U.S. Pat. No. 4,970,198) and derivatives thereof (e.g., gamma calicheamicin hydrazide derivatives), ozogamicins, duocarmycins and derivatives thereof (e.g., CC-1065 (NSC 298223), or an achiral analogue of duocarmycin (for example AS-1-145 or centanamycin)), taxanes and derivatives thereof, and enediynes and derivatives thereof (See, e.g., PCT International Patent Application Publication Nos. WO 2009/017394, WO 2010/062171, WO 2007/089149, WO 2011/021146, WO 2008/150261, WO 2006/031653, WO 2005/089809, WO 2005/089807, and WO 2005/089808, each of which is incorporated by reference herein in its entirety). In a specific embodiment, an antibody that is conjugated to such therapeutic/drug moiety is one that comprises the CDRs set forth in Table 1 (e.g., VL CDR1, VL CDR2, and VL CDR3 having the amino acid sequence of SEQ ID NO: 20, 21, and 22, respectively, and/or a VH chain region comprising VH CDR1, VH CDR2, and VH CDR3 having the amino acid sequence of SEQ ID NO: 23, 24, and 25, respectively). In a specific embodiment, an antibody that is conjugated to such therapeutic/drug moiety is one that comprises a VL comprising SEQ ID NO: 7, 8, 9, 10, or 12 or a sequence set forth in Tables 5B and 5D, and/or VH comprising SEQ ID NO: 2, 3, 4, 5, 6, or 11 or a sequence set forth in Tables 5A and 5C. In a specific embodiment, the antibody and therapeutic agent are conjugated by way of one or more linkers. In another specific embodiment, the antibody and therapeutic agent are conjugated directly.

Non-limiting examples of calicheamicins suitable for conjugation to an antibody described herein are disclosed, for example, in U.S. Pat. Nos. 4,671,958; 5,053,394; 5,037,651; 5,079,233; and 5,108,912; and PCT International Patent Application Publication Nos. WO 2011/021146, WO 2008/150261, WO 2006/031653, WO 2005/089809, WO 2005/089807, and WO 2005/089808; each of which is incorporated herein by reference for such calicheamcin disclosure. In particular embodiments, these compounds may contain a methyltrisulfide that reacts with appropriate thiols to form disulfides, and at the same time introduces a functional group such as a hydrazide or other functional group that may be useful for conjugating calicheamicin to an antibody described herein. In certain embodiments, stabilizing the disulfide bond that is present in calicheamicin conjugates by adding dimethyl substituents may yield an improved antibody/drug conjugate. In specific embodiments, the calicheamicin derivative is N-acetyl gamma calicheamicin dimethyl hydrazide, or NAc-gamma DMH (CL-184,538), as one of the optimized derivatives for conjugation. Disulfide analogs of calicheamicin which can be conjugated to an antibody described herein are described, for example, in U.S. Pat. Nos. 5,606,040 and 5,770,710, each of which is incorporated herein by reference for such compound disclosure. In a certain embodiment, a moiety (e.g., calicheamicin or a derivative thereof) is conjugated to an antibody by a linker. In a particular embodiment, a moiety (e.g., calicheamicin or a derivative thereof) is hydrolyzed from the antibody-drug conjugate at the linker. In one embodiment, a moiety (e.g., calicheamicin or a derivative thereof) is hydrolyzed from an antibody conjugate at the linker between about a pH of 3.0 and pH 4.0 for 1-24 hours at a temperature from 20 to 50° C., preferably 37° C.

In specific embodiments, non-limiting examples of therapeutic moieties or drug moieties for conjugation to an antibody described herein include pyrrolobenzodiazepines (PBDs) and derivatives thereof, for example, PBD dimers (e.g., SJG-136 or SG2000), C2-unsaturated PBD dimers, pyrrolobenzodiazepine dimers bearing C2 aryl substitutions (e.g., SG2285), PBD dimer pro-drug that is activated by hydrolysis (e.g., SG2285), and polypyrrole-PBD (e.g., SG2274) (see, e.g., PCT International Patent Application Publication Nos. WO 2000/012507, WO 2007/039752, WO 2005/110423, WO 2005/085251, and WO 2005/040170, and U.S. Pat. No. 7,612,062, each of which is incorporated herein by reference for such compound disclosure). In a specific embodiment, an antibody that is conjugated to such therapeutic/drug moiety is one that comprises the CDRs set forth in Table 1 (e.g., VL CDR1, VL CDR2, and VL CDR3 having the amino acid sequence of SEQ ID NO: 19, 20, and 21, respectively, and/or a VH chain region comprising VH CDR1, VH CDR2, and VH CDR3 having the amino acid sequence of SEQ ID NO: 16, 17, and 18, respectively), or Table 2, or Table 3. In a specific embodiment, an antibody that is conjugated to such therapeutic/drug moiety is one that comprises a VL comprising SEQ ID NO: 7, 8, 9, 10, or 12 or a sequence set forth in Tables 5B and 5D, and/or VH comprising SEQ ID NO: 2, 3, 4, 5, 6, or 11 or a sequence set forth in Tables 5A and 5C. In a specific embodiment, the antibody and therapeutic agent is conjugated by way of one or more linkers.

Further, an antibody described herein can be conjugated or recombinantly fused to a therapeutic moiety or drug moiety that modifies a given biological response. Therapeutic moieties or drug moieties are not to be construed as limited to classical chemical therapeutic agents. For example, the drug moiety can be a protein, peptide, or polypeptide possessing a desired biological activity. Such proteins can include, for example, a toxin such as abrin, ricin A, pseudomonas exotoxin, cholera toxin, or diphtheria toxin; a protein such as tumor necrosis factor, γ-interferon, α-interferon, nerve growth factor, platelet derived growth factor, tissue plasminogen activator, an apoptotic agent, e.g., TNF-γ, TNF-γ, AIM I (see, International Publication No. WO 97/33899), AIM II (see, International Publication No. WO 97/34911), Fas Ligand (Takahashi et al., 1994, J. Immunol., 6:1567-1574), and VEGF (see, International Publication No. WO 99/23105), an anti-angiogenic agent, e.g., angiostatin, endostatin or a component of the coagulation pathway (e.g., tissue factor); or, a biological response modifier such as, for example, a lymphokine (e.g., interferon gamma, interleukin-1 ("IL-1"), interleukin-2 ("IL-2"), interleukin-5 ("IL-5"), interleukin-6 ("IL-6"), interleukin-7 ("IL-7"), interleukin 9 ("IL-9"), interleukin-10 ("IL-10"), interleukin-12 ("IL-12"), interleukin-15 ("IL-15"), interleukin-23 ("IL-23"), granulocyte macrophage colony stimulating factor ("GM-CSF"), and granulocyte colony stimulating factor ("G-CSF")), or a growth factor (e.g., growth hormone ("GH")), or a coagulation agent (e.g., calcium, vitamin K, tissue factors, such as but not limited to, Hageman factor (factor XII), high-molecular-weight kininogen (HMWK), prekallikrein (PK), coagulation proteins-factors II (prothrombin), factor V, XIIa, VIII, XIIIa, XI, XIa, IX, IXa, X, phospholipid, and fibrin monomer).

Provided herein are antibodies recombinantly fused or chemically conjugated (covalent or non-covalent conjugations) to a heterologous protein or polypeptide (or fragment thereof, preferably to a polypeptide of about 10, about 20, about 30, about 40, about 50, about 60, about 70, about 80, about 90 or about 100 amino acids) to generate fusion proteins. In particular, provided herein are fusion proteins comprising an antigen-binding fragment of an antibody described herein (e.g., a Fab fragment, Fd fragment, Fv fragment, F(ab)$_2$ fragment, a VH domain, a VH CDR, a VL domain or a VL CDR) and a heterologous protein, polypeptide, or peptide. In one embodiment, the heterologous protein, polypeptide, or peptide that the antibody is fused to is useful for targeting the antibody to a particular cell type, such as a cell that expresses KIT. For example, an antibody that immunospecifically binds to a cell surface receptor expressed by a particular cell type (e.g., an immune cell) can be fused or conjugated to a modified antibody described herein. In specific embodiments, the heterologous protein or polypeptide (or fragment thereof) binds to a second target (e.g., a target other than KIT) (see, e.g., PCT International Patent Application Publication No. WO 2009/088805 and U.S. Patent Application Publication No. US 2009/0148905).

Provided herein is a conjugated or fusion protein comprising any antibody described herein, or an antigen-binding fragment thereof, and a heterologous polypeptide (e.g., a polypeptide other than KIT). In one embodiment, a conjugated or fusion protein described herein comprises an anti-KIT antibody described herein, and a heterologous polypeptide. In another embodiment, a conjugated or fusion protein provided herein comprises an antigen-binding fragment of an anti-KIT antibody described herein, and a heterologous polypeptide. In another embodiment, a conjugated or fusion protein described herein comprises a VH domain having the amino acid sequence of any one of the VH domains of an anti-KIT antibody described herein, and/or a VL domain having the amino acid sequence of any one of the VL domains of an anti-KIT antibody described herein, and a heterologous polypeptide. In another embodiment, a conjugated or fusion protein described herein comprises one or more VH CDRs having the amino acid sequence of any one of SEQ ID NO: 16, 17, and 18 (see, e.g., Table 1), or the amino acid sequence of any one of the CDRs set forth in Table 2 or 3, and a heterologous polypeptide. In another embodiment, a conjugated or fusion protein comprises one or more VL CDRs having the amino acid sequence of any one of the VL CDRs of an anti-KIT antibody described herein (e.g., VL CDRs in Table 1, SEQ ID NOs: 19, 20, and 21, or VL CDRs of Table 2 or Table 3), and a heterologous polypeptide. In another embodiment, a conjugated or fusion protein described herein comprises at least one VH domain and at least one VL domain of an anti-KIT antibody described herein, and a heterologous polypeptide. In another embodiment, a conjugated or fusion protein described herein comprises at least one VH domain and at least a VL domain comprising SEQ ID NO: 7, 8, 9, 10, or 12 or a sequence set forth in Tables 5B and 5D, and/or VH domain comprising SEQ ID NO: 2, 3, 4, 5, 6, or 11 or a sequence set forth in Tables 5A and 5C, and a heterologous polypeptide. In yet another embodiment, a conjugated or fusion protein described herein comprises at least one VH CDR and at least one VL CDR of an anti-KIT antibody described herein (e.g., VL CDRs and VH CDRs in Table 1 or Table 2 or Table 3), and a heterologous polypeptide.

In addition, an antibody described herein can be conjugated to therapeutic moieties such as a radioactive metal ion, such as alpha-emitters such as $^{213}$Bi or macrocyclic chelators useful for conjugating radiometal ions, including but not limited to, $^{131}$In, $^{131}$LU, $^{131}$Y, $^{131}$Ho, $^{131}$Sm, to polypeptides. In certain embodiments, the macrocyclic chelator is 1,4,7,10-tetraazacyclododecane-N,N',N'',N'''-tetraacetic acid (DOTA) which can be attached to the antibody via a linker molecule. Such linker molecules are commonly known in the art and described in Denardo et al., 1998, Clin Cancer Res. 4(10):2483-90; Peterson et al., 1999, Bioconjug. Chem. 10(4):553-7; and Zimmerman et al., 1999, Nucl. Med. Biol. 26(8):943-50, each incorporated by reference in their entireties.

In certain embodiments, an antibody described herein, or an antigen-binding fragment thereof, is conjugated to one or more molecules (e.g., therapeutic or drug moiety) directly or indirectly via one or more linker molecules. In particular embodiments, a linker is an enzyme-cleavable linker or a disulfide linker. In a specific embodiment, the cleavable linker is cleavable via an enzyme such an aminopeptidase, an aminoesterase, a dipeptidyl carboxy peptidase, or a protease of the blood clotting cascade. In particular embodiments, a linker comprises 1, 2, 3, 4, 5, 6, 7, 8, 9, 10, 11, 12, 13, 14, 15, or 20 amino acid residues. In certain embodiments, a linker consists of 1 to 10 amino acid residues, 1 to 15 amino acid residues, 5 to 20 amino acid residues, 10 to 25 amino acid residues, 10 to 30 amino acid residues, or 10 to 50 amino acid residues.

In certain embodiments, a moiety is conjugated to an antibody by one or more linkers. In a particular embodiment, a moiety is hydrolyzed from the antibody-drug conjugate at the linker. In one embodiment, a moiety is hydrolyzed from the antibody conjugate at the linker between about a pH of 3.0 and pH 4.0 for about 1-24 hours, and at a temperature from about 20 to 50° C., preferably 37° C. In a specific embodiment, a linker is stable in the blood stream but releases the conjugated moiety once it is inside the targeted cells. In certain embodiments, a moiety is conjugated to an antibody described herein via one or more triazole-containing linkers (see, e.g., International Patent Application Publication No. WO 2007/018431, which is incorporated herein by reference). Non-limiting examples of linkers and spacers for incorporation into antibody-drug conjugates described herein are disclosed in PCT International Patent Application Publication Nos. WO 2007/018431, WO 2004/043493, and WO 2002/083180.

Moreover, antibodies described herein can be fused to marker sequences, such as a peptide to facilitate purification. In preferred embodiments, the marker amino acid sequence is a hexa-histidine peptide, such as the tag provided in a pQE vector (QIAGEN, Inc.), among others, many of which are commercially available. As described in Gentz et al., 1989, Proc. Natl. Acad. Sci. USA 86:821-824, for instance, hexa-histidine provides for convenient purification of the fusion protein. Other peptide tags useful for purification include, but are not limited to, the hemagglutinin ("HA") tag, which corresponds to an epitope derived from the influenza hemagglutinin protein (Wilson et al., 1984, Cell 37:767), and the "FLAG" tag.

Methods for fusing or conjugating therapeutic moieties (including polypeptides) to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies 84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), Thorpe et al., 1982, Immunol. Rev. 62:119-58; U.S. Pat. Nos. 5,336,603, 5,622,929, 5,359,046, 5,349,053, 5,447,851, 5,723,125, 5,783,181, 5,908,626, 5,844,095, and 5,112,946; EP 307,434; EP 367, 166; EP 394,827; PCT publications WO 91/06570, WO 96/04388, WO 96/22024, WO 97/34631, and WO 99/04813; Ashkenazi et al., Proc. Natl. Acad. Sci. USA, 88: 10535-10539, 1991; Traunecker et al., Nature, 331:84-86, 1988; Zheng et al., J. Immunol., 154:5590-5600, 1995; Vil et al., Proc. Natl. Acad. Sci. USA, 89:11337-11341, 1992, which are incorporated herein by reference in their entireties.

Fusion proteins can be generated, for example, through the techniques of gene-shuffling, motif-shuffling, exon-shuffling, and/or codon-shuffling (collectively referred to as "DNA shuffling"). DNA shuffling can be employed to alter the activities of antibodies described herein (e.g., antibodies with higher affinities and lower dissociation rates). See, generally, U.S. Pat. Nos. 5,605,793, 5,811,238, 5,830,721, 5,834,252, and 5,837,458; Patten et al., 1997, Curr. Opinion Biotechnol. 8:724-33; Harayama, 1998, Trends Biotechnol. 16(2):76-82; Hansson et al., 1999, J. Mol. Biol. 287:265-76; and Lorenzo and Blasco, 1998, Biotechniques 24(2):308-313 (each of these patents and publications is hereby incorporated by reference). Antibodies, or the encoded antibodies, can be altered by being subjected to random mutagenesis by error-prone PCR, random nucleotide insertion or other methods prior to recombination. A polynucleotide encoding an antibody described herein can be recombined with one or more components, motifs, sections, parts, domains, fragments, etc. of one or more heterologous molecules.

An antibody described herein can also be conjugated to a second antibody to form an antibody heteroconjugate as described in U.S. Pat. No. 4,676,980, which is incorporated herein by reference.

The therapeutic moiety or drug conjugated or recombinantly fused to an antibody described herein that immunospecifically binds to a KIT antigen can be chosen to achieve the desired prophylactic or therapeutic effect(s), e.g., reducing tumor size or burden, reducing cancer cell growth or proliferation, or inducing death of cancer cells. In certain embodiments, the antibody is a modified antibody. A clinician or other medical personnel should consider the following when deciding on which therapeutic moiety or drug to conjugate or recombinantly fuse to an antibody described herein: the nature of the disease, the severity of the disease, and the condition of the subject.

Antibodies described herein can also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

In a certain aspect, an antibody described herein or an antigen-binding fragment thereof is an extracellular drug conjugate (ECD) comprising an antibody linked to a drug, optionally by a linker (see, e.g., PCT International Patent Application Publication No. WO 2011/031870). The drug can act outside of the cell, and thus internalization of the conjugate is not required. After an ECD binds a target cell, the drug sends a signal into the cell.

In one embodiment, the linker of the ECD is a non-cleavable linker. Examples of non-cleavable linkers include linkers that contain polyethylene glycol chains or polyethylene chains that are not acid or base sensitive (such as hydrazone containing linkers), are not sensitive to reducing or oxidizing agents (such as those containing disulfide linkages), and are not sensitive to enzymes that may be found in cells or circulatory system. Specific examples of non-cleavable linkers include SMCC linker (US Patent Application 20090202536). For illustrative purposes, examples of cleavable linkers include linkers that contain non-hindered glutathione sensitive disulfides, esters, peptide sequences sensitive to the peptidases such as cathepsin or plasmin, pH sensitive hydrazones (see Bioconjugate Chem., 2010, 21 (1), pp 5-13) and non-hindered disulfide linker SPP (US Patent Application 20090202536).

In certain aspects, an ECD comprises a drug or agent that is a cardiac glycoside, for example, proscillaridin or a sugar-enhanced proscillaridin. In one embodiment, the agent is composed from a cardiac glycoside which is void a sugar. In various embodiments, the cardiac glycoside is a compound identified in PCT Pub. No. WO 2010/017480 (PCT/US2009/053159).

5.2 Polynucleotides

In certain aspects, provided herein are polynucleotides comprising a nucleotide sequence encoding an antibody (e.g., human or humanized antibody) described herein or a fragment thereof (e.g., a variable light chain region and/or variable heavy chain region) that immunospecifically binds to a KIT antigen, and vectors, e.g., vectors comprising such polynucleotides for recombinant expression in host cells (e.g., E. coli and mammalian cells). Provided herein are polynucleotides comprising nucleotide sequences encoding any of the antibodies provided herein, as well as vectors comprising such polynucleotide sequences, e.g., expression vectors for their efficient expression in host cells, e.g., mammalian cells. Also provided herein are polynucleotides encoding KIT antigens (e.g., SEQ ID NO: 14 or 15) for generating anti-KIT antibodies described herein.

As used herein, an "isolated" polynucleotide or nucleic acid molecule is one which is separated from other nucleic acid molecules which are present in the natural source (e.g., in a human) of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. For example, the language "substantially free" includes preparations of polynucleotide or nucleic acid molecule having less than about 15%, 10%, 5%, 2%, 1%, 0.5%, or 0.1% (in particular less than about 10%) of other material, e.g., cellular material, culture medium, other nucleic acid molecules, chemical precursors and/or other chemicals. In a specific embodiment, a nucleic acid molecule(s) encoding an antibody described herein is isolated or purified.

In particular aspects, provided herein are polynucleotides comprising nucleotide sequences encoding antibodies (e.g., a humanized antibody) or antigen-binding fragments thereof, which immunospecifically bind to a KIT polypeptide (e.g., the D4 region of KIT, for example, human KIT) and comprises an amino acid sequence as described herein, as well as antibodies which compete with such antibodies for binding to a KIT polypeptide (e.g., in a dose-dependent manner), or which binds to the same epitope as that of such antibodies.

In certain aspects, provided herein are polynucleotides comprising a nucleotide sequence encoding the light chain or heavy chain of an antibody described herein. The polynucleotides can comprise nucleotide sequences encoding a light chain comprising the VL FRs and CDRs of antibodies described herein (see, e.g., Tables 1 and 5B). The polynucleotides can comprise nucleotide sequences encoding a heavy chain comprising the VH FRs and CDRs of antibodies described herein (see, e.g., Tables 1 and 5A). In specific embodiments, a polynucleotide described herein encodes a VL chain region comprising the amino acid sequence of SEQ ID NO: 7, 8, 9 or 10. In specific embodiments, a polynucleotide described herein encodes a VH chain region comprising the amino acid sequence of any one of SEQ ID NOs: 2-6.

In particular embodiments, a polynucleotide described herein encodes a VL chain region, wherein the polynucleotide comprises the nucleic acid sequence of SEQ ID NO: 27, 28, 29, or 30. In particular embodiments, a polynucleotide described herein encodes a VH chain region, wherein the polynucleotide comprises the nucleic acid sequence of SEQ ID NO: 22, 23, 24, 25, or 26. In particular embodiments, a polynucleotide encodes an antibody described herein, wherein the polynucleotide comprises the nucleic acid sequence of SEQ ID NO: 28 encoding a L2 VL chain region and the nucleic acid sequence of SEQ ID NO: 24 encoding a H3 VH chain region. In particular embodiments, one or more polynucleotides comprise the nucleic acid sequence of SEQ ID NO: 28 encoding a VL chain region and the nucleic acid sequence of SEQ ID NO: 24 encoding a VH chain region. In particular embodiments, a polynucleotide encodes an antibody described herein, wherein the polynucleotide comprises the nucleic acid sequence of SEQ ID NO: 27 encoding a L1 VL chain region and the nucleic acid sequence of SEQ ID NO: 25 encoding a H4 VH chain region. In particular embodiments, one or more polynucleotides comprise the nucleic acid sequence of SEQ ID NO: 27 encoding a VL chain region and the nucleic acid sequence of SEQ ID NO: 25 encoding a VH chain region. In particular embodiments, a polynucleotide described herein encodes a VL chain region, wherein the polynucleotide comprises a nucleic acid sequence that is at least 80%, at least 85%, at least 90%, at least 95%, or at least 98% identical to the nucleic acid sequence of SEQ ID NO: 27, 28, 29, or 30. In particular embodiments, a polynucleotide described herein encodes a VH chain region, wherein the polynucleotide comprises a nucleic acid sequence that is at least 80%, at least 85%, at least 90%, at least 95%, or at least 98% identical to the nucleic acid sequence of SEQ ID NO: 22, 23, 24, 25, or 26.

In particular embodiments, provided herein are polynucleotides comprising a nucleotide sequence encoding an anti-KIT antibody comprising a VL chain region, e.g., containing FR1-CDR1-FR2-CDR2-FR3-CDR3-FR4, comprising an amino acid sequences described herein (e.g., see Tables 1, 5A-5B, and 6A-6B). In specific embodiments, provided herein are polynucleotides comprising a nucleotide sequence encoding an anti-KIT antibody comprising a VH chain region, e.g., containing FR1-CDR1-FR2-CDR2-FR3-CDR3-FR4, comprising an amino acid sequence described herein (e.g., see Tables 1, 5A-5B, and 6A-6B).

In certain embodiments, a polynucleotide described herein comprises a nucleotide sequence encoding an antibody provided herein comprising a variable light (VL) chain region comprising an amino acid described herein (e.g., see FIGS. 3A-3I), wherein the antibody immunospecifically binds to a KIT polypeptide, e.g., a human KIT polypeptide, for example, a D4 region of KIT (e.g., human KIT), for example SEQ ID NO: 15.

In certain embodiments, a polynucleotide described herein comprises a nucleotide sequence encoding an antibody provided herein comprising a variable heavy (VH) chain region comprising an amino acid sequence described herein (e.g., see FIGS. 3A-3I), wherein the antibody immunospecifically binds to a KIT polypeptide, e.g., a human KIT polypeptide, for example, a D4 region of KIT (e.g., human KIT), for example SEQ ID NO: 15.

In certain aspects, a polynucleotide comprises a nucleotide sequence encoding an antibody (e.g., human or humanized antibody) described herein comprising a VL chain region comprising one or more VL FRs having the amino acid sequence described herein (e.g., see Tables 5B and 5D), wherein the antibody immunospecifically binds to a KIT polypeptide, e.g., a human KIT polypeptide, for example, a D4 region of KIT (e.g., human KIT), for example SEQ ID NO: 15. In certain aspects, a polynucleotide comprises a nucleotide sequence encoding an antibody described herein comprising a VH chain region comprising one or more VH FRs having the amino acid sequence described herein (e.g., see Tables 5A and 5C), wherein the antibody immunospecifically binds to a KIT polypeptide, e.g., a human KIT polypeptide, for example, a D4 region of KIT (e.g., human KIT), for example SEQ ID NO: 15.

In specific embodiments, a polynucleotide provided herein comprises a nucleotide sequence encoding an antibody (e.g., human or humanized antibody) described herein comprising: framework regions (e.g., framework regions of the VL domain and VH domain) that are human framework regions, wherein the antibody immunospecifically binds to a KIT polypeptide, e.g., a human KIT polypeptide, for example, a D4 region of KIT (e.g., human KIT, for example SEQ ID NO: 15).

In specific aspects, provided herein is a polynucleotide comprising a nucleotide sequence encoding an antibody comprising a light chain and a heavy chain, e.g., a separate light chain and heavy chain. With respect to the light chain, in a specific embodiment, a polynucleotide provided herein comprises a nucleotide sequence encoding a kappa light chain. In another specific embodiment, a polynucleotide provided herein comprises a nucleotide sequence encoding a lambda light chain. In yet another specific embodiment, a polynucleotide provided herein comprises a nucleotide sequence encoding an antibody described herein comprising a human kappa light chain or a human lambda light chain. In a particular embodiment, a polynucleotide provided herein comprises a nucleotide sequence encoding an antibody described herein, which immunospecifically binds to a KIT polypeptide (e.g., a KIT polypeptide comprising a D4 region of KIT, for example human KIT (e.g., SEQ ID NO: 15)), wherein the antibody comprises a light chain, and wherein the amino acid sequence of the VL chain region can comprise any amino acid sequence described herein (e.g., SEQ ID NO: 7, 8, 9, or 10 or 12), and wherein the constant region of the light chain comprises the amino acid sequence of a human kappa light chain constant region. In a particular embodiment, the light chain comprises the amino acid sequence of SEQ ID NO: 12. In another particular embodiment, a polynucleotide provided herein comprises a nucleotide sequence encoding an antibody described herein, which immunospecifically binds to a KIT polypeptide (e.g., a KIT polypeptide comprising a D4 region of KIT, for example human KIT (e.g., SEQ ID NO: 15)), and comprises a light chain, wherein the amino acid sequence of the VL chain region can comprises any amino acid sequence described herein (e.g., SEQ ID NO: 7, 8, 9, or 10 or 12), and wherein the constant region of the light chain comprises the amino acid sequence of a human lambda light chain constant region. For example, human constant region sequences can be those described in U.S. Pat. No. 5,693,780.

In a particular embodiment, a polynucleotide provided herein comprises a nucleotide sequence encoding an antibody described herein, which immunospecifically binds to a KIT polypeptide (e.g., a KIT polypeptide comprising a KIT polypeptide comprising a D4 region of KIT, for example human KIT (e.g., SEQ ID NO: 15)), wherein the antibody comprises a heavy chain, wherein the amino acid sequence of the VH chain region can comprise any amino acid sequence described herein (e.g., SEQ ID NO: 2, 3, 4, 5, or 6 or 11), and wherein the constant region of the heavy chain comprises the amino acid sequence of a human gamma (γ) heavy chain constant region.

In yet another specific embodiment, a polynucleotide provided herein comprises a nucleotide sequence encoding an antibody described herein (or an antigen-binding fragment thereof), which immunospecifically binds to a KIT polypeptide (e.g., a D4 region of KIT, for example human KIT), wherein the antibody comprises a VL chain region and a VH chain region comprising any amino acid sequences described herein, and wherein the constant regions comprise the amino acid sequences of the constant regions of a human IgG1 (e.g., isotype a, z, or f) or human IgG4.

In a specific embodiment, provided herein are polynucleotides comprising a nucleotide sequence encoding an anti-KIT antibody, or an antigen-binding fragment or domain thereof, designated herein, see, e.g., Tables 1-6B and FIGS. 3A-3I, for example antibody Hum1-Hum20.

Also provided herein are polynucleotides encoding an anti-KIT antibody or a fragment thereof that are optimized, e.g., by codon/RNA optimization, replacement with heterologous signal sequences, and elimination of mRNA instability elements. Methods to generate optimized nucleic acids encoding an anti-KIT antibody or a fragment thereof (e.g., light chain, heavy chain, VH domain, or VL domain) for recombinant expression by introducing codon changes and/ or eliminating inhibitory regions in the mRNA can be carried out by adapting the optimization methods described in, e.g., U.S. Pat. Nos. 5,965,726; 6,174,666; 6,291,664; 6,414,132; and 6,794,498, accordingly. For example, potential splice sites and instability elements (e.g., A/T or A/U rich elements) within the RNA can be mutated without altering the amino acids encoded by the nucleic acid sequences to increase stability of the RNA for recombinant expression. The alterations utilize the degeneracy of the genetic code, e.g., using an alternative codon for an identical amino acid. In some embodiments, it can be desirable to alter one or more codons to encode a conservative mutation, e.g., a similar amino acid with similar chemical structure and properties and/or function as the original amino acid. Such methods can increase expression of an anti-KIT antibody or fragment thereof by at least 1 fold, 2 fold, 3 fold, 4 fold, 5 fold, 10 fold, 20 fold, 30 fold, 40 fold, 50 fold, 60 fold, 70 fold, 80 fold, 90 fold, or 100 fold or more relative to the expression of an anti-KIT antibody encoded by polynucleotides that have not been optimized.

In certain embodiments, an optimized polynucleotide sequence encoding an anti-KIT antibody described herein or a fragment thereof (e.g., VL domain and/or VH domain) can hybridize to an antisense (e.g., complementary) polynucleotide of an unoptimized polynucleotide sequence encoding an anti-KIT antibody described herein or a fragment thereof (e.g., VL domain and/or VH domain). In specific embodiments, an optimized nucleotide sequence encoding an anti-KIT antibody described herein or a fragment hybridizes under high stringency conditions to antisense polynucleotide of an unoptimized polynucleotide sequence encoding an anti-KIT antibody described herein or a fragment thereof. In a specific embodiment, an optimized nucleotide sequence encoding an anti-KIT antibody described herein or a fragment thereof hybridizes under high stringency, intermediate or lower stringency hybridization conditions to an antisense polynucleotide of an unoptimized nucleotide sequence encoding an anti-KIT antibody described herein or a fragment thereof. Information regarding hybridization conditions have been described, see, e.g., U.S. Patent Application Publication No. US 2005/0048549 (e.g., paragraphs 72-73), which is incorporated herein by reference.

In certain embodiments, an optimized polynucleotide sequence encoding a VL region of an antibody described herein is at least 75%, at least 80%, at least 85%, at least 90%, at least 95%, at least 98% identical to the nucleotide sequence of SEQ ID NO: 27, 28, 29, or 30. In certain embodiments, an optimized polynucleotide sequence encoding a VH region of an antibody described herein is at least 75%, at least 80%, at least 85%, at least 90%, at least 95%, at least 98% identical to the nucleotide sequence of SEQ ID NO: 22, 23, 24, 25, or 26.

The polynucleotides can be obtained, and the nucleotide sequence of the polynucleotides determined, by any method known in the art. Nucleotide sequences encoding antibodies described herein, e.g., antibodies described in Tables 1-6B and FIGS. 3A-3I, and modified versions of these antibodies can be determined using methods well known in the art, i.e., nucleotide codons known to encode particular amino acids are assembled in such a way to generate a nucleic acid that encodes the antibody. Such a polynucleotide encoding the antibody can be assembled from chemically synthesized oligonucleotides (e.g., as described in Kutmeier et al., 1994, BioTechniques 17:242), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody described herein can be generated from nucleic acid from a suitable source (e.g., a hybridoma) using methods well known in the art (e.g., PCR and other molecular cloning methods). For example, PCR amplification using synthetic primers hybridizable to the 3' and 5' ends of a known sequence can be performed using genomic DNA obtained from hybridoma cells producing the antibody of interest. Such PCR amplification methods can be used to obtain nucleic acids comprising the sequence encoding the light chain and/or heavy chain of an antibody. Such PCR amplification methods can be used to obtain nucleic acids comprising the sequence encoding the variable light chain region and/or the variable heavy chain region of an antibody. The amplified nucleic acids can be cloned into vectors for expression in host cells and for further cloning, for example, to generate chimeric and humanized antibodies.

If a clone containing a nucleic acid encoding a particular antibody is not available, but the sequence of the antibody molecule is known, a nucleic acid encoding the immunoglobulin can be chemically synthesized or obtained from a suitable source (e.g., an antibody cDNA library or a cDNA library generated from, or nucleic acid, preferably poly A+RNA, isolated from, any tissue or cells expressing the antibody, such as hybridoma cells selected to express an antibody described herein) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR can then be cloned into replicable cloning vectors using any method well known in the art.

DNA encoding anti-KIT antibodies described herein can be readily isolated and sequenced using conventional procedures (e.g., by using oligonucleotide probes that are capable of binding specifically to genes encoding the heavy and light chains of the anti-KIT antibodies). Hybridoma cells can serve as a source of such DNA. Once isolated, the DNA can be placed into expression vectors, which are then transfected into host cells such as E. coli cells, simian COS cells, Chinese hamster ovary (CHO) cells (e.g., CHO cells from the CHO GS System™ (Lonza)), or myeloma cells that do not otherwise produce immunoglobulin protein, to obtain the synthesis of anti-KIT antibodies in the recombinant host cells.

To generate whole antibodies, PCR primers including VH or VL nucleotide sequences, a restriction site, and a flanking sequence to protect the restriction site can be used to amplify the VH or VL sequences in scFv clones. Utilizing cloning techniques known to those of skill in the art, the PCR amplified VH domains can be cloned into vectors expressing a heavy chain constant region, e.g., the human gamma 4 constant region, and the PCR amplified VL domains can be cloned into vectors expressing a light chain constant region, e.g., human kappa or lambda constant regions. In certain embodiments, the vectors for expressing the VH or VL domains comprise an EF-1α promoter, a secretion signal, a cloning site for the variable domain, constant domains, and a selection marker such as neomycin. The VH and VL domains can also be cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

The DNA also can be modified, for example, by substituting the coding sequence for human heavy and light chain constant domains in place of the murine sequences, or by covalently joining to the immunoglobulin coding sequence all or part of the coding sequence for a non-immunoglobulin polypeptide.

Also provided are polynucleotides that hybridize under high stringency, intermediate or lower stringency hybridization conditions to polynucleotides that encode an antibody described herein. In specific embodiments, polynucleotides described herein hybridize under high stringency, intermediate or lower stringency hybridization conditions to polynucleotides encoding a VH chain region (e.g., SEQ ID NO: 2, 3, 4, 5, or 6) and/or VL chain region (e.g., SEQ ID NO: 7, 8, 9, or 10) provided herein. In specific embodiments, polynucleotides described herein hybridize under high stringency or intermediate stringency hybridization conditions to polynucleotides which are complements to polynucleotides encoding a VH chain region (e.g., SEQ ID NO: 3 or 5) and/or VL chain region (e.g., a SEQ ID NO: 2) provided herein.

In specific embodiments, polynucleotides described herein hybridize under high stringency, intermediate or lower stringency hybridization conditions to polynucleotides which are complements to a polynucleotide comprising SEQ ID NO: 27, 28, 29, or 30 encoding a VL domain. In specific embodiments, polynucleotides described herein hybridize under high stringency or intermediate stringency hybridization conditions to polynucleotides which are complements to a polynucleotide comprising SEQ ID NO: 22, 23, 24, 25, or 26 encoding a VH domain.

Hybridization conditions have been described in the art and are known to one of skill in the art. For example, hybridization under stringent conditions can involve hybridization to filter-bound DNA in 6× sodium chloride/sodium citrate (SSC) at about 45° C. followed by one or more washes in 0.2×SSC/0.1% SDS at about 50-65° C.; hybridization under highly stringent conditions can involve hybridization to filter-bound nucleic acid in 6×SSC at about 45° C. followed by one or more washes in 0.1×SSC/0.2% SDS at about 68° C. Hybridization under other stringent hybridization conditions are known to those of skill in the art and have been described, see, for example, Ausubel, F. M. et al., eds., 1989, Current Protocols in Molecular Biology, Vol. I, Green Publishing Associates, Inc. and John Wiley & Sons, Inc., New York at pages 6.3.1-6.3.6 and 2.10.3.

5.3 Host Cells and Recombinant Expression of Antibodies

In certain aspects, provided herein are host cells recombinantly expressing the antibodies described herein (or an antigen-binding fragment thereof) and related expression vectors. Provided herein are vectors (e.g., expression vectors) comprising polynucleotides comprising nucleotide sequences encoding anti-KIT antibodies or a fragment for recombinant expression in host cells, preferably in mammalian cells. Also provided herein are host cells comprising such vectors for recombinantly expressing anti-KIT antibodies described herein (e.g., human or humanized antibody). In a particular aspect, provided herein are methods for producing an antibody described herein, comprising expressing such antibody from a host cell.

Recombinant expression of an antibody described herein (e.g., a full-length antibody, heavy and/or light chain of an antibody, or a single chain antibody described herein) that immunospecifically binds to a KIT antigen involves construction of an expression vector containing a polynucleotide that encodes the antibody. Once a polynucleotide encoding an antibody molecule, heavy and/or light chain of an antibody, or fragment thereof (preferably, but not necessarily, containing the heavy and/or light chain variable domain) described herein has been obtained, the vector for the production of the antibody molecule can be produced by recombinant DNA technology using techniques well-known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. Also provided are replicable vectors comprising a nucleotide sequence encoding an antibody molecule described herein, a heavy or light chain of an antibody, a heavy or light chain variable domain of an antibody or a fragment thereof, or a heavy or light chain CDR, operably linked to a promoter. Such vectors can, for example, include the nucleotide sequence encoding the constant region of the antibody molecule (see, e.g., International Publication Nos. WO 86/05807 and WO 89/01036; and U.S. Pat. No. 5,122,464) and the variable domain of the antibody can be cloned into such a vector for expression of the entire heavy, the entire light chain, or both the entire heavy and light chains.

An expression vector can be transferred to a cell (e.g., host cell) by conventional techniques and the resulting cells can then be cultured by conventional techniques to produce an antibody described herein or a fragment thereof. Thus, provided herein are host cells containing a polynucleotide encoding an antibody described herein or fragments thereof, or a heavy or light chain thereof, or fragment thereof, or a single chain antibody described herein, operably linked to a promoter for expression of such sequences in the host cell. In certain embodiments, for the expression of double-chained antibodies, vectors encoding both the heavy and light chains, individually, can be co-expressed in the host cell for expression of the entire immunoglobulin molecule, as detailed below. In certain embodiments, a host cell contains a vector comprising a polynucleotide encoding both the heavy chain and light chain of an antibody described herein, or a fragment thereof. In specific embodiments, a host cell contains two different vectors, a first vector comprising a polynucleotide encoding a heavy chain of an antibody described herein, or a fragment thereof, and a second vector comprising a polynucleotide encoding a light chain of an antibody described herein, or a fragment thereof. In other embodiments, a first host cell comprises a first vector comprising a polynucleotide encoding a heavy chain of an antibody described herein, or a fragment thereof, and a second host cell comprises a second vector comprising a polynucleotide encoding a light chain of an antibody described herein.

A variety of host-expression vector systems can be utilized to express antibody molecules described herein (see, e.g., U.S. Pat. No. 5,807,715). Such host-expression systems represent vehicles by which the coding sequences of interest can be produced and subsequently purified, but also represent cells which can, when transformed or transfected with the appropriate nucleotide coding sequences, express an antibody molecule described herein in situ. These include but are not limited to microorganisms such as bacteria (e.g., *E. coli* and *B. subtilis*) transformed with recombinant bacteriophage DNA, plasmid DNA or cosmid DNA expression vectors containing antibody coding sequences; yeast (e.g., *Saccharomyces Pichia*) transformed with recombinant yeast expression vectors containing antibody coding sequences; insect cell systems infected with recombinant virus expression vectors (e.g., baculovirus) containing antibody coding sequences; plant cell systems (e.g., green algae such as *Chlamydomonas reinhardtii*) infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, MDCK, HEK 293, NS0, PER.C6, VERO, CRL7O3O, HsS78Bst, HeLa, and NIH 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). In a specific embodiment, cells for expressing antibodies described herein (e.g., Hum1-Hum20) or an antigen-binding fragment thereof are CHO cells, for example CHO cells from the CHO GS System™ (Lonza). In a specific embodiment, a mammalian expression vector is pOptiVEC™ or pcDNA3.3. Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary (CHO) cells, in conjunction with a vector such as the major intermediate early gene promoter element from human cytomegalovirus is an effective expression system for antibodies (Foecking et al., 1986, Gene 45:101; and Cockett et al., 1990, Bio/Technology 8:2). In certain embodiments, antibodies described herein are produced by CHO cells or NS0 cells. In a specific embodiment, the expression of nucleotide sequences encoding antibodies described herein which immunospecifically bind to a KIT antigen is regulated by a constitutive promoter, inducible promoter or tissue specific promoter.

In bacterial systems, a number of expression vectors can be advantageously selected depending upon the use intended for the antibody molecule being expressed. For example, when a large quantity of such an antibody is to be produced, for the generation of pharmaceutical compositions of an antibody molecule, vectors which direct the expression of high levels of fusion protein products that are readily purified can be desirable. Such vectors include, but are not limited to, the *E. coli* expression vector pUR278 (Ruther et al., 1983, EMBO 12:1791), in which the antibody coding sequence can be ligated individually into the vector in frame with the lac Z coding region so that a fusion protein is produced; pIN vectors (Inouye & Inouye, 1985, Nucleic Acids Res. 13:3101-3109; Van Heeke & Schuster, 1989, J. Biol. Chem. 24:5503-5509); and the like. pGEX vectors can also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence can be cloned individually into non-essential regions (for example the polyhedrin gene) of the virus and placed under control of an AcNPV promoter (for example the polyhedrin promoter).

In mammalian host cells, a number of viral-based expression systems can be utilized. In cases where an adenovirus is used as an expression vector, the antibody coding sequence of interest can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts (e.g., see Logan & Shenk, 1984, Proc. Natl. Acad. Sci. USA 8 1:355-359). Specific initiation signals can also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, etc. (see, e.g., Bittner et al., 1987, Methods in Enzymol. 153:51-544).

In addition, a host cell strain can be chosen which modulates the expression of the inserted sequences, or modifies and processes the gene product in the specific fashion desired. Such modifications (e.g., glycosylation) and processing (e.g., cleavage) of protein products can be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product can be used. Such mammalian host cells include but are not limited to CHO, VERO, BHK, Hela, COS, MDCK, HEK 293, NIH 3T3, W138, BT483, Hs578T, HTB2, BT2O and T47D, NS0 (a murine myeloma cell line that does not endogenously produce any immunoglobulin chains), CRL7O3O and HsS78Bst cells. In certain embodiments, humanized monoclonal anti-KIT antibodies described herein are produced in mammalian cells, such as CHO cells.

For long-term, high-yield production of recombinant proteins, stable expression is preferred. For example, cell lines which stably express the antibody molecule can be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells can be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method can advantageously be used to engineer cell lines which express the antibody molecule. Such engineered cell lines can be particularly useful in screening and evaluation of compositions that interact directly or indirectly with the antibody molecule.

A number of selection systems can be used, including but not limited to, the herpes simplex virus thymidine kinase (Wigler et al., 1977, Cell 11:223), hypoxanthineguanine phosphoribosyltransferase (Szybalska & Szybalski, 1992, Proc. Natl. Acad. Sci. USA 48:202), and adenine phosphoribosyltransferase (Lowy et al., 1980, Cell 22:8-17) genes can be employed in tk-, hgprt- or aprt-cells, respectively. Also, antimetabolite resistance can be used as the basis of selection for the following genes: dhfr, which confers resistance to methotrexate (Wigler et al., 1980, Natl. Acad. Sci. USA 77:357; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Wu and Wu, 1991, Biotherapy 3:87-95; Tolstoshev, 1993, Ann. Rev. Pharmacol. Toxicol. 32:573-596; Mulligan, 1993, Science 260:926-932; and Morgan and Anderson, 1993, Ann. Rev. Biochem. 62:191-217; May, 1993, TIB TECH 11(5):155-215); and hygro, which confers resistance to hygromycin (Santerre et al., 1984, Gene 30:147). Methods commonly known in the art of recombinant DNA technology can be routinely applied to select the desired recombinant clone, and such methods are described, for example, in Ausubel et al. (eds.), *Current Protocols in Molecular Biology*, John Wiley & Sons, N Y (1993); Kriegler, *Gene Transfer and Expression*, A Laboratory Manual, Stockton Press, N Y (1990); and in Chapters 12 and 13, Dracopoli et al. (eds.), *Current Protocols in Human Genetics*, John Wiley & Sons, N Y (1994); Colberre-Garapin et al., 1981, J. Mol. Biol. 150:1, which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol. 3 (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., 1983, Mol. Cell. Biol. 3:257).

The host cell can be co-transfected with two or more expression vectors described herein, the first vector encoding a heavy chain derived polypeptide and the second vector encoding a light chain derived polypeptide. The two vectors can contain identical selectable markers which enable equal expression of heavy and light chain polypeptides. The host cells can be co-transfected with different amounts of the two or more expression vectors. For example, host cells can be transfected with any one of the following ratios of a first expression vector and a second expression vector: 1:1, 1:2, 1:3, 1:4, 1:5, 1:6, 1:7, 1:8, 1:9, 1:10, 1:12, 1:15, 1:20, 1:25, 1:30, 1:35, 1:40, 1:45, or 1:50.

Alternatively, a single vector can be used which encodes, and is capable of expressing, both heavy and light chain polypeptides. In such situations, the light chain should be placed before the heavy chain to avoid an excess of toxic free heavy chain (Proudfoot, 1986, Nature 322:52; and Kohler, 1980, Proc. Natl. Acad. Sci. USA 77:2197-2199). The coding sequences for the heavy and light chains can comprise cDNA or genomic DNA. The expression vector can be monocistronic or multicistronic. A multicistronic nucleic acid construct can encode 2, 3, 4, 5, 6, 7, 8, 9, 10 or more, or in the range of 2-5, 5-10 or 10-20 genes/nucleotide sequences. For example, a bicistronic nucleic acid construct can comprise in the following order a promoter, a first gene (e.g., heavy chain of an antibody described herein), and a second gene and (e.g., light chain of an antibody described herein). In such an expression vector, the transcription of both genes can be driven by the promoter, whereas the translation of the mRNA from the first gene can be by a cap-dependent scanning mechanism and the translation of the mRNA from the second gene can be by a cap-independent mechanism, e.g., by an IRES.

Once an antibody molecule described herein has been produced by recombinant expression, it can be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies described herein can be fused to heterologous polypeptide sequences described herein or otherwise known in the art to facilitate purification.

In specific embodiments, an antibody described herein is isolated or purified. Generally, an isolated antibody is one that is substantially free of other antibodies with different antigenic specificities than the isolated antibody. For example, in a particular embodiment, a preparation of an antibody described herein is substantially free of cellular material and/or chemical precursors. The language "substantially free of cellular material" includes preparations of an antibody in which the antibody is separated from cellular components of the cells from which it is isolated or recombinantly produced. Thus, an antibody that is substantially free of cellular material includes preparations of antibody having less than about 30%, 20%, 10%, 5%, 2%, 1%, 0.5%, or 0.1% (by dry weight) of heterologous protein (also referred to herein as a "contaminating protein") and/or variants of an antibody, for example, different post-translational modified forms of an antibody or other different versions of an antibody (e.g., antibody fragments). When the antibody is recombinantly produced, it is also generally substantially free of culture medium, i.e., culture medium represents less than about 20%, 10%, 2%, 1%, 0.5%, or 0.1% of the volume of the protein preparation. When the antibody is produced by chemical synthesis, it is generally substantially free of chemical precursors or other chemicals, i.e., it is separated from chemical precursors or other chemicals which are involved in the synthesis of the protein. Accordingly, such preparations of the antibody have less than about 30%, 20%, 10%, or 5% (by dry weight) of chemical precursors or compounds other than the antibody of interest. In a specific embodiment, antibodies described herein are isolated or purified.

5.4 Methods of Producing Antibodies

Antibodies (e.g., human or humanized antibodies) described herein (or an antigen-binding fragment thereof) that immunospecifically bind to a KIT antigen can be produced by any method known in the art for the synthesis of antibodies, for example, by chemical synthesis or by recombinant expression techniques. The methods described herein employs, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described in the references cited herein and are fully explained in the literature. See, e.g., Maniatis et al. (1982) *Molecular Cloning: A Laboratory Manual*, Cold Spring Harbor Laboratory Press; Sambrook et al. (1989), *Molecular Cloning: A Laboratory Manual*, Second Edition, Cold Spring Harbor Laboratory Press; Sambrook et al. (2001) *Molecular Cloning: A Laboratory Manual*, Cold Spring Harbor Laboratory Press, Cold Spring Harbor, N.Y.; Ausubel et al., *Current Protocols in Molecular Biology*, John Wiley & Sons (1987 and annual updates); *Current Protocols in Immunology*, John Wiley & Sons (1987 and annual updates) Gait (ed.) (1984) *Oligonucleotide Synthesis: A Practical Approach*, IRL Press; Eckstein (ed.) (1991) *Oligonucleotides and Analogues: A Practical Approach*, IRL Press; Birren et al. (eds.) (1999) *Genome Analysis: A Laboratory Manual*, Cold Spring Harbor Laboratory Press.

For example, humanized antibodies can be produced using a variety of techniques known in the art, including but not limited to, CDR-grafting (European Patent No. EP 239,400; International publication No. WO 91/09967; and U.S. Pat. Nos. 5,225,539, 5,530,101, and 5,585,089), veneering or resurfacing (European Patent Nos. EP 592,106 and EP 519,596; Padlan, 1991, Molecular Immunology 28(4/5):489-498; Studnicka et al., 1994, Protein Engineering 7(6):805-814; and Roguska et al., 1994, PNAS 91:969-973), chain shuffling (U.S. Pat. No. 5,565,332), and techniques disclosed in, e.g., U.S. Pat. Nos. 6,407,213, 5,766,886, WO 9317105, Tan et al., J. Immunol. 169:1119 25 (2002), Caldas et al., Protein Eng. 13(5):353-60 (2000), Morea et al., Methods 20(3):267 79 (2000), Baca et al., J. Biol. Chem. 272(16):10678-84 (1997), Roguska et al., Protein Eng. 9(10):895 904 (1996), Couto et al., Cancer Res. 55 (23 Supp):5973s-5977s (1995), Couto et al., Cancer Res. 55(8): 1717-22 (1995), Sandhu J S, Gene 150(2):409-10 (1994), and Pedersen et al., J. Mol. Biol. 235(3):959-73 (1994). See also U.S. Patent Pub. No. US 2005/0042664 A1 (Feb. 24, 2005), which is incorporated herein by reference.

In specific aspects, a humanized antibody is capable of binding to a predetermined antigen and which comprises a framework region having substantially the amino acid sequence of a human immunoglobulin and CDRs having substantially the amino acid sequence of a non-human immunoglobulin (e.g., a murine immunoglobulin). In particular embodiments, a humanized antibody also comprises at least a portion of an immunoglobulin constant region (Fc), typically that of a human immunoglobulin. The antibody also can include the CH1 hinge, CH2, CH3, and CH4 regions of the heavy chain. A humanized antibody can be selected from any class of immunoglobulins, including IgM, IgG, IgD, IgA and IgE, and any isotype, including $IgG_1$, $IgG_2$, $IgG_3$ and $IgG_4$.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., *Antibodies: A Laboratory Manual*, (Cold Spring Harbor Laboratory Press, 2nd ed. 1988); Hammerling et al., in: *Monoclonal Antibodies and T-Cell Hybridomas* 563 681 (Elsevier, N.Y., 1981). The term "monoclonal antibody" as used herein is not limited to antibodies produced through hybridoma technology. For example, monoclonal antibodies can be produced by recombinant technology, e.g., recombinant monoclonal antibodies expressed by a host cell, such as a mammalian host cell.

Methods for producing and screening for specific antibodies using hybridoma technology are routine and well known in the art. For example, in the hybridoma method, a mouse or other appropriate host animal, such as a sheep, goat, rabbit, rat, hamster or macaque monkey, is immunized to elicit lymphocytes that produce or are capable of producing antibodies that will specifically bind to the protein (e.g., D4 region of human KIT) used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp. 59-103 (Academic Press, 1986)). Additionally, a RIMMS (repetitive immunization multiple sites) technique can be used to immunize an animal (Kilptrack et al., 1997 Hybridoma 16:381-9, which is incorporated herein by reference).

Non-limiting examples of myeloma cell lines include murine myeloma lines, such as those derived from MOPC-21 and MPC-11 mouse tumors available from the Salk Institute Cell Distribution Center, San Diego, Calif., USA, and SP-2 or X63-Ag8.653 cells available from the American Type Culture Collection, Rockville, Md., USA. Human myeloma and mouse-human heteromyeloma cell lines also have been described for the production of human monoclonal antibodies (Kozbor, *J. Immunol.*, 133:3001 (1984); Brodeur et al., *Monoclonal Antibody Production Techniques and Applications*, pp. 51-63 (Marcel Dekker, Inc., New York, 1987)).

Antibodies described herein include antibody fragments which recognize specific KIT antigens and can be generated by any technique known to those of skill in the art. For example, Fab and F(ab')$_2$ fragments described herein can be produced by proteolytic cleavage of immunoglobulin molecules, using enzymes such as papain (to produce Fab fragments) or pepsin (to produce F(ab')$_2$ fragments). A Fab fragment corresponds to one of the two identical arms of an antibody molecule and contains the complete light chain paired with the VH and CH1 domains of the heavy chain. A F(ab')$_2$ fragment contains the two antigen-binding arms of an antibody molecule linked by disulfide bonds in the hinge region.

In one aspect, to generate whole antibodies, PCR primers including VH or VL nucleotide sequences, a restriction site, and a flanking sequence to protect the restriction site can be used to amplify the VH or VL sequences from a template, e.g., scFv clones. Utilizing cloning techniques known to those of skill in the art, the PCR amplified VH domains can be cloned into vectors expressing a VH constant region, and the PCR amplified VL domains can be cloned into vectors expressing a VL constant region, e.g., human kappa or lambda constant regions. The VH and VL domains can also be cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

Single domain antibodies, for example, antibodies lacking the light chains, can be produced by methods well-known in the art. See Riechmann et al., 1999, J. Immunol. 231:25-38; Nuttall et al., 2000, Curr. Pharm. Biotechnol. 1(3):253-263; Muylderman, 2001, J. Biotechnol. 74(4):277302; U.S. Pat. No. 6,005,079; and International Publication Nos. WO 94/04678, WO 94/25591, and WO 01/44301.

In certain aspects, antibodies described herein, such as heteroconjugate antibodies, single chain antibodies, and bispecific antibodies, can be produced through recombinant technology known in the art. For example, mammalian host cells comprising vectors expressing an antibody described herein are cultured under conditions suitable for antibody production.

Further, antibodies that immunospecifically bind to a KIT antigen can, in turn, be utilized to generate anti-idiotype antibodies that "mimic" an antigen using techniques well known to those skilled in the art. (See, e.g., Greenspan & Bona, 1989, FASEB J. 7(5):437-444; and Nissinoff, 1991, J. Immunol. 147(8):2429-2438).

5.5 Pharmaceutical Compositions and Kits

Provided herein are compositions, pharmaceutical compositions, and kits comprising one or more antibodies (e.g., humanized antibodies) described herein, or antigen-binding fragments thereof, or conjugates thereof. In particular aspects, compositions described herein can be for in vitro, in vivo, or ex vivo uses. In specific embodiments, provided herein is a pharmaceutical composition comprising an antibody (e.g., a humanized antibody) described herein (or an antigen-binding fragment thereof) and a pharmaceutically acceptable carrier or excipient.

As used herein, the term "pharmaceutically acceptable" means being approved by a regulatory agency of the Federal or a state government, or listed in the U.S. Pharmacopeia, European Pharmacopeia or other generally recognized Pharmacopeia for use in animals, and more particularly in humans.

Therapeutic formulations containing one or more antibodies (e.g., humanized antibodies) provided herein can be prepared for storage by mixing the antibody having the desired degree of purity with optional physiologically acceptable carriers, excipients or stabilizers (*Remington's Pharmaceutical Sciences* (1990) Mack Publishing Co., Easton, Pa.; *Remington: The Science and Practice of Pharmacy*, 21st ed. (2006) Lippincott Williams & Wilkins, Baltimore, Md.), in the form of lyophilized formulations or aqueous solutions. Acceptable carriers, excipients, or stabilizers are nontoxic to recipients at the dosages and concentrations employed, and include buffers such as phosphate, citrate, and other organic acids; and/or non-ionic surfactants such as TWEEN™, PLURONICS™ or polyethylene glycol (PEG).

Formulations, such as those described herein, can also contain more than one active compounds (for example, molecules, e.g., antibody or antibodies described herein) as necessary for the particular indication being treated. In certain embodiments, formulations comprise an antibody provided herein and one or more active compounds with complementary activities that do not adversely affect each other. Such molecules are suitably present in combination in amounts that are effective for the purpose intended. For example, an antibody described herein can be combined with one or more other therapeutic agents (e.g., a tyrosine kinase inhibitor such as imatinib mesylated or sunitinib, or a histone deacetylase inhibitor such as vorinostat). Such combination therapy can be administered to the patient serially or simultaneously or in sequence.

The formulations to be used for in vivo administration can be sterile. This is readily accomplished by filtration through, e.g., sterile filtration membranes.

In specific aspects, the pharmaceutical compositions provided herein contain therapeutically effective amounts of one or more of the antibodies (e.g., humanized antibodies) provided herein, and optionally one or more additional prophylactic of therapeutic agents, in a pharmaceutically acceptable carrier. Such pharmaceutical compositions are useful in the prevention, treatment, management or amelioration of a KIT-associated disorder or disease, such as cancer (e.g., GIST) or an inflammatory bowel disease, or one or more of the symptoms thereof.

Pharmaceutical carriers suitable for administration of the antibodies provided herein include any such carriers known to those skilled in the art to be suitable for the particular mode of administration.

In addition, the antibodies described herein can be formulated as the sole pharmaceutically active ingredient in the composition or can be combined with other active ingredients (such as one or more other prophylactic or therapeutic agents).

The compositions can contain one or more antibodies provided herein. In one embodiment, the antibodies are formulated into suitable pharmaceutical preparations, such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers.

In the compositions, one or more antibodies provided herein (or conjugates thereof) is (are) mixed with a suitable pharmaceutical carrier. The concentrations of the antibody or antibodies in the compositions can, for example, be effective for delivery of an amount, upon administration, that treats, prevents, or ameliorates a KIT-associated disorder or disease or a symptom thereof. In particular embodiments, concentrations of an antibody-drug conjugate or antibody-drug conjugates in the compositions can, for example, be effective for delivery of an amount of a drug(s), upon administration, that treats, prevents, or ameliorates a KIT-associated disorder or disease or a symptom thereof.

In one embodiment, the compositions are formulated for single dosage administration. To formulate a composition, the weight fraction of compound is dissolved, suspended, dispersed or otherwise mixed in a selected carrier at an effective concentration such that the treated condition is relieved, prevented, or one or more symptoms are ameliorated.

In certain aspects, an antibody (e.g., a humanized antibody) provided herein (or an antibody-drug conjugate thereof) is included in the pharmaceutically acceptable carrier in an effective amount sufficient to exert a therapeutically useful effect in the absence of, or with minimal or negligible, undesirable side effects on the patient treated. A therapeutically effective concentration can be determined empirically by testing the compounds in in vitro and in vivo systems using routine methods and then extrapolated therefrom for dosages for humans.

The concentration of antibody in the pharmaceutical composition will depend on, e.g., the physicochemical characteristics of the antibody, the dosage schedule, and amount administered as well as other factors known to those of skill in the art. In certain aspects, the concentration of antibody-drug conjugate in the pharmaceutical composition will depend on, e.g., the physicochemical characteristics of the antibody and/or the drug, the dosage schedule, and amount administered as well as other factors known to those of skill in the art.

In one embodiment, a therapeutically effective dosage produces a serum concentration of antibody of from about 0.1 ng/ml to about 50-100 µg/ml. The pharmaceutical compositions, in another embodiment, provide a dosage of from about 0.001 mg to about 2000 mg of antibody per kilogram of body weight for administration over a period of time, e.g., every day, every week, every 2 weeks, or every 3 weeks. Pharmaceutical dosage unit forms can be prepared to provide from about 0.01 mg to about 2000 mg, and in one embodiment from about 10 mg to about 500 mg of the antibody and/or a combination of other optional essential ingredients per dosage unit form.

In a particular embodiment, an antibody-drug conjugate described herein is administered at an effective dosage of about 1 to 100 mg of antibody-drug conjugate per kilogram of body weight for administration over a period of time, e.g., every day, every week, every 2 weeks, or every 3 weeks.

The antibody can be administered at once, or can be divided into a number of smaller doses to be administered at intervals of time. It is understood that the precise dosage and duration of treatment is a function of the disease being treated and can be determined empirically using known testing protocols or by extrapolation from in vivo or in vitro test data. It is to be noted that concentrations and dosage values can also vary with the severity of the condition to be alleviated. It is to be further understood that for any particular subject, specific dosage regimens can be adjusted over time according to the individual need and the professional judgment of the person administering or supervising the administration of the compositions, and that the concentration ranges set forth herein are exemplary only and are not intended to limit the scope or practice of the claimed compositions.

Upon mixing or addition of the antibody, the resulting mixture can be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and can be empirically determined.

The pharmaceutical compositions are provided for administration to humans and animals in unit dosage forms, such as sterile parenteral (e.g., intravenous) solutions or suspensions containing suitable quantities of the compounds or pharmaceutically acceptable derivatives thereof. Pharmaceutical compositions are also provided for administration to humans and animals in unit dosage form, such as tablets, capsules, pills, powders, granules, and oral solutions or suspensions, and oil-water emulsions containing suitable quantities of the compounds or pharmaceutically acceptable derivatives thereof. The antibody is, in one embodiment, formulated and administered in unit-dosage forms or multiple-dosage forms. Unit-dose forms as used herein refers to physically discrete units suitable for human and animal subjects and packaged individually as is known in the art. Each unit-dose contains a predetermined quantity of the antibody sufficient to produce the desired therapeutic effect, in association with the required pharmaceutical carrier, vehicle or diluent. Examples of unit-dose forms include ampoules and syringes and individually packaged tablets or capsules. Unit-dose forms can be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

In certain embodiments, one or more anti-KIT antibodies described herein are in a liquid pharmaceutical formulation. Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered can also contain minor amounts of nontoxic auxiliary substances such as wetting agents, emulsifying agents, solubilizing agents, and pH buffering agents and the like.

Actual methods of preparing such dosage forms are known, or will be apparent, to those skilled in this art; for example, see, e.g., *Remington's Pharmaceutical Sciences* (1990) Mack Publishing Co., Easton, Pa.; *Remington: The Science and Practice of Pharmacy,* 21st ed. (2006) Lippincott Williams & Wilkins, Baltimore, Md.

Dosage forms or compositions containing antibody in the range of 0.005% to 100% with the balance made up from non-toxic carrier can be prepared. Methods for preparation of these compositions are known to those skilled in the art.

Parenteral administration, in one embodiment, is characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the pharmaceutical compositions to be administered can also contain minor amounts of non-toxic auxiliary substances such as wetting or emulsifying agents, pH buffering agents, stabilizers, solubility enhancers, and other such agents. Other routes of administration may include, enteric administration, intracerebral administration, nasal administration, intraarterial administration, intracardiac administration, intraosseous infusion, intrathecal administration, and intraperitoneal administration.

Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions can be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Pharmaceutical carriers also include ethyl alcohol, polyethylene glycol and propylene glycol for water miscible vehicles; and sodium hydroxide, hydrochloric acid, citric acid or lactic acid for pH adjustment.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

The antibody can be suspended in micronized or other suitable form. The form of the resulting mixture depends upon a number of factors, including the intended mode of administration and the solubility of the compound in the selected carrier or vehicle. The effective concentration is sufficient for ameliorating the symptoms of the condition and can be empirically determined.

In other embodiments, the pharmaceutical formulations are lyophilized powders, which can be reconstituted for administration as solutions, emulsions and other mixtures. They can also be reconstituted and formulated as solids or gels.

The lyophilized powder is prepared by dissolving a antibody provided herein, in a suitable solvent. In some embodiments, the lyophilized powder is sterile. The solvent can contain an excipient which improves the stability or other pharmacological component of the powder or reconstituted solution, prepared from the powder. Excipients that can be used include, but are not limited to, dextrose, sorbital, fructose, corn syrup, xylitol, glycerin, glucose, sucrose or other suitable agent. The solvent can also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. In one embodiment, the resulting solution will be apportioned into vials for lyophilization. Each vial will contain a single dosage or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined.

Antibodies provided herein can be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered.

The antibodies and other compositions provided herein can also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874. In some embodiments, the anti-KIT antibodies described herein are targeted (or otherwise administered) to the bone marrow, such as in a patient having or at risk of having leukemia. In some embodiments, anti-KIT antibodies described herein are targeted (or otherwise administered) to the gastrointestinal tract, such as in a patient having or at risk of having gastrointestinal stromal tumors. In some embodiments, anti-KIT antibodies described herein are targeted (or otherwise administered) to the lungs, such as in a patient having or at risk of lung cancer (e.g., small cell lung cancer). In some embodiments, anti-KIT antibodies described herein are targeted (or otherwise administered) to the brain, such as in a patient having or at risk of having neuroblastoma. In specific embodiments, an anti-KIT antibody described herein is capable of crossing the blood-brain barrier.

Provided herein is a pharmaceutical pack or kit comprising one or more containers filled with one or more of the ingredients of the pharmaceutical compositions described herein, such as one or more antibodies provided herein. Optionally associated with such container(s) can be a notice in the form prescribed by a governmental agency regulating the manufacture, use or sale of pharmaceuticals or biological products, which notice reflects approval by the agency of manufacture, use or sale for human administration.

Also provided herein are kits that can be used in the above methods. In one embodiment, a kit comprises an antibody described herein, preferably a purified antibody, in one or more containers. In a specific embodiment, the kits described herein contain a substantially isolated KIT antigen as a control. In another specific embodiment, the kits described herein further comprise a control antibody which does not react with the KIT antigen. In another specific embodiment, the kits described herein contain one or more elements for detecting the binding of a modified antibody to a KIT antigen (e.g., the antibody can be conjugated to a detectable substrate such as a fluorescent compound, an enzymatic substrate, a radioactive compound or a luminescent compound, or a second antibody which recognizes the first antibody can be conjugated to a detectable substrate). In specific embodiments, the kit can include a recombinantly produced or chemically synthesized KIT antigen. The KIT antigen provided in the kit can also be attached to a solid support. In a more specific embodiment the detecting means of the above described kit includes a solid support to which KIT antigen is attached. Such a kit can also include a non-attached reporter-labeled anti-human antibody. In this embodiment, binding of the antibody to the KIT antigen can be detected by binding of the said reporter-labeled antibody.

5.6 Methods

Provided herein are methods for impeding, preventing, treating and/or managing a KIT-associated disorder or disease (e.g., cancer). Such methods comprise administering to a subject in need thereof a therapeutically effective amount of an anti-KIT antibody described herein (e.g., humanized antibodies, and antigen-binding fragments thereof, or conjugates thereof). In certain aspects, also provided herein are methods for preventing, impeding, treating or managing one or more symptoms of a KIT-associated disorder or disease.

As used herein, "administer" or "administration" refers to the act of injecting or otherwise physically delivering a substance (e.g., a humanized anti-KIT antibody provided herein or an antigen-binding fragment thereof or a conjugate thereof) to a subject or a patient (e.g., human), such as by mucosal, topical, intradermal, intravenous, intramuscular delivery and/or any other method of physical delivery described herein or known in the art.

As used herein, the terms "effective amount" or "therapeutically effective amount" refer to an amount of a therapy (e.g., a humanized antibody or pharmaceutical composition provided herein) which is sufficient to reduce and/or ameliorate the severity and/or duration of a given disease and/or a symptom related thereto. These terms also encompass an amount necessary for the reduction or amelioration of the advancement or progression of a given disease, reduction or amelioration of the recurrence, development or onset of a given disease, and/or to improve or enhance the prophylactic or therapeutic effect(s) of another therapy (e.g., a therapy other than an anti-KIT antibody provided herein). In some embodiments, "effective amount" as used herein also refers to the amount of an antibody described herein to achieve a specified result (e.g., inhibition (e.g., partial inhibition) of a KIT biological activity of a cell, such as inhibition of cell proliferation or cell survival, or enhancement or induction of apoptosis or cell differentiation).

As used herein, the term "in combination" in the context of the administration of other therapies refers to the use of more than one therapy. The use of the term "in combination" does not restrict the order in which therapies are administered. The therapies may be administered, e.g., serially, sequentially, concurrently, or concomitantly.

As used herein, the terms "manage," "managing," and "management" refer to the beneficial effects that a subject derives from a therapy (e.g., a prophylactic or therapeutic agent), which does not result in a cure of a KIT-associated disease or disorder. In certain embodiments, a subject is administered one or more therapies (e.g., prophylactic or therapeutic agents, such as an antibody described herein) to "manage" a KIT-associated disease (e.g., cancer, inflammatory condition, or fibrosis), one or more symptoms thereof, so as to prevent the progression or worsening of the disease.

As used herein, the terms "impede" or "impeding" in the context of a KIT-associated disorder or disease refer to the total or partial inhibition (e.g., less than 100%, 95%, 90%, 80%, 70%, 60%, 50%, 40%, 30%, 20%, 10%, or 5%) or blockage of the development, recurrence, onset or spread of a KIT-associated disease and/or symptom related thereto, resulting from the administration of a therapy or combination of therapies provided herein (e.g., a combination of prophylactic or therapeutic agents, such as an antibody described herein).

As used herein, the term "prophylactic agent" refers to any agent that can totally or partially inhibit the development, recurrence, onset or spread of a KIT-associated disease and/or symptom related thereto in a subject. In certain embodiments, the term "prophylactic agent" refers to an antibody described herein. In certain other embodiments, the term "prophylactic agent" refers to an agent other than an antibody described herein. Generally, a prophylactic agent is an agent which is known to be useful to or has been or is currently being used to prevent a KIT-associated disease and/or a symptom related thereto or impede the onset, development, progression and/or severity of a KIT-associated disease and/or a symptom related thereto. In specific embodiments, the prophylactic agent is a human anti-KIT antibody, such as a humanized or a fully human anti-KIT monoclonal antibody.

As used herein, the term "side effects" encompasses unwanted and adverse effects of a therapy (e.g., a prophylactic or therapeutic agent). Unwanted effects are not necessarily adverse. An adverse effect from a therapy (e.g., a prophylactic or therapeutic agent) can be harmful or uncomfortable or risky. Examples of side effects include, diarrhea, cough, gastroenteritis, wheezing, nausea, vomiting, anorexia, abdominal cramping, fever, pain, loss of body weight, dehydration, alopecia, dyspenea, insomnia, dizziness, mucositis, nerve and muscle effects, fatigue, dry mouth, and loss of appetite, rashes or swellings at the site of administration, flu-like symptoms such as fever, chills and fatigue, digestive tract problems and allergic reactions. Additional undesired effects experienced by patients are numerous and known in the art. Many are described in the *Physician's Desk Reference* (63$^{rd}$ ed., 2009).

As used herein, the terms "subject" and "patient" are used interchangeably. As used herein, a subject is preferably a mammal such as a non-primate (e.g., cows, pigs, horses, cats, dogs, goats, rabbits, rats, mice, etc.) or a primate (e.g., monkey and human), most preferably a human. In one embodiment, the subject is a mammal, preferably a human, having a KIT-associated disorder or disease. In another embodiment, the subject is a mammal, preferably a human, at risk of developing a KIT-associated disorder or disease. In another embodiment, the subject is a non-human primate. In a specific embodiment, the subject is an adult human subject at least 18 years old.

As used herein, the terms "therapies" and "therapy" can refer to any protocol(s), method(s), compositions, formulations, and/or agent(s) that can be used in the prevention, treatment, management, or amelioration of a condition or disorder or symptom thereof (e.g., cancer or one or more symptoms or condition associated therewith; inflammatory condition or one or more symptoms or condition associated therewith; fibrosis or one or more symptoms or condition associated therewith). In certain embodiments, the terms "therapies" and "therapy" refer to drug therapy, adjuvant therapy, radiation, surgery, biological therapy, supportive therapy, and/or other therapies useful in treatment, management, prevention, or amelioration of a condition or disorder or one or more symptoms thereof (e.g., cancer or one or more symptoms or condition associated therewith; inflammatory condition or one or more symptoms or condition associated therewith; fibrosis or one or more symptoms or condition associated therewith). In certain embodiments, the term "therapy" refers to a therapy other than an anti-KIT antibody described herein or pharmaceutical composition thereof. In specific embodiments, an "additional therapy" and "additional therapies" refer to a therapy other than a treatment using an anti-KIT antibody described herein or pharmaceutical composition. In a specific embodiment, a therapy includes the use of an anti-KIT antibody described herein as an adjuvant therapy. For example, using an anti-KIT antibody described herein in conjunction with a drug therapy, biological therapy, surgery, and/or supportive therapy.

As used herein, the term "therapeutic agent" refers to any agent that can be used in the treatment, management or amelioration of a KIT-associated disease and/or a symptom related thereto. In certain embodiments, the term "therapeutic agent" refers to an anti-KIT antibody described herein (e.g., any one of antibodies Hum1-Hum20), an antigen-binding fragment thereof, or a conjugate thereof. In certain other embodiments, the term "therapeutic agent" refers to an agent other than an antibody described herein. Preferably, a therapeutic agent is an agent which is known to be useful for, or has been or is currently being used for the treatment, management or amelioration of a KIT-associated disease or one or more symptoms related thereto. In specific embodiments, the therapeutic agent is a human anti-KIT antibody, such as a fully human anti-KIT monoclonal antibody.

As used herein, the terms "KIT-associated disorder" or "KIT-associated disease" are used interchangeably and refer to any disease that is completely or partially caused by, associated with, or is the result of, KIT expression and/or activity or lack thereof. In one aspect, a KIT-associated disorder or disease can be known to one of skill in the art or can be ascertained by one of skill in the art. In a certain embodiment, a KIT-associated disease or disorder is associated with KIT expression and/or activity. For example, KIT expression and/or activity may contribute, in combination with one or more other factors (e.g., mutation or expression and/or activity of another gene), to development and/or progression of a KIT-associated disease or disorder. In a certain embodiment, a KIT-associated disease or disorder is associated with one or more mutations of KIT.

In certain embodiments, a KIT-associated disease is fibrosis or an inflammatory disorder, e.g., inflammatory bowel disease (IBD), such as Crohn's disease (CD) or ulcerative colitis (UC). In other embodiments, a KIT-associated disease is cancer, such as lung cancer (e.g., small cell lung cancer), leukemia, neuroblastoma, melanoma, sarcoma (e.g., Ewing's sarcoma) or gastrointestinal stromal tumor (GIST).

As used herein, the terms "treat," "treatment" and "treating" refer to the reduction or amelioration of the progression, severity, and/or duration of a KIT-associated disease (e.g., cancer, inflammatory disorder, or fibrosis) resulting from the administration of one or more therapies (including, but not limited to, the administration of one or more prophylactic or therapeutic agents, such as an antibody provided herein).

In specific embodiments, methods described herein for treating a KIT-associated disorder or disease provide for the reduction or amelioration of the progression, severity, and/or duration of a KIT-associated disorder or disease (e.g., cancer, inflammatory condition, or fibrosis) resulting from the administration of one or more therapies (including, but not limited to, the administration of one or more prophylactic or therapeutic agents, such as an anti-KIT antibody described herein). In further specific embodiments, methods described herein for treating a KIT-associated disorder or disease relate to reducing one or more symptoms of a KIT-associated disorder or disease. In specific embodiments, an antibody described herein, for example any one of antibodies Hum1-Hum20, e.g., antibody Hum8 or Hum4 or Hum17 or Hum10, or an antigen-binding fragment thereof, or a conjugate thereof, is for use in treating or managing a KIT-associated disorder (e.g., cancer). In a particular embodiment, a KIT-associated disease or disorder being treated or managed with an anti-KIT antibody described herein, or an antigen-binding fragment thereof, or a conjugate thereof, is associated with KIT expression and/or activity, e.g., involves cells expressing KIT and/or exhibiting KIT activity, but is not caused by or the result of KIT expression or activity.

In a particular embodiment, provided herein is an antibody (e.g., a humanized anti-KIT antibody), for example any one of antibodies Hum1-Hum20, or Hum17, Hum10, Hum8 or Hum4, or an antigen-binding fragment thereof, or a conjugate thereof, for use in treating or managing a KIT-associated disorder (e.g., cancer), wherein the antibody comprises (i) a VL chain region having the amino acid sequence of SEQ ID NO: 7, 8, 9, or 10, and/or (ii) a VH chain region having the amino acid sequence of SEQ ID NO: 2, 3, 4, 5, or 6. In another particular embodiment, provided herein is an antibody, or an antigen-binding fragment thereof, for use in treating or managing a KIT-associated disorder (e.g., cancer), wherein the antibody comprises a combination of VH domain (e.g., H1-H5, SEQ ID NOs: 2-6) and VL domain (L1-L4, SEQ ID NOs: 7-10) selected from the group presented in Table 4. In a particular embodiment, provided herein is an antibody (e.g., a humanized anti-KIT antibody) for example, any one of antibodies Hum1-Hum20, such as Hum17, Hum10, Hum8 or Hum4, or an antigen-binding fragment thereof, or a conjugate thereof, for use in treating or managing a KIT-associated disorder (e.g., cancer), wherein the antibody comprises (i) a VL chain region comprising the amino acid sequence of SEQ ID NO: 12 (see, e.g., FIG. 4B), and/or (ii) a VH chain region comprising the consensus amino acid sequence of SEQ ID NO: 11 (see, e.g., FIG. 4A). In a particular embodiment, provided herein is an antibody (e.g., a humanized anti-KIT antibody) for example, any one of antibodies Hum1-Hum20, such as Hum17, Hum10, Hum8 or Hum4, or an antigen-binding fragment thereof, or a conjugate thereof, for use in treating or managing a KIT-associated disorder (e.g., cancer), wherein the antibody comprises (i) a VL chain region comprising an amino acid sequence set forth in Table 6A (e.g., L1-L4 and LL1-LL62), and/or (ii) a VH chain region comprising the amino acid sequence set forth in Table 6B (e.g., H1-H5 and HH1-HH256).

In a specific embodiment, the antibody used in the methods described herein is internalized by the cell to which it binds. In a particular embodiment, a conjugate is used in the methods described herein, wherein the conjugate comprises an antibody described herein (e.g., a humanized anti-KIT antibody, for example Hum4 or Hum8), or a KIT-binding fragment thereof. In a specific embodiment, the conjugate comprises an antibody described herein (e.g., a humanized anti-KIT antibody) for example, any one of antibodies Hum1-Hum20, such as Hum17, Hum10, Hum8 or Hum4, or a KIT-binding fragment thereof, linked, covalently or non-covalently, to a therapeutic agent, such as a toxin. In a certain embodiment, the conjugate used in the methods described herein is internalized into a cell to which it binds.

In certain embodiments, KIT is aberrantly (e.g., highly) expressed by cells, for example, KIT is overexpressed. In particular embodiments, KIT expression (e.g., on the cell surface) is at least about 10%, 20%, 30%, 40%, 50%, 60%, 70%, 80%, 90%, or 100% higher than KIT expression on the surface of a control cell (e.g., a cell expressing normal levels of KIT, for example, a normal, e.g., human, mast cell, stem cell, brain cell, melanoblast, or ovary cell). In particular embodiments, KIT expression yields at least about 10%, 20%, 30%, 40%, 50%, 60%, 70%, 80%, 90%, or 100% higher cell surface KIT expression than the average KIT expression on the surface of a control cell population (e.g., a cell population expressing normal levels of KIT, for example, a normal, e.g., human, mast cell population, stem cell population, brain cell population, melanoblast population, or ovary cell population). In specific embodiments, such control cells can be obtained or derived from a healthy individual (e.g., healthy human). In some embodiments, KIT can be aberrantly upregulated in a particular cell type, whether or not KIT is aberrantly expressed on the cell surface. In particular embodiments, KIT signaling or activity can be aberrantly upregulated in a particular cell type, whether or not KIT is aberrantly expressed on the cell surface. In particular embodiments, KIT signaling is at least about 10%, 20%, 30%, 40%, 50%, 60%, 70%, 80%, 90%, or 100% higher than KIT signaling of a control cell (e.g., a cell containing normal KIT signaling, for example, a mast cell, stem cell, brain cell, melanoblast, or ovary cell). In particular embodiments, KIT signaling is at least about 10%, 20%, 30%, 40%, 50%, 60%, 70%, 80%, 90%, or 100% higher than average KIT signaling of a control cell population (e.g., a cell population exhibiting normal KIT signaling, for example, a normal, e.g., human, mast cell population, stem cell population, brain cell population, melanoblast population, or ovary cell population). In certain embodiments, normal, aberrant or excessive cell signaling is caused by binding of KIT to a KIT ligand. In other embodiments, aberrant or excessive cell signaling occurs independent of binding of KIT to a KIT ligand.

In certain aspects, a KIT-associated disorder or disease can be characterized by gain-of-function KIT activity, increase in KIT activity, or overexpression of KIT. In one embodiment, a KIT-associated disorder or disease is completely or partially caused by or is the result of gain-of-function KIT activity or expression, e.g., overexpression, of KIT. In certain embodiments, the gain-of-function KIT activity can occur independent of KIT ligand (e.g., SCF) binding KIT receptor. In particular aspects, high or overexpression of KIT in a cell refers to an expression level which is at least about 35%, 45%, 55%, or 65% more than the expression level of a reference cell known to have normal KIT expression or KIT activity or more than the average expression level of KIT in a population of cells or samples known to have normal KIT expression or KIT activity. Expression levels of KIT can be assessed by methods described herein or known to one of skill in the art (e.g., Western blotting or immunohistory chemistry). In particular embodiments, a KIT-associated disorder or disease is characterized by KIT activity which is higher than normal KIT activity and contributes to cellular transformation, neoplasia, and tumorogenesis. In particular aspects, high or increase of KIT activity in a cell refers to a KIT activity level which is at least about 35%, 45%, 55%, or 65% more than the expression level of a reference cell known to have normal KIT activity or more than the average level of KIT activity in a population of cells or samples known to have normal KIT activity. Non-limiting examples of a KIT activity includes tyrosine phosphorylation of the cytoplasmic domain of KIT, and signaling downstream of KIT, such as Stat or Akt signaling.

Non-limiting examples of disorders or KIT-associated disorders or diseases include cancers such as breast cancer, leukemia (e.g., chronic myelogenous leukemia, acute myeloid leukemia, mast cell leukemia), lung cancer (e.g., small cell lung cancer), neuroblastoma, gastrointestinal stromal tumors (GIST), melanoma, colorectal cancer, sarcoma (e.g., Ewing's sarcoma), and germ cell tumors (e.g., seminoma). In a particular embodiment, a cancer which is treated or managed by the methods provided herein is characterized by a gain-of-function KIT mutation or overexpression of KIT.

In a specific embodiment, a method described herein is for treating cancer (e.g., GIST, lung cancer, or sarcoma (e.g., Ewing's sarcoma)), wherein said method comprises administering to a subject in need thereof a therapeutically effective amount of an antibody described herein (e.g., a humanized anti-KIT antibody) for example, any one of antibodies Hum1-Hum20, such as Hum17, Hum10, Hum8 or Hum4, or an antigen-binding fragment thereof, or a conjugate thereof. In certain aspects, also provided herein are methods for preventing, treating or managing one or more symptoms of cancer, wherein said methods comprise administering to a subject in need thereof a therapeutically effective amount of an antibody described herein (e.g., a humanized anti-KIT antibody), for example, any one of antibodies Hum1-Hum20, such as Hum17, Hum10, Hum8 or Hum4, or an antigen-binding fragment thereof, or a conjugate thereof. In a specific embodiment, an antibody for use in the methods of treating cancer described herein comprises a VL domain comprising the amino acid sequence of SEQ ID NO: 8 (L2), and/or a VH domain comprising the amino acid sequence of SEQ ID NO: 4 (H3). In a specific embodiment, an antibody for use in the methods of treating cancer described herein comprises a VL domain comprising the amino acid sequence of SEQ ID NO: 7 (L1), and/or a VH domain comprising the amino acid sequence of SEQ ID NO: 5 (H4).

In a specific embodiment, a method described herein is for treating GIST, wherein said method comprises administering to a subject in need thereof a therapeutically effective amount of an antibody described herein (e.g., a humanized anti-KIT antibody) for example, any one of antibodies Hum1-Hum20, such as Hum17, Hum10, Hum8 or Hum4, or an antigen-binding fragment thereof, or a conjugate thereof. In certain aspects, also provided herein are methods for preventing, treating or managing one or more symptoms of GIST, wherein said methods comprise administering to a subject in need thereof a therapeutically effective amount of an antibody described herein (e.g., a humanized anti-KIT antibody) for example, any one of antibodies Hum1-Hum20, such as Hum17, Hum10, Hum8 or Hum4, or an antigen-binding fragment thereof, or a conjugate thereof. In a specific embodiment, an antibody for use in the methods of treating GIST described herein comprises a VL domain comprising the amino acid sequence of SEQ ID NO: 8 (L2), and/or a VH domain comprising the amino acid sequence of SEQ ID NO: 4 (H3). In a specific embodiment, an antibody for use in the methods of treating GIST described herein comprises a VL domain comprising the amino acid sequence of SEQ ID NO: 7 (L1), and/or a VH domain comprising the amino acid sequence of SEQ ID NO: 5 (H4).

In a specific embodiment, a method described herein is for treating lung cancer (e.g., small cell lung carcinoma), wherein said method comprises administering to a subject in need thereof a therapeutically effective amount of an antibody described herein (e.g., a humanized anti-KIT antibody) for example, any one of antibodies Hum1-Hum20, such as Hum17, Hum10, Hum8 or Hum4, or an antigen-binding fragment thereof, or a conjugate thereof. In certain aspects, also provided herein are methods for preventing, treating or managing one or more symptoms of lung cancer (e.g., small cell lung carcinoma), wherein said methods comprise administering to a subject in need thereof a therapeutically effective amount of an antibody described herein (e.g., a humanized anti-KIT antibody) for example, any one of antibodies Hum1-Hum20, such as Hum17, Hum10, Hum8 or Hum4, or an antigen-binding fragment thereof, or a conjugate thereof. In a specific embodiment, an antibody for use in the methods of treating lung cancer (e.g., small cell lung cancer) comprises a VL domain comprising the amino acid sequence of SEQ ID NO: 8 (L2), and/or a VH domain comprising the amino acid sequence of SEQ ID NO: 4 (H3). In a specific embodiment, an antibody for use in the methods of treating lung cancer (e.g., small cell lung cancer) comprises a VL domain comprising the amino acid sequence of SEQ ID NO: 7 (L1), and/or a VH domain comprising the amino acid sequence of SEQ ID NO: 5 (H4).

In a specific embodiment, a method described herein is for treating melanoma, wherein said method comprises administering to a subject in need thereof a therapeutically effective amount of an antibody described herein (e.g., a humanized anti-KIT antibody) for example, any one of antibodies Hum1-Hum20, such as Hum17, Hum10, Hum8 or Hum4, or an antigen-binding fragment thereof, or a conjugate thereof. In certain aspects, also provided herein are methods for preventing, treating or managing one or more symptoms of melanoma, wherein said methods comprise administering to a subject in need thereof a therapeutically effective amount of an antibody described herein (e.g., a humanized anti-KIT antibody) for example, any one of antibodies Hum1-Hum20, such as Hum17, Hum10, Hum8 or Hum4, or an antigen-binding fragment thereof, or a conjugate thereof. In a specific embodiment, an antibody for use in the methods of treating melanoma described herein comprises a VL domain comprising the amino acid sequence of SEQ ID NO: 8 (L2), and/or a VH domain comprising the amino acid sequence of SEQ ID NO: 4 (H3). In a specific embodiment, an antibody for use in the methods of treating melanoma described herein comprises a VL domain comprising the amino acid sequence of SEQ ID NO: 7 (L1), and/or a VH domain comprising the amino acid sequence of SEQ ID NO: 5 (H4).

In specific embodiments, a cancer treated in accordance with the methods described herein can be any type of cancer which comprises cancer or tumor cells expressing cell surface KIT or a mutated form thereof, which can be confirmed by any histologically or cytologically method known to one of skill in the art.

In certain embodiments, a cancer is metastatic. In certain embodiments, a cancer is an advanced cancer which has spread outside the site or organ of origin, either by local invasion or metastasis.

In particular embodiments, a cancer is a recurrent cancer which has regrown, either at the initial site or at a distant site, after a response to initial therapy (e.g., after surgery to remove the tumor and adjuvant therapy following surgery). In some embodiments, a cancer is a refractory cancer which progresses even though an anti-tumor agent, such as a chemotherapeutic agent, is being administered, or has been administered, to the cancer patient. A non-limiting example of a refractory cancer is one which is refractory to a tyrosine kinase inhibitor, such as GLEEVEC® (imatinib mesylate), SUTENT® (SU11248 or sunitinib), IRESSA™ (gefitinib), TARCEVA® (erlotinib), NEXAVAR® (sorafenib), or VOTRIENT™ (pazopanib). In some embodiments, a cancer is a refractory cancer which progresses even though radiation or chemotherapy is being administered, or has been administered, to the cancer patient.

In specific embodiments, provided herein are methods for treating a refractory cancer in a patient in need thereof comprising administering to the patient a therapeutically effective amount of an antibody described herein, wherein the refractory cancer is refractory or resistant to an anti-cancer agent such as a tyrosine kinase inhibitor (e.g., GLEEVEC® (imatinib mesylate) or SUTENT® (SU11248 or Sunitinib)). Other non-limiting examples of tyrosine kinase inhibitors include 706 and AMNI07 (nilotinib). RAD00I, PKC412, gefitinib (IRESSA™) erlotinib (TARCEVA®), sorafenib (NEXAVAR®), pazopanib (VOTRIENT™), axitinib, bosutinib, cediranib (RECENTIN®), SPRYCEL® (dasatinib), lapatinib (TYKERB®), lestaurtinib, neratinib, nilotinib (TASIGNA®), semaxanib, toceranib (PALLADIA™), vandetanib (ZACTIMA™), and vatalanib. In certain embodiments, the refractory cancer was initially responsive to an anti-cancer agent, such as a tyrosine kinase inhibitor (e.g., GLEEVEC® or SU11248 (i.e., sunitinib)), but has developed resistance the anti-cancer agent. In certain embodiments, a subject has one or more mutations in KIT that confers resistance to an anti-cancer agent such as a tyrosine kinase inhibitor.

In particular embodiments, an antibody described herein is administered to a patient who has previously received, or is currently receiving, one or more anti-cancer therapies, for example, a chemotherapeutic agent, or a tyrosine kinase inhibitor (e.g., GLEEVEC® (imatinib mesylate), SUTENT® (SU11248 or sunitinib), IRESSA™ (gefitinib), TARCEVA® (erlotinib), NEXAVAR® (sorafenib), or VOTRIENT™ (pazopanib)) or a histone deacetylase inhibitor (e.g., vorinostat or suberoylanilide hydroxamic acid (SAHA)). In other particular embodiments, an antibody described herein is administered to a patient who is, or is suspected of being, resistant or refractory to an anti-cancer therapy, for example, a tyrosine kinase inhibitor, e.g., GLEEVEC® (imatinib mesylate), SUTENT® (SU11248 or sunitinib), IRESSA™ (gefitinib), TARCEVA® (erlotinib), NEXAVAR® (sorafenib), or VOTRIENT™ (pazopanib).

In particular embodiments, an antibody described herein (e.g., any one of antibodies Hum1-Hum20, or an antigen binding fragment thereof (e.g., KIT-binding fragment thereof), or a conjugate thereof) is administered to a patient who has previously received, or is currently receiving, one or more anti-cancer therapies, for example, an anti-growth factor receptor antibody (e.g., anti-HER2 antibody, anti-EGFR antibody, anti-VEGFR antibody, or anti-KIT antibody), or anti-growth factor antibody (e.g., anti-EGF antibody, anti-VEGF antibody). In other particular embodiments, an antibody described herein is administered to a patient who is, or is suspected of being, resistant or refractory to an anti-cancer therapy, for example, an anti-growth factor receptor antibody (e.g., anti-HER2 antibody, anti-EGFR antibody, anti-VEGFR antibody, or anti-KIT antibody) or anti-growth factor antibody (e.g., anti-EGF antibody, anti-VEGF antibody).

In a particular embodiment, a method described herein for treating or managing cancer in a subject in need thereof, can achieve at least one, two, three, four or more of the following effects due to administration of a therapeutically effective amount of an anti-KIT antibody described herein: (i) the reduction or amelioration of the severity of cancer (e.g., leukemia, lung cancer, or gastrointestinal stromal cancer) and/or one or more symptoms associated therewith; (ii) the reduction in the duration of one or more symptoms associated with a cancer (e.g., leukemia, lung cancer, or gastrointestinal stromal cancer); (iii) the prevention in the recurrence of a tumor (e.g., lung tumor or gastrointestinal stromal tumor); (iv) the regression of a cancer (e.g., leukemia, lung cancer, or gastrointestinal stromal tumor) and/or one or more symptoms associated therewith; (v) the reduction in hospitalization of a subject; (vi) the reduction in hospitalization length; (vii) the increase in the survival of a subject; (viii) the inhibition of the progression of a cancer (e.g., leukemia, lung cancer, or gastrointestinal stromal tumor) and/or one or more symptoms associated therewith; (ix) the enhancement or improvement of the therapeutic effect of another therapy (e.g., surgery, radiation, chemotherapy, or another tyrosine kinase inhibitor); (x) a reduction or elimination in the cancer cell population (e.g., leukemia cell population, lung cancer cell population, gastrointestinal stromal tumor cell population); (xi) a reduction in the growth of a tumor or neoplasm; (xii) a decrease in tumor size (e.g., volume or diameter); (xiii) a reduction in the formation of a newly formed tumors; (xiv) eradication, removal, or control of primary, regional and/or metastatic cancer; (xv) ease in removal of a tumor by reducing tumor and/or edema-related vascularization prior to surgery; (xvi) a decrease in the number or size of metastases; (xvii) a reduction in mortality; (xviii) an increase in tumor-free survival rate of patients; (xvix) an increase in relapse-free survival; (xx) an increase in the number of patients in remission; (xxi) a decrease in hospitalization rate; (xxii) the size of the tumor is maintained and does not increase or increases by less than the increase of a tumor after administration of a standard therapy as measured by conventional methods available to one of skill in the art, such as computed tomography (CT) scan, magnetic resonance imaging (MRI), dynamic contrast-enhanced MM (DCE-MRI), or a positron emission tomography (PET) scan; (xxiii) the prevention of the development or onset of one or more symptoms associated cancer; (xxiv) an increase in the length of remission in patients; (xxv) the reduction in the number of symptoms associated with cancer; (xxvi) an increase in symptom-free survival of cancer patients; (xxvii) a decrease in the concentration of one or more inflammatory mediators (e.g., cytokines or interleukins) in biological specimens (e.g., plasma, serum, cerebral spinal fluid, urine, or any other biofluids) of a subject with a cancer (e.g., leukemia, lung cancer, or gastrointestinal stromal cancer); (xxviii) a decrease in circulating tumor cells (CTCs) in the blood of a subject with cancer (e.g., leukemia, lung cancer, or gastrointestinal stromal cancer); (xxix) inhibition (e.g., partial inhibition) or decrease in tumor metabolism or perfusion; and (xxx) improvement in the quality of life as assessed by methods well known in the art, e.g., questionnaires.

In certain aspects, provided herein are methods for killing cancer cells in an individual, wherein said method comprises administering to an individual in need thereof an effective amount of an antibody described herein (e.g., a humanized anti-KIT antibody) for example, any one of antibodies Hum1-Hum20, such as Hum17, Hum10, Hum8 or Hum4, or an antigen-binding fragment thereof, or a conjugate thereof. In certain aspects, provided herein are methods for inhibiting growth or proliferation of cancer cells in an individual, wherein said method comprises administering to an individual in need thereof an effective amount of an antibody described herein (e.g., a humanized anti-KIT antibody) for example, any one of antibodies Hum1-Hum20, such as Hum17, Hum10, Hum8 or Hum4, or an antigen-binding fragment thereof, or a conjugate thereof. In certain embodiments, partial inhibition of growth or proliferation of cancer cells is achieved, for example, inhibition of at least about 20% to about 55% of growth or proliferation of cancer cells.

In certain aspects, provided herein are methods for reducing tumor size or load in an individual in need thereof, wherein said method comprises administering to said individual an effective amount of an antibody described herein (e.g., a humanized anti-KIT antibody) for example, any one of antibodies Hum1-Hum20, such as Hum17, Hum10, Hum8 or Hum4, or an antigen-binding fragment thereof, or a conjugate thereof.

Other non-limiting examples of KIT-associated disorders or diseases include systemic mast cell disorders (e.g., mastocytosis), hematologic disorders, fibrosis (e.g., idiopathic pulmonary fibrosis (TPF), scleroderma, or myelofibrosis) and inflammatory conditions such as asthma, rheumatoid arthritis, inflammatory bowel disease, and allergic inflammation.

In a particular embodiment, a method described herein for treating or managing a KIT-associated disorder, e.g., fibrosis or an inflammatory condition (e.g., asthma, rheumatoid arthritis, inflammatory bowel disease, and allergic inflammation), in a subject in need thereof, can achieve at least one, two, three, four or more of the following effects due to administration of a therapeutically effective amount of an anti-KIT antibody described herein: (i) the reduction or amelioration of the severity of fibrosis or an inflammatory condition (e.g., asthma, rheumatoid arthritis, inflammatory bowel disease, and allergic inflammation) and/or one or more symptoms associated therewith; (ii) the reduction in the duration of one or more symptoms associated with fibrosis or an inflammatory condition (e.g., asthma, rheumatoid arthritis, inflammatory bowel disease, and allergic inflammation); (iii) the prevention in the recurrence of fibrosis or an inflammatory condition (e.g., asthma, rheumatoid arthritis, inflammatory bowel disease, and allergic inflammation); (iv) the reduction in hospitalization of a subject; (v) the reduction in hospitalization length; (vi) the inhibition (e.g., partial inhibition) of the progression of fibrosis or an inflammatory condition (e.g., asthma, rheumatoid arthritis, inflammatory bowel disease, and allergic inflammation) and/or one or more symptoms associated therewith; (vii) the enhancement or improvement of the therapeutic effect of another therapy (e.g., anti-inflammatory therapy such as steroids); (viii) an increase in the number of patients in remission (i.e., a time period characterized by no or minimal symptoms associated with the inflammatory condition); (ix) an increase in the length of remission in patients; (x) a decrease in hospitalization rate; (xi) the reduction in the number of symptoms associated with fibrosis or an inflammatory condition (e.g., asthma, rheumatoid arthritis, inflammatory bowel disease, and allergic inflammation); (xii) a decrease in the concentration of one or more inflammatory mediators (e.g., cytokines or interleukins) in biological specimens (e.g., plasma, serum, cerebral spinal fluid, urine, or any other biofluids) of a subject with fibrosis or an inflammatory condition (e.g., asthma, rheumatoid arthritis, inflammatory bowel disease, and allergic inflammation); and (xiii) improvement in the quality of life as assessed by methods well known in the art, e.g., questionnaires.

In certain embodiments, an anti-KIT antibody described herein may be administered by any suitable method to a subject in need thereof. Non-limiting examples of administration methods include mucosal, intradermal, intravenous, intratumoral, subcutaneous, intramuscular delivery and/or any other method of physical delivery described herein or known in the art. In one embodiment, an anti-KIT antibody or a pharmaceutical composition thereof is administered systemically (e.g., parenterally) to a subject in need thereof. In another embodiment, an anti-KIT antibody or a pharmaceutical composition thereof is administered locally (e.g., intratumorally) to a subject in need thereof. Each dose may or may not be administered by an identical route of administration. In some embodiments, an anti-KIT antibody described herein can be administered via multiple routes of administration simultaneously or subsequently to other doses of the same or a different an anti-KIT antibody described herein.

When a disease, or a symptom thereof, is being treated, administration of the substance typically occurs after the onset of the disease or symptoms thereof. When a disease, or symptoms thereof, are being prevented, administration of the substance typically occurs before the onset of the disease or symptoms thereof. In certain embodiments, an anti-KIT antibody described herein is administered prophylactically or therapeutically to a subject. An anti-KIT antibody described herein can be prophylactically or therapeutically administered to a subject so as to prevent, lessen or ameliorate a KIT-associated disorder or disease (e.g., cancer, inflammatory condition, fibrosis) or symptom thereof.

The dosage and frequency of administration of an anti-KIT antibody described herein or a pharmaceutical composition thereof is administered to a subject in need thereof in accordance with the methods for treating a KIT-associated disorder or disease provided herein will be efficacious while minimizing side effects. The exact dosage of an anti-KIT antibody described herein to be administered to a particular subject or a pharmaceutical composition thereof can be determined by a practitioner, in light of factors related to the subject that requires treatment. Factors which can be taken into account include the severity of the disease state, general health of the subject, age, and weight of the subject, diet, time and frequency of administration, combination(s) with other therapeutic agents or drugs, reaction sensitivities, and tolerance/response to therapy. The dosage and frequency of administration of an anti-KIT antibody described herein or a pharmaceutical composition thereof can be adjusted over time to provide sufficient levels of the anti-KIT antibody or to maintain the desired effect.

The precise dose to be employed in the formulation will also depend on the route of administration, and the seriousness of a KIT-associated disorder or disease (e.g., cancer, inflammatory condition, fibrosis), and should be decided according to the judgment of the practitioner and each patient's circumstances.

In one embodiment, for the anti-KIT antibodies described herein, the dosage administered to a patient, to manage a KIT-associated disorder or disease (e.g., cancer, inflammatory condition, fibrosis) is typically 0.1 mg/kg to 100 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of the antibodies described herein can be reduced by enhancing uptake and tissue penetration of the antibodies by modifications such as, for example, lipidation.

In one embodiment, approximately 0.001 mg/kg (mg of antibody per kg weight of a subject) to approximately 500 mg/kg of an anti-KIT antibody described herein is administered to manage a KIT-associated disorder or disease (e.g., cancer, inflammatory condition, fibrosis).

In some embodiments, an effective amount of an antibody provided herein is from about 0.01 mg to about 1,000 mg. In specific embodiments, an "effective amount" of an anti-KIT antibody described herein refers to an amount of an anti-KIT antibody described herein which is sufficient to achieve at least one, two, three, four or more of the following effects: (i) the reduction or amelioration of the severity of a KIT-associated disorder or disease (e.g., cancer, inflammatory condition, fibrosis) and/or one or more symptoms associated therewith; (ii) the reduction in the duration of one or more symptoms associated with a KIT-associated disorder or disease (e.g., cancer, inflammatory condition, fibrosis); (iii) the prevention in the recurrence of a tumor (e.g., gastrointestinal stromal tumor); (iv) the regression of a KIT-associated disorder or disease (e.g., cancer, inflammatory condition, fibrosis) and/or one or more symptoms associated therewith; (v) the reduction in hospitalization of a subject; (vi) the reduction in hospitalization length; (vii) the increase in the survival of a subject; (viii) the inhibition (e.g., partial inhibition) of the progression of a KIT-associated disorder or disease (e.g., cancer, inflammatory condition, fibrosis) and/or one or more symptoms associated therewith; (ix) the enhancement or improvement of the therapeutic effect of another therapy; (x) a reduction or elimination in the cancer cell population (e.g., leukemia cell population, lung cancer cell population, gastrointestinal stromal cancer cell population); (xi) a reduction in the growth of a tumor or neoplasm; (xii) a decrease in tumor size (e.g., volume or diameter); (xiii) a reduction in the formation of a newly formed tumors; (xiv) eradication, removal, or control of primary, regional and/or metastatic cancer; (xv)

ease in removal of a tumor by reducing tumor and/or edema-related vascularization prior to surgery; (xvi) a decrease in the number or size of metastases; (xvii) a reduction in mortality; (xviii) an increase in tumor-free survival rate of patients; (xvix) an increase in relapse-free survival; (xx) an increase in the number of patients in remission; (xxi) a decrease in hospitalization rate; (xxii) the size of the tumor is maintained and does not increase or increases by less than the increase of a tumor after administration of a standard therapy as measured by conventional methods available to one of skill in the art, such as computed tomography (CT) scan, magnetic resonance imaging (MRI), dynamic contrast-enhanced MM (DCE-MRI), or a positron emission tomography (PET) scan; (xxiii) the prevention of the development or onset of one or more symptoms associated cancer; (xxiv) an increase in the length of remission in patients; (xxv) the reduction in the number of symptoms associated with cancer; (xxvi) an increase in symptom-free survival of cancer patients; (xxvii) a decrease in the concentration of one or more inflammatory mediators (e.g., cytokines or interleukins) in biological specimens (e.g., plasma, serum, cerebral spinal fluid, urine, or any other biofluids) of a subject with a KIT-associated disorder or disease (e.g., cancer, inflammatory condition, fibrosis); (xxviii) a decrease in circulating tumor cells (CTCs) in the blood of a subject with cancer; (xxix) inhibition (e.g., partial inhibition) or decrease in tumor metabolism or perfusion; and (xxx) improvement in the quality of life as assessed by methods well known in the art, e.g., questionnaires. In some embodiments, "effective amount" as used herein also refers to the amount of an antibody described herein to achieve a specified result (e.g., inhibition of one or more KIT biological activities of a cell, such as inhibition of cell proliferation).

In some embodiments, an anti-KIT antibody described herein is administered as necessary, e.g., weekly, biweekly (i.e., once every two weeks), monthly, bimonthly, trimonthly, etc., as determined by a physician.

In some embodiments, a single dose of an anti-KIT antibody described herein is administered one or more times to a patient to impede, prevent, manage, treat and/or ameliorate a KIT-associated disorder or disease (e.g., cancer, inflammatory condition, fibrosis).

In particular embodiments, an anti-KIT antibody or pharmaceutical composition thereof is administered to a subject in accordance with the methods for treating a KIT-associated disorder or disease (e.g., cancer, inflammatory condition, fibrosis) presented herein in cycles, wherein the anti-KIT antibody or pharmaceutical composition is administered for a period of time, followed by a period of rest (i.e., the anti-KIT antibody or pharmaceutical composition is not administered for a period of time).

Also, presented herein are combination therapies for the treatment of a KIT-associated disorder or disease (e.g., cancer, inflammatory condition, fibrosis) which involve the administration of an anti-KIT antibody described herein (e.g., a humanized anti-KIT antibody) for example, any one of antibodies Hum1-Hum20, such as Hum10, Hum17, Hum8 or Hum4, or an antigen-binding fragment thereof (e.g., KIT-binding fragment thereof), or an antibody conjugate thereof in combination with one or more additional therapies (e.g., chemotherapeutic agent, tyrosine kinase inhibitor, PGP inhibitors, HSP-90 inhibitors, proteosome inhibitors, or histone deacetylase inhibitor) to a subject in need thereof. In a specific embodiment, presented herein are combination therapies for the treatment of a KIT-associated disorder or disease (e.g., cancer, inflammatory condition, fibrosis) which involve the administration of an amount (e.g., a therapeutically effective amount or a sub-optimal amount) of an anti-KIT antibody described herein in combination with an amount (e.g., a therapeutically effective amount or a sub-optimal amount) of another therapy (e.g., chemotherapeutic agent, tyrosine kinase inhibitor, or histone deacetylase inhibitor) to a subject in need thereof.

In combination therapies, one or more anti-KIT antibodies provided herein (e.g., a humanized anti-KIT antibody) for example, any one of antibodies Hum1-Hum20, such as Hum10, Hum17, Hum8 or Hum4, or an antigen-binding fragment thereof (e.g., KIT-binding fragment thereof), or an antibody conjugate thereof can be administered prior to, concurrently with, or subsequent to the administration of one or more additional therapies (e.g., agents, surgery, or radiation) for use in treating, managing, and/or ameoliorating a KIT-associated disorder or disease (e.g., cancer, inflammatory condition, fibrosis). The use of the term "in combination" does not restrict the order in which one or more anti-KIT antibodies and one or more additional therapies are administered to a subject. In specific embodiments, the therapies can be administered serially or sequentially.

In specific embodiments, one or more anti-KIT antibodies provided herein (e.g., a humanized anti-KIT antibody) for example, any one of antibodies Hum1-Hum20, such as Hum10, Hum17, Hum8 or Hum4, or an antigen-binding fragment thereof (e.g., KIT-binding fragment thereof), or an antibody conjugate thereof can be administered prior to, concurrently with, or subsequent to the administration of one or more additional therapies such as anticancer agents, for example, tyrosine kinase inhibitors (e.g., imatinib myselyate (Gleevec®) or sunitinib (SUTENT), or histone deacetylase inhibitors (e.g., vorinostat or suberoylanilide hydroxamic acid (SAHA)), for treating, managing, and/or ameoliorating a KIT-associated disorder or disease (e.g., cancer, for example, GIST, melanoma, or lung cancer).

In another specific embodiment, presented herein are combination therapies for the treatment of a KIT-associated disorder or disease (e.g., cancer, inflammatory condition, fibrosis) which involve the administration of an amount of an anti-KIT antibody described herein (e.g., a humanized anti-KIT antibody) for example, any one of antibodies Hum1-Hum20, such as Hum10, Hum17, Hum8 or Hum4, or an antigen-binding fragment thereof (e.g., KIT-binding fragment thereof), or an antibody conjugate thereof in combination with an amount of another therapy (e.g., chemotherapeutic agent, tyrosine kinase inhibitor, or histone deacetylase inhibitor) to a subject in need thereof. In a specific embodiment, the combination therapies result in a synergistic effect. In certain embodiments, the combination therapies result in an additive effect.

In a specific embodiment, presented herein are combination therapies for the treatment of cancer which involve the administration of an amount of an anti-KIT antibody described herein in combination with an amount of another therapy (e.g., surgery, radiation, stem cell transplantation, or chemotherapy) to a subject in need thereof. In a specific embodiment, the combination therapies result in a synergistic effect. In another specific embodiment, the combination therapies result in an additive effect.

In a specific embodiment, presented herein are combination therapies for the treatment of an inflammatory condition which involve the administration of an amount of an anti-KIT antibody described herein in combination with an amount of another therapy (e.g., anti-inflammatory therapy, for example, steroid therapy) to a subject in need thereof. In a specific embodiment, the combination therapies result in a synergistic effect. In another specific embodiment, the combination therapies result in an additive effect.

Non-limiting examples of another therapy for use in combination with antibodies described herein include, another anti-KIT antibody that immunospecifically binds to a different epitope of KIT, one or more other antibodies (e.g., anti-HER2 antibody, anti-EGFR antibody, anti-VEGF antibody), anti-inflammatory therapy, chemotherapy (e.g., microtubule disassembly blocker, antimetabolite, topisomerase inhibitor, and DNA crosslinker or damaging agent), radiation, surgery, PGP inhibitors (e.g., cyclosporine A, Verapamil), HSP-90 inhibitors (e.g., 17-AAG, STA-9090), proteosome inhibitors (e.g., Bortezomib), and tyrosine kinase inhibitors (e.g., imatinib mesylate (GLEEVEC®), sunitinib (SUTENT® or SU11248), gefitinib (IRESSA™) erlotinib (TARCEVA®), sorafenib (NEXAVAR®), pazopanib (VOTRIENT™), axitinib, bosutinib, cediranib (RECENTIN®), SPRYCEL® (dasatinib), lapatinib)(TYKERB®), lestaurtinib, neratinib, nilotinib (TASIGNA®), semaxanib, toceranib (PALLADIA™), vandetanib (ZACTIMA™), and vatalanib). In a specific embodiment, another therapy for use in combination with antibodies described herein is imatinib mesylate.

Other non-limiting examples of another therapy for use in combination with antibodies described herein (e.g., a humanized anti-KIT antibody) for example, any one of antibodies Hum1-Hum20, such as Hum10, Hum17, Hum8 or Hum4, or an antigen-binding fragment thereof (e.g., KIT-binding fragment thereof), or an antibody conjugate thereof include a histone deacetylase inhibitor, such as vorinostat or suberoylanilide hydroxamic acid (SAHA) or a compound having the chemical formula (I), (II), or (III) as set forth below. In a specific embodiment, provided herein is a method for treating cancer (e.g., GIST or lung cancer) comprising (i) administering an antibody described herein (e.g., a humanized anti-KIT antibody) for example, any one of antibodies Hum1-Hum20, such as Hum10, Hum17, Hum8 or Hum4, or an antigen-binding fragment thereof (e.g., KIT-binding fragment thereof), or an antibody conjugate thereof; and (ii) a histone deacetylase inhibitor, for example, vorinostat or suberoylanilide hydroxamic acid (SAHA) or a compound having the chemical formula (I), (II), or (III) as set forth below.

In one embodiment, provided herein for use in the methods described herein in combination with anti-KIT antibodies are compounds of Formula (I)

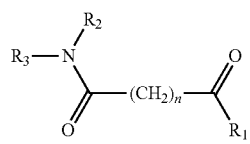

Formula (I)

or a pharmaceutically acceptable salt, hydrate, or solvate thereof, wherein
$R_1$ is hydroxylamino;
each of $R_2$ and $R_3$ are independently the same as or different from each other, substituted or unsubstituted, branched or unbranched, and are hydrogen, hydroxyl, alkyl, alkenyl, cycloalkyl, aryl, alkyloxy, aryloxy, arylalkyloxy or pyridine; or $R_2$ and $R_3$ are bonded together to form a piperidine; and
n is an integer from 5 to 7.

In one embodiment, $R_2$ is hydrogen atom and $R_3$ is substituted or unsubstituted phenyl. In a certain embodiment, $R_3$ is phenyl substituted with methyl, cyano, nitro, trifluoromethyl, amino, aminocarbonyl, methylcyano, chloro, fluoro, bromo, iodo, 2,3-difluoro, 2,4-difluoro, 2,5-difluoro, 3,4-difluoro, 3,5-difluoro, 2,6-difluoro, 1,2,3-trifluoro, 2,3,6-trifluoro, 2,4,6-trifluoro, 3,4,5-trifluoro, 2,3,5,6-tetrafluoro, 2,3,4,5,6-pentafluoro, azido, hexyl, t-butyl, phenyl, carboxyl, hydroxyl, methoxy, phenyloxy, benzyloxy, phenylaminooxy, phenylaminocarbonyl, methoxycarbonyl, methylaminocarbonyl, dimethylamino, dimethylaminocarbonyl, or hydroxylaminocarbonyl. In another embodiment, $R_3$ is unsubstituted phenyl. In a further embodiment, n is 6.

In one embodiment, provided herein for use in the methods described herein in combination with anti-KIT antibodies are compounds of Formula (II)

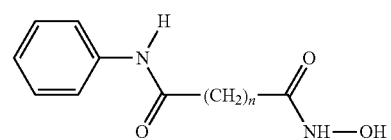

Formula (II)

or a pharmaceutically acceptable salt, or solvate thereof, wherein n is an integer from 5 to 8. In one embodiment n is 6.

In one embodiment, provided herein for use in the methods described herein in combination with anti-KIT antibodies is a compound of Formula (III) (SAHA)

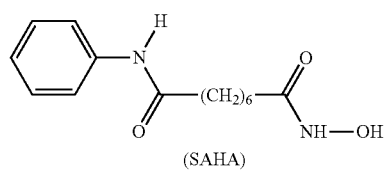

Formula (III)

(SAHA)

or a pharmaceutically acceptable salt, hydrate or solvate thereof.

Compounds of Formulae I-III can be synthesized according to the methods described in U.S. Reissued Pat. No. RE38,506 and U.S. Pat. No. 6,087,367, each of which is herewith incorporated by reference in its entirety.

In one embodiment, provided herein for use in the methods described herein in combination with anti-KIT antibodies is a Form I polymorph of SAHA characterized by an X-ray diffraction pattern substantially similar to that set forth in FIG. 13A of U.S. Pat. No. 7,456,219, which is herewith incorporated by reference in its entirety. In one embodiment the Form I polymorph of SAHA is characterized by an X-ray diffraction pattern including characteristic peaks at about 9.0, 9.4, 17.5, 19.4, 20.0, 24.0, 24.4, 24.8, 25.0, 28.0, and 43.3 degrees 2θ, as measured with a Siemens D500 Automated Powder Diffractometer (range: 4-40 degrees 2θ; source: Cu; λ=1.54 Angstrom, 50 kV, 40 mA).

In a certain embodiment, the Form I polymorph of SAHA is characterized by a Differential Scanning calorimetry (DSC) thermogram having a single maximum value at about 164.4±2.0° C., as measured by a Perkins Elmer DSC 6 Instrument at a heating rate of 10° C./min from 50° C. to at least 30° C. above the observed melting temperature.

The Form I polymorph of SAHA can be synthesized according to the methods described in U.S. Pat. No. 7,456,219.

In one embodiment, provided herein is a crystalline composition comprising Lysine and SAHA characterized by an X-ray diffraction pattern substantially similar to that set forth in FIG. 1 of International Patent Application Publication No. WO2008/042146, which is herewith incorporated by reference in its entirety. In another embodiment, the crystalline composition is characterized by an X-ray diffraction pattern including characteristic peaks at about 6.8, 20.1 and 23.2 degrees 2θ, as measured with a PANanalytical X'Pert Pro X-ray powder diffractometer (range: 2-40 degrees 2θ; source: Cu Kα1 and Kα2). In another embodiment, the crystalline composition is characterized by an X-ray diffraction pattern including characteristic peaks at about 6.8, 12.6, 18.7, 20.1 23.2, and 24.0 degrees 2θ, as measured with a PANanalytical X'Pert Pro X-ray powder diffractometer (range: 2-40 degrees 2θ; source: Cu Kα1 and Kα2). In another embodiment, the crystalline composition is characterized by an X-ray diffraction pattern including characteristic peaks at about 6.8, 12.0, 12.6, 16.4, 18.7, 20.1 23.2, 24.0, 29.3 degrees 2θ, as measured with a PANanalytical X'Pert Pro X-ray powder diffractometer (range: 2-40 degrees 2θ; source: Cu Kα1 and Kα2).

In a certain embodiment, the crystalline composition comprising Lysine and SAHA is characterized by a Differential Scanning calorimetry (DSC) thermogram, wherein the endotherm of the crystalline composition exhibits an extrapolated onset temperature of approximately 182° C., as measured by a TA Instruments Q1000 differential scanning calorimeter at a heating rate of 10° C./min from room temperature to 300° C.

The crystalline composition comprising Lysine and SAHA can be synthesized according to the methods described in International Patent Application Publication No. WO2008/042146.

In certain embodiments, combination therapies described herein result in synergy or a synergistic effect. In a specific embodiment, a synergistic effect of a combination therapy permits the use of lower dosages (e.g., sub-optimal doses) of an anti-KIT antibody described herein and/or an additional therapy and/or less frequent administration of an anti-KIT antibody described herein or an additional therapy to a subject. In certain embodiments, the ability to utilize lower dosages of an anti-KIT antibody and/or of an additional therapy and/or to administer an anti-KIT antibody or said additional therapy less frequently reduces the toxicity associated with the administration of an anti-KIT antibody or of said additional therapy, respectively, to a subject without reducing the efficacy of an anti-KIT antibody or of said additional therapy, respectively, in the treatment of a KIT-associated disorder or disease. In some embodiments, a synergistic effect results in improved efficacy of an anti-KIT antibody described herein and/or of said additional therapies in treating a KIT-associated disorder or disease. In some embodiments, a synergistic effect of a combination of an anti-KIT antibody described herein and one or more additional therapies avoids or reduces adverse or unwanted side effects associated with the use of any single therapy.

Provided herein are methods for inhibiting KIT activity in a cell expressing KIT comprising contacting the cell with an effective amount of an antibody described herein (e.g., a humanized anti-KIT antibody) for example, any one of antibodies Hum1-Hum20, such as Hum10, Hum17, Hum8 or Hum4, or an antigen-binding fragment thereof (e.g., KIT-binding fragment thereof), or an antibody conjugate thereof. Also provided herein are methods for inducing or enhancing apoptosis in a cell expressing KIT comprising contacting the cell with an effective amount of an antibody described herein. Also provided herein are methods for inducing or enhancing cell differentiation in a cell expressing KIT comprising contacting the cell with an effective amount of an antibody described herein.

KIT activity and, for example, the effect of an antibody on KIT activity can routinely be assessed using, e.g., cell-based assays such as those described herein.

Non-limiting examples of KIT activity which can be inhibited by the methods provided herein can include any activity of KIT known or described in the art, e.g., KIT receptor dimerization, KIT receptor phosphorylation (tyrosine phosphorylation), signaling downstream of the KIT receptor (e.g., Stat, AKT, MAPK, or Ras signaling), KIT ligand (e.g., SCF) induced transcriptional regulation (e.g., SCF-induced transcriptional activation of c-Myc), induction or enhancement of cell proliferation, or cell survival.

In certain embodiments, a method for inhibiting (e.g., partially inhibiting) KIT activity in a cell expressing KIT comprises contacting the cell with an effective amount of an antibody described herein (e.g., a humanized anti-KIT antibody) for example, any one of antibodies Hum1-Hum20, such as Hum10, Hum17, Hum8 or Hum4, or an antigen-binding fragment thereof (e.g., KIT-binding fragment thereof), or an antibody conjugate thereof, sufficient to inhibit or antagonize KIT activity by at least about 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein and/or known to one of skill in the art (e.g., ELISA). In certain embodiments, a method for inhibiting (e.g., partially inhibiting) KIT activity in a cell expressing KIT comprises contacting the cell with an effective amount of an antibody described herein (e.g., a humanized anti-KIT antibody) for example, any one of antibodies Hum1-Hum20, such as Hum10, Hum17, Hum8 or Hum4, or an antigen-binding fragment thereof (e.g., KIT-binding fragment thereof), or an antibody conjugate thereof, sufficient to inhibit or antagonize KIT activity by at least about 25%, 35%, 45%, 50%, 55%, or 65%, as assessed by methods described herein and/or known to one of skill in the art (e.g., ELISA). Non-limiting examples of KIT activity can include KIT receptor phosphorylation, KIT receptor signaling, KIT ligand (e.g., SCF) mediated cell proliferation, KIT ligand (e.g., SCF) mediated cell survival, and transcriptional activation of a KIT target gene (e.g., c-Myc).

In a particular embodiment, a method for inhibiting KIT activity in a cell expressing KIT comprises contacting the cell with an effective amount of an antibody described herein (e.g., a humanized anti-KIT antibody) for example, any one of antibodies Hum1-Hum20, such as Hum10, Hum17, Hum8 or Hum4, or an antigen-binding fragment thereof (e.g., KIT-binding fragment thereof), or an antibody conjugate thereof, sufficient to inhibit (e.g., partially inhibit) or antagonize downstream KIT signaling, for example, signaling of a member of the Src family kinases, PI3-kinases, or Ras-MAPK.

In another particular embodiment, a method for inhibiting (e.g., partially inhibiting) one or more KIT activities in a cell expressing KIT, comprises contacting the cell with an effective amount of an antibody described herein sufficient to inhibit or antagonize downstream KIT signaling such as phosphorylation of MAPK, phosphorylation of AKT, or phosphorylation of Stat1, Stat3, or Stat5.

In certain embodiments, a method for inhibiting (e.g., partially inhibiting) KIT activity in a cell expressing KIT comprises contacting the cell with an effective amount of an antibody described herein sufficient to inhibit or to reduce phosphorylation of AKT (e.g., KIT ligand (e.g., SCF) induced phosphorylation of AKT) by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art, e.g., Western blot or ELISA assay as described in section 6 or immunoblotting assay. In certain embodiments, a method for inhibiting e.g., partially inhibiting) KIT activity in a cell expressing KIT comprises contacting the cell with an effective amount of an antibody described herein sufficient to inhibit or to reduce phosphorylation of AKT (e.g., KIT ligand (e.g., SCF) induced phosphorylation of AKT) by at least about 25%, 35%, 45%, 55%, or 65%, as assessed by methods described herein or known to one of skill in the art, e.g., Western blot or ELISA assay as described in section 6 or immunoblotting assay.

In certain aspects, a method for inhibiting (e.g., partially inhibiting) KIT activity in a cell (e.g., cancer cell) expressing KIT comprises contacting the cell with an effective amount of an antibody described herein sufficient to inhibit proliferation of the cell. Cell proliferation assays are described in the art and can be readily carried out by one of skill in the art. For example, cell proliferation can be assayed by measuring Bromodeoxyuridine (BrdU) incorporation (see, e.g., Hoshino et al., 1986, Int. J. Cancer 38, 369; Campana et al., 1988, J. Immunol. Meth. 107:79) or (3H) thymidine incorporation (see, e.g., Blechman et al., Cell, 1995, 80:103-113; Chen, J., 1996, Oncogene 13:1395-403; Jeoung, J., 1995, J. Biol. Chem. 270:18367 73), by direct cell count at various time intervals (e.g., 12-hour or 24-hour intervals), or by detecting changes in transcription, translation or activity of known genes such as proto-oncogenes (e.g., fos, myc) or cell cycle markers (Rb, cdc2, cyclin A, D1, D2, D3, E, etc). The levels of such protein and mRNA and activity can be determined by any method well known in the art. For example, protein can be quantitated by known immunodiagnostic methods such as ELISA, Western blotting or immunoprecipitation using antibodies, including commercially available antibodies. mRNA can be quantitated using methods that are well known and routine in the art, for example, using northern analysis, RNase protection, or polymerase chain reaction in connection with reverse transcription.

In specific embodiments, a method for inhibiting (e.g., partially inhibiting) KIT activity in cells (e.g., cancer cells) expressing KIT comprises contacting the cells with an effective amount of an antibody described herein sufficient to inhibit cell proliferation by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art (e.g., BrdU incorporation assay). In specific embodiments, a method for inhibiting (e.g., partially inhibiting) KIT activity in cells expressing KIT comprises contacting the cells with an effective amount of an antibody described herein sufficient to inhibit cell proliferation by at least about 25%, 35%, 45%, 55%, or 65%, as assessed by methods described herein or known to one of skill in the art (e.g., BrdU incorporation assay). In specific embodiments, a method for an inhibiting or antagonizing KIT activity in cells expressing KIT comprises contacting the cells with an effective amount of an antibody described herein sufficient to inhibit cell proliferation by at least about 1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold as assessed by methods described herein or known to one of skill in the art (e.g., BrdU incorporation assay).

In certain aspects, a method provided herein for inhibiting KIT activity in a cell (e.g., cancer cell) expressing KIT comprises contacting the cell with an effective amount of an antibody described herein sufficient to reduce or to inhibit survival of the cell. Cell survival assays are described in the art and can be readily carried out by one of skill in the art. For example, cell viability can be assessed by using trypan-blue staining or other cell death or viability markers known in the art. In a specific embodiment, the level of cellular ATP is measured to determined cell viability. In specific embodiments, cell viability is measured in three-day and seven-day periods using an assay standard in the art, such as the CellTiter-Glo Assay Kit (Promega) which measures levels of intracellular ATP. A reduction in cellular ATP is indicative of a cytotoxic effect. In another specific embodiment, cell viability can be measured in the neutral red uptake assay. In other embodiments, visual observation for morphological changes can include enlargement, granularity, cells with ragged edges, a filmy appearance, rounding, detachment from the surface of the well, or other changes. These changes are given a designation of T (100% toxic), PVH (partially toxic—very heavy—80%), PH (partially toxic—heavy—60%), P (partially toxic—40%), Ps (partially toxic—slight—20%), or 0 (no toxicity—0%), conforming to the degree of cytotoxicity seen. A 50% cell inhibitory (cytotoxic) concentration ($IC_{50}$) is determined by regression analysis of these data.

In specific embodiments, a method provided herein for inhibiting (e.g., partially inhibiting) KIT activity in cells expressing KIT comprises contacting the cells with an effective amount of an antibody described herein sufficient to reduce or to inhibit survival of the cells by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art (e.g., trypan blue exclusion assay). In specific embodiments, a method provided herein for inhibiting (e.g., partially inhibiting) KIT activity in cells expressing KIT comprises contacting the cells with an effective amount of an antibody described herein sufficient to reduce or to inhibit survival of the cells by at least about 25%, 35%, 45%, 55%, or 65%, as assessed by methods described herein or known to one of skill in the art (e.g., trypan blue exclusion assay). In specific embodiments, a method provided herein for inhibiting KIT activity in cells expressing KIT comprises contacting the cells with an effective amount of an antibody described herein sufficient to reduce or to inhibit survival of the cells by at least about 1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold as assessed by methods described herein or known to one of skill in the art (e.g., trypan blue assay).

In a specific embodiment, a method provided herein for inhibiting (e.g., partially inhibiting) KIT activity in cells expressing KIT comprises contacting the cells with an effective amount of an antibody described herein sufficient to induce apoptosis (i.e., programmed cell death). Methods for detecting apoptosis are described in the art and can be readily carried out by one of skill in the art. For example, flow cytometry can be used to detect activated caspase 3, an apoptosis-mediating enzyme, in cells undergoing apoptosis, or Western blotting can be used to detect cleavage of poly(ADP-ribose) polymerase (PARP (see, e.g., Smolich et al., Blood, 2001, 97:1413-1421). Cleavage of PARP is an indicator of apoptosis. In specific embodiments, a method provided herein for an inhibiting or antagonizing KIT activity in cells expressing KIT comprises contacting the cells with an effective amount of an antibody described herein sufficient to induce or enhance apoptosis by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art (e.g., flow cytometry to detect activated caspases 3). In specific embodiments, a method provided herein for an inhibiting or antagonizing KIT activity in cells expressing KIT comprises contacting the cells with an effective amount of an antibody described herein sufficient to induce or enhance apoptosis by at least about 25%, 35%, 45%, 55%, or 65%, as assessed by methods described herein or known to one of skill in the art (e.g., flow cytometry to detect activated caspases 3). In specific embodiments, antibodies a method provided herein for inhibiting KIT activity in cells expressing KIT comprises contacting the cells with an effective amount of an antibody described herein sufficient to induce or enhance apoptosis by at least about 1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold as assessed by methods described herein or known to one of skill in the art (e.g., flow cytometry to detect activated caspase 3).

In a specific embodiment, a method provided herein for inhibiting (e.g., partially inhibiting) KIT activity in a cell expressing KIT comprises contacting the cells with an effective amount of an antibody described herein sufficient to induce differentiation. Methods for detecting differentiation are described in the art and can be readily carried out by one of skill in the art. For example, flow cytometry can be used to detect expression of one or more differentiation markers, or the lack of expression of one or more undifferentiated markers, in a cell contacted with an antibody described herein. Similarly, Western blotting can also be used to detect differentiation markers. Suitable differentiation markers and undifferentiated markers have been described and are one of skill in the art.

In specific embodiments, a method provided herein for inhibiting (e.g., partially inhibiting) KIT activity in cells expressing KIT comprises contacting the cells with an effective amount of an antibody described herein sufficient to induce differentiation by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art (e.g., flow cytometry). In specific embodiments, a method provided herein for inhibiting (e.g., partially inhibiting) KIT activity in cells expressing KIT comprises contacting the cells with an effective amount of an antibody described herein sufficient to induce differentiation by at least about 25%, 35%, 45%, 55%, or 65%, as assessed by methods described herein or known to one of skill in the art (e.g., flow cytometry). In specific embodiments, a method provided herein for inhibiting KIT activity in cells expressing KIT comprises contacting the cells with an effective amount of an antibody described herein sufficient to induce differentiation by at least about 1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold as assessed by methods described herein or known to one of skill in the art (e.g., flow cytometry).

Non-limiting examples of cells which can be differentiated by the methods described herein include stem cells (e.g., embryonic stem cells, hematopoietic stem cells) and progenitor cells. Exemplary hematopoietic stem cell markers include CD38, CD34, CD59, CD133, Sca-1, and ABCG2. Non-limiting examples of neural stem cell markers include Nestin, PSA-NCAM, p75 Neurotrophin R, and Vimentin. Other non-limiting examples of stem cell markers include, Oct4, Sox2, Klf4, LIN28, Nanog, SSEA-3, SSEA-4, Notch, and Wnt.

5.7 Diagnostic Methods

Labeled or otherwise detectable antibodies, which immunospecifically bind to a KIT antigen (e.g., the D4 region of KIT, for example, human KIT) can be used for diagnostic purposes to detect, diagnose, or monitor a KIT-associated disease.

Provided herein are methods for detecting KIT expression in samples obtained from patients with a KIT-associated disorder or disease. In a particular embodiment, a method for detecting KIT expression in a sample obtained from a patient comprises contacting the sample with an anti-KIT antibody described herein and detecting the expression level of KIT in the samples, for example, by correlating the binding of anti-KIT antibody to KIT with KIT expression levels. Methods for detection are known to one of skill in the art.

In certain aspects, provided herein are methods for diagnosing a patient with a KIT-associated disorder or disease. In a certain aspect, a method for diagnosing a subject with a KIT-associated disorder or disease comprises contacting a sample obtained from the subject with an anti-KIT antibody described herein (or an antigen-binding fragment thereof) and detecting the expression level of KIT in the sample. In certain embodiments, a method for diagnosing a patient with a KIT-associated disorder or disease is an in vitro method. In particular embodiments, a method for diagnosing a patient with a KIT-associated disorder or disease is an ex vivo method.

In certain aspects, provided herein are methods for the detection of a KIT-associated disease comprising: (a) assaying the expression of a KIT antigen in cells or a tissue sample of a subject using one or more antibodies described herein; and (b) comparing the level of the KIT antigen with a control level, e.g., levels in normal tissue samples (e.g., from a patient not having a KIT-associated disease, or from the same patient before disease onset), whereby an increase in the assayed level of KIT antigen compared to the control level of the KIT antigen is indicative of a KIT-associated disease.

Methods for detection are known to one of skill in the art. For example, the anti-KIT antibody can be conjugated to a detectable molecule (e.g., as described in section 5.1.1), and the detectable molecule can be visualized using standard techniques (e.g., microscopy). Antibodies described herein can be used to assay KIT antigen levels in a biological sample using classical immunohistological methods as described herein or as known to those of skill in the art (e.g., see Jalkanen et al., 1985, J. Cell. Biol. 101:976-985; and Jalkanen et al., 1987, J. Cell. Biol. 105:3087-3096). Other antibody-based methods useful for detecting protein gene expression include immunoassays, such as ELISA and the radioimmunoassay (MA). Suitable antibody assay labels are known in the art and include enzyme labels, such as, glucose oxidase; radioisotopes, such as iodine ($^{125}$I, $^{121}$I) carbon ($^{14}$C), sulfur ($^{35}$S), tritium ($^{3}$H), indium ($^{121}$In), and technetium ($^{99}$Tc); luminescent labels, such as luminol; and fluorescent labels, such as fluorescein and rhodamine, and biotin. In specific embodiments, diagnostic methods described herein involve using naked or unlabeled antibodies not conjugated to a detectable marker, and the naked or unlabeled antibodies are detected indirectly, e.g., by using a secondary antibody, which can be labeled.

In certain embodiments, high expression of KIT in a sample relative to a normal control sample (e.g., sample obtained from a healthy patient not suffering from a KIT-associated disorder or disease) indicates that the patient is suffering from a KIT-associated disorder or disease.

A method for diagnosing a patient with a KIT-associated disorder or disease, such as cancer, in a sample obtained from a patient comprises contacting the sample with an anti-KIT antibody described herein and detecting the expression level of KIT in the sample. In certain embodiments, high expression of KIT in a sample relative to a normal control sample (e.g., sample obtained from a healthy patient not suffering from a KIT-associated disorder or disease) indicates that the patient is suffering from a KIT-associated disorder or disease.

In certain embodiments, a sample can be a tumor sample derived from, or comprising tumor cells from, a patient's tumor. Examples of tumor samples herein include, but are not limited to, tumor biopsies, circulating tumor cells, circulating plasma proteins, ascitic fluid, primary cell cultures or cell lines derived from tumors or exhibiting tumor-like properties, as well as preserved tumor samples, such as formalin-fixed, paraffin-embedded tumor samples or frozen tumor samples. In certain embodiments, a sample is a fixed tumor sample which has been histologically preserved using a fixative. In some embodiments, a sample is a formalin-fixed tumor sample which has been preserved using formaldehyde as the fixative. In certain embodiments, a sample is an embedded tumor sample which is surrounded by a firm and generally hard medium such as paraffin, wax, celloidin, or a resin. Embedding makes possible the cutting of thin sections for microscopic examination or for generation of tissue microarrays (TMAs). In particular embodiments, a sample is a paraffin-embedded tumor sample which is surrounded by a purified mixture of solid hydrocarbons derived from petroleum. In certain embodiments, a sample is a frozen tumor sample which is, or has been, frozen. In a specific embodiment, a sample, for example, a paraffin-embedded sample or frozen sample, is sectioned.

In certain aspects, a cancer or biological sample which displays KIT expression, amplification, or activation is one which, in a diagnostic test, expresses (including overexpresses) a KIT receptor, has amplified KIT gene, and/or otherwise demonstrates activation or phosphorylation of a KIT receptor.

Also provided herein is the detection and diagnosis of a KIT-associated disease in a human. In one embodiment, diagnosis comprises: a) administering (for example, parenterally, subcutaneously, or intraperitoneally) to a subject an effective amount of a labeled antibody described herein; b) waiting for a time interval following the administering for permitting the labeled antibody to preferentially concentrate at sites in the subject where the KIT antigen is expressed (and for unbound labeled molecule to be cleared to background level); c) determining background level; and d) detecting the labeled antibody in the subject, such that detection of labeled antibody above the background level indicates that the subject has a KIT-mediated disease. Background level can be determined by various methods including, comparing the amount of labeled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99}$Tc. The labeled antibody will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982)).

Depending on several variables, including the type of label used and the mode of administration, the time interval following the administration for permitting the labeled antibody to preferentially concentrate at sites in the subject and for unbound labeled antibody to be cleared to background level is 6 to 48 hours or 6 to 24 hours or 6 to 12 hours. In another embodiment the time interval following administration is 5 to 20 days or 5 to 10 days.

In one embodiment, monitoring of a KIT-mediated disease is carried out by repeating the method for diagnosing the a KIT-mediated disease, for example, one month after initial diagnosis, six months after initial diagnosis, one year after initial diagnosis, etc.

Presence of the labeled molecule can be detected in the subject using methods known in the art for in vivo scanning. These methods depend upon the type of label used. Skilled artisans will be able to determine the appropriate method for detecting a particular label. Methods and devices that can be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patient using positron emission-tomography. In yet another embodiment, the molecule is labeled with a paramagnetic label and is detected in a patient using magnetic resonance imaging (MRI).

6. EXAMPLES

The examples in this section (i.e., section 6) are offered by way of illustration, and not by way of limitation.

6.1 Example 1: Generating Anti-KIT Antibodies

Anti-KIT antibodies were designed using Composite Human Antibody™ technology (Antitope Ltd., Cambridge, United Kingdom) and the amino acid sequence of the mouse antibody 37M (U.S. patent application Ser. No. 13/358,210 filed Jan. 25, 2012) which immunospecifically binds to a human KIT D4 region, to produce anti-KIT antibodies with human amino acid sequences, wherein the antibodies bind a human KIT D4 region. Five heavy chain variable region sequences (H1, H2, H3, H4 and H5) and four light chain variable region sequences (L1, L2, L3 and L4) were selected to be used for gene synthesis, expression in mammalian cells and testing for direct binding to recombinant KIT domains as well as activity in blocking stem cell factor (SCF)-induced phosphorylation. Amino acid sequences for H1-H5, L1-L4 and nucleic acid sequences encoding them are shown in FIGS. 3A-3I.

Nucleic acid molecules encoding the H (heavy chain) and L (light chain) variable region amino acid sequences were cloned directly into expression vectors for human IgG1 VH chains and human $V_\kappa$ chains. All constructs were confirmed by sequencing. Vectors encoding IgG1 VH (H1-H5) and $V_\kappa$ (L1-L4) chains were transfected into CHO cells (e.g., CHOdhfr− cells) in different combinations to produce twenty antibodies (see Table 4, antibodies Hum1-Hum20). Vectors encoding the chimeric antibody 37C, a chimeric antibody with human constant domains and mouse 37M variable domains (U.S. patent application Ser. No. 13/358,210 filed Jan. 25, 2012), were also transfected into CHO cells. Cells transiently transfected with non-linearized DNA were incubated for four days prior to harvesting supernatants which were used directly in assays or for purification. Stable transfections to establish cell lines expressing the antibodies were carried out using linearized DNA and were subsequently drug-selected. Supernatants from drug-resistant colonies for each construct were tested for IgG titre using an IgG1 ELISA, and the best expressing lines were selected based on an above-background (usually >0.1 µg/ml) IgG titre in the supernatant, and expanded in the presence of drug selection through 24-well and 6-well plates, T75 and T175 tissue culture flasks, with screening for IgG expression at every stage. Titers of 0.1-1 µg/ml are typical for non-optimised CHOdhfr− cell lines. Antibody expression was confirmed by Coomassie Blue stained SDS-PAGE.

In these particular cells, a majority of the antibodies were expressed with a titer in the range of 0.1-1.0 µg/ml, and in particular, antibody Hum4 was expressed at a titer of 1.2 µg/ml.

6.2 Example 2: Binding Affinity to Human KIT Ig-Like Domains D4/D5

The binding affinity of the anti-KIT antibodies to the target antigen KIT Ig-like domains D4/D5 was assessed by direct binding ELISA. A dilution series (three-fold) of chimeric antibody 37C and Hum1-Hum20 antibodies from approximately $1 \times 10^{-8}$ M to $4.7 \times 10^{13}$ M was incubated for 1 hour at room temperature on a flat bottom microtitre plate pre-coated with 50 ng/well recombinant c-Kit Ig-like domains D4/D5 (see FIG. 2) diluted in borate buffer and pre-blocked for 1 hour with 1% BSA. Bound antibody was detected with anti-human Ig-HRP followed by detection using TMB substrate. Results are presented in Table 7 below.

TABLE 7

Binding characterization of anti-KIT antibodies.

| Antibody | Relative binding activity assay #1 (sup) | Relative binding activity assay #2 (sup) | Relative binding activity assay #3 (purified) | Relative binding activity assay #4 (purified) |
|---|---|---|---|---|
| Hum1 |  | 0.64 |  |  |
| Hum2 |  | 0.79 |  |  |
| Hum3 |  | 0.88 |  |  |
| Hum4 |  | 0.91 | 1.07 | 0.83 |
| Hum5 |  | 0.93 |  |  |
| Hum6 | 1.15 | 0.70 |  |  |
| Hum7 | 1.12 | 0.80 |  |  |
| Hum8 | 1.02 | 0.62 | 0.89 | 0.75 |
| Hum9 | 1.08 | 1.00 | 0.85 |  |
| Hum10 | 1.10 | 0.88 | 0.87 | 0.72 |
| Hum11 |  | 0.74 |  |  |
| Hum12 | 1.23 | 0.72 |  |  |
| Hum13 | 1.11 | 0.78 |  |  |
| Hum14 | 1.14 | 1.03 | 0.74 |  |
| Hum15 | 0.87 | 0.76 | 0.87 |  |
| Hum16 | 1.2 | 1.02 |  |  |
| Hum17 | 1.17 | 0.76 | 0.98 | 0.72 |
| Hum18 | 1.22 | 0.79 | 0.99 |  |
| Hum19 | 1.11 | 1.05 | 0.95 | 0.85 |
| Hum20 | 0.80 | 0.70 |  |  |
| $EC_{50}$ (pM) chimeric (replicates) | 380.74 ± 18.3 (×4) | 411.66 ± 183.7 (×5) | 462.35 ± 28 (×2) | 567.76 (×1) |

EC50 values (pM) were calculated for anti-KIT antibodies Hum1-20, and values for antibodies were normalized against those for the chimeric antibody 37 C in the corresponding experiment. Higher values indicate stronger binding activity. Actual $EC_{50}$ values for the chimeric antibody in each experiment are shown at the foot of the table along with the number of replicates averaged to achieve that value.
(sup) = supernatant containing antibody;
(purified) = antibody purified from supernatant.

The binding activity of certain of the antibodies as well as chimeric antibody 37C was further characterized by solid phase ELISA using an antigen containing the D4/D5 region (see FIG. 2) of human KIT. The general protocol used for the solid phase ELISA experiments is described below.

Materials:
Recombinant antigen: Recombinant IG domain four and five of the extracellular region of KIT
TBS-T: 50 mM Tris pH 7.4, 150 mM NaCl, 0.1% Tween 20
TBS: 50 mM Tris pH 7.4, 150 mM NaCl
Blocking solution: 1% bovine serum albumin (BSA) in TBS
Dilution buffer: 1% BSA in TBS-T
Detection antibody solution: Goat anti-mouse IgG HRP antibody and Pierce goat anti-human F(ab')$_2$ specific conjugated with horseradish peroxidase (Thermo scientific 31414)
Detection Substrate: TMB (3,3',5,5'-tetramethylbenzidine) Substrate kit (Thermo scientific #34021)

Recombinant antigen corresponding to the D4/D5 region of the KIT extracellular domain (see FIG. 2) was absorbed onto 96-well microtiter plates. In particular, recombinant antigen (5 µg) were diluted into 10 mL of borate buffer, and 100 µL of the antigen solution were added to each well of a 96 well plate and were incubated at 4° C. overnight.

Serial dilutions of antibody samples were prepared with dilution buffer for ELISA.

ELISA: Following one rinse with TBS-T, blocking buffer (200 µL) was added to each well of the plate with the adsorbed antigen and was incubate at room temperature for one hour. Then, the blocking buffer was removed, and the serially diluted solutions of test antibodies and controls were added to the plate in a volume of 50 µL and incubated at room temperature for one hour. The antibody solutions were removed, and the plate was washed three times with 100 µL of wash buffer on a plate washer. After the last wash, the plate was blotted dry. Secondary antibody solution was diluted 1:8000 and was added to each well in a volume of 100 μL and allowed to incubate for one hour at room temperature. The diluted secondary antibody solution was removed, and the plate was washed three times with 100 μL of wash buffer on a plate washer. Then, freshly mixed TMB substrate solution was added to each well in a volume of 100 μL and was allowed to incubate at room temperature for 30 minutes. Subsequently, 100 μL of 2N $H_2SO_4$ were added to each well and immediately read on the plate reader. An irrelevant antibody served as the negative control, and an anti-KIT antibody against the D4 and/or D5 domain of the extracellular region of KIT served as the positive control. OD values for each sample were obtained at a wavelength of 450 nm.

Results were analyzed using Graph Pad Prism and Excel to obtain the concentration of antibodies at 50% binding to antigen.

Figure 5:
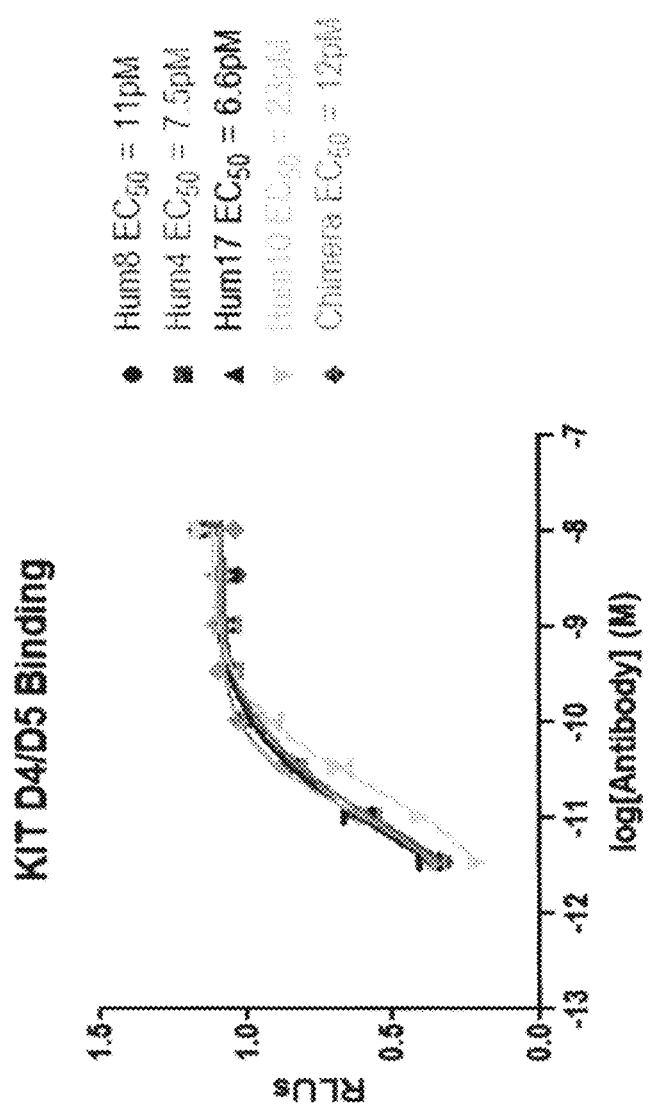
FIG. 5 depicts the binding activity of antibodies Hum17, Hum8, Hum4, and Hum10, as well as a chimera of antibody 37M ("chimera"), to a recombinant polypeptide of the D4/D5 region of human KIT as determined by solid phase ELISA. The $EC_{50}$ value for each antibody is indicated.

FIG. 5 depicts a graph plotting $OD_{450}$ versus log concentration (M) of anti-KIT antibodies. The effective concentration at 50% binding ($EC_{50}$) for the binding affinity of a chimera of antibody 37M and antibodies Hum17, Hum8, Hum4, and Hum10 to the D4/D5 region of human KIT was calculated to be approximately 12 pM, 6.6 pM, 11 pM, 7.5 pM, and 23 pM, respectively.

The results presented in FIG. 5 show that the binding affinities of a chimera of antibody 37M and and antibodies Hum17, Hum8, Hum4, and Hum10 are comparable.

Additional binding assays demonstrated that Hum17, Hum8, Hum4, and Hum10 exhibited specific binding to canine KIT and monkey KIT, in addition to human KIT, but they did not exhibit specific binding to murine KIT.

6.3 Example 3: Binding Affinity of Anti-KIT Antibodies for Human KIT Expressed on CHO Cells To confirm that the anti-KIT antibodies can bind to KIT expressed on the surface of cells, flow cytometry assays were carried out using CHO cells that do (CHO/KIT-WT) and do not (parental CHO cells) exogenously express the full-length, wild-type human KIT receptor. Briefly, parental CHO cells and CHO/KIT-WT cells were washed and incubated with 0.01 nM, 0.1 nM, 1 nM or 10 nM of a chimeric (human-mouse) 37M antibody, antibody Hum17, Hum8, Hum4, or Hum10, a negative control isotype IgG antibody, or a commercial anti-KIT antibody as a positive control. The samples were processed for flow cytometry analysis. More specifically, cells were removed from the culture flasks using EDTA, and washed with PBS. Then, the cells were resuspended in media and counted. Each sample containing approximately 200,000 to 250,000 cells was spun, the media was removed, and the cells were resuspended in FC buffer (1% BSA, 0.01% sodium azide in 1×PBS) for the blocking step. The cells were incubated in FC buffer for 1 hour on ice. Then, primary antibody (e.g., a chimeric (human-mouse) 37M antibody, Hum17, Hum8, Hum4, Hum10, positive control anti-KIT antibody, or negative control antibody) was added to the cells in FC buffer as described above. The samples were mixed and incubated on ice for 1 hour, followed by washing the cells with 0.5-1 mL FC buffer. The FC buffer was removed by spinning the cells at 1200 rpm for 3 minutes at 4° C., decanting the liquid. The cell pellets were resuspended in 200 μL FC buffer, and secondary antibody (DyLight 488 AffiniPure Goat Anti-Mouse IgG Jackson Laboratories) was added to the cells at a 1:1000 to 1:2000 dilution. The samples were mixed and incubated on ice for 1 hour, and then washed as described above. The samples were run on a fluorescence activated cell sorter (FACS) machine (Accuri FlowCytometer C6). Samples were analyzed by following channel FLA-1 for DyLight-conjugated samples.

Figure 6:
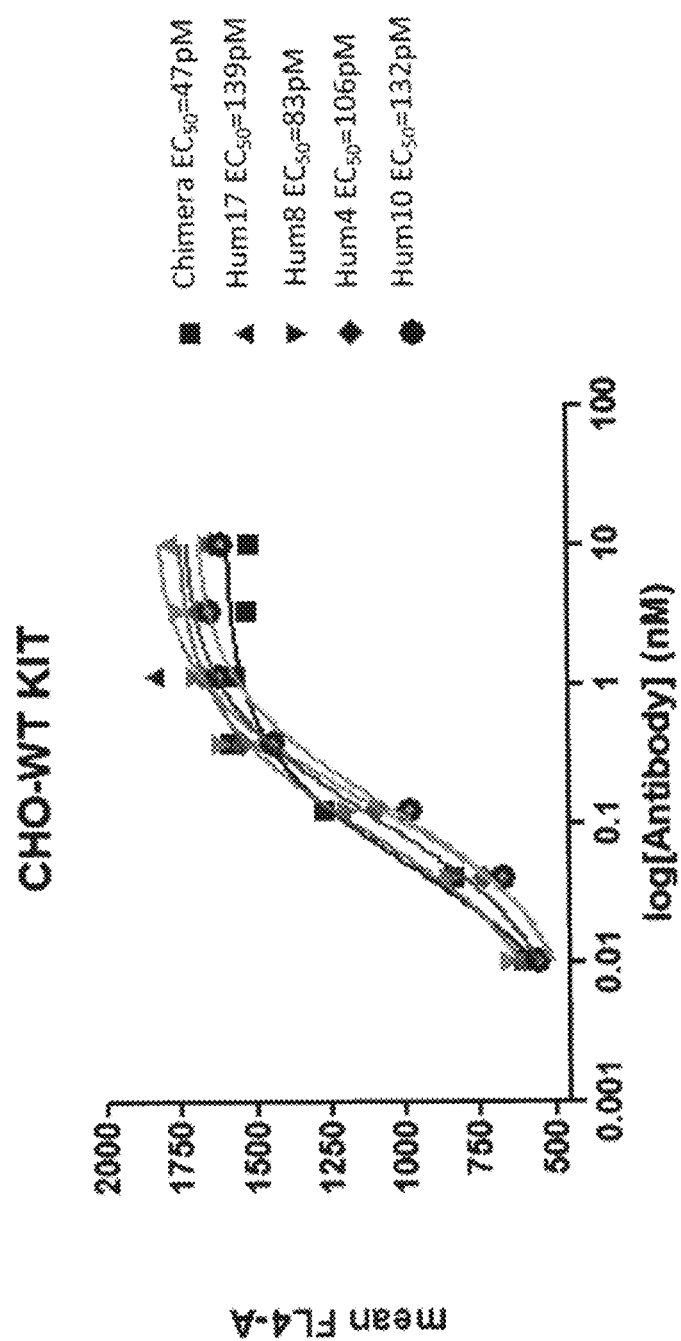
FIG. 6 depicts a graph of the results of binding assays performed by flow cytometry with CHO cells recombinantly expressing wild-type human KIT to characterize the KIT binding activity of antibodies Hum17, Hum8, Hum4, and Hum10, in comparison to a chimera of antibody 37M ("chimera"). The $EC_{50}$ value for each antibody is indicated.

FIG. 6 summarizes the results from the flow cytometry analysis. The effective concentration at 50% binding ($EC_{50}$) for the binding affinity of a chimera (human-mouse) of antibody 37M and antibodies Hum17, Hum8, Hum4, and Hum10 to the D4/D5 region of human KIT was calculated to be approximately 47 pM, 139 pM, 83 pM, 106 pM, and 132 pM, respectively.

The results presented in FIG. 6 show that the binding affinities of the chimeric 37M antibody and antibodies Hum17, Hum8, Hum4, and Hum10 for cell surface expressed human KIT are comparable.

6.4 Example 4: Inhibition of KIT Phosphorylation Induced by SCF in Cell-Based Phospho-KIT Assays The inhibition of stem cell factor (SCF)-mediated phosphorylation of cell-surface KIT by anti-KIT chimeric 37M antibody and certain anti-KIT antibodies described herein was assessed in a cell-based assay as follows: CHO-KIT cells, sorted for high cell surface antigen expression, were cultured overnight in 24-well or 96-well plates in the absence of serum before addition of a three-fold dilution series from $1 \times 10^{-8}$ M-$1.4 \times 10^{11}$ M of test antibody (chimeric or anti-KIT antibodies described herein purified from supernatant) or control blocking antibody (BioLegend, clone A3C6E2).

Following incubation for 2 hours at 37° C., cells were stimulated with 30 ng/mL SCF (R&D Systems, cat. no. 255-SC/CF) for 10 min at 37° C., lysed in the presence of protease and phosphatase inhibitors, and KIT protein was captured from whole lysates onto white-walled 96-well Maxisorp plates pre-coated with KIT capture antibody (Thermo Scientific, cat. no. LVMS289-PABX). For the 96-well format, duplicate wells were set up for each condition and lysed and transferred separately to the capture plate whilst for the 24-well format, duplicate samples of lysate were taken from the same well. Following overnight incubation at 4° C. and extensive washing of the plate, tyrosine phosphorylated KIT was detected using HRP-conjugated anti-phosphotyrosine clone 4G10 (Millipore, cat. no. 16-105) and West PICO chemiluminescent substrate (Fisher, cat. no. PN34087). The results are presented in Table 8 below.

TABLE 8

| | Blocking Assays | | | |
|---|---|---|---|---|
| Antibody | Relative blocking activity, assay #1 (24-well) | Relative blocking activity, assay #2 (24-well) | Relative blocking activity, assay #3 (96-well) | Relative blocking activity, assay #4 (96-well) |
| Hum4 | 1.2 | | | 0.86 |
| Hum8 | | 1.01 | | 1.12 |

TABLE 8-continued

Blocking Assays

| Antibody | Relative blocking activity, assay #1 (24-well) | Relative blocking activity, assay #2 (24-well) | Relative blocking activity, assay #3 (96-well) | Relative blocking activity, assay #4 (96-well) |
|---|---|---|---|---|
| Hum9 | | | 1.05 | |
| Hum10 | | 0.82 | | 0.86 |
| Hum13 | | | 1.00 | |
| Hum14 | | 0.94 | | |
| Hum15 | 0.98 | | 0.99 | |
| Hum17 | | 1.39 | | 1.07 |
| Hum18 | | 1.22 | | |
| Hum19 | 1.09 | | 0.98 | 1.40 |

$IC_{50}$ values (pM) were calculated for these antibodies and values for were normalized against those for the chimeric 37 M antibody in the corresponding experiment. Higher values indicate stronger blocking activity. "(96-well)" refers to assays carried out in 96-well plate format as opposed to 24-well format (24-well).

The results in Table 8 shows that the blocking activities of antibodies Hum4, Hum8, Hum9, Hum10, Hum13, Hum14, Hum15, Hum17, Hum18, and Hum19 are comparable to the blocking activity of a chimera of antibody 37M.

To further characterize the effect of these antibodies on KIT activity, specifically, SCF-induced tyrosine phosphorylation of the cytoplasmic domain of KIT, cell-based phospho-KIT assays were carried out as follows.

Materials:
CHO cells stably transfected with a plasmid encoding full-length human KIT (see FIG. 1), which was cloned from a human ovary cDNA library (OriGene, Rockville, Md.)
Complete cell culture media (see Table 9)
Starving media: Cell culture media described in Table 9 without FBS
Trypsin-EDTA
PBS
SCF solution: rhSCF (RD Systems 255-SC/CF); final concentration 30 ng/mL
Lysis buffer: 50 mM Tris pH 7.4, 150 mM NaCl, 1 mM EDTA, 1% Triton X-100, protease inhibitor cocktail tables EDTA free (Roche Diagnostics 04693132001), 1 mM $NaVO_4$
TBS-T: 50 mM Tris pH 7.4, 150 mM NaCl, 0.1% Tween 20
Blocking solution: 5% bovine serum albumin (BSA) in TBS-T
Dilution buffer: 1% BSA in TBS-T containing 1 mM $NaVO_4$
Detection antibody solution: anti-phospho-tyrosine antibody conjugated with horse radish peroxidase (Millipore, 4G10); dilution factor 1:500
Capture antibody: anti-KIT antibody Ab3 from Thermo Scientific (MS-289-PABX)

TABLE 9

Cell Culture Media

| | |
|---|---|
| Cell line | CHO (parental or KIT transfected) |
| Basic medium | Gibco F12 Nutrient Mixture (Ham) 1 × 11765 |
| Penicillin/Streptomycin (Cellgro 30-001-CI) | 50 IU/mL penicillin 50 μg/mL streptomycin |
| 100 × GlutaMAX ™-I (Gibco 35050) | 1 × GlutaMAX ™ |
| Geneticin (Invitrogen 10131027) | 1 mg/mL Geneticin (for selection of transfected cells only) |

Passaging of CHO/KIT-WT cells: Confluent cells were washed once with sterile PBS, incubated with 0.25% Trypsin-EDTA at room temperature until cells detached from the plastic tissue culture plates. Complete culture medium, which contains FBS, was added to the plate to end the tryptic digestion.

Counting Cells: Ten microliters of cell suspension were mixed with 10 μL of 0.4% trypan blue. Half of this mixture (10 μL) was transferred into a cell counting chamber (Invitrogen), and the cells were counted. Cells (200,000 per well) were transferred into a 24-well cell culture plate, and were cultivated in complete medium (Table 9) for 24 hours under normal cell culture conditions (i.e., humidified 95% air and 5% $CO_2$ atmosphere at 37° C.).

Cell Treatment: After the cells were plated in the 24-well plates and cultured overnight, the medium was removed, and the cell monolayer was washed once with starvation medium. The cells were then cultured for 24 hours in starvation medium under normal cell culture conditions. Then the cells were treated with a chimeric (human-mouse) 37M antibody, Hum4, Hum8, Hum10, Hum17, or control antibody solutions for 2 hours under normal cell culture conditions. The final concentration for the antibody solution was 100 nM (5 μg/mL) or less. Subsequently, SCF solution was added to the cells pretreated with anti-KIT antibodies or control antibody at a final concentration of 30 ng/mL for 10 minutes under normal cell culture conditions.

Controls:
Negative controls: starved, untreated and non-stimulated cells
Positive control: starved, untreated and SCF-stimulated cells
Drug control: starved cells, treated with 1 μM Gleevec and stimulated with SCF
Antibody control: cells starved, treated with 100 nM blocking antibody (purified mouse anti-human KIT antibody (BioLegend A3C6E2) that binds to the SCF binding site)

Preparation of cell lysates: After stimulation, cells in the 24-well plate were placed on ice immediately, the cells were washed once with cold PBS, and lysed with 100 μL of cold lysis buffer.

Preparation of 96-well ELISA plate with capture antibody: Capture antibody (5 μL) was diluted in 10 mL 50 mM Borate buffer, and the capture antibody solution (100 μL or 50 ng/well) was added to each well of the 96-well ELISA plate. The 96-well plate was incubated at room temperature for 5-6 hours or overnight at 4° C. The capture antibody solution was removed prior to the blocking step. Blocking was carried out by adding 100 μL of blocking solution to each well and allowed to incubate at room temperature for 1 hour. The blocking solution was removed, the wells were washed once with dilution buffer, and 50 μL of dilution buffer were added to each well.

Phospho-KIT assay: 50 μL of the cell lysates of each sample from a well of the 24-well plate were transferred into 1 well of the prepared 96-well plate containing 50 μL dilution buffer, and the 96-well plate was incubated overnight at 4° C. Following the overnight incubation, the supernatant was removed, and the plate was washed 3 times (5 minute incubation each time) with TBS-T. Detection antibody dilution (100 μL) was added to each well and incubated for 1 hour at room temperature in the dark. The plate was washed 3 times with TBS-T, washed once with TBS, and the TBS was removed. The "SuperSignal West Dura Extended Duration Substrate" reagents (Thermo Scientific) were mixed (1:1), and 100 µL of the mix were added to each well.

Luminescence was detected in the ELISA plate reader using the GEN5™ protocol "Luminescence Glow" and the data were analyzed using Microsoft Excel.

Figure 7:
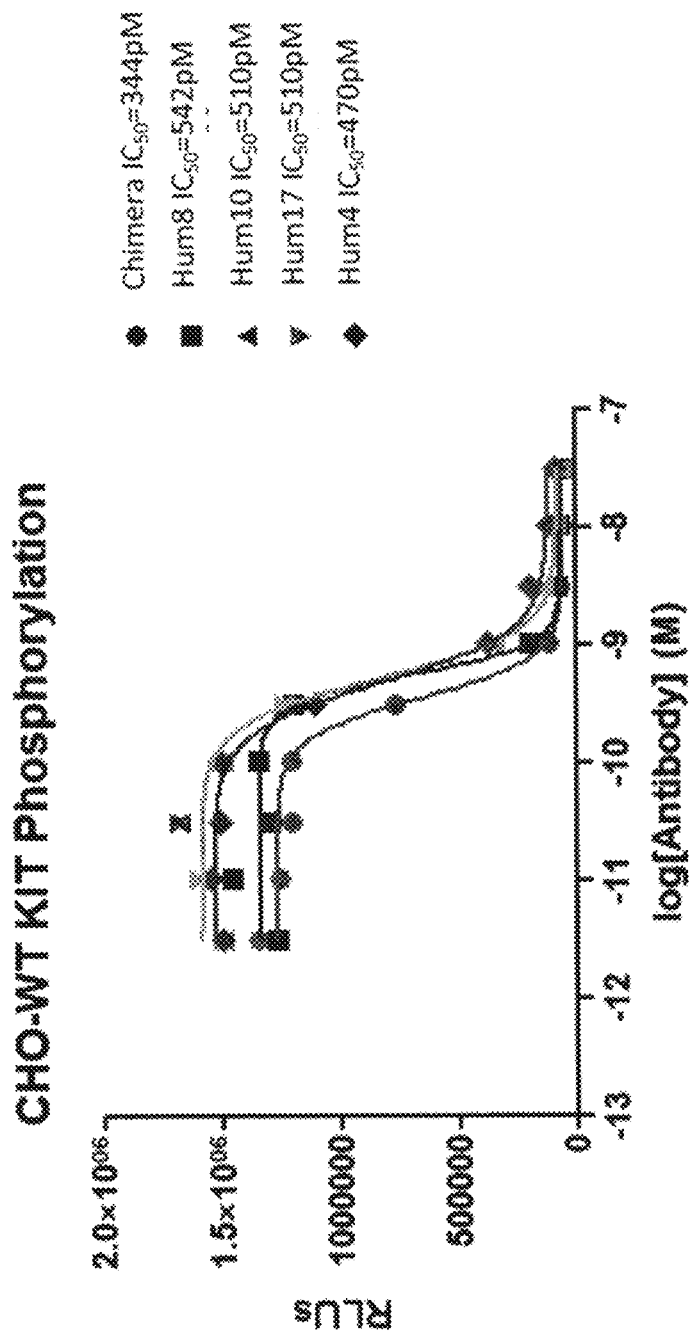
FIG. 7 depicts a graph of the results of KIT phosphorylation inhibition assays performed by ELISA with CHO cells recombinantly expressing wild-type KIT to characterize the phosphorylation blocking activity of antibodies Hum17, Hum8, Hum4, and Hum10, in comparison to a chimera of antibody 37M ("chimera"). The $IC_{50}$ values for each antibody are indicated.

FIG. 7 depicts a graph plotting the data from these experiments. The graph is a plot of arbitrary luminescence units versus log concentration (M) of either a chimera (human-mouse) of antibody 37M or antibody Hum17, Hum8, Hum4, or Hum10. The 50% inhibition concentrations ($IC_{50}$) of the chimera 37M, Hum17, Hum8, Hum4, and Hum10 antibodies were calculated to be approximately 344 pM, 510 pM, 542 pM, 470 pM, and 510 pM, respectively. The results indicate that antibodies Hum17, Hum8, Hum4, and Hum10, like the 37M chimera antibody, are effective inhibitors of ligand (SCF)-induced tyrosine phosphorylation of the cytoplasmic domain of KIT.

These anti-KIT antibodies can be expressed in a variety of different cell types without substantially affecting the properties of the antibody, for example, binding activity and blocking activity. For example, anti-KIT antibodies Hum17, Hum8, Hum4, and Hum10 were expressed in a different recombinant expression system based on HEK293-Freestyle (293F) cells, and exhibited blocking activity as determined by KIT phosphorylation inhibition assays. These results indicate that a variety of cell systems can be used for expressing anti-KIT antibodies described herein, such as antibodies Hum1-Hum20, without compromising antibody activity.

6.5 Example 5: Antibody Internalization by CHO Cells Expressing Wild-Type KIT Immunofluorescence staining assays were carried out to assess internalization of antibodies Hum4, Hum10, Hum17, and Hum8 by CHO cells expressing wild-type KIT ("CHO/KIT-WT").

The immunofluorescence staining assays were carried out essentially as described below. Materials and reagents for the immunofluorescence assays included the following:

Primary antibodies: antibodies Hum4, Hum8, Hum10, Hum17, 37M, and β-Tubulin (9F3) rabbit monoclonal antibody (mAb) (Cell Signaling #2128).

Secondary antibodies: goat anti-mouse antibody conjugated to Oregon Green® 488 (Invitrogen #011038), goat anti-rabbit antibody conjugated to Texas Red (Invitrogen # T2767), and goat anti-human antibody conjugated to Alexa Fluor 488 (Invitrogen # A11013).

Fixative: 4% paraformaldehyde (PFA) (store 40% PFA microscopy grade in fridge and dilute 1:10 with PBS just before use)

Permeabilization solution: PBS with 0.1% Triton X-100 and 0.5% BSA, sterile filtered Blocking/dilution solution: 2% BSA in PBS, sterile filtered Mounting media: ProLong® Gold antifade reagent with DAPI (P36931 Invitrogen) (4',6-diamidino-2-phenylindole)

CHO cells engineered to express exogenous human, wild-type KIT (full-length) ("CHO/KIT-WT")

CHO cells (e.g., 75,000 cells per well) were seeded into a 24-well tissue culture plate containing one round glass coverslip per well. The cells were cultivated for at least 6 hours before overnight starvation in media containing no fetal bovine serum. Following starvation, the culture media was removed from the cells and antibody 37M, Hum4, Hum10, Hum17, or Hum8 diluted to 33.3 nM in starvation media containing 1% bovine serum albumin, was transferred onto the cell layer at time 0 minute, 30 minutes, 45 minutes or 55 minutes to generate a time course. Cells were incubated for the indicated times under standard culture conditions (37° C. and 5% $CO_2$). Cell layers were washed once with PBS (room temperature) 5 to 60 minutes after addition of the antibody. Cell layers were fixed for 20 minutes with 4% PFA at room temperature, and were washed 3 times with PBS. Cell membranes were permeabilized by the addition of permeabilization solution for 3 minutes followed by 3 washes with PBS. Blocking solution was added to each well, and cells were blocked for 20 minutes at room temperature. The β-Tubulin (9F3) rabbit mAb was diluted 1:100 in dilution solution and incubated with the cell layers for 1 hour at room temperature followed by 2 washes with PBS and one with blocking solution. Both secondary antibodies were diluted together at 1:200 in dilution solution before being added to the cells. Cells were incubated in secondary antibody in the dark at room temperature for 1 hour followed by 3 PBS washes. The cells on the coverslips were mounted against the glass slides using one drop of ProLong® Gold antifade reagent with DAPI and were kept at room temperature overnight. Internalization of the antibody was analyzed by fluorescence microscopy at various time point, e.g., 5 minutes and 60 minutes of exposure to antibody 37M, Hum4, Hum10, Hum17, or Hum8.

The immunofluorescence staining assays demonstrated that, in CHO/KIT-WT cells, antibodies Hum4, Hum10, Hum17, and Hum8, similarly to antibody 37M, bound to the surface of these cells, and were internalized by these cells. In particular, images of cells exposed to these antibodies show staining of membrane-associated structures at early time points, such as at 5 minutes after exposure to anti-KIT antibodies, and show staining of internal structures (e.g., vesicles) at later time points, such as at 60 minutes after exposure to antibody. In contrast, images of cells exposed with anti-β-Tubulin antibody, as a control, showed staining of elongated structures throughout the cytoplasm of the cells. These results indicate that antibodies Hum4, Hum10, Hum17, and Hum8 are internalized by cells expressing KIT. Effective internalization of antibodies is useful, e.g., for delivering toxins to cells, for example cancer cells, expressing KIT.

6.6 Example 6: Stability Data

Successful development of therapeutic antibodies is, in part, dependent on the characterization of the antibody stability in vivo. To this end, both the relative thermal stability and relative stability under mimicked physiological conditions (i.e., serum, 37° C.) of a subset of anti-KIT antibodies described herein was characterized.

Differential Scanning calorimetry:

Differential Scanning calorimetry (DSC) is a thermoanalytical technique used to determine the point at which a sample of interest undergoes phase transition, such as melting or crystallization. Therefore, DSC is a useful tool to compare the relative thermal stability of multiple antibodies. To this end, a subset of anti-KIT antibodies described herein (e.g., antibodies Hum1-Hum20) were analyzed using DSC, and the melting temperatures of these antibodies were determined. The melting profiles of each anti-KIT antibody revealed one major melting peak, and one or two minor peaks. The prevalent melting points ranged from 85.7° C. to 86.6° C., while the minor peaks were calculated to be from 71.6° C.-71.9° C. These results, showing that the melting temperatures are significantly higher than 37° C., indicate that these anti-KIT antibodies can be stable in a therapeutic setting, for example, at 37° C.

Serum Stability:

To better understand the stability of anti-KIT antibodies described herein under physiological conditions, antibody activity was assessed following long-term incubation in fetal calf serum at 37° C. Briefly, anti-KIT antibodies were diluted to 0.2 mg/mL in serum-free media or media containing 50% fetal calf serum. Samples were incubated at 37° C. for 1, 2 and 3 weeks, at which point aliquots were compared to antibody stored at 4° C. for the same duration in both binding ELISA and cell-based phosphorylation assays as described in earlier examples. Using the 4° C. antibody as a reference, binding ELISA assays revealed that following one week, the maximum change in $EC_{50}$ value was 4-fold, but was as low as 1.1-fold, while after two weeks, the maximum change was 4-fold, using the 4° C. antibody as a control. Consistently, $IC_{50}$ values in cell-based phosphorylation assays for these same anti-KIT antibodies stored at 37° C. with or without serum varied by less than two-fold from those of the antibodies stored at 4° C.

Together, these data suggest long-term stability of anti-KIT antibodies described herein, as the binding and blocking activity of each antibody is maintained following incubation both in serum and at an elevated temperature. These results indicate that anti-KIT antibodies described herein (e.g., Hum1-Hum20) can exhibit maintained activity and can, for example, be used in a less-frequent dosing regimen.

6.7 Example 7: Blocking Ligand-Induced AKT Phosphorylation

Anti-KIT antibodies described herein (e.g., Hum1-Hum20) are assayed for the ability to inhibit or block AKT phosphorylation, which is a downstream signaling event of KIT signaling. The assay is carried out as described above with the following modifications. First, a mouse anti-AKT antibody is immobilized on ELISA plates as a capture antibody. Second, the detection of AKT phosphorylation (phospho-AKT) is performed using a two-step method. After incubation of the cell lysates with the coated ELISA plate, a biotinylated mouse monoclonal antibody recognizing phospho-AKT (Ser473) is added to each well for 1 hour at room temperature at a dilution of 1:500. Following this incubation and subsequent washes, the phospho-AKT antibody is detected with Protein Western C Streptavidin-HRP antibody (BioRad) at a dilution of 1:2500. The final detection step with TMB substrate solution is performed as described herein (e.g., sections 6.2 and 6.4).

6.8 Example 8: Animal Model Study of Anti-KIT Antibodies in Treating Cancer

The anti-tumor effects of anti-KIT antibodies described herein are confirmed using mouse models, such as xenograft mouse models, of human tumors. Various mouse models for studying cancer have been described (see, e.g., Fernandez et al., J. Clin. Invest., 2007, 117(12): 4044-4054). Below, mouse models, e.g., xenograft mouse models, derived from a variety of patient-derived, human cell lines are described. Mouse models for assessing toxicity are also described below.

Gastrointestinal Stromal Tumor (GIST)

Mouse models of GIST have been described, for example, see, Fernandez et al, J. Clin. Invest., 2007, 117(12): 4044-4054. For example, GIST cells are harvested from subconfluent cultures by a brief exposure to 0.05% trypsin-EDTA (Invitrogen). Trypsinization is stopped with medium containing 10% FBS. The cells are then washed twice in serum-free medium and resuspended in serum-free HBSS (Invitrogen). Single-cell suspensions with greater than 95% viability, as determined by Trypan blue exclusion, are used for the injections. To produce tumors, $1 \times 10^5$ to $1 \times 10^7$ GIST cells, for example $6 \times 10^6$ GIST cells per 100 µl are injected subcutaneously into the unilateral flank of each SCID mouse (e.g., female C.B-17/IcrHsd-Prkdc$^{SCID}$ mice purchased from Harlan Sprague Dawley Inc.; housed in facilities approved by and in accordance with the American Association for Assessment and Accreditation of Laboratory Animal Care, the United States Department of Agriculture, the United States Department of Health and Human Services, and the NIH; and used according to institutional guidelines). Five to ten mice per group in the vehicle and anti-KIT antibody groups are used. Once tumors are palpable (e.g., approximately 8-11 weeks from injection), mice are started on therapy with injections of normal saline (vehicle) or anti-KIT antibodies (e.g., antibodies Hum1-Hum20 or antibody-drug conjugates thereof), for example, daily, weekly, or bi-weekly intraperitoneal injections). Treatment is continued for a period of time, e.g., approximately 6 weeks, with weekly 2-dimensional measurements of tumor size. Imaging methods for detecting tumor size can also be used, e.g., MM. All mice are sacrificed when the tumor size approach approximately 1.5 cm in the control group. Tumors are collected, are fixed in formalin, and are analyzed by H&E staining. Representative images are taken from each tumor using a light microscope at ×40 and ×100 magnification.

A graph of tumor size or volume of each mouse plotted against time (e.g., days or weeks) after tumor injection is generated to ascertain the effect of the anti-KIT antibodies on tumor growth in the mice relative to the vehicle negative control.

Non-limiting examples of GIST cells which may be used in these mouse models include, GIST 430 cells (human GIST cells that express mutated KIT having a deletion of exon 11 (V560-L576) and V654A mutation in exon 13) and GIST882 cells (immortal GIST cells that possess a homozygous exon 13 missense mutation (i.e., K642E) in KIT (see, e.g., Tuveson et al., Oncogene, 2001, 20: 5054-5058)).

Leukemia

To study the effects of anti-KIT antibodies on leukemia, a xenograft mouse model using human leukemia cells (e.g., K562, HEL, or HL60 cells) is established essentially as described above, except that leukemia cells (e.g., K562, HEL, or HL60 cells) are injected into the mice instead of GIST cells. In particular, the tumor cells are collected from subconfluent suspensions. To produce tumors, $1 \times 10^5$ to $1 \times 10^7$ tumor cells per 100 µl are injected into each SCID mouse. The mice are then randomized into the following groups (n=5-10 per group): (a) normal saline daily; and (b) anti-KIT antibodies (e.g., antibodies Hum1-Hum20 or antibody-drug conjugates thereof). The mice are started on therapy (e.g., at day 0, 7, or 14 or when tumors are detectable) with injections of normal saline (vehicle) or anti-KIT antibodies (e.g., daily, weekly, or bi-weekly intraperitoneal injections). Treatment is continued for a period of time, e.g., approximately 6 weeks, with weekly 2-dimensional measurements of tumor size. Imaging methods for detecting tumor size can also be used, e.g., MRI. Tumors are measured weekly during treatment and at necropsy.

A graph of tumor size or volume of each mouse plotted against time (e.g., days or weeks) after tumor injection is generated to ascertain the effect of the anti-KIT antibodies on tumor growth in the mice relative to the vehicle negative control.

Mouse models of human leukemia also can be generated by injecting human leukemia cells into nude mice or irradiated mice, via other routes, such as intravenous route, and monitoring animal death as an indication of progression of leukemia in the presence or absence of treatment with anti-KIT antibodies. A survival curve is generated for each mouse to ascertain the effect of anti-KIT antibodies on survival.

Lung Cancer (e.g., Small Cell Lung Cancer)

A xenograft mouse model using human lung cancer cells, e.g., human small cell lung carcinoma cells (e.g., H526 cells, WBA cells, or NCI-H209 cells) is established essentially as described above, except for a few modifications. For example, lung cancer cells (e.g., small cell lung cancer cells) are injected into mice instead of GIST cells. Lung cancer cells, e.g., H526 tumor cells, are collected, and $1 \times 10^5$ to $1 \times 10^7$ lung cancer cells per 100 µl are injected into each mouse (e.g., SCID mouse). The mice are then randomized into the following groups (e.g. n=5-10 per group): (a) normal saline daily; and (b) anti-KIT antibodies (e.g., antibodies Hum1-Hum20 or antibody-drug conjugates thereof). The mice are started on therapy (e.g., at day 0, 7, or 14 or when tumors are detectable) with injections (e.g., daily, weekly, or bi-weekly intraperitoneal injections) of normal saline (vehicle) or anti-KIT antibodies. Treatment is continued for a period of time (e.g., approximately 6 weeks or more), with weekly 2-dimensional measurements of tumor size. Imaging methods for detecting tumor size can also be used, e.g., MRI. Tumors are measured weekly during treatment and at necropsy.

A graph of tumor size or volume of each mouse plotted against time (e.g., days or weeks) after tumor injection is generated to ascertain the effect of the anti-KIT antibodies on tumor growth in the mice relative to the vehicle negative control. A survival curve is generated to ascertain the effect of the anti-KIT antibodies (e.g., any one of antibodies Hum1-Hum20, or an antigen-binding fragment thereof, or a conjugate thereof) on animal survival.

Mouse models for lung cancer (e.g., small cell lung cancer) have been described (see, e.g., Garton et al., 2006, Cancer Res. 66(2):1015-24; and Wolff et al., 2004, Clin Cancer Res. 10:3528-3534), and may be adapted accordingly to study the effects of anti-KIT antibodies described herein.

Sarcoma

Xenograft models are established using cell lines derived from Ewing's family of tumors, such as RD-ES, SK-ES-1 or SK-N-MC, or rhabdomyosarcomas, such as A-673. Cell lines are available from the American Type Culture Collection (ATCC; Manassas, Va.). Generally, methods similar to those described above are utilized. For example, $2.5-5 \times 10^6$ cells are suspended with trypsin/EDTA or re-suspended in 100-2004, growth medium and implanted subcutaneously into the flank of 6-8 week old immunodeficient mice (NuNu, SCID) (Charles River Laboratories, Wilmington, Mass.). Five to ten mice per group in both the vehicle and anti-KIT antibody groups are used. Once tumors are palpable or have reached 100-200 mm³, mice are started on therapy with injections (e.g., daily, weekly, or bi-weekly intraperitoneal injections) of normal saline (vehicle) or anti-KIT antibodies (e.g., antibodies Hum1-Hum20 or antibody-drug conjugates thereof). Treatment is continued for a period of time, e.g., approximately 6 weeks or more, and tumor size is evaluated (e.g., twice weekly by way of 2-dimensional measurements). Imaging methods for detecting tumor size can be used, e.g., MRI. Mice are sacrificed when the tumor size approach a certain size (, e.g., approximately 1.5 cm) in the control group. Tumors are collected, are fixed in formalin, and are analyzed by H&E staining. Representative images are taken from each tumor using a light microscope at, e.g., at ×40 and ×100 magnification.

A graph of tumor size or volume of each mouse plotted against time (e.g., days or weeks) after tumor injection is generated to ascertain the effect of the anti-KIT antibodies on tumor growth in the mice relative to the vehicle negative control.

Mouse models for sarcoma (e.g., Ewing's sarcoma) have been described, for example, see the following list of publications, and may be adapted accordingly to evaluate the effects of anti-KIT antibodies (e.g., any one of antibodies Hum1-Hum20):

González et al., 2004, Clin Cancer Res. 10(2):751-61;
Landuzzi et al., 2000, Am J Pathol. 157(6):2123-31 (6647 cells);
Merchant et al., 2002, JNCI 94(22):1673-1679 (TC71 cells);
Sturla et al., 2000, Cancer Res. 60(21):6160-70 (TC32 and RD-ES cells);
Powis et al., 2006, Mol Cancer Ther. 5(3):630-636 (A-673 cells);
Watanabe et al., 2008, Hum Gene Ther. 19(3):300-10 (A-673 cells);
Rouleau et al., 2008, Clin Cancer Res. 14(22):7223-7236 (A-673 cells);
Karmakar et al, 2011, World J Oncol. 2(2):53-63 (RD-ES and SK-N-MC cells);
Wang et al., 2009, In vivo 23(6):903-9 (TC71 cells); and
Ikeda et al., 2010, Mol Cancer Ther. (3):653-60 (TC71 cells and A4573 cells).

Humanized Mouse Model

Studies with anti-KIT antibodies, including anti-KIT antibody drug conjugates, for example, Hum1-Hum20 antibodies, including antibody-drug conjugates thereof are carried out with mouse models generated by engraftment of immunodeficient mice with components of human immune system, e.g., humanized NSG mice (The Jackson Laboratory, Bar Harbor, Me.). Humanized NSG mice are NOD scid IL-2 receptor gamma chain knockout mice (NSG) engrafted with human hematopoietic stem cells (hCD34$^+$ cells) to reconstitute a human immune system.

These mice can serve as a platform for studying toxicity of anti-KIT antibodies. For example, groups of mice (e.g., 1-5 mice) are injected with various concentrations of anti-KIT antibodies over a period of time (e.g., 4-16 weeks). The mice are assessed for toxicity indicators, e.g., body weight, survival length.

6.9 Example 9: Inhibition of Colony Formation by KIT Expressing CHO Cells in Soft Agar Assays Anti-KIT antibodies described herein, for example Hum1-Hum20, are tested for their ability to inhibit anchorage independent cell growth in soft agar assays of CHO/KIT-WT cells. Soft agar assay for colony formation is an anchorage independent growth assay, which is a useful assay for detecting malignant transformation of cells. In vitro transformation is associated with certain phenotypic changes such as loss of contact inhibition (cells can grow over one another) and anchorage independence (cells form colonies in soft agar). In general, nontransformed cells fail to grow when suspended in a viscous fluid or gel (e.g. agar or agarose), however when these cells are transformed, they are able to grow in a viscous fluid or gel and become anchorage-independent. The process by which these phenotypic changes occur, is assumed to be closely related to the process of in vivo carcinogenesis.

The soft agar assays are carried out as follows. Base agar layer (containing agar and cell culture medium) is added to each well of a 96 well plate. Cell agar layer (containing agar, cell culture medium and cell suspension) is added on top of the base agar layer. Anti-KIT antibodies are diluted in cell culture medium and pipetted on top of the layers. The control samples do not contain any antibodies. Plates are incubated at 37° C. and 5% $CO_2$ for 5-8 days in the presence or absence of 30 ng/mL SCF. The ligand SCF and anti-KIT antibodies (100 nM) are added concurrently to the agar.

When treatment is completed, the agar is solubilized and the cells are lysed. The green fluorescent Cyquant® GR dye is mixed with the lysates. This dye exhibits fluorescence when bound to cellular nucleic acids. Fluorescence is measured at 480 nm excitation and 520 nm emission.

The embodiments described herein are intended to be merely exemplary, and those skilled in the art will recognize, or be able to ascertain using no more than routine experimentation, numerous equivalents to the specific procedures described herein. All such equivalents are considered to be within the scope of the present invention and are covered by the following claims. Furthermore, as used in this specification and claims, the singular forms "a," "an" and "the" include plural forms unless the content clearly dictates otherwise. Thus, for example, reference to "an antibody" includes a mixture of two or more such antibodies, and the like. Additionally, ordinarily skilled artisans will recognize that operational sequences must be set forth in some specific order for the purpose of explanation and claiming, but the present invention contemplates various changes beyond such specific order.

All references (including patent applications, patents, and publications) cited herein are incorporated herein by reference in their entirety and for all purposes to the same extent as if each individual publication or patent or patent application was specifically and individually indicated to be incorporated by reference in its entirety for all purposes.

What is claimed:

1. A method for treating or managing a KIT-associated disorder, wherein the KIT-associated disorder is associated with KIT expression and/or activity, the method comprising administering to a subject in need thereof a therapeutically effective amount of an isolated antibody, or an antigen-binding fragment thereof, which immunospecifically binds to human KIT and comprises:
   (i) a light chain variable region ("VL") comprising the amino acid sequence: DIVMTQSPSX$_{K1}$LSASVGDRVTITCKASQN VRTNVAWYQQKPGKAPKX$_{K2}$LIYSASYRY SGVPDRFX$_{K3}$GSGSGTDFTLTISSLQX$_{K4}$ED FAX$_{K5}$YX$_{K6}$CQQY NSYPRTFGGGTKVEIK (SEQ ID NO: 12), wherein X$_{K1}$ is an amino acid with an aromatic or aliphatic hydroxyl side chain, X$_{K2}$ is an amino acid with an aliphatic or aliphatic hydroxyl side chain, X$_{K3}$ is an amino acid with an aliphatic hydroxyl side chain, X$_{K4}$ is an amino acid with an aliphatic hydroxyl side chain or is P, X$_{K5}$ is an amino acid with a charged or acidic side chain, and X$_{K6}$ is an amino acid with an aromatic side chain; and
   (ii) a heavy chain variable region ("VH") comprising the amino acid sequence: QVQLVQSGAEX$_{H1}$KKPGASVKX$_{H2}$SCKASG YTFTDYYINAVVX$_{H3}$QAPGKG LEWIARIYPGSGNTYYNEKFKGRX$_{H4}$TX$_{H5}$ TAX$_{H6}$KSTSTAYMX$_{H7}$LSSLRSE DX$_{H8}$AVYFCARGVYYFDYWGQGTTVTVSS (SEQ ID NO: 11), wherein X$_{H1}$ is an amino acid with an aliphatic side chain, X$_{H2}$ is an amino acid with an aliphatic side chain, X$_{H3}$ is an amino acid with a polar or basic side chain, X$_{H4}$ is an amino acid with an aliphatic side chain, X$_{H5}$ is an amino acid with an aliphatic side chain, X$_{H6}$ is an amino acid with an acidic side chain, X$_{H7}$ is an amino acid with an acidic or amide derivative side chain, and X$_{H8}$ is an amino acid with an aliphatic hydroxyl side chain.

2. The method of claim 1, wherein the KIT-associated disorder is systemic mast cell disorder, an inflammatory condition, or fibrosis.

3. The method of claim 1, wherein the method further comprises administering a second therapeutic agent.

4. The method of claim 3, wherein the second therapeutic agent is a chemotherapeutic agent, tyrosine kinase inhibitor, a histone deacetylase inhibitor, an antibody, or a cytokine.

5. The method of claim 4, wherein the tyrosine kinase inhibitor is imatinib mesylate or SU11248.

6. The method of claim 1, wherein X$_{K1}$ is the amino acid F or S, X$_{K2}$ is the amino acid A or S, X$_{K3}$ is the amino acid T or S, X$_{K4}$ is the amino acid S or P, X$_{K5}$ is the amino acid D or T, and X$_{K6}$ is the amino acid F or Y.

7. The method of claim 1, wherein X$_{H1}$ is the amino acid L or V, X$_{H2}$ is the amino acid L or V, X$_{H3}$ is the amino acid K or R, X$_{H4}$ is the amino acid V or A, X$_{H5}$ is the amino acid L or I, X$_{H6}$ is the amino acid E or D, X$_{H7}$ is the amino acid Q or E, and X$_{H8}$ is the amino acid S or T.

8. The method of claim 1, wherein the antibody is a human IgG1 or IgG4 antibody.

9. The method of claim 1, wherein the antibody is a monoclonal antibody.

10. The method of claim 1, wherein the antibody or antigen-binding fragment thereof is an antigen-binding fragment or a Fab fragment.

11. The method of claim 1, wherein the antibody is a bispecific antibody.

12. The method of claim 1, wherein the antibody is fused to a heterologous polypeptide.

13. The method of claim 1, wherein the antibody or antigen-binding fragment thereof is a conjugate linked to an agent.

14. A method for treating or managing a KIT-associated disorder, wherein the KIT-associated disorder is a disorder associated with KIT expression and/or activity, the method comprising administering to a subject in need thereof a therapeutically effective amount of an isolated antibody, or an antigen-binding fragment thereof, which immunospecifically binds to human KIT and comprises a VL and a VH, wherein:
  (i) the VL comprises the amino acid sequence of SEQ ID NO: 8 and the VH comprises the amino acid sequence of SEQ ID NO: 4;
  (ii) the VL comprises the amino acid sequence of SEQ ID NO: 10 and the VH comprises the amino acid sequence of SEQ ID NO: 3;
  (iii) the VL comprises the amino acid sequence of SEQ ID NO: 8 and the VH comprises the amino acid sequence of SEQ ID NO: 6;
  (iv) the VL comprises the amino acid sequence of SEQ ID NO: 7 and the VH comprises the amino acid sequence of SEQ ID NO: 5;
  (v) the VL comprises the amino acid sequence of SEQ ID NO: 7 and the VH comprises the amino acid sequence of SEQ ID NO: 2;
  (vi) the VL comprises the amino acid sequence of SEQ ID NO: 7 and the VH comprises the amino acid sequence of SEQ ID NO: 3;
  (vii) the VL comprises the amino acid sequence of SEQ ID NO: 7 and the VH comprises the amino acid sequence of SEQ ID NO: 4;
  (viii) the VL comprises the amino acid sequence of SEQ ID NO: 7 and the VH comprises the amino acid sequence of SEQ ID NO: 6;
  (ix) the VL comprises the amino acid sequence of SEQ ID NO: 8 and the VH comprises the amino acid sequence of SEQ ID NO: 2;
  (x) the VL comprises the amino acid sequence of SEQ ID NO: 8 and the VH comprises the amino acid sequence of SEQ ID NO: 3;
  (xi) the VL comprises the amino acid sequence of SEQ ID NO: 8 and the VH comprises the amino acid sequence of SEQ ID NO: 5;
  (xii) the VL comprises the amino acid sequence of SEQ ID NO: 9 and the VH comprises the amino acid sequence of SEQ ID NO: 2;
  (xiii) the VL comprises the amino acid sequence of SEQ ID NO: 9 and the VH comprises the amino acid sequence of SEQ ID NO: 3;
  (xiv) the VL comprises the amino acid sequence of SEQ ID NO: 9 and the VH comprises the amino acid sequence of SEQ ID NO: 4;
  (xv) the VL comprises the amino acid sequence of SEQ ID NO: 9 and the VH comprises the amino acid sequence of SEQ ID NO: 5;
  (xvi) the VL comprises the amino acid sequence of SEQ ID NO: 9 and the VH comprises the amino acid sequence of SEQ ID NO: 6;
  (xvii) the VL comprises the amino acid sequence of SEQ ID NO: 10 and the VH comprises the amino acid sequence of SEQ ID NO: 2;
  (xviii) the VL comprises the amino acid sequence of SEQ ID NO: 10 and the VH comprises the amino acid sequence of SEQ ID NO: 4;
  (xix) the VL comprises the amino acid sequence of SEQ ID NO: 10 and the VH comprises the amino acid sequence of SEQ ID NO: 5; or
  (xx) the VL comprises the amino acid sequence of SEQ ID NO: 10 and the VH comprises the amino acid sequence of SEQ ID NO: 6.

15. The method of claim 14, wherein the KIT-associated disorder is systemic mast cell disorder, an inflammatory condition, or fibrosis.

16. The method of claim 14, wherein the method further comprises administering a second therapeutic agent.

17. A method for treating or managing a KIT-associated disorder, wherein the KIT-associated disorder is a disorder associated with KIT expression and/or activity, the method comprising administering to a subject in need thereof a therapeutically effective amount of an isolated antibody, or an antigen-binding fragment thereof, which immunospecifically binds to human KIT, wherein said antibody or antigen-binding fragment thereof comprises:
  (i) a VL comprising a VL CDR1, VL CDR2, and VL CDR3 comprising the amino acid sequences of SEQ ID NOs: 19, 20, and 21, respectively; and a VH comprising the amino acid sequence of SEQ ID NO: 2;
  (ii) a VL comprising a VL CDR1, VL CDR2, and VL CDR3 comprising the amino acid sequences of SEQ ID NOs: 19, 20, and 21, respectively; and a VH comprising the amino acid sequence of SEQ ID NO: 3;
  (iii) a VL comprising a VL CDR1, VL CDR2, and VL CDR3 comprising the amino acid sequences of SEQ ID NOs: 19, 20, and 21, respectively; and a VH comprising the amino acid sequence of SEQ ID NO: 4;
  (iv) a VL comprising a VL CDR1, VL CDR2, and VL CDR3 comprising the amino acid sequences of SEQ ID NOs: 19, 20, and 21, respectively; and a VH comprising the amino acid sequence of SEQ ID NO: 5;
  (v) a VL comprising a VL CDR1, VL CDR2, and VL CDR3 comprising the amino acid sequences of SEQ ID NOs: 19, 20, and 21, respectively; and a VH comprising the amino acid sequence of SEQ ID NO: 6;
  (vi) a VL comprising a VL CDR1, VL CDR2, and VL CDR3 comprising the amino acid sequences of SEQ ID NOs: 59, 60, and 61, respectively; and a VH comprising the amino acid sequence of SEQ ID NO: 2;
  (vii) a VL comprising a VL CDR1, VL CDR2, and VL CDR3 comprising the amino acid sequences of SEQ ID NOs: 59, 60, and 61, respectively; and a VH comprising the amino acid sequence of SEQ ID NO: 3;
  (viii) a VL comprising a VL CDR1, VL CDR2, and VL CDR3 comprising the amino acid sequences of SEQ ID NOs: 59, 60, and 61, respectively; and a VH comprising the amino acid sequence of SEQ ID NO: 4;
  (ix) a VL comprising a VL CDR1, VL CDR2, and VL CDR3 comprising the amino acid sequences of SEQ ID NOs: 59, 60, and 61, respectively; and a VH comprising the amino acid sequence of SEQ ID NO: 5;
  (x) a VL comprising a VL CDR1, VL CDR2, and VL CDR3 comprising the amino acid sequences of SEQ ID NOs: 59, 60, and 61, respectively; and a VH comprising the amino acid sequence of SEQ ID NO: 6;
  (xi) a VL comprising a VL CDR1, VL CDR2, and VL CDR3 comprising the amino acid sequences of SEQ ID NOs: 66, 67, and 68, respectively; and a VH comprising the amino acid sequence of SEQ ID NO: 2;
  (xii) a VL comprising a VL CDR1, VL CDR2, and VL CDR3 comprising the amino acid sequences of SEQ ID NOs: 66, 67, and 68, respectively; and a VH comprising the amino acid sequence of SEQ ID NO: 3;
  (xiii) a VL comprising a VL CDR1, VL CDR2, and VL CDR3 comprising the amino acid sequences of SEQ ID NOs: 66, 67, and 68, respectively; and a VH comprising the amino acid sequence of SEQ ID NO: 4;
(xiv) a VL comprising a VL CDR1, VL CDR2, and VL CDR3 comprising the amino acid sequences of SEQ ID NOs: 66, 67, and 68, respectively; and a VH comprising the amino acid sequence of SEQ ID NO: 5;
(xv) a VL comprising a VL CDR1, VL CDR2, and VL CDR3 comprising the amino acid sequences of SEQ ID NOs: 66, 67, and 68, respectively; and a VH comprising the amino acid sequence of SEQ ID NO: 6;
(xvi) a VL comprising the amino acid sequence of SEQ ID NO: 7, and a VH comprising a VH CDR1, VH CDR2, and VH CDR3 comprising the amino acid sequences of SEQ ID NOs: 16, 17, and 18, respectively;
(xvii) a VL comprising the amino acid sequence of SEQ ID NO: 8, and a VH comprising a VH CDR1, VH CDR2, and VH CDR3 comprising the amino acid sequences of SEQ ID NOs: 16, 17, and 18, respectively;
(xviii) a VL comprising the amino acid sequence of SEQ ID NO: 9, and a VH comprising a VH CDR1, VH CDR2, and VH CDR3 comprising the amino acid sequences of SEQ ID NOs: 16, 17, and 18, respectively;
(xix) a VL comprising the amino acid sequence of SEQ ID NO: 10, and a VH comprising a VH CDR1, VH CDR2, and VH CDR3 comprising the amino acid sequences of SEQ ID NOs: 16, 17, and 18, respectively;
(xx) a VL comprising the amino acid sequence of SEQ ID NO: 7, and a VH comprising a VH CDR1, VH CDR2, and VH CDR3 comprising the amino acid sequences of SEQ ID NOs: 56, 57, and 58, respectively;
(xxi) a VL comprising the amino acid sequence of SEQ ID NO: 8, and a VH comprising a VH CDR1, VH CDR2, and VH CDR3 comprising the amino acid sequences of SEQ ID NOs: 56, 57, and 58, respectively;
(xxii) a VL comprising the amino acid sequence of SEQ ID NO: 9, and a VH comprising a VH CDR1, VH CDR2, and VH CDR3 comprising the amino acid sequences of SEQ ID NOs: 56, 57, and 58, respectively;
(xxiii) a VL comprising the amino acid sequence of SEQ ID NO: 10, and a VH comprising a VH CDR1, VH CDR2, and VH CDR3 comprising the amino acid sequences of SEQ ID NOs: 56, 57, and 58, respectively;
(xxiv) a VL comprising the amino acid sequence of SEQ ID NO: 7, and a VH comprising a VH CDR1, VH CDR2, and VH CDR3 comprising the amino acid sequences of SEQ ID NOs: 56, 62, and 63, respectively;
(xxv) a VL comprising the amino acid sequence of SEQ ID NO: 8, and a VH comprising a VH CDR1, VH CDR2, and VH CDR3 comprising the amino acid sequences of SEQ ID NOs: 56, 62, and 63, respectively;
(xxvi) a VL comprising the amino acid sequence of SEQ ID NO: 9, and a VH comprising a VH CDR1, VH CDR2, and VH CDR3 comprising the amino acid sequences of SEQ ID NOs: 56, 62, and 63, respectively;
(xxvii) a VL comprising the amino acid sequence of SEQ ID NO: 10, and a VH comprising a VH CDR1, VH CDR2, and VH CDR3 comprising the amino acid sequences of SEQ ID NOs: 56, 62, and 63, respectively;
(xxviii) a VL comprising the amino acid sequence of SEQ ID NO: 7, and a VH comprising a VH CDR1, VH CDR2, and VH CDR3 comprising the amino acid sequences of SEQ ID NOs: 64, 65, and 58, respectively;
(xxix) a VL comprising the amino acid sequence of SEQ ID NO: 8, and a VH comprising a VH CDR1, VH CDR2, and VH CDR3 comprising the amino acid sequences of SEQ ID NOs: 64, 65, and 58, respectively;
(xxx) a VL comprising the amino acid sequence of SEQ ID NO: 9, and a VH comprising a VH CDR1, VH CDR2, and VH CDR3 comprising the amino acid sequences of SEQ ID NOs: 64, 65, and 58, respectively;
(xxxi) a VL comprising the amino acid sequence of SEQ ID NO: 10, and a VH comprising a VH CDR1, VH CDR2, and VH CDR3 comprising the amino acid sequences of SEQ ID NOs: 64, 65, and 58, respectively;
(xxxii) a VL comprising the amino acid sequence of SEQ ID NO: 7, and a VH comprising a VH CDR1, VH CDR2, and VH CDR3 comprising the amino acid sequences of SEQ ID NOs: 70, 71, and 72, respectively;
(xxxiii) a VL comprising the amino acid sequence of SEQ ID NO: 8, and a VH comprising a VH CDR1, VH CDR2, and VH CDR3 comprising the amino acid sequences of SEQ ID NOs: 70, 71, and 72, respectively; or
(xxxiv) a VL comprising the amino acid sequence of SEQ ID NO: 9, and a VH comprising a VH CDR1, VH CDR2, and VH CDR3 comprising the amino acid sequences of SEQ ID NOs: 70, 71, and 72, respectively.

18. The method of claim 17, wherein the KIT-associated disorder is systemic mast cell disorder, an inflammatory condition, or fibrosis.

19. The method of claim 17, wherein the method further comprises administering a second therapeutic agent.

20. The method of claim 2, wherein the KIT-associated disorder is systemic mast cell disorder.

21. The method of claim 15, wherein the KIT-associated disorder is systemic mast cell disorder.

22. The method of claim 18, wherein the KIT-associated disorder is systemic mast cell disorder.

* * * * *

UNITED STATES PATENT AND TRADEMARK OFFICE
CERTIFICATE OF CORRECTION

PATENT NO.         : 10,781,267 B2                                              Page 1 of 1
APPLICATION NO.    : 16/221002
DATED              : September 22, 2020
INVENTOR(S)        : Hadari et al.

It is certified that error appears in the above-identified patent and that said Letters Patent is hereby corrected as shown below:

In the Claims

In Column 353, Claim 1, Line 45, replace "CQQY NSYPRTFGGGTKVEIK" with --CQQYNSYPRTFGGGTKVEIK--;
In Column 353, Claim 1, Line 57, replace "YTFTDYYINAVVX$_{H3}$" with --YTFTDYYINWVX$_{H3}$--.

Signed and Sealed this
Twenty-ninth Day of December, 2020

Andrei Iancu
*Director of the United States Patent and Trademark Office*